(12) United States Patent
Georgiou

(10) Patent No.: US 9,314,445 B2
(45) Date of Patent: Apr. 19, 2016

(54) USE OF OMEGA FATTY ACIDS FOR TREATING DISEASE

(76) Inventor: Tassos Georgiou, Nicosia (CY)

( * ) Notice: Subject to any disclaimer, the term of this patent is extended or adjusted under 35 U.S.C. 154(b) by 0 days.

(21) Appl. No.: 14/343,863

(22) PCT Filed: Sep. 12, 2012

(86) PCT No.: PCT/EP2012/067771
§ 371 (c)(1),
(2), (4) Date: Mar. 10, 2014

(87) PCT Pub. No.: WO2013/037794
PCT Pub. Date: Mar. 21, 2013

(65) Prior Publication Data
US 2014/0227261 A1   Aug. 14, 2014

(30) Foreign Application Priority Data
Sep. 12, 2011   (EP) ..................... 11390001

(51) Int. Cl.
*A61K 31/20*   (2006.01)
*A61K 31/202*   (2006.01)
*A61K 31/58*   (2006.01)
*A61K 38/13*   (2006.01)
*A61K 39/395*   (2006.01)

(52) U.S. Cl.
CPC ............... *A61K 31/202* (2013.01); *A61K 31/58* (2013.01); *A61K 38/13* (2013.01); *A61K 39/3955* (2013.01)

(58) Field of Classification Search
CPC .................................................. A61K 31/202
USPC ........................................................ 514/560
See application file for complete search history.

(56) References Cited

U.S. PATENT DOCUMENTS

| 2005/0249821 A1 | 11/2005 | Paul |
| 2006/0009522 A1* | 1/2006 | Dana et al. .................. 514/560 |
| 2009/0226547 A1 | 9/2009 | Gilbard et al. |

FOREIGN PATENT DOCUMENTS

| EP | 1932521 A1 * | 6/2008 |
| WO | 2004004599 A2 | 1/2004 |
| WO | 2009098186 A1 | 8/2009 |
| WO | 2010106571 A2 | 9/2010 |

OTHER PUBLICATIONS

Decision to Grant dated Jul. 23, 2015 and translated claims, letter, and fees submitted on Jul. 9, 2015 for the corresponding European Patent Application No. 12773237.8.
Georgiou et al., "Pilot study for treating dry age-related macular degeneration (AMD) with high-dose omega-3 fatty acids", PharmaNutrition 2 (2014) 8-11.
"Lutein + Zeaxanthin and Omega-3 Fatty Acids for Age-Related Macular Degeneration—The Age-Related Eye Disease Study 2 (AREDS2) Randomized Clinical Trial", JAMA. 2013;309(19)2005-2015.
Intention to Grant and Text for Grant dated Feb. 27, 2015 for EP12773237.8.

* cited by examiner

*Primary Examiner* — Kevin E Weddington
(74) *Attorney, Agent, or Firm* — Ella Cheong Hong Kong; Sam T. Yip

(57) ABSTRACT

Eicosapentaenoic acid (EPA) and docosahexaenoic acid (DHA), or a salt or an ester thereof, are provided for use in the treatment and/or prophylaxis of a condition selected from macular oedema, conditions causing damage to retinal photoreceptors and/or retinal pigment epithelial cells, and dry eyes in a mammal, wherein the combined dosage of eicosapentaenoic acid and docosahexaenoic acid is from 5 mmol to 25 mmol per day, and wherein the molar ratio of eicosapentaenoic acid to docosahexaenoic acid is in the range of from 1:1 to 5:1. Compositions comprising EPA and DHA and at least one pharmaceutically acceptable excipient, and kits containing EPA, DHA and further therapeutic agents are also provided. The EPA and DHA, or composition comprising the EPA and DHA may be administered orally.

13 Claims, 270 Drawing Sheets

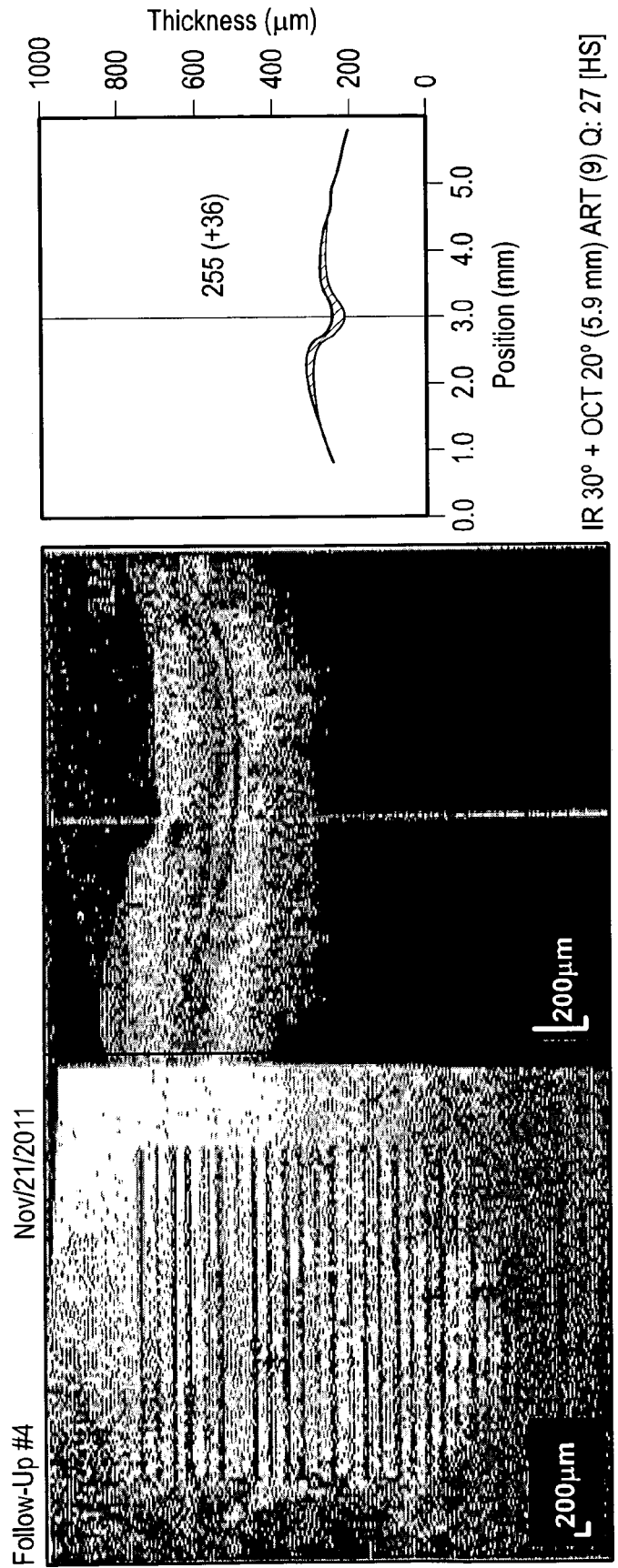
FIG. 19 *Cont'd*

USE OF OMEGA FATTY ACIDS FOR TREATING DISEASE

FIELD OF INVENTION

The invention relates to the use of eicosapentaenoic acid (EPA) and docosahexaenoic acid (DHA) for treating disease, in particular for the treatment or prophylaxis of certain eye conditions.

BACKGROUND OF INVENTION

The macula is the part of the retina which is responsible for sharp vision, due to the presence of a high density of cone photoreceptors. Macular oedema is a condition characterised by swelling of the macula due to leakage from small blood vessels. There is a breakdown of blood retinal bathers with changes in microvascular permeability, which leads to extracellular oedema, photoreceptor damage and loss of vision.

Macular oedema is caused by a wide range of retinal diseases which include:
1) Wet age-related macular degeneration,
2) Diabetic maculopathy,
3) Retinal vascular occlusions (branch or central),
4) Epiretinal membranes, and
5) Inflammation within the eye such as after recent eye surgery.

Vision loss associated with the above conditions is due to macular oedema, and the main strategy to reduce visual loss in patients having the above conditions has been the treatment of macular oedema. Age-related macular degeneration is the leading cause of visual impairment and blindness in persons over the age of 65 in the world. The condition, which occurs in dry and wet forms, usually affects older adults resulting in a loss of vision in the centre of the visual field, due to retina damage. In dry age-related macular degeneration, drusen (cellular debris) builds up between the retina and choroid. In the more severe wet form, blood vessels may grow up from the choroid behind the retina, leading to blood and protein leakage beneath the macula and consequences such as vision loss and detached retinas.

Diabetic retinopathy (also referred to as diabetic maculopathy) is the most common cause of blindness among adults of working age, and involves swelling of the central part of the retina or the macula. Diabetic retinopathy is caused by changes in the blood vessels of the retina. For some people with the condition, blood vessels may swell and leak fluid and/or abnormal new blood vessels may grow on the surface of the retina. Diabetic retinopathy has been classified as having four stages:

i) Mild non-proliferative diabetic retinopathy (in which microaneurysms occur—small areas of balloon-like swelling in the blood vessels of the retina);

ii) Moderate non-proliferative diabetic retinopathy (in which some blood vessels which nourish the retina are blocked);

iii) Severe non-proliferative diabetic retinopathy (in which many more blood vessels are blocked depriving areas of the retina of blood supply); and iv) Proliferative diabetic retinopathy (in which the growth of new blood vessels takes place. The blood vessels can leak blood resulting in severe vision loss and/or blindness).

Diabetic retinopathy is responsible for 12,000 to 24,000 new cases of blindness each year in the USA. Macular oedema affects 14% of patients with diabetes.

Retinal vascular occlusion diseases (e.g. by thrombus formation blocking blood supply in arteries to the retina) are the second most common cause of visual loss due to retinal vascular disease. They affect around 1.1 million people in the USA alone, thus representing a serious public health problem.

Epiretinal membrane is a condition affecting the macula in which a layer of tissue forms across the macula which contracts to create tension, and can lead to macula oedema.

The main strategy to reduce visual loss in these patients has been by treatment with VEGF inhibitors. VEGF inhibitors have revolutionised the way in which patients with wet age-related macular degeneration are treated in the last 5 years. Intravitreal injections of VEGF inhibitors (e.g. Avastin® (bevacizumab), Lucentis® (ranibizumab)) have been used to treat macular oedema, and give visual outcomes superior to previous treatments. However, although positive effects are observed whilst patients are on treatment, oedema tends to return when treatment is stopped. Frequent monthly intravitreal injections lead to better outcomes for patients. However, side effects such as endophthalmitis, retinal tears leading to retinal detachments, vitreous haemorrhages and cataracts are observed with repeated injections.

Intravitreal injections of steroids, such as Kenalog® (triamcinolone) have also been used to treat macular oedema. However treatment effects are usually temporary and therapy needs to be repeated. Intravitreal steroids can also cause side effects such as increased intraocular pressure, cataracts, retinal detachment, vitreous haemorrhages and endophthalmitis. In diabetic retinopathy, focal or grid laser photocoagulation is the standard of care for the past 25 years. From the ETDRS study it is known that performing focal or grid laser reduces the risk of moderate vision loss as compared with no treatment. However, only 17% of patients gained vision. This means that nine patients have to be treated, for one to have improved vision.

Conditions causing damage to retinal photoreceptors and/or retinal pigment epithelial cells include inherited diseases such as retinitis pigmentosa and Stargardt's disease, damage caused by exposure to extreme light, damage associated with surgery (e.g. cataract surgery), damage associated with exposure to chemical toxins (e.g. quinines, such as chloroquine) and other conditions such as macular dystrophy and macular degeneration (e.g. dry age-related macular degeneration).

Dry eyes (also known as dry eye disease, dry eye syndrome) is a condition in which the eyes do not produce enough tears, and can lead to the eyes becoming inflamed or swollen. The condition has been defined as being a multifactorial disease of the tears and ocular surface that results in symptoms of discomfort, visual disturbance, and tear flim instability with potential damage to the ocular surface. It is accompanied by increased osmolarity of the tear film and inflammation of the ocular surface (The Definition and Classification of Dry Eye Disease, Guidelines from the 2007 International Dry Eye Workshop, Lemp and Foulks). Dry eyes can cause irritation, reduced visual acuity, superficial punctuate keratitis and poor tear break-up time. The disease has been classified based on severity into 4 levels, ranging from levels 1 and 2 (mild), to levels 3 (moderate) and 4 (severe) (The Definition and Classification of Dry Eye Disease, supra).

Known therapies for dry eyes include treatment with artificial tear drops, steroidal and non-steroidal eye drops, cyclosporine eye drops, use of punctal plugs, use of specialized eyewear, and/or surgery. However, there are still patients with dry eyes who remain very symptomatic despite the use of such treatments.

The use of compositions containing omega-3 fatty acids in treating and/or preventing eye conditions has been investigated. For example, WO2010/118761 (Eolas Science Limited) discloses processes for preparing certain compositions rich in the omega-3 fatty acid docosahexaenoic acid (DHA) and which contain only low amounts of phytanic acid. WO2010/118761 also discloses the use of those compositions for treating certain eye conditions. US 2009/0226547 (Gilbard & Seddon) discloses a nutritional supplement for eye health comprising EPA and DHA together with anti-oxidant and anti-angiogenic components.

However, there remains a need for effective alternative therapies for treating conditions such as macular oedema, conditions causing damage to retinal photoreceptors and/or retinal pigment epithelial cells, and dry eyes.

SUMMARY OF THE INVENTION

Accordingly, in a first aspect, the invention provides eicosapentaenoic acid (EPA) and docosahexaenoic acid (DHA), or a salt or an ester thereof, for use in the treatment and/or prophylaxis of a condition selected from the group consisting of macular oedema, conditions causing damage to retinal photoreceptors and/or retinal pigment epithelial cells, and dry eyes in a mammal, wherein the combined dosage of eicosapentaenoic acid and docosahexaenoic acid is from 5 mmol to 25 mmol per day, and wherein the molar ratio of eicosapentaenoic acid to docosahexaenoic acid is in the range of from 1:1 to 5:1.

It has been found by the inventor that significant improvements in the symptoms of those conditions can be achieved using EPA and DHA in the indicated ratios and dosage amounts. The therapy of the invention is surprisingly effective, even for patients with severe forms of those conditions, and even for patients who are non-responsive or poorly responsive to other therapies. The therapy of the invention is particularly suitable for oral administration, and so avoids the need for frequent intravitreal injections (associated with other therapies such as VEGF inhibitors and steroids). The use of EPA and DHA in the indicated ratios and dosage amounts also avoids or reduces the side effects experienced with the known treatments (e.g. endophthalmitis, retinal tears leading to retinal detachments, vitreous haemorrhages and cataracts).

In some preferred embodiments, the EPA and DHA is for use in the treatment of macular oedema in a patient or patient population that is poorly responsive or non-responsive to treatment with a VEGF inhibitor. In some preferred embodiments, the EPA and DHA is for use in the treatment of moderate and/or severe dry eyes. In some preferred embodiments, the EPA and DHA is for use in the treatment of dry eyes in a patient or patient population that is poorly responsive or non responsive to treatment with steroid eye drops, artificial tear drops, tear lubricating ointments, steroid ointments, punctual plugs and/or cyclosporine eye drops.

In some embodiments, the EPA and DHA is for use together with a further therapeutic agent, for simultaneous, sequential or separate administration. Preferably the further therapeutic agent is a VEGF inhibitor, a steroid, a carbonic anhydrase inhibitor and/or cyclosporine.

In a second aspect, the invention provides a kit comprising i) eicosapentaenoic acid (EPA) and docosahexaenoic acid (DHA), or a salt or an ester thereof; and ii) a VEGF inhibitor, a steroid, a carbonic anhydrase inhibitor and/or cyclosporine, wherein the combined dosage of eicosapentaenoic acid and docosahexaenoic acid is from 5 mmol to 25 mmol per day, and wherein the molar ratio of eicosapentaenoic acid to docosahexaenoic acid is in the range of from 1:1 to 5:1. The kit is for use in treating the conditions mentioned above.

In a third aspect, the invention provides a composition comprising eicosapentaenoic acid (EPA) and docosahexaenoic acid (DHA), or a salt or an ester thereof, and at least one pharmaceutically acceptable excipient, wherein the molar ratio of EPA (or salt or ester thereof) to DHA (or salt or ester thereof) in the composition is in the range of from 1:1 to 5:1, for use in the treatment and/or prophylaxis of a condition selected from the group consisting of macular oedema, conditions causing damage to retinal photoreceptors and/or retinal pigment epithelial cells and dry eyes in a mammal, and wherein the composition is for administration in a combined daily dosage of EPA (or salt or ester thereof) to DHA (or salt or ester thereof) of from 5 mmol to 25 mmol per day. Preferably the composition is for oral administration. Preferably, the composition comprises at least 50 weight % omega-3 fatty acids. Preferably, the composition is substantially free from anti-oxidants. In one embodiment, the composition consists of, per 100 g:

TABLE 1

| Fats | | 100 g |
|---|---|---|
| Of which: | Saturated | 3.1 g |
| | Monounsaturated | 11.5 g |
| | Polyunsaturated | 85.4 g |
| Total omega-3 fatty acid | | 75 g |
| Of which: | EPA (eicosapentaenoic acid) | 40 g |
| | DHA (docosahexaenoic acid) | 20 g |
| | Other omega-3 fatty acid | 15 g |

DETAILED DESCRIPTION OF INVENTION

Figure 1:
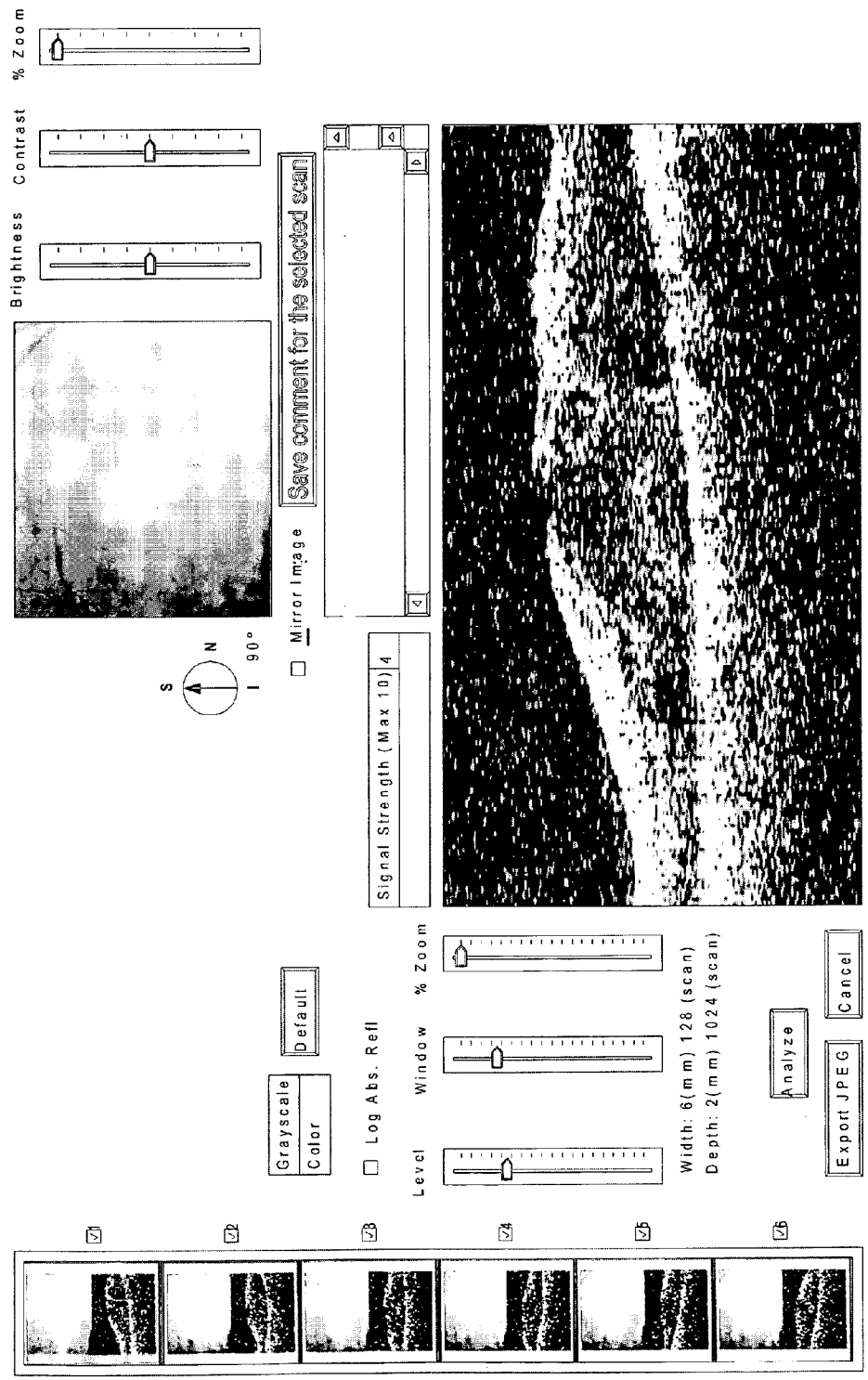
FIGS. 1 to 38 show Optical Coherence Tomography (OCT) scans in patients before, during, and after treatment with EPA and DHA in accordance with the invention.

The invention provides eicosapentaenoic acid (EPA) and docosahexaenoic acid (DHA), or a salt or an ester thereof, for use in the treatment and/or prophylaxis of a condition selected from the group consisting of macular oedema, conditions causing damage to retinal photoreceptors and/or retinal pigment epithelial cells, and dry eyes in a mammal, wherein the combined dosage of eicosapentaenoic acid and docosahexaenoic acid is from 5 mmol to 25 mmol per day, and wherein the molar ratio of eicosapentaenoic acid to docosahexaenoic acid is in the range of from 1:1 to 5:1. The use of eicosapentaenoic acid and docosahexaenoic acid, in the indicated ratios and dosages, provides a particularly effective therapy for those conditions, avoids or reduces the requirement for intravitreal injections associated with VEGF inhibitor and steroid therapies, and avoids or reduces side effects such as endophthalmitis, retinal tears leading to retinal detachments, vitreous haemorrhages and cataracts associated with those known therapies.

The invention also provides the use of EPA and DHA, or a salt or an ester thereof, for the manufacture of a medicament for the treatment and/or prophylaxis of a condition selected from macular oedema, conditions causing damage to retinal photoreceptors and/or retinal pigment epithelial cells, and dry eyes in a mammal, wherein the combined dosage of EPA and DHA is from 5 mmol to 25 mmol per day, and wherein the molar ratio of EPA to DHA is in the range of from 1:1 to 5:1.

The invention also provides a method for the treatment and/or prevention of a condition selected from macular oedema, conditions causing damage to retinal photoreceptors and/or retinal pigment epithelial cells, and dry eyes in a mammal, which comprises administering to the mammal EPA and DHA, or a salt or an ester thereof, wherein the combined dosage of EPA and DHA is from 5 mmol to 25 mmol per day, and wherein the molar ratio of EPA to DHA is in the range of from 1:1 to 5:1. Preferably, the mammal is a human. The method is preferably for treatment and/or prevention of macular oedema, conditions causing damage to retinal photoreceptors and/or retinal pigment epithelial cells, and/or dry eyes in a patient or patient population who have or are at risk of developing at least one of those conditions.

EPA and DHA are omega-3 fatty acids. An omega-3 fatty acid is an unsaturated fatty acid containing a final carbon-carbon double bond as the third bond from the alkyl end of the molecule (i.e. the end that is remote from the carboxylic acid group). Examples of omega-3 fatty acids are indicated in Table 2.

TABLE 2

| Omega-3 fatty acids | | | |
|---|---|---|---|
| Common name | Lipid name | Chemical name | MW |
| Tetracosahexaenoic acid | 24:6 (n-3) | all-cis-6,9,12,15,18,21-tetracosahexaenoic acid | 357 |
| Tetracosapentaenoic acid | 24:5 (n-3) | all-cis-9,12,15,18,21-tetracosapentaenoic acid | 359 |
| Docosahexaenoic acid (DHA) | 22:6 (n-3) | all-cis-4,7,10,13,16,19-docosahexaenoic acid | 328 |
| Docosapentaenoic acid (DPA) | 22:5 (n-3) | all-cis-7,10,13,16,19-docosapentaenoic acid | 331 |
| Eicosapentaenoic acid (EPA) | 20:5 (n-3) | all-cis-5,8,11,14,17-eicosapentaenoic acid | 302 |
| Eicosatetraenoic acid (ETA) | 20:4 (n-3) | all-cis-8,11,14,17-eicosatetraenoic acid | 304 |
| Eicosatrienoic acid (ETE) | 20:3 (n-3) | all-cis-11,14,17-eicosatrienoic acid | 306 |
| Stearidonic acid (SDA) | 18:4 (n-3) | all-cis-6,9,12,15-octadecatetraenoic acid | 276 |
| α-Linolenic acid (ALA) | 18:3 (n-3) | all-cis-9,12,15-octadecatrienoic acid | 278 |
| Hexadecatrienoic acid | 16:3 (n-3) | all-cis-7,10,13-hexadecatrienoic acid | 250 |

In some embodiments, the EPA and/or DHA is in the form of a salt. Suitable salts include those formed with organic or inorganic bases. Pharmaceutically acceptable base salts include ammonium salts, alkali metal salts, for example those of potassium and sodium, alkaline earth metal salts, for example those of calcium and magnesium, and salts with organic bases, for example dicyclohexylamine, N-methyl-D-glucomine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine.

In other embodiments, the EPA and/or DHA is in the form of an ester. Ester groups include those formed from the terminal carboxylic acid moiety of the omega-3 fatty acid and an alcohol, such as a $C_{1-12}$ alkyl ester, formed by reaction of the omega-3 fatty acid with an alcohol having from 1 to 12 carbons, preferably a $C_{1-6}$ alkyl ester formed by reaction of the omega-3 fatty acid with an alcohol having from 1 to 6 carbons, for example a methyl, ethyl, n-propyl, isopropyl, butyl, pentyl, or hexyl ester, formed by reaction of the omega-3 fatty acid with methanol, ethanol, n-propanol, isopropanol, butanol, pentanol or hexanol. Preferably, the ester is an ethyl ester or a methyl ester, more preferably an ethyl ester.

In one preferred embodiment the EPA or salt or ester thereof comprises EPA and/or EPA ethyl ester, and the DHA or salt or ester thereof comprises DHA and/or DHA ethyl ester. More preferably, a combination of eicosapentaenoic acid and docosahexaenoic acid is used (i.e. the free acids of EPA and DHA are used, rather than salts or esters).

The therapy of the invention has been shown to be particularly effective for treatment of the indicated conditions. Thus, preferably the EPA and DHA, or a salt or an ester thereof, are for use in the treatment of a condition selected from macular oedema, conditions causing damage to retinal photoreceptors and/or retinal pigment epithelial cells, and dry eyes. However, the invention also encompasses the use of EPA and DHA in the indicated ratios and dosages as a prophylactic therapy.

In a preferred embodiment, the condition is macular oedema. In a preferred embodiment, the condition is cystoid macular oedema. In a preferred embodiment, the condition is diabetic macular oedema. In a preferred embodiment, the condition is macular oedema caused by/associated with wet age-related macular degeneration, diabetic retinopathy, retinal vascular occlusions, epiretinal membranes, inflammation in the eye causing oedema and/or retinal pigment epithelial atrophy in a mammal, preferably wet age-related macular degeneration, diabetic retinopathy, retinal vascular occlusions and/or inflammation of the eye. In one embodiment, the condition is macular oedema caused by/associated with wet age-related macular degeneration. In another embodiment, the condition is macular oedema caused by/associated with diabetic retinopathy, preferably proliferative diabetic retinopathy. In another embodiment, the condition is macular oedema caused by/associated with retinal vascular occlusions. In another embodiment, the condition is macular oedema caused by/associated with epiretinal membranes. In another embodiment, the condition is macular oedema caused by/associated with inflammation of the eye. In another embodiment, the condition is macular oedema caused by/associated with retinal pigment epithelial atrophy.

In a preferred embodiment, the EPA and DHA, or salt or ester thereof, is for use in the treatment of macular oedema in a patient or patient population that is poorly responsive or non-responsive to treatment with a VEGF inhibitor. Examples of VEGF inhibitors include Lucentis® (ranibizumab) and Avastin® (bevacizumab). In another embodiment, the EPA and DHA, or salt or ester thereof, is for use in the treatment of macular oedema in a patient or patient population that is poorly responsive or non-responsive to treatment with a steroid. Examples of steroids include Kenalog® (triamcinolone).

Administration of EPA and DHA has been shown to result in improved vision (determined by a gain in lines on a Snellen chart) in patients who have macular oedema, or a reversal or partial reversal in vision loss associated with/caused by macular oedema. Accordingly, in certain embodiments, the EPA and DHA, or salt or ester thereof, finds use in improving visual acuity in patients who have macular oedema and/or finds use reducing or reversing vision loss associated with/caused by macular oedema. Patients with macular oedema treated with EPA and DHA have also demonstrated reduced retinal fluid levels and/or reduced retinal swelling. In certain embodiments, the EPA and DHA, or salt or ester thereof, finds use in reducing retinal fluid levels in patients who have macular oedema. In certain embodiments, the EPA and DHA, or salt or ester thereof, finds use in reducing retinal swelling in patients with macular oedema.

In a preferred embodiment, the condition is dry eyes. The therapy of the invention has been shown to be particularly effective in treating patients with more severe forms of that condition. Accordingly, in a preferred embodiment the condition is moderate or severe dry eyes (i.e. dry eyes of disease severity level 3 or 4). More preferably, the condition is severe dry eyes (i.e. dry eyes of disease severity level 4). In a preferred embodiment, the EPA and DHA, or salt or ester thereof, is for use in the treatment of dry eyes in a patient or patient population that is poorly responsive or non-responsive to treatment with steroid eye drops, artificial tear drops, tear lubricating ointments, steroid ointments, punctual plugs and/or cyclosporine eye drops.

In a preferred embodiment, the condition is a condition causing damage to retinal photoreceptors and/or retinal pigment epithelial cells, e.g. an inherited disease (such as retinitis pigmentosa or Stargardt's disease), an eye tumour, damage caused by exposure to extreme light, damage associated with surgery (e.g. cataract surgery), damage associated with exposure to chemical toxins (e.g. quinines, such as chloroquine) or other conditions such as macular dystrophy, macular degeneration (e.g. dry age-related macular degeneration), optic neuropathy, and vascular disturbance. More preferably, the condition is selected from the group consisting of retinitis pigmentosa, Stargardt's disease, damage caused by exposure to extreme light, damage associated with surgery, damage associated with exposure to a chemical toxin, macular dystrophy and dry age-related macular degeneration.

Administration of EPA and DHA has been shown to result in improved vision (as determined by a gain in lines on a Snellen chart) in patients having photoreceptor damage following cataract surgery or due to chloroquin therapy, or a reversal or partial reversal in vision loss caused by cataract surgery and/or chloroquin therapy. Accordingly, in certain embodiments, the EPA and DHA, or salt or ester thereof, finds use in improving visual acuity in patients who have a condition causing damage to retinal photoreceptors and/or retinal pigment epithelial cells (e.g. photoreceptor damage following cataract surgery, or following quinine therapy) and/or finds use reducing or reversing vision loss associated with/caused by those conditions.

The combined dosage of EPA and DHA, or a salt or an ester thereof, is from 5 mmol to 25 mmol per day (for an adult human) Preferably, the combined dosage is from 5 mmol to 20 mmol per day, more preferably from 6 mmol to 18 mmol, still more preferably from 7 mmol to 17 mmol. In one preferred embodiment, the combined dosage of EPA and DHA, or a salt or an ester thereof, is about 7 mmol to 8 mmol per day. In another preferred embodiment, the combined dosage of EPA and DHA, or a salt or an ester thereof, is about 10 mmol to 11 mmol per day. In another preferred embodiment, the combined dosage of EPA and DHA, or a salt or an ester thereof, is about 16 mmol to 17 mmol per day. In another embodiment, the combined dosage of EPA and DHA, or a salt or an ester thereof, is from 5 mmol to 15 mmol per day.

The molar ratio of EPA to DHA, or a salt or ester thereof, is in the range of from 1:1 to 5:1. Preferably the molar ratio is in the range of from 1:1 to 4:1, more preferably 1:1 to 3:1, still more preferably 1.5:1 to 2.5:1, yet more preferably 2.1:1 to 2.4:1, most preferably in the range of from 2.1:1 to 2.2:1.

The ratio of EPA to DHA may alternatively be expressed in terms of a weight ratio. Preferably, EPA and DHA are present in a weight ratio of from 1:1 to 4:1, more preferably from 1:1 to 3:1, most preferably about 2:1.

Preferably, the dosage of EPA, or a salt or an ester thereof, is in the range of from 4 mmol per day to 15 mmol per day, and the dosage of DHA, or a salt or an ester thereof, is in the range of from 2 mmol per day to 7.5 mmol per day. In one preferred embodiment, the dosage of EPA, or a salt or an ester thereof, is in the range of from 5 mmol per day to 6 mmol per day, and the dosage of DHA, or a salt or an ester thereof, is in the range of from 2 mmol per day to 3 mmol per day. In another preferred embodiment, the dosage of EPA, or a salt or an ester thereof, is in the range of from 7.2 mmol per day to 8.2 mmol per day, and the dosage of DHA, or a salt or an ester thereof, is in the range of from 3 mmol per day to 4 mmol per day. In another preferred embodiment, the dosage of EPA, or a salt or an ester thereof, is in the range of from 10.5 mmol per day to 11.5 mmol per day, and the dosage of DHA, or a salt or an ester thereof, is in the range of from 4.6 mmol per day to 5.6 mmol per day.

The omega fatty acids EPA and DHA, or salts or esters thereof, may be administered simultaneously, sequentially or separately. Whilst those omega fatty acids may be used as the sole active ingredients in a medicament, it is also possible for them to be used in combination with one or more further active ingredients, for simultaneous, sequential or separate administration. Such further active ingredients may be an agent useful in the prevention or treatment of macular oedema, conditions causing damage to retinal photoreceptors and/or retinal pigment epithelial cells, and/or dry eyes. Such agents are known in the art. Preferably the further therapeutic agent is selected from the group consisting of a VEGF inhibitor (such as bevacizumab or ranibizumab), a steroid (such as triamcinolone), a carbonic anhydrase inhibitor (such as acetazolamide, methazolamide or dorzolamide), and cyclosporine. More preferably, the further active ingredient is a VEGF inhibitor and/or a steroid. In one preferred embodiment, the further active ingredient is a VEGF inhibitor, such as bevacizumab or ranibizumab. In one preferred embodiment, the further active ingredient is a steroid, such as triamcinolone.

The precise dosage of the further active ingredient will vary with the dosing schedule, the oral potency of the particular agent chosen, the age, size, sex and condition of the subject, the nature and severity of the disorder to be treated, and other relevant medical and physical factors. Thus, a precise pharmaceutically effective amount cannot be specified in advance, but can be readily determined by the caregiver or clinician. An appropriate amount can be determined by routine experimentation from animal models and human clinical studies. For humans, an effective dose will be known or otherwise able to be determined by one of ordinary skill in the art.

The individual components of such combinations can be administered separately at different times during the course of therapy or concurrently in divided or single combination forms. The present invention is therefore to be understood as embracing all such regimes of simultaneous or alternating treatment and the term "administering" is to be interpreted accordingly. It will be understood that the scope of combinations of the omega-3 fatty acids EPA and DHA with other agents includes in principle any combination with any pharmaceutical composition useful for treating macular oedema, conditions causing damage to retinal photoreceptors and/or retinal pigment epithelial cells, and/or dry eyes.

The above further therapeutic agent, when employed in combination with the omega-3 fatty acids EPA and DHA, may be used, for example, in those amounts indicated in the Physicians' Desk Reference (PDR) or as otherwise determined by one of ordinary skill in the art.

The present invention also provides a kit comprising i) eicosapentaenoic acid (EPA) and docosahexaenoic acid (DHA), or a salt or an ester thereof and ii) a VEGF inhibitor (e.g. bevacizumab or ranibizumab), a steroid (e.g. triamcinolone), a carbonic anhydrase inhibitor (such as acetazolamide, methazolamide or dorzolamide), and cyclosporine, wherein the combined dosage of eicosapentaenoic acid and docosahexaenoic acid is from 5 mmol to 25 mmol per day, and wherein the molar ratio of eicosapentaenoic acid to docosahexaenoic acid is in the range of from 1:1 to 5:1. The kit is for use in treating and/or preventing one or more of the conditions mentioned above.

The therapy comprising EPA and DHA, or salts or esters thereof, is preferably for oral administration. A treatment that does not require administration of therapeutic agents via intravitreal administration is particularly advantageous. The administration regime is thus greatly simplified compared to treatment with known agents and is likely to lead to improved patient compliance.

The medicament of the invention may advantageously be administered in a single daily dose, or the total daily dosage may be administered in doses of two, three or four times daily. Preferably, the EPA and DHA, or a salt or an ester thereof, is for administration once per day or twice per day.

In one preferred embodiment there is provided EPA and DHA, or a salt or an ester thereof, for use in the treatment of a condition selected from the group consisting of macular oedema, conditions causing damage to retinal photoreceptors and/or retinal pigment epithelial cells and dry eyes in a mammal, wherein the dosage of EPA (or salt or ester thereof) is from 4 to 15 mmol per day and wherein the dosage of DHA (or salt or ester thereof) is from 2 to 7.5 mmol per day. In another preferred embodiment there is provided EPA and DHA, or a salt or an ester thereof, for use in the treatment of macular oedema in a mammal, wherein the dosage of EPA (or salt or ester thereof) is from 4 to 15 mmol per day and wherein the dosage of DHA (or salt or ester thereof) is from 2 to 7.5 mmol per day. In one preferred embodiment, the condition is macular oedema in a patient or patient population that is poorly responsive or non-responsive to treatment with a VEGF inhibitor. In another preferred embodiment, the condition is macular oedema in a patient or patient population that is poorly responsive or non-responsive to treatment with a steroid.

In another preferred embodiment there is provided EPA and DHA, or a salt or an ester thereof, for use in the treatment of dry eyes in a mammal, wherein the dosage of EPA (or salt or ester thereof) is from 4 to 15 mmol per day and wherein the dosage of DHA (or salt or ester thereof) is from 2 to 7.5 mmol per day. More preferably the condition is moderate and/or severe dry eyes.

In another preferred embodiment there is provided EPA and DHA, or a salt or an ester thereof, for use in the treatment of conditions causing damage damage to retinal photoreceptors and/or retinal pigment epithelial cells in a mammal, wherein the dosage of EPA (or salt or ester thereof) is from 4 to 15 mmol per day and wherein the dosage of DHA (or salt or ester thereof) is from 2 to 7.5 mmol per day.

In another preferred embodiment, there is provided EPA and DHA for use in the treatment and/or prophylaxis of a condition selected from the group consisting of macular oedema and dry eyes in a mammal, wherein the combined dosage of EPA and DHA is from 5 mmol to 25 mmol per day (more preferably from 5 mmol to 15 mmol per day), and wherein the weight ratio of EPA to DHA is in the range of from 1:1 to 4:1 (more preferably from 1:1 to 3:1, most preferably about 2:1).

In another preferred embodiment, there is provided EPA and DHA, for use in the treatment of a condition selected from the group consisting of macular oedema and dry eyes in a mammal, wherein the combined dosage of EPA and DHA is from 5 mmol to 25 mmol per day (more preferably from 5 mmol to 15 mmol per day), and wherein the weight ratio of EPA to DHA is in the range of from 1:1 to 4:1 (more preferably from 1:1 to 3:1, most preferably about 2:1).

In another preferred embodiment, there is provided EPA and DHA for use in the treatment of macular oedema in a mammal, wherein the combined dosage of EPA and DHA is from 5 mmol to 25 mmol per day (more preferably from 5 to 15 mmol per day), and wherein the weight ratio of EPA to DHA is in the range of from 1:1 to 4:1 (more preferably from 1:1 to 3:1, most preferably about 2:1).

In another preferred embodiment, there is provided EPA and DHA for use in the treatment of dry eyes in a mammal wherein the combined dosage of EPA and DHA is from 5 mmol to 25 mmol per day (more preferably from 5 to 15 mmol per day), and wherein the weight ratio of EPA to DHA is in the range of from 1:1 to 4:1 (more preferably from 1:1 to 3:1, most preferably about 2:1).

The invention also provides a composition comprising eicosapentaenoic acid (EPA) and docosahexaenoic acid (DHA), or a salt or an ester thereof, and at least one pharmaceutically acceptable excipient, wherein the molar ratio of EPA (or salt or ester thereof) to DHA (or salt or ester thereof) in the composition is in the range of from 1:1 to 5:1, for use in the treatment and/or prophylaxis of a condition selected from the group consisting of macular oedema, conditions causing damage to retinal photoreceptors and/or retinal pigment epithelial cells and dry eyes in a mammal, and wherein the composition is for administration in a combined daily dosage of EPA (or salt or ester thereof) to DHA (or salt or ester thereof) of from 5 mmol to 25 mmol per day.

Preferred pharmaceutical formulations useful according to the invention are those suitable for oral administration, and include compositions in liquid or solid form. Where the formulation is a solid composition it may be, for example, in the form of a capsule, caplet, tablet, pill, lozenge or powder. Preferably, the formulation is a composition having liquid form, and most preferably the composition is a liquid that is suitable for oral administration. Liquid compositions may be provided in unit-dose or multi-dose containers such as bottles, vials or ampoules. Preferred unit dosage formulations are those containing an effective dose, as hereinbefore recited, or an appropriate fraction thereof, of the omega-3 fatty acids.

Preferably the composition comprises EPA and/or EPA ethyl ester, and comprises DHA and/or DHA ethyl ester. More preferably, the composition comprises eicosapentaenoic acid and docosahexaenoic acid (i.e. the free acids of EPA and DHA are used, rather than salts or esters).

Preferably, the composition comprises eicosapentaenoic acid and docosahexaenoic acid in a molar ratio of from 1:1 to 4:1, more preferably 1:1 to 3:1, still more preferably 1.5:1 to 2.5:1, yet more preferably 2.1:1 to 2.4:1, most preferably from 2.1:1 to 2.2:1. Preferably, the composition comprises eicosapentaenoic acid and docosahexaenoic acid in a weight ratio of from 1:1 to 4:1, more preferably from 1:1 to 3:1, most preferably about 2:1.

Preferably, the composition comprises at least 30 weight % omega-3 fatty acid, more preferably at least 40 weight % omega-3 fatty acid, still more preferably at least 50 weight % omega-3 fatty acid. Preferably, the composition comprises at least 40 weight % of a combination of eicosapentaenoic acid and docosahexaenoic acid in a weight ratio of from 1:1 to 4:1, optionally in liquid form, more preferably at least 50 weight % of a combination of eicosapentaenoic acid and docosahexaenoic acid in a weight ratio of from 1:1 to 4:1, optionally in liquid form. In one particularly preferred embodiment, the composition comprises about 60 weight % of a combination of eicosapentaenoic acid and docosahexaenoic acid in a weight ratio of about 2:1, optionally in liquid form.

In one preferred embodiment, the composition is substantially free from anti-oxidants selected from the list consisting of vitamin E (including tocopherols and tocotrienols), epigallocatechin-3-gallate (EGCG), vitamin C, lutein and zeaxanthin. In one preferred embodiment, the composition is substantially free from anti-oxidants. In one preferred embodiment, the composition contains no anti-oxidants.

In one embodiment the composition consists of, per 100 g:

TABLE 3

| Fats | | 100 g |
|---|---|---|
| Of which: | Saturated | 3.1 g |
| | Monounsaturated | 11.5 g |
| | Polyunsaturated | 85.4 g |
| Total omega-3 fatty acid | | 75 g |
| Of which: | EPA (eicosapentaenoic acid) | 40 g |
| | DHA (docosahexaenoic acid) | 20 g |
| | Other omega-3 fatty acid | 15 g |

The composition of Table 3 is referred to as Omega 3RX®, and may be provided in liquid form. In certain preferred embodiments the composition is Omega 3RX®, and the dosage is from 5 ml to 10 ml per day (for example about 5 ml, about 6 ml, about 7 ml, about 8 ml, about 9 ml, or about 10 ml per day). Preferably the Omega 3RX® is for administration once per day or twice per day (e.g. for twice daily dosing, 2 doses of 2.5 ml, 2 doses of 3 ml, 2 doses of 3.5 ml, 2 doses of 4 ml, 2 doses of 4.5 ml or 2 doses of 5 ml may be administered).

In one preferred embodiment there is provided a composition comprising EPA and DHA, or a salt or an ester thereof, and at least one pharmaceutically acceptable excipient, wherein the molar ratio of EPA (or salt or ester thereof) to DHA (or salt or ester thereof) in the composition is in the range of from 1.5:1 to 2.5:1 (more preferably 2.1:1 to 2.4:1, most preferably from 2.1:1 to 2.2:1), for use in the treatment of a condition selected from the group consisting of macular oedema, conditions causing damage to retinal photoreceptors and/or retinal pigment epithelial cells and dry eyes in a mammal, and wherein the composition is for administration in a combined daily dosage of EPA (or salt or ester thereof) to DHA (or salt or ester thereof) of from 5 mmol to 25 mmol per day (more preferably from 5 to 15 mmol per day).

In one preferred embodiment there is provided a composition comprising EPA and DHA, or a salt or an ester thereof, and at least one pharmaceutically acceptable excipient, wherein the molar ratio of EPA (or salt or ester thereof) to DHA (or salt or ester thereof) in the composition is in the range of from 1.5:1 to 2.5:1 (more preferably 2.1:1 to 2.4:1, most preferably from 2.1:1 to 2.2:1), for use in the treatment of macular oedema in a mammal, and wherein the composition is for administration in a combined daily dosage of EPA (or salt or ester thereof) to DHA (or salt or ester thereof) of from 5 mmol to 25 mmol per day (more preferably from 5 to 15 mmol per day). In one preferred embodiment, the composition is for use in the treatment of macular oedema in a patient or patient population that is poorly responsive or non-responsive to treatment with a VEGF inhibitor. In another preferred embodiment, the composition is for use in the treatment of macular oedema in a patient or patient population that is poorly responsive or non-responsive to treatment with a steroid.

In one preferred embodiment there is provided a composition comprising EPA and DHA, or a salt or an ester thereof, and at least one pharmaceutically acceptable excipient, wherein the molar ratio of EPA (or salt or ester thereof) to DHA (or salt or ester thereof) in the composition is in the range of from 1.5:1 to 2.5:1 (more preferably 2.1:1 to 2.4:1, most preferably from 2.1:1 to 2.2:1), for use in the treatment of conditions causing damage to retinal photoreceptors and/or retinal pigment epithelial cells in a mammal, and wherein the composition is for administration in a combined daily dosage of EPA (or salt or ester thereof) to DHA (or salt or ester thereof) of from 5 mmol to 25 mmol per day (more preferably from 5 to 15 mmol per day).

In one preferred embodiment there is provided a composition comprising EPA and DHA, or a salt or an ester thereof, and at least one pharmaceutically acceptable excipient, wherein the molar ratio of EPA (or salt or ester thereof) to DHA (or salt or ester thereof) in the composition is in the range of from 1.5:1 to 2.5:1 (more preferably 2.1:1 to 2.4:1, most preferably from 2.1:1 to 2.2:1), for use in the treatment of dry eyes in a mammal, and wherein the composition is for administration in a combined daily dosage of EPA (or salt or ester thereof) to DHA (or salt or ester thereof) of from 5 mmol to 25 mmol per day (more preferably from 5 to 15 mmol per day). More preferably, the condition is moderate and/or severe dry eyes.

In one embodiment there is provided a composition comprising EPA and DHA in a weight ratio of from 1:1 to 4:1, and at least one pharmaceutically acceptable excipient, for use in the treatment and/or prophylaxis of a condition selected from macular oedema and dry eyes in a mammal, wherein the composition comprises at least 50 weight % omega-3 fatty acid. In another embodiment there is provided a composition comprising EPA and DHA in a weight ratio of from 1:1 to 4:1, and at least one pharmaceutically acceptable excipient, for use in the treatment of a condition selected from macular oedema and dry eyes in a mammal, wherein the composition comprises at least 50 weight % omega-3 fatty acid.

In another embodiment there is provided a composition comprising EPA and DHA in a weight ratio of from 1:1 to 4:1, and at least one pharmaceutically acceptable excipient, for use in the treatment of macular oedema in a mammal, in a patient or patient population that is poorly responsive or non-responsive to treatment with a VEGF inhibitor and/or a steroid, wherein the composition comprises at least 50 weight % omega-3 fatty acid. In one embodiment, the patient or patient population is poorly responsive or non-responsive to treatment with a VEGF inhibitor. In another embodiment, the patient or patient population is poorly responsive or non-responsive to treatment with a steroid.

It should be understood that in addition to the ingredients particularly mentioned above, the formulations of this invention may include other agents conventional in the art having regard to the type of formulation in question, for example those suitable for oral administration may include flavouring agents.

EXAMPLES

The following non-limiting Examples illustrate the invention.

Example 1

Omega Fatty Acid Composition

An example omega fatty acid composition is indicated in Table 4 below and is sold under the name Omega 3RX® (Enerzona):

TABLE 4

| Composition | Amount per 100 g |
|---|---|
| Calories/Energy | 3700 KJ |
| Protein | 0 g |
| Fats | 100 g |

TABLE 4-continued

| Composition | | Amount per 100 g |
|---|---|---|
| Of which: | Saturated | 3.1 g |
| | Monounsaturated | 11.5 g |
| | Polyunsaturated | 85.4 g |
| Total omega-3 fish oil | | 75 g |
| Of which: | EPA (eicosapentaenoic acid) | 40 g |
| | DHA (docosahexaenoic acid) | 20 g |
| | Other omega-3 fatty acid | 15 g |

5 ml of Omega 3RX® contains 3.13 g of omega-3 fatty acids, of which 1.67 g is EPA (5.53 mmol), 0.83 g is DHA (2.53 mmol), and 0.63 g is other omega-3 fatty acids.

Example 2

Case Studies Showing Treatment of Macular Oedema with Omega Fatty Acids 14 cases of macular oedema that demonstrate the efficacy of orally taken Omega 3RX® for treatment are presented.

The omega fatty acids were given orally. The form of omega fatty acid used was Omega 3RX®, in liquid form. Omega 3RX® was dosed twice per day. The daily dose of Omega 3RX® was 5-7 ml (i.e. two doses of 2.5-3.5 ml Omega 3RX® daily).

OCT (Optical Coherence Tomography) can accurately measure the oedema in the macular area and has become an invaluable tool for assessment and therapeutic decision making for patients with macular oedema. OCT scans were used to monitor patients' response to treatment.

Case 1
Presentation

Patient 1 is a 61 year old gentleman with diabetes who was treated for macular oedema since Sep. 28, 2009.

Treatment

He was treated with intravitreal injections of Lucentis® and Kenalog® in Sep. 28, 2009 and May 5, 2010 in the left eye. He also had grid laser treatment on Jun. 2, 2010. On Aug. 4, 2010 he was started on Omega 3RX®.

Result

Figure 2:
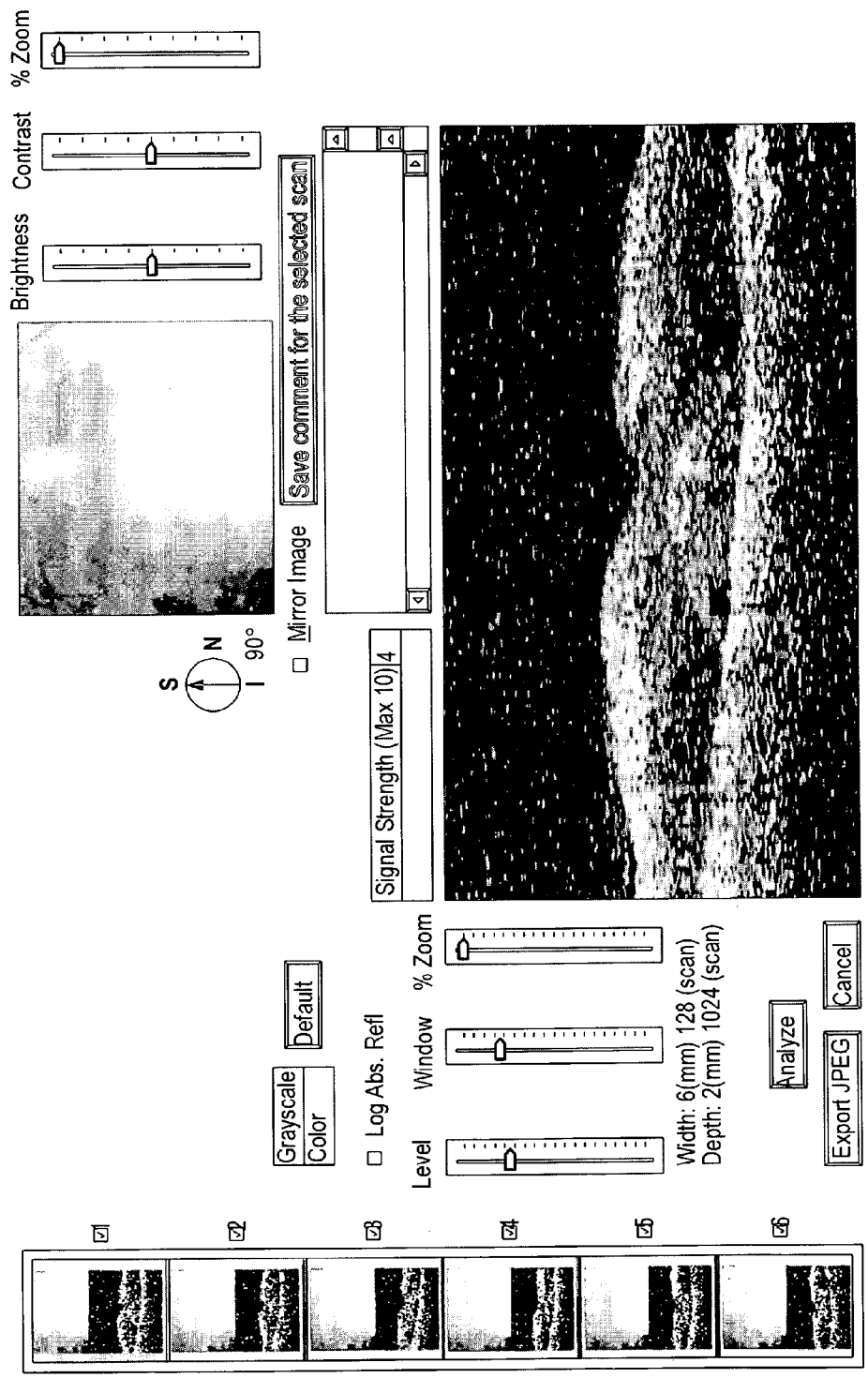

There was marked improvement in macular oedema and visual acuity in the left eye. FIG. 1 shows the macular oedema before treatment with Omega 3RX® and FIG. 2 after treatment. The vision improved from 6/18 to 6/12 in the left eye.

Case 2
Presentation

Patient 2 is a 65 year old gentleman who presented in March 2008 with bilateral pigment epithelial detachment (PED, a type of age-related macular degeneration (AMD)). His visual acuities were 6/18 right eye and 6/12 left eye.

Treatment

From March 2008 until January 2010 he was treated with intravitreal injections of anti-VEGF (Avastin®). He had twelve injections in each eye. In four of the times anti-VEGF was combined with a steroid injection (Kenalog® 2 mg). In March 2010 he was started on Omega 3RX® 2.5 ml twice per day.

Result

On the $3^{rd}$ of March 2010 his visual acuites were 6/12 right eye and counting fingers in the left eye. There was minimal to moderate improvement of macular oedema in each eye with each intravitreal injection but the oedema returned one to two months following treatment with injections. There was never complete resolution of macular oedema while he was treated with intravitreal injections. Since he was started with Omega 3RX® the macular oedema gradually reduced and completely resolved in both eyes over a period of 2-4 months. He has been without any macular oedema since May 2010 in the right eye and since June 2010 in the left eye.

Case 3

Presentation

Patient 3 is a 73 year old lady who presented with choroidal neovascular membrane (wet AMD) in June 2008 in her right eye. Her visual acuities at presentation were 6/36 in the right eye and 6/6 in the left eye.

Treatment

She was treated with intravitreal anti-VEGF injections (Lucentis®) on Jun. 9, 2008, Jul. 9, 2008, Aug. 6, 2008, Jan. 5, 2009, Feb. 2, 2009, Dec. 30, 2009, Jan. 27, 2010, and Mar. 1, 2010. She was started on Omega 3RX® on Jul. 26, 2010.

Results

Good short term results were achieved with resolution of macular oedema. This patient needed many repeat intravitreal anti-VEGF injections. The visual acuities in the right eye on Jul. 26, 2010 was counting fingers. It was decided not to proceed with any further injections and she was started on Omega 3RX®. OCT scan showed marked improvement of macular oedema between the period of Jul. 26, 2010 and Nov. 29, 2010 (Figures not shown). Vision improved from counting fingers to 3/60.

Case 4

Presentation

Patient 4 is a 78 year old gentleman who presented on Mar. 22, 2010 with reduced vision in the right eye. On examination he had right choroidal neovascular membrane (wet AMD) and visual acuity of 3/60.

Treatment

He was treated with combined intravitreal anti-VEGF and steroid (Lucentis® and Kenalog®) on Mar. 22, 2010, Apr. 21, 2010, May 19, 2010, Jun. 16, 2010, Jul. 14, 2010, and Aug. 11, 2010. He was started on Omega 3RX® on Oct. 6, 2010.

Results

There was marked reduction of macular oedema (and PED) since the treatment with Omega 3RX® and improved visual acuity. H is visual acuity in this eye was 6/36 in Mar. 22, 2010 (Figure not shown), 6/18 in Jun. 16, 2010, 6/18 in Oct. 6, 2010 (Figure not shown), 6/12+2 in Nov. 3, 2010 and 6/9+2 in Dec. 1, 2010 (Figure not shown). This marked improvement occurred within two months of starting the treatment.

Case 5

Presentation

Patient 5 is a 58 year old gentleman who has insulin dependent diabetes. He presented on Mar. 19, 2008 with reduced vision in both eyes due to macular oedema.

Treatment

He was treated with six intravitreal injections of Lucentis® and Kenalog® in the right eye and five intravitreal injections of Lucentis® and Kenalog® in the left eye from the period of March 2008 to January 2010. Grid laser treatment was performed twice in each eye in 2008 and 2009. He was started on Omega 3RX® on Sep. 13, 2010.

Results

There was marked improvement of macular oedema in both eyes since the treatment with Omega 3RX®. Complete resolution of the oedema in both eyes was observed (Figure not shown). Visual acuity in the right eye remained 6/60 probably due to long standing oedema causing damage to the photoreceptors. In the left eye visual acuity improved from 6/24 in Sep. 13, 2010 to 6/12 in Nov. 24, 2010.

Case 6

Presentation

Patient 6 is a 41 year old gentleman with insulin diabetes who presented on Apr. 26, 2010 with macular oedema. The macular oedema was at the fovea and not possible for focal laser treatment. H is vision was 6/12 in the right eye.

Treatment

He had intravitreal injection of Lucentis® with Kenalog® on Apr. 26, 2010. On Jun. 30, 2010 he was started on Omega 3RX®.

Results

Intravitreal injection of Lucentis® with Kenalog® did not resolve the macular oedema. H is vision was 6/12 on Apr. 26, 2010 and worsened to 6/12 on May 26, 2010. On Aug. 30, 2010 his vision was 6/6 and there was marked improvement of macular oedema. Gradual reduction of macular oedema was observed (Figures not shown).

Case 7

Presentation

Patient 7 is a 69 year old gentleman who had a right branch retinal vein occlusion in 2002 and left branch retinal vein occlusion in 2003. He had a scar in the right macular and macular oedema in the left eye.

Treatment

He was treated with 3 intravitreal injections of Avastin® and Kenalog® in the left eye over the periods from Sep. 10, 2008 to May 6, 2009 with no improvement of macular oedema. He was started on Omega 3RX® on Sep. 15, 2010.

Results

Since the treatment of Omega 3RX®, the macular oedema has nearly resolved over a period of 2 months. H is vision in the left eye has improved from 6/18+1 to 6/18+4. Two months following Omega 3RX®, the oedema has nearly resolved.

Case 8

Presentation

Patient 8 is a 77 year old who had a branch retinal vein occlusion in her only one eye in Dec. 8, 2008.

Treatment

Figure 30:
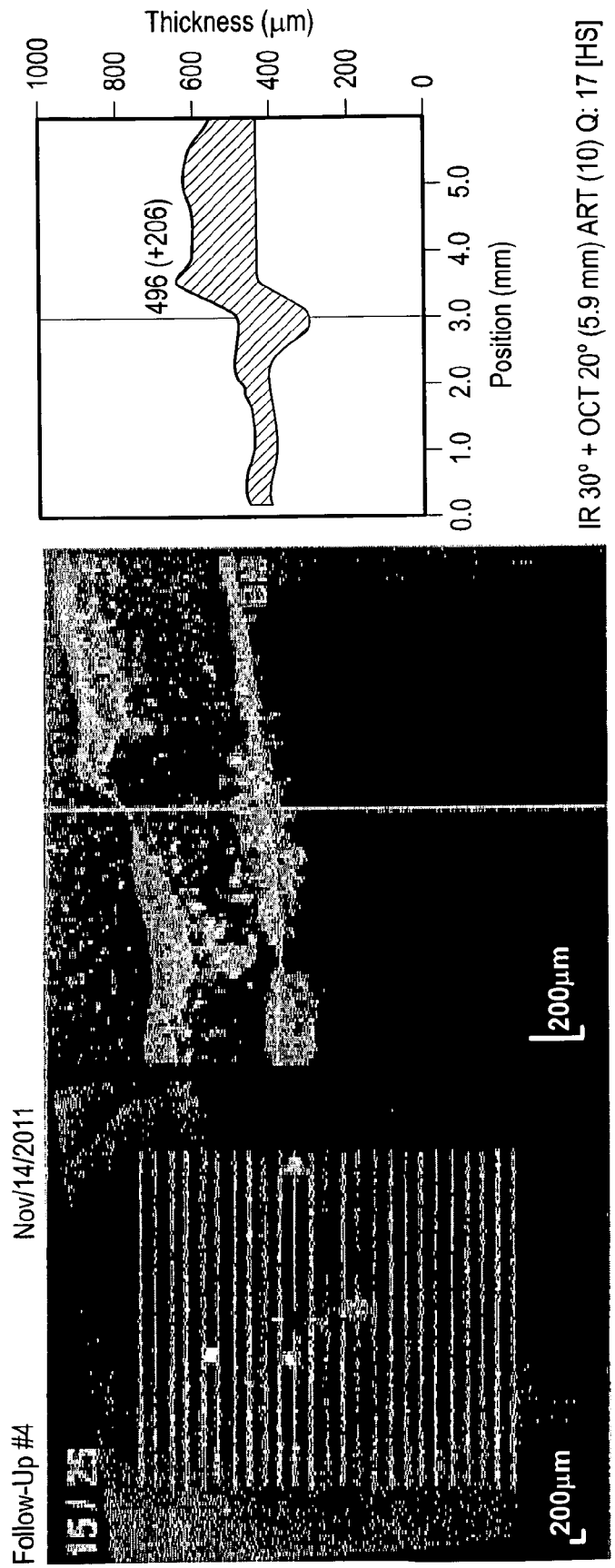
Figure 30:
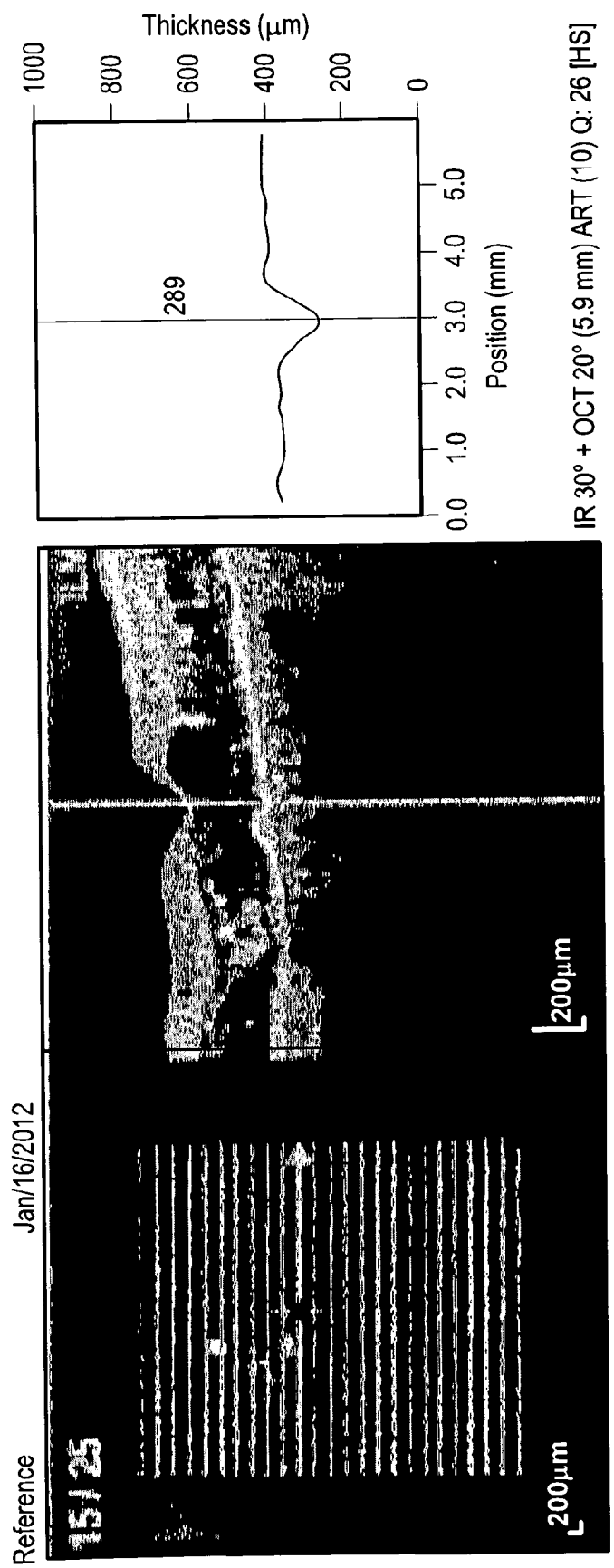
Figure 30:
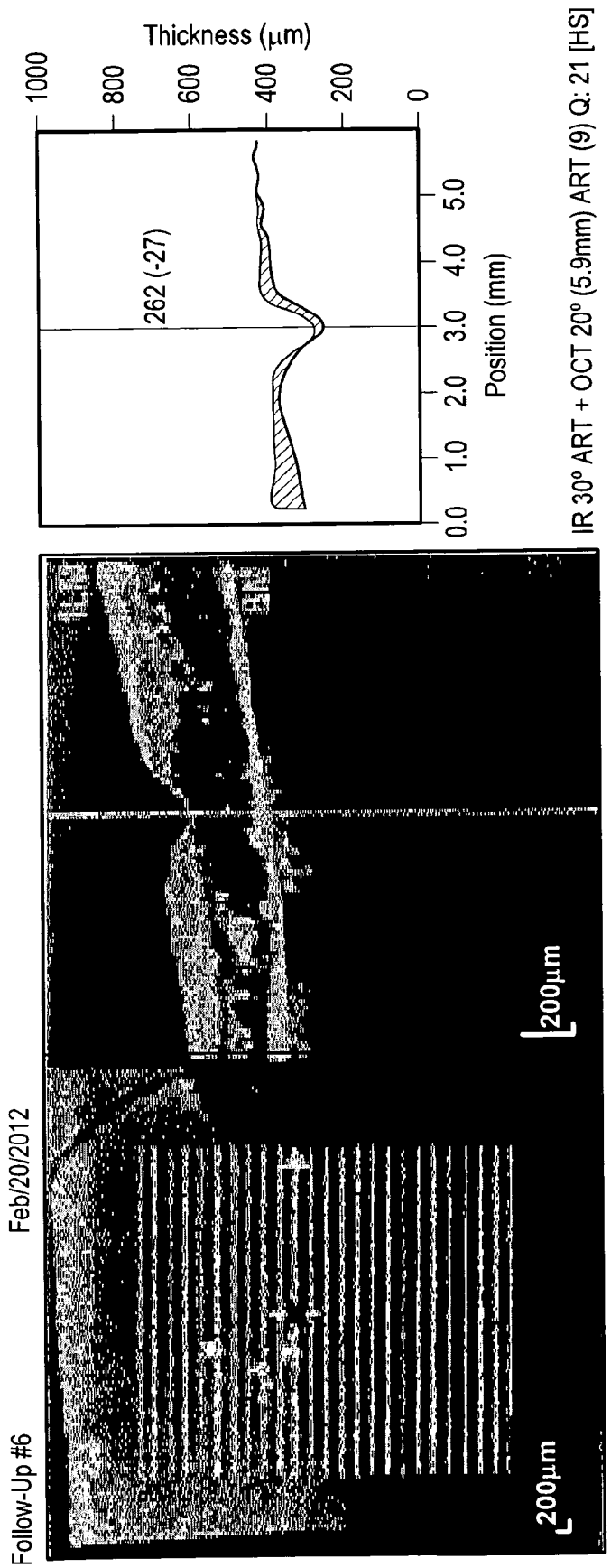

She was treated with five intravitreal injections of Lucentis® and Kenalog® between the periods of Dec. 8, 2008 and Dec. 29, 2009. The effect of resolution of macular oedema with the injection was short lived. FIG. 30 show macular oedema in Aug. 5, 2009. Her vision was 6/18. She was started on Omega 3RX® on Aug. 3, 2010.

Result

Reduction and complete resolution of macular oedema following Omega 3RX® treatment was observed (Figures not shown). Vision improved from 6/18 on Aug. 5, 2010 to 6/12 on Nov. 1, 2010.

Case 9

Presentation

Patient 9 is a gentleman who had central retinal vein occlusion in the right eye in October 2007 and presented on Jan. 30, 2008. H is visual acuity in the right eye was hand movements on presentation.

Treatment

He was treated with ten intravitreal Lucentis® and Kenalog® injections between the periods of Jan. 30, 2008 and Nov. 3, 2009. He was started on Omega 3RX® on Jul. 7, 2010.

Results

Moderate improvements of macular oedema was seen following intravitreal injections but the effect was lasting each time one month approximately. Since the treatment with Omega 3RX® the macular oedema has much improved. Gradual reduction of macular oedema with Omega 3RX® treatment was observed (Figures not shown). Vision has improved from counting fingers on Jul. 7, 2010 to 6/60 on Nov. 29, 2010.

Case 10
Presentation

Patient 10 is an 82 year old lady who had a cataract surgery in the right eye on Nov. 24, 2009 and anterior chamber implant was used due to zonular weakness of the capcular bag. She developed macular oedema following surgery.

Treatment

She was treated with steroid and non-steroidal eye drops with no improvements of the macular oedema. She also had intravitreal injections of Avastin® and Kenalog® on May 26, 2010 and Jun. 23, 2010 with no improvement. She was started on Omega 3RX® on Jul. 21, 2010.

Results

She had moderate reduction of macular oedema following treatment with Omega 3RX®. Less macular oedema was observed following one month of treatment (Figure not shown). Vision improved from 6/36 to 6/18 following treatment.

Case 11
Presentation

Patient 11 is a 60 year old diabetic gentleman who developed macular oedema due to epiretinal membrane in the left eye.

Results

Macular oedema was reduced following one month treatment of Omega 3RX®, Visual acuity also improved from 6/18 to 6/9. Usually epiretinal membranes are treated with surgery involving vitrectomy with peel of the membrane. This type of surgery has risks of around 5% including retinal detachment, cataract, vitreous haemorrhages etc. Marked reduction of macular oedema was observed (Figure not shown).

Case 12
Presentation

Patient 12 is a 67 year old man with diabetes presented with reduced vision in the right eye. On examination he had macular oedema due to diabetes and visual acuity of 6/18.

Treatment

He was treated on Nov. 12, 2010 with intravitreal Lucentis® and Kenalog®. H is vision improved from 6/18 to 6/9 on Dec. 22, 2010. On Mar. 28, 2011 he presented with macular oedema and visual acuity of 6/18. He was started on Omega 3RX®.

Results

There was reduction of macular oedema since the treatment with Omega 3RX®. Reduction of macular oedema from Mar. 28, 2011 to May 2, 2011 was observed with the Spectralis OCT scan (Figure not shown). Vision improved from 6/18 to 6/9–.

Case 13
Presentation

Patient 13 is a 79 old man presented on Mar. 1, 2010 with vision of counting fingers in the left eye. On examination he had macular oedema due to wet macular degeneration.

Treatment

He was treated with intravitreal Lucentis® and Kenalog® on Mar. 31, 2010 and Apr. 28, 2010. He was started on Nov. 29, 2010 with Omega 3RX®.

Results

The intravitreal injections resolved the macular oedema temporarily. Examination on Nov. 29, 2010 showed recurrent fluid. On Mar. 2, 2011 there was no fluid seen on OCT scan (Figures not shown). Vision improved to 6/60.

Case 14
Presentation

Patient 14 is a 60 year old lady presented on Jan. 10, 2006 with reduced vision. On examination her vision was 6/24 in the left eye and had macular oedema due to diabetes Treatment She was treated with twelve intravitreal Avastin® and Kenalog® injections in the left eye between Jan. 10, 2006 and Apr. 19, 2010. She also had focal laser treatments. On May 6, 2008 she had vitrectomy in the left eye to try and reduce the oedema which always recurred with the above treatments. On Oct. 27, 2010 she was started on Omega3RX®.

Results

Macular oedema was observed despite treatments with intravitreal avastin and Kenalog® injections, focal laser treatments and vitrectomy surgery from the period Nov. 10, 2008 to Jan. 10, 2011 (Figures not shown). Near resolution of oedema after 5 months of treatment with Omega3RX® was observed (Figure not shown). Vision improved to 6/9– on Mar. 21, 2011.

SUMMARY

Macular oedema is often associated with decreased visual acuity and is a frequent cause of visual impairment for patients.

Intravitreal administration of steroids/VEGF have been shown to reduce oedema and improve or at least stabilize visual acuity but these effects are often transient. There are also risks involved with injections such as endophthalmitis, cataract, retinal tears, retinal detachments and high intraocular pressure.

The cases presented show, using OCT scan documentation, that treatment with liquid Omega 3RX® can be of a significant benefit to patients with macular oedema. Macular thickness can be reduced or even eliminated in patients with macular oedema resulting in improvement of visual acuity. In addition, no ocular or systemic side effects were shown. Each patient in this case presentation had a marked and favourable response with reduction in macular oedema during treatment.

Example 3

Improvements have been observed in patients with dry eyes, who were treated with omega fatty acids in the form of Omega 3RX®.

Example 4

Further case studies showing treatment of eye conditions with omega fatty acids

Case a)

Figure 3:
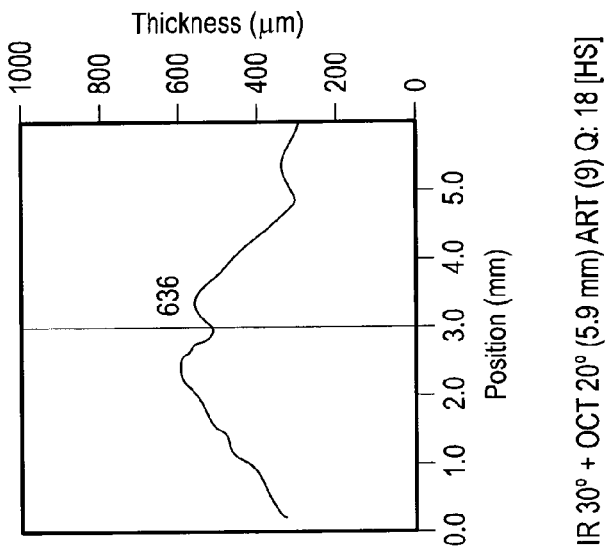
Figure 3:
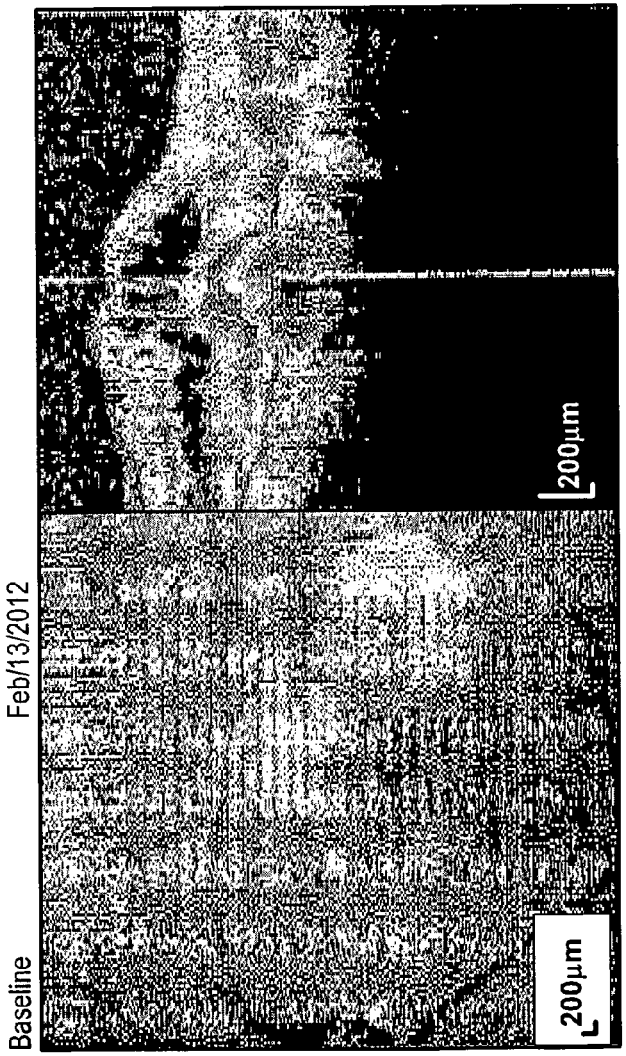
Figure 3:
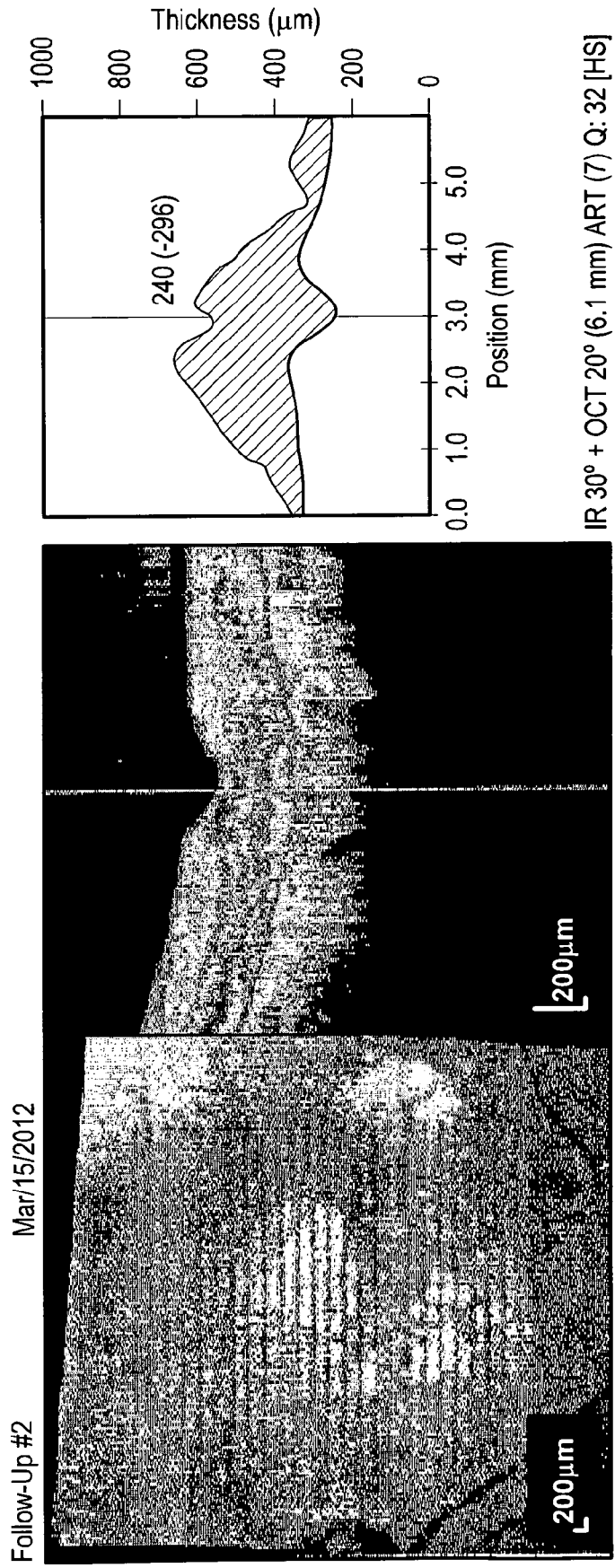

79 year old female presented on Feb. 13, 2012 with left reduced vision due to wet AMD (macular degeneration). Visual acuity was 6/60. She was treated with intravitreal Avastin injection and started on Omega 3RX®. One month following treatment there was no fluid on OCT scan and she gained one line of vision on Snellen chart (FIG. 3).

Case b)

Figure 4:
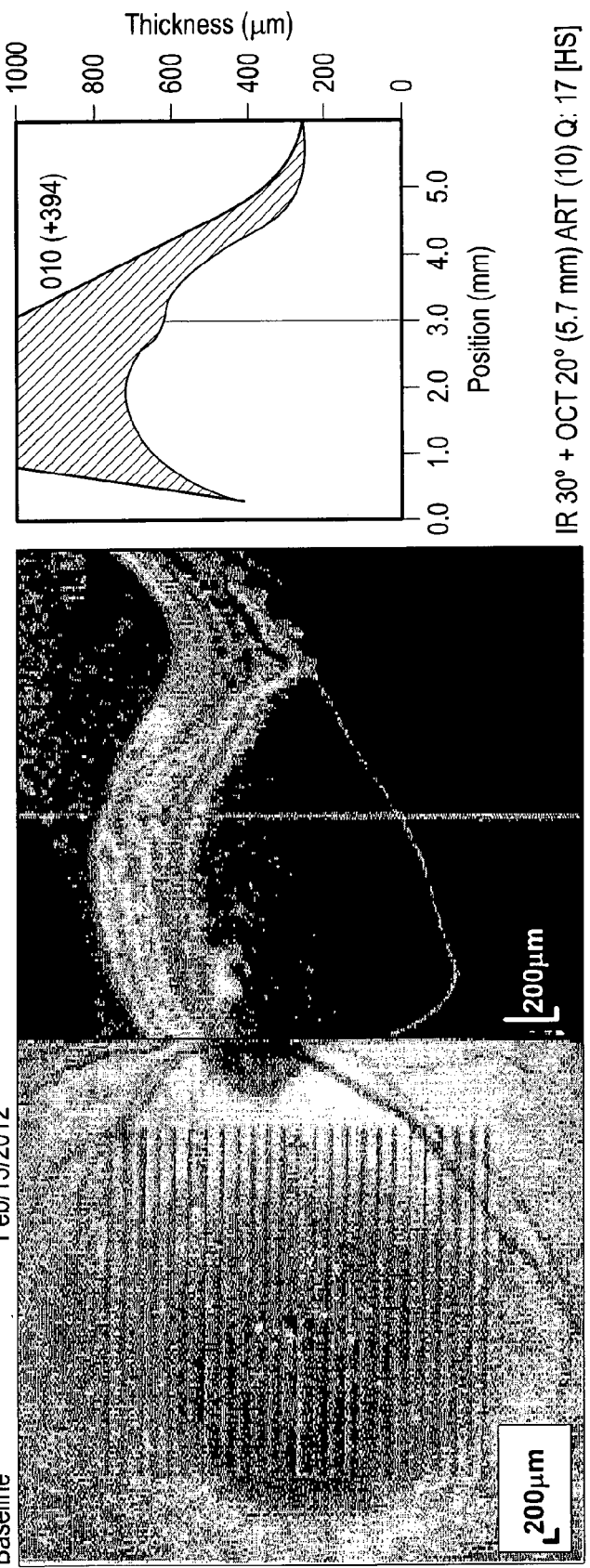
Figure 4:
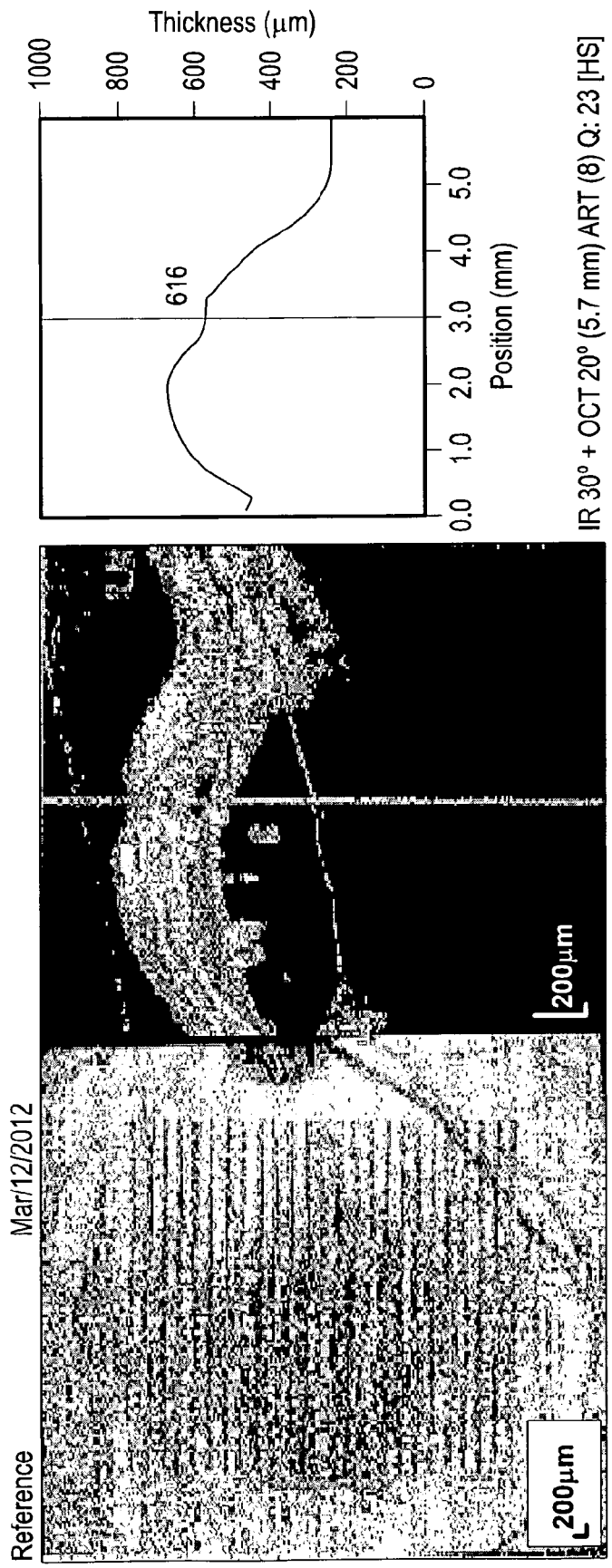
Figure 4:
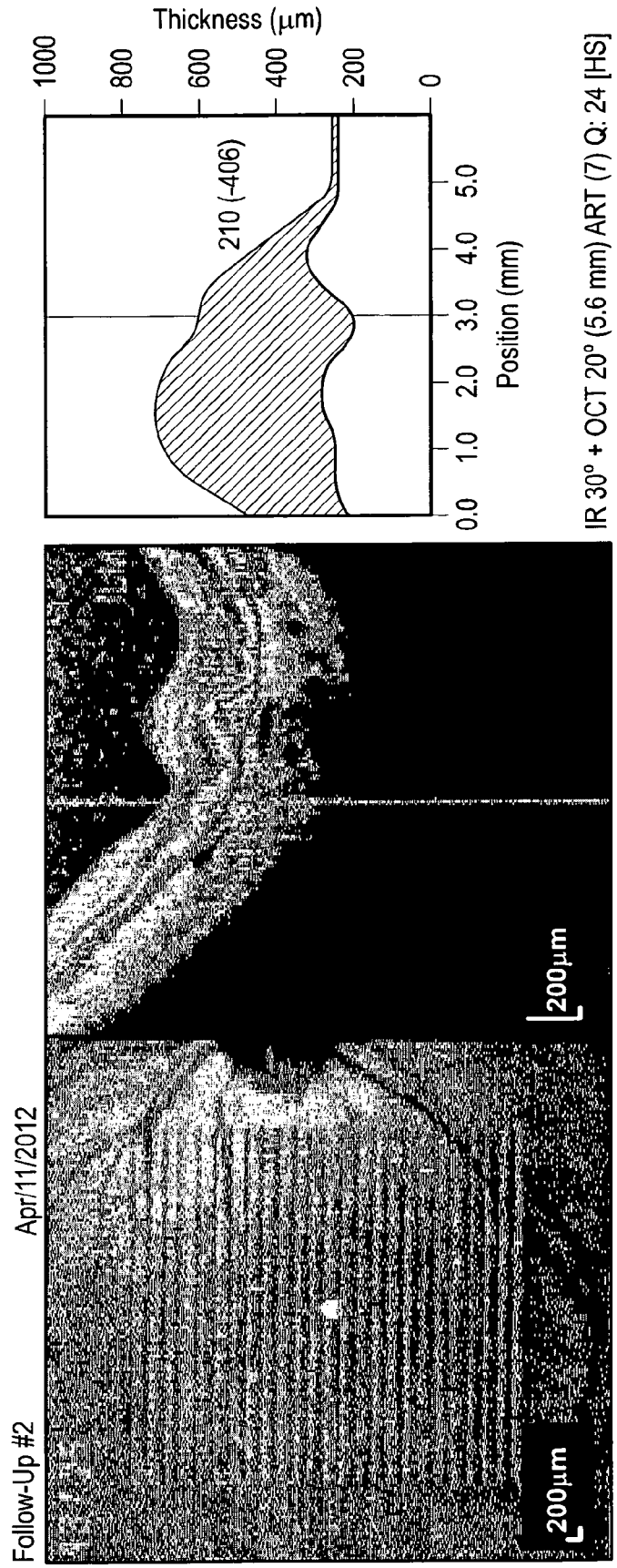

77 year old female presented with right wet AMD on Feb. 13, 2012. Her visual acuity was 6/30. She was treated with intravitreal Avastin injection and Omega 3RX®. Two months following treatment there was no fluid and she gained six lines of vision on Snellen chart (FIG. 4).

Case c)

Figure 5:
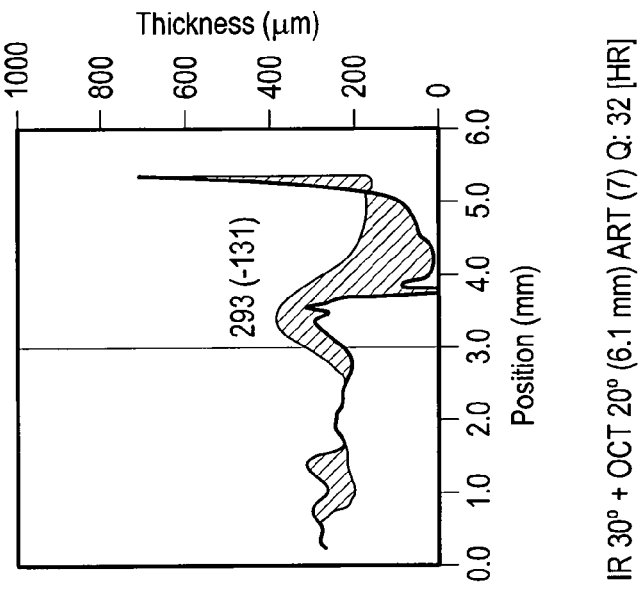
Figure 5:
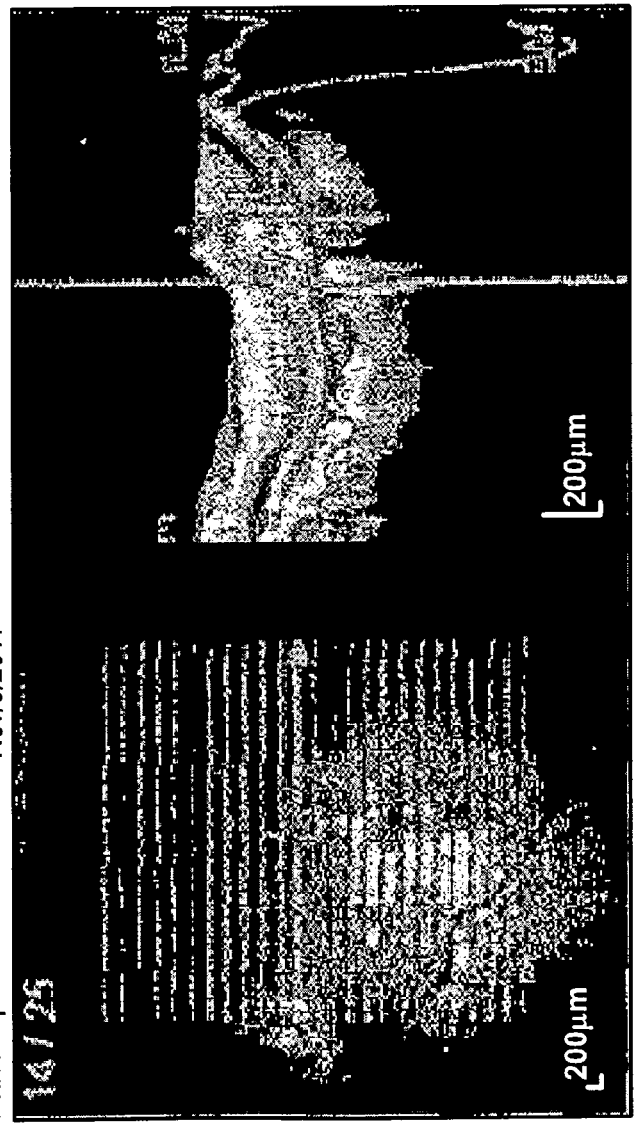
Figure 5:
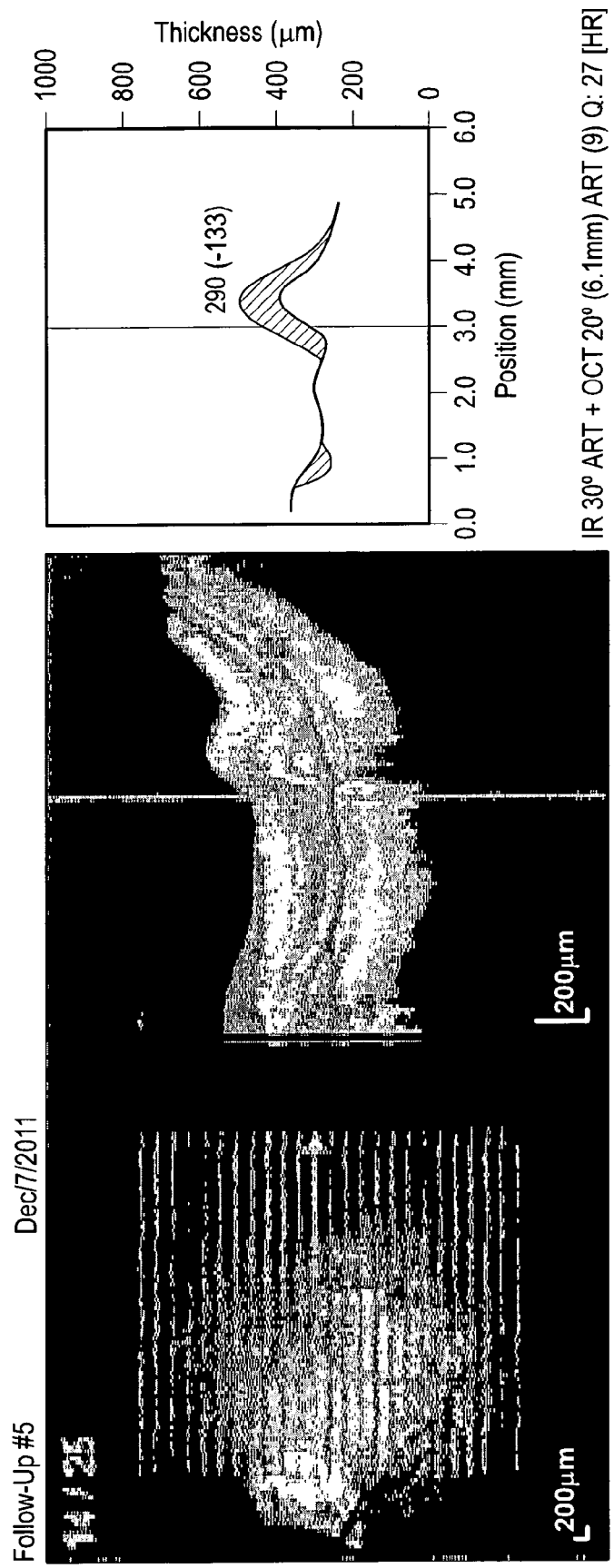
Figure 5:
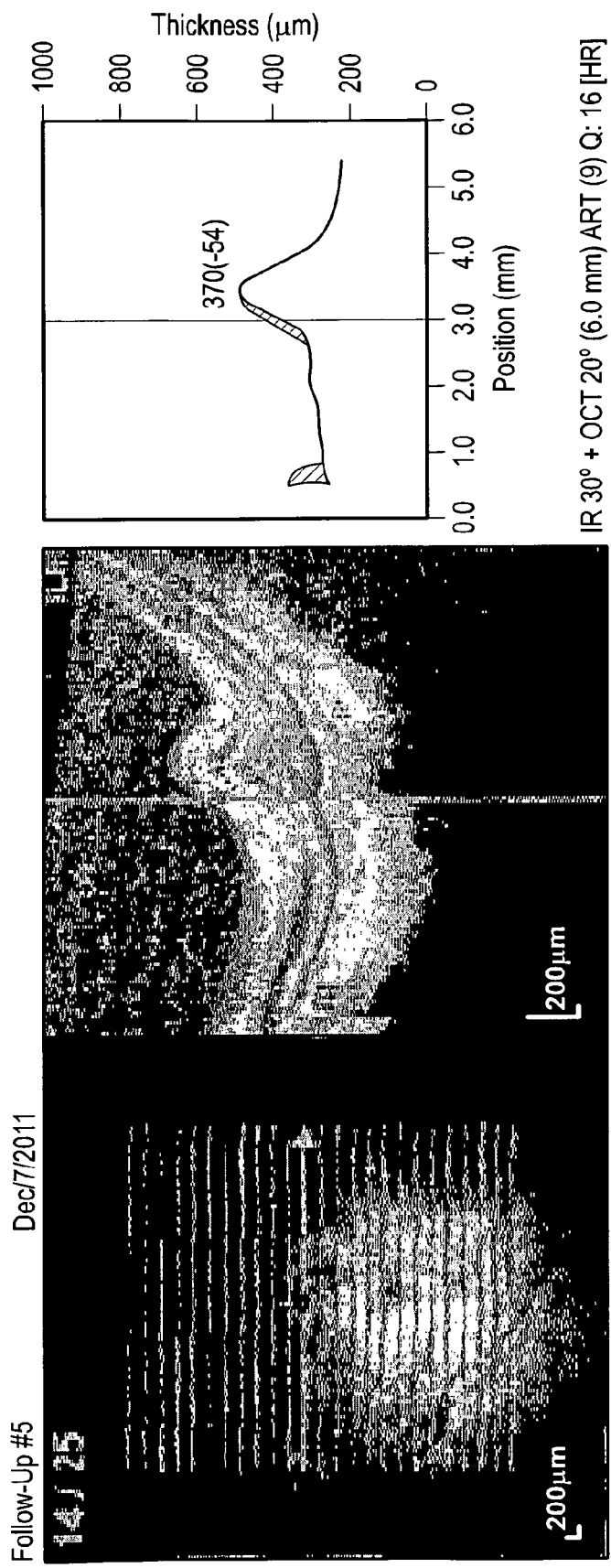
Figure 5:
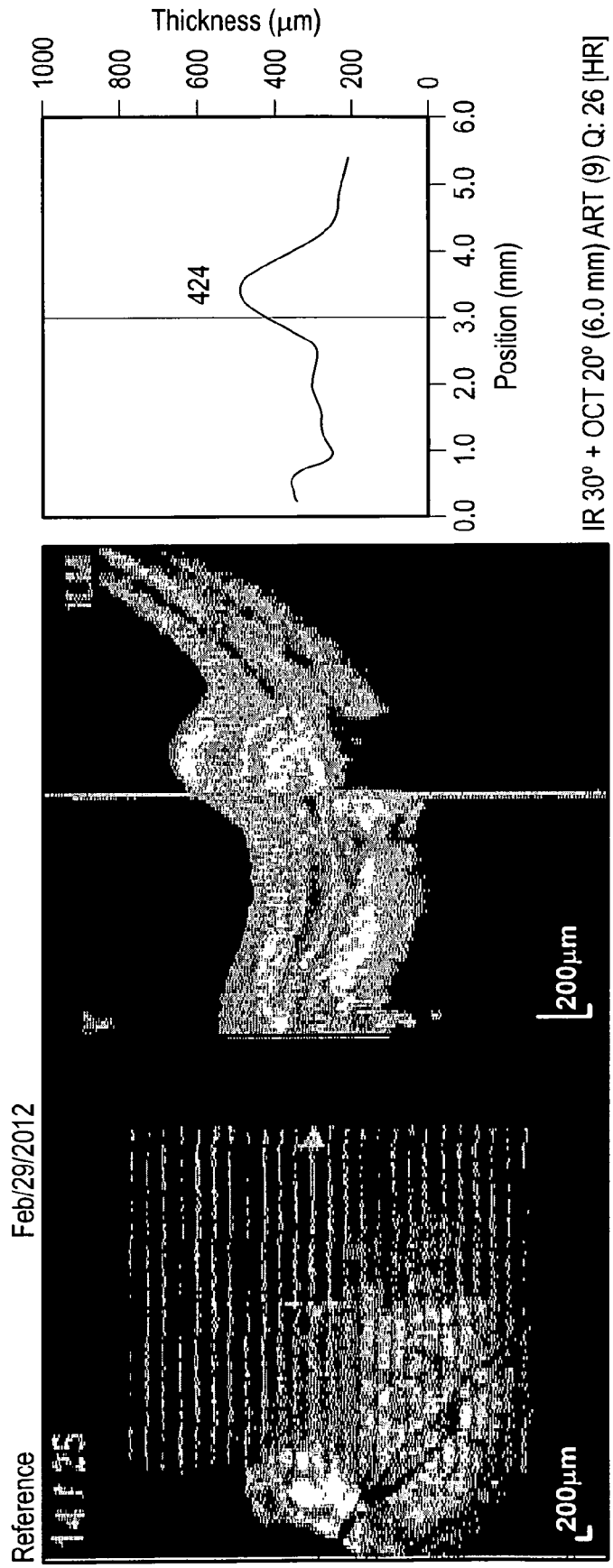
Figure 5:
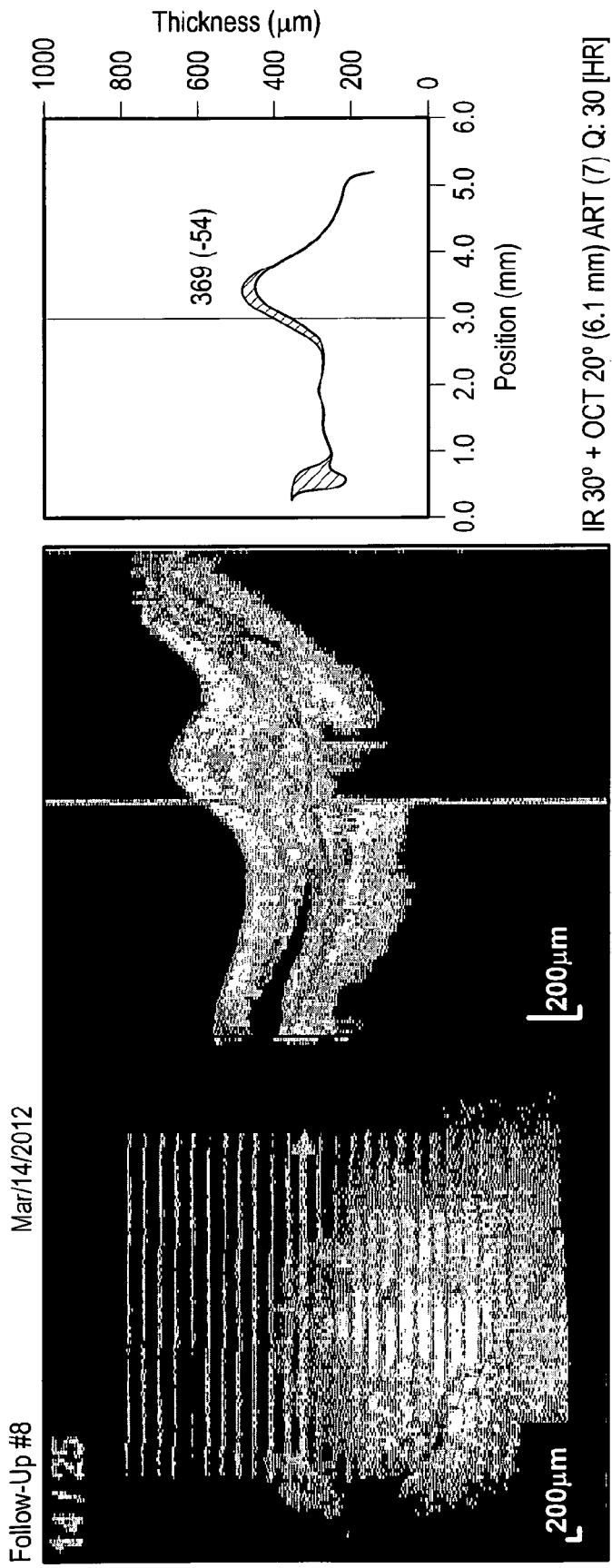

54 year old female had bilateral cataract surgery in November 2008. She presented in July 2001 with reduced vision due to wet AMD. Visual acuity was 6/60. She was treated with four intravitreal Avastin injections between July and November 2011. She presented again on Feb. 29, 2012 with reduced vision in the left eye. She was started on Omega 3RX®, and two weeks later there was no fluid with vision 6/21 (FIG. 5).

Figure 6:
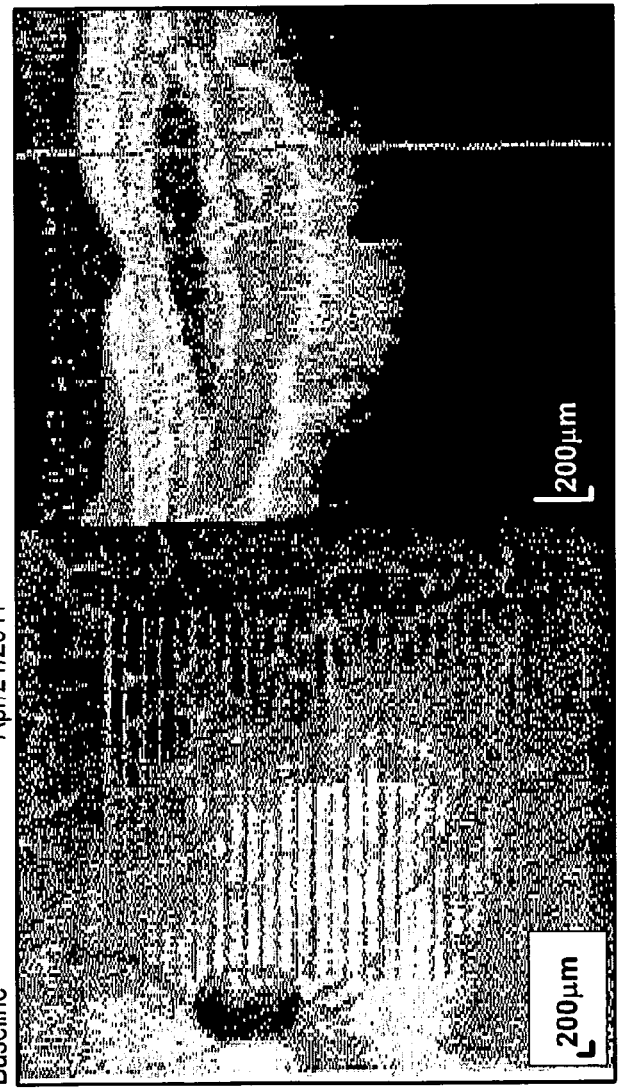
Figure 6:
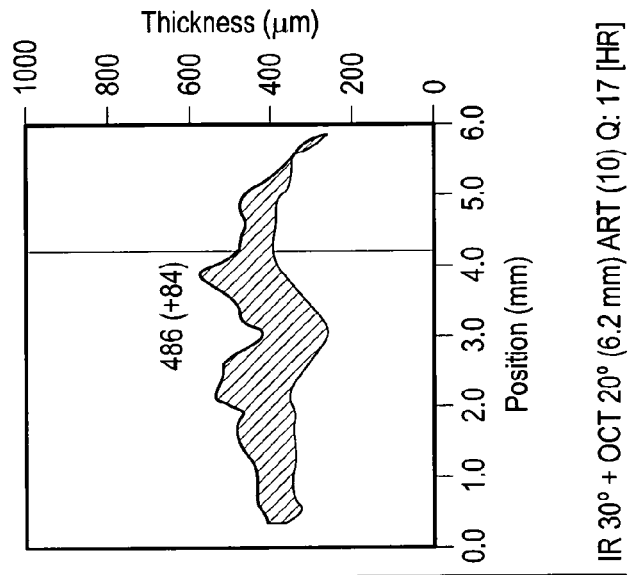
Figure 6:
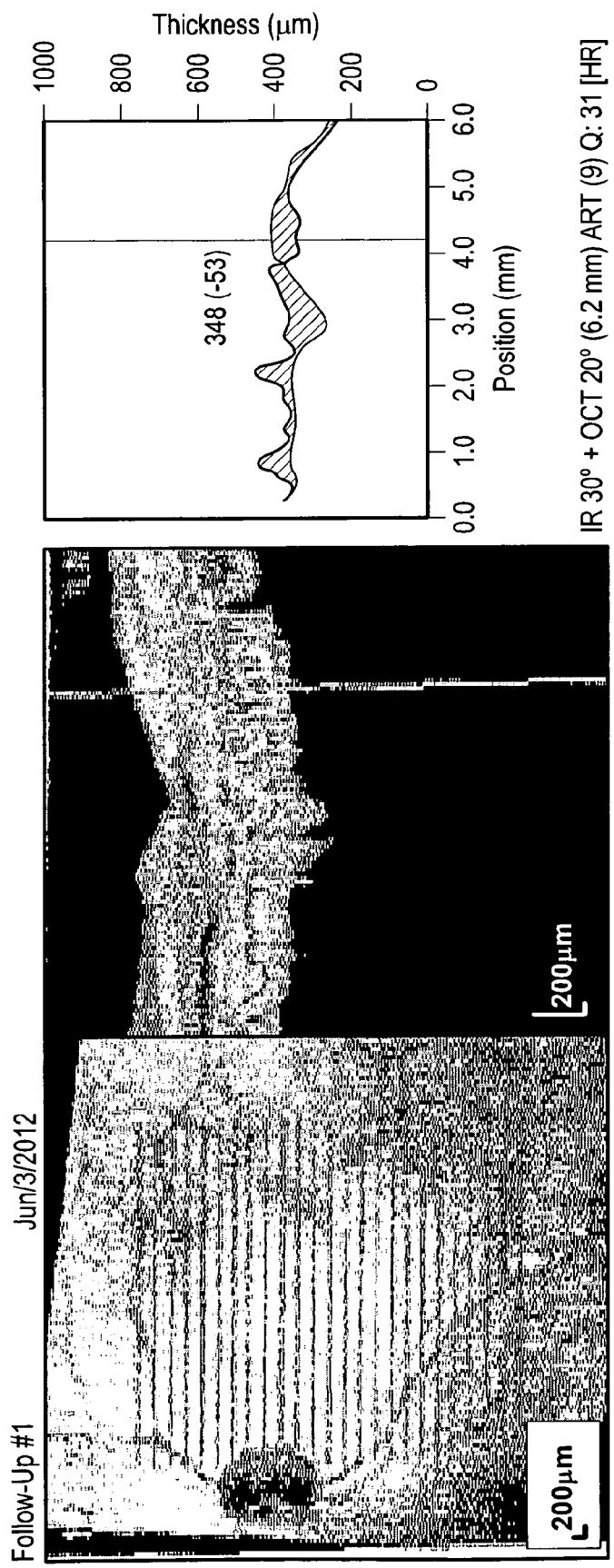
Figure 6:
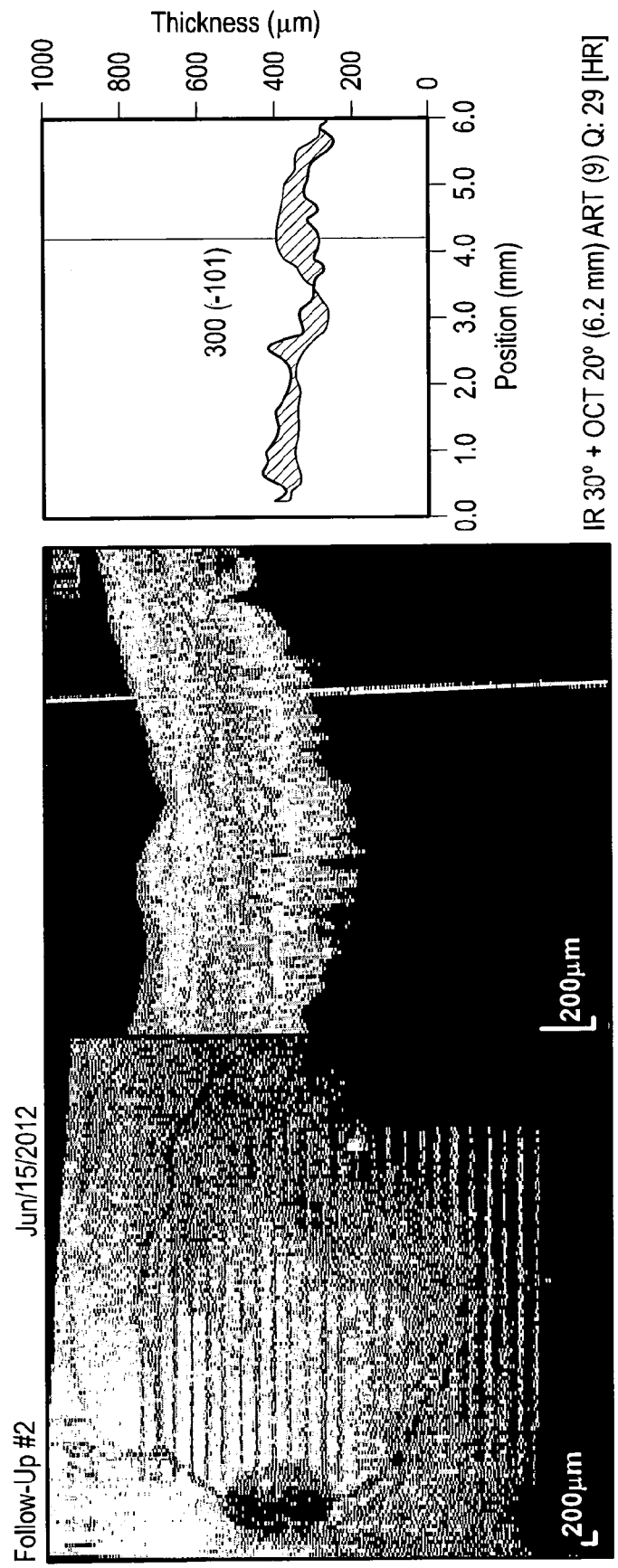
Figure 6:
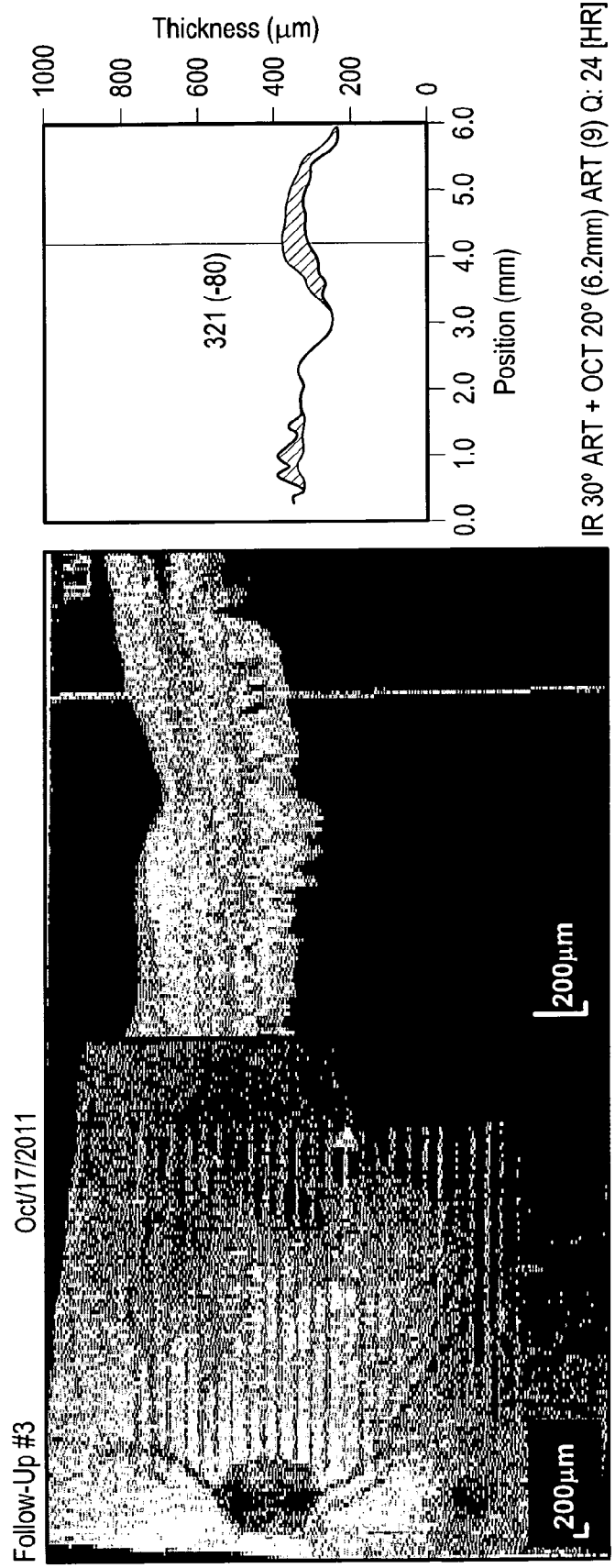
Figure 6:
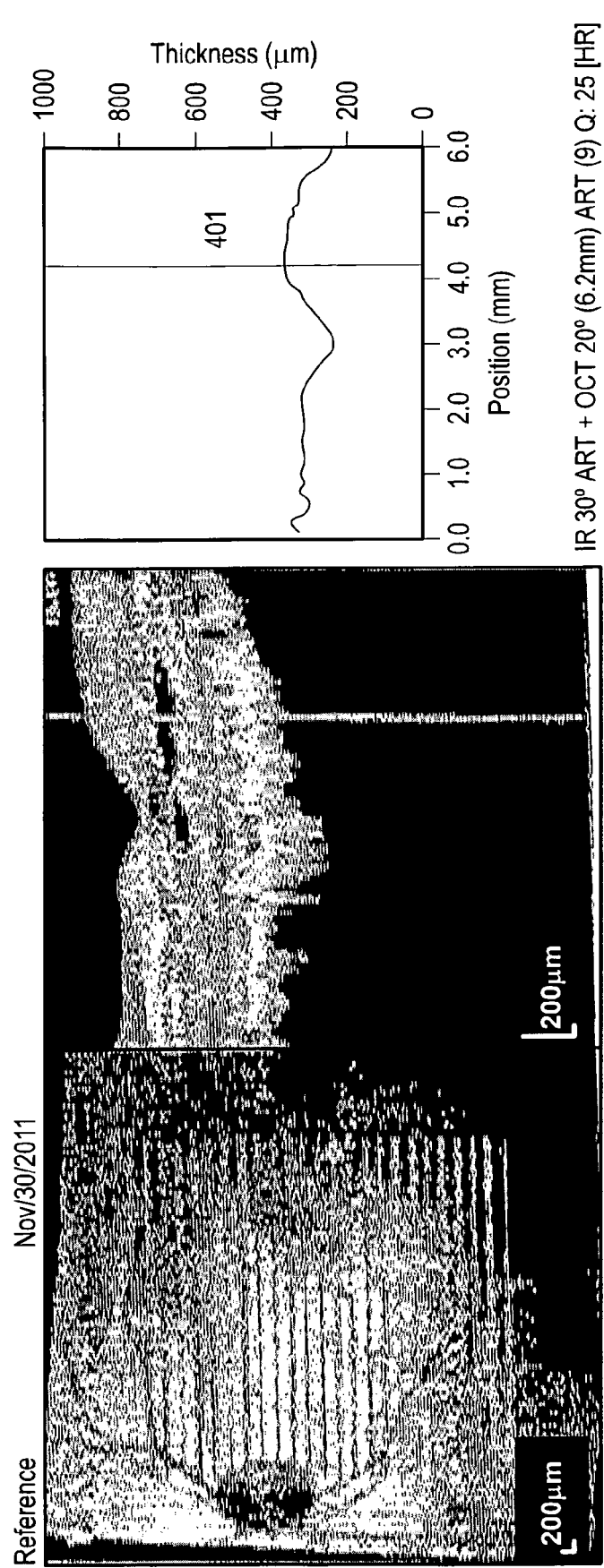
Figure 6:
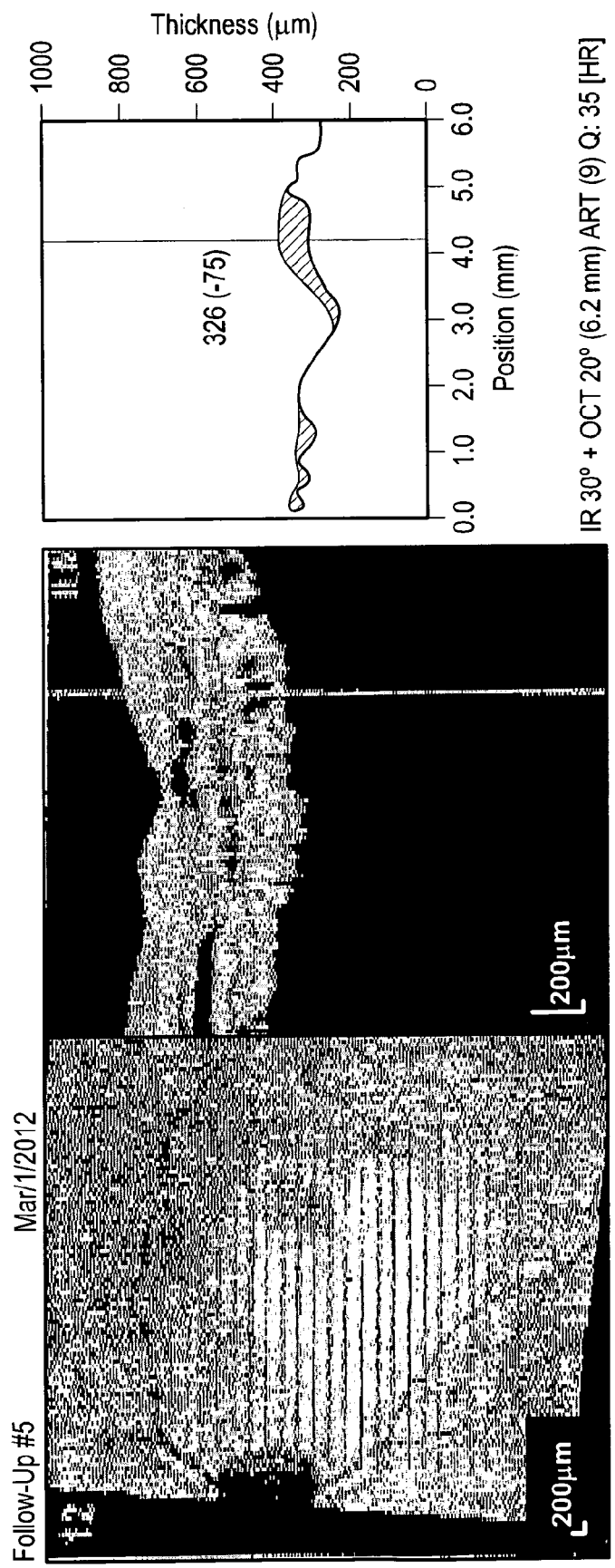

Case d)
61 year old female had twenty three intravitreal Avastin injections for left wet AMD. Her last injection was in June 2011. Her right eye is blind due to retinal detachment. On Nov. 30, 2011 she presented with reduced vision and wet AMD. She was started on Omega 3RX®. Three months following treatment there was minimal fluid with one line gain of vision (FIG. 6).

Figure 7:
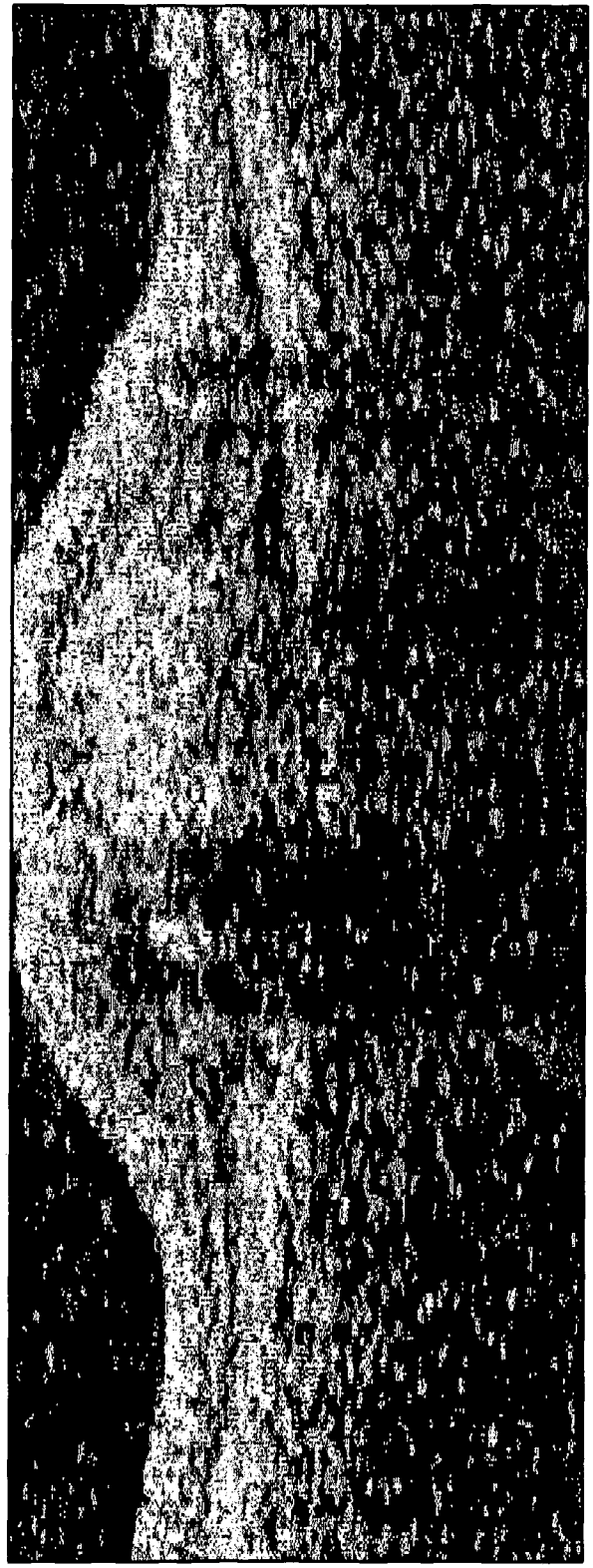
Figure 7:
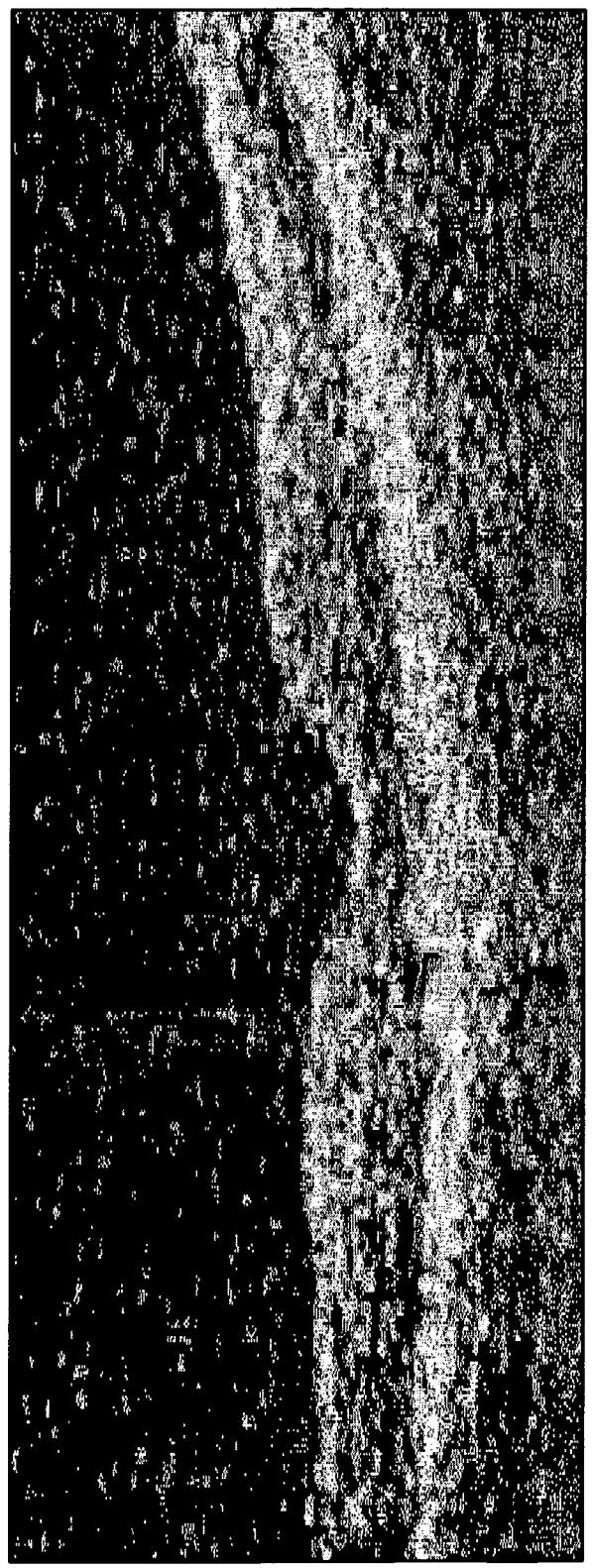
Figure 7:
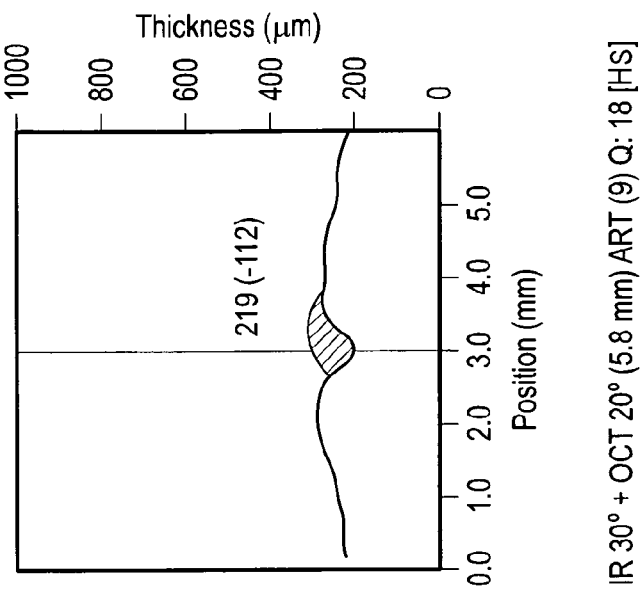
Figure 7:
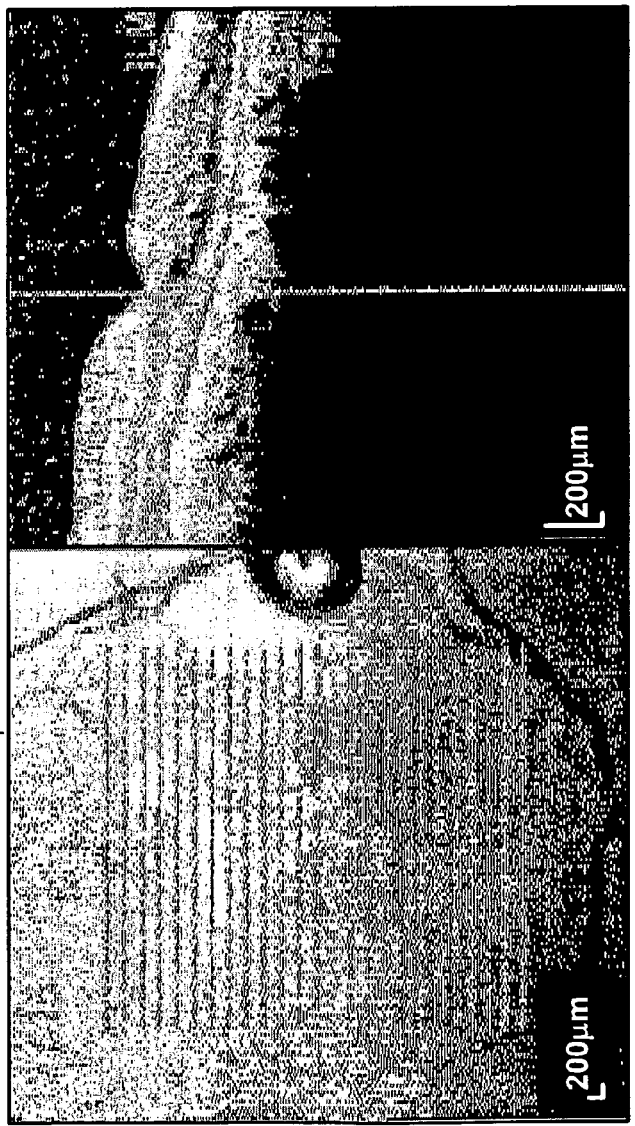
Figure 7:
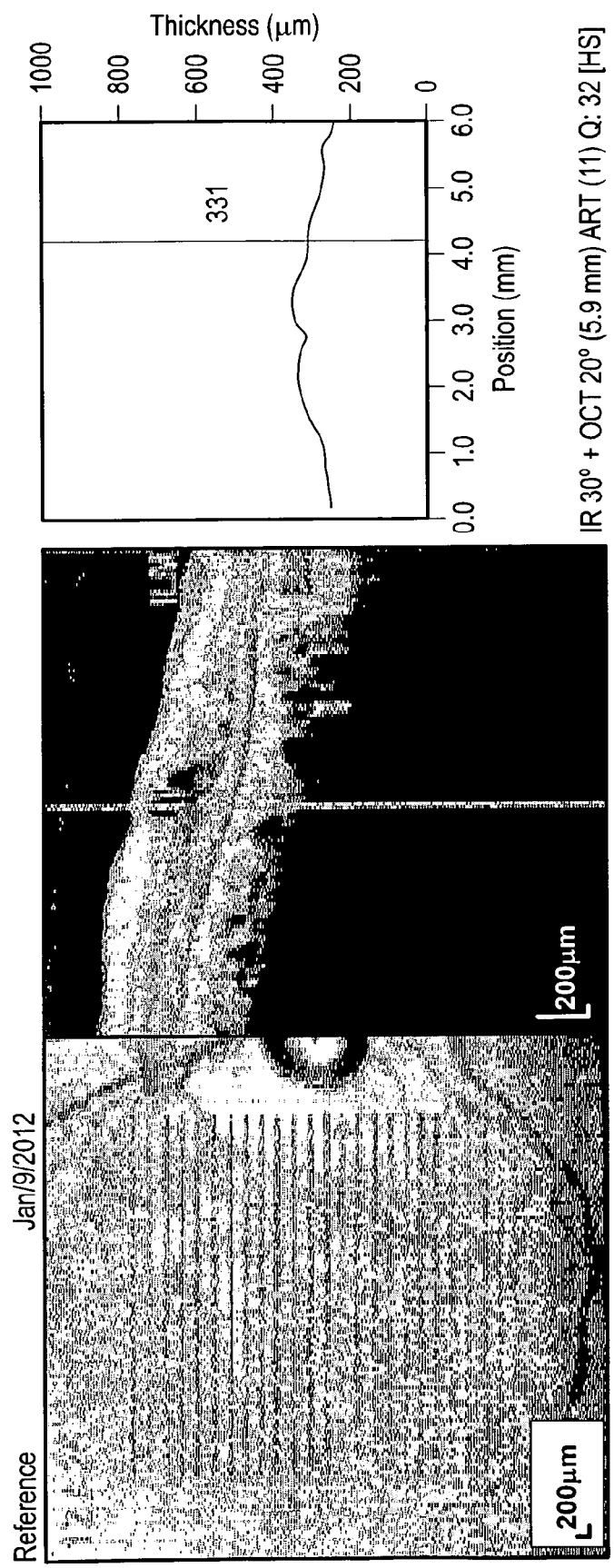
Figure 7:
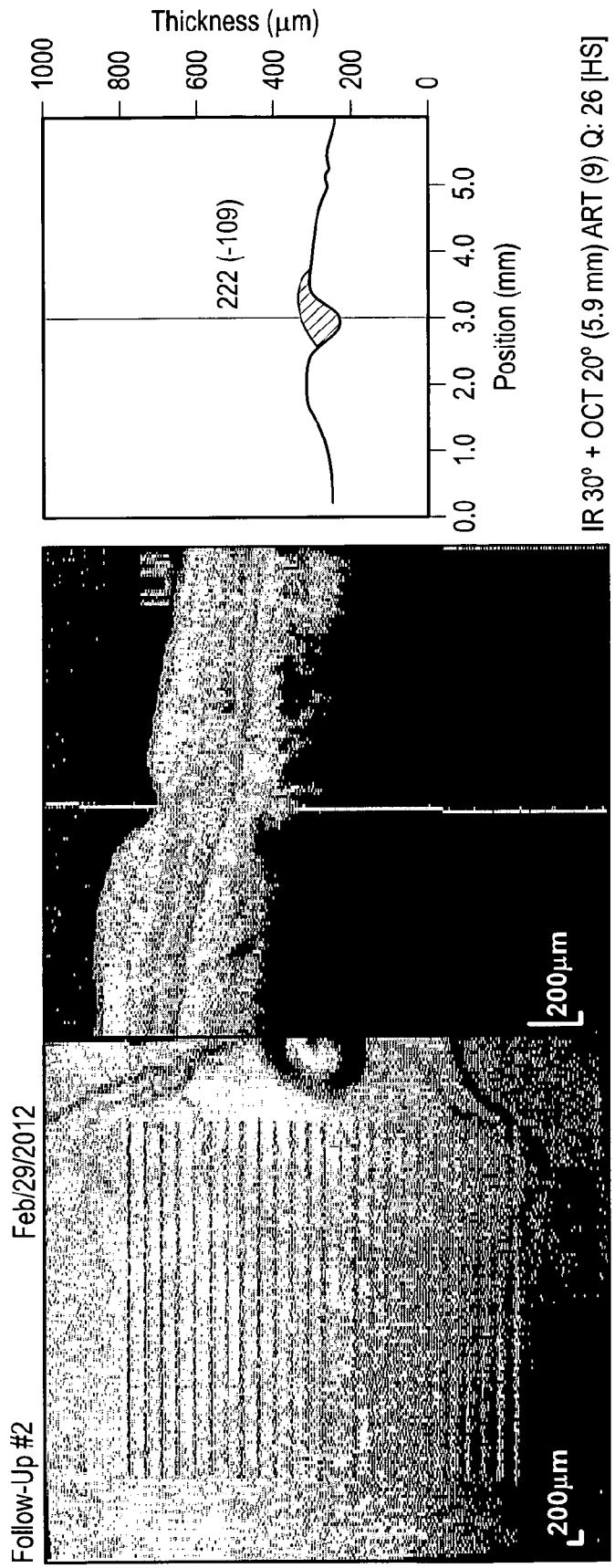

Case e)
92 year old male presented in 2009 with right wet AMD. He had three intravitreal Lucentis injections. H is left eye is blind. He presented again on Jan. 9, 2012 with wet AMD and he was treated with Omega 3RX®. Six weeks following treatment there was no fluid on OCT scan (FIG. 7).

Figure 8:
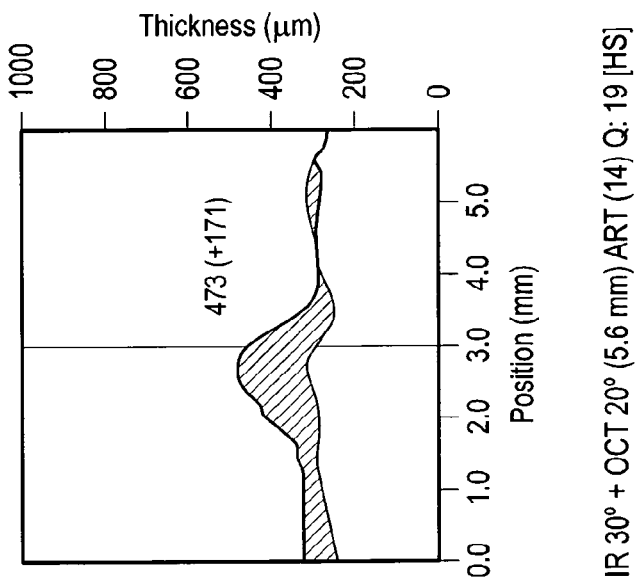
Figure 8:
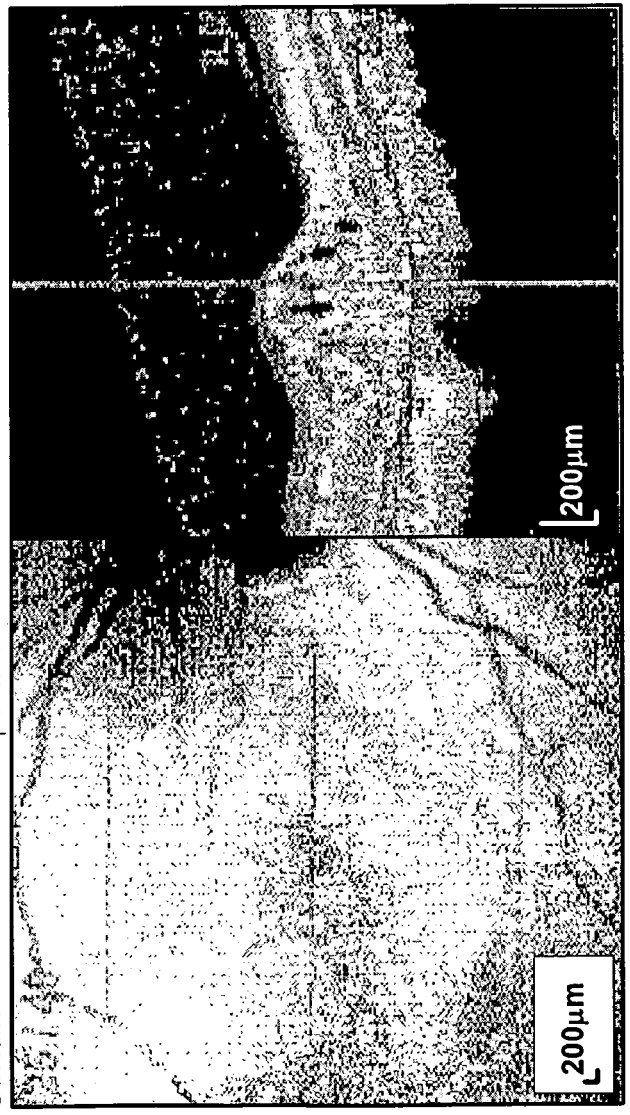
Figure 8:
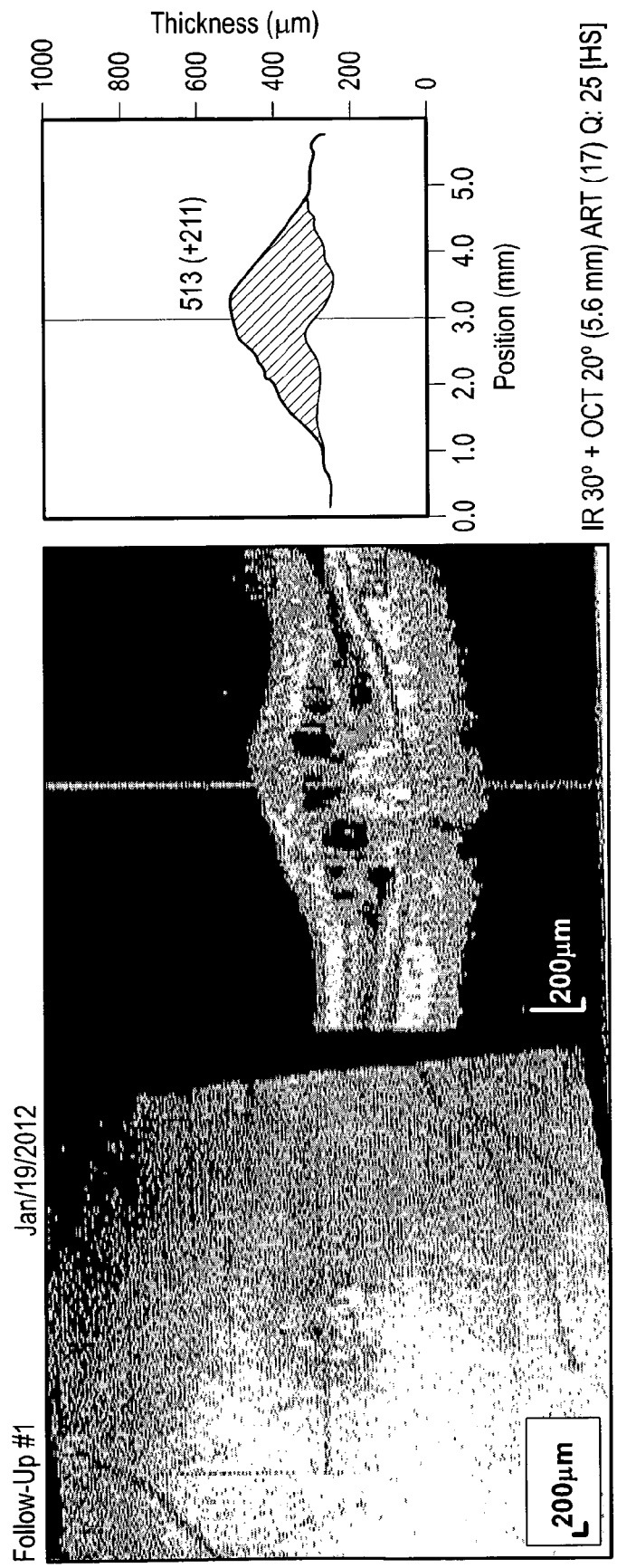
Figure 8:
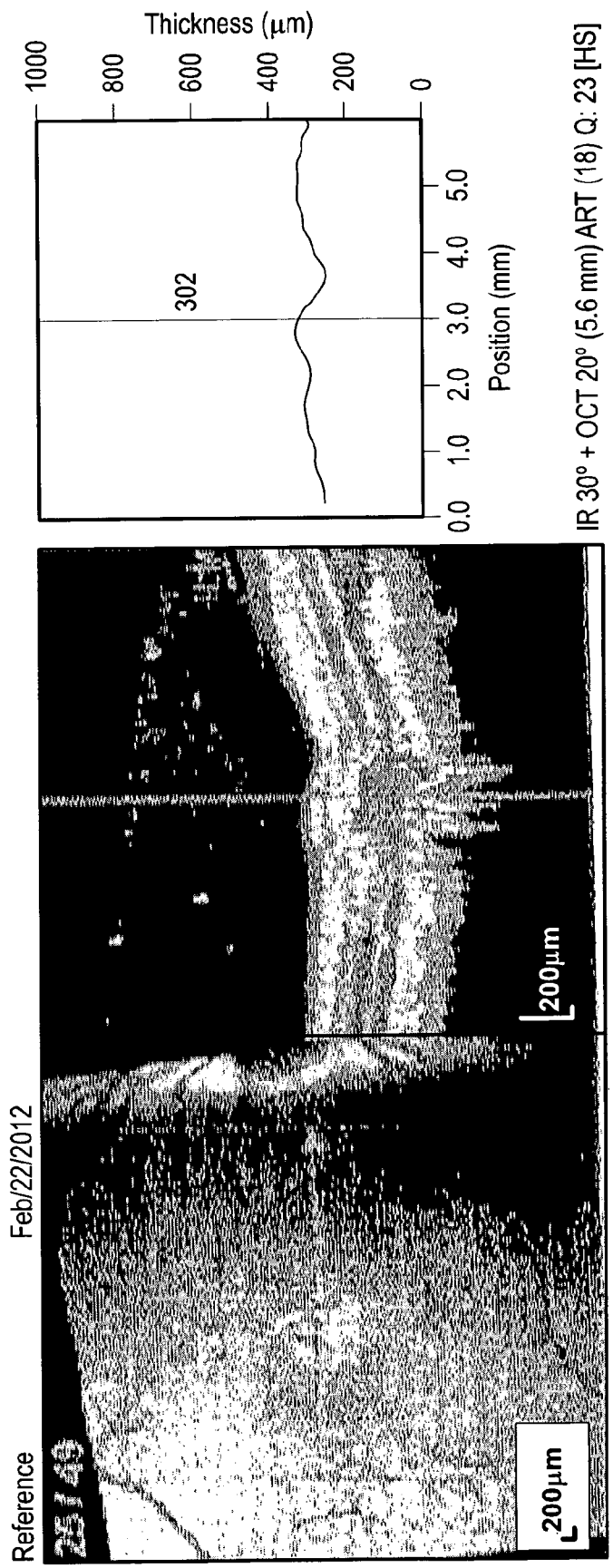
Figure 8:
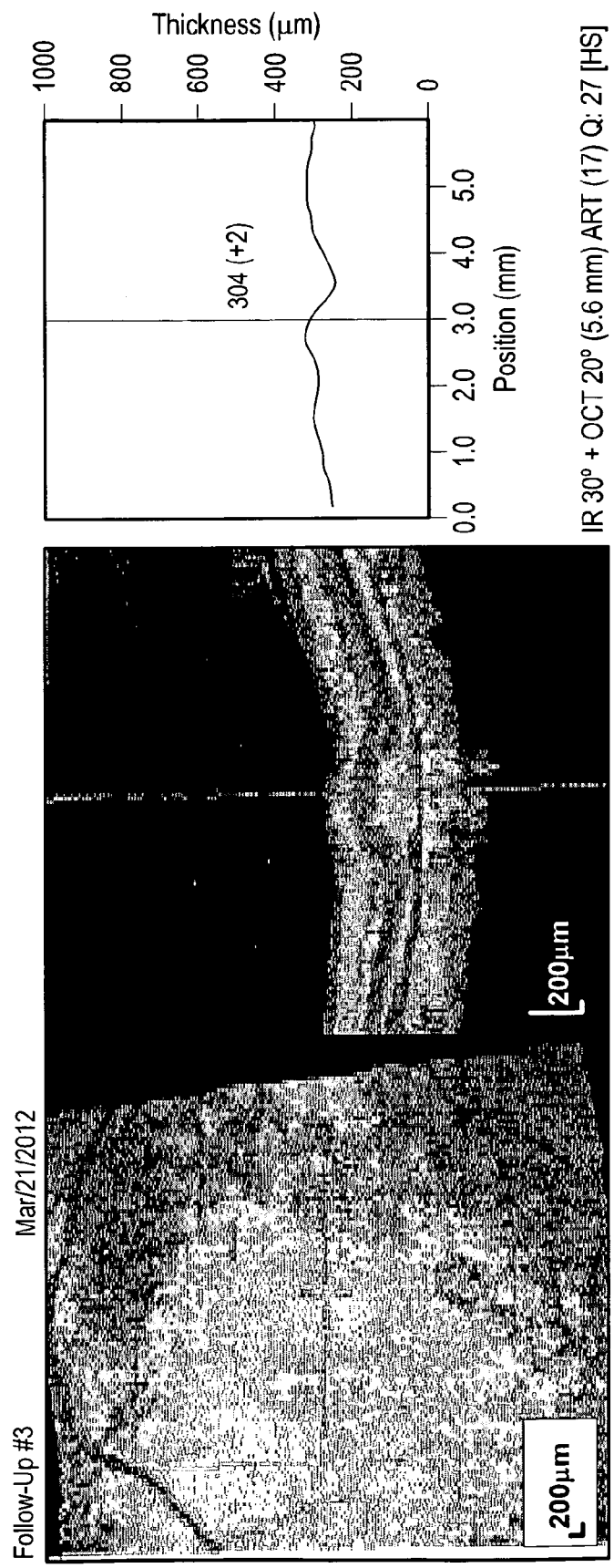

Case f)
74 year old female presented in April 2011 with right wet AMD. She was treated with intravitreal Avastin injection. She presented again on Jan. 19, 2012 with wet macular degeneration and vision of 6/120. She was treated with Avastin intravitreal injection and Omega 3RX®. A month following treatment there was no fluid on OCT and she gained one line of vision (FIG. 8).

Figure 9:
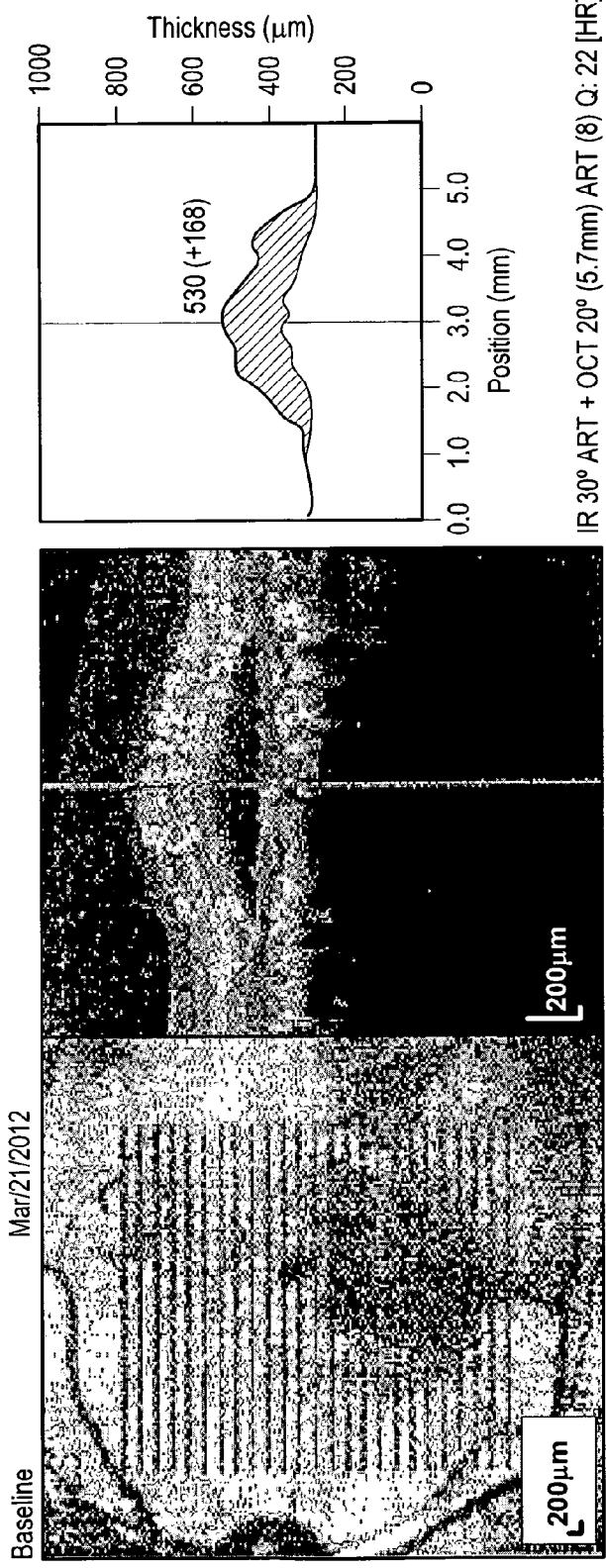
Figure 9:
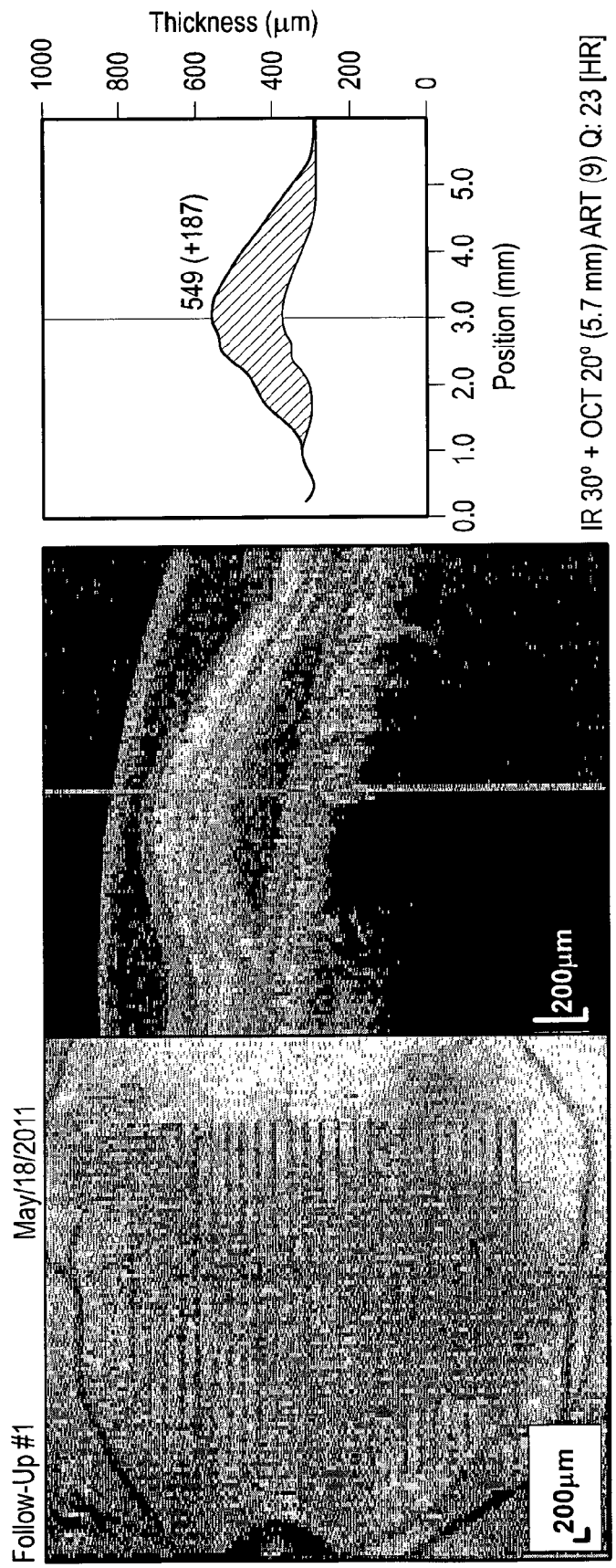
Figure 9:
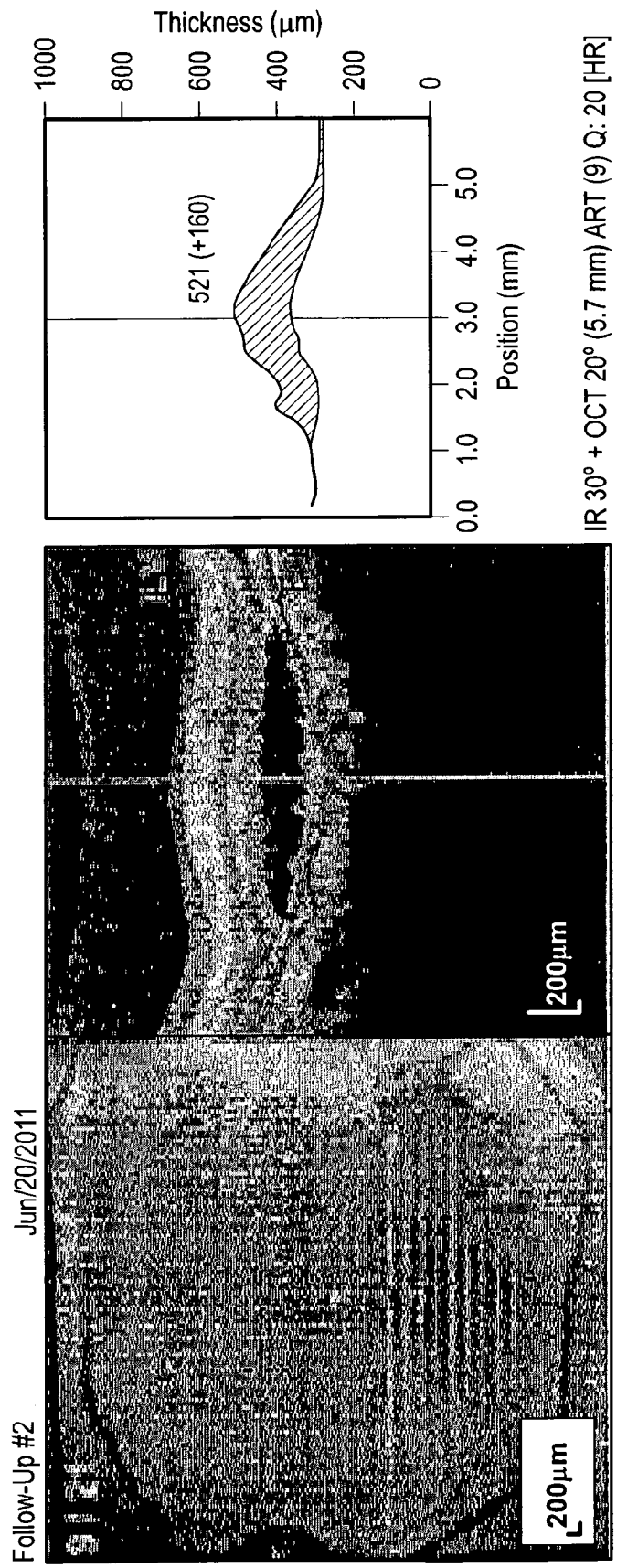
Figure 9:
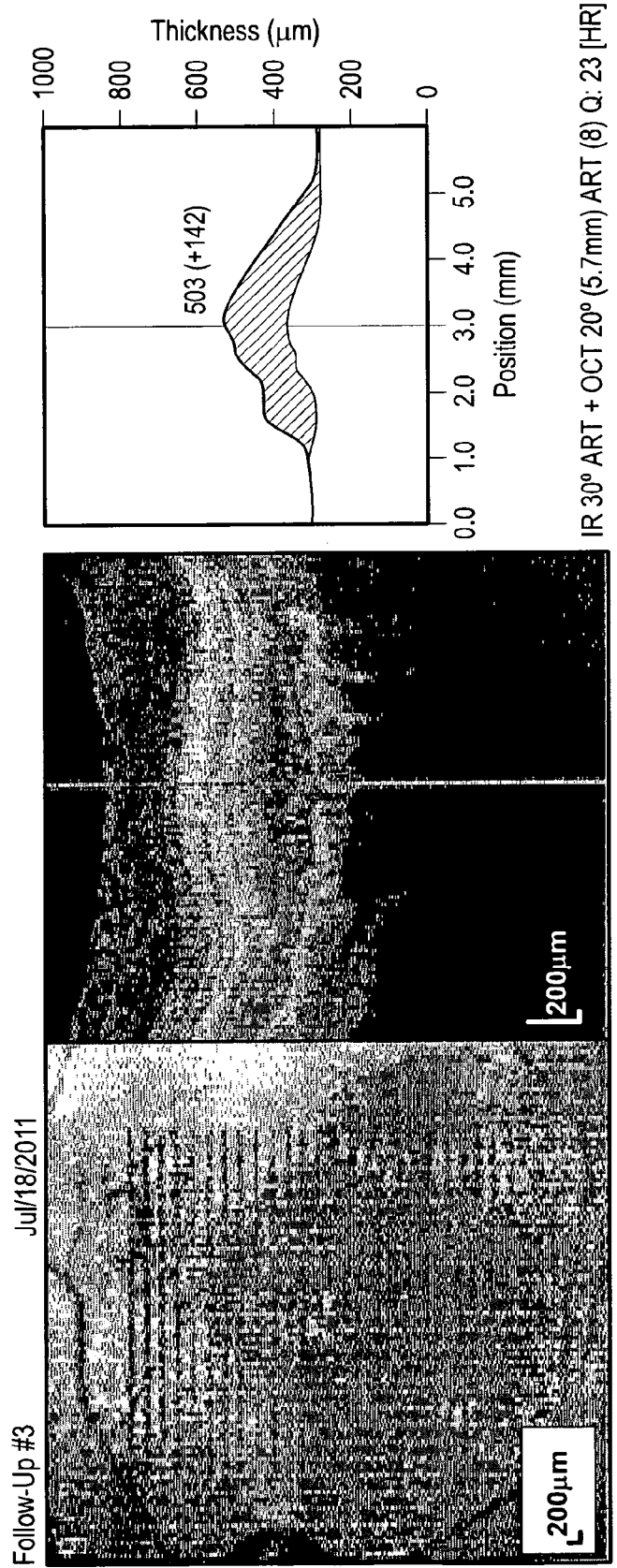
Figure 9:
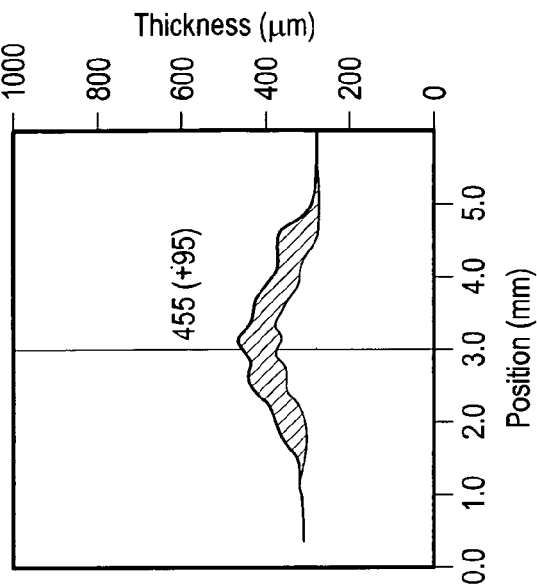
Figure 9:
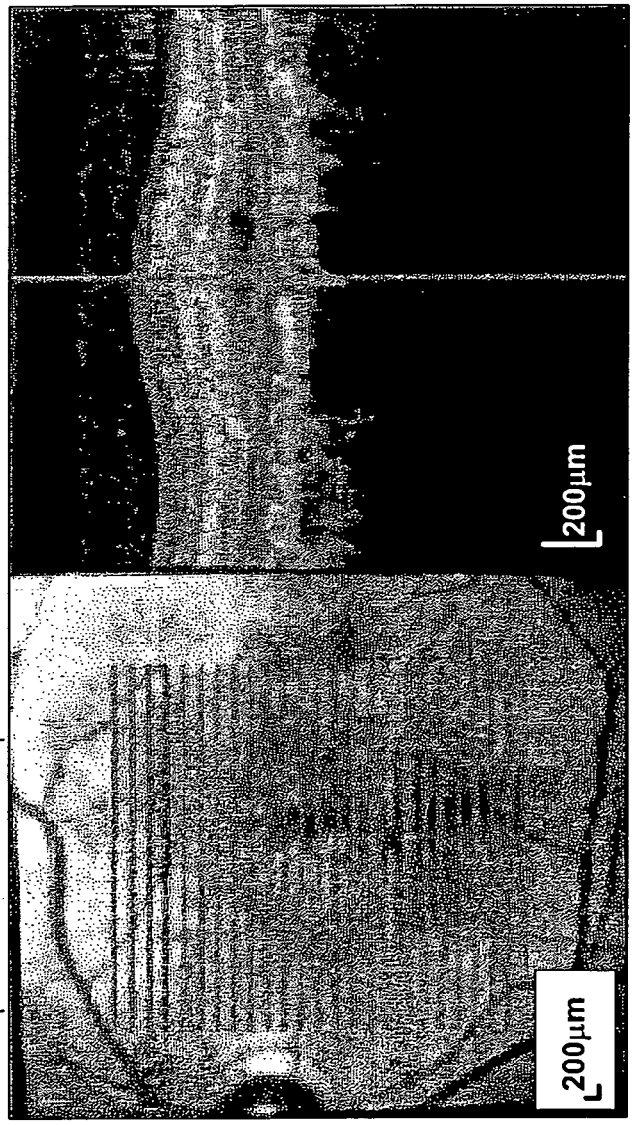
Figure 9:
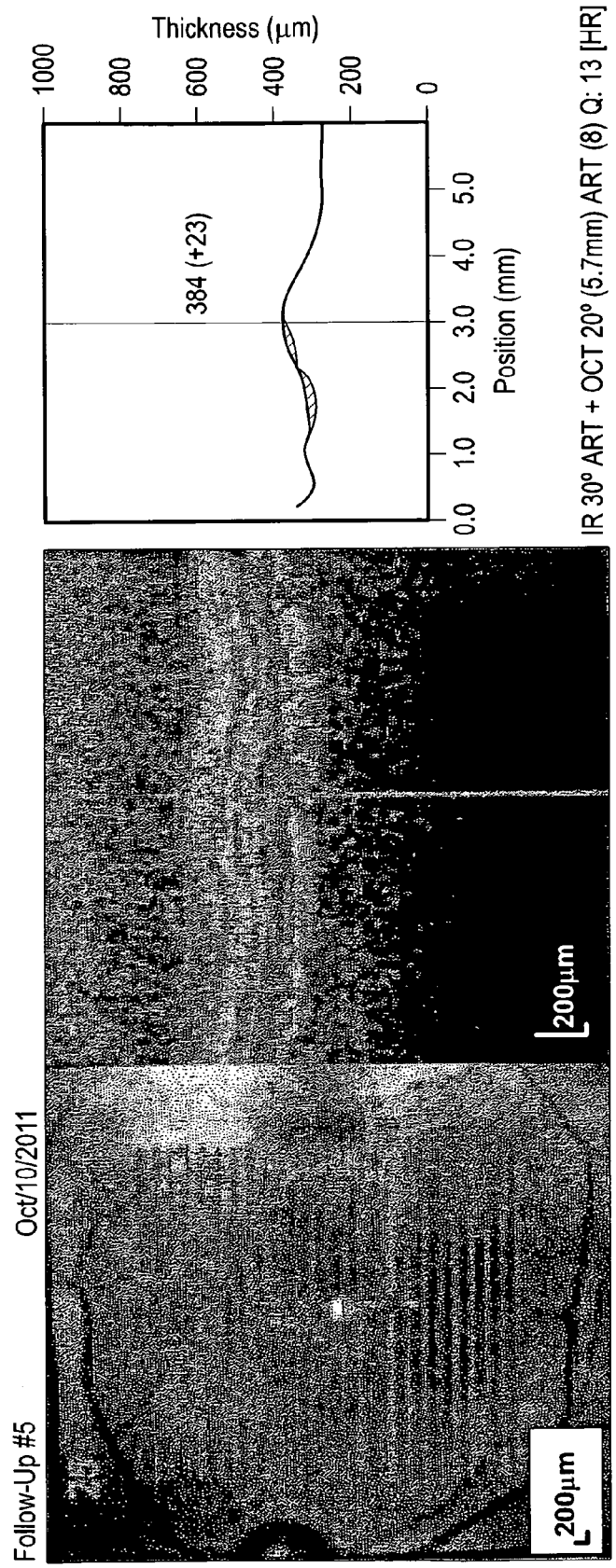
Figure 9:
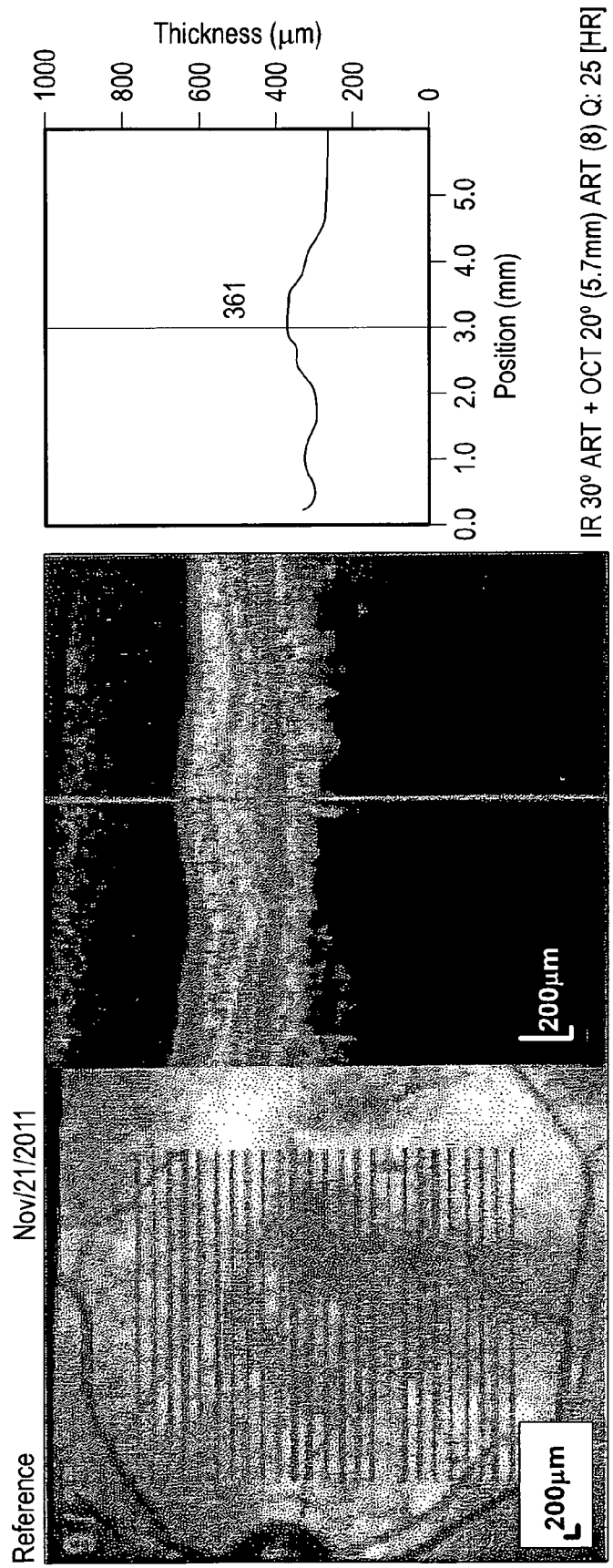
Figure 9:
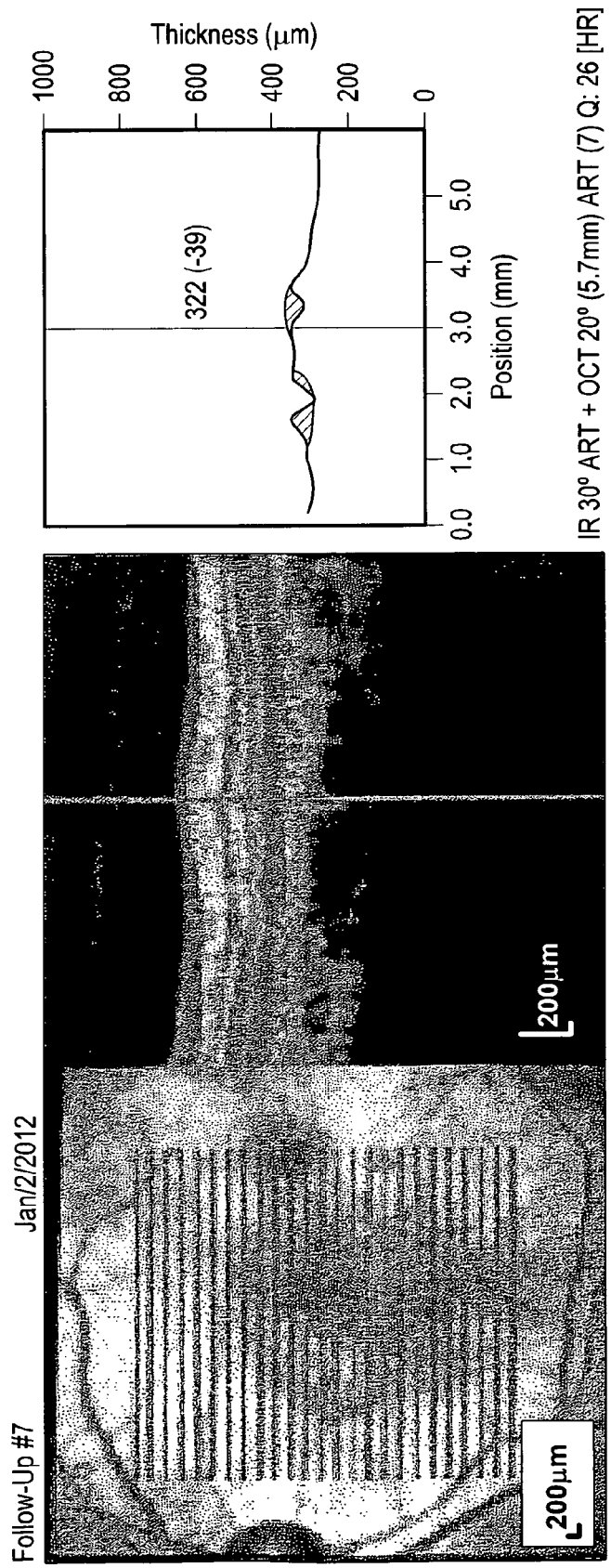

Case g)
60 year old male presented in 2009 with left wet AMD. He was treated with ten intravitreal Lucentis injections. In April 2011 he was started on Omega 3RX®. In November 2011 there was no fluid on OCT scan and he gained four lines of vision (FIG. 9).

Figure 10:
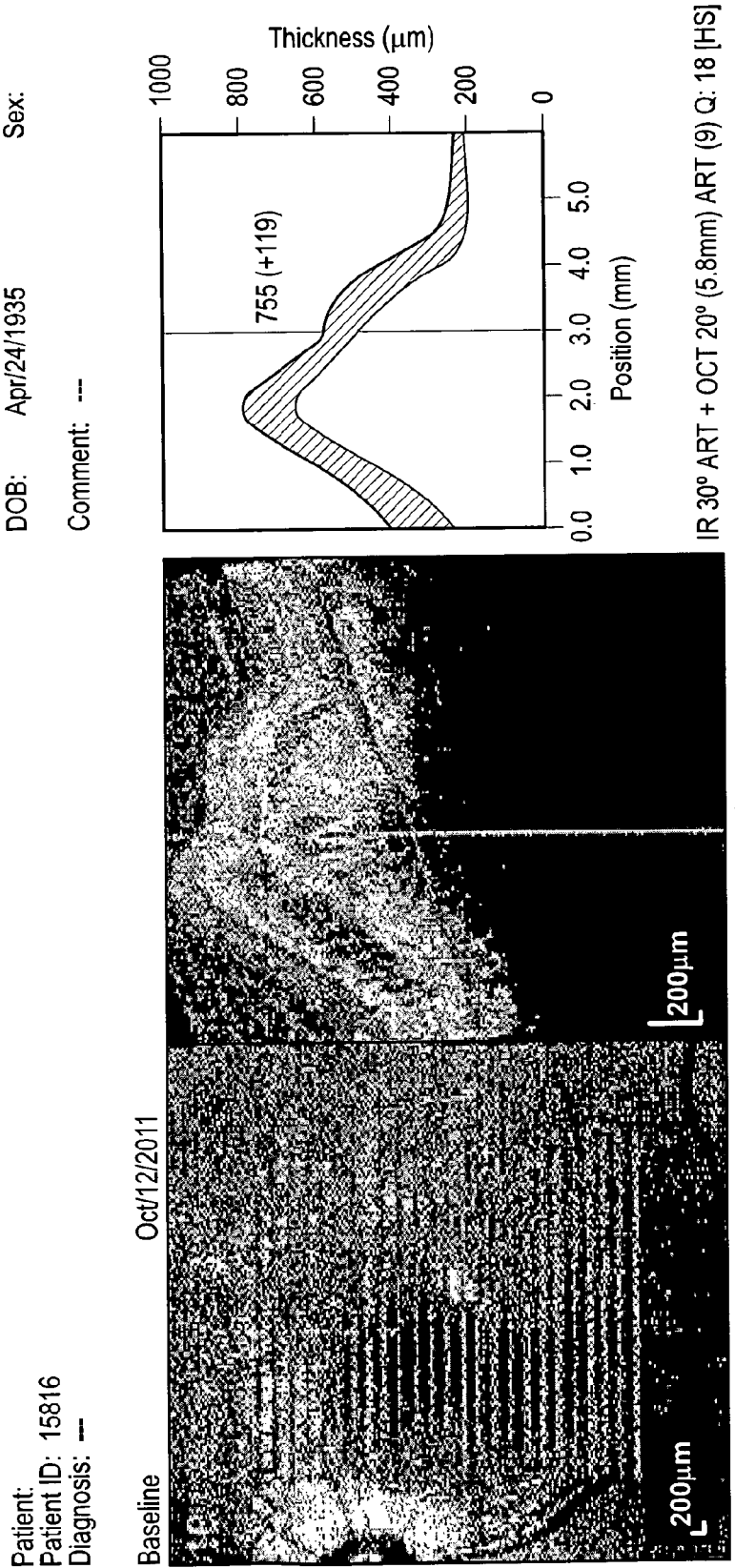
Figure 10:
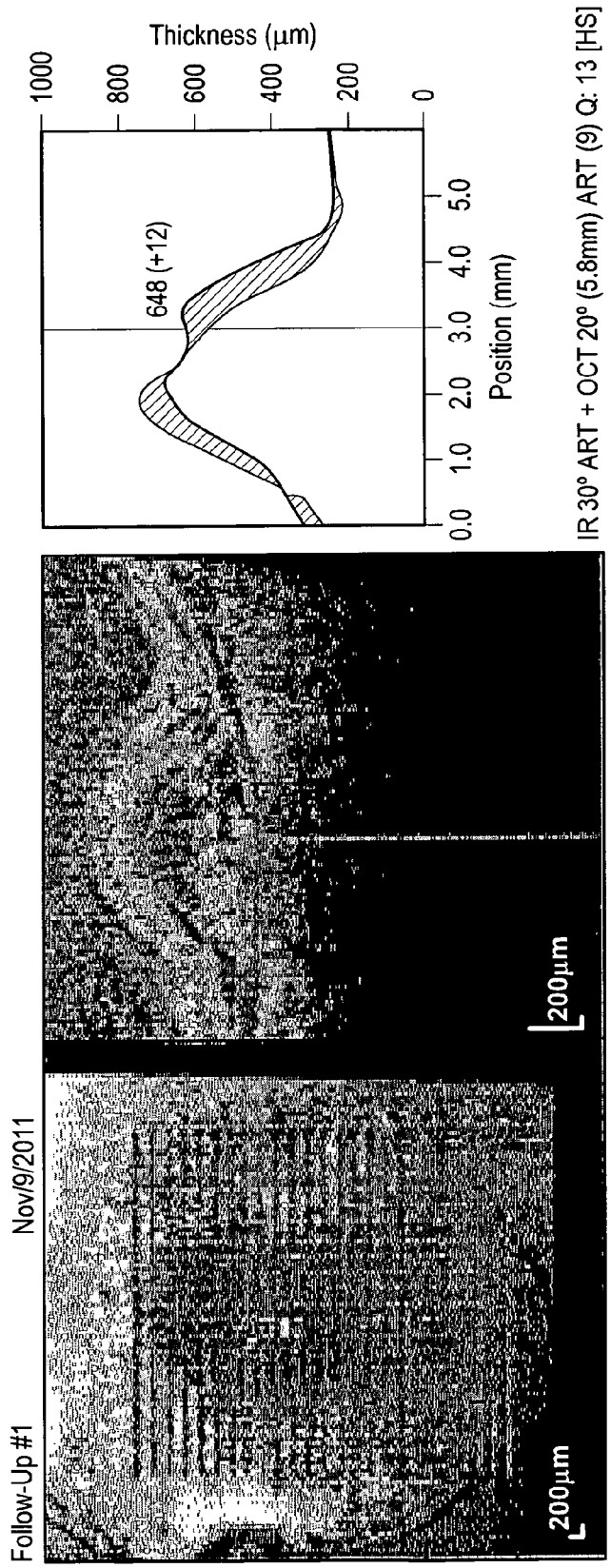
Figure 10:
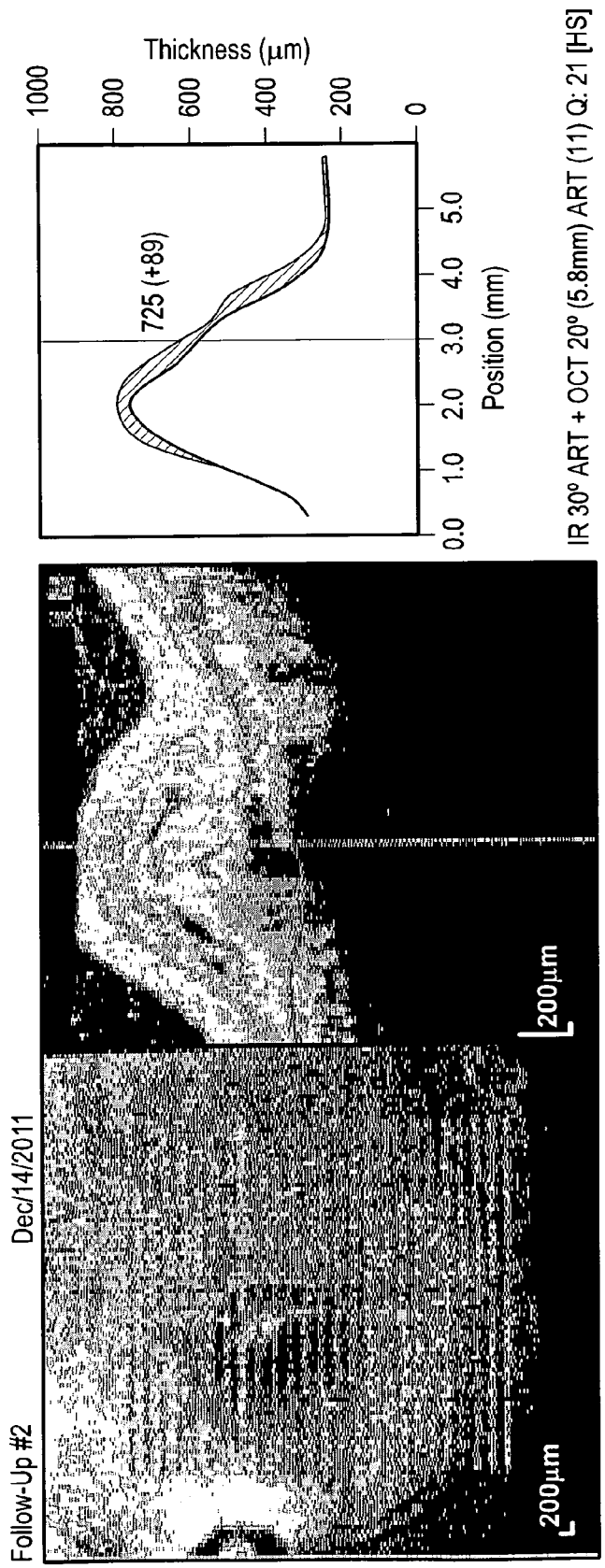
Figure 10:
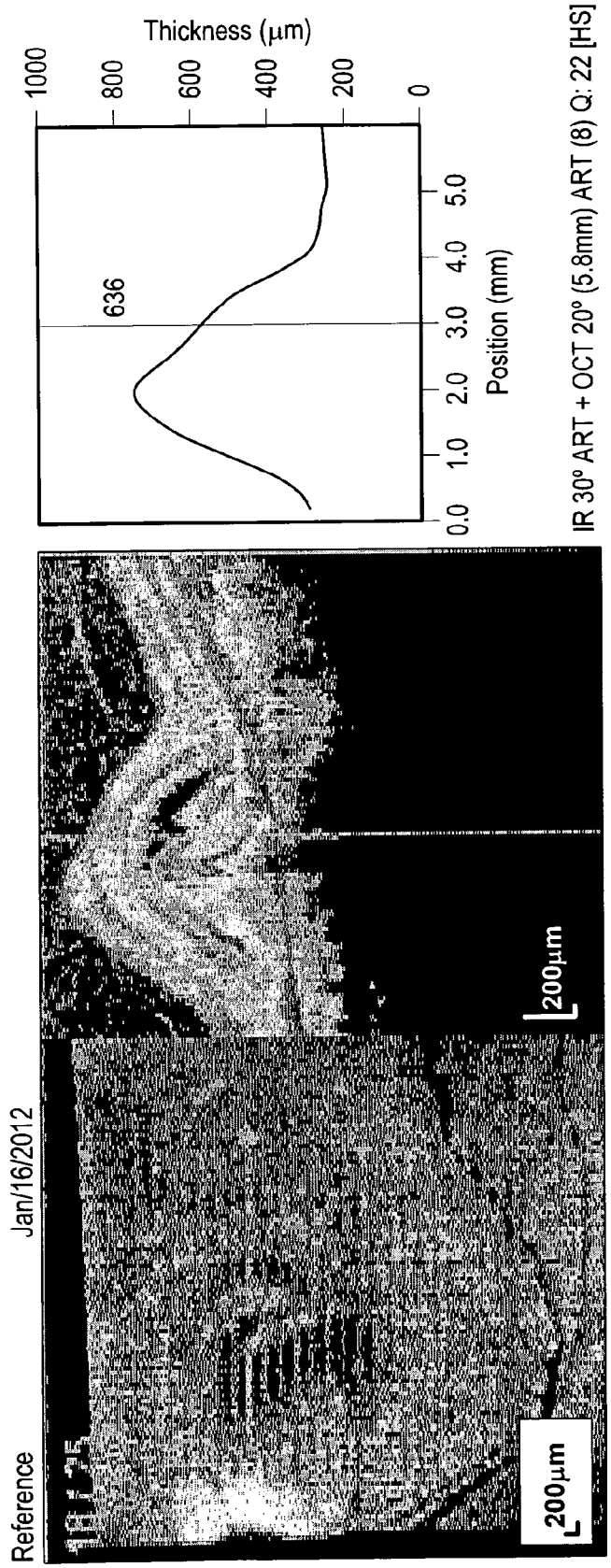
Figure 10:
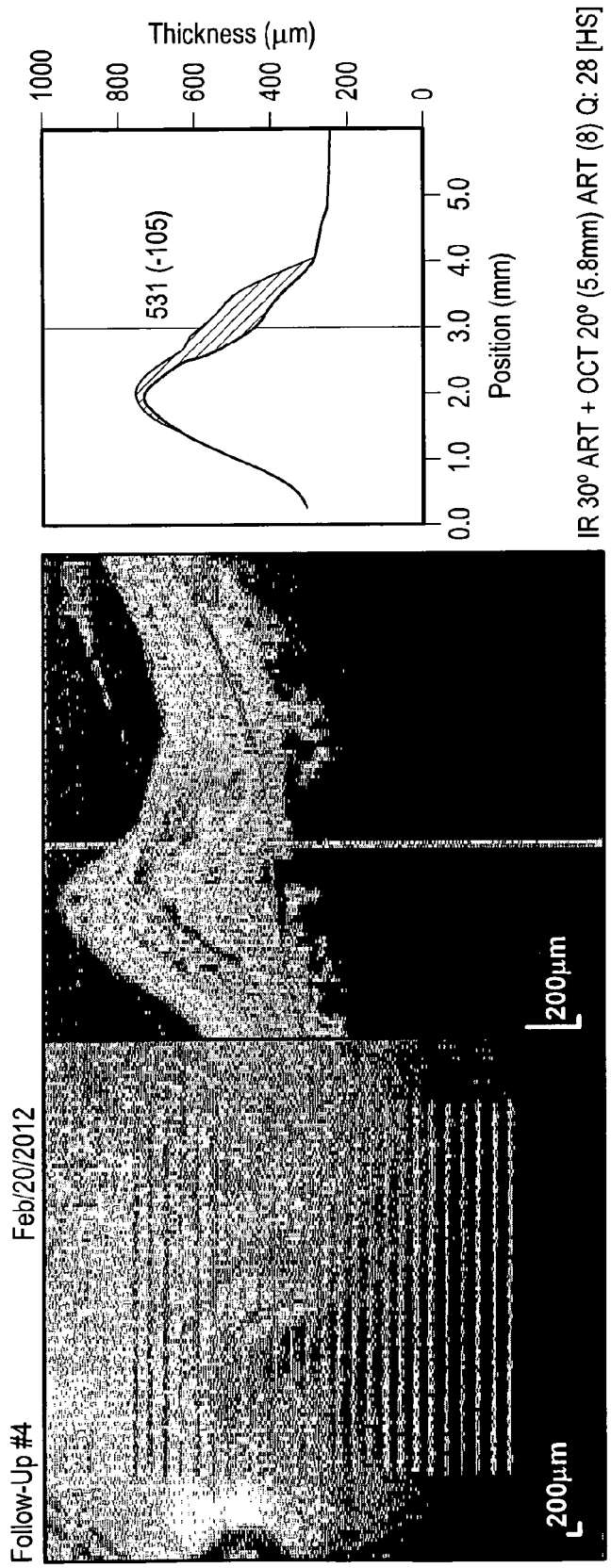

Case h)
76 year old female presented in October 2011 with left wet AMD. She was treated with three intravitreal Avastin injections. On Feb. 14, 2011 she was started on Omega 3RX® with the last intravitreal Avastin injection. Two months following treatment there was minimal fluid and she gained one line of vision (FIG. 10).

Figure 11:
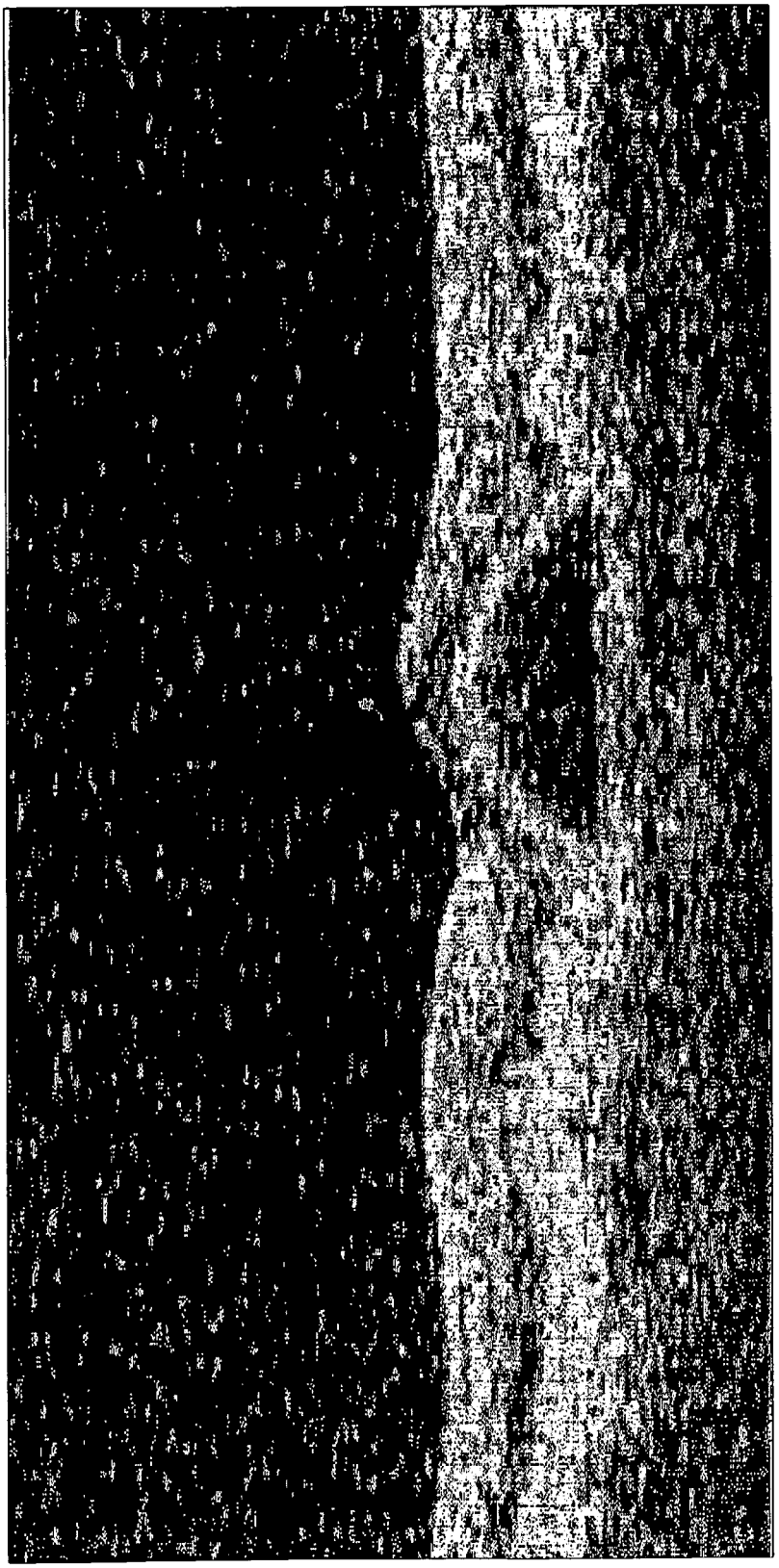
Figure 11:
Figure 11:
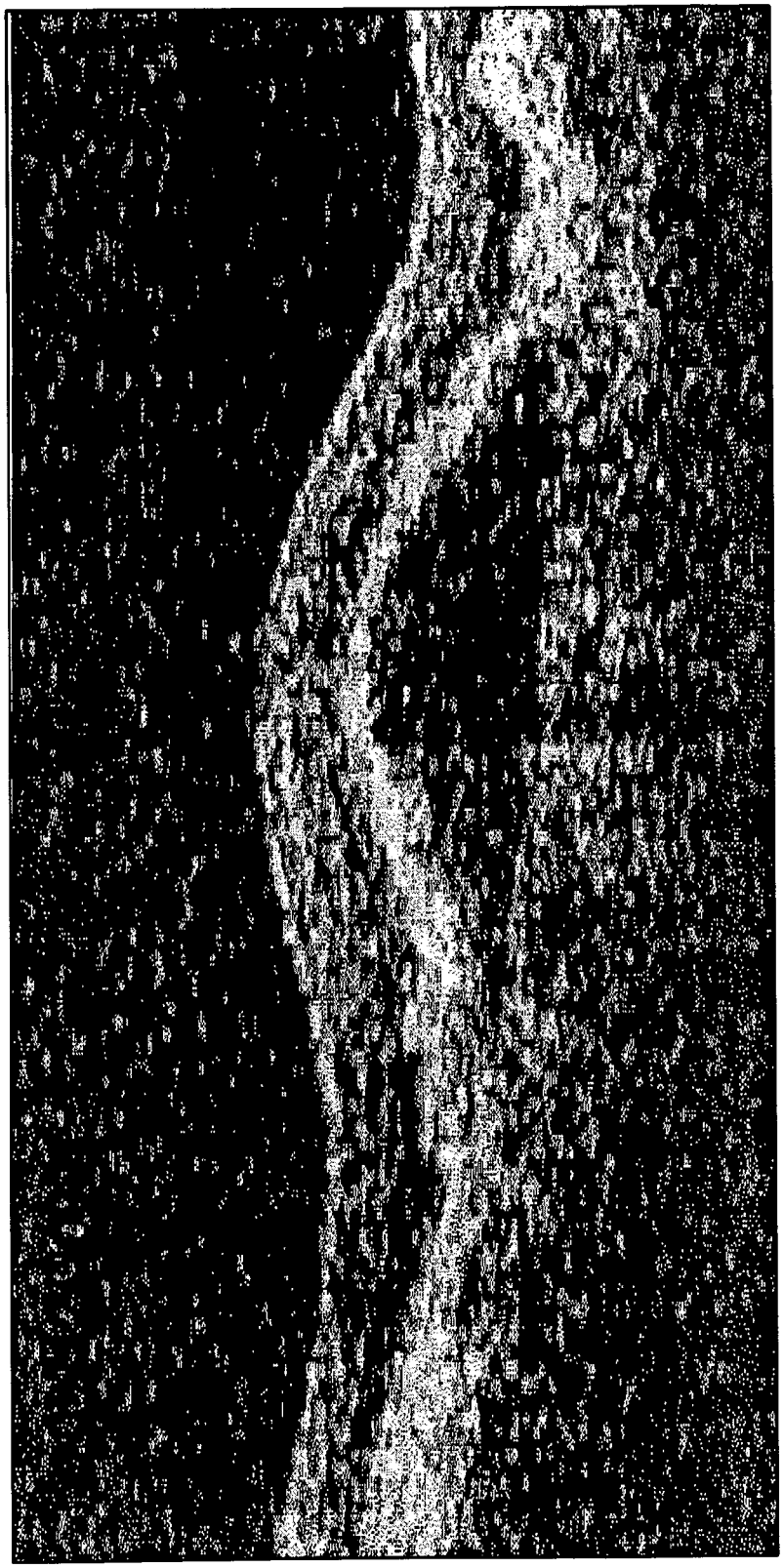
Figure 11:
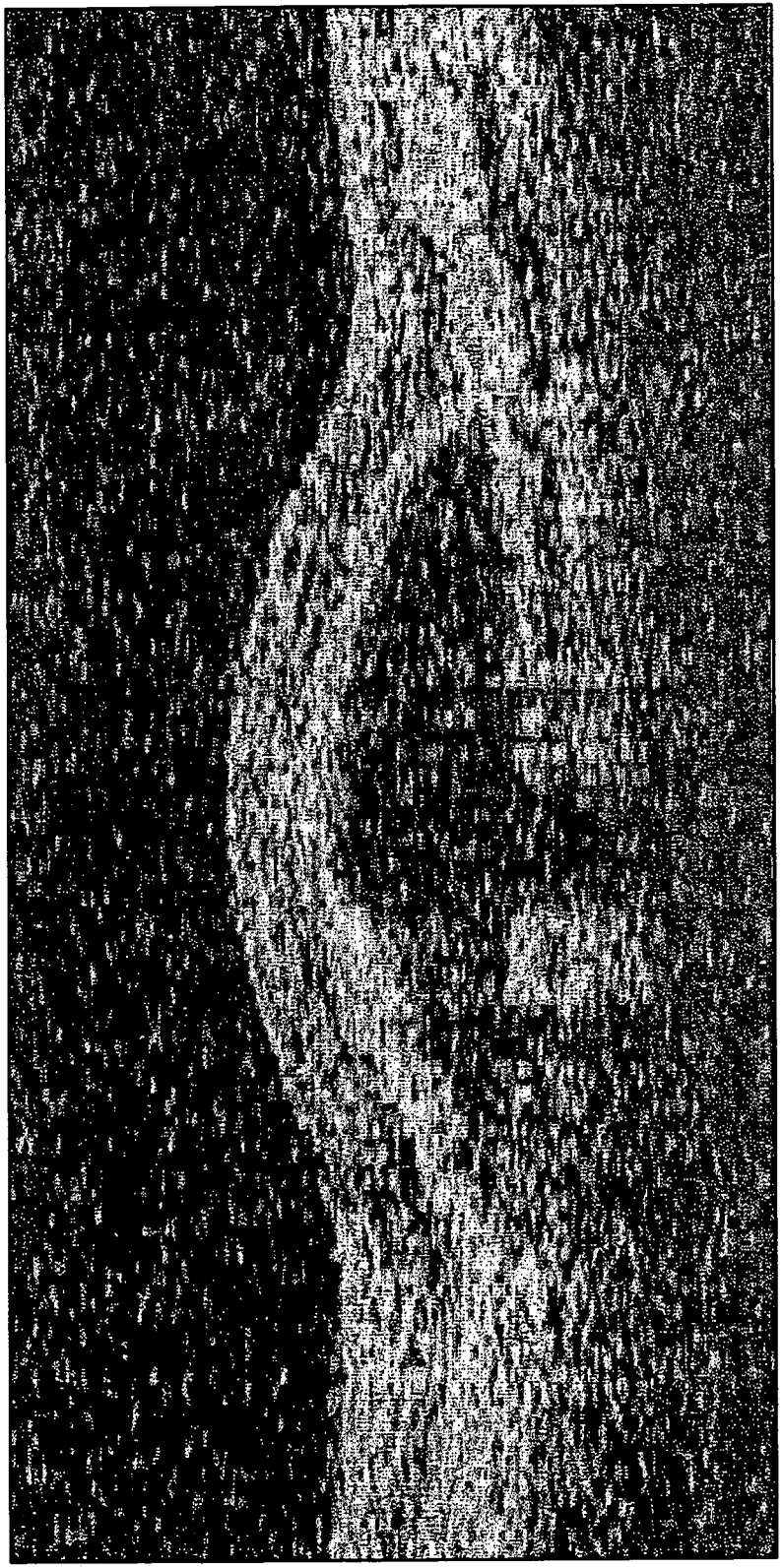
Figure 11:
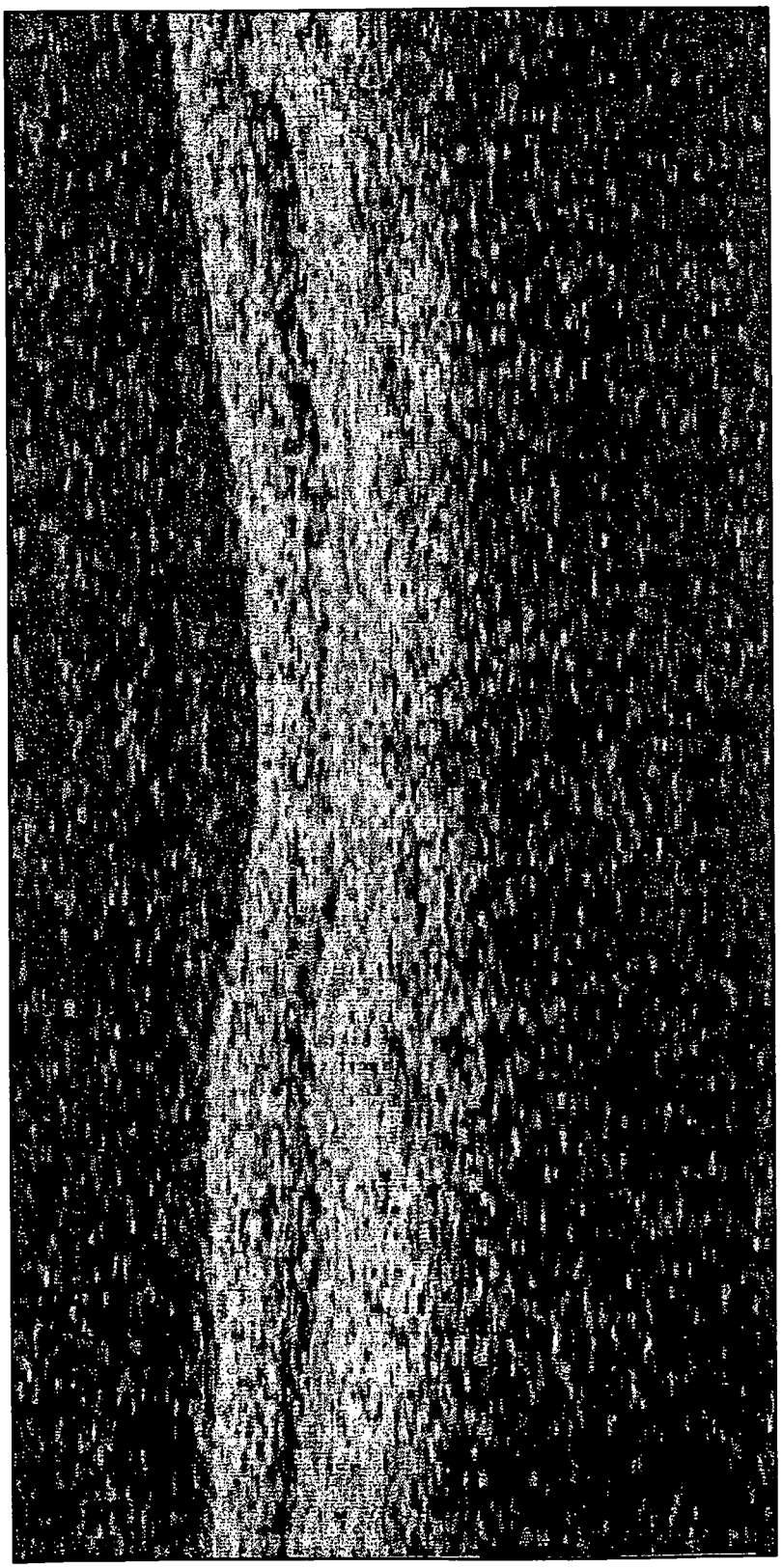
Figure 11:
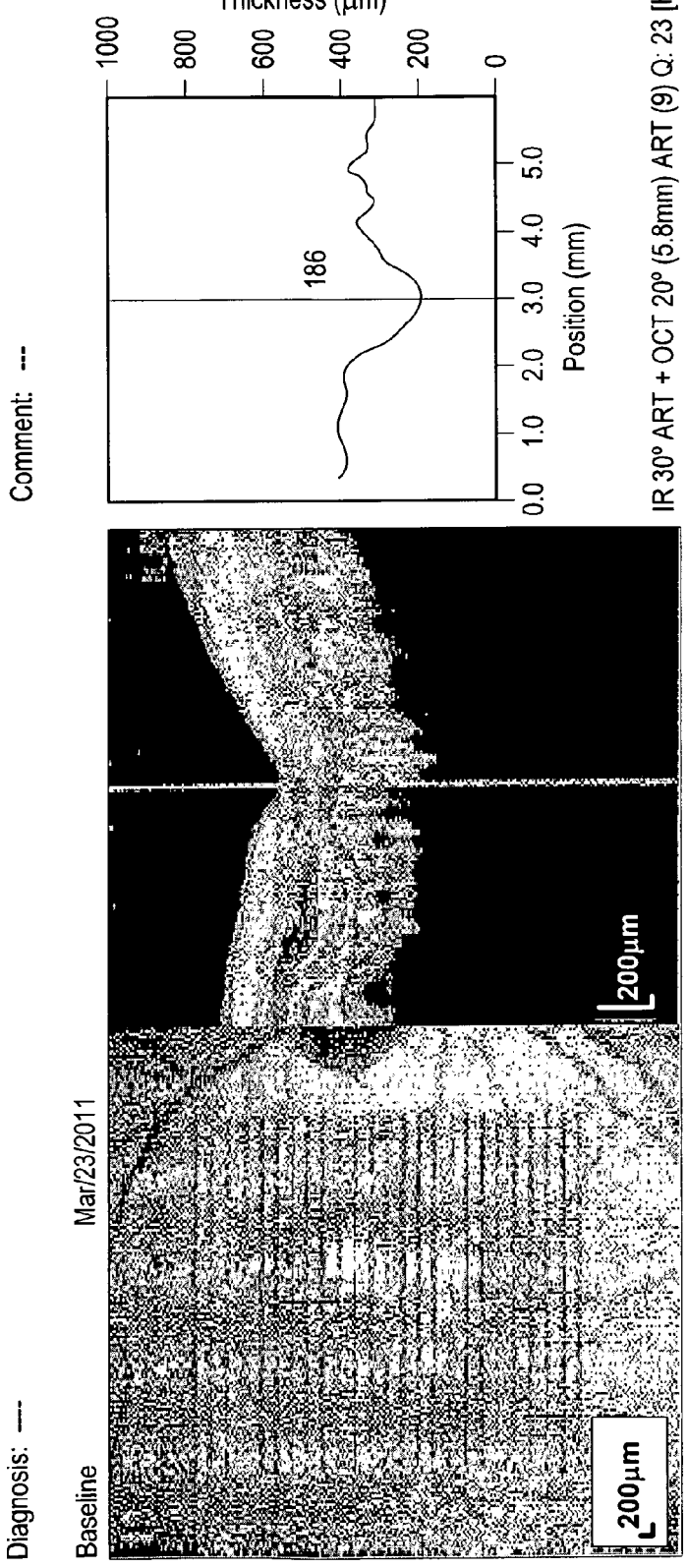
Figure 11:
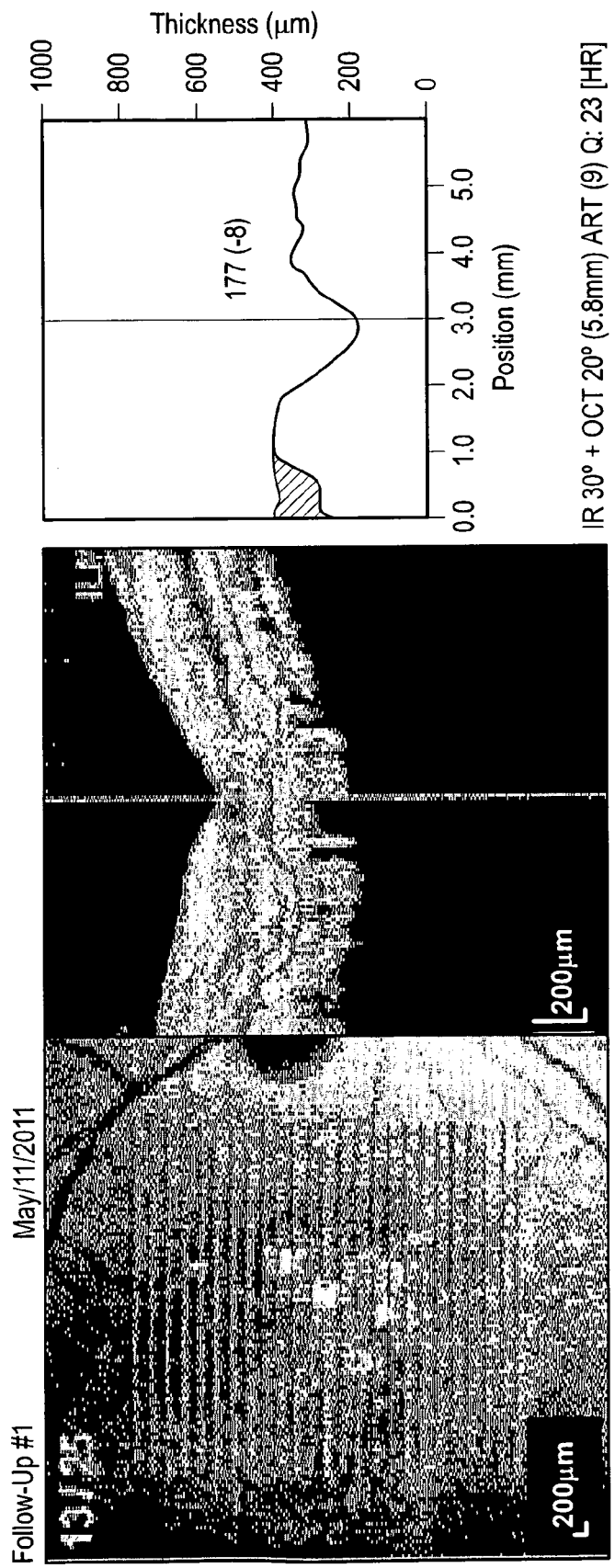
Figure 11:
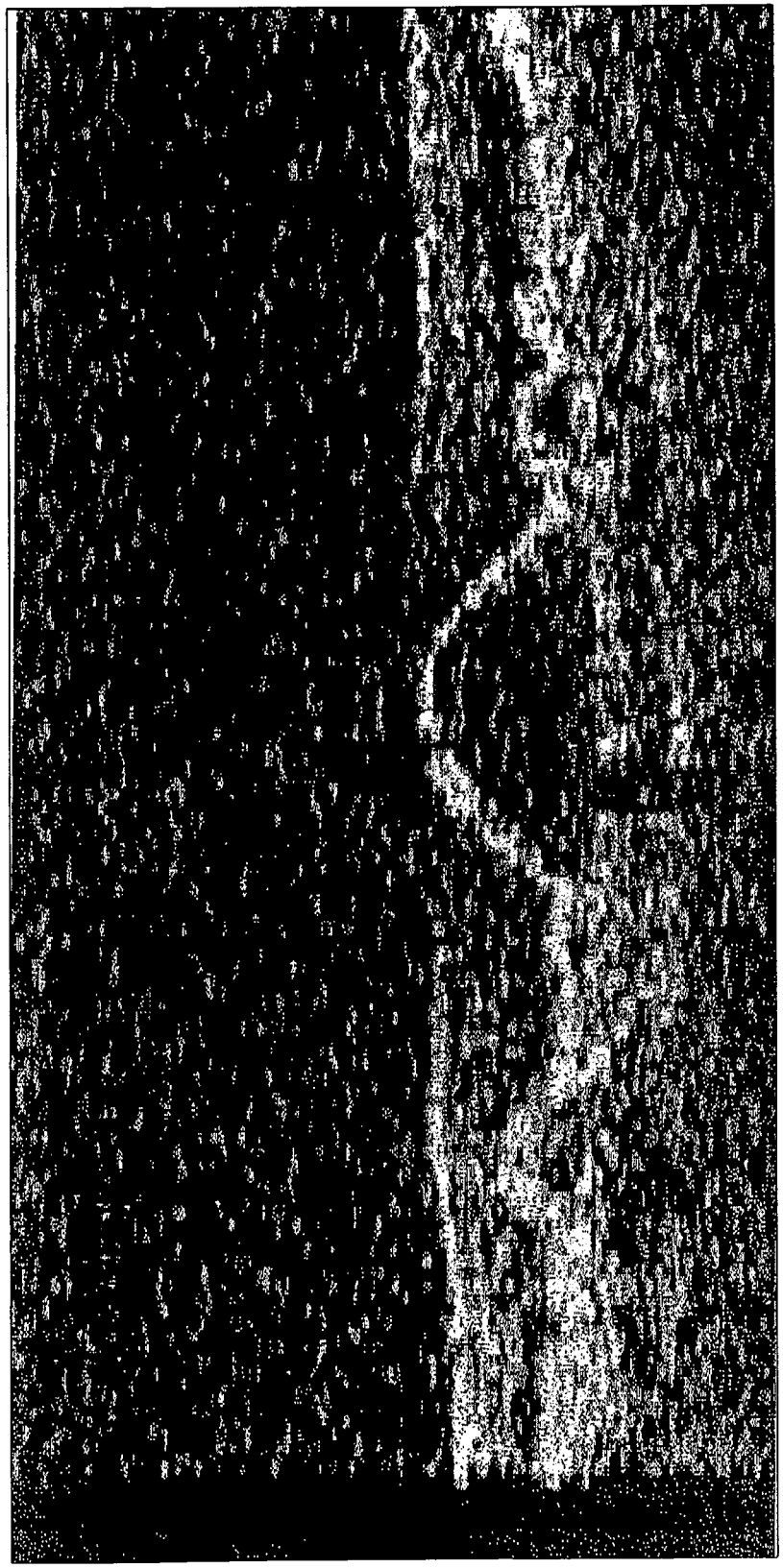
Figure 11:
Figure 11:
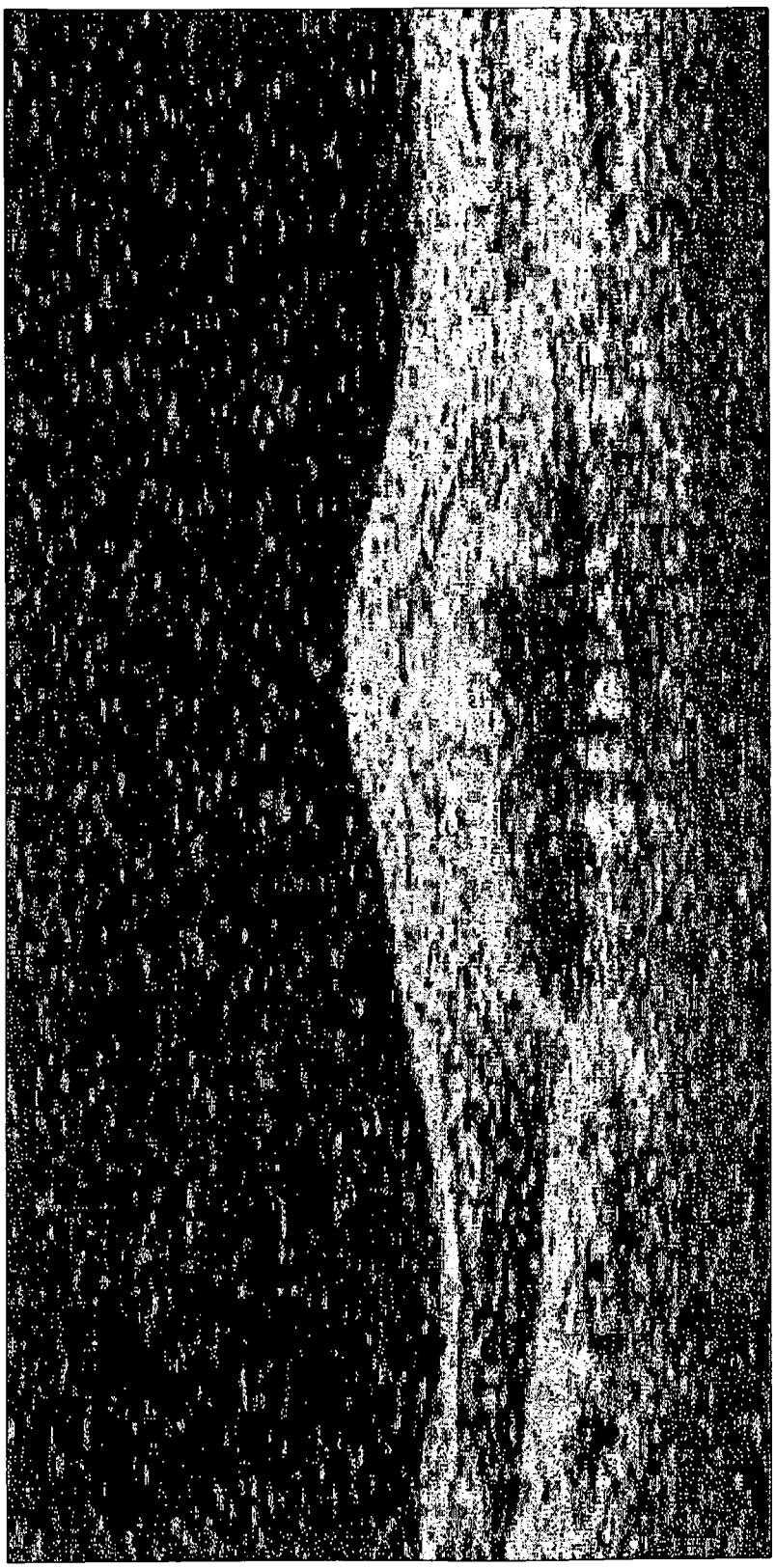
Figure 11:
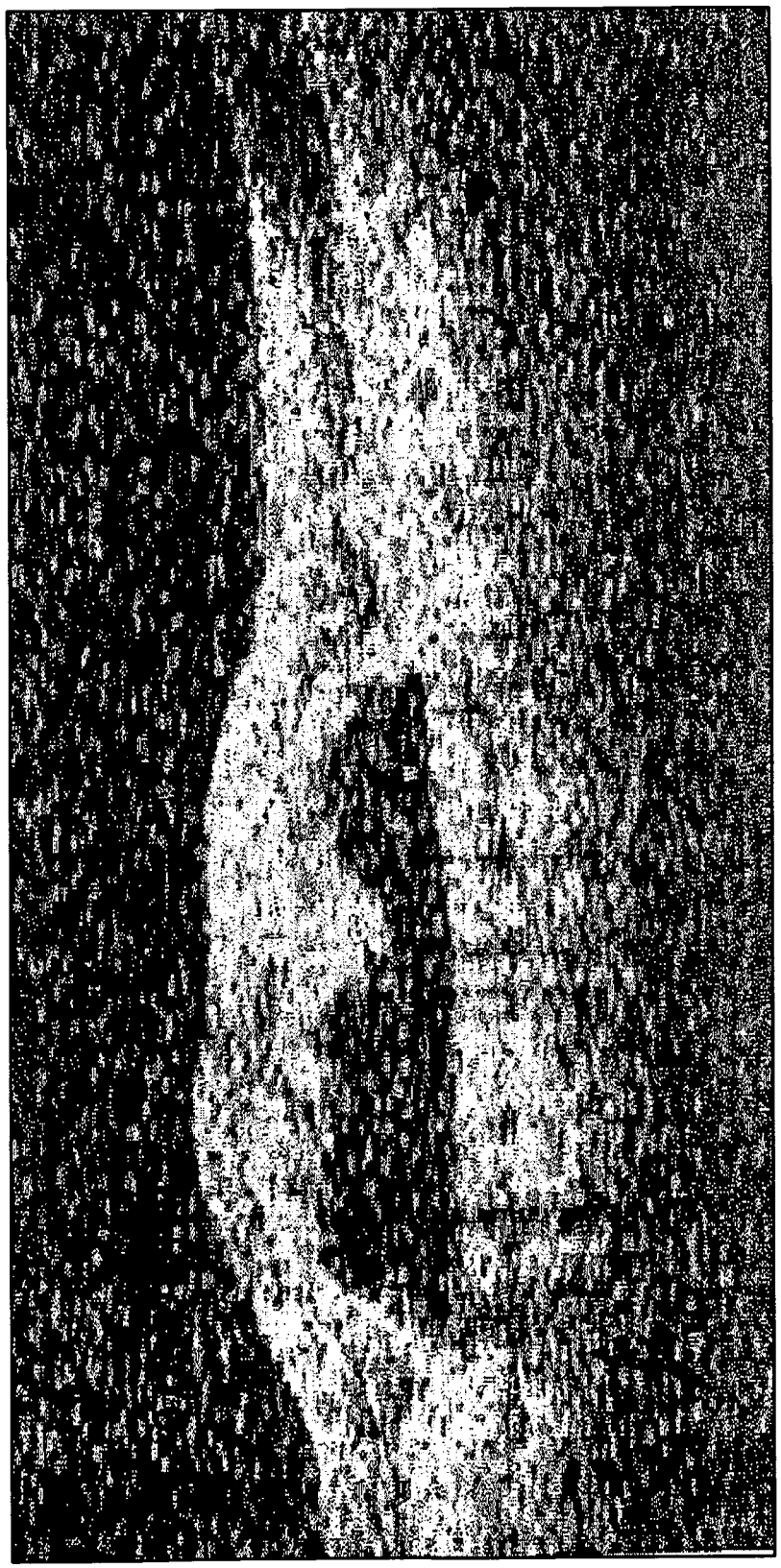
Figure 11:
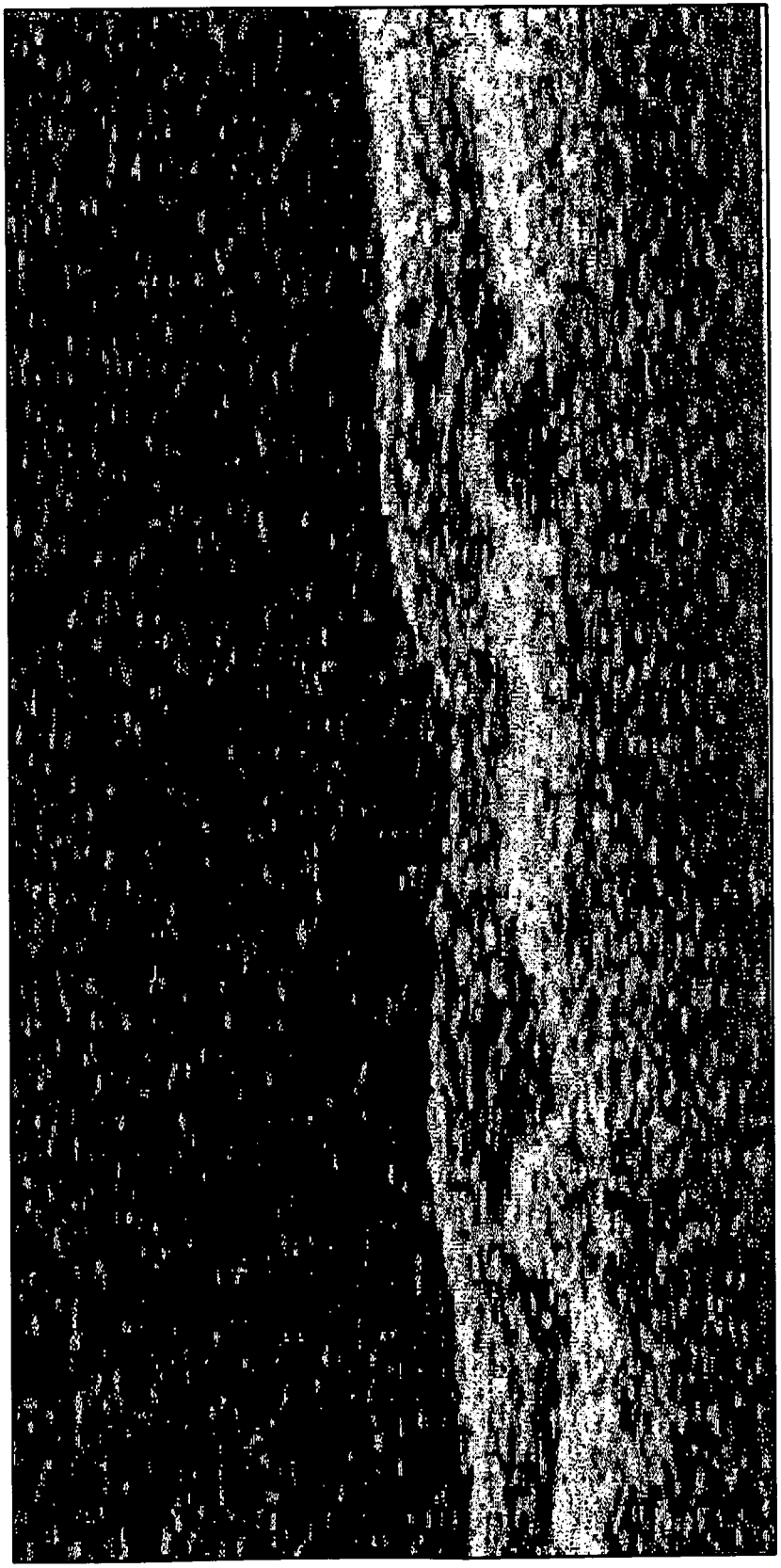
Figure 11:
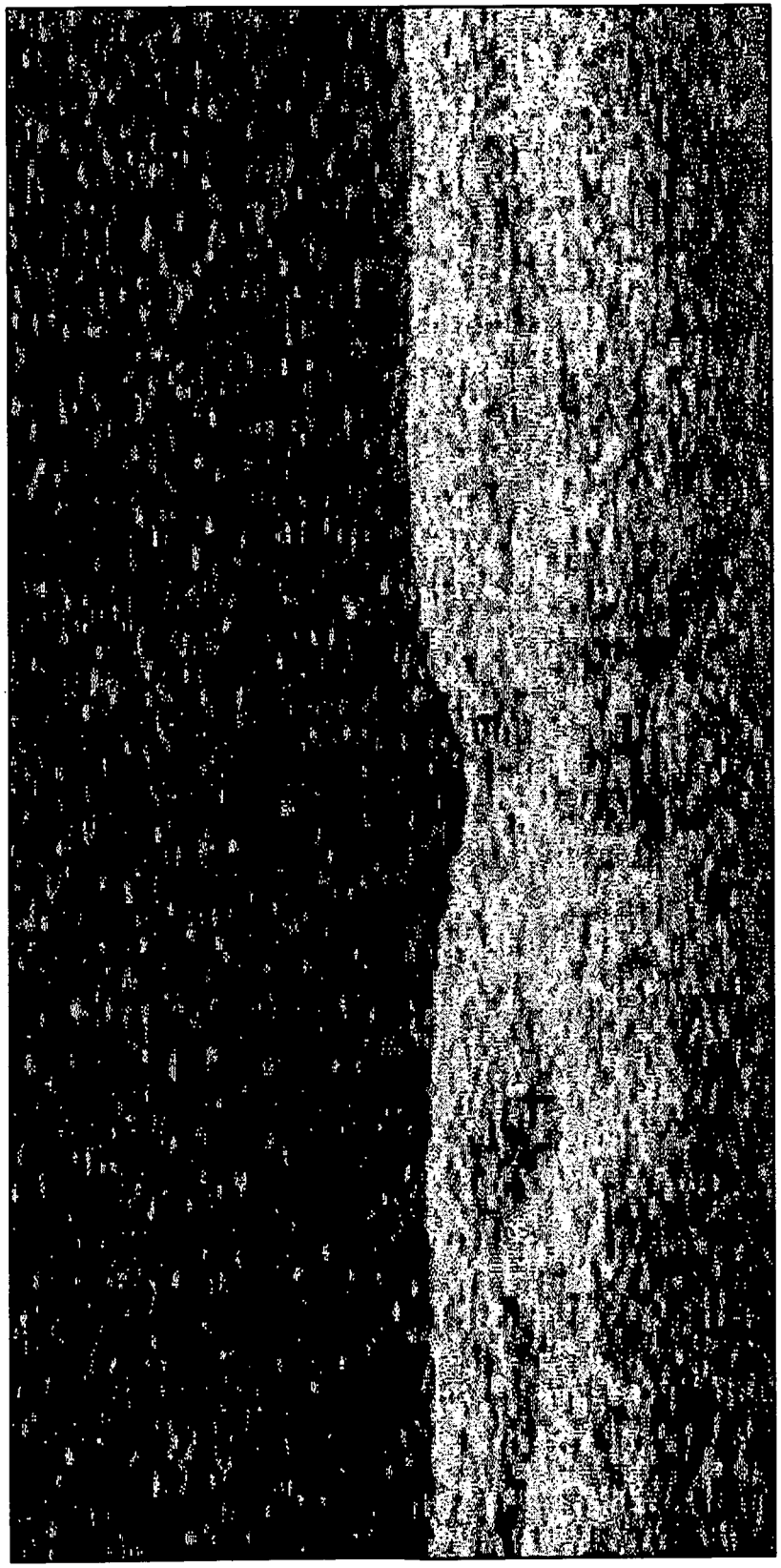
Figure 11:
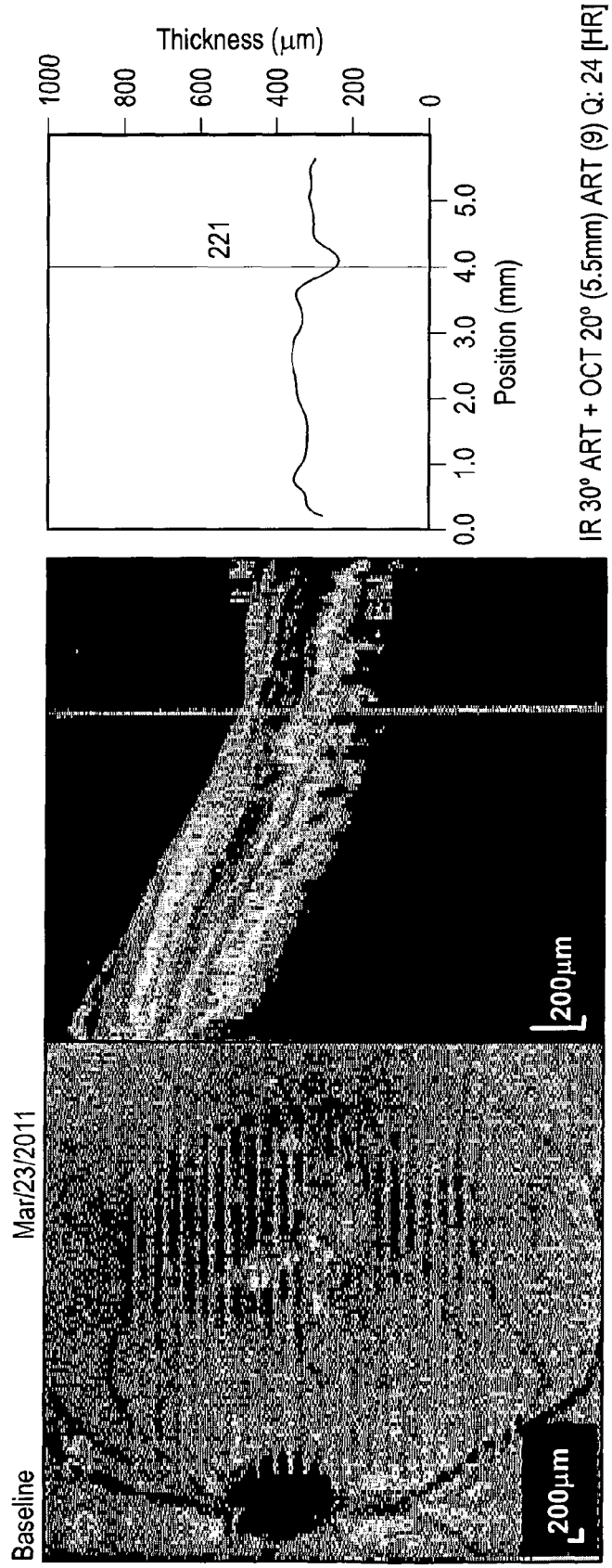
Figure 11:
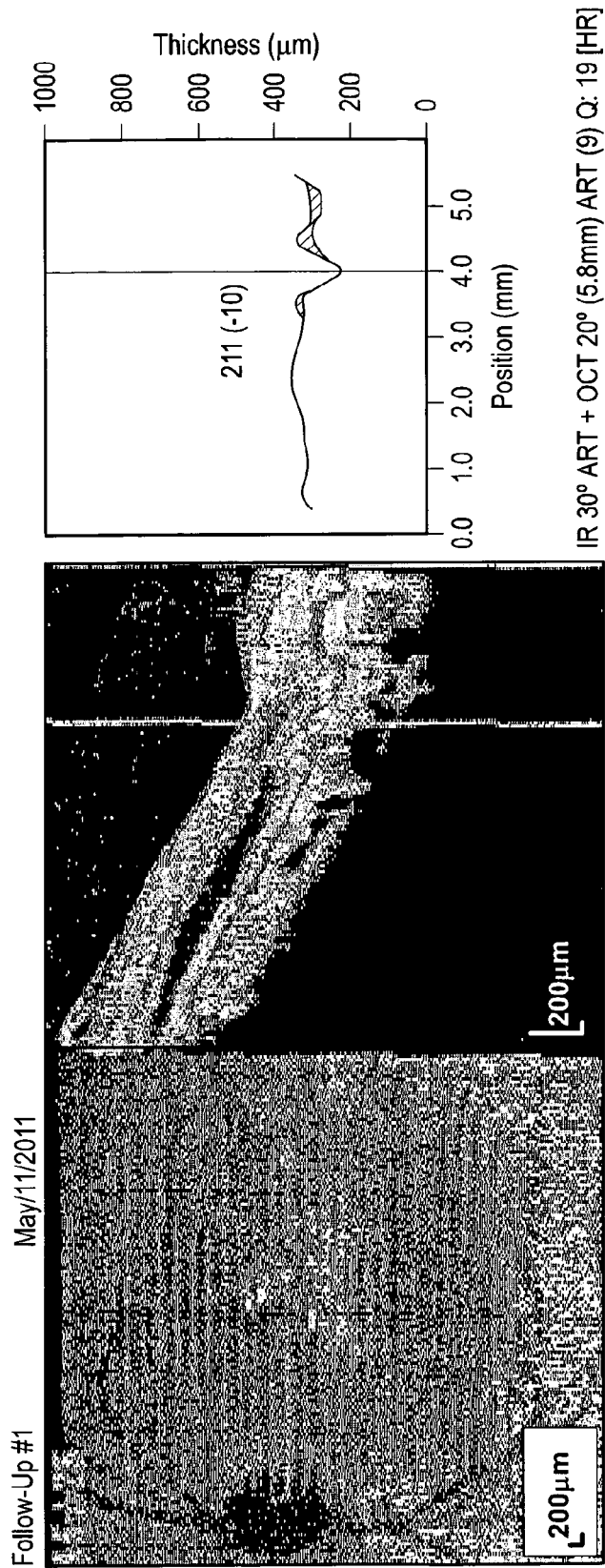

Case i)
67 year old man presented in 2008 initially with left wet AMD and then with right wet AMD. He had more than twelve intravitreal Avastin injections in each eye. In March 2010 he was started with Omega 3RX®. Two months following treatment there was no fluid in the right eye and gained one line of vision. Four months following treatment there was no fluid in the left eye and he gained three lines of vision (FIG. 11).

Figure 12:
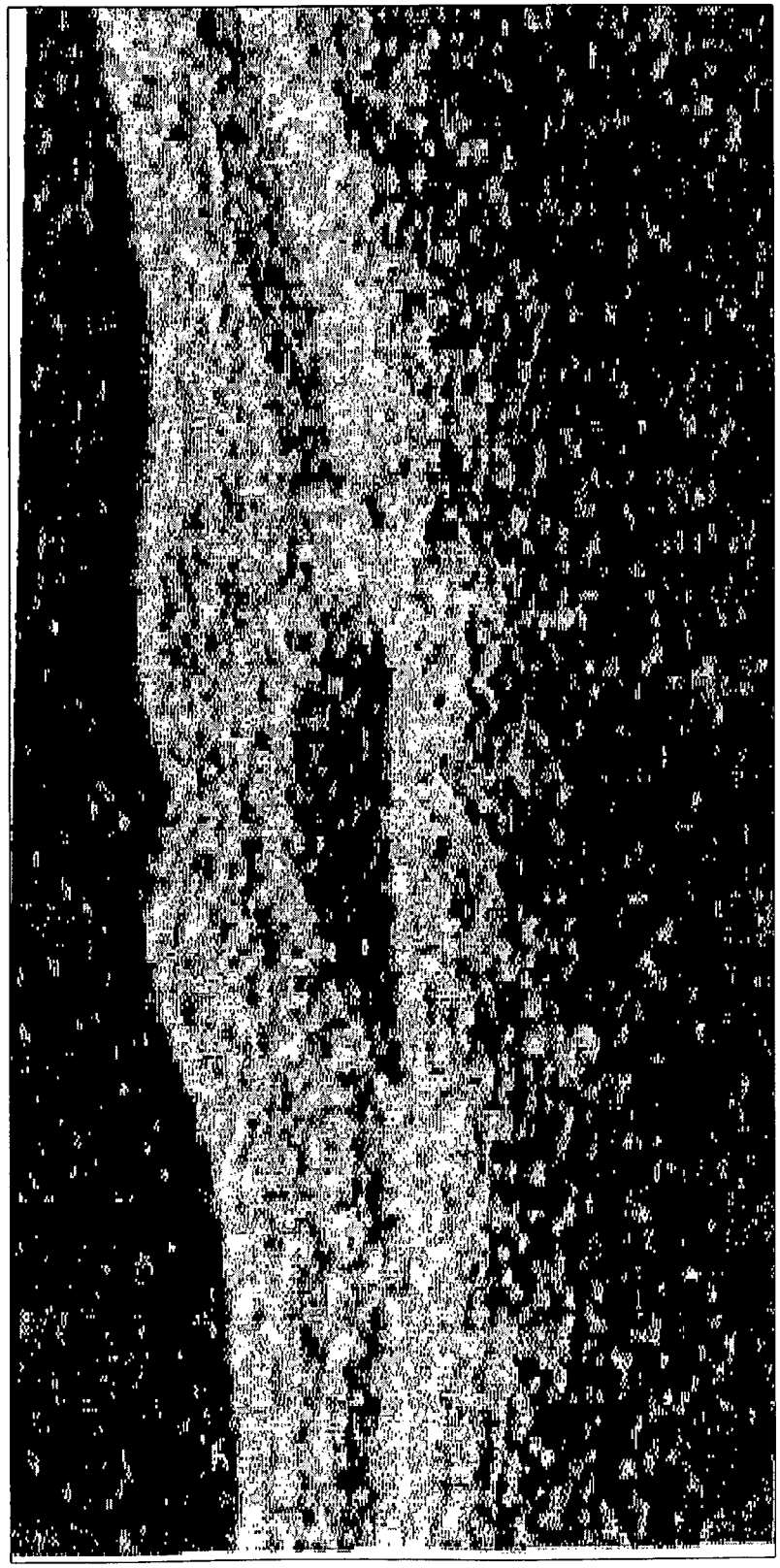
Figure 12:
Figure 12:
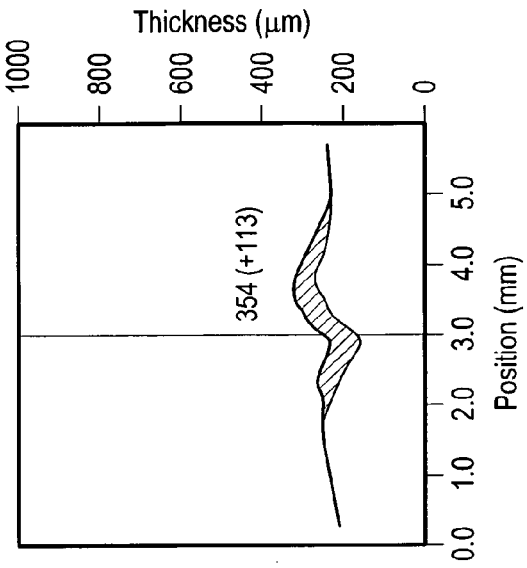
Figure 12:
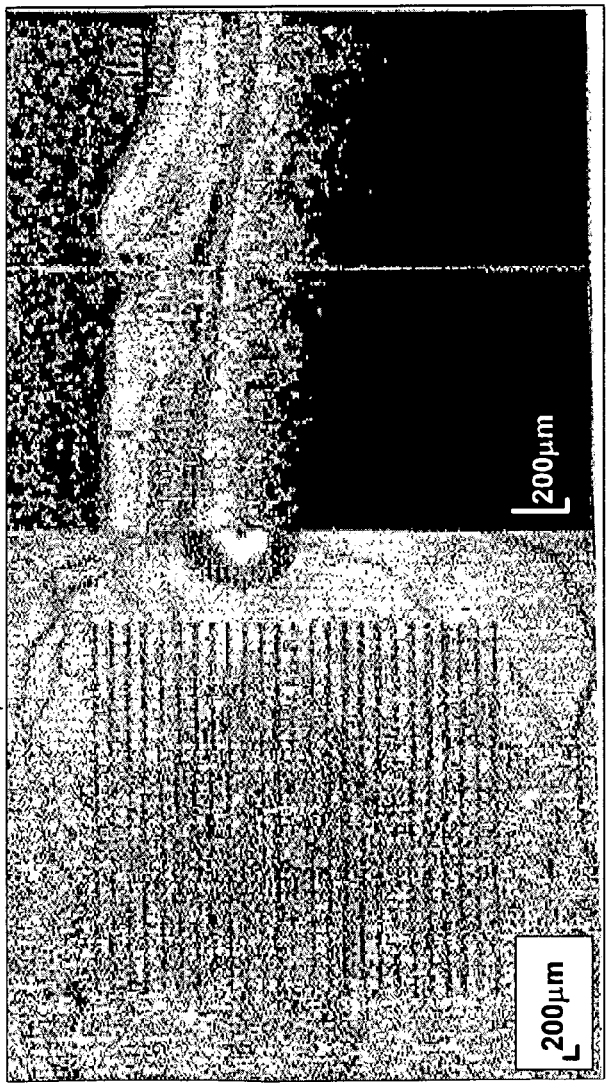
Figure 12:
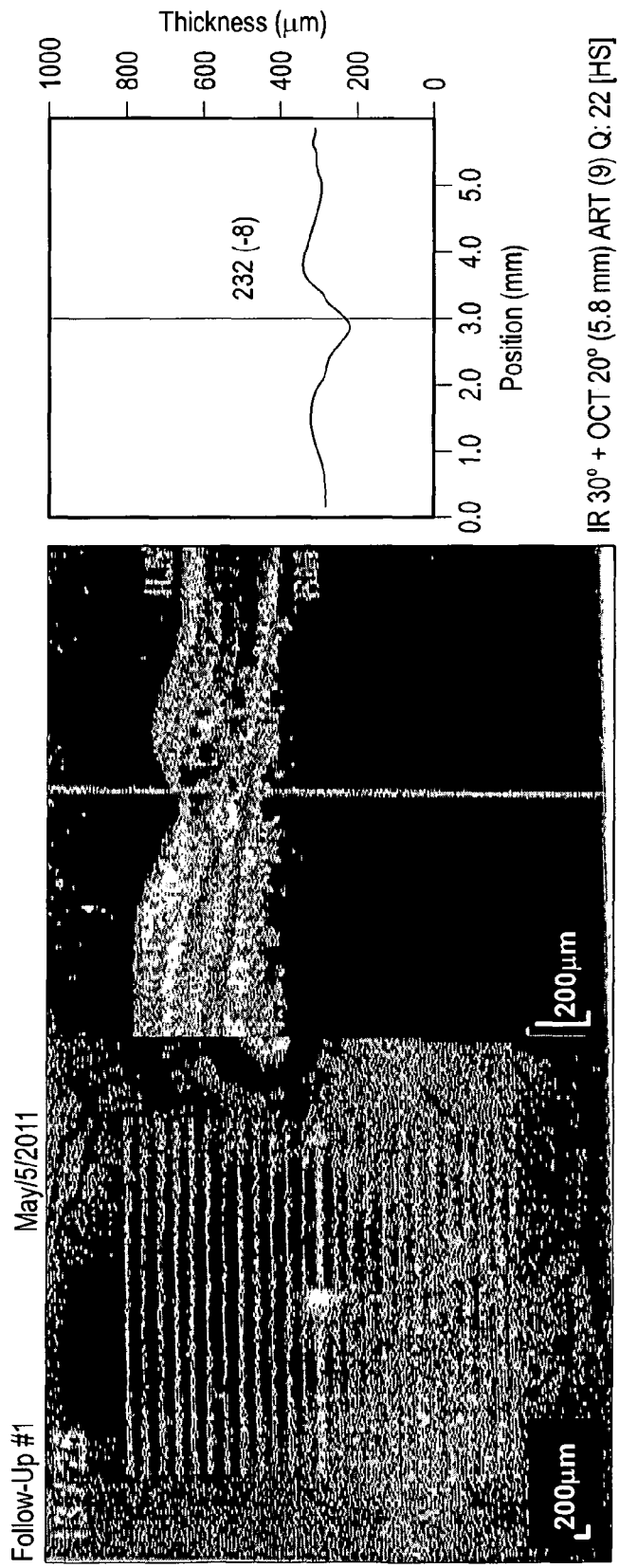
Figure 12:
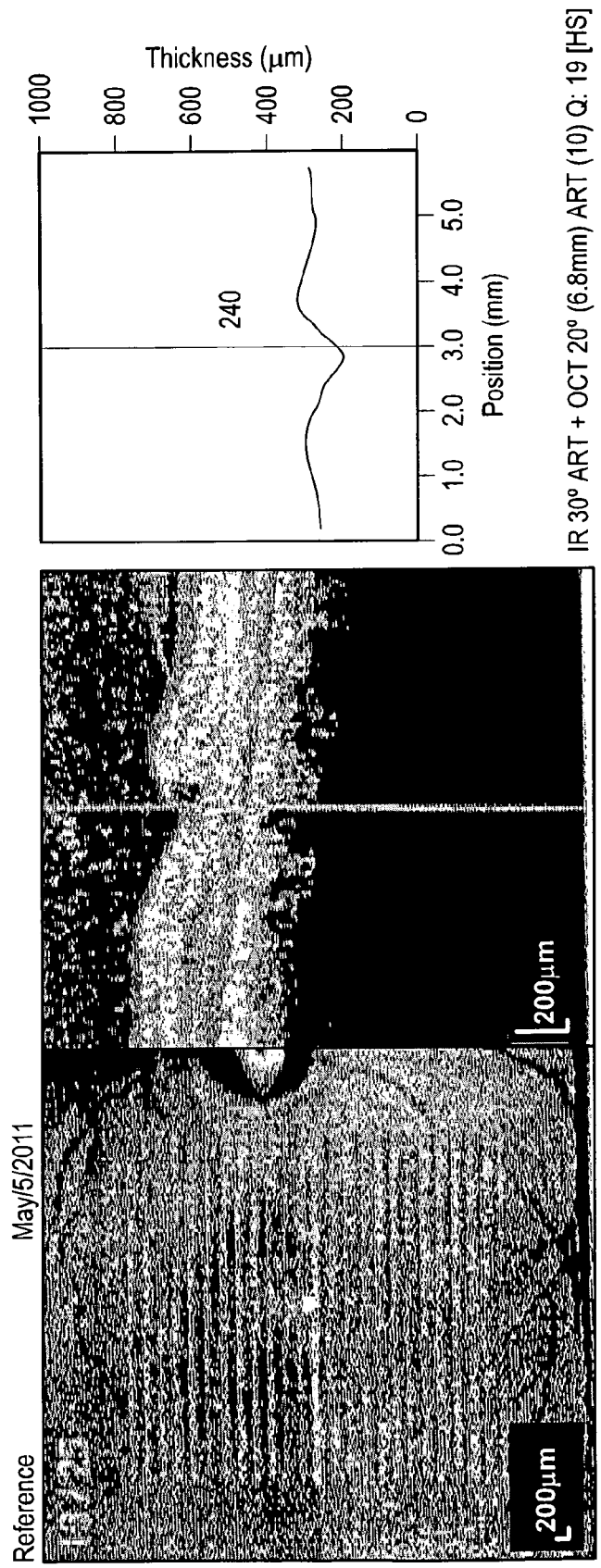
Figure 12:
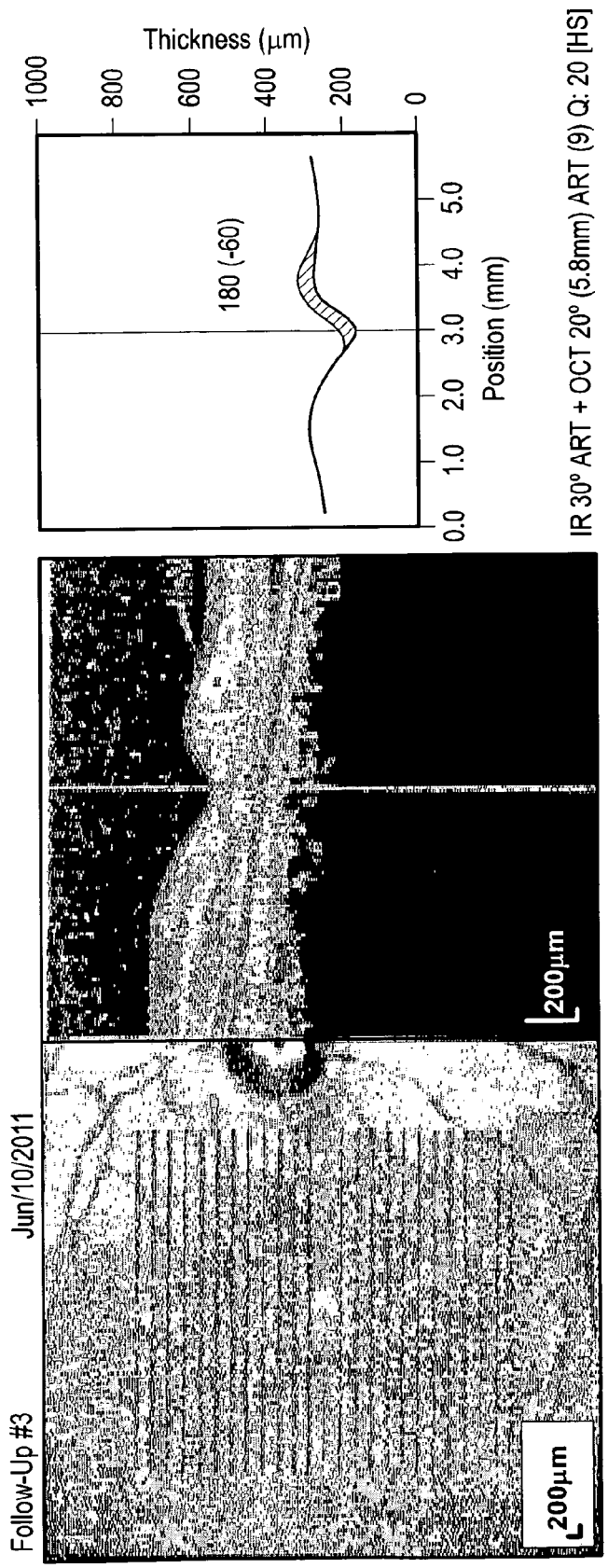
Figure 12:
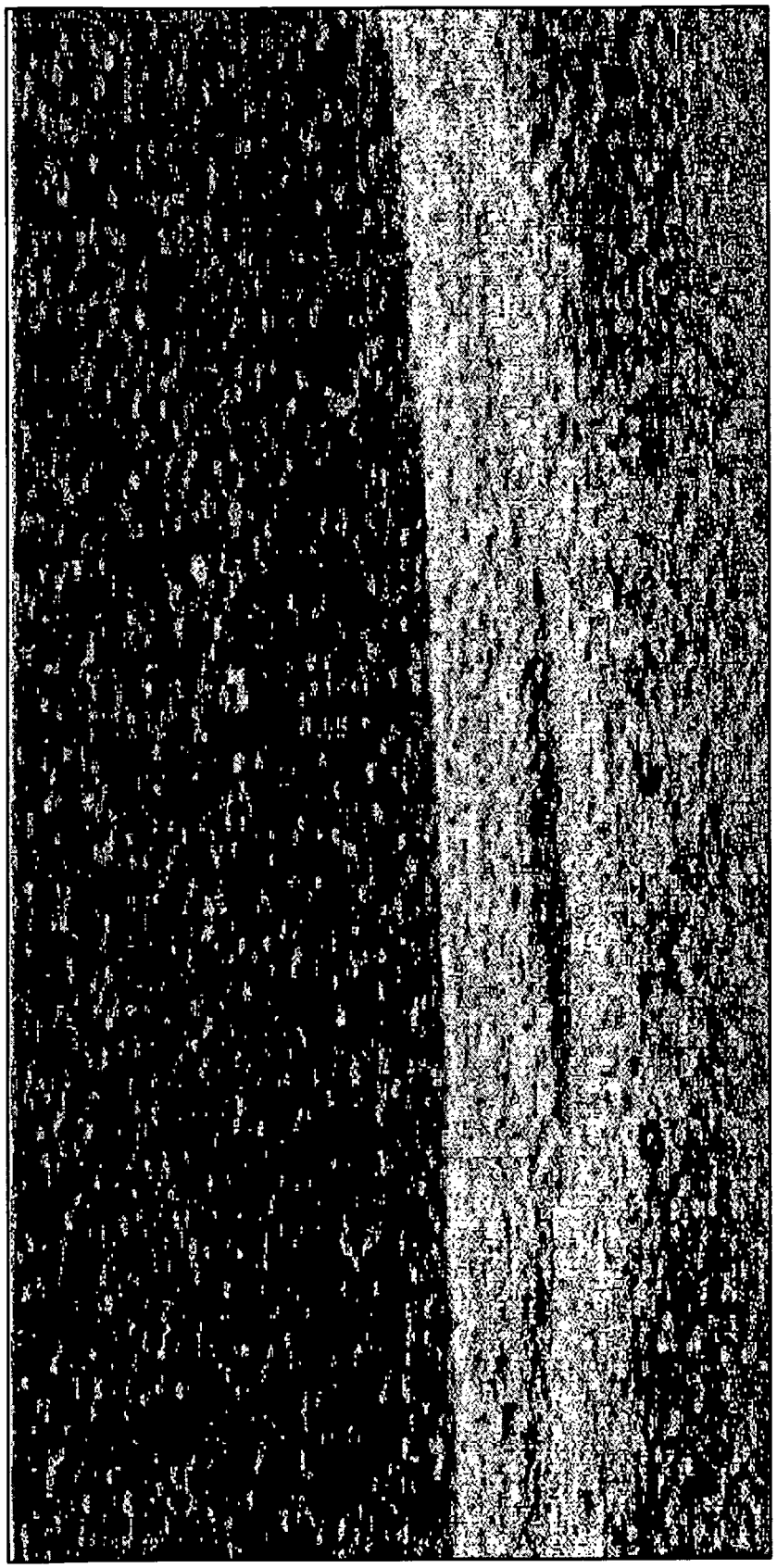
Figure 12:
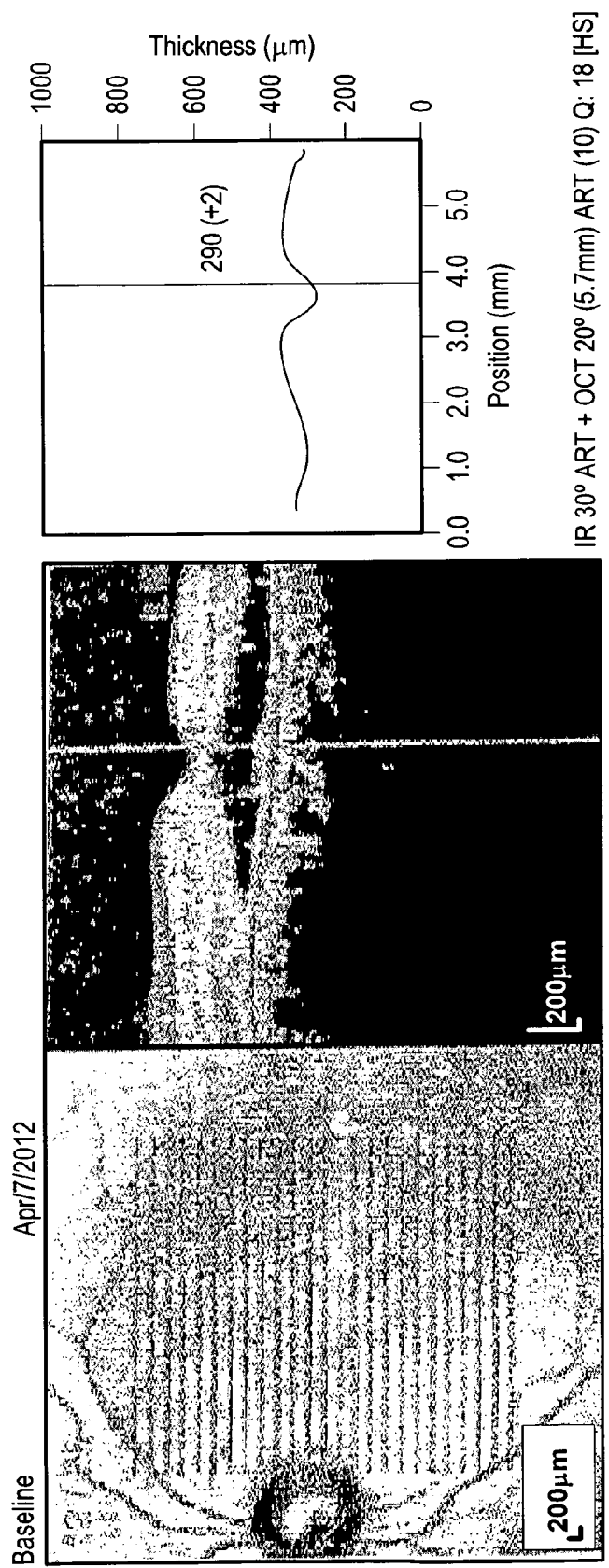
Figure 12:
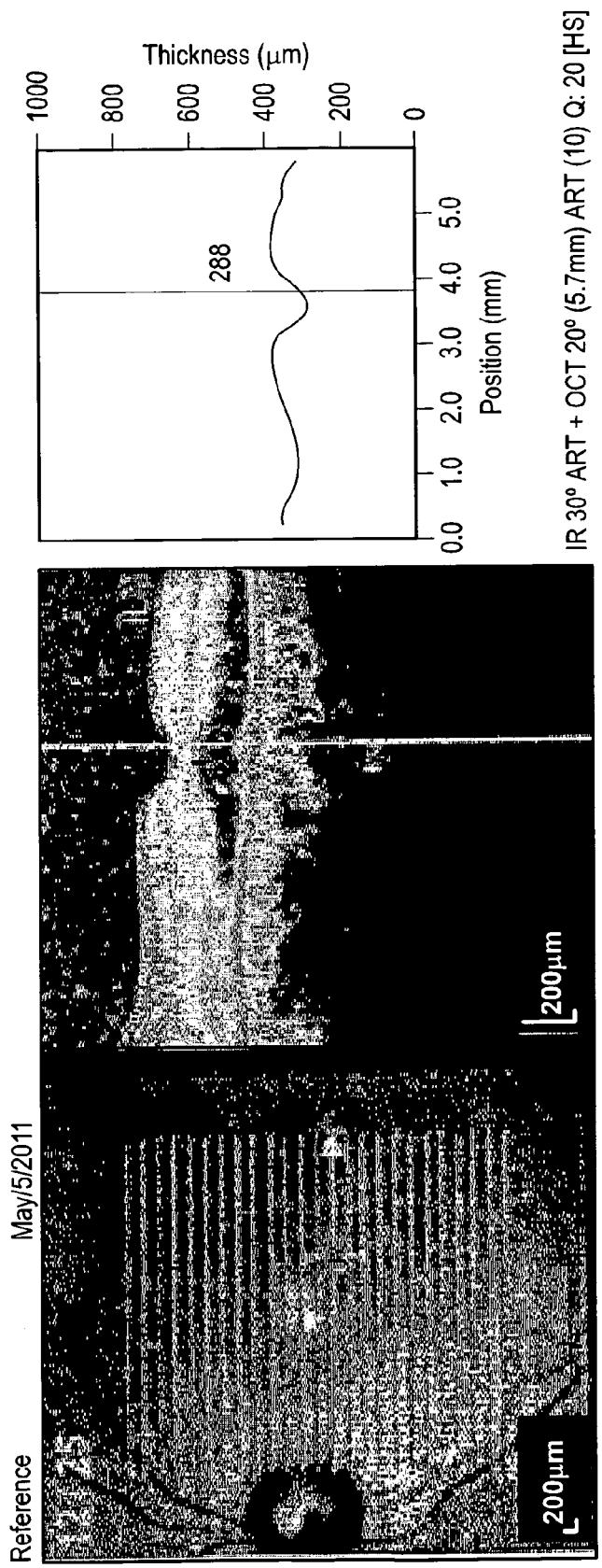
Figure 12:
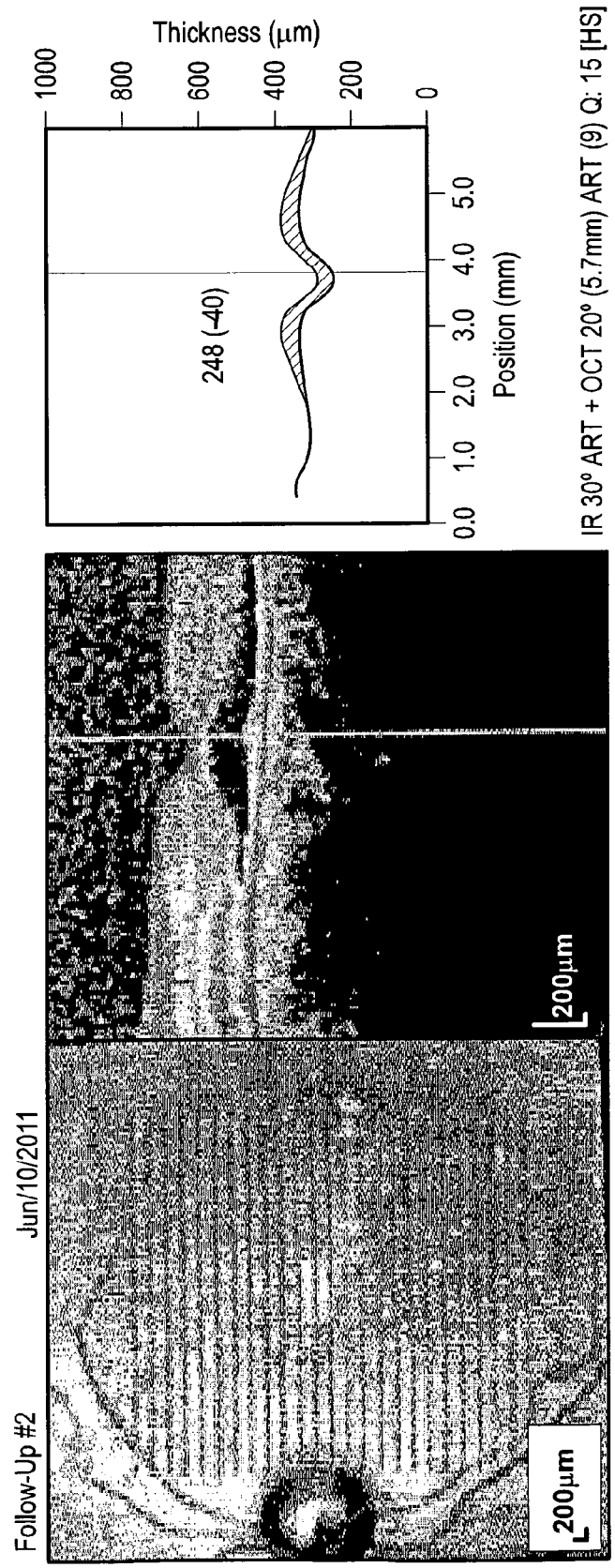

Case j)
74 year old man presented with left wet AMD in 2008 and right AMD at the end of 2008. He had more than fifteen intravitreal Lucentis injections in each eye. He started on Omega 3RX® on 1.2.11. Four months following treatment there was no fluid on the right eye and he gained one line of vision. In the left eye there was minimal fluid and his vision was stable (FIG. 12).

Figure 13:
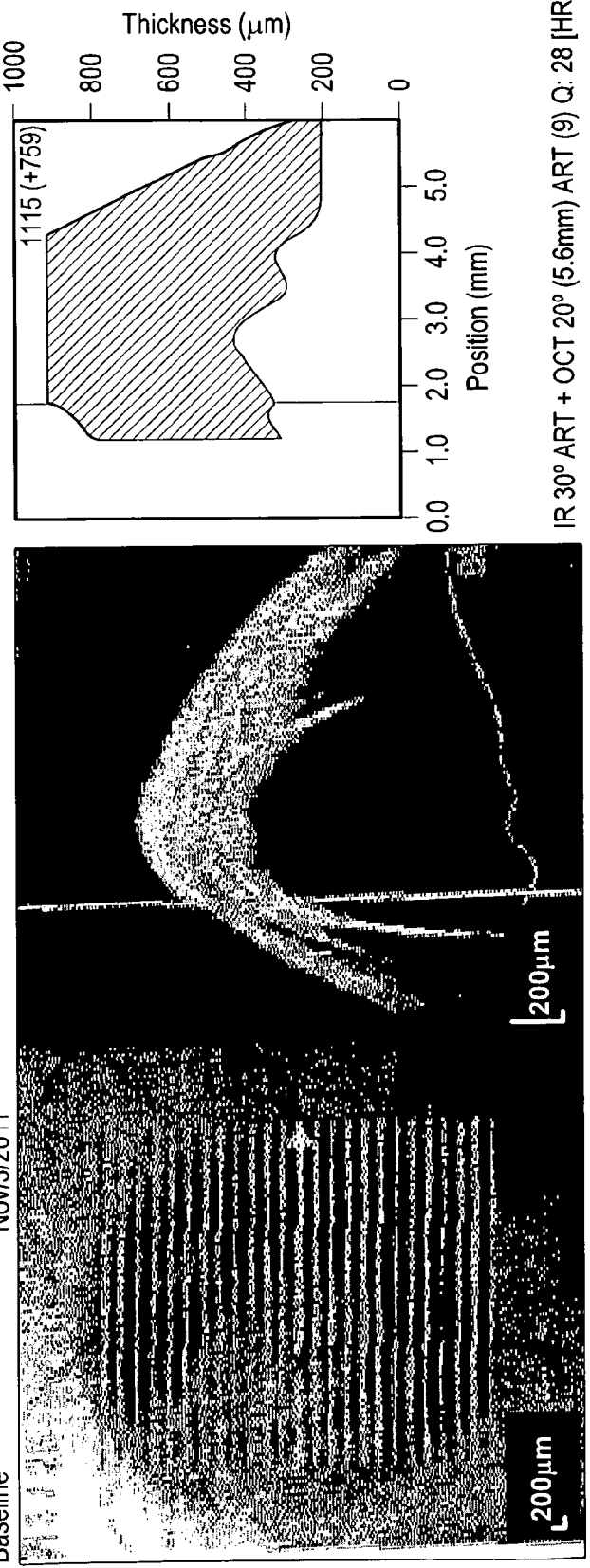
Figure 13:
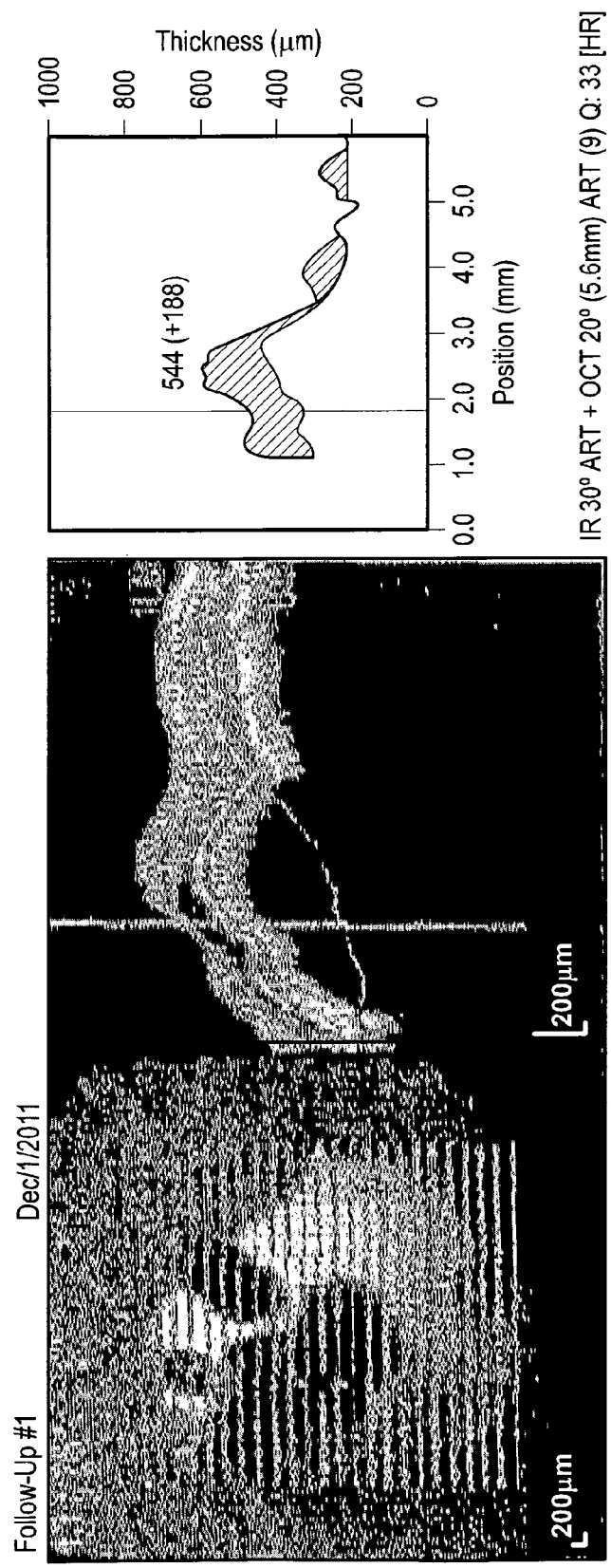
Figure 13:
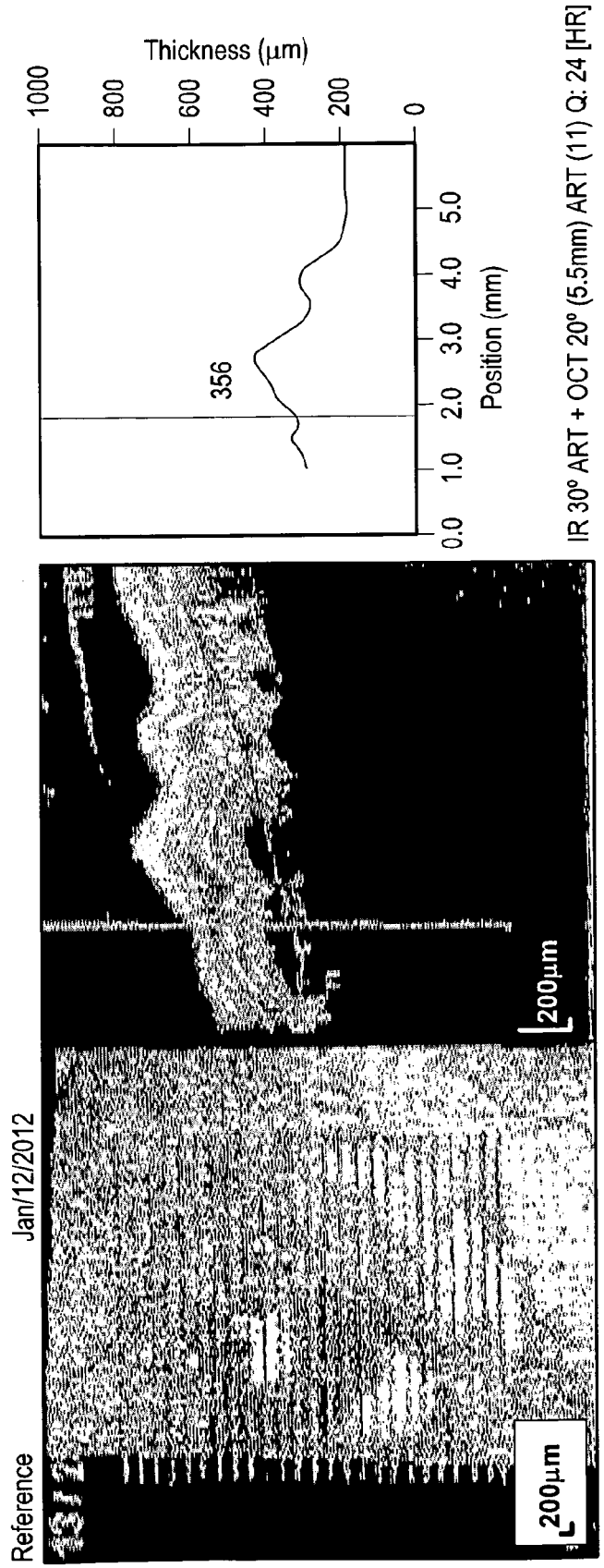
Figure 13:
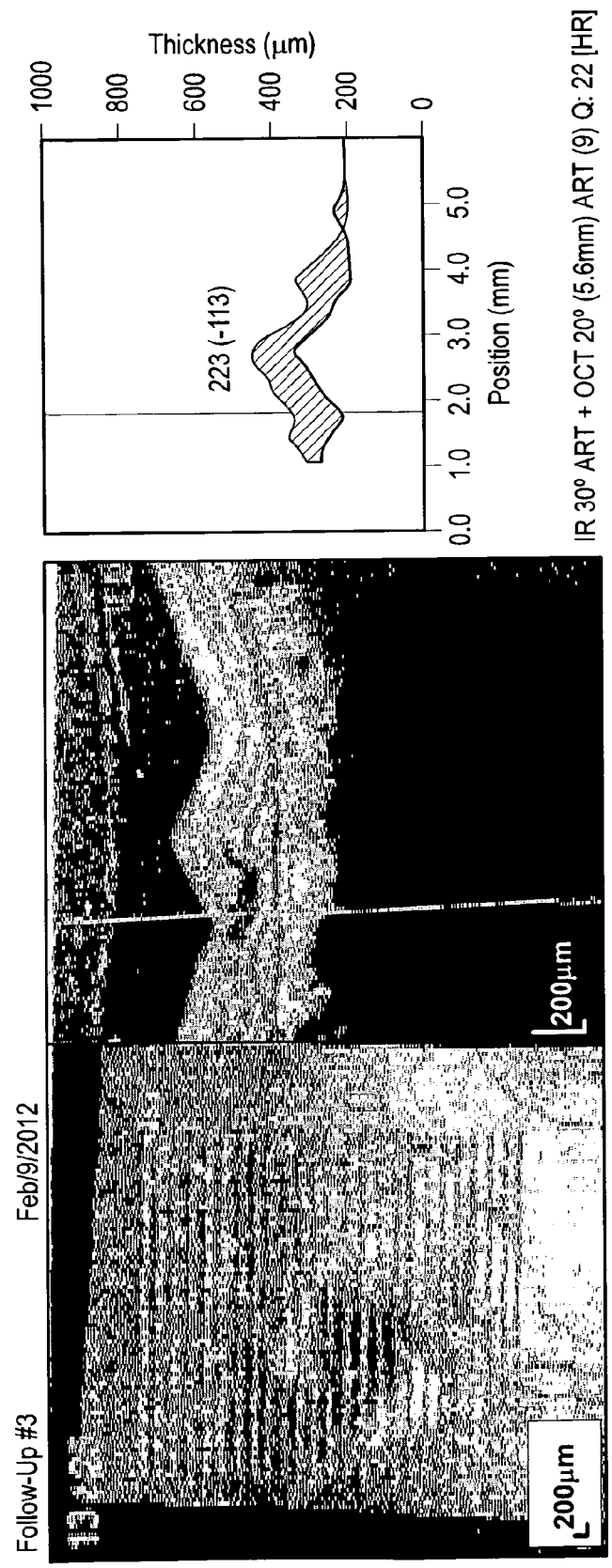
Figure 13:
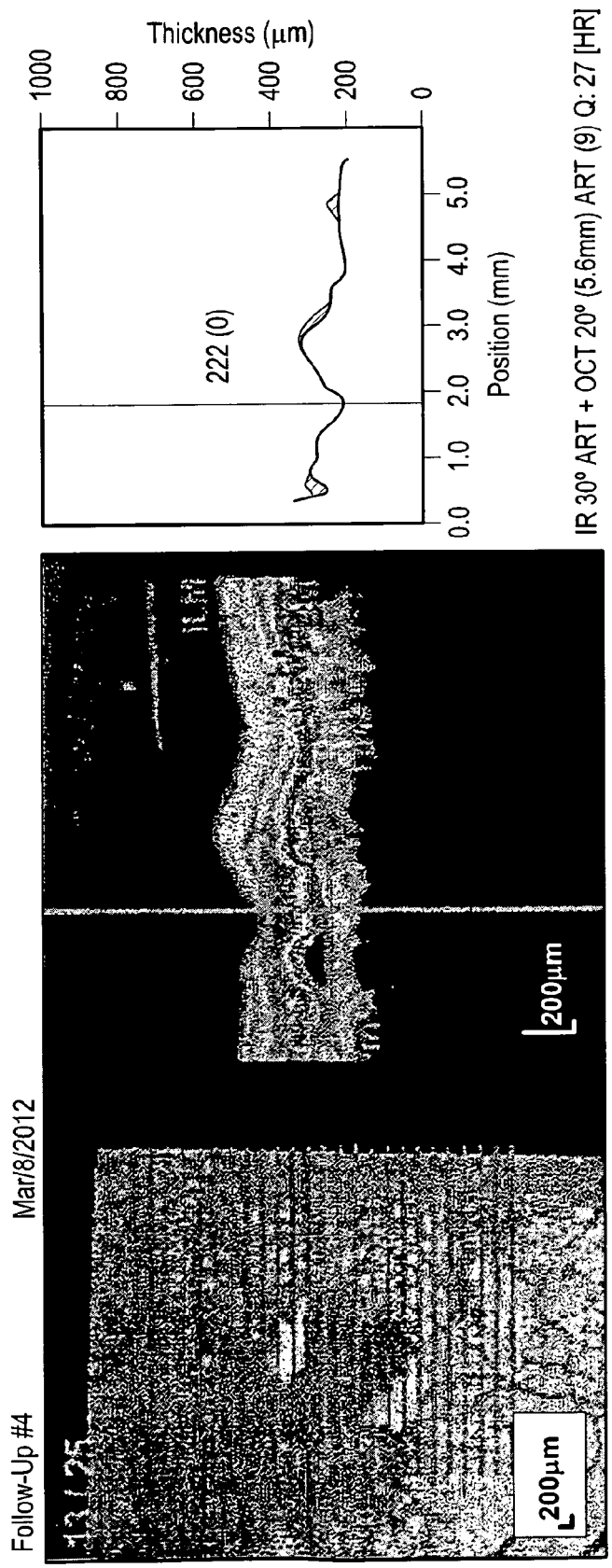
Figure 13:
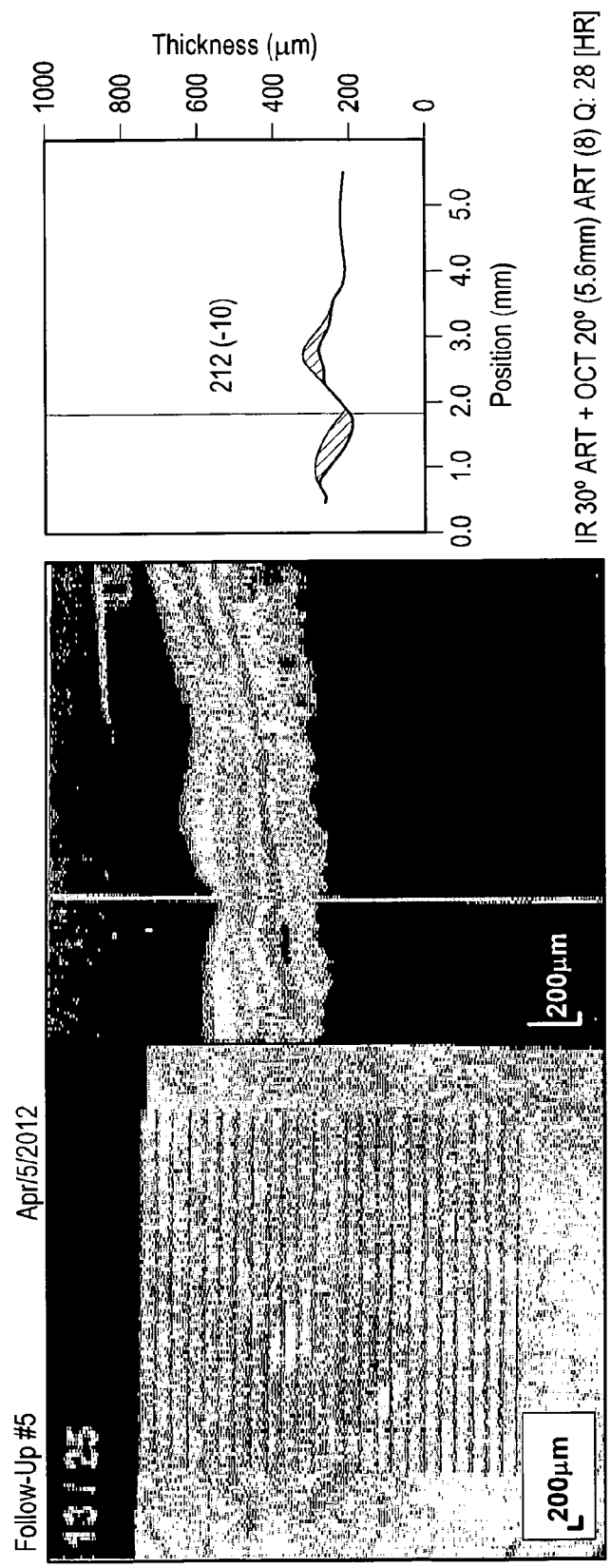

Case k)
71 year old man presented with left wet AMD on Nov. 3, 2011. He was treated with three intravitreal Avastin injections. His last injection was on 12.1.12 and was also started on Omega 3RX®. Three months following treatment the fluid nearly resolved and he gained one line of vision since the treatment of Omega 3RX® (FIG. 13).

Figure 14:
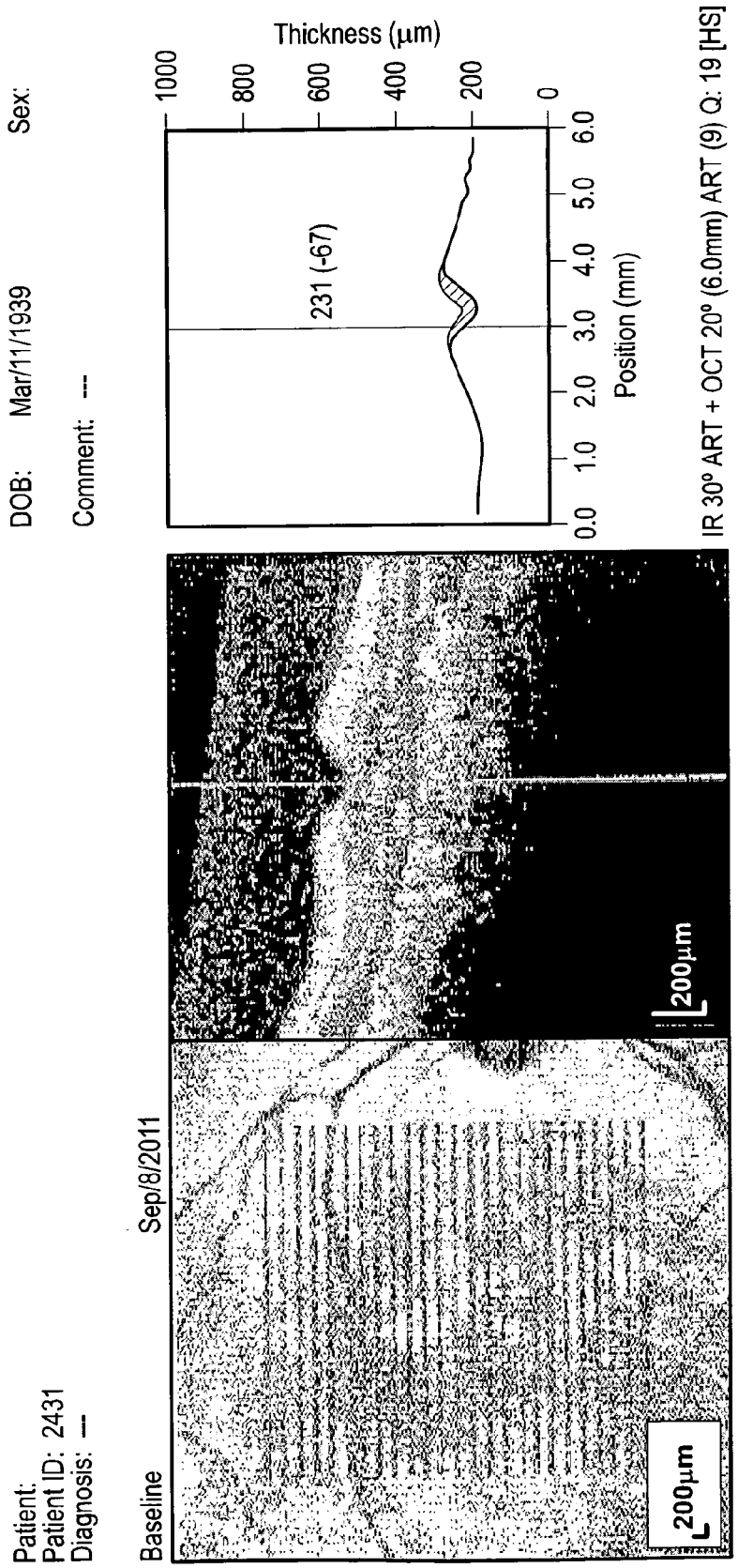
Figure 14:
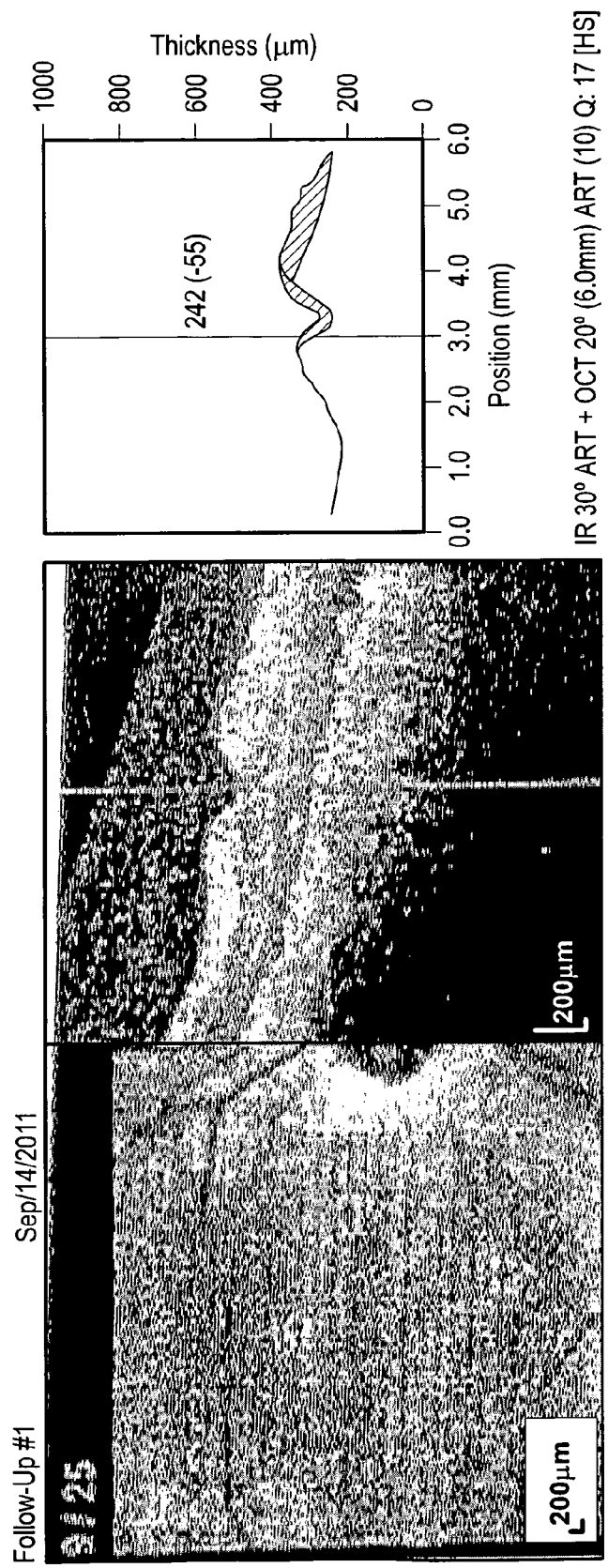
Figure 14:
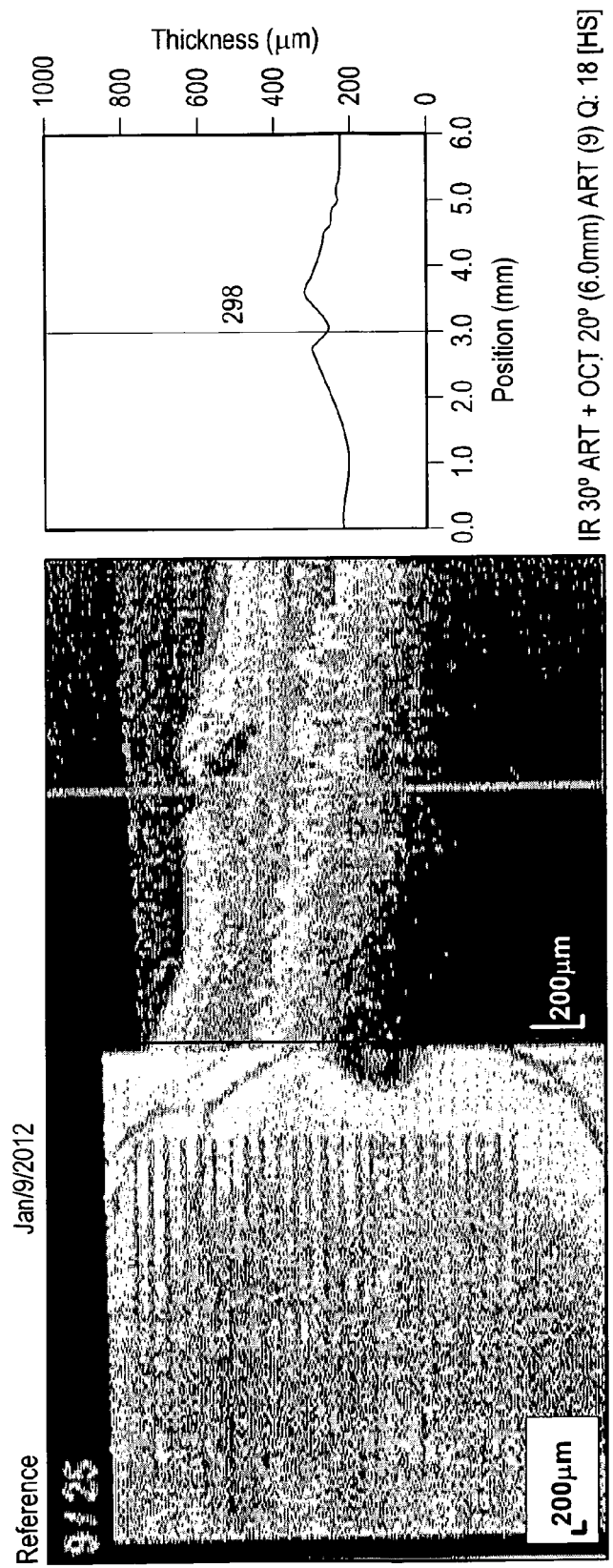
Figure 14:
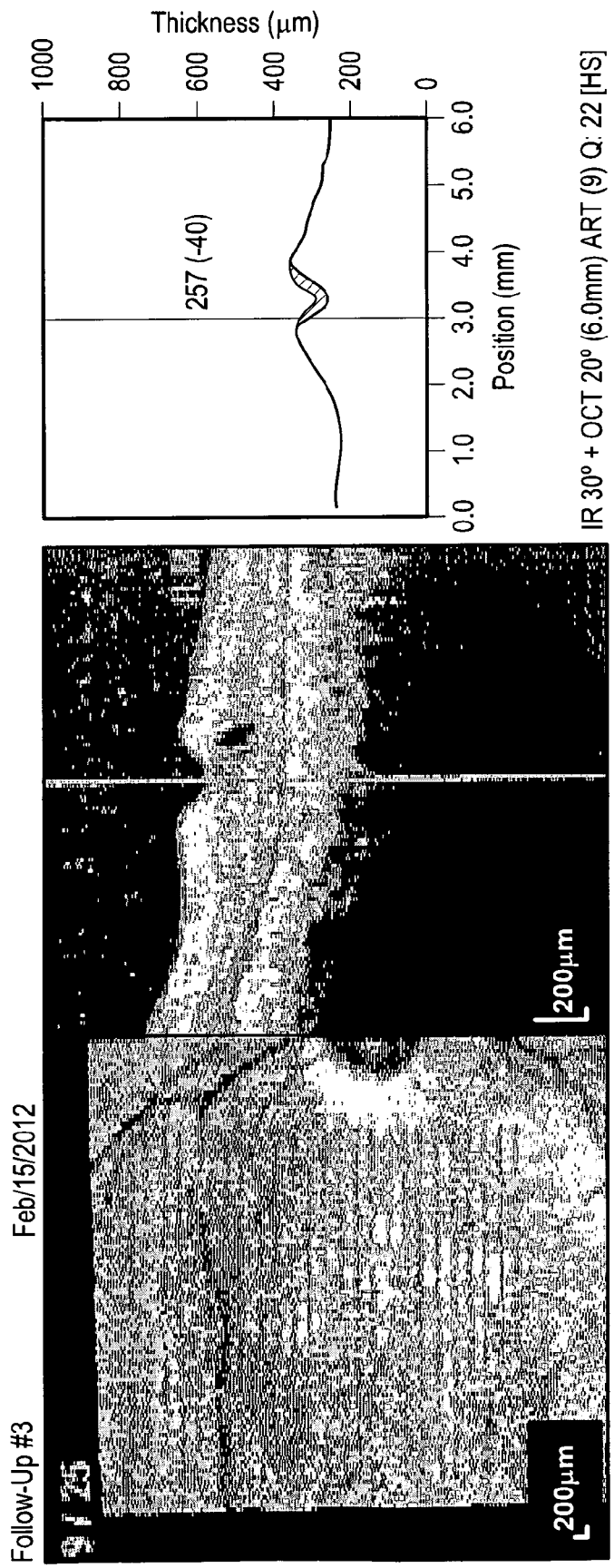
Figure 14:
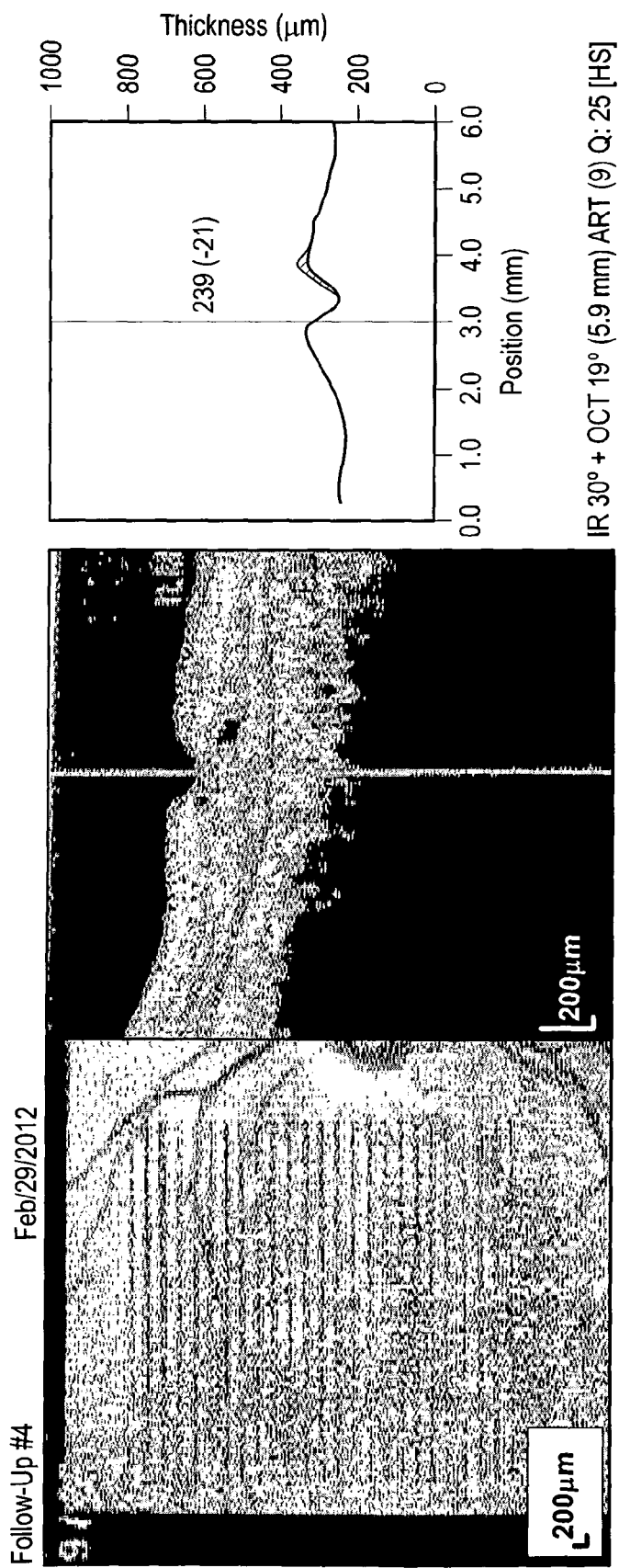

Case l)
72 year old man presented in 2008 with right wet AMD. He was treated with eight intravitreal Avastin injections the last one at the end of 2010. He presented on Jan. 9, 2012 with wet AMD and started on Omega 3RX®. Six weeks following treatment there was minimal fluid with one line vision gained (FIG. 14).

Figure 15:
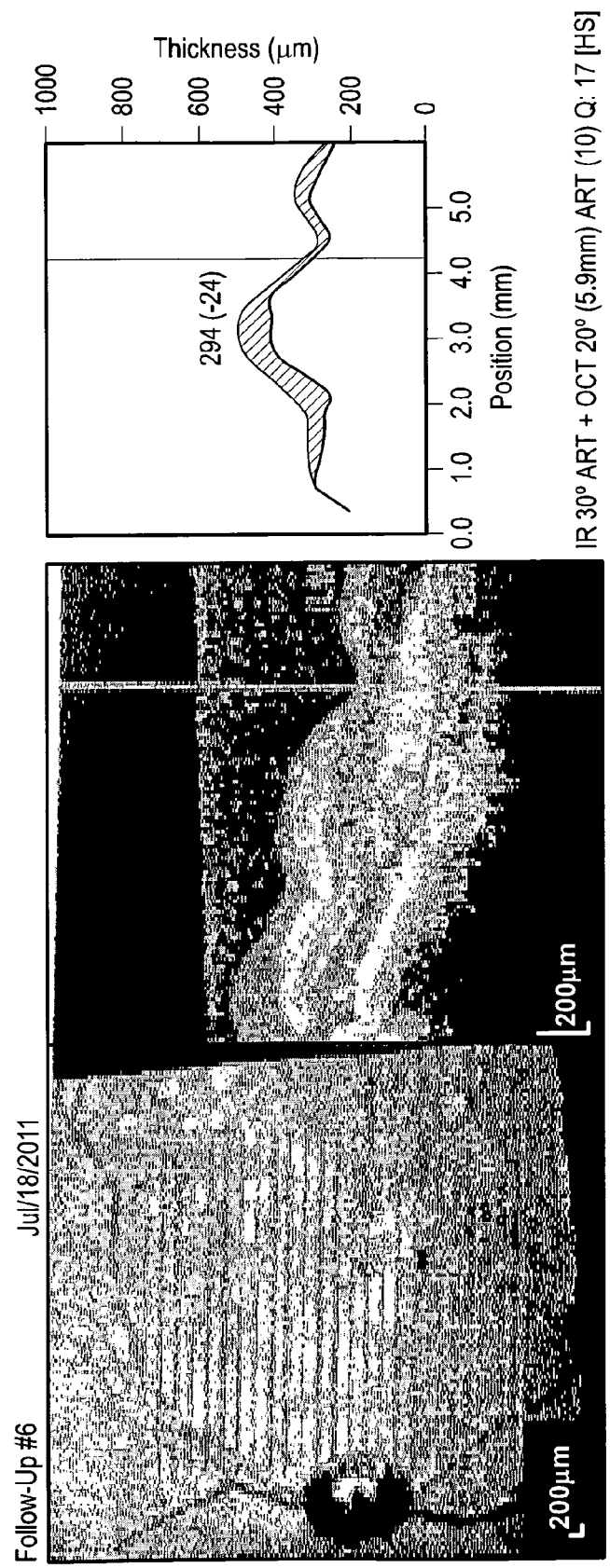
Figure 15:
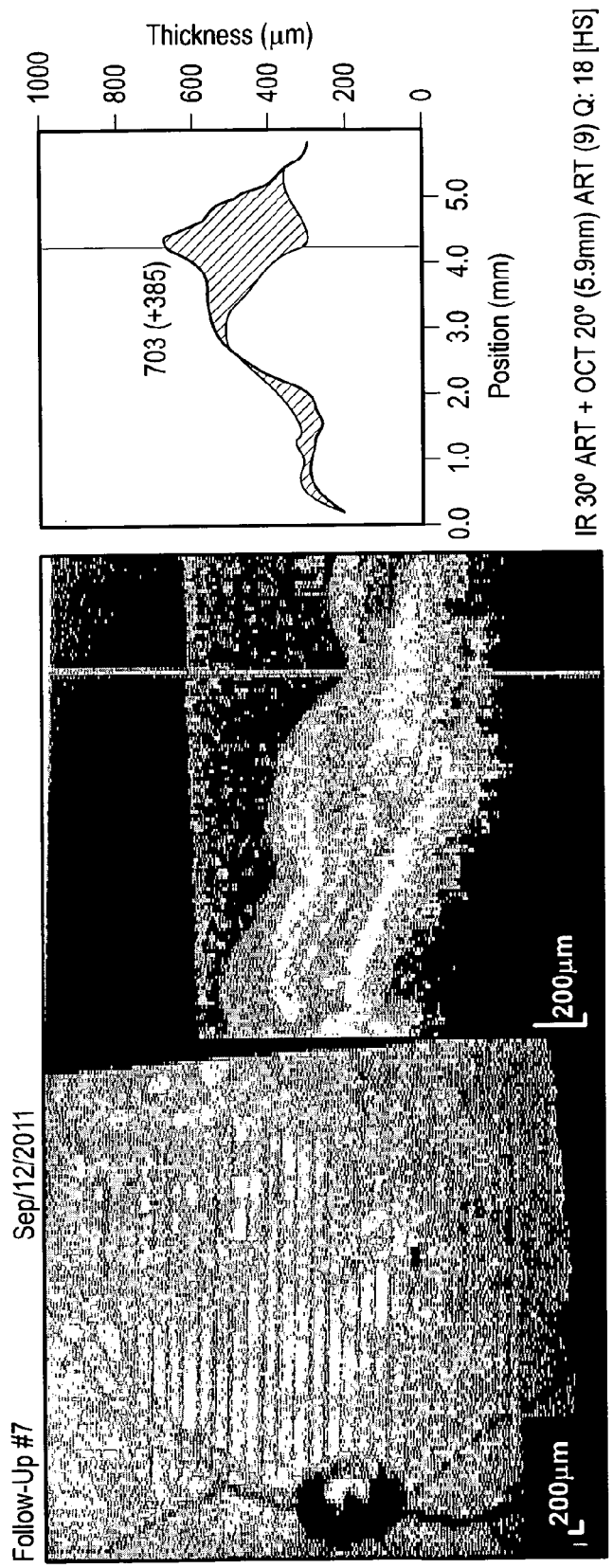
Figure 15:
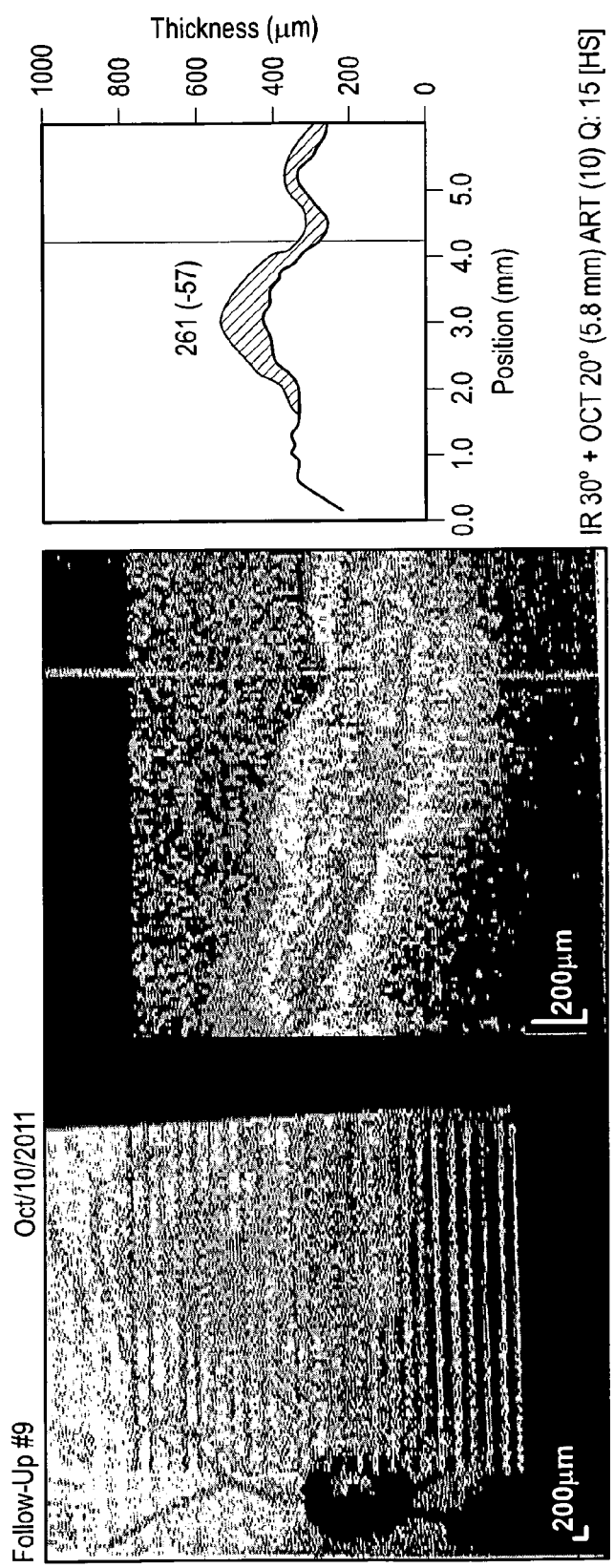
Figure 15:
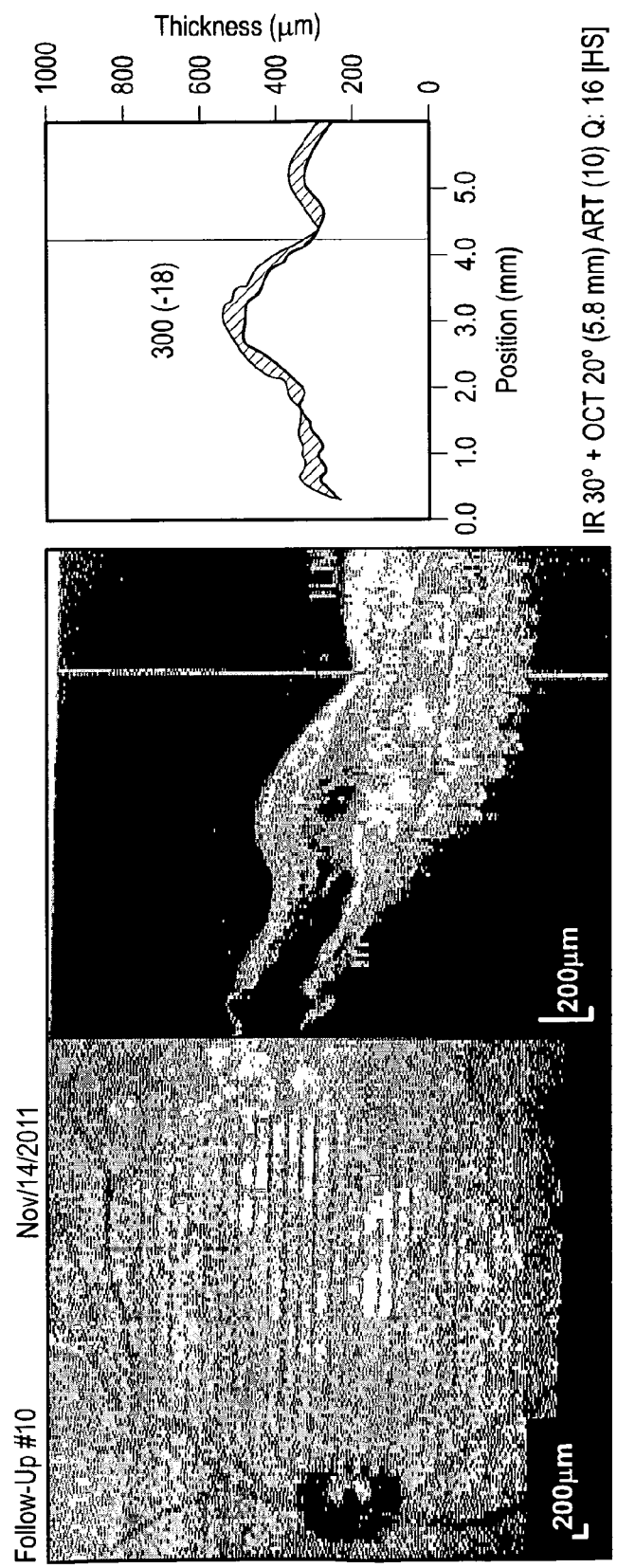
Figure 15:
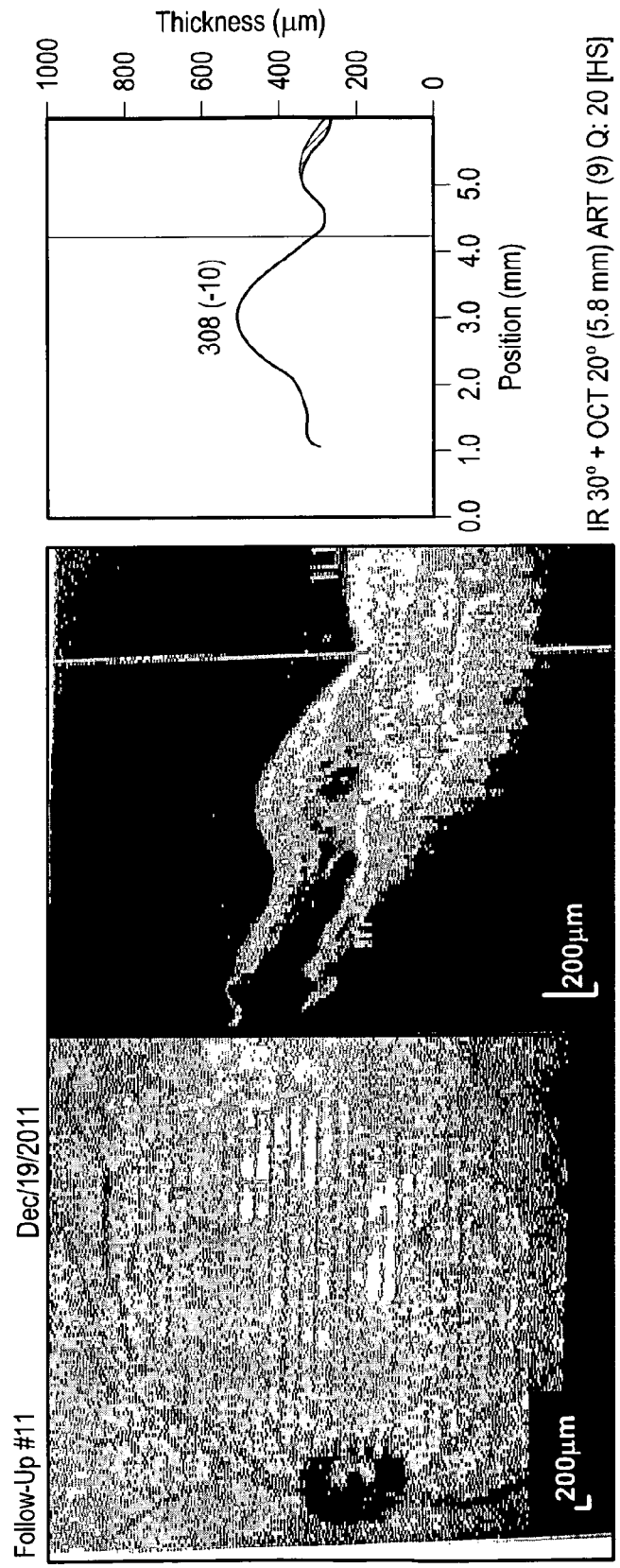
Figure 15:
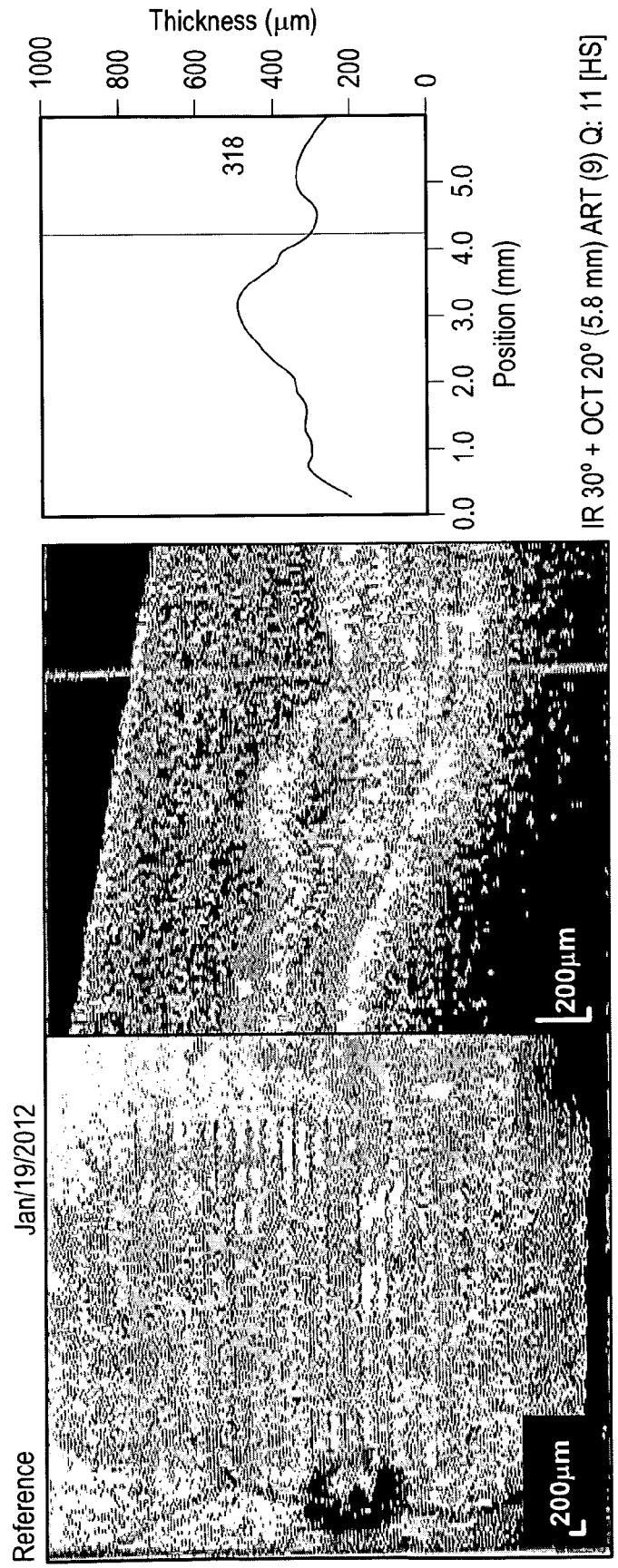
Figure 15:
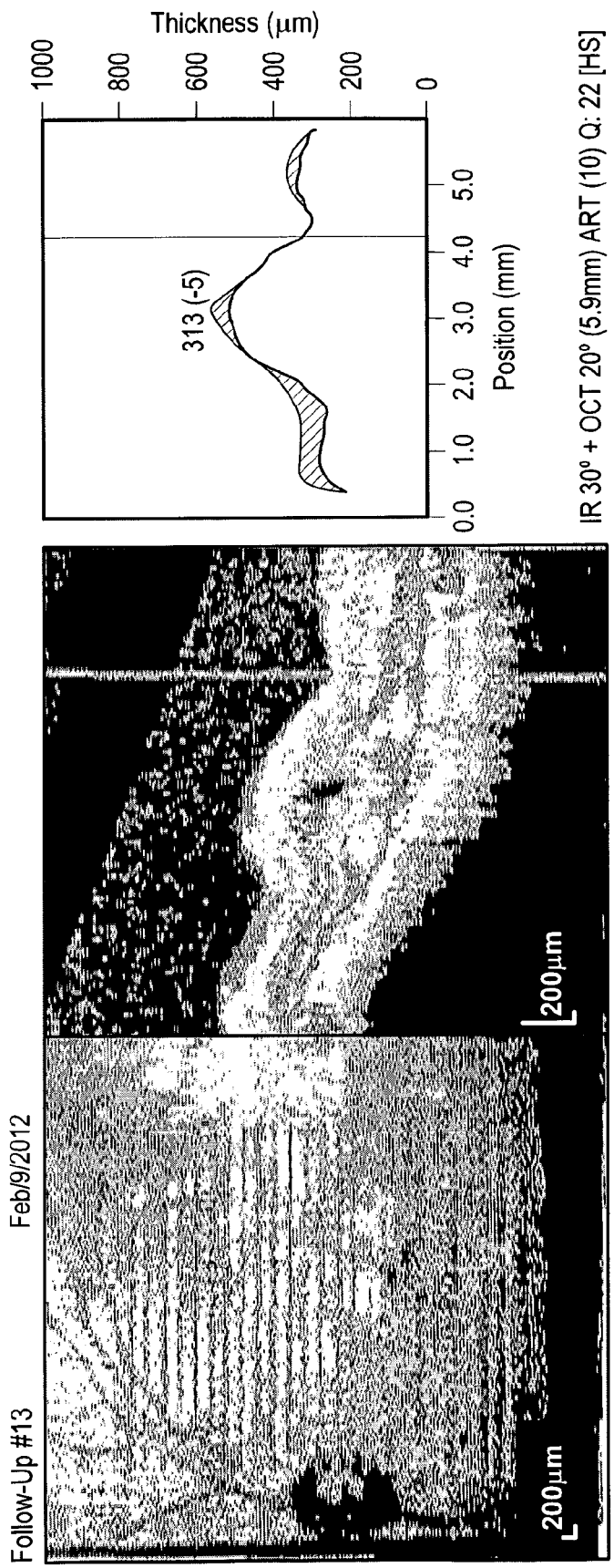

Case m)
74 year old man presented on 22.2.10 with left wet AMD. He was treated with six intravitreal Avastin injections. On Sep. 12, 2011 he had the last Avastin injection and started on Omega 3RX®. A month following treatment there was no fluid on OCT scan and he gained two lines of vision (FIG. 15).

Figure 16:
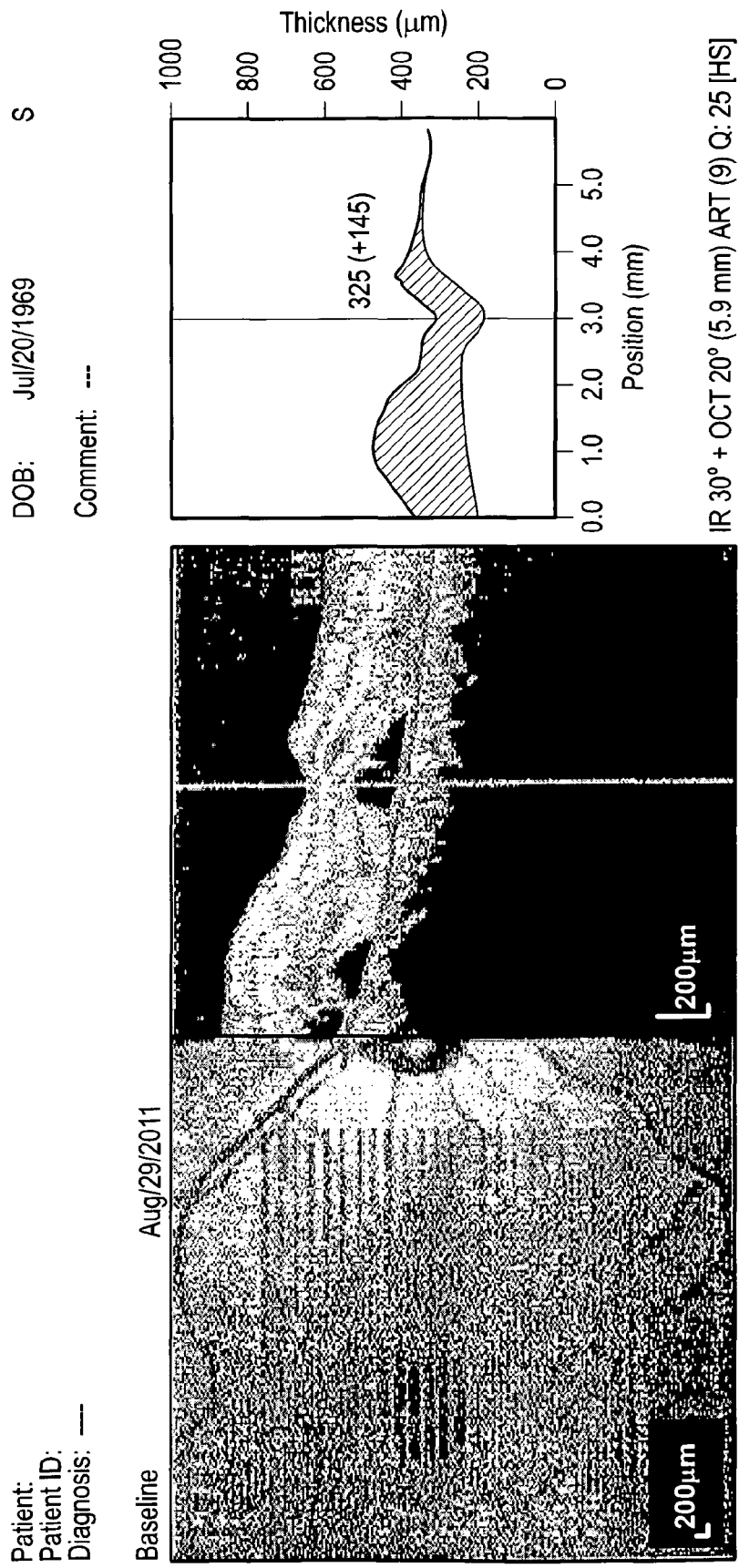
Figure 16:
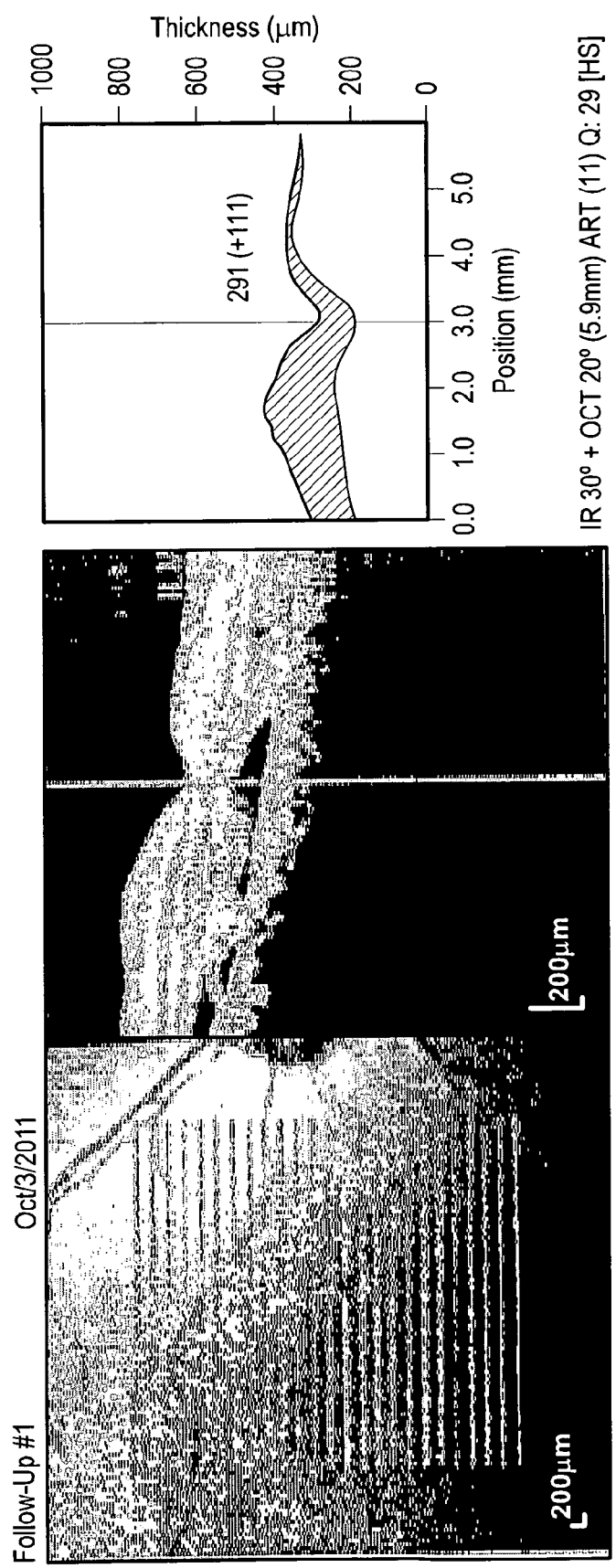
Figure 16:
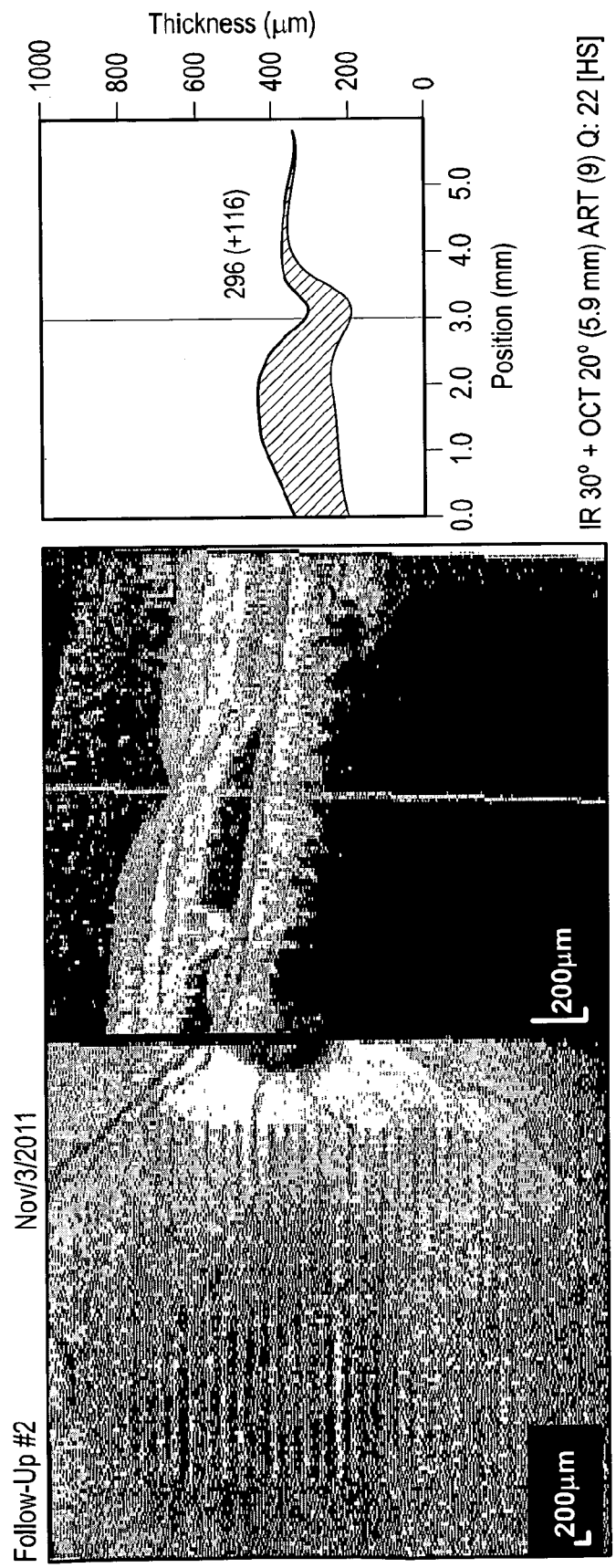
Figure 16:
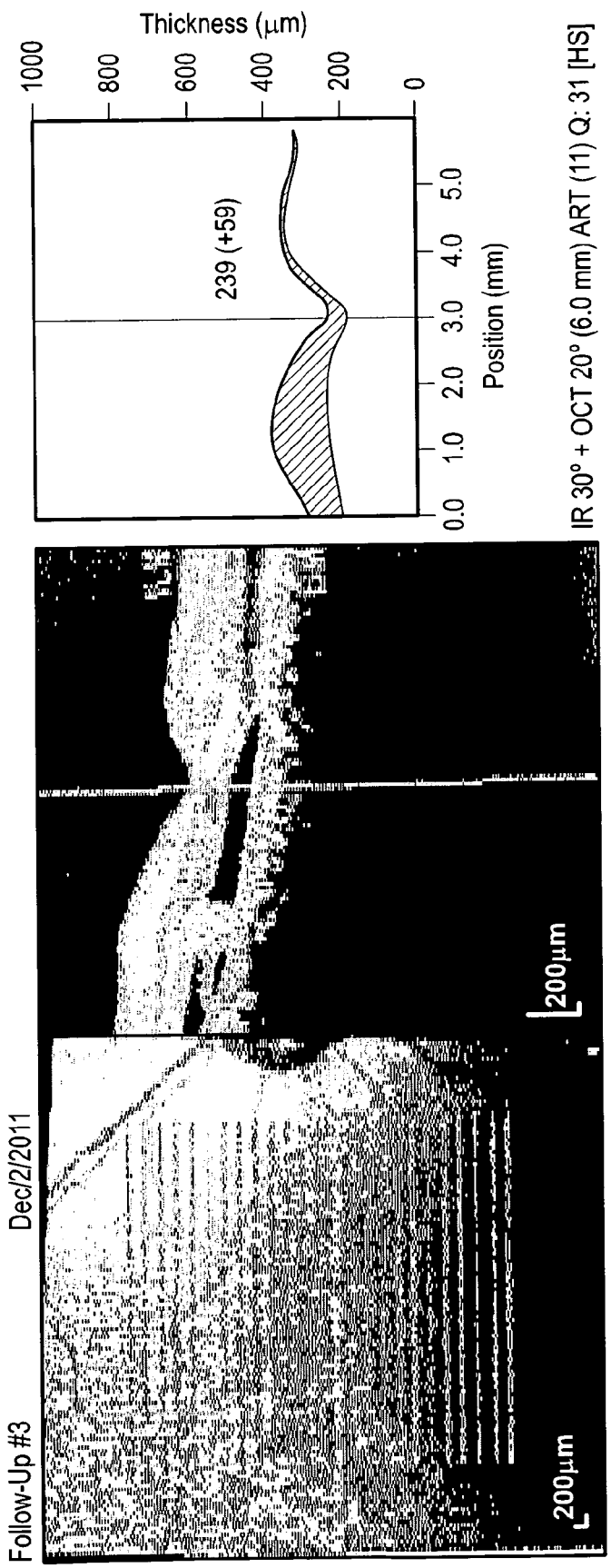
Figure 16:
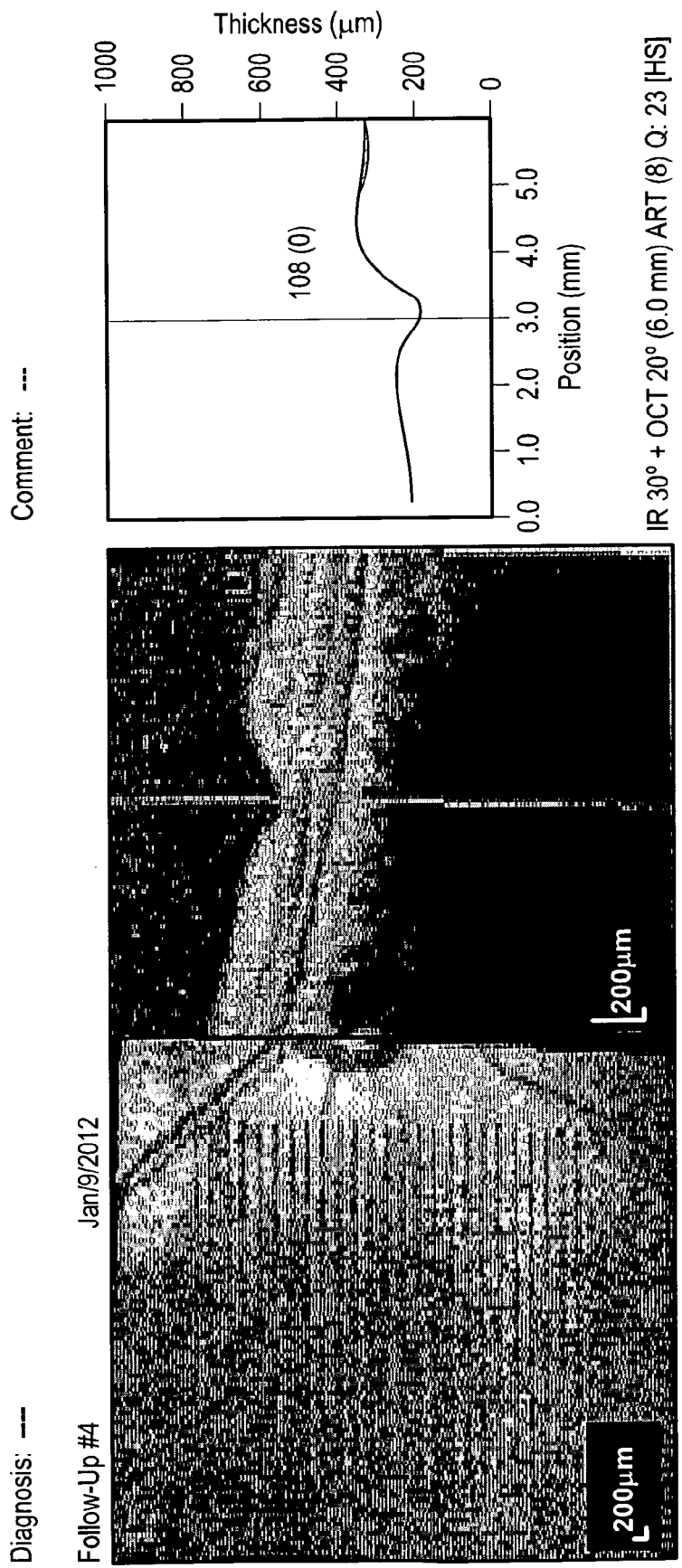
Figure 16:
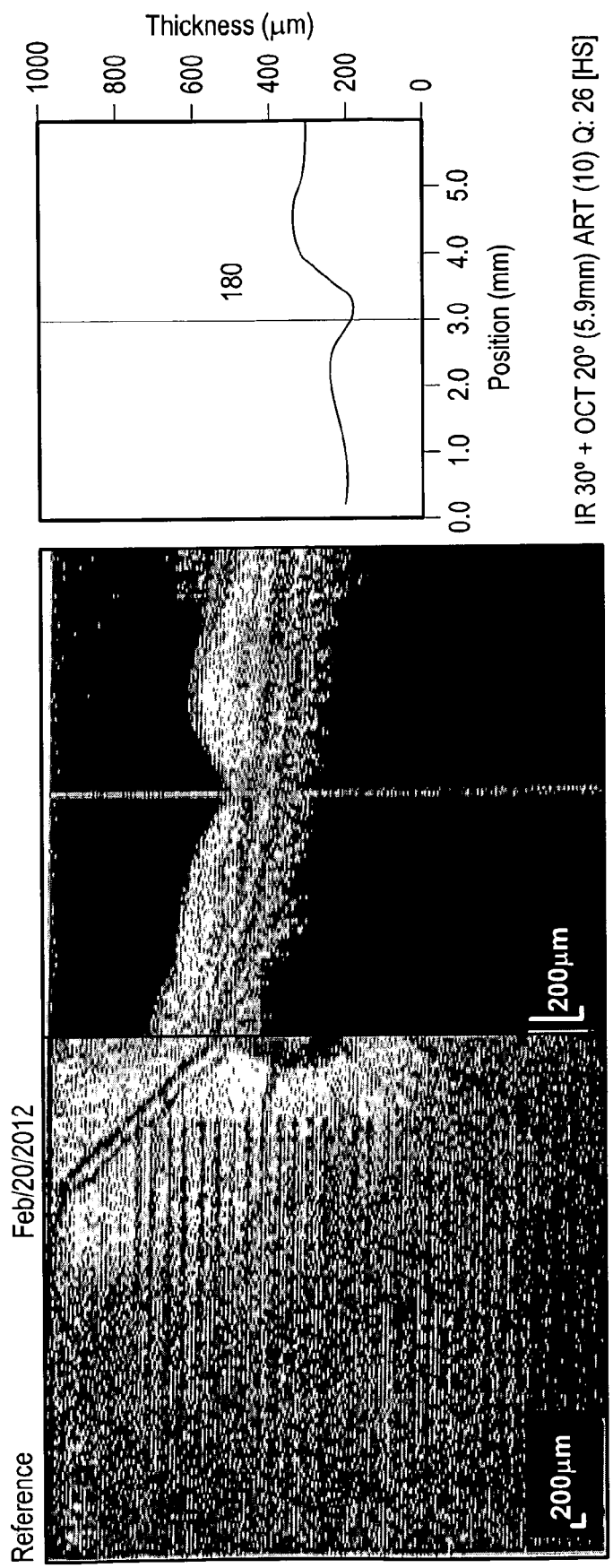
Figure 16:
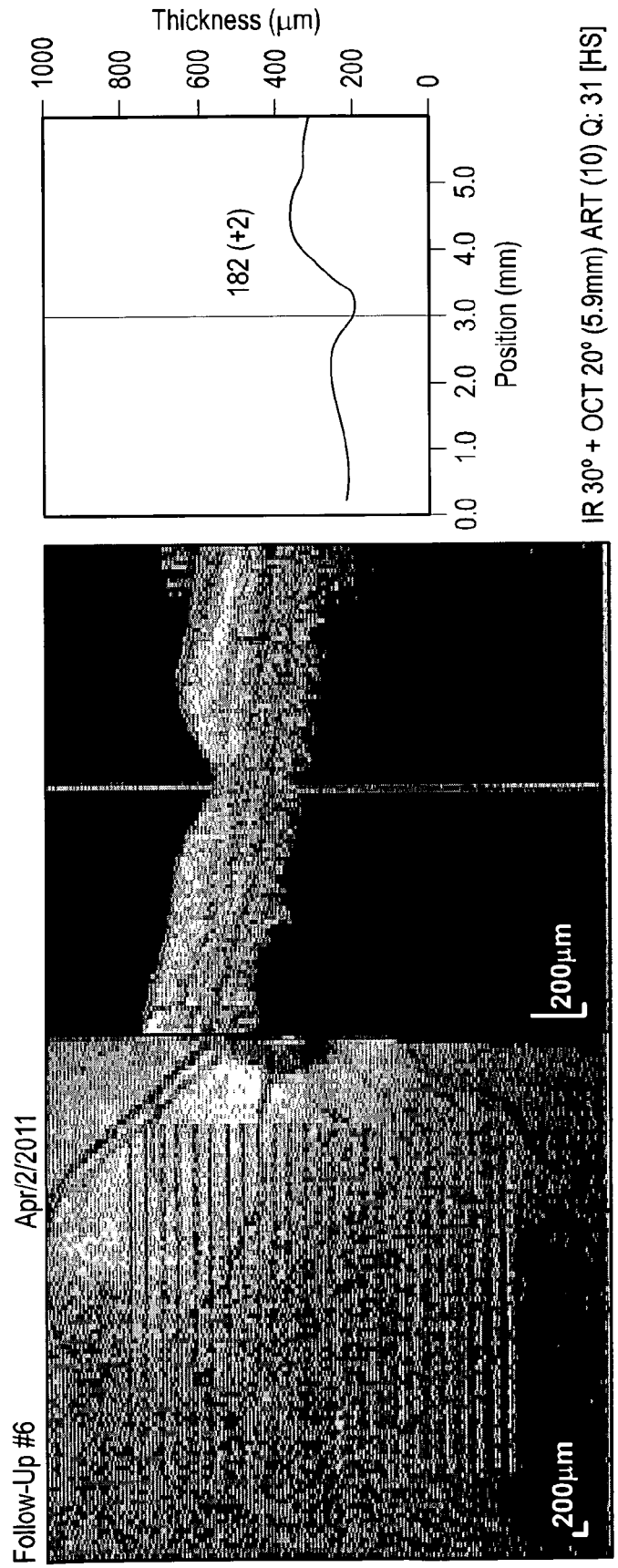

Case n)
43 year old man with right central serous retinopathy. He was treated with three intravitreal Avastin injections and started on Omega 3RX® on Dec. 2, 2011. A month following treatment with Omega 3RX® the fluid resolved and he gained two lines of vision (FIG. 16).

Figure 17:
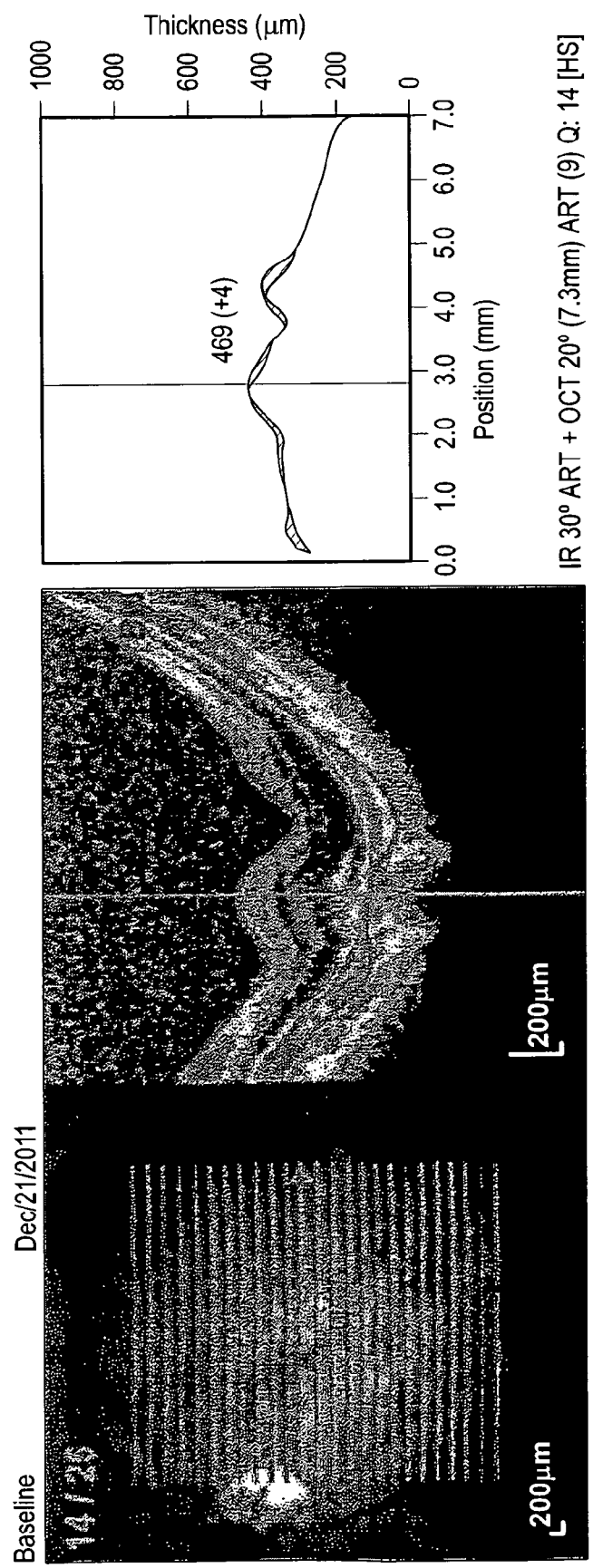
Figure 17:
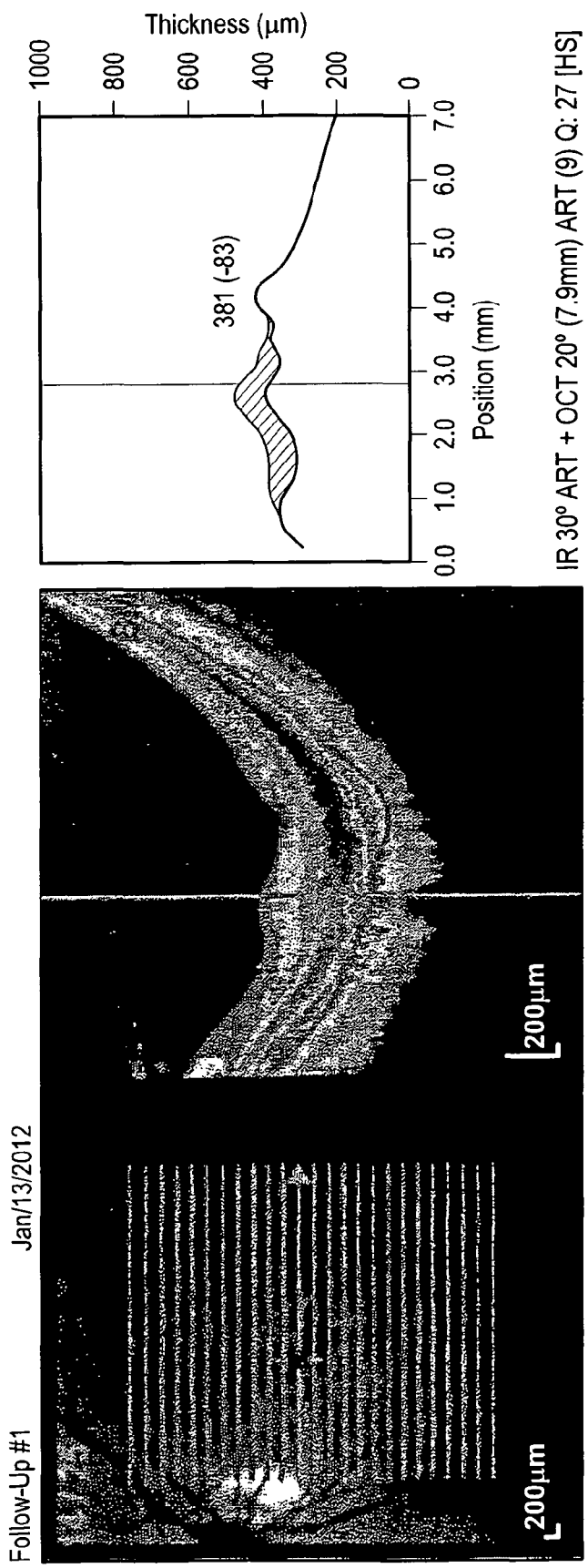
Figure 17:
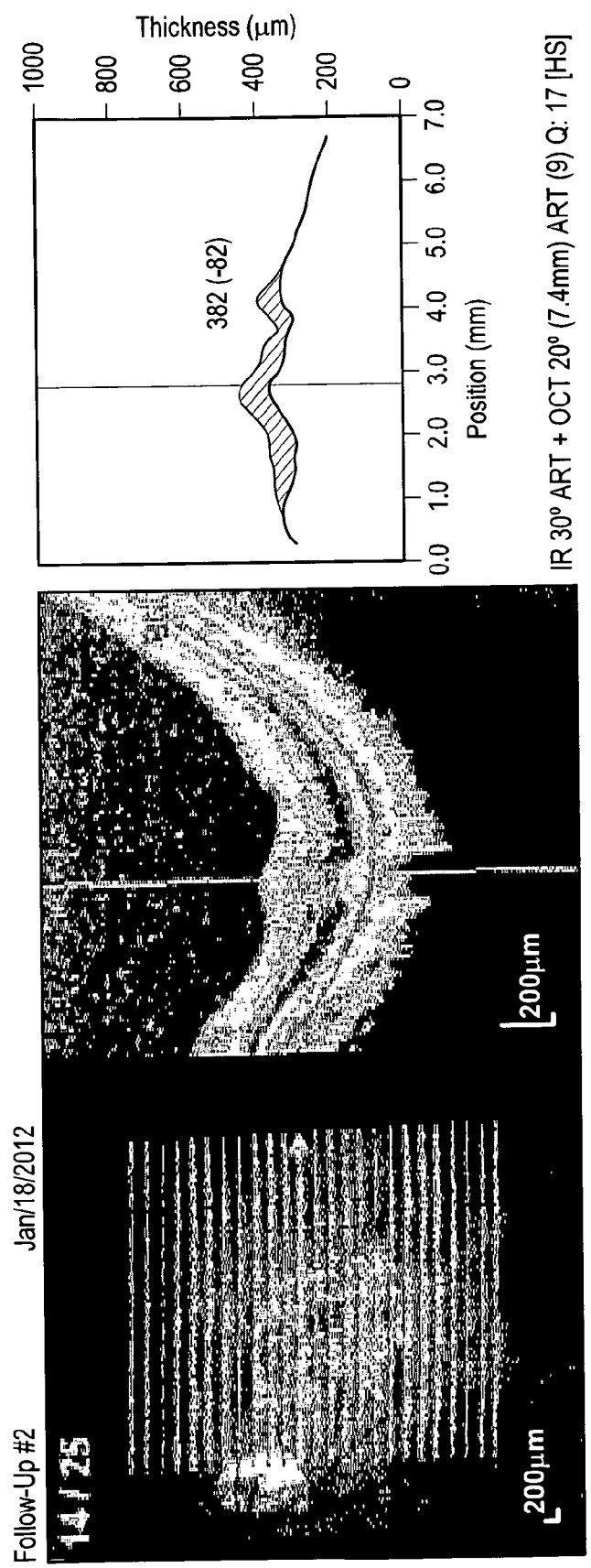
Figure 17:
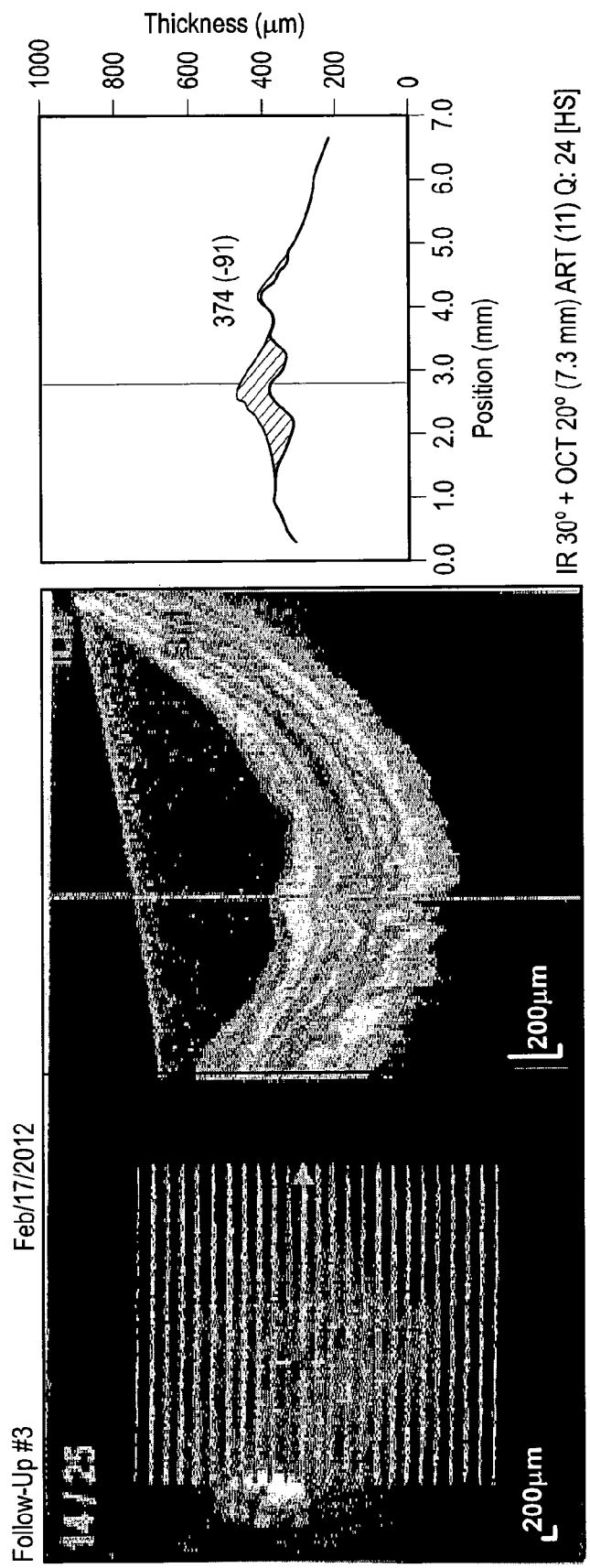
Figure 17:
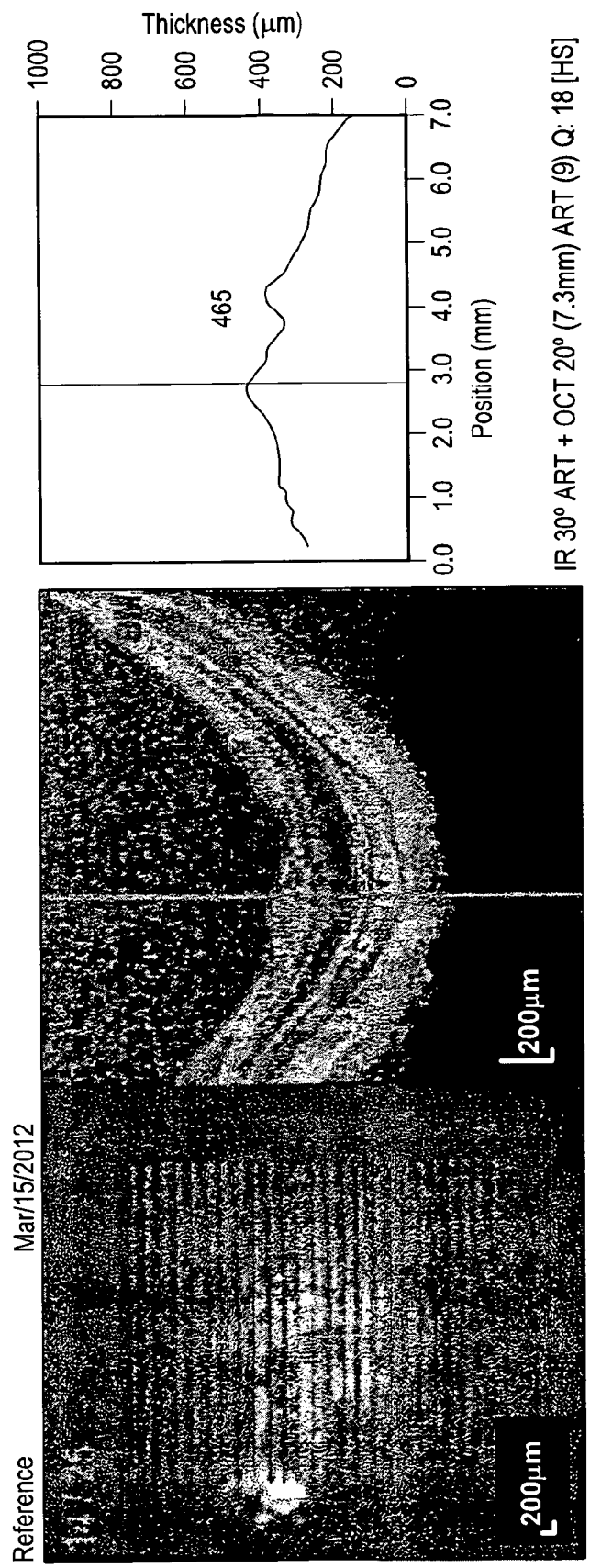
Figure 17:
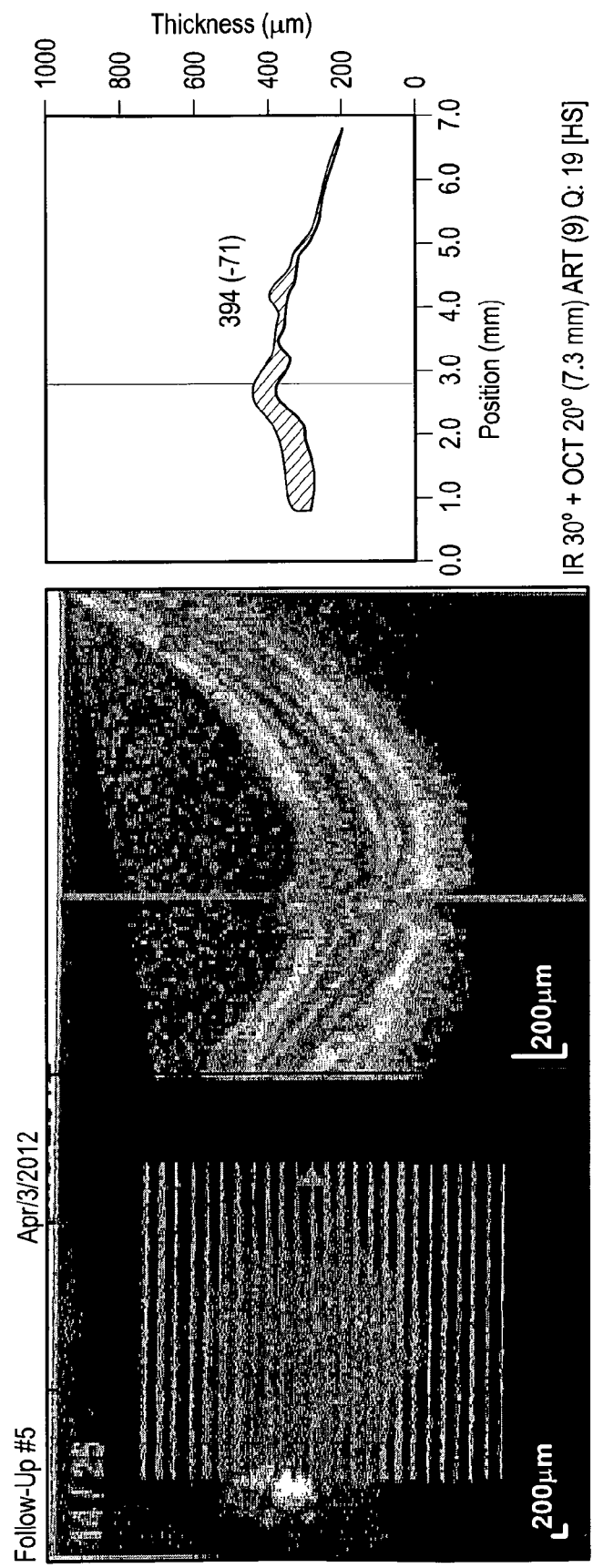

Case o)
60 year old man presented with left wet AMD on Dec. 21, 2012. He was treated with one intravitreal Avastin injection and Omega 3RX®. The fluid resolved in a month and he gained two lines of vision (FIG. 17).

Figure 18:
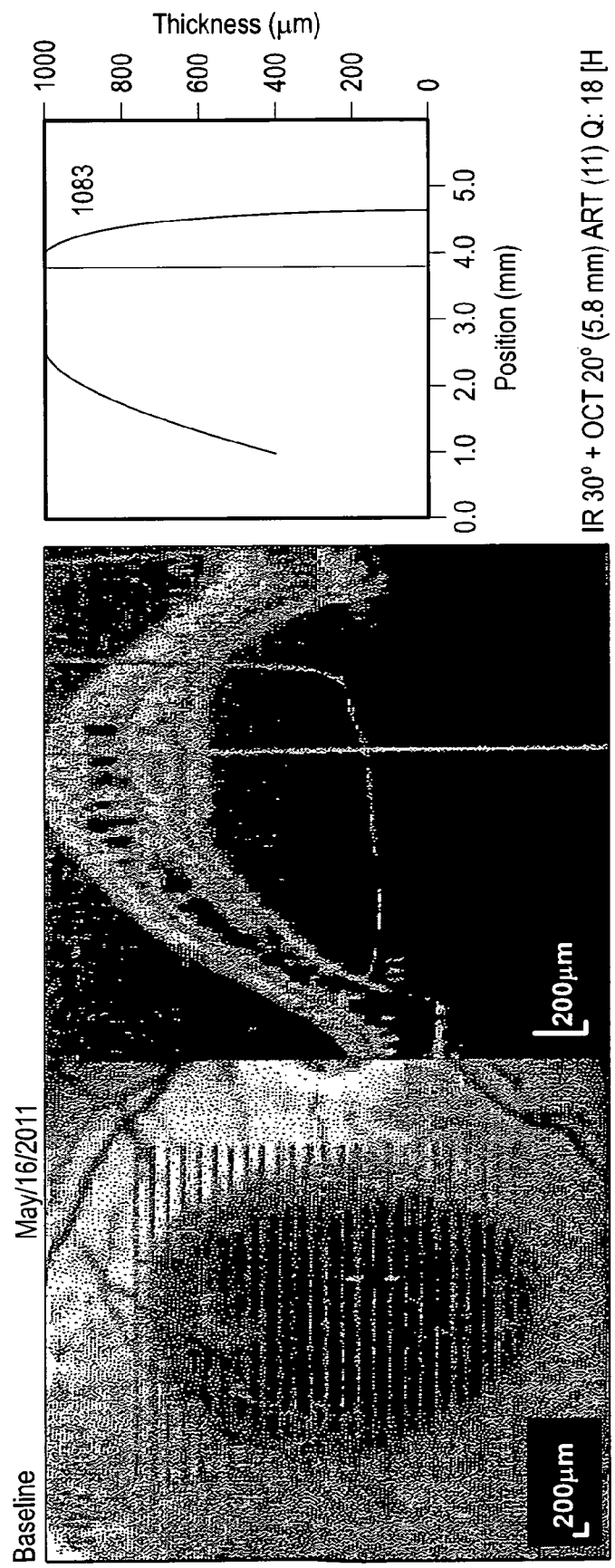
Figure 18:
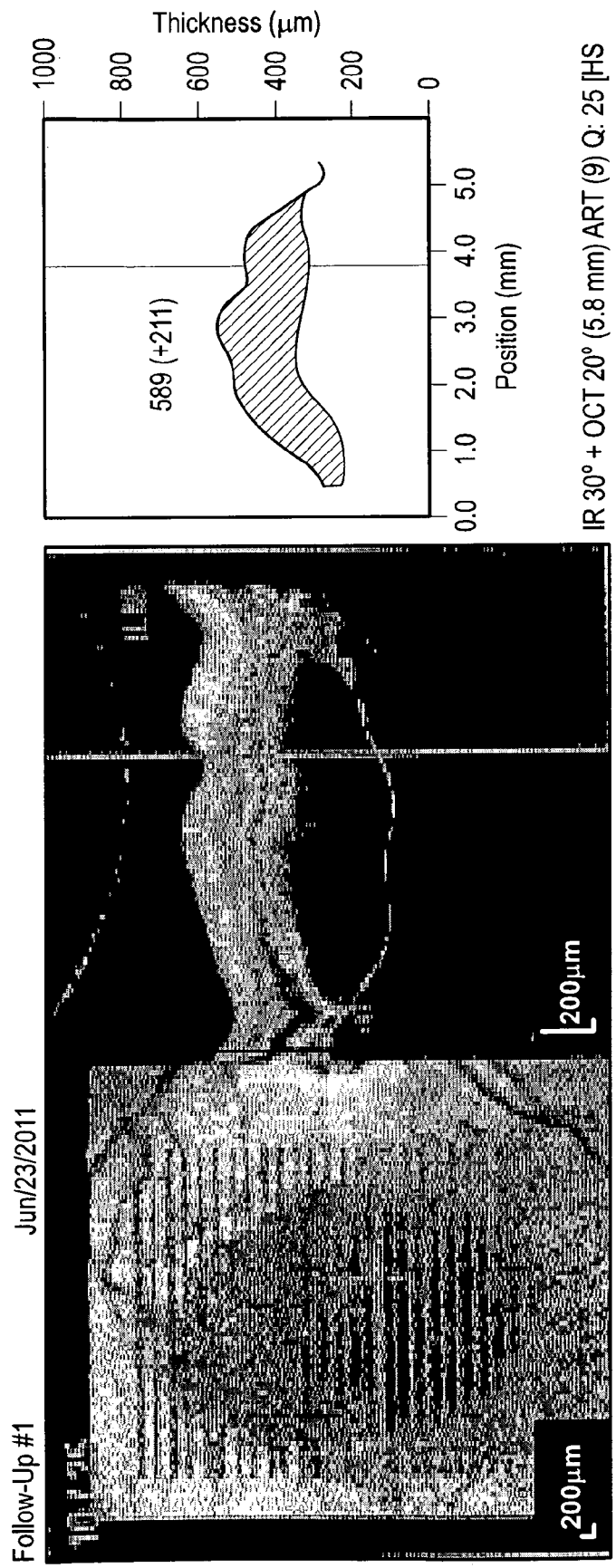
Figure 18:
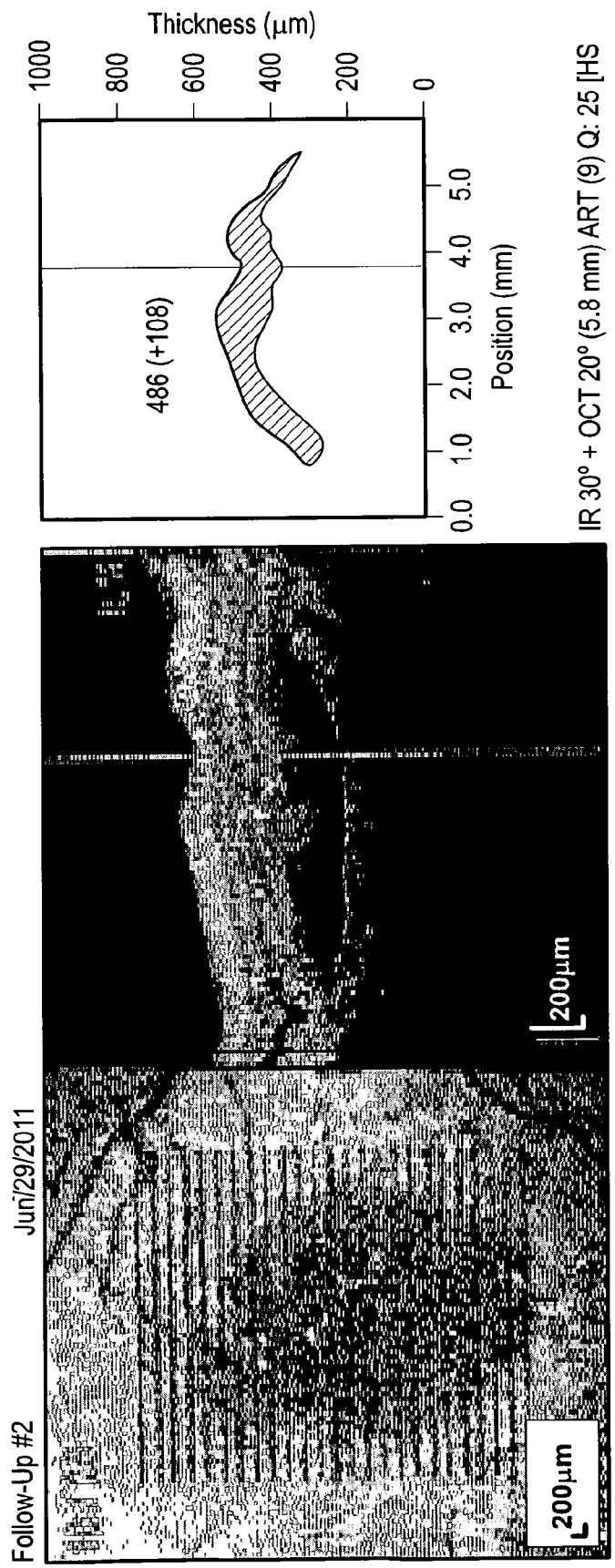
Figure 18:
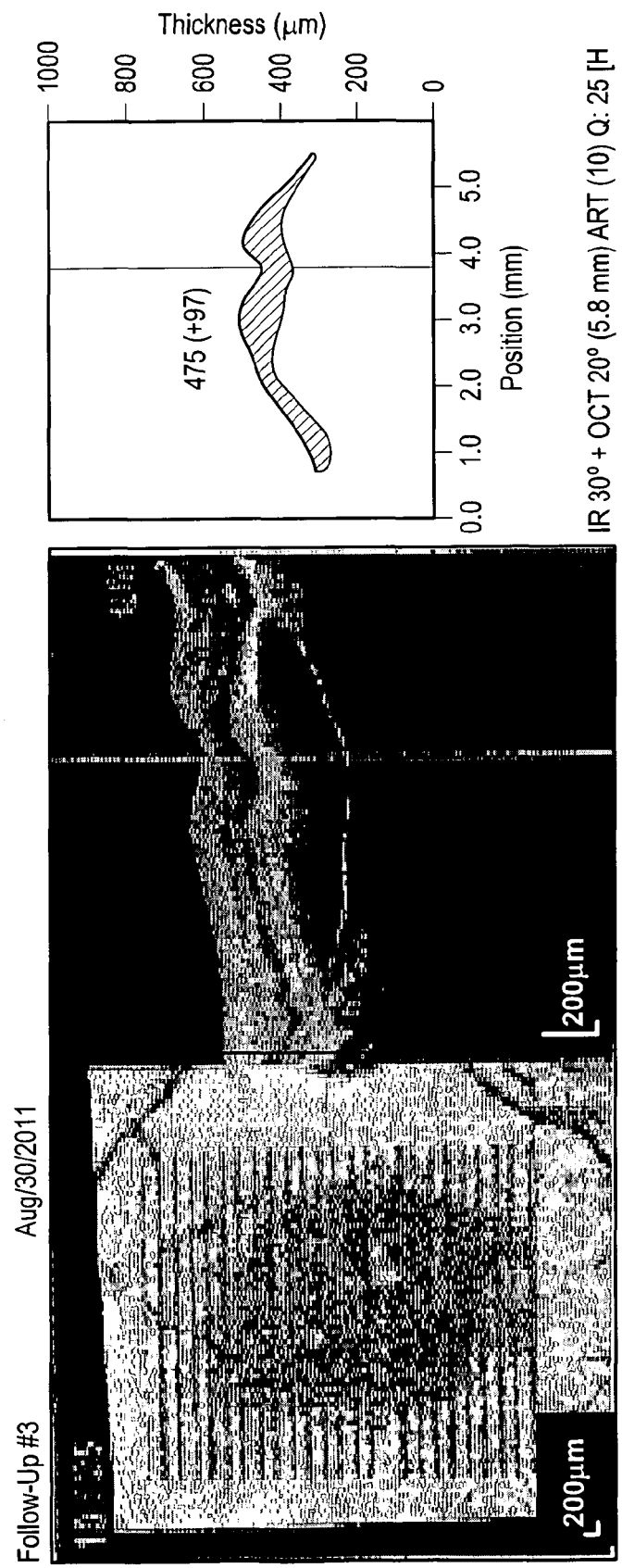
Figure 18:
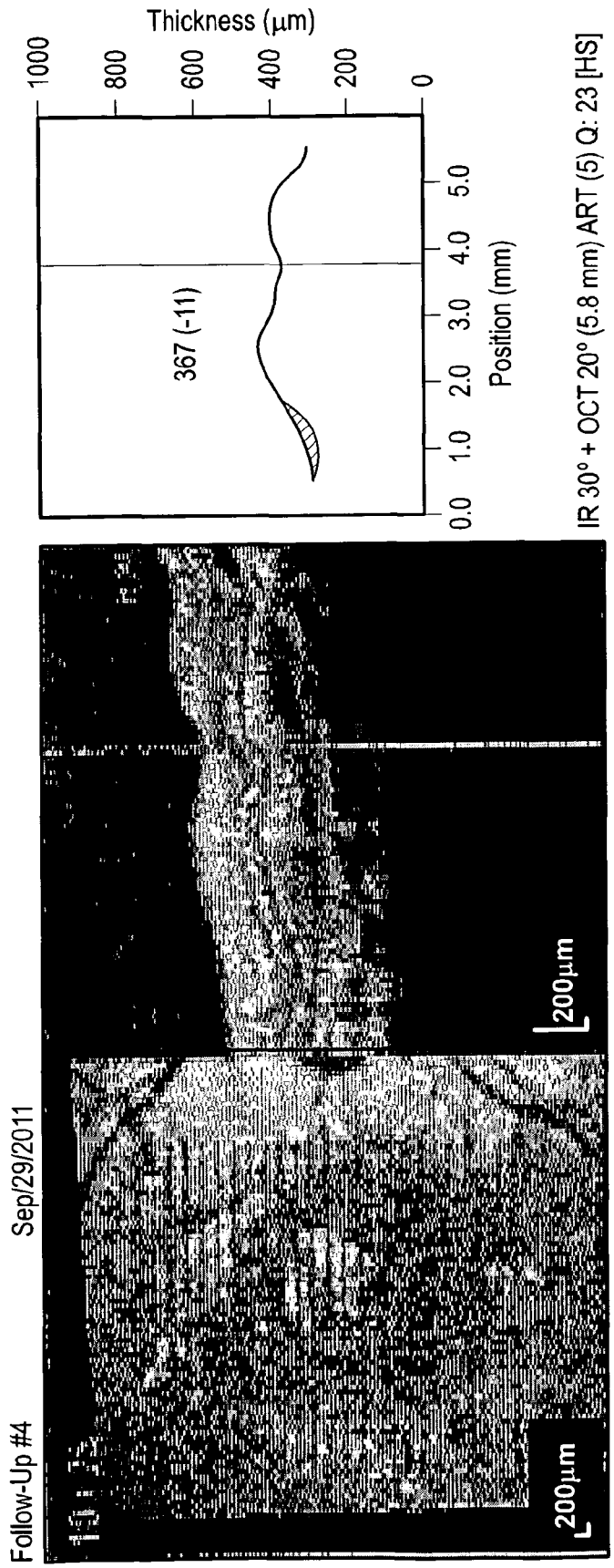
Figure 18:
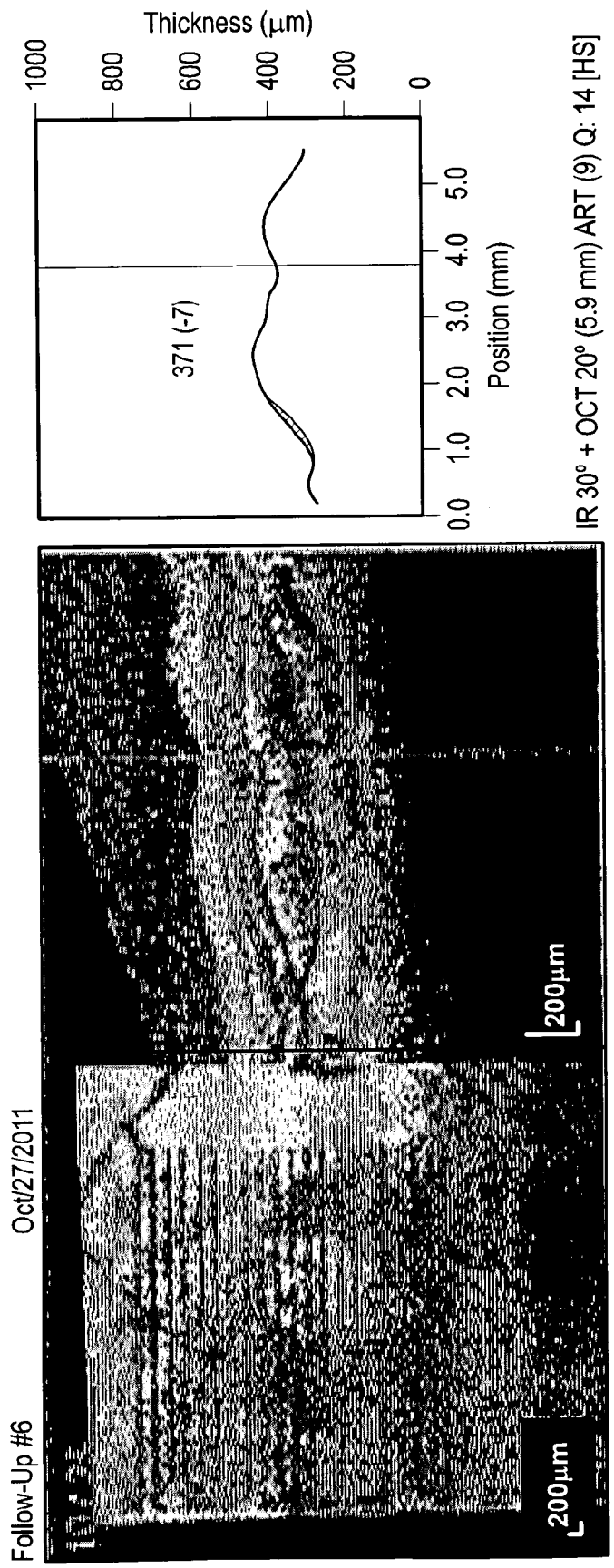
Figure 18:
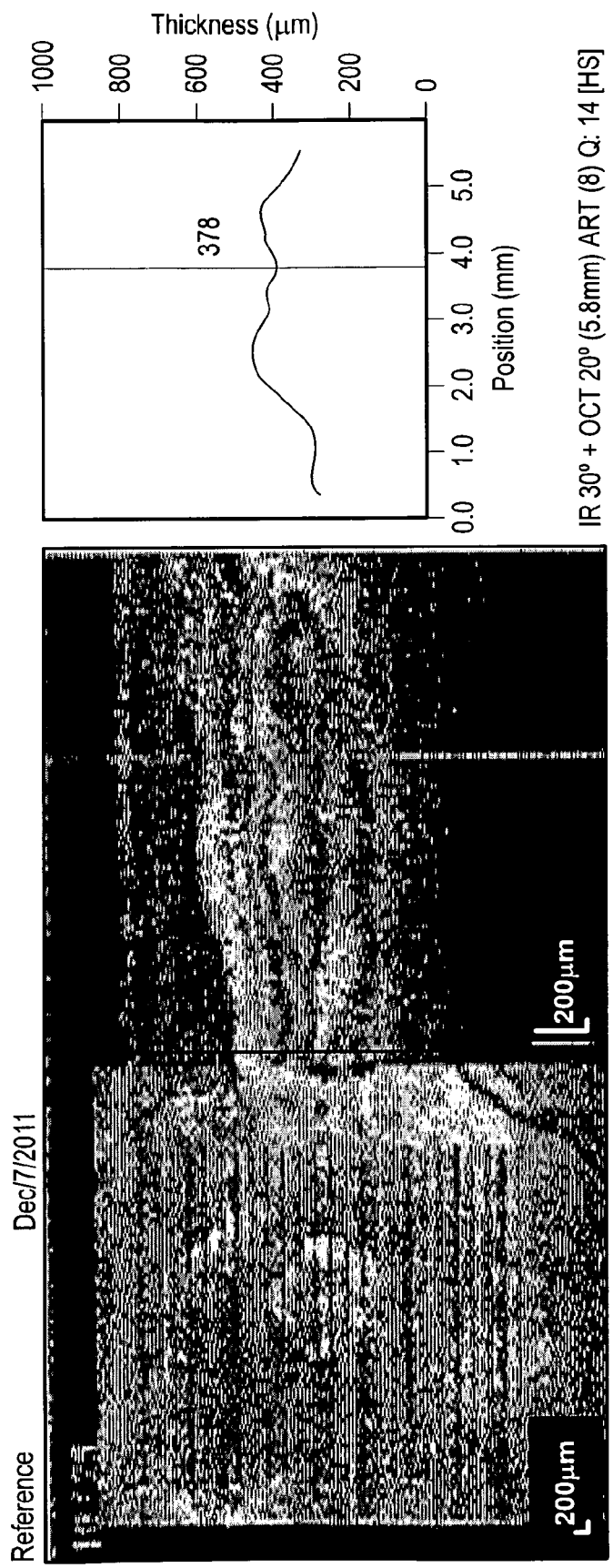
Figure 18:
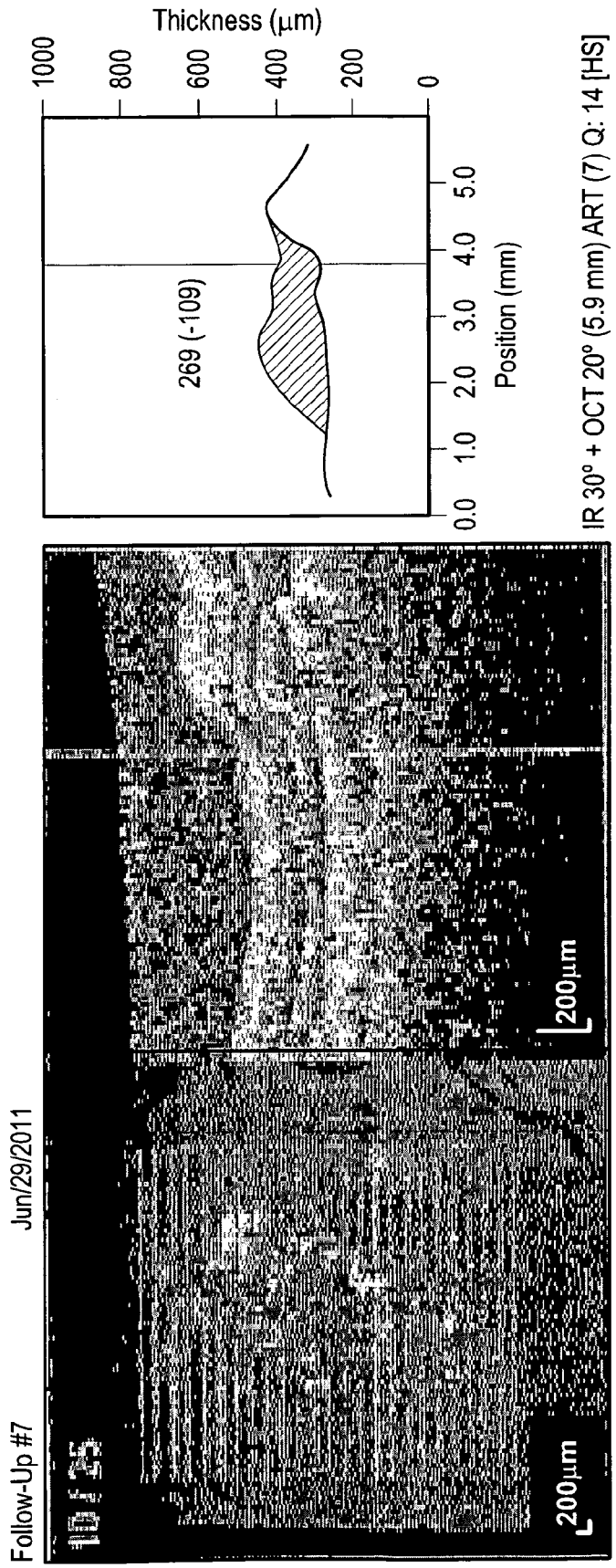

Case p)
69 year old female presented with left wet AMD on May 12, 2010. She was treated with nine intravitreal Avastin injections the last one on Jan. 27, 2011. She started on Omega 3RX® on Dec. 7, 2011. Six weeks following treatment there was minimal fluid on OCT scan (FIG. 18).

Figure 19:
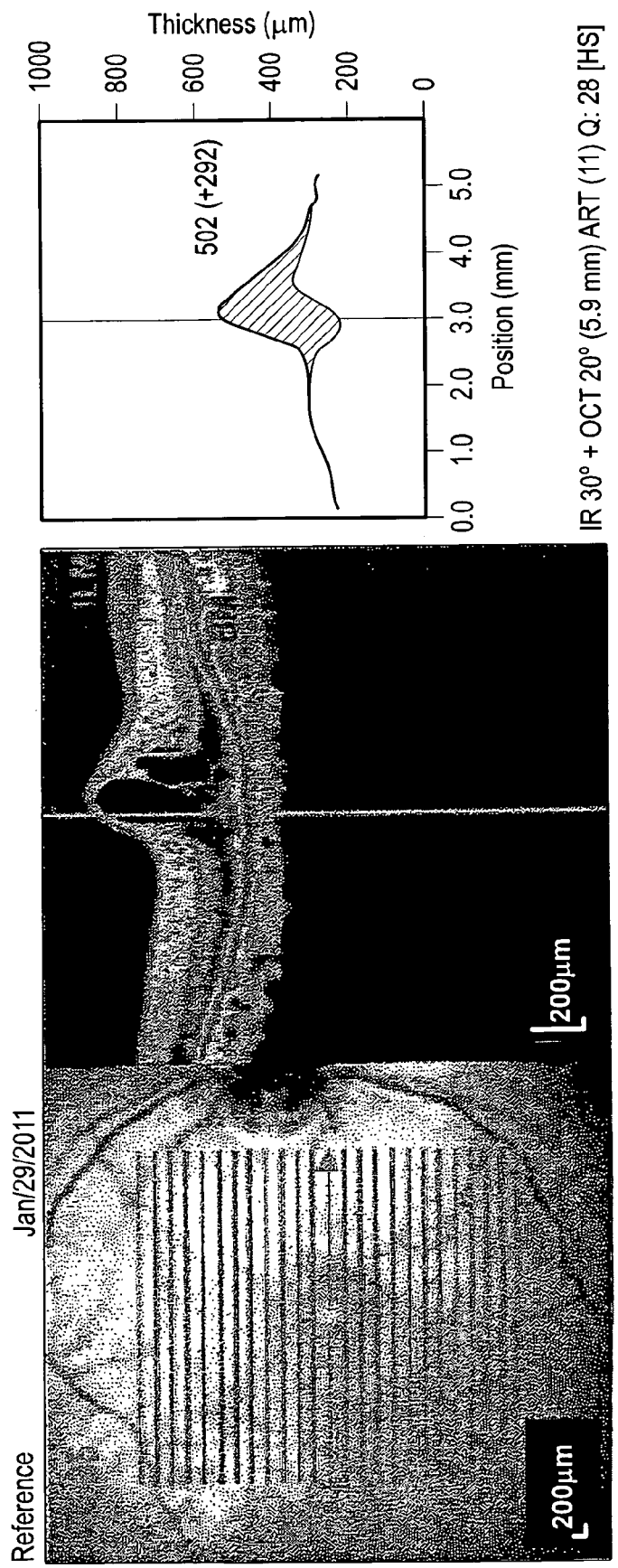
Figure 19:
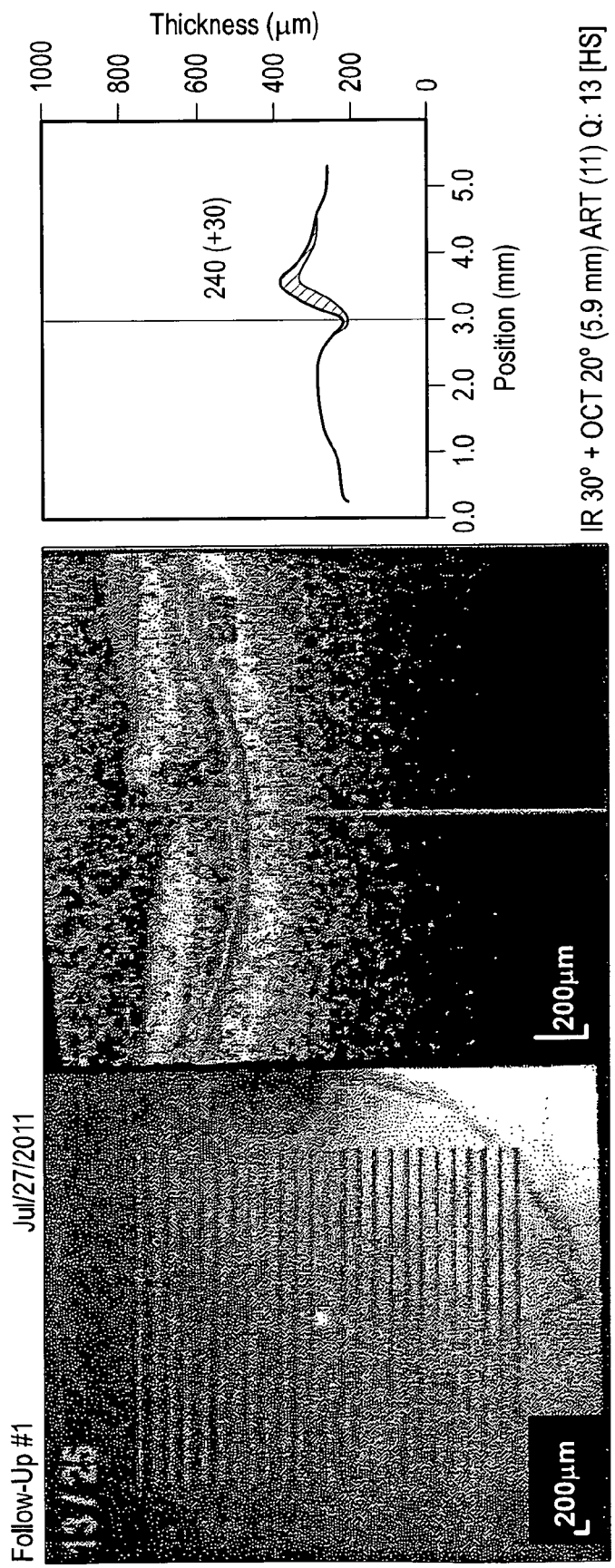
Figure 19:
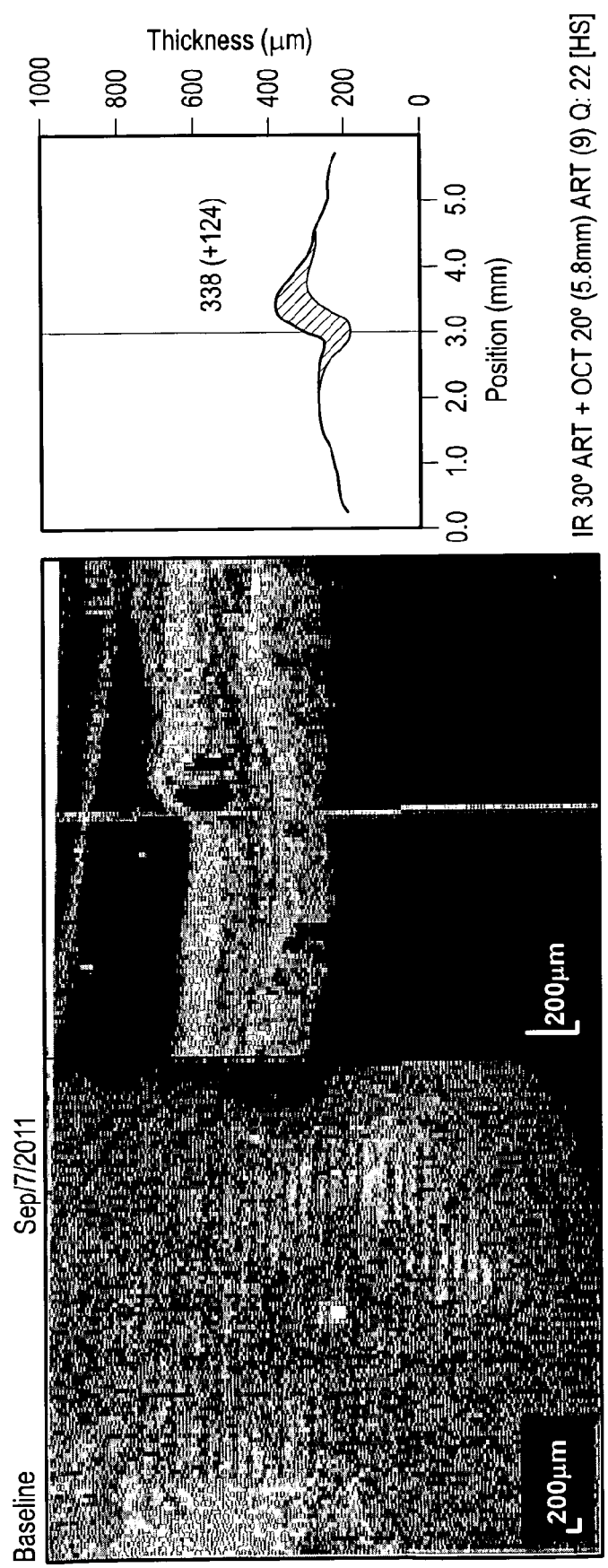
Figure 19:
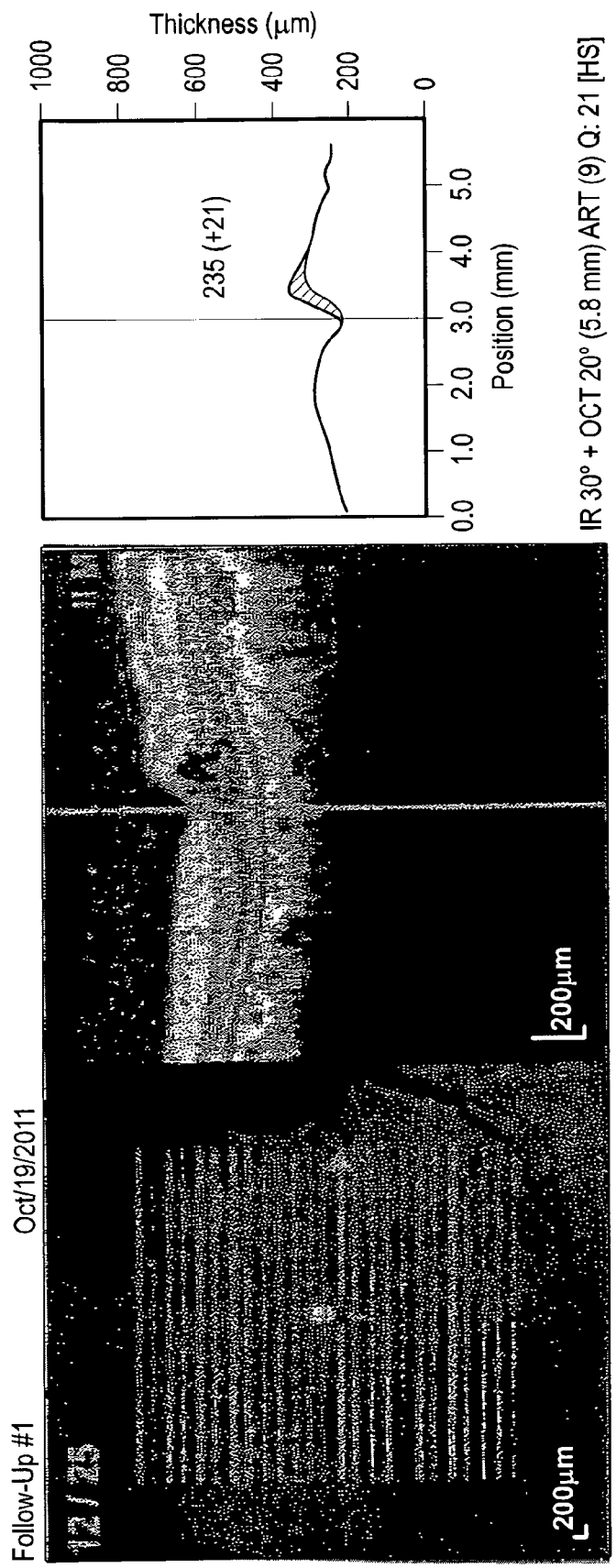
Figure 19:
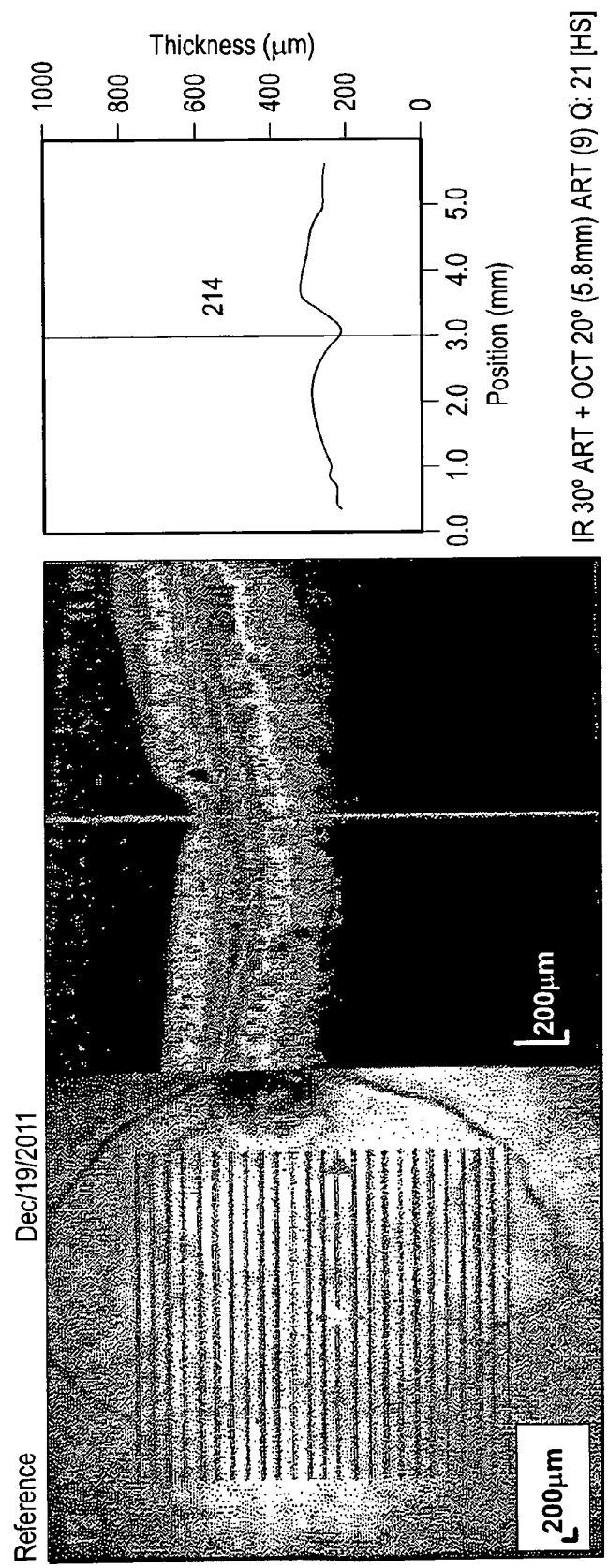
Figure 19:
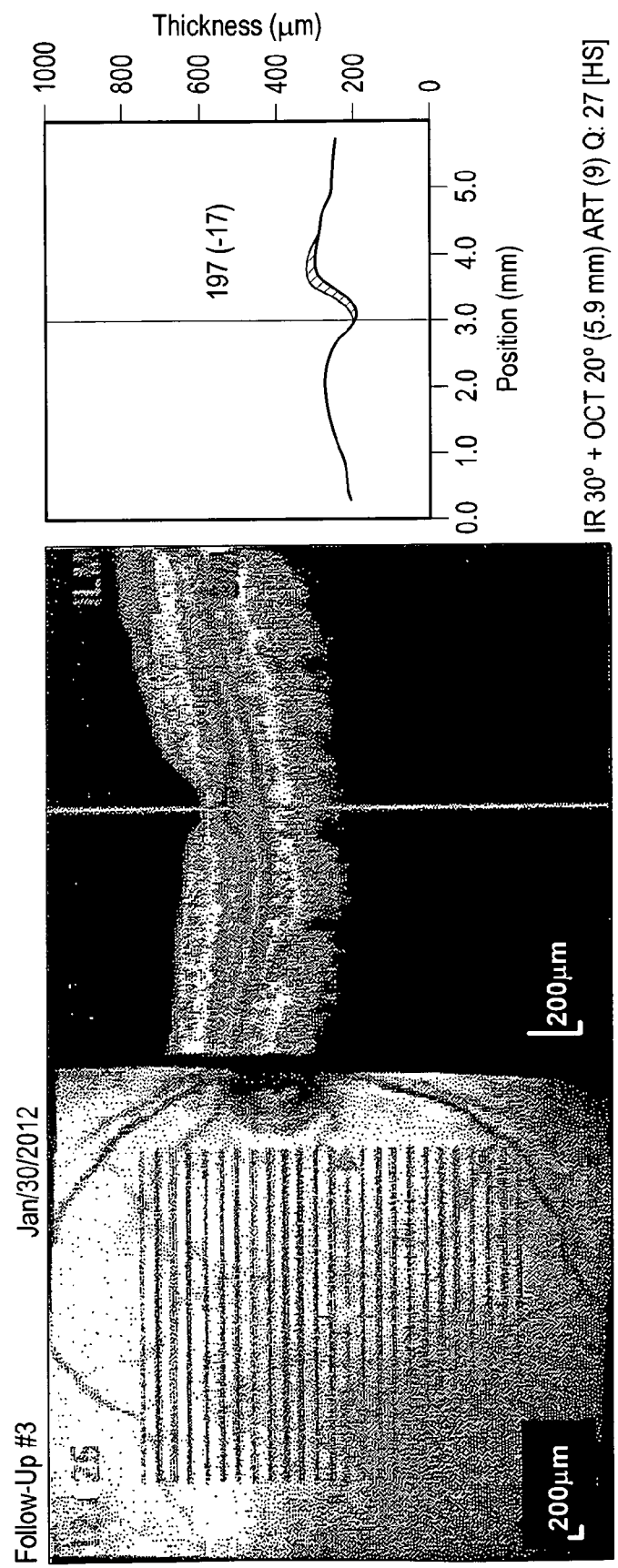
Figure 19:
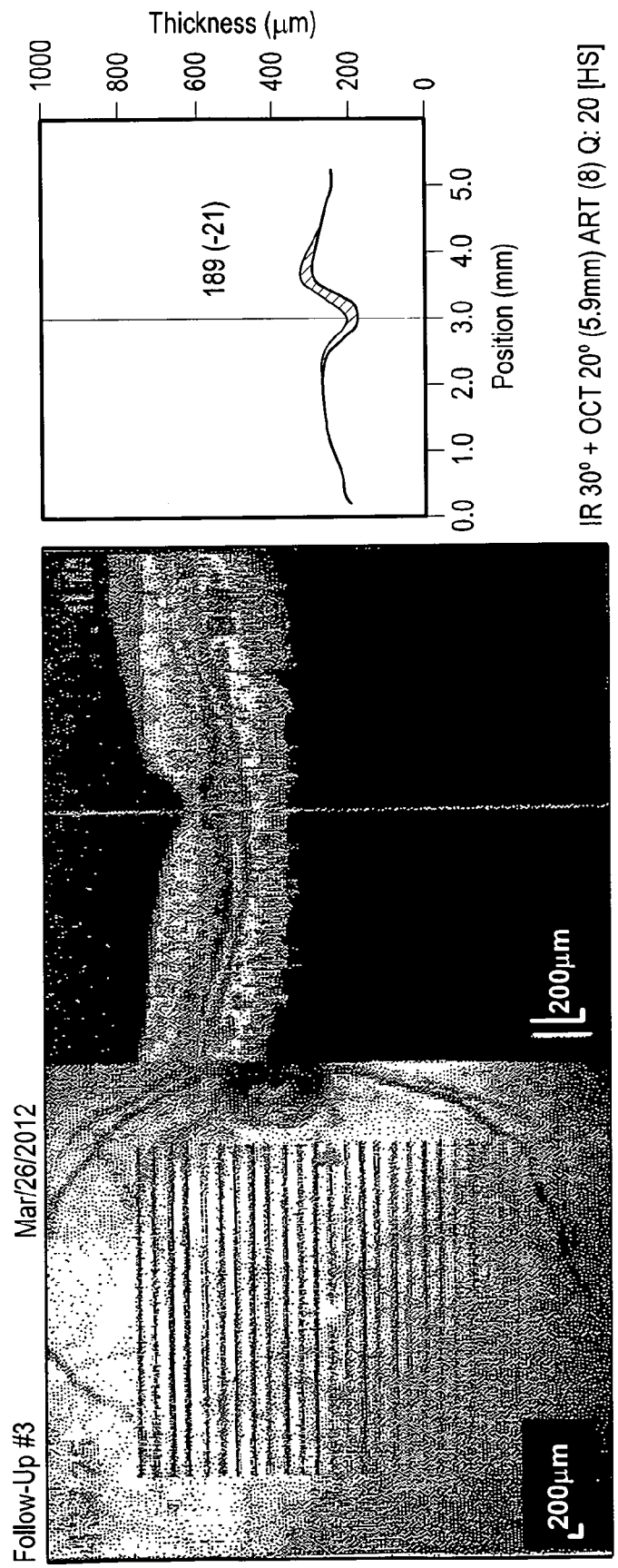
Figure 19:
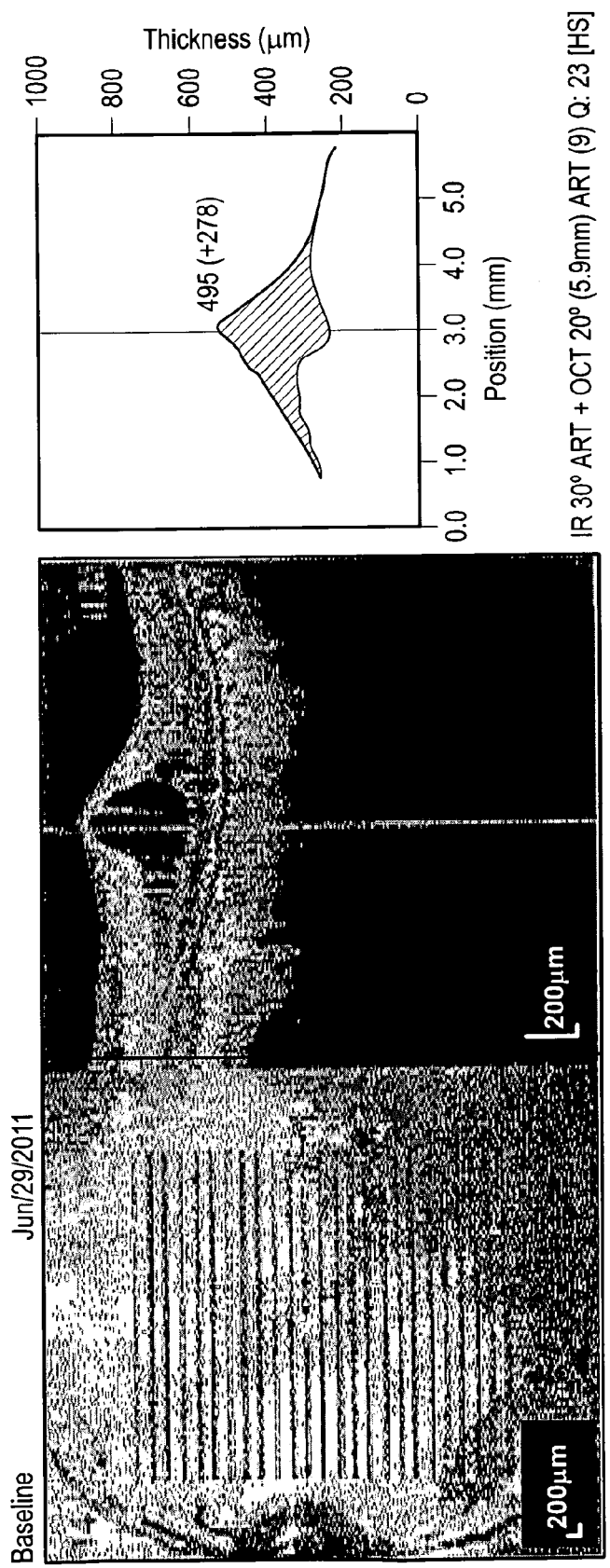
Figure 19:
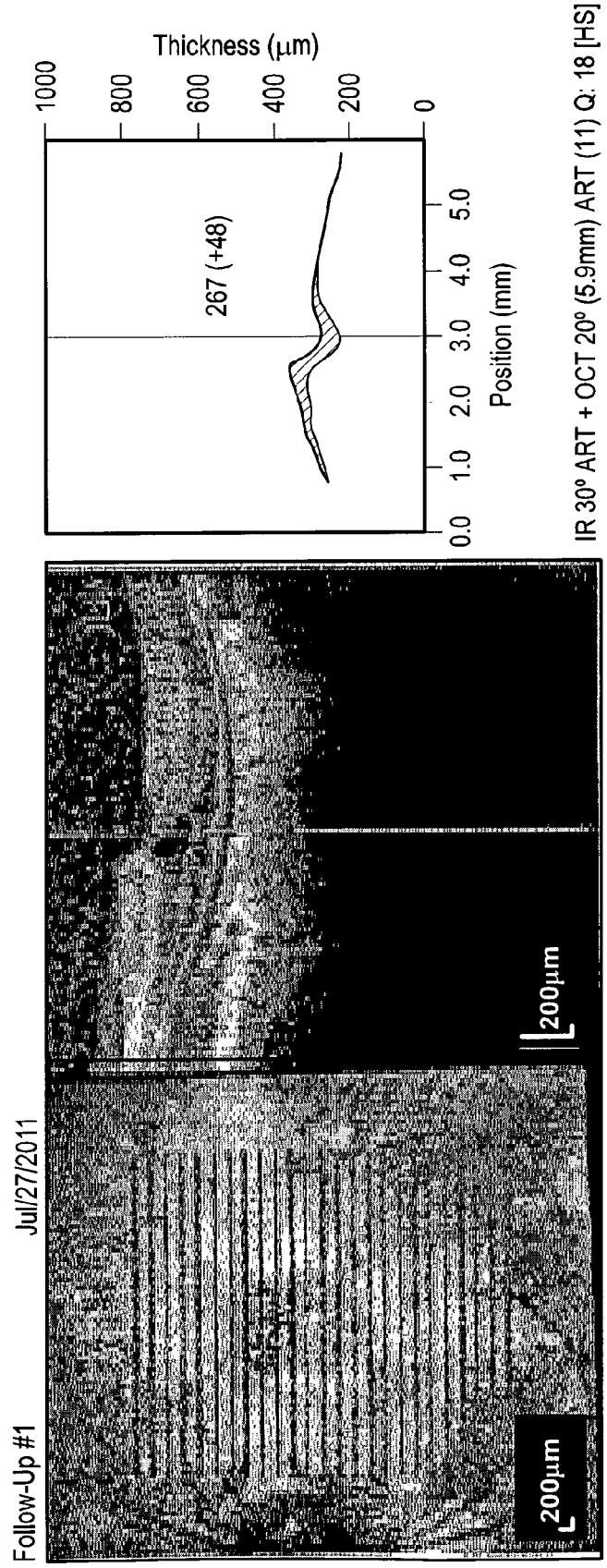
Figure 19:
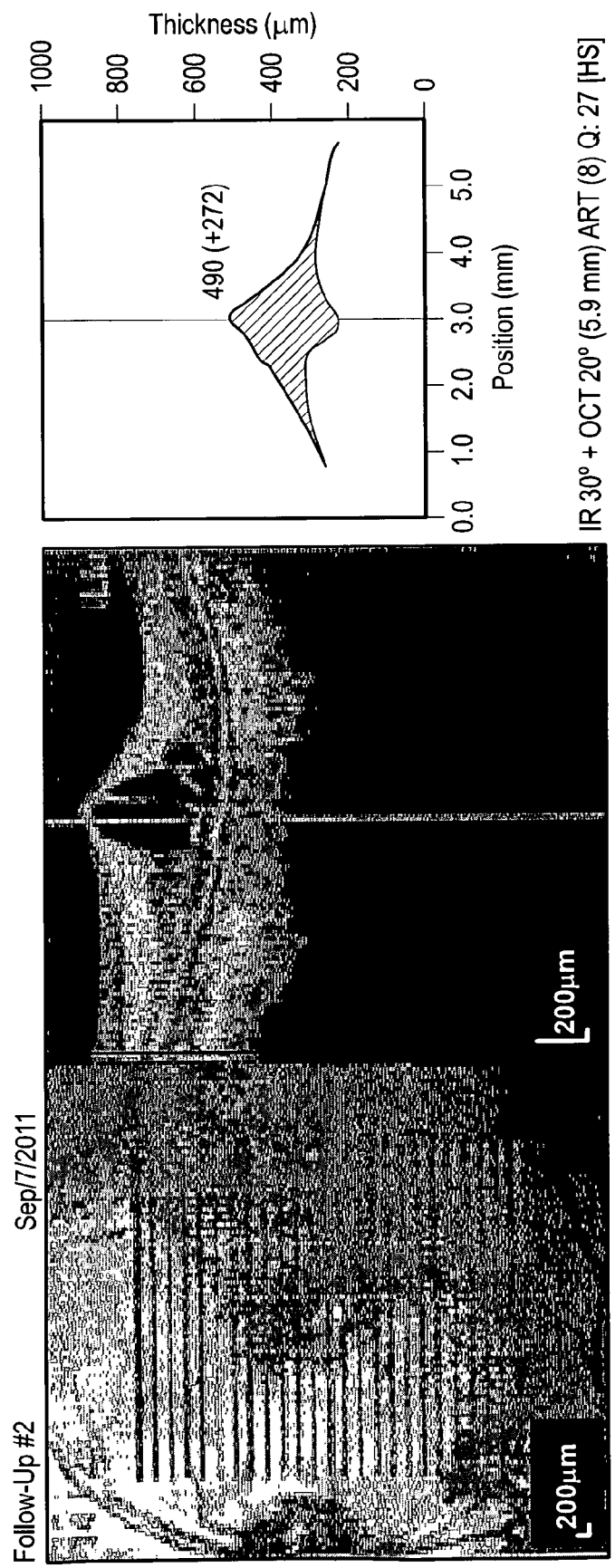
Figure 19:
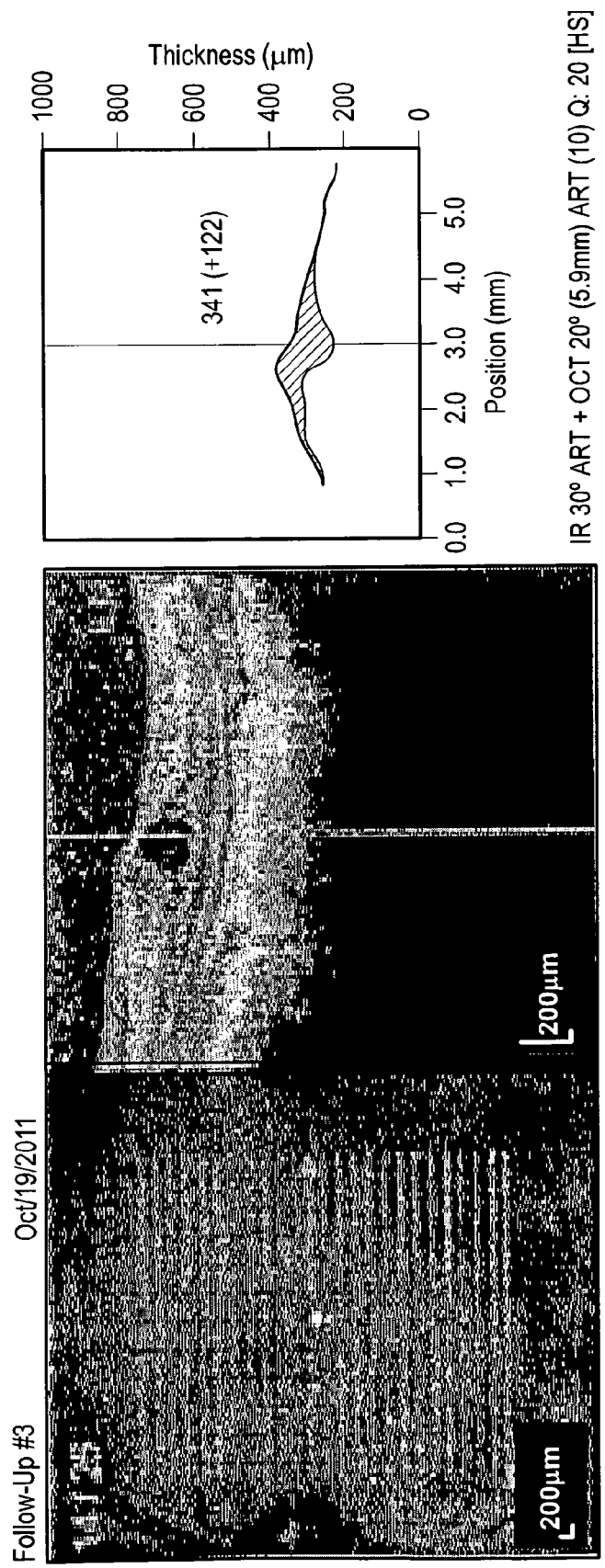
Figure 19:
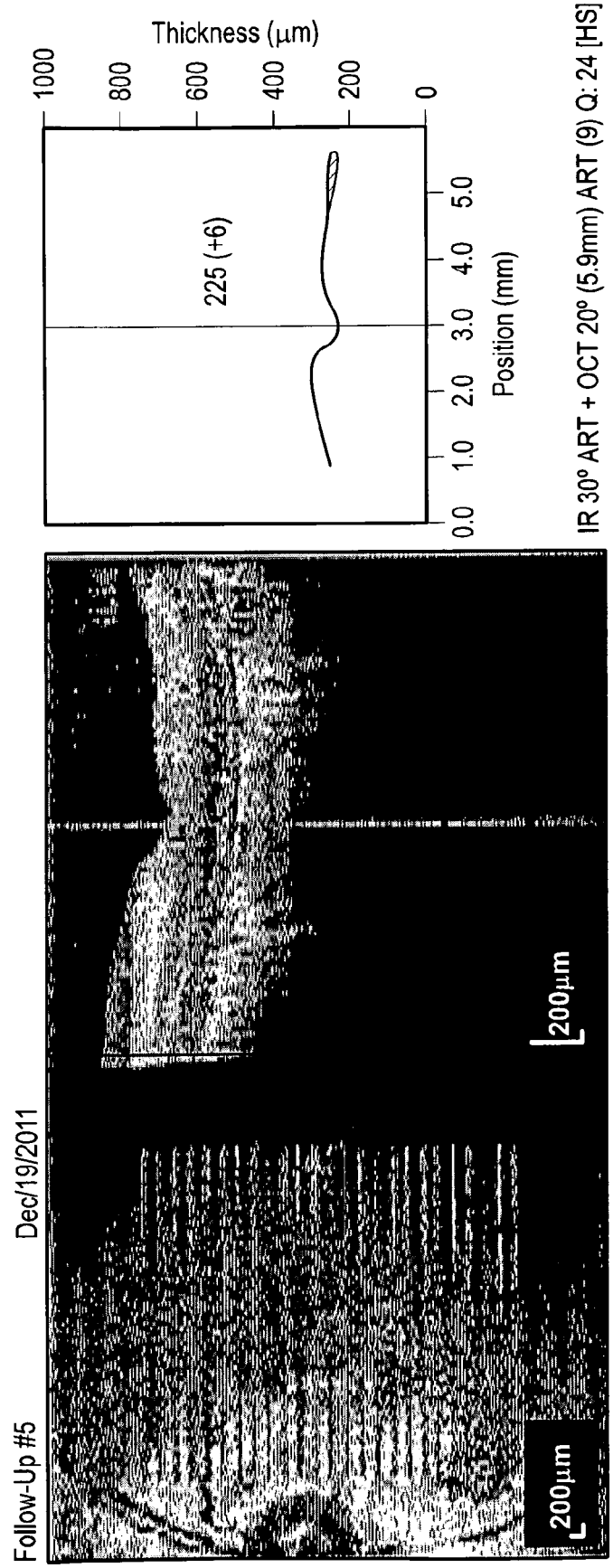
Figure 19:
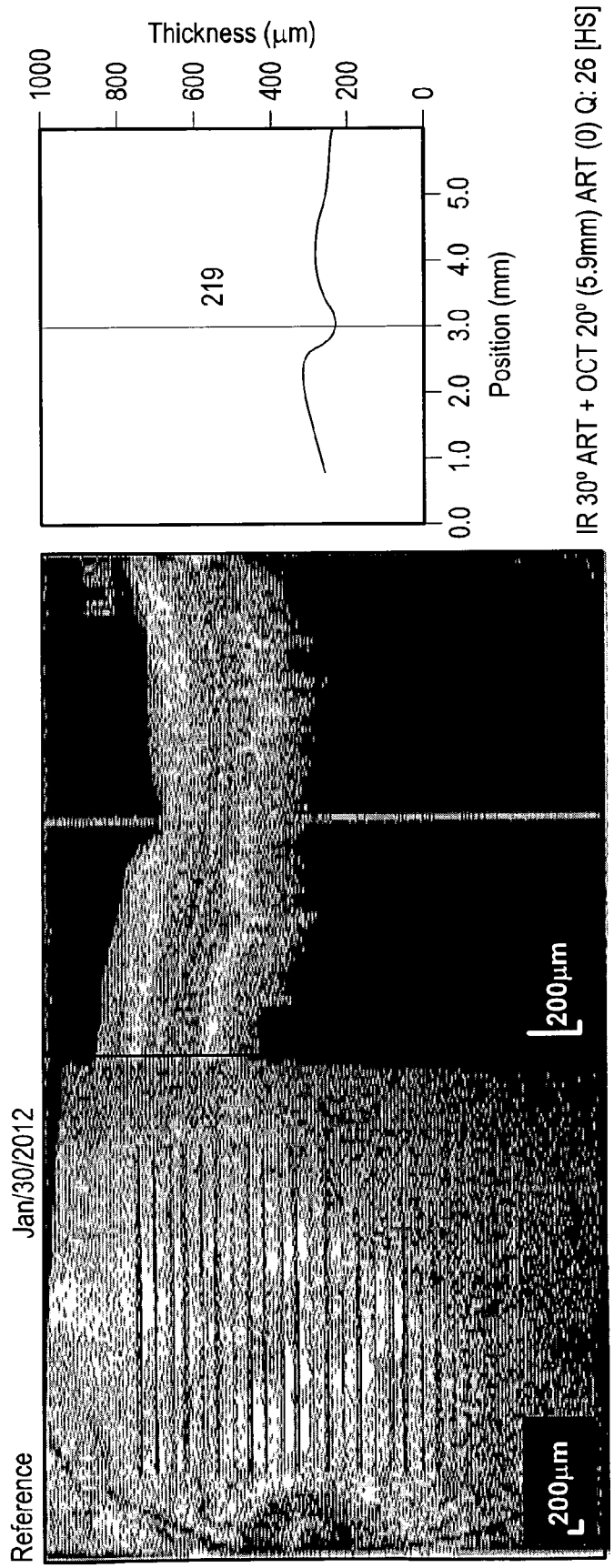
Figure 19:
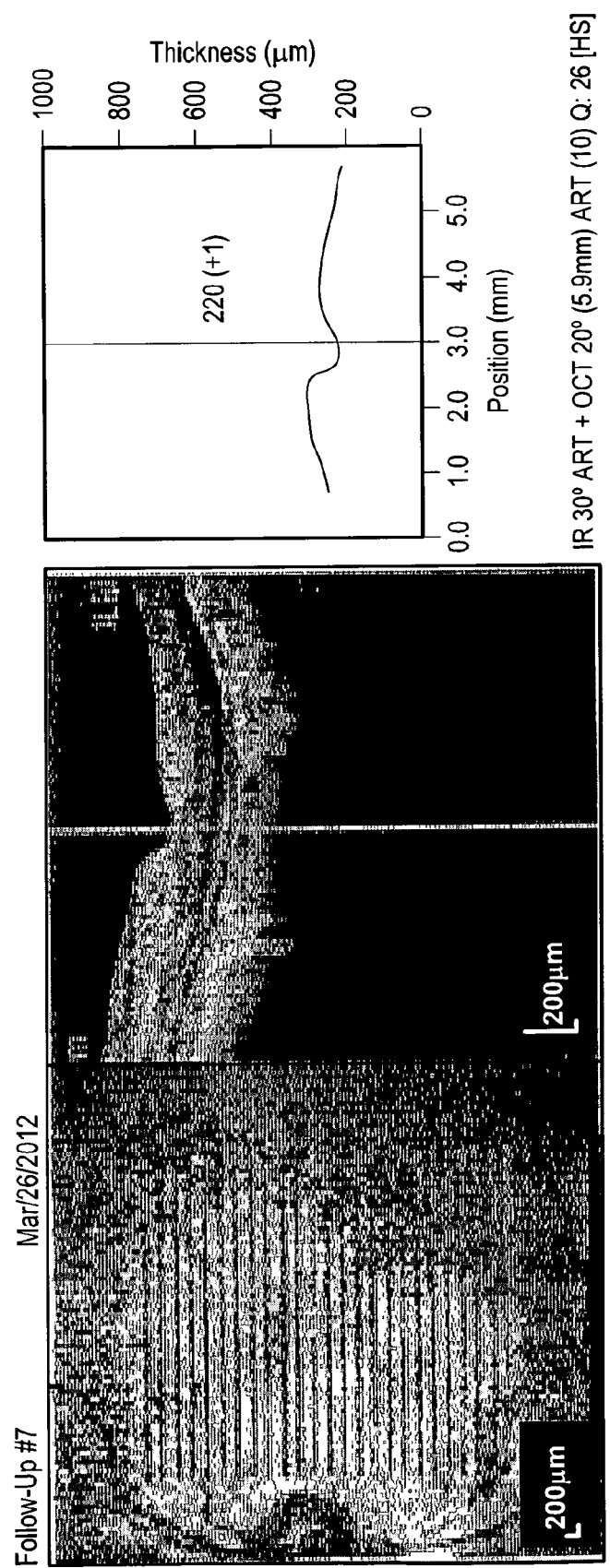

Case q)
82 year old female presented with right wet AMD in 2007 and left wet AMD in 2008. She was treated with more than fifteen intravitreal injections in each eye. She started on Omega 3RX® on Oct. 19, 2011. Within two months of starting Omega 3RX® the fluid resolved in both eyes. She gained one line of vision in each eye (FIG. 19).

Figure 20:
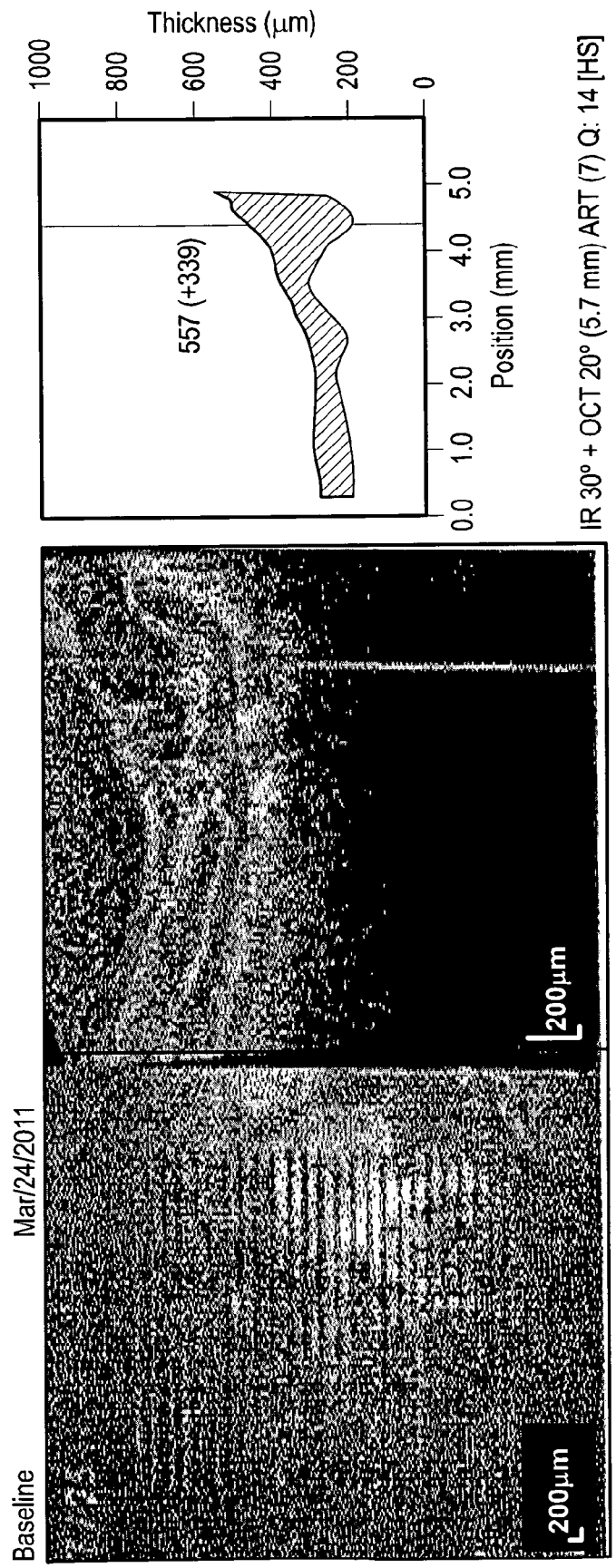
Figure 20:
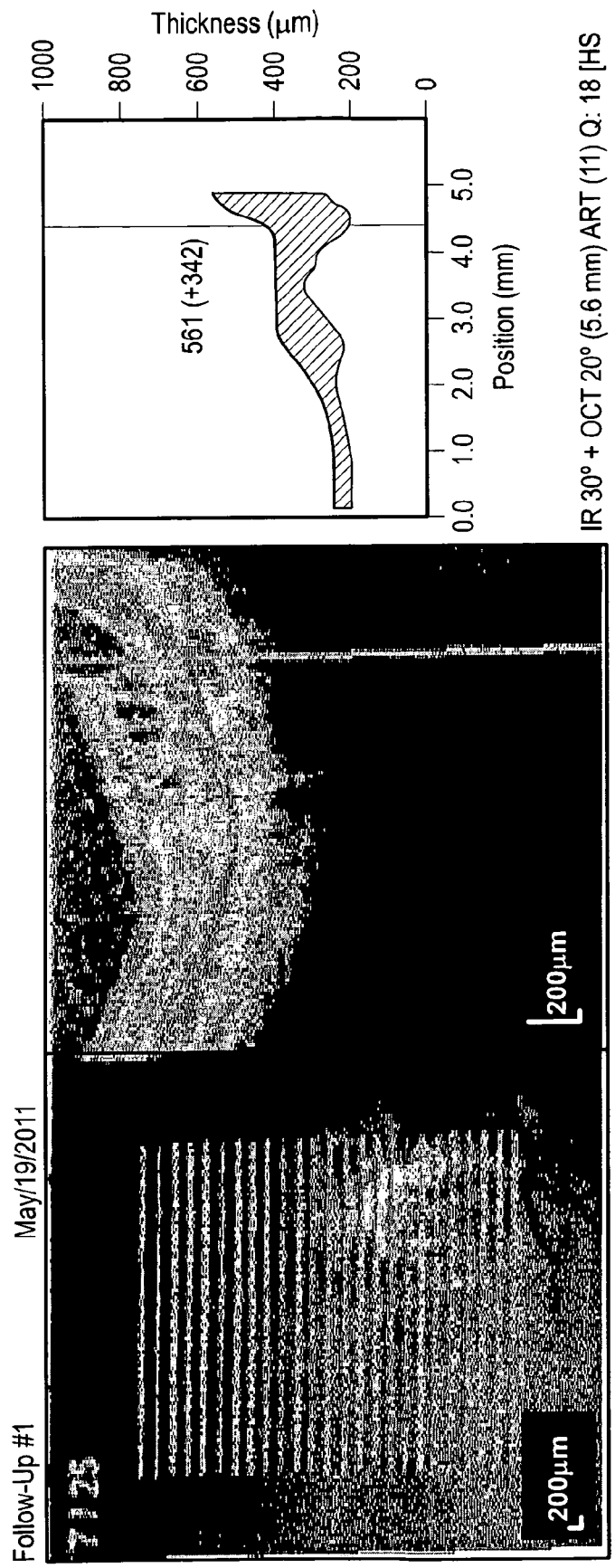
Figure 20:
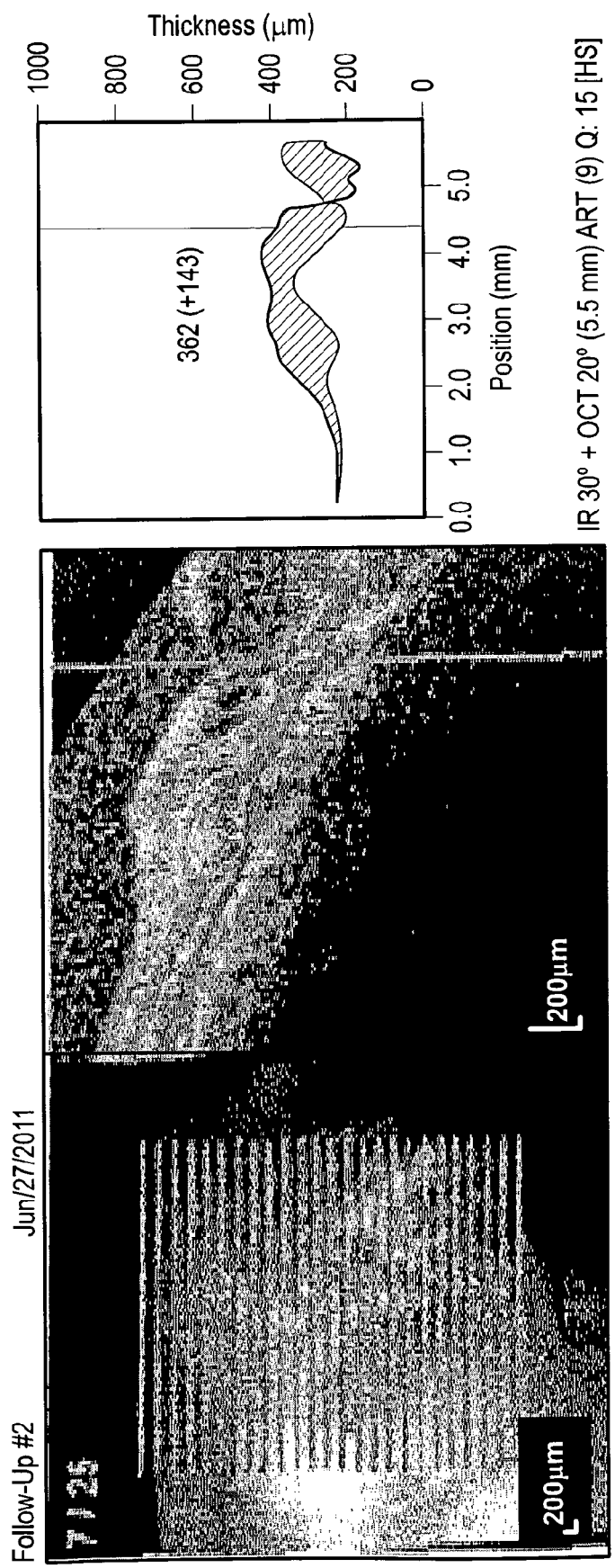
Figure 20:
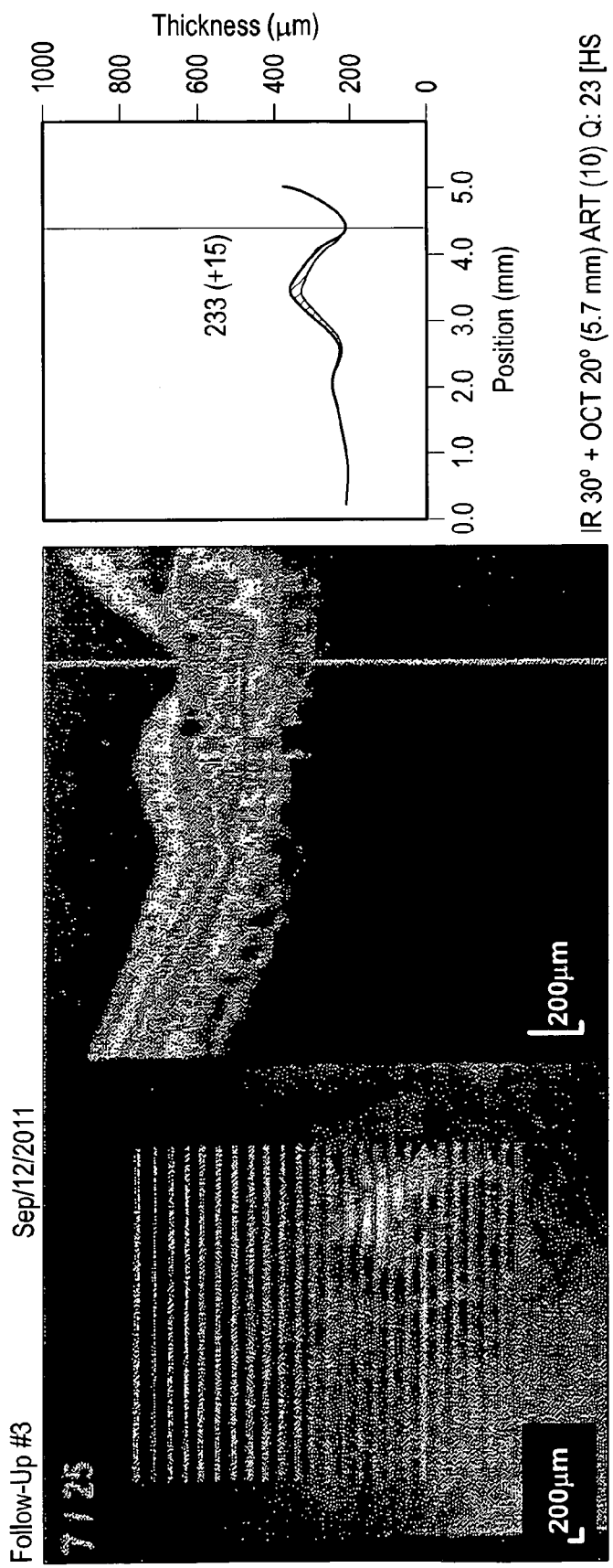
Figure 20:
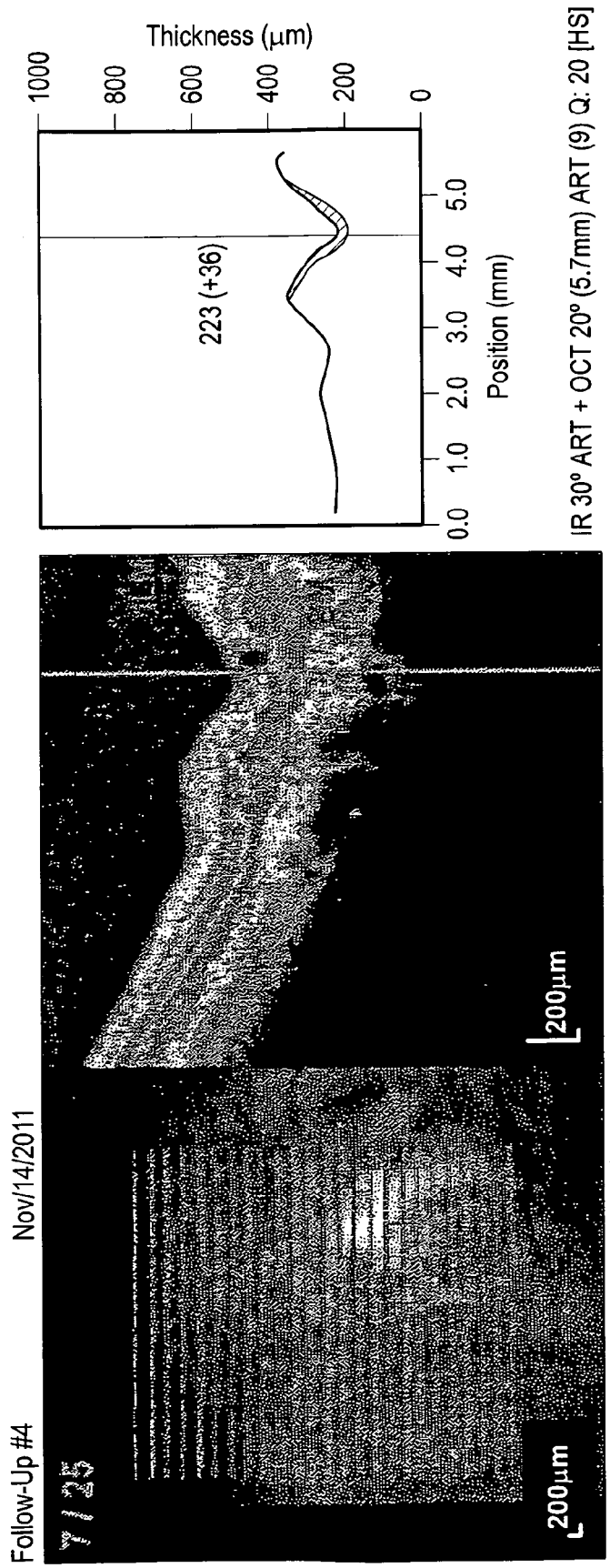
Figure 20:
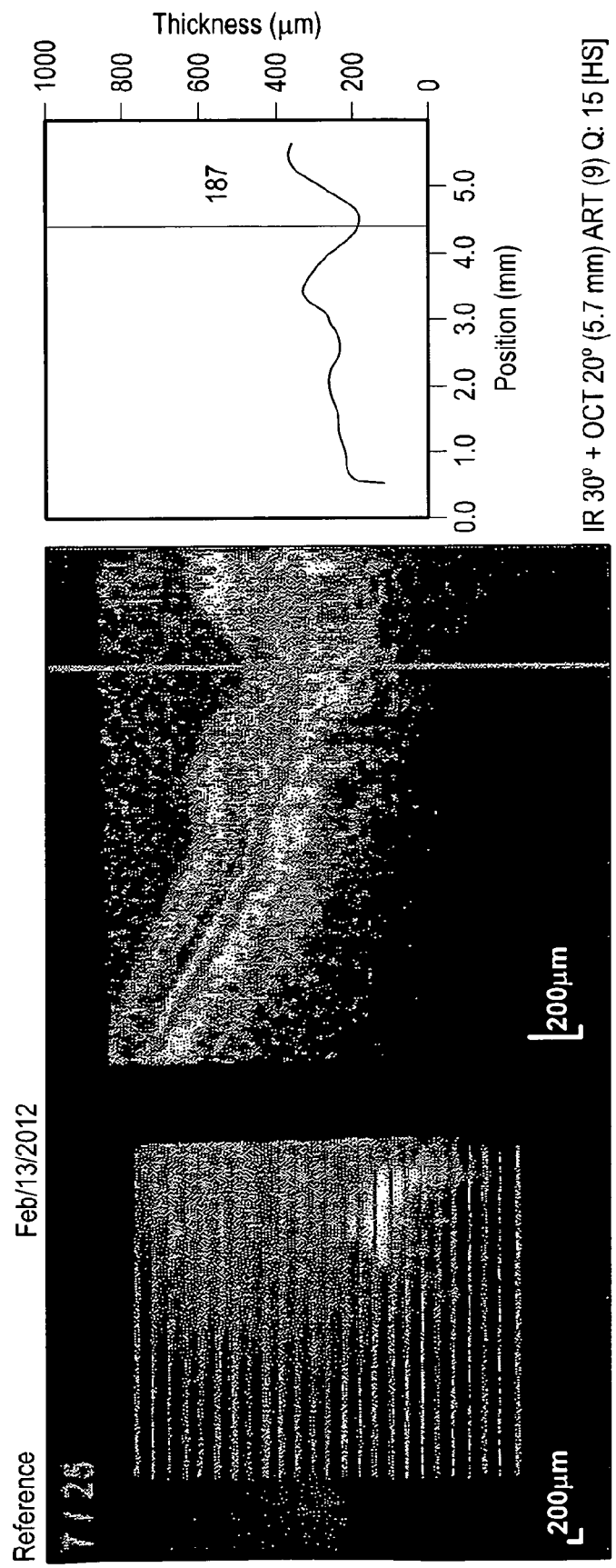
Figure 20:
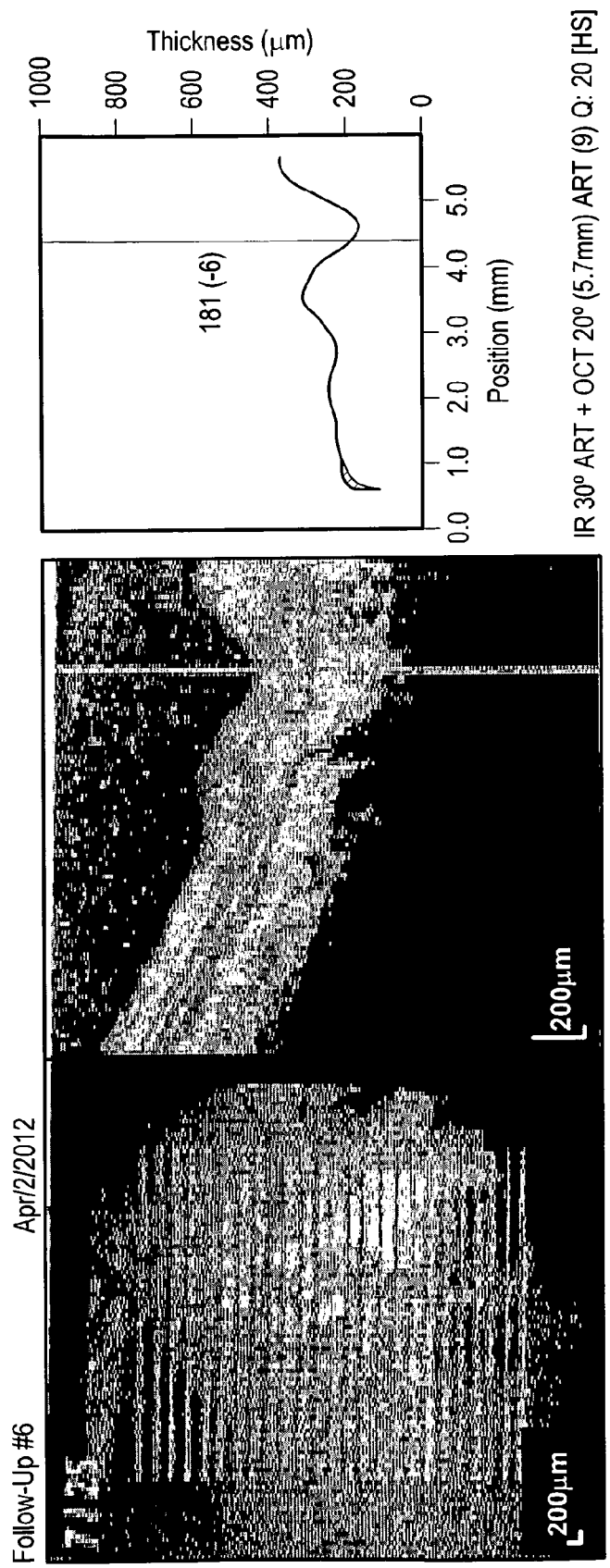

Case r)
74 year old female presented in 2008 with right wet AMD. She had eight intravitreal Lucentis injections. She was started on Omega 3RX® on May 19, 2011. The fluid resolved within five months of treatment and she gained one line of vision (FIG. 20).

Figure 21:
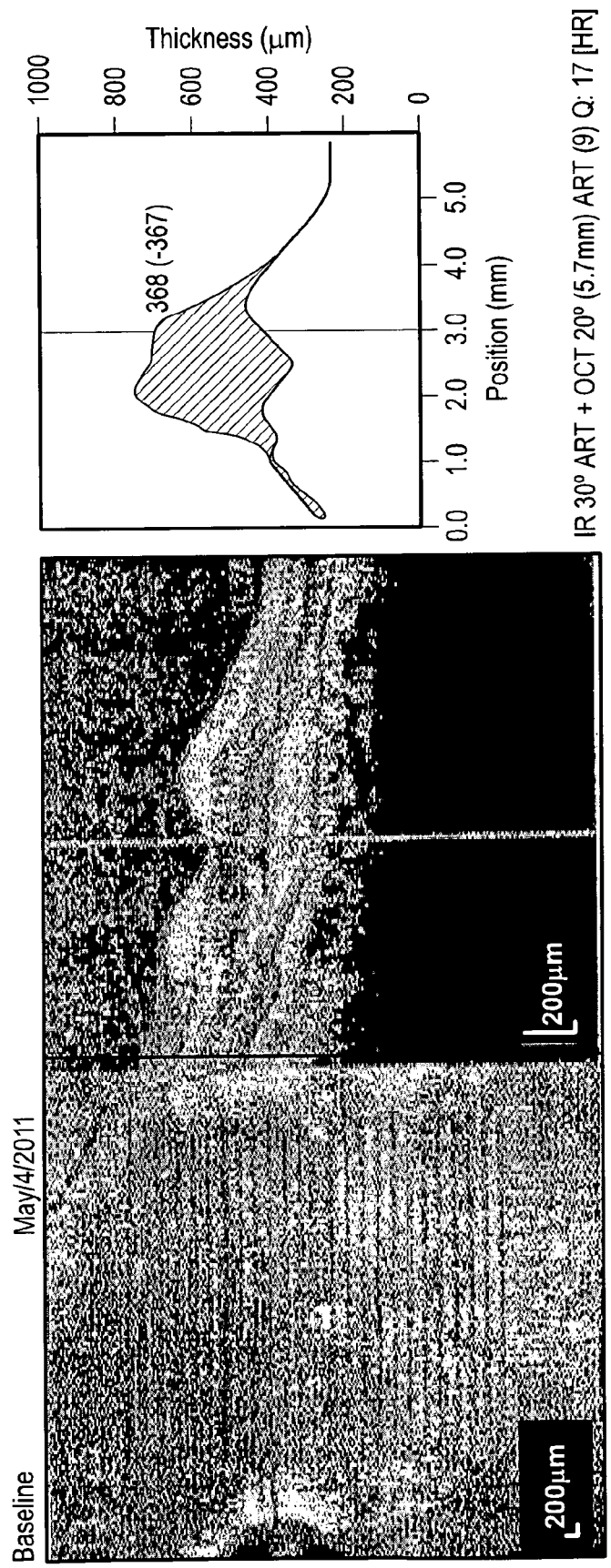
Figure 21:
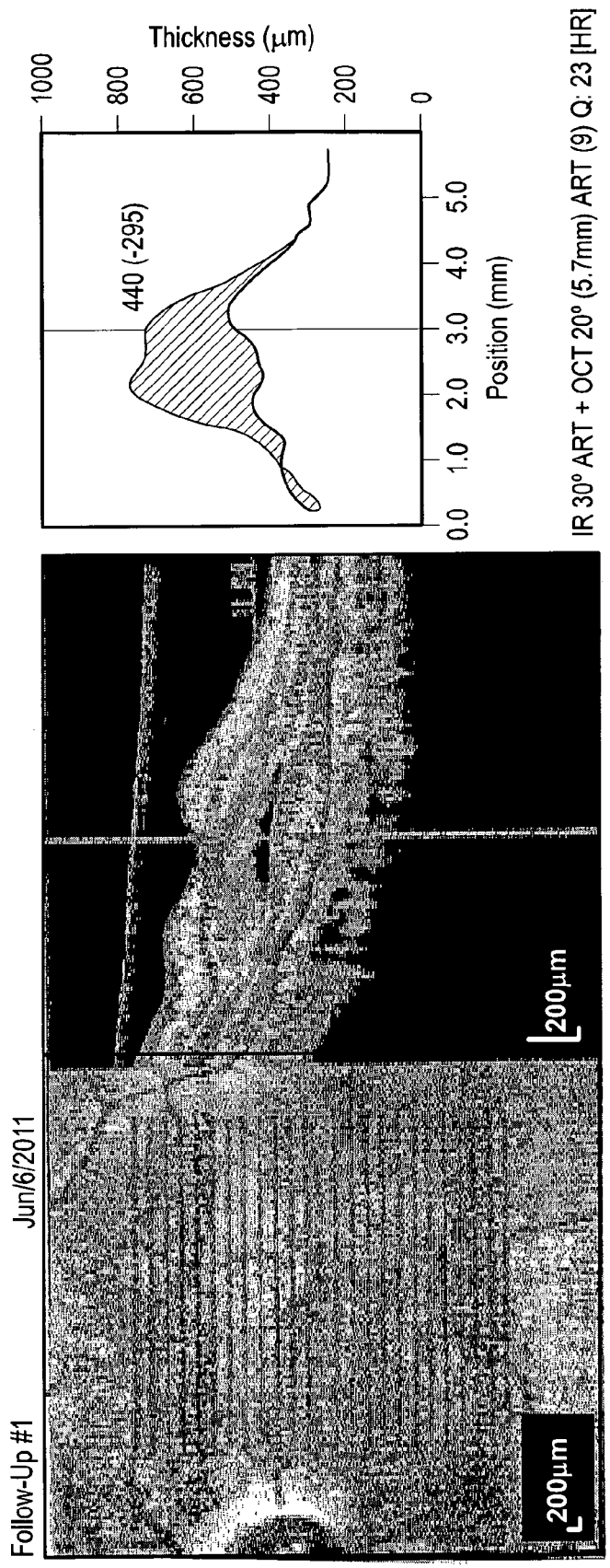
Figure 21:
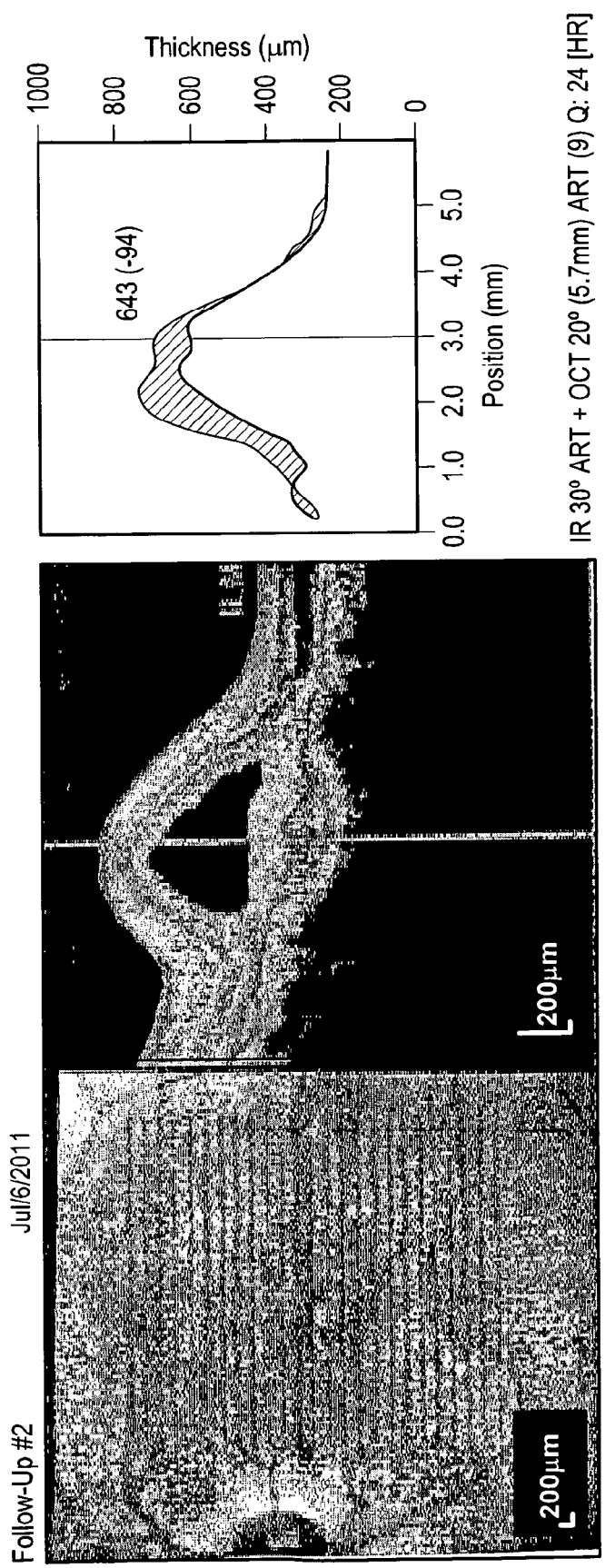
Figure 21:
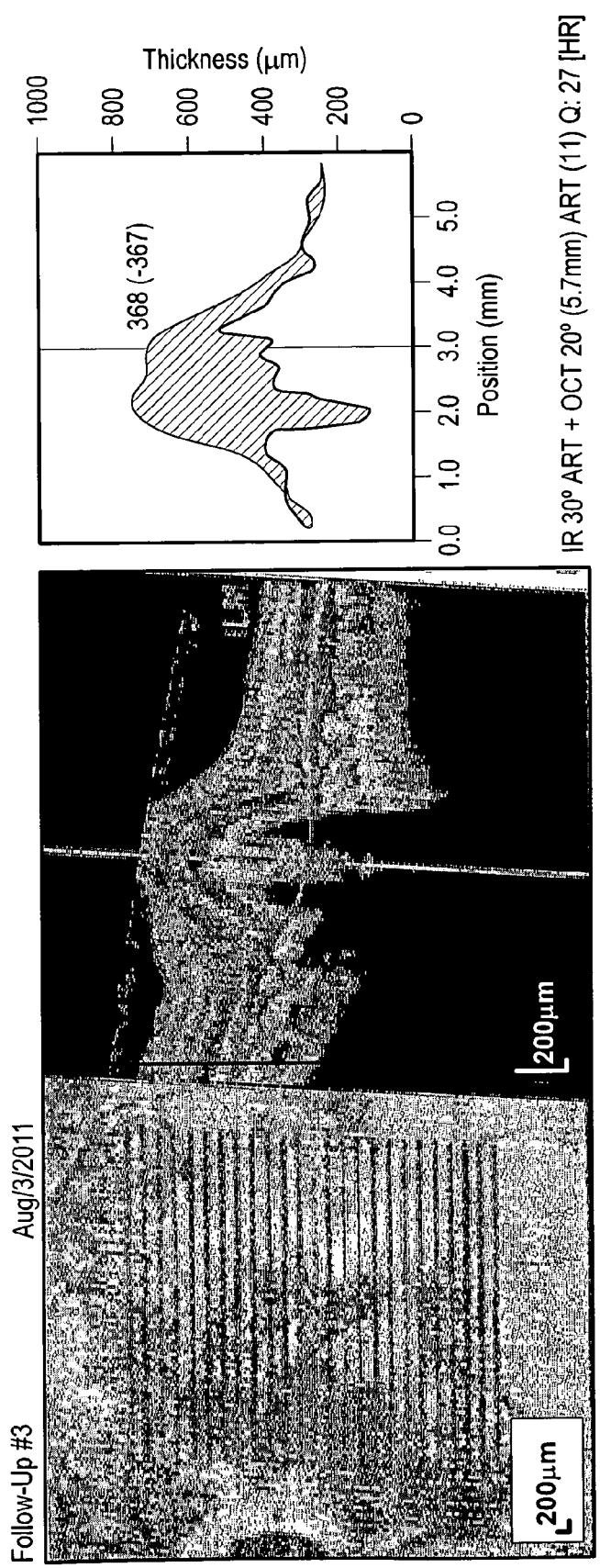
Figure 21:
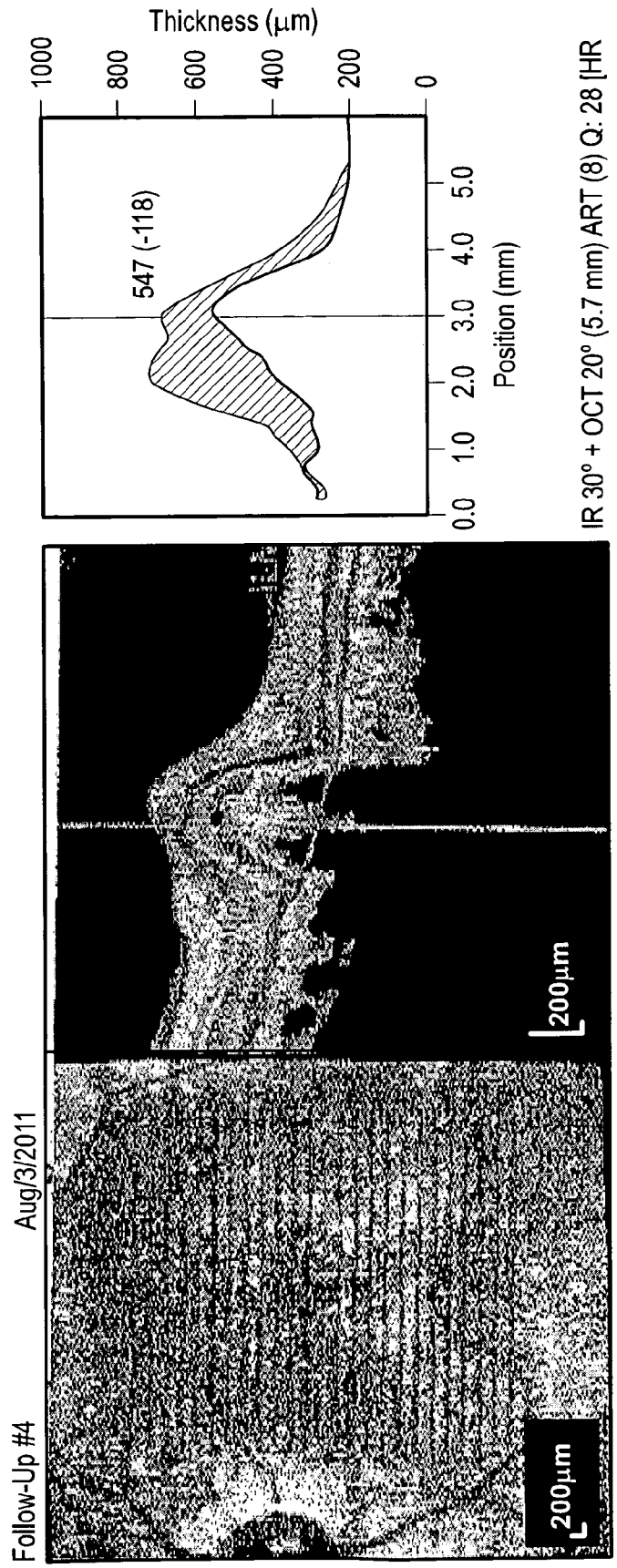
Figure 21:
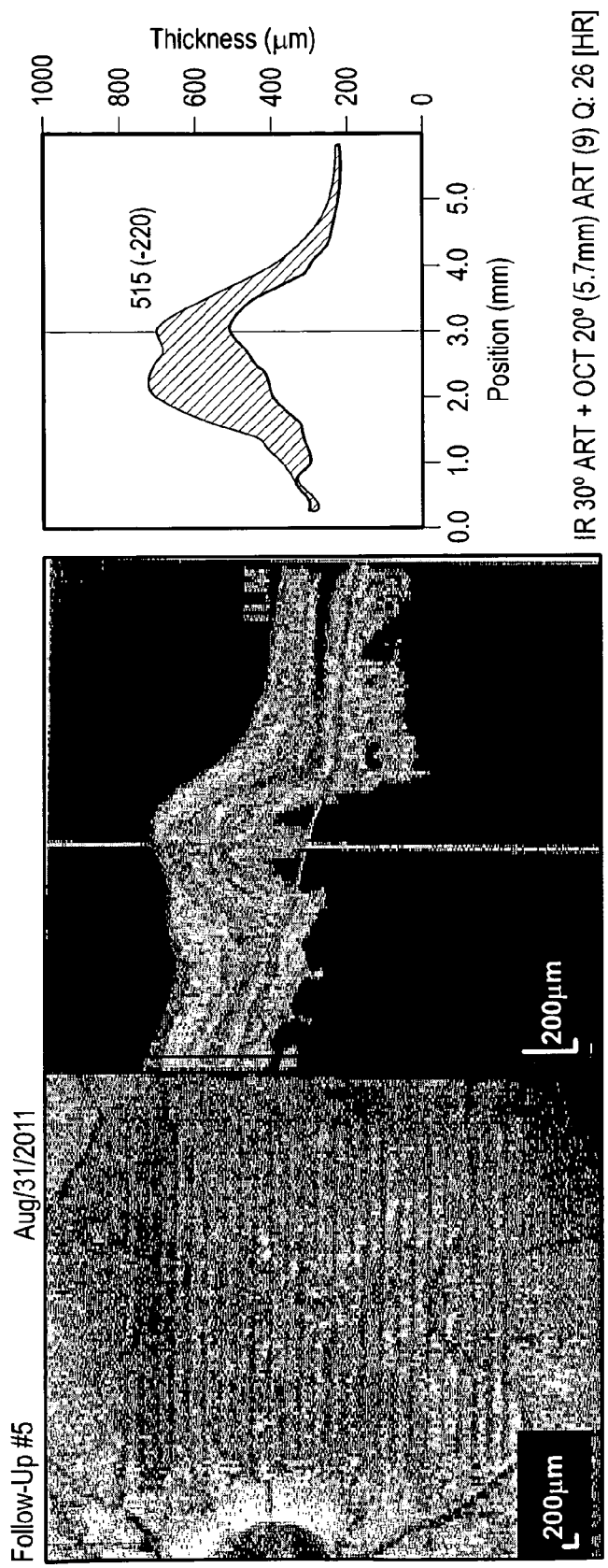
Figure 21:
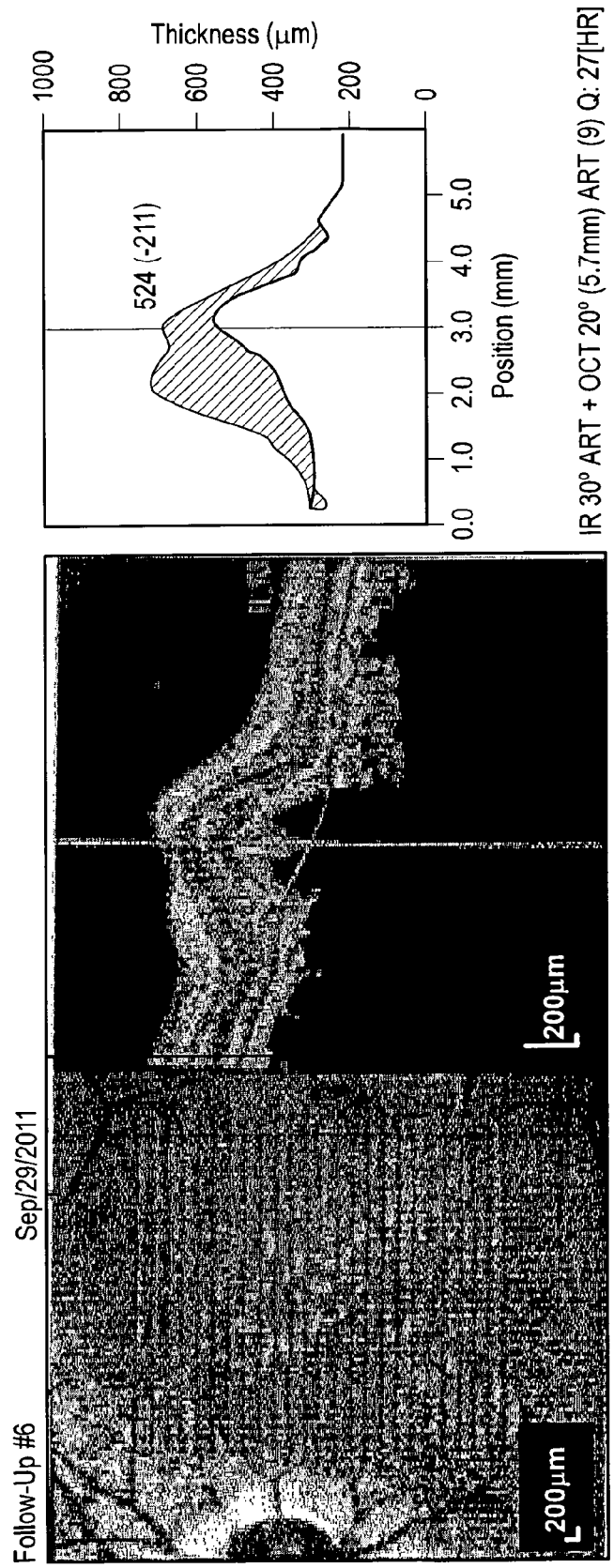
Figure 21:
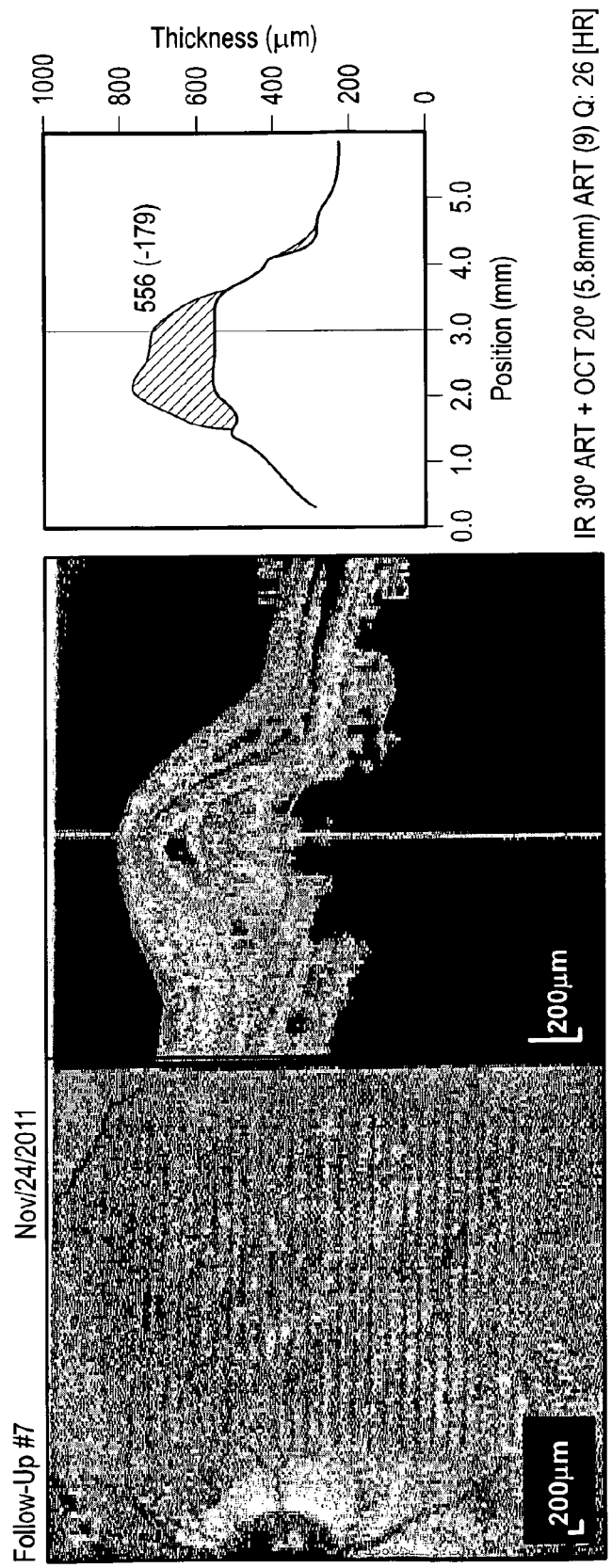
Figure 21:
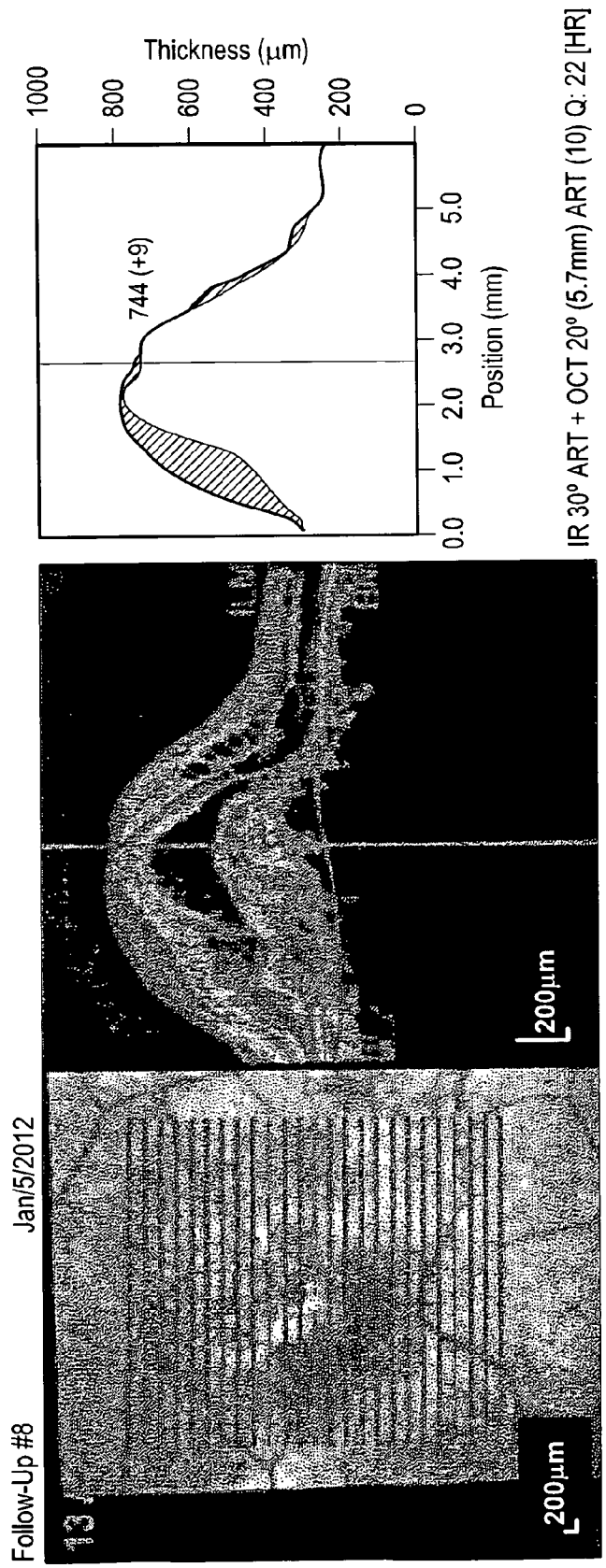
Figure 21:
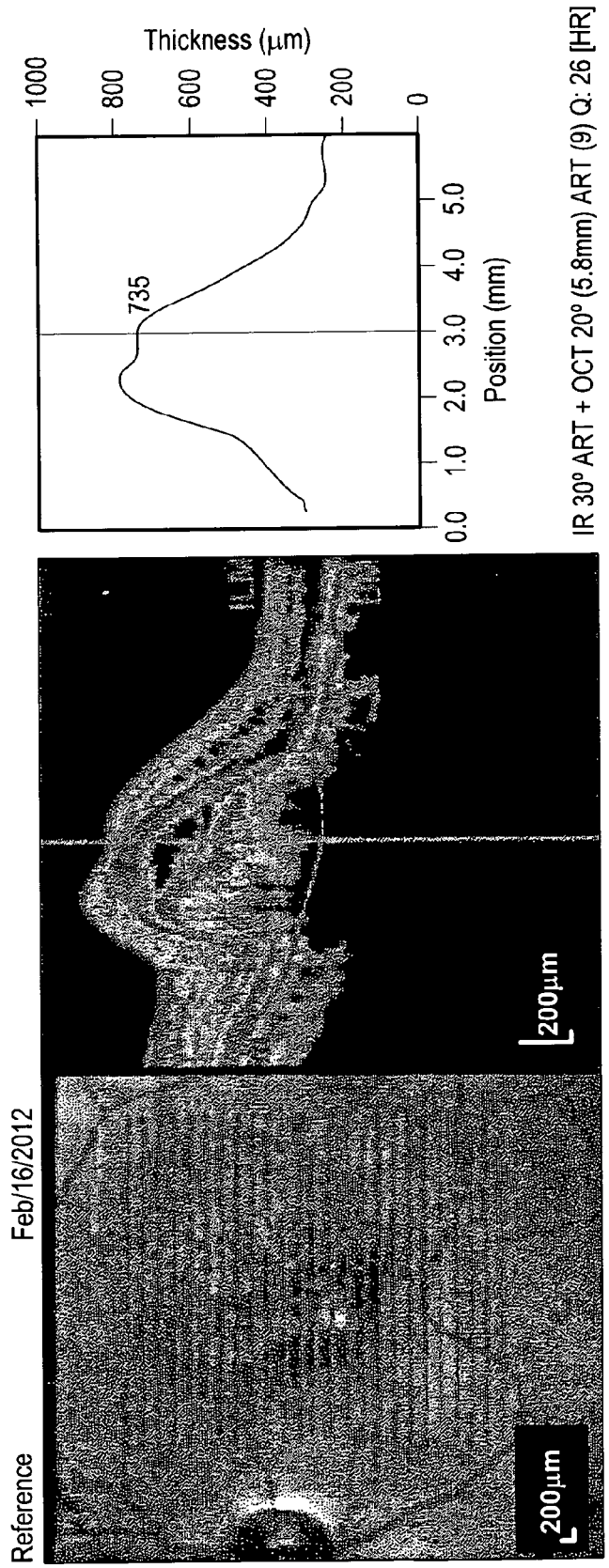
Figure 21:
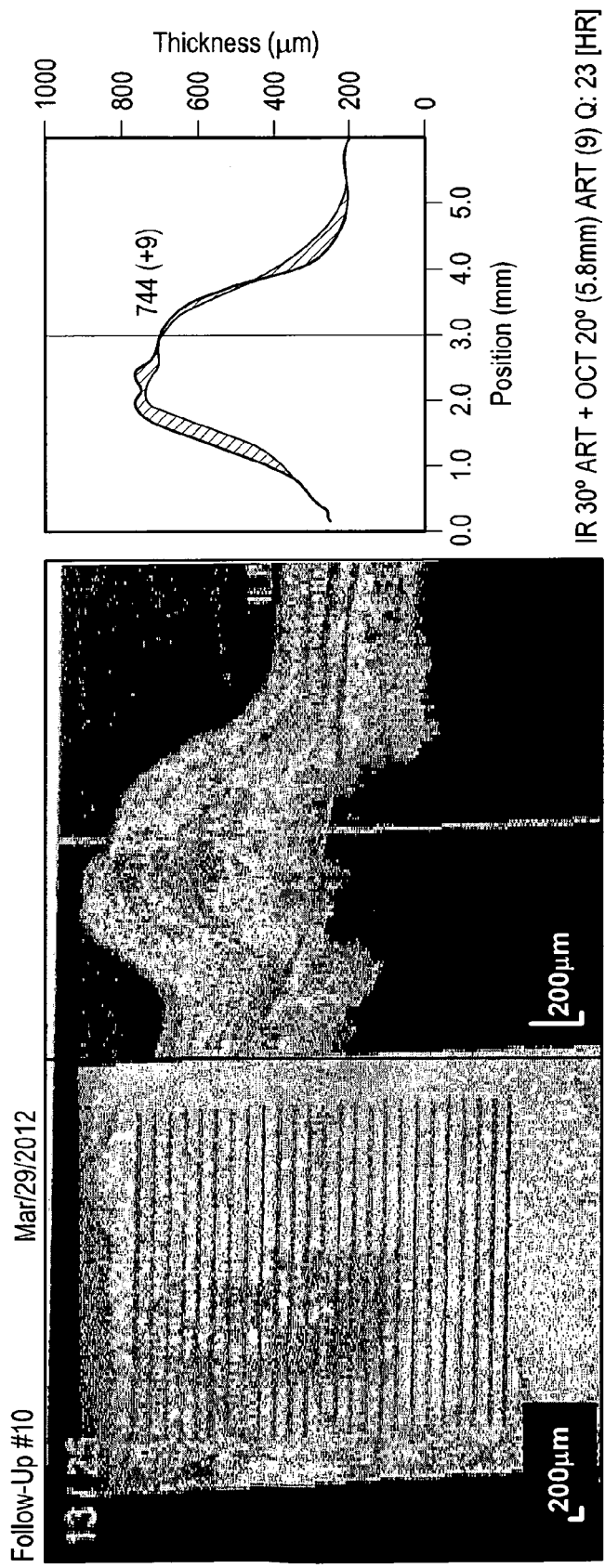

Case s)
72 year old male presented with left wet AMD. He had eight intravitreal Lucentis injections, the last one on Jan. 5, 2012, also started on Omega 3RX®. Three months following treatment there was no fluid (FIG. 21).

Figure 22:
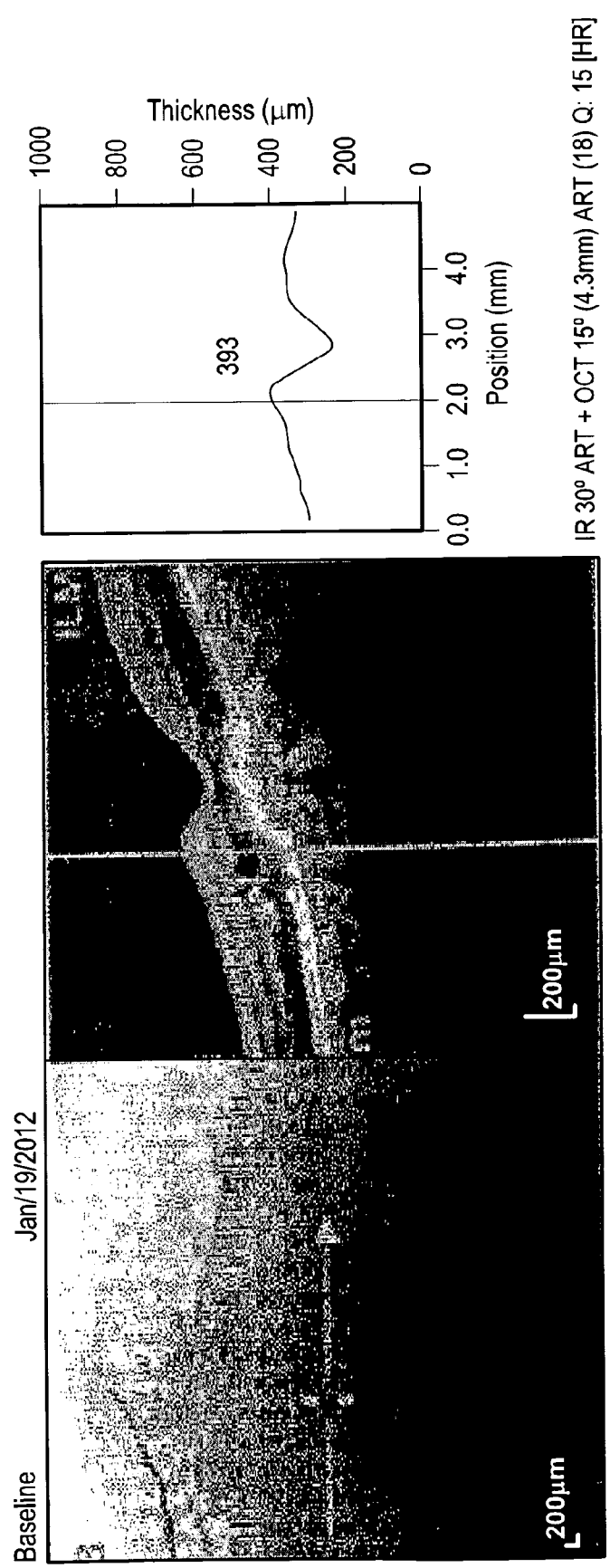
Figure 22:
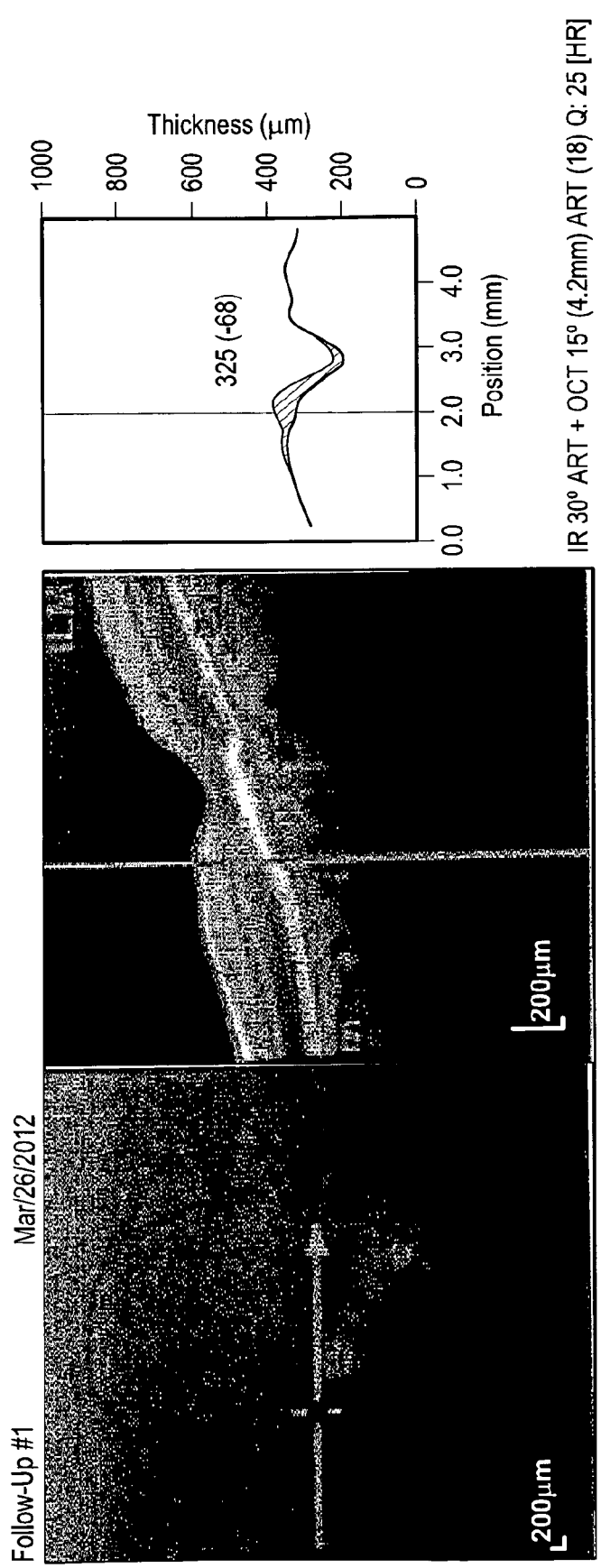

Case t)
72 year old man presented with left wet AMD. He was treated with intravitreal Avastin and was started with Omega 3RX®. Two months following treatment the fluid resolved and he gained four lines of vision (FIG. 22).

Figure 23:
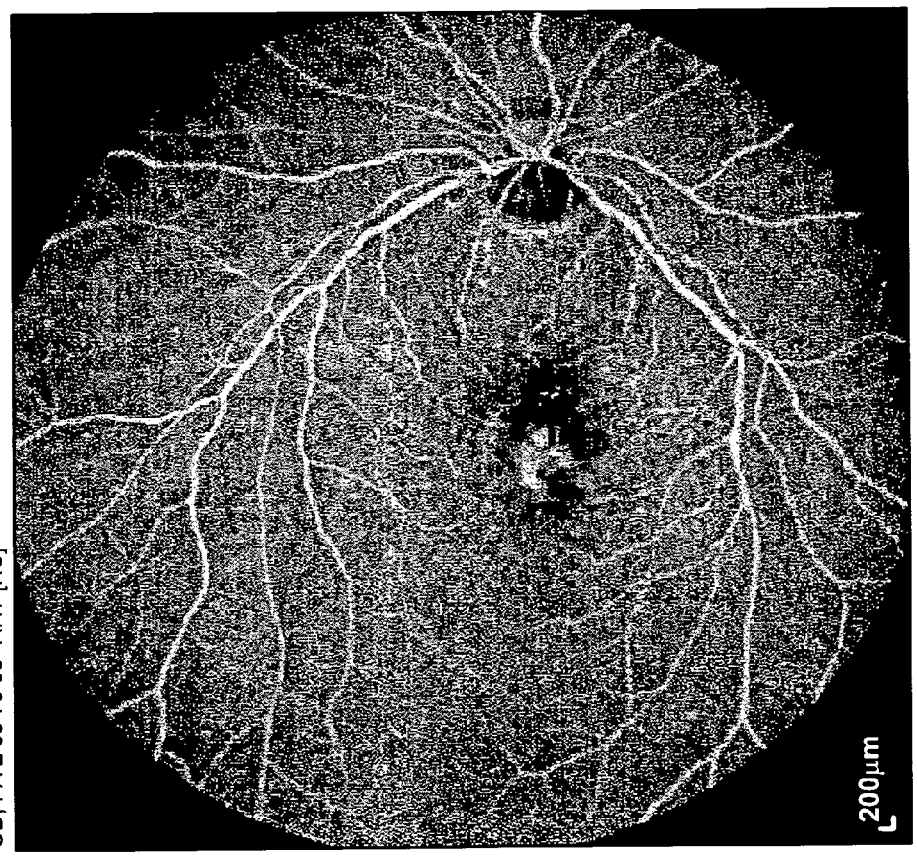
Figure 23:
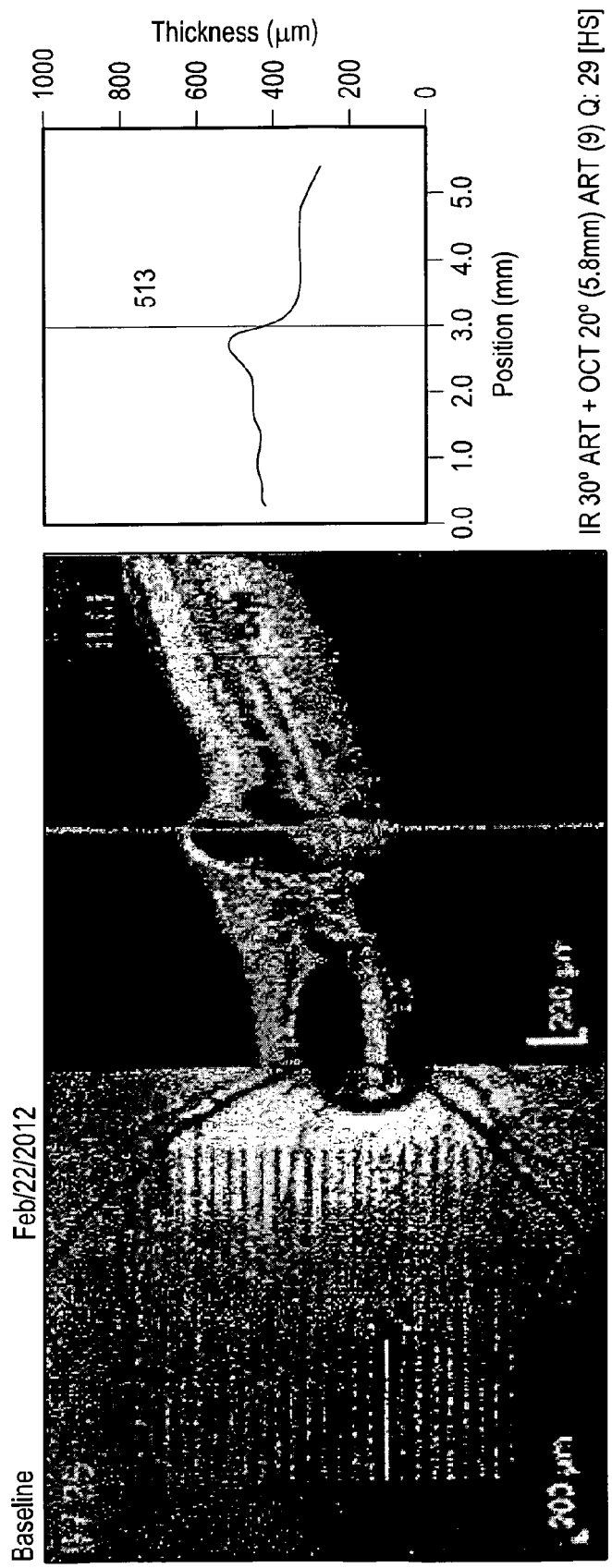
Figure 23:
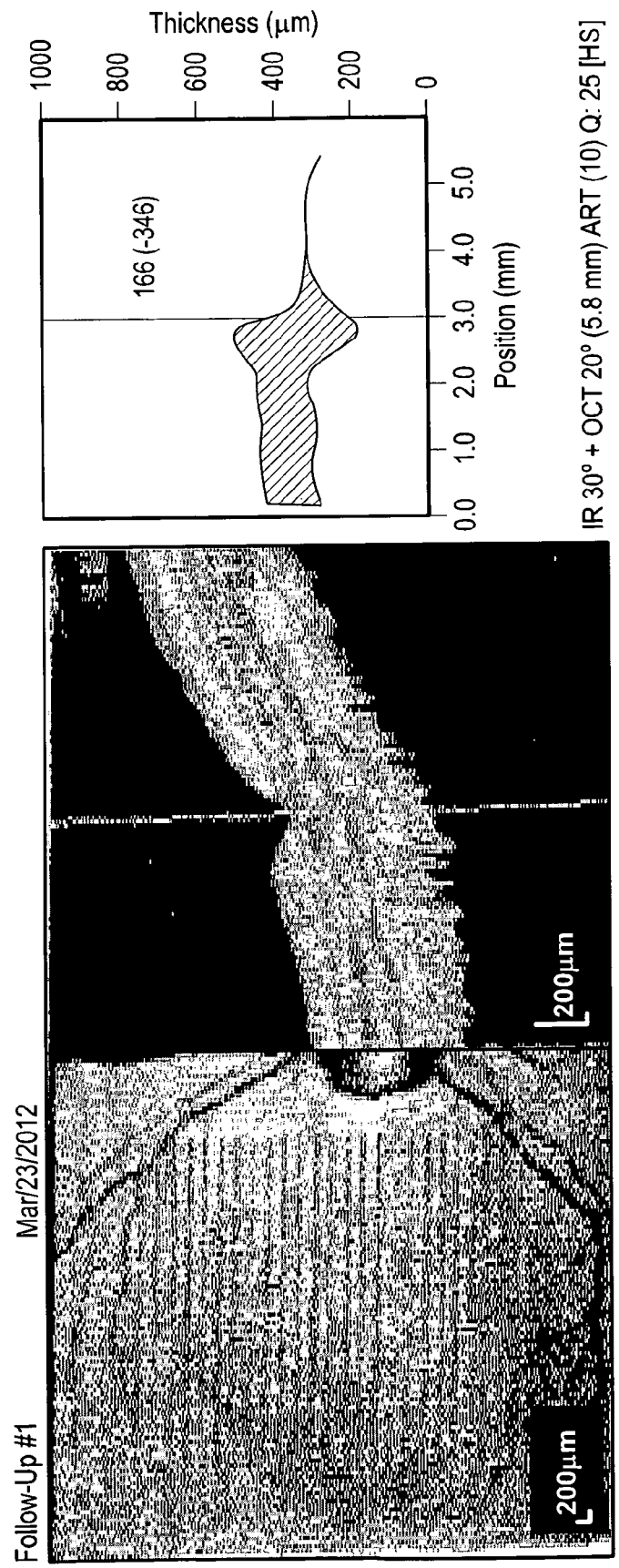
Figure 23:
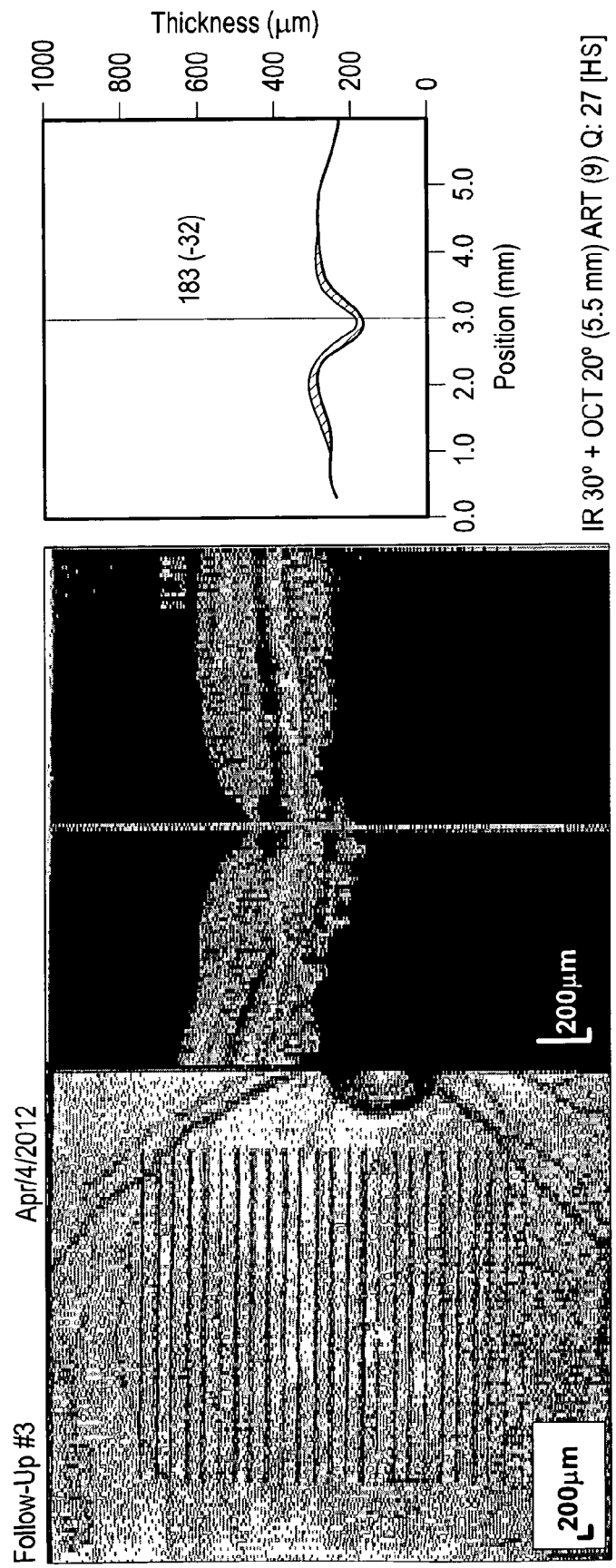
Figure 23:
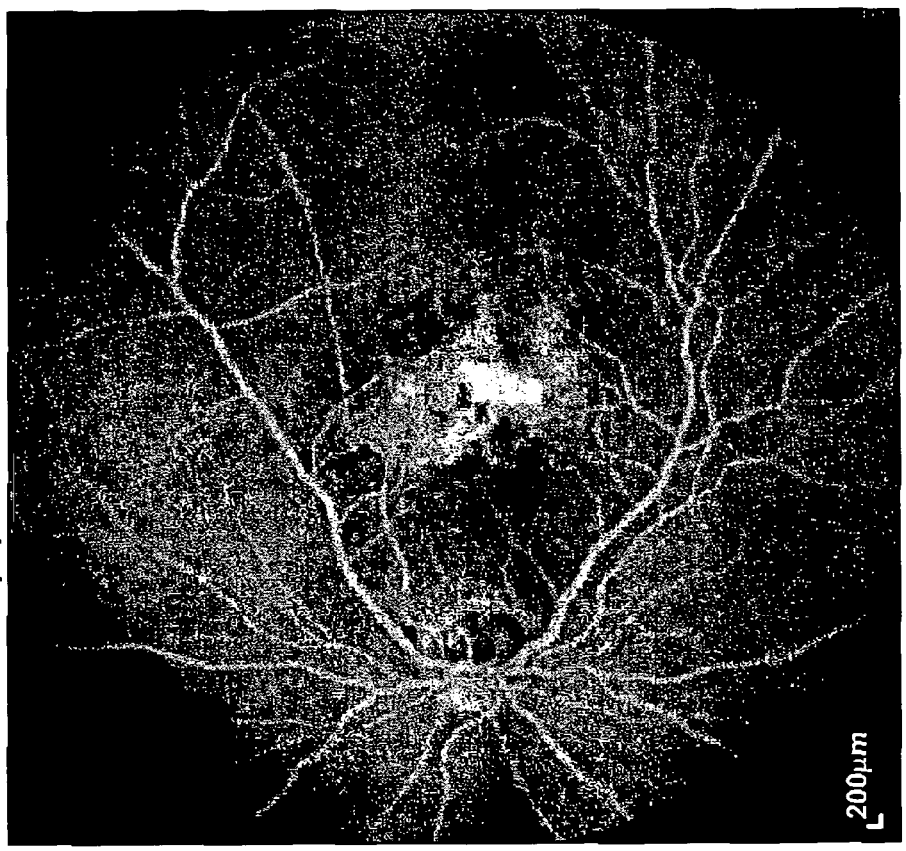
Figure 23:
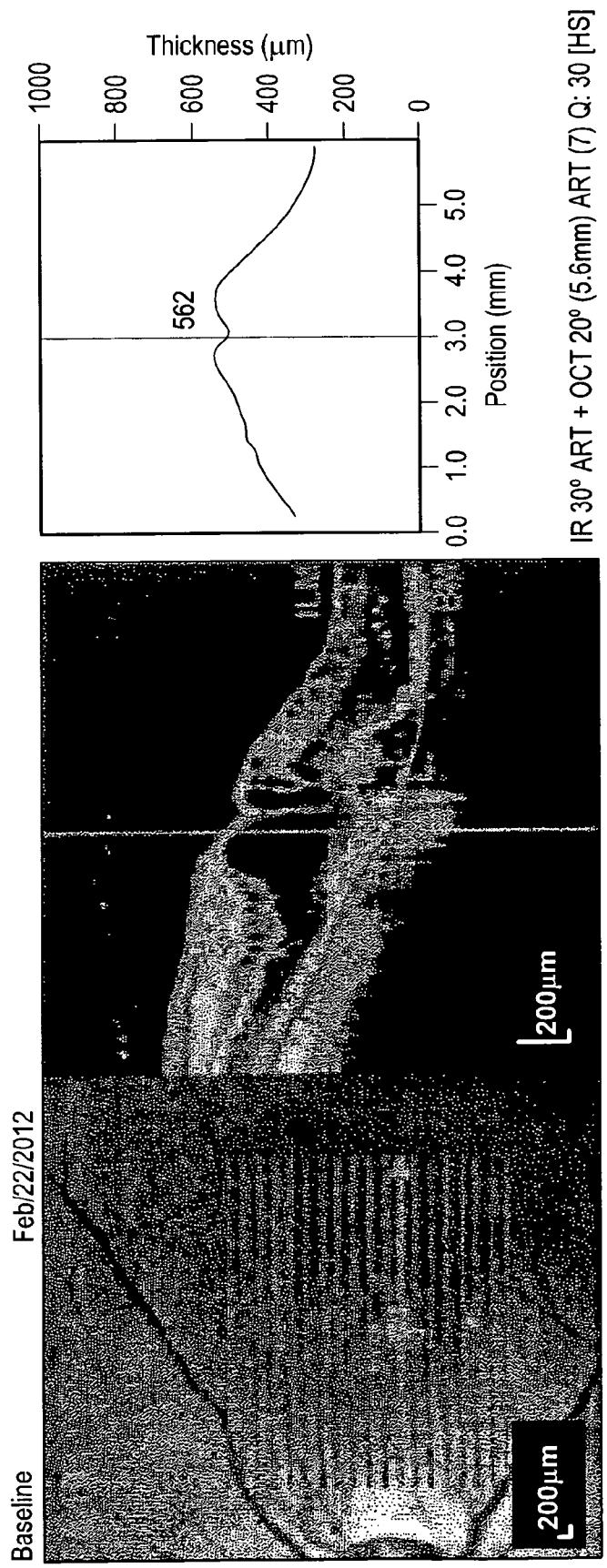
Figure 23:
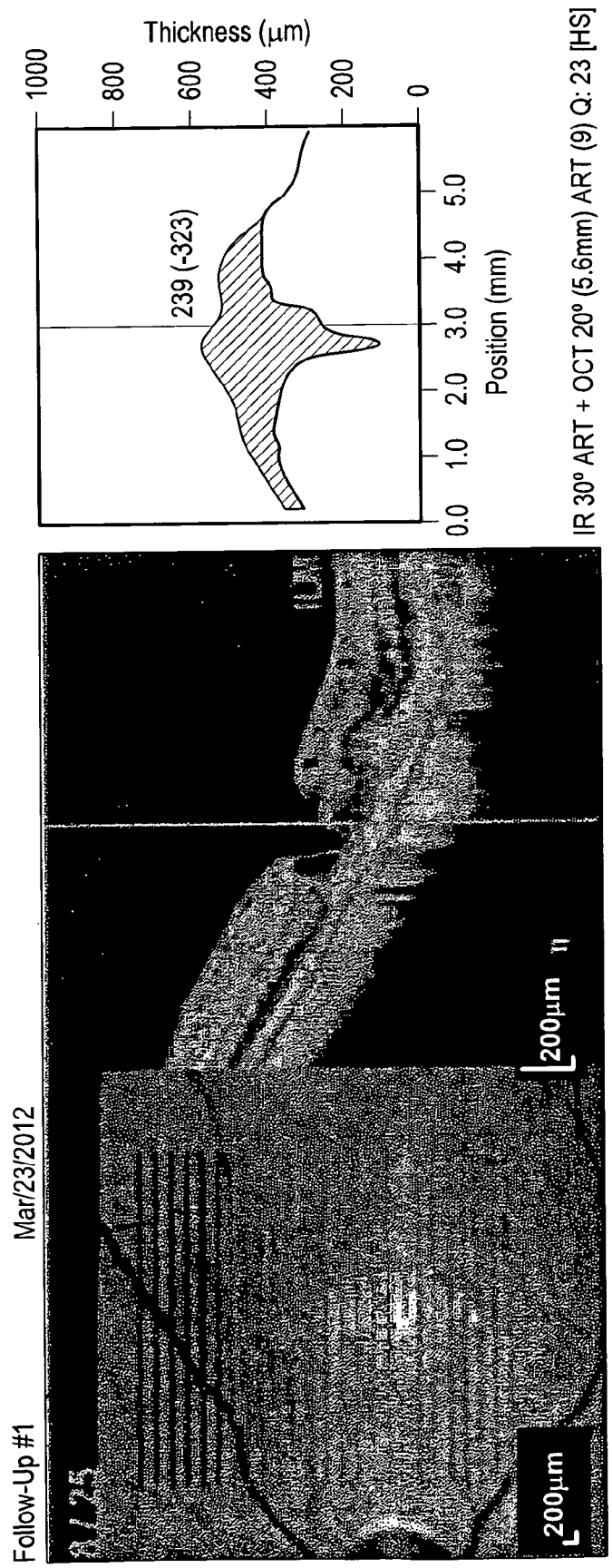
Figure 23:
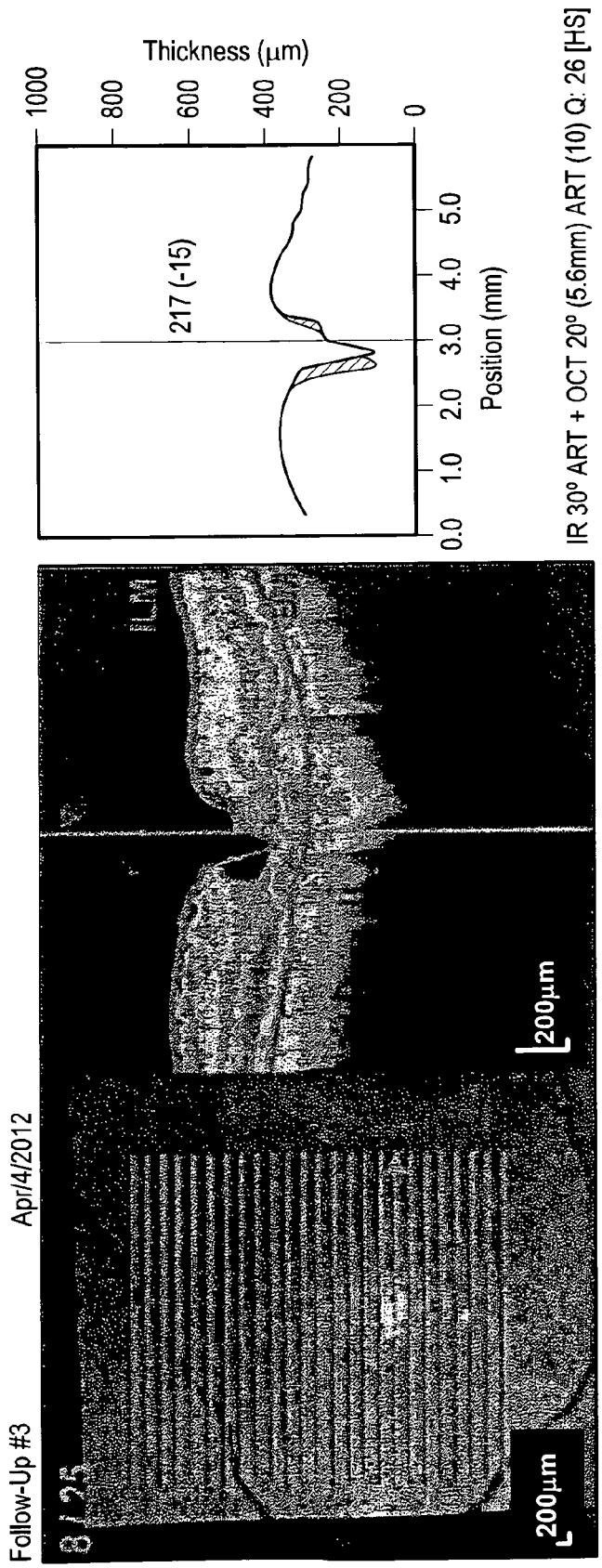

Case u)
72 year old female presented on Feb. 22, 2012 with bilateral wet AMD. She was treated with bilateral intravitreal Avastin injections and was started on Omega 3RX®. A month following treatment there was resolution of fluid and she gained one line vision in each eye (FIG. 23).

Figure 24:
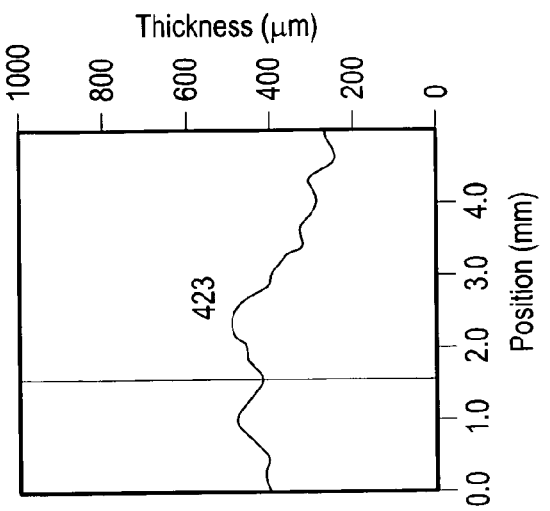
Figure 24:
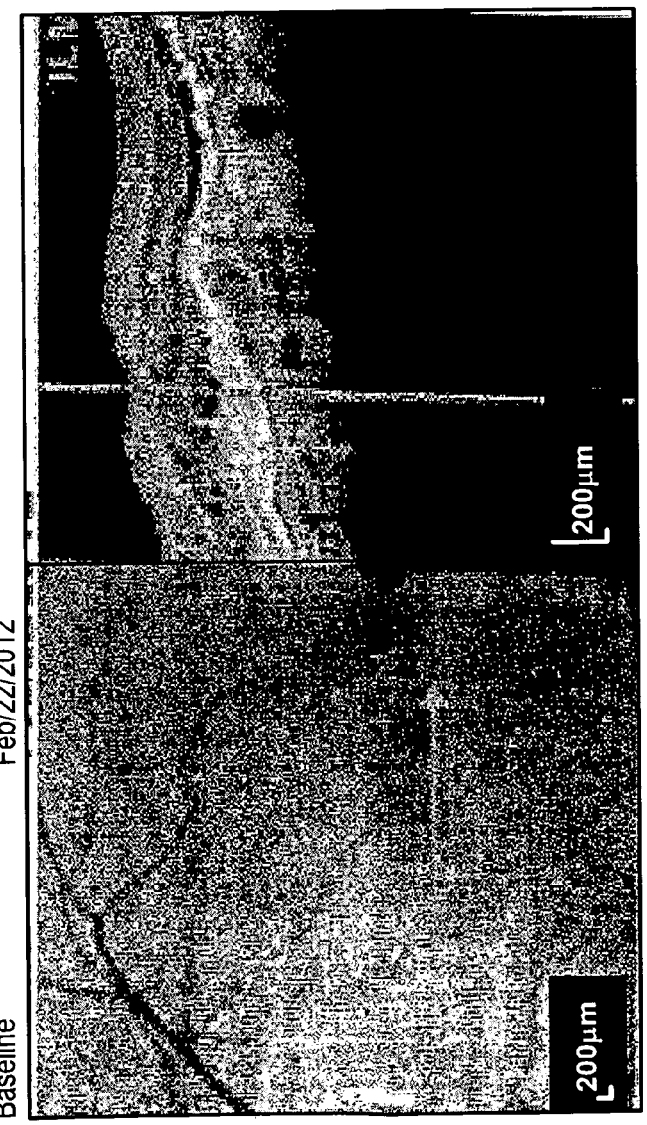
Figure 24:
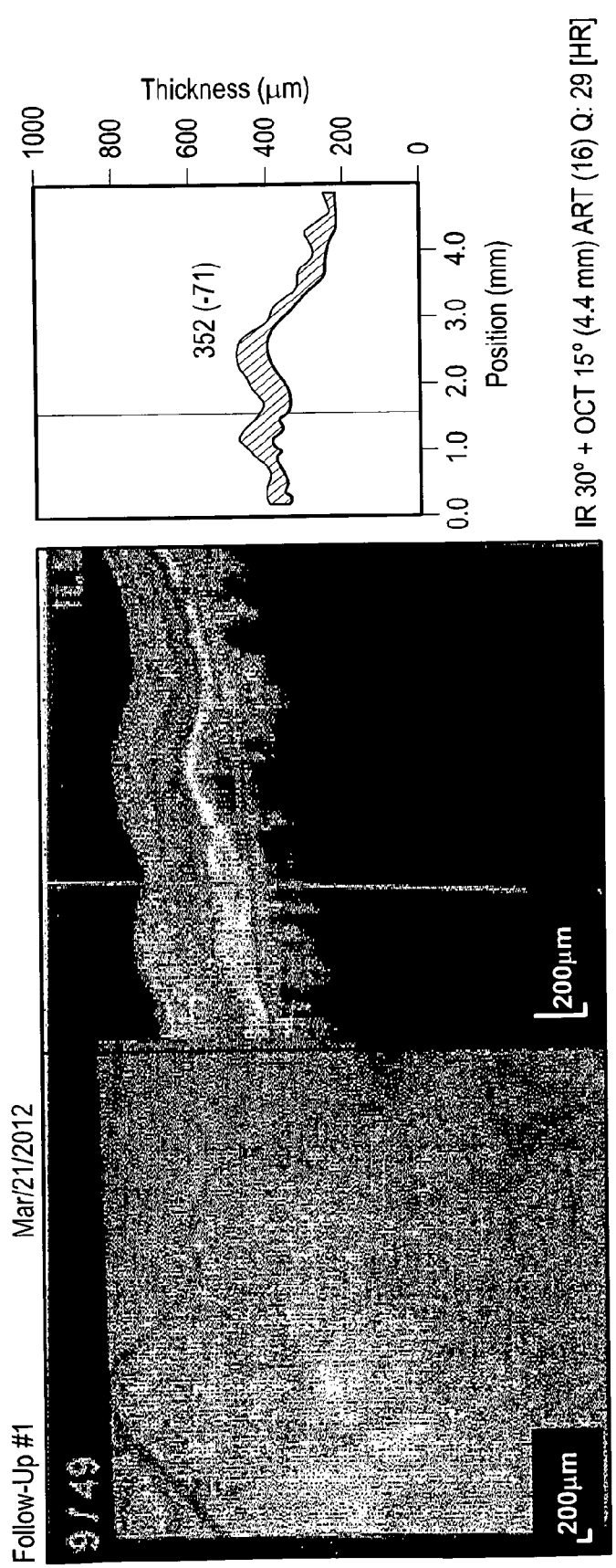

Case v)
82 year old male presented with a left eye wet AMD on 29.4.09 was treated with four intravitreal Lucentis injections. He presented again on Feb. 22, 2012 with left wet AMD and vision of 6/18. He was treated with intravitreal Avastin and Omega 3RX®, and a month later there was no fluid and he gained one line of vision (FIG. 24).

Figure 25:
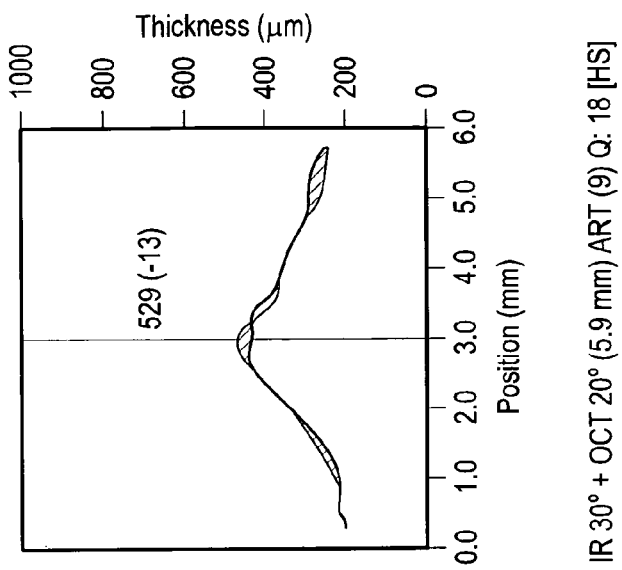
Figure 25:
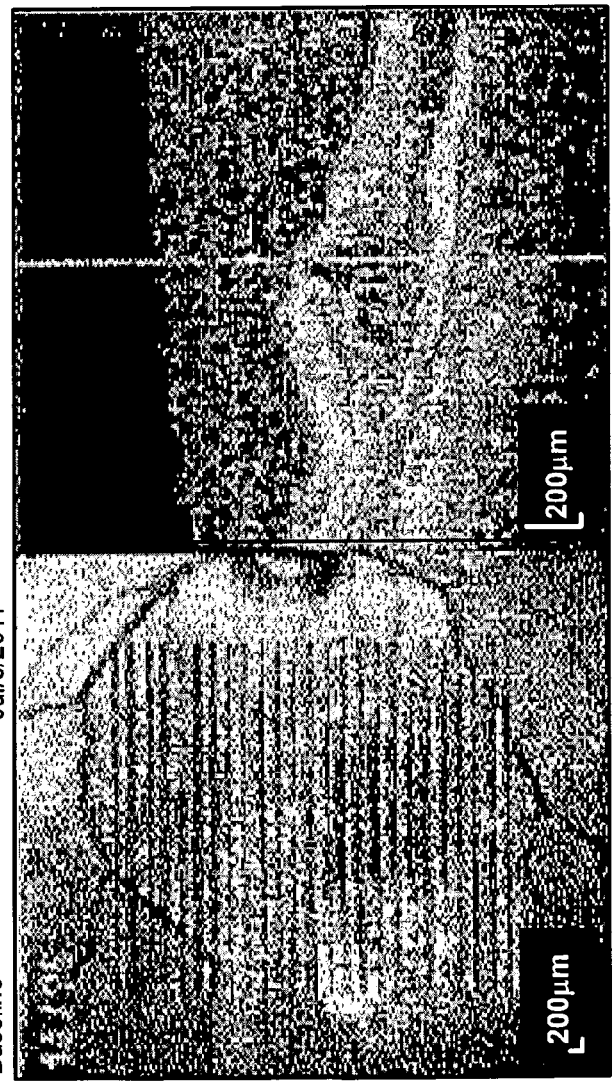
Figure 25:
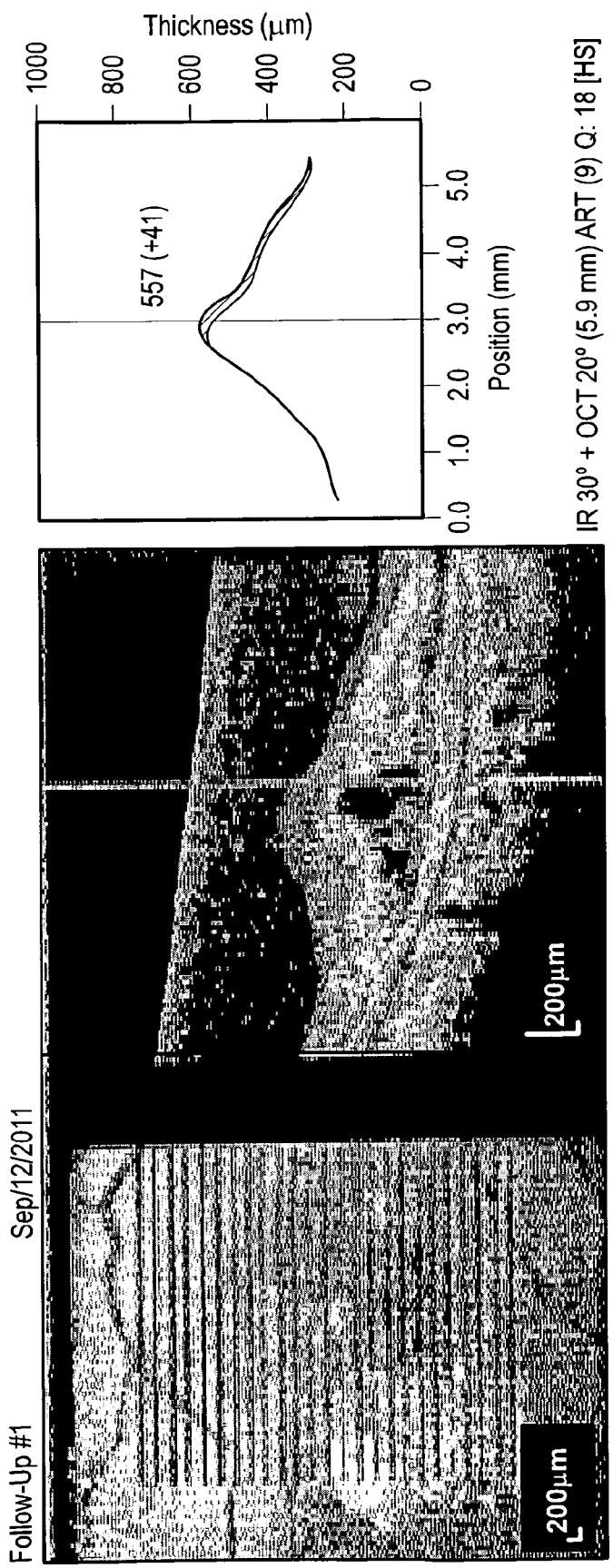
Figure 25:
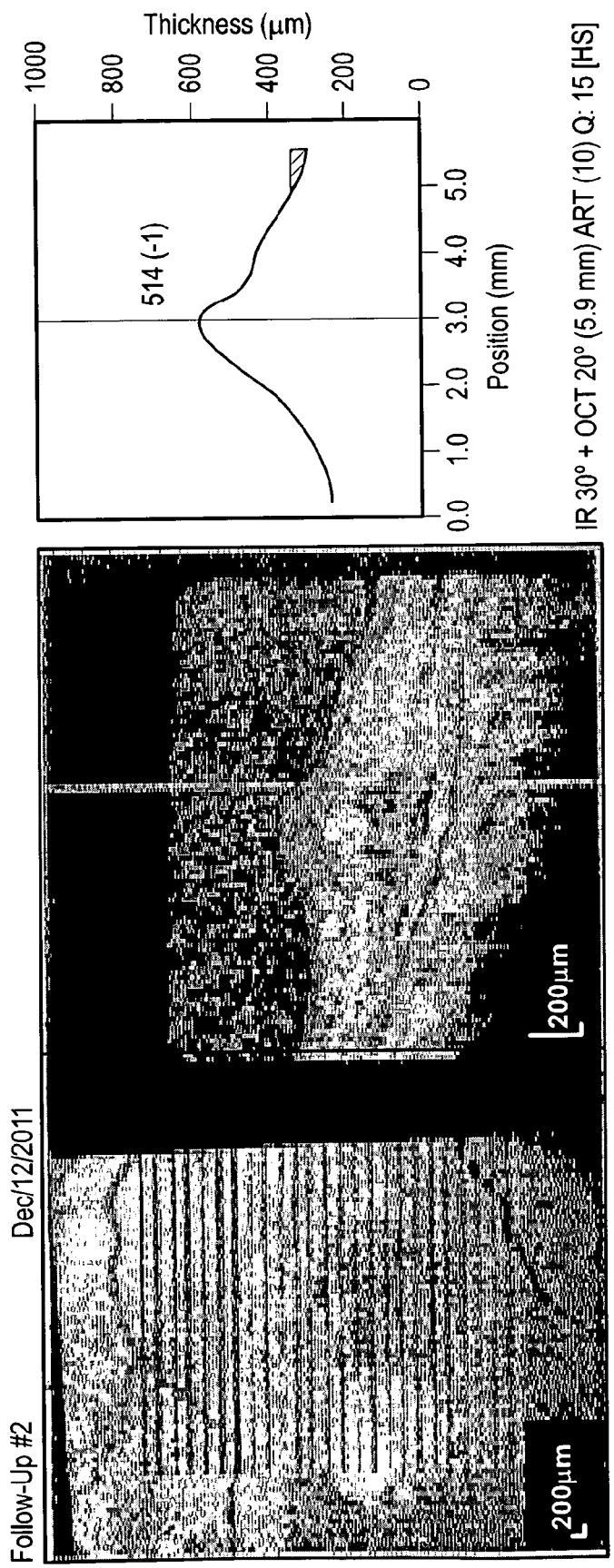
Figure 25:
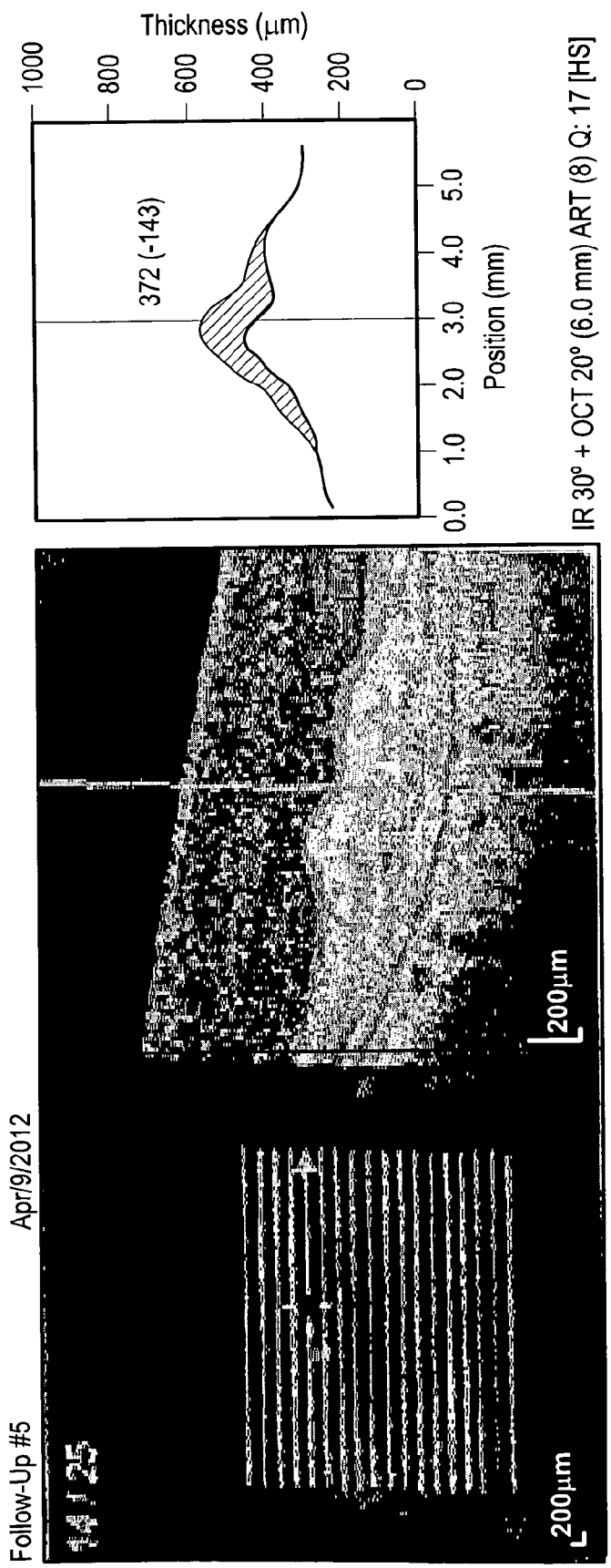

Case w)
78 year old female presented with right wet AMD in 2008. She was treated with eleven intravitreal Avastin injections. On Dec. 12, 2011 she was started on Omega 3RX®. Three months following treatment there was no fluid and she gained one line of vision (FIG. 25).

Case x)

Figure 26:
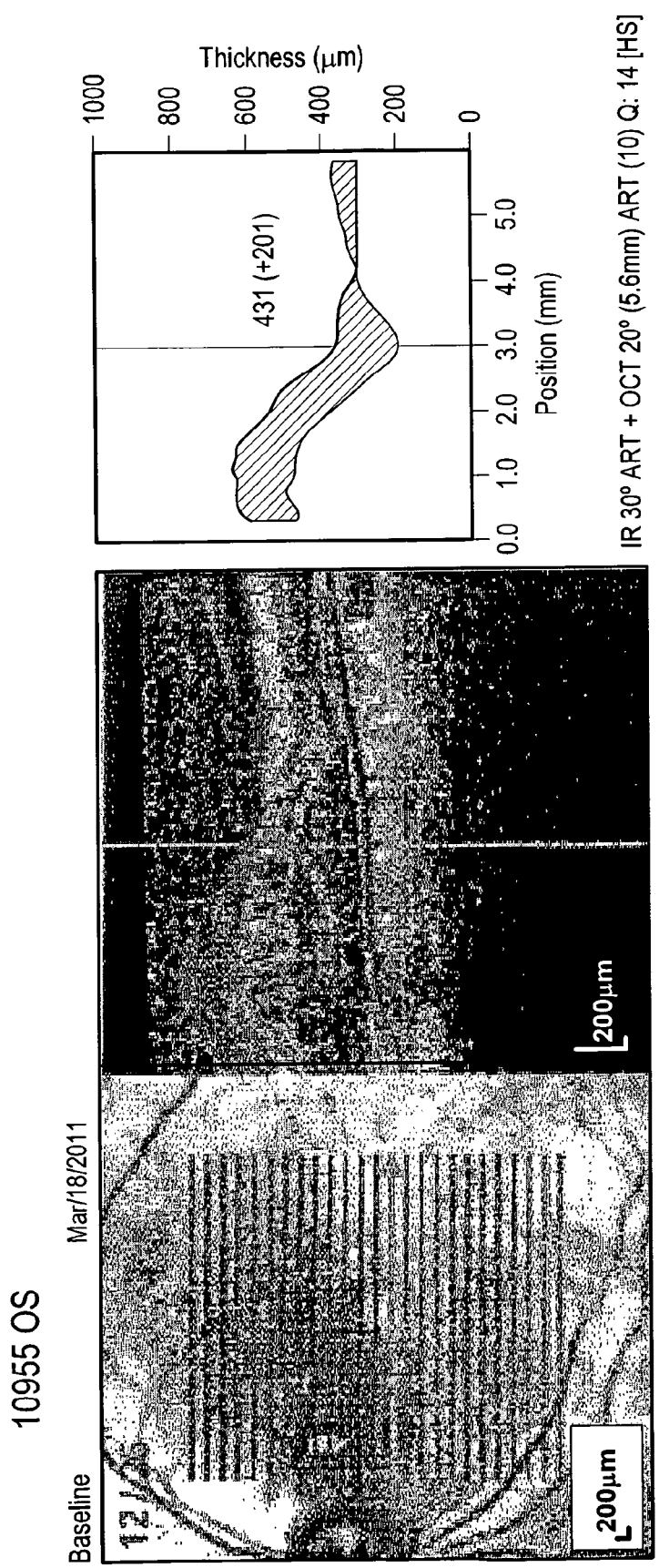
Figure 26:
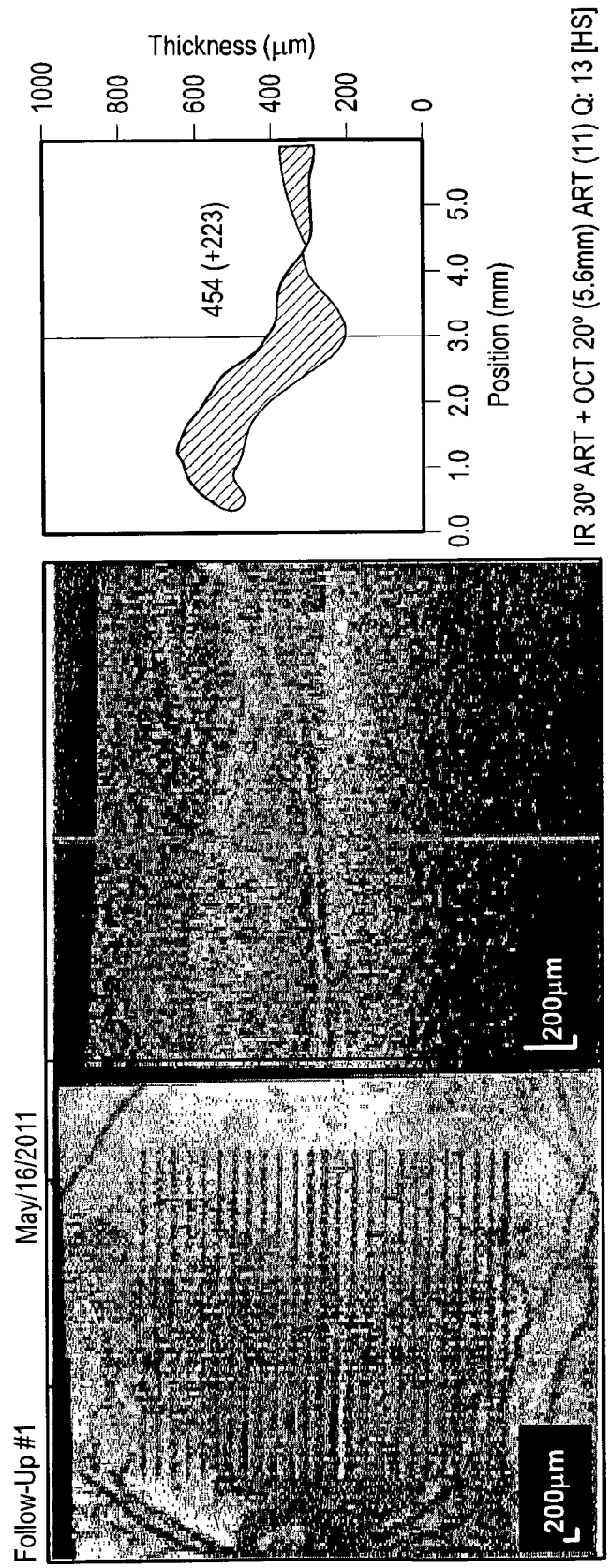
Figure 26:
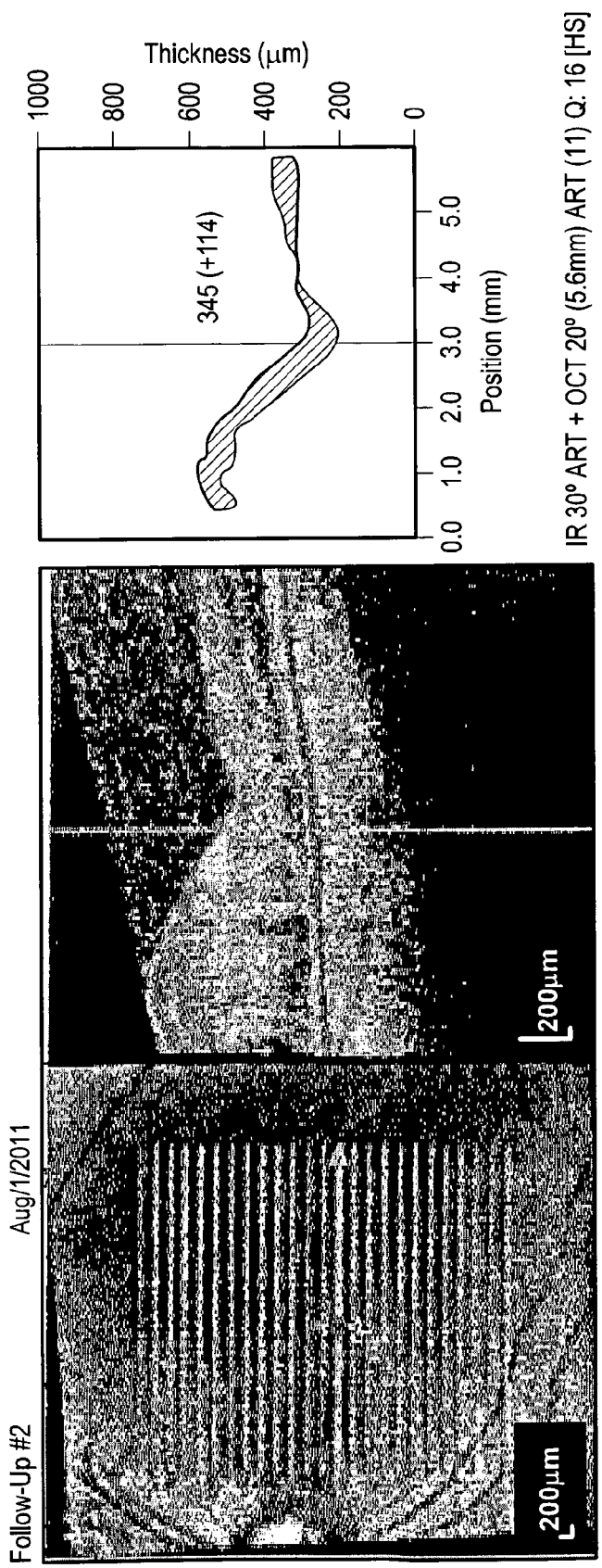
Figure 26:
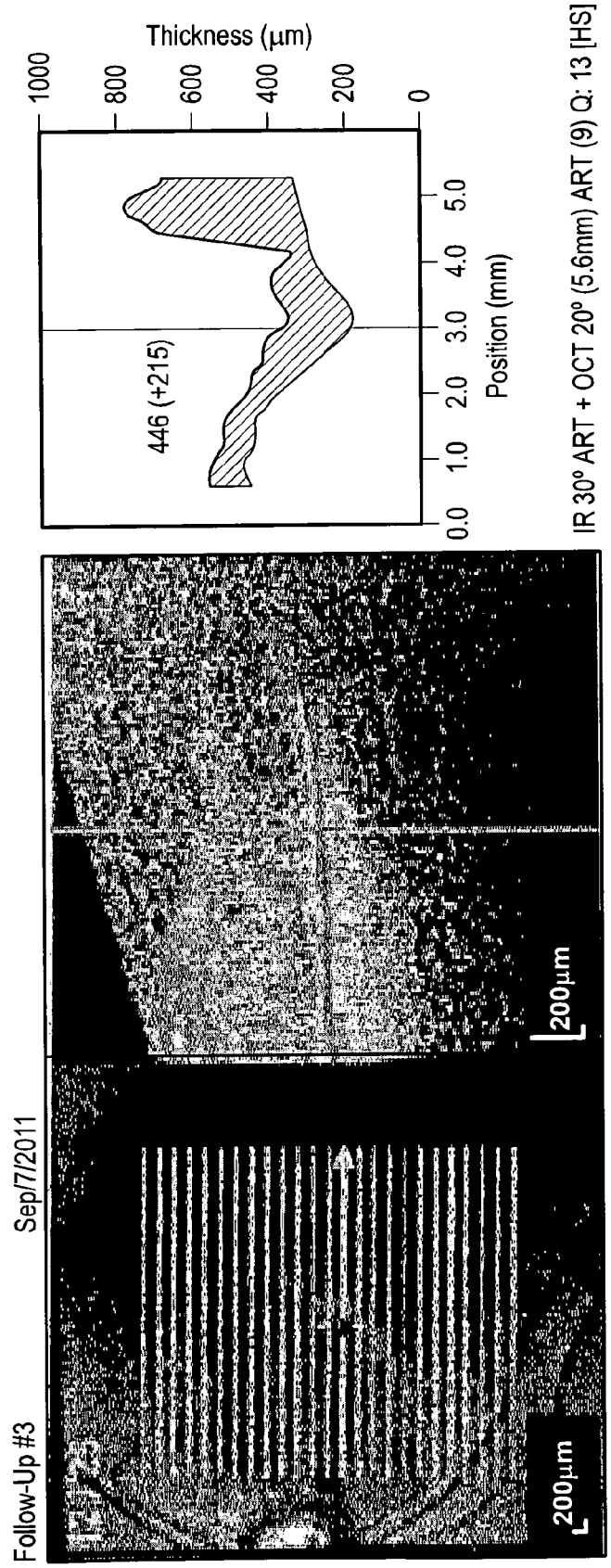
Figure 26:
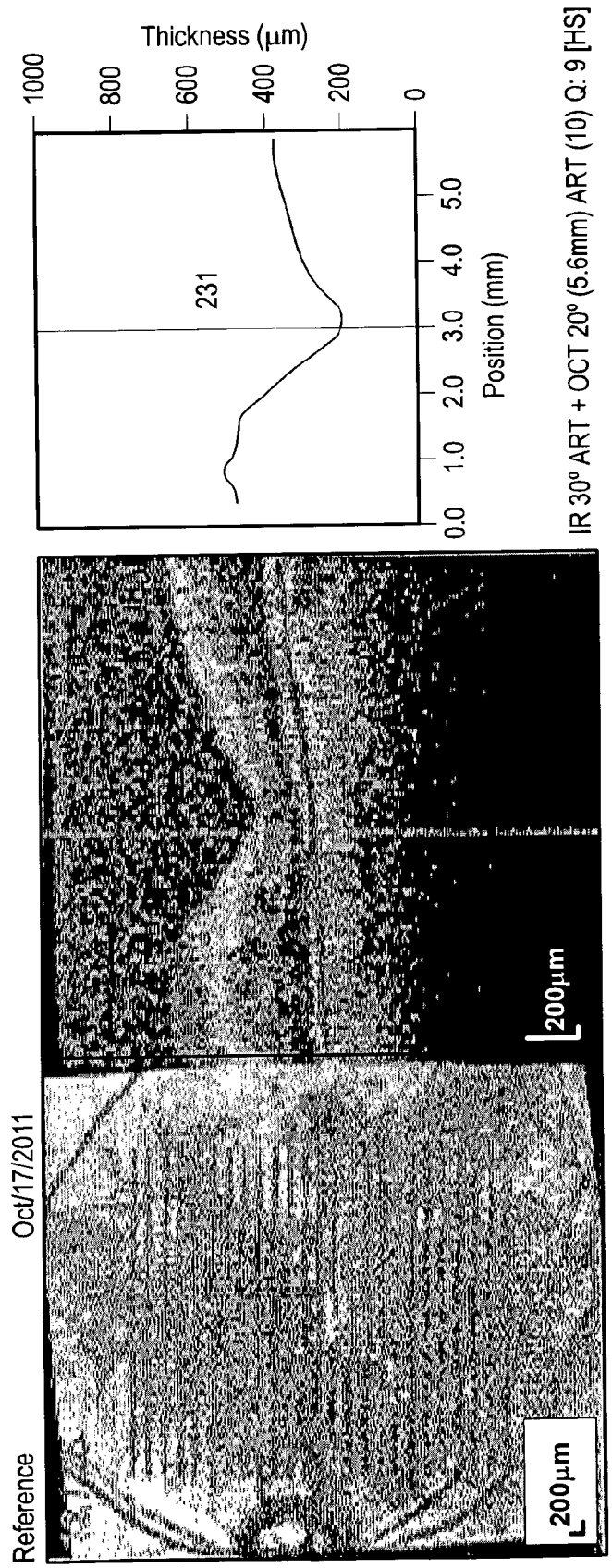
Figure 26:
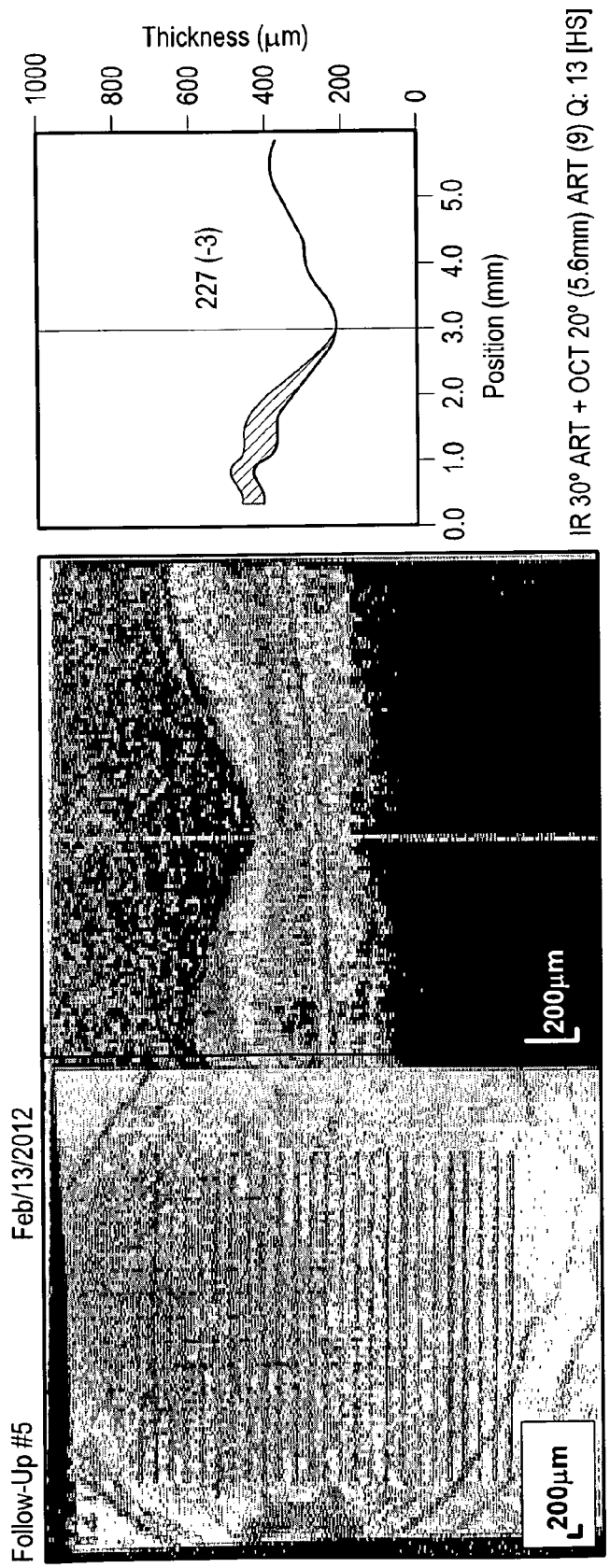
Figure 26:
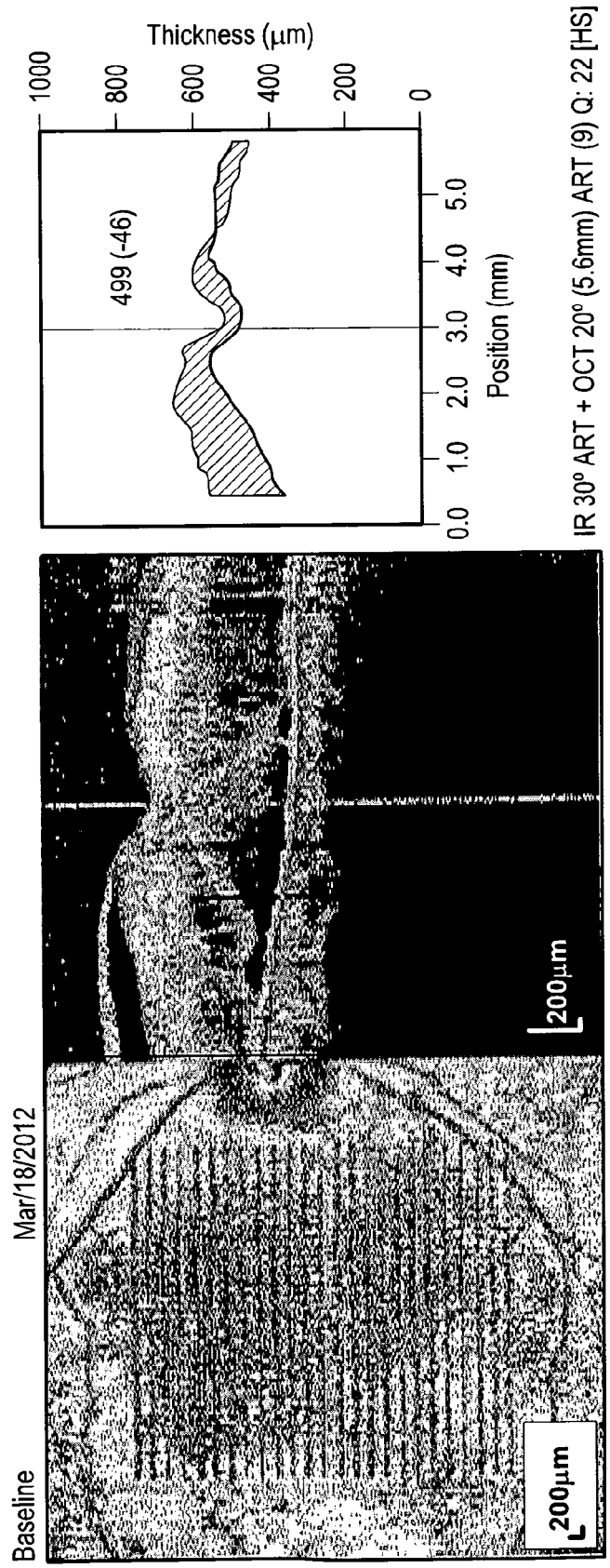
Figure 26:
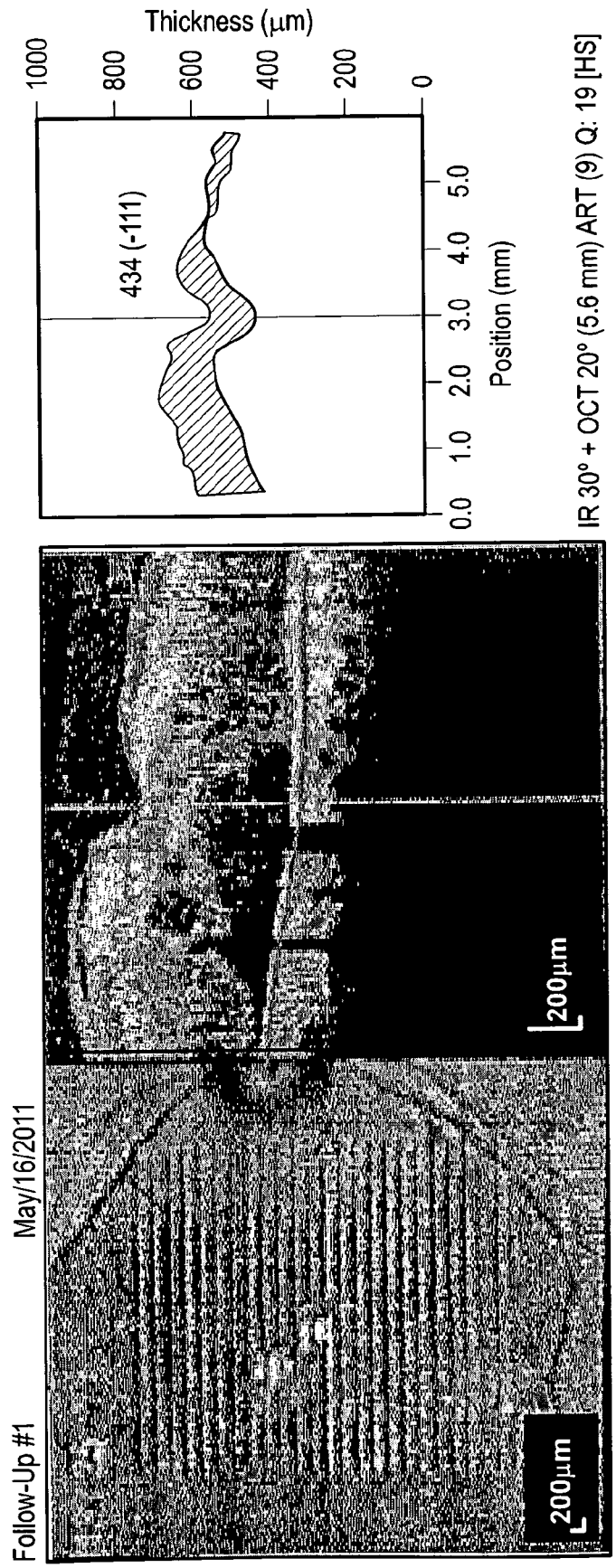
Figure 26:
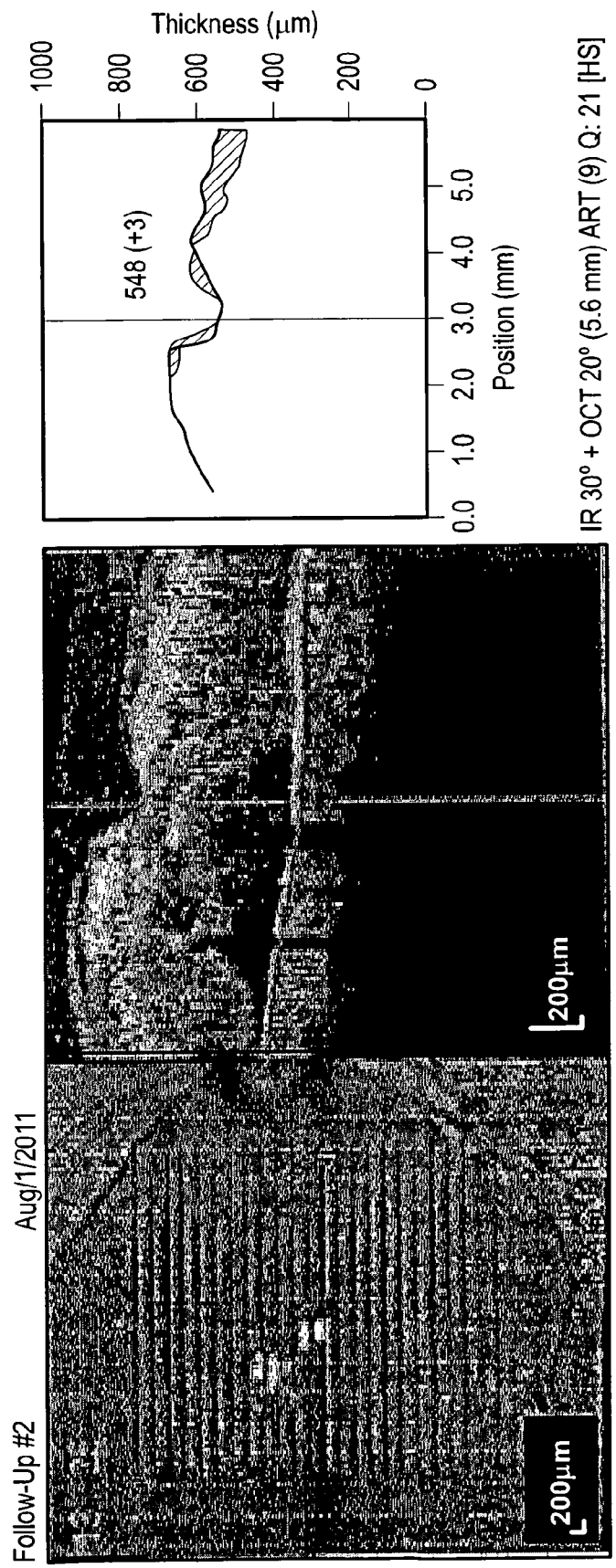
Figure 26:
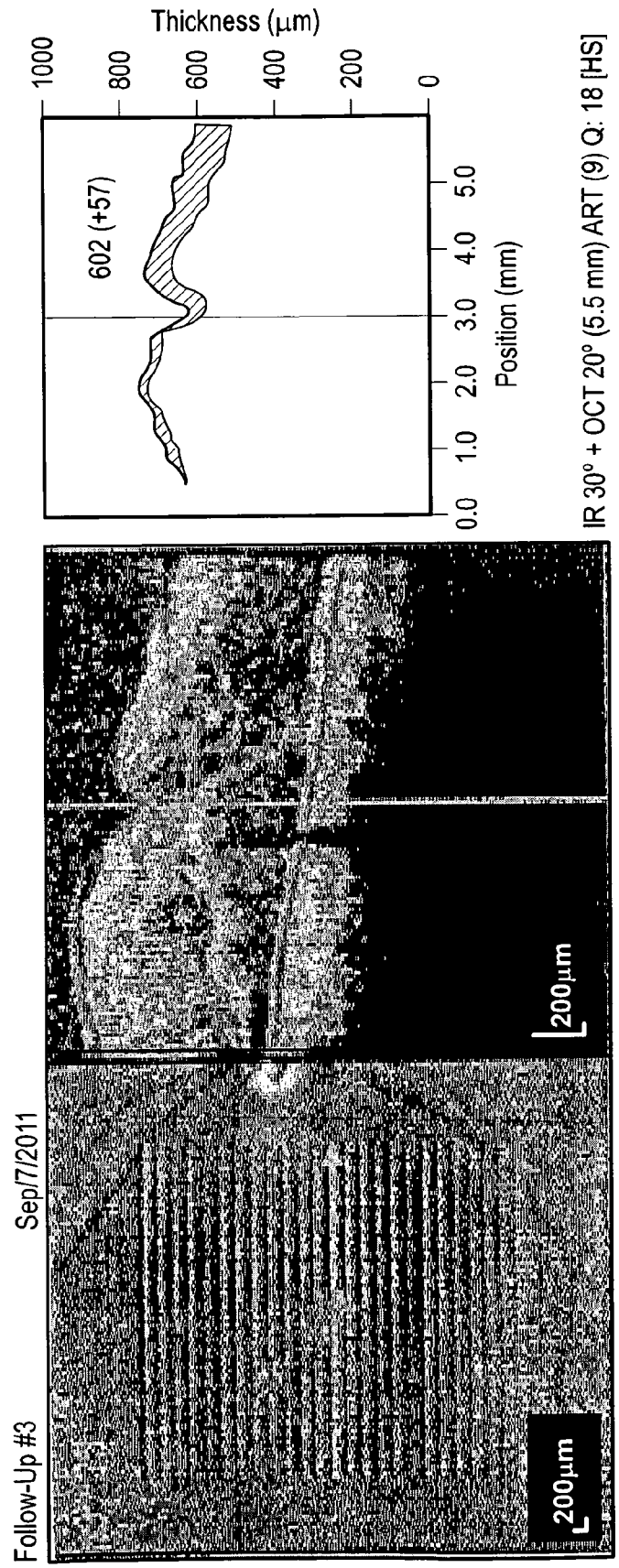
Figure 26:
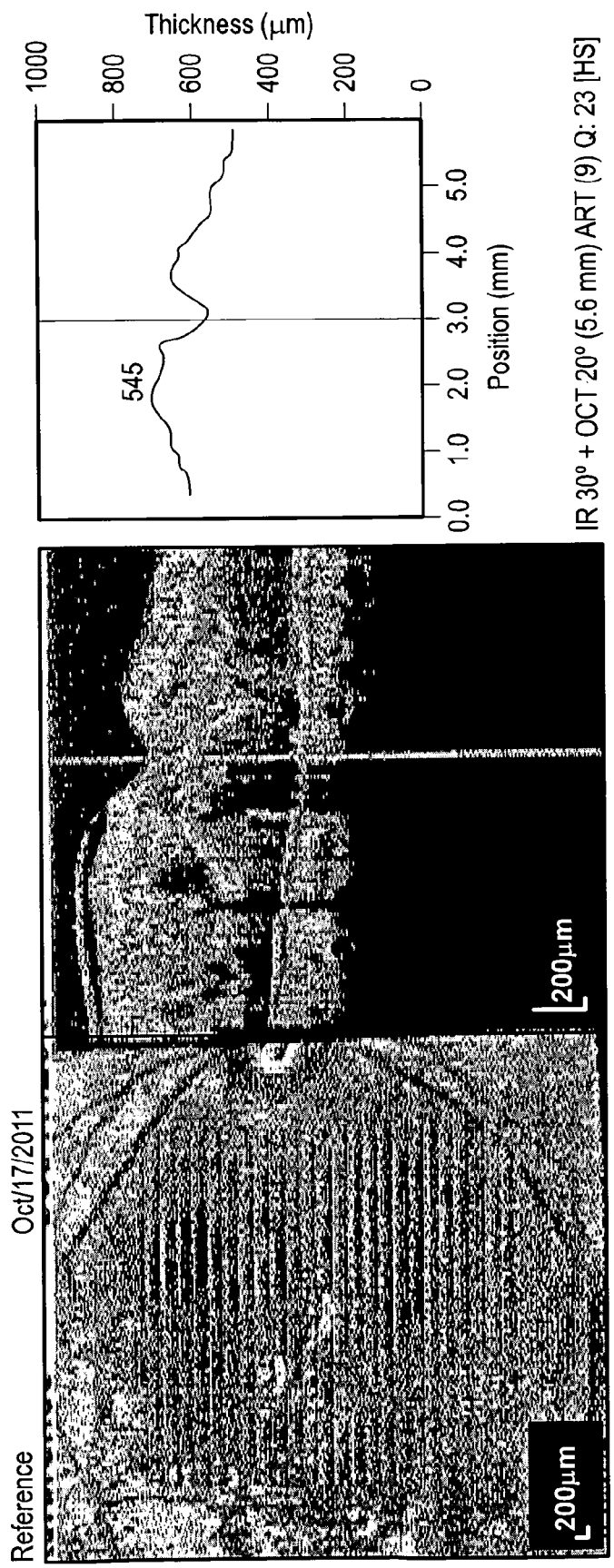
Figure 26:
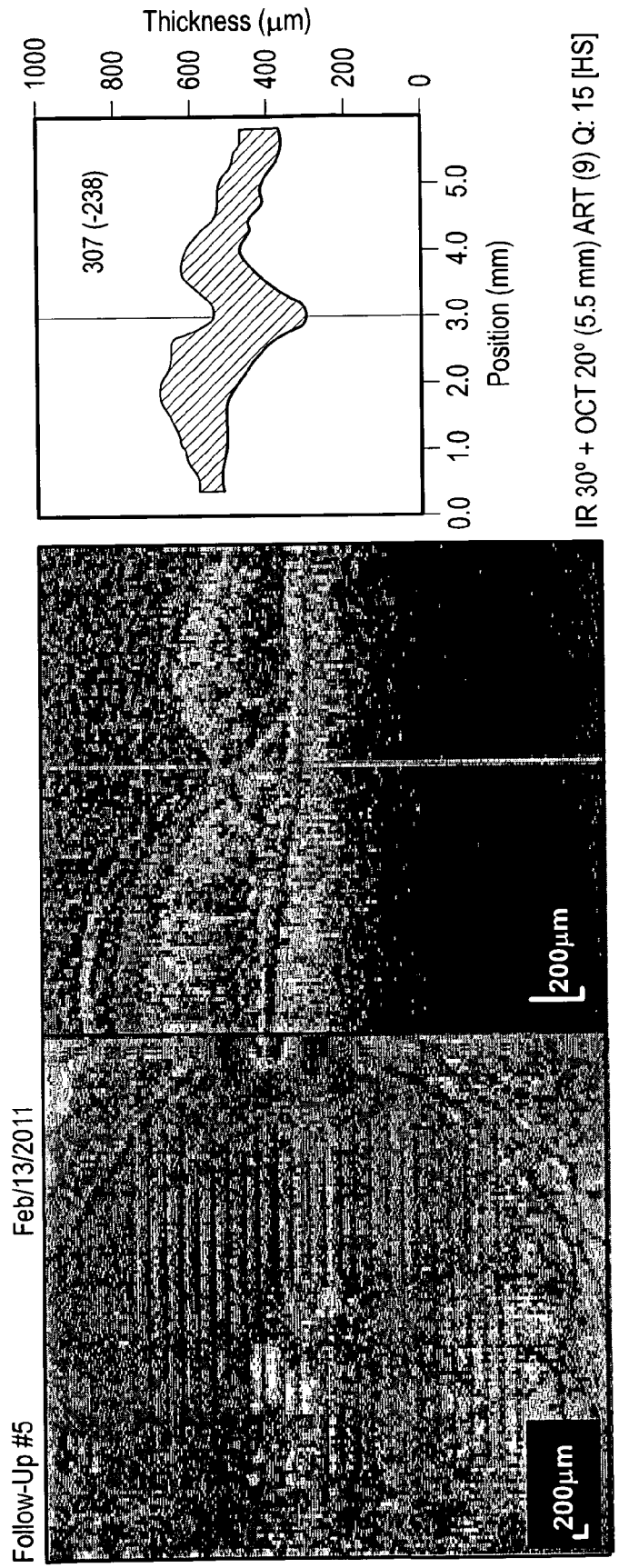

63 year old lady with diabetes presented in 2009 with diabetic macular oedema. She was treated with two introvitreal Avastin injection and two focal LASER treatments in each eye. On Sep. 7, 2011 she was started on Omega 3RX®. Six weeks following treatment there was no fluid in the right eye and minimal fluid in the left eye. She gained four lines of vision in the right eye and four lines of vision in the left eye (FIG. 26).

Case y)

Figure 27:
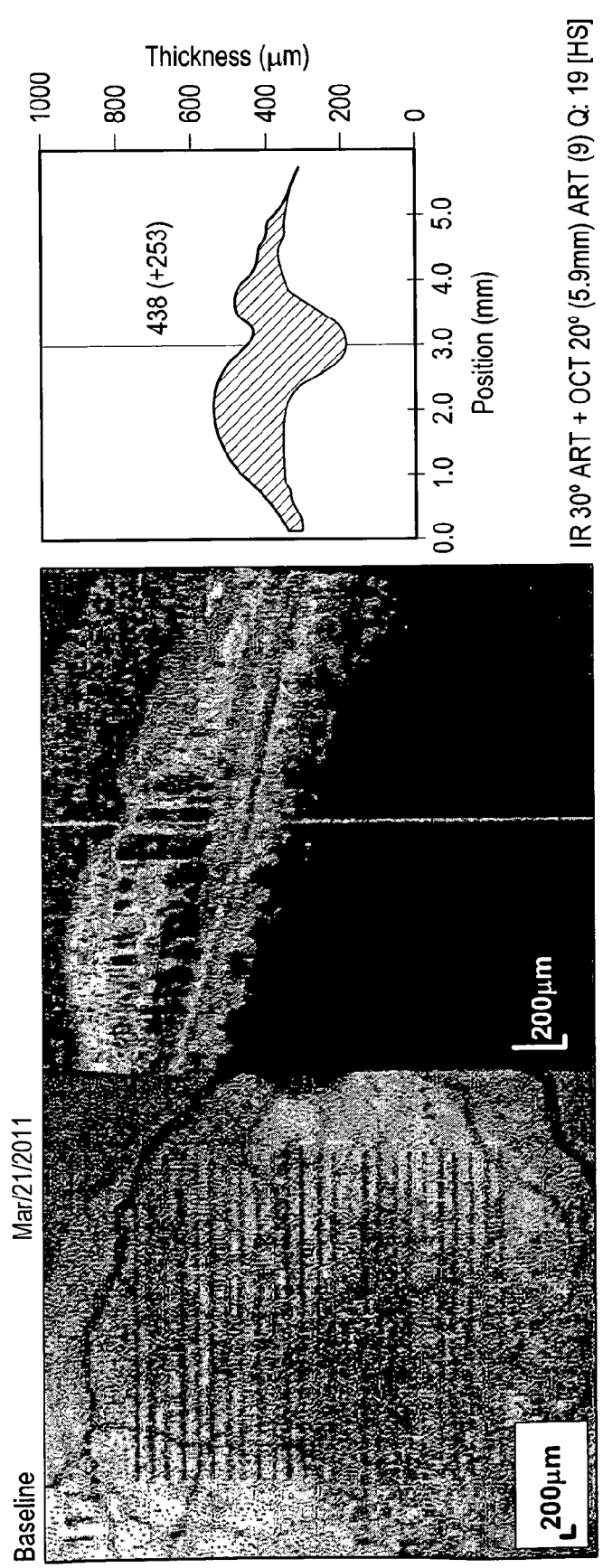
Figure 27:
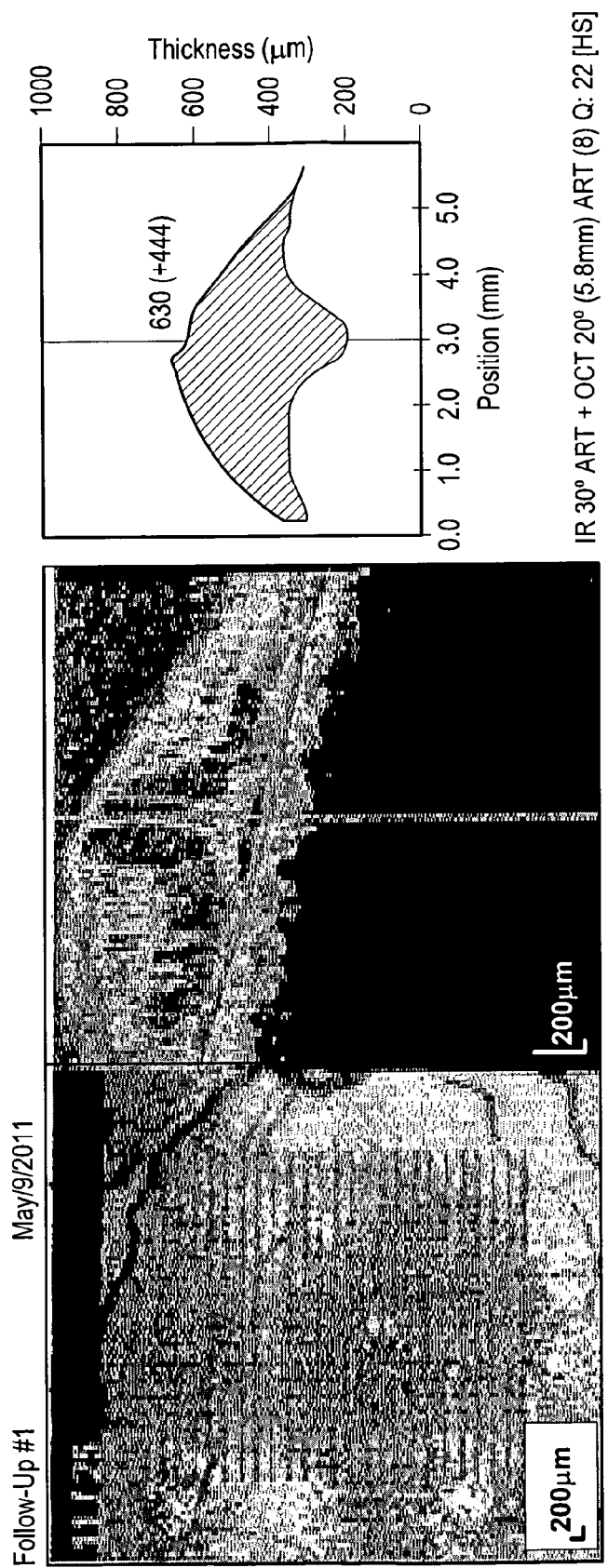
Figure 27:
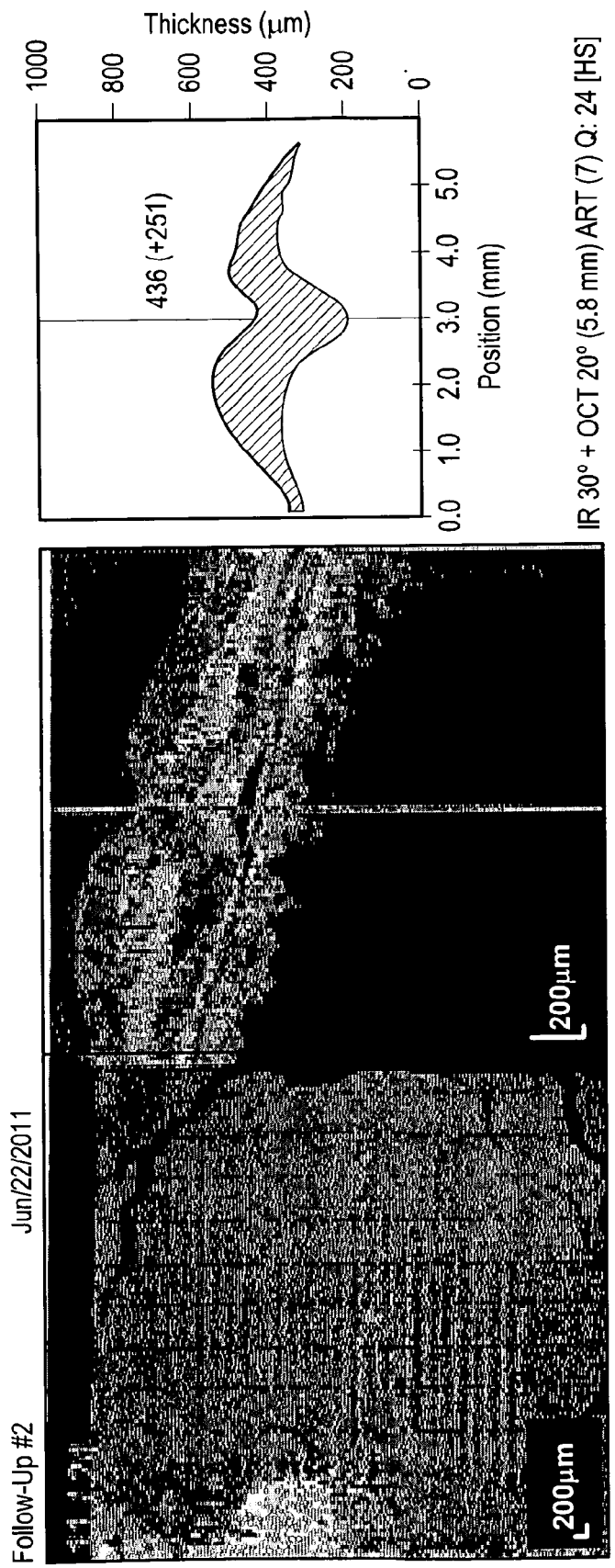
Figure 27:
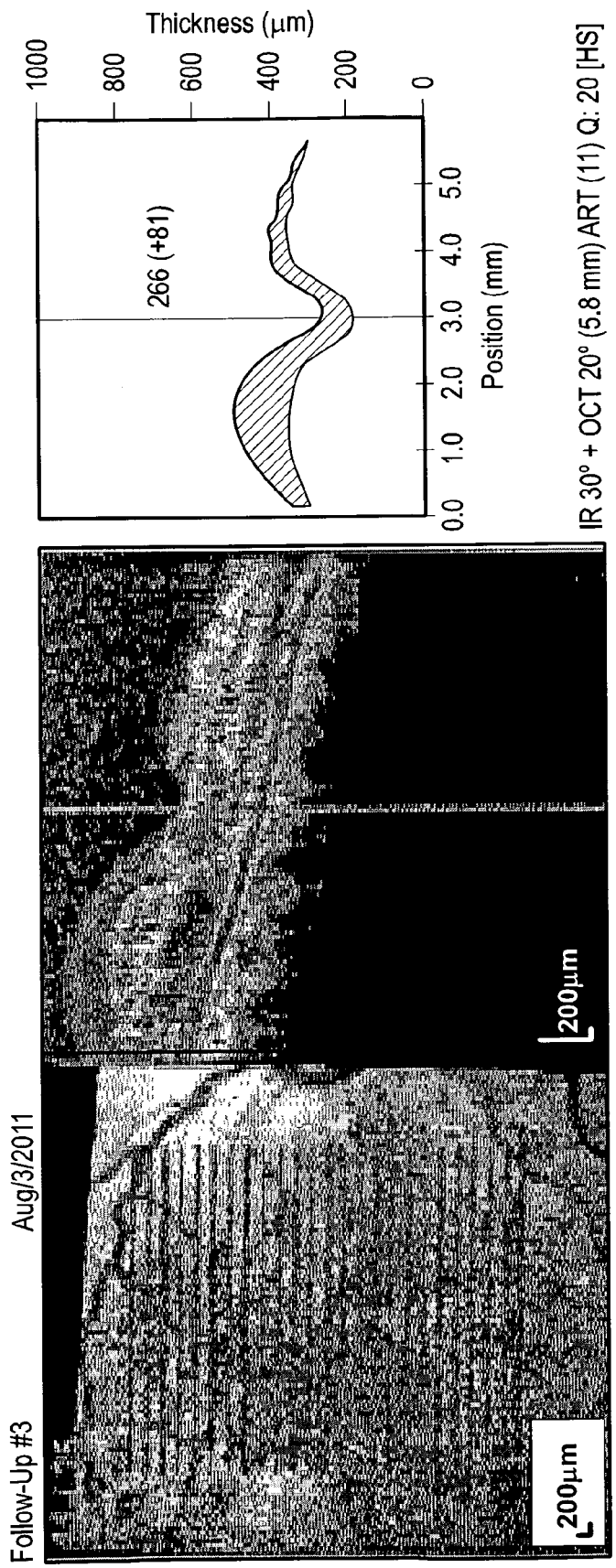
Figure 27:
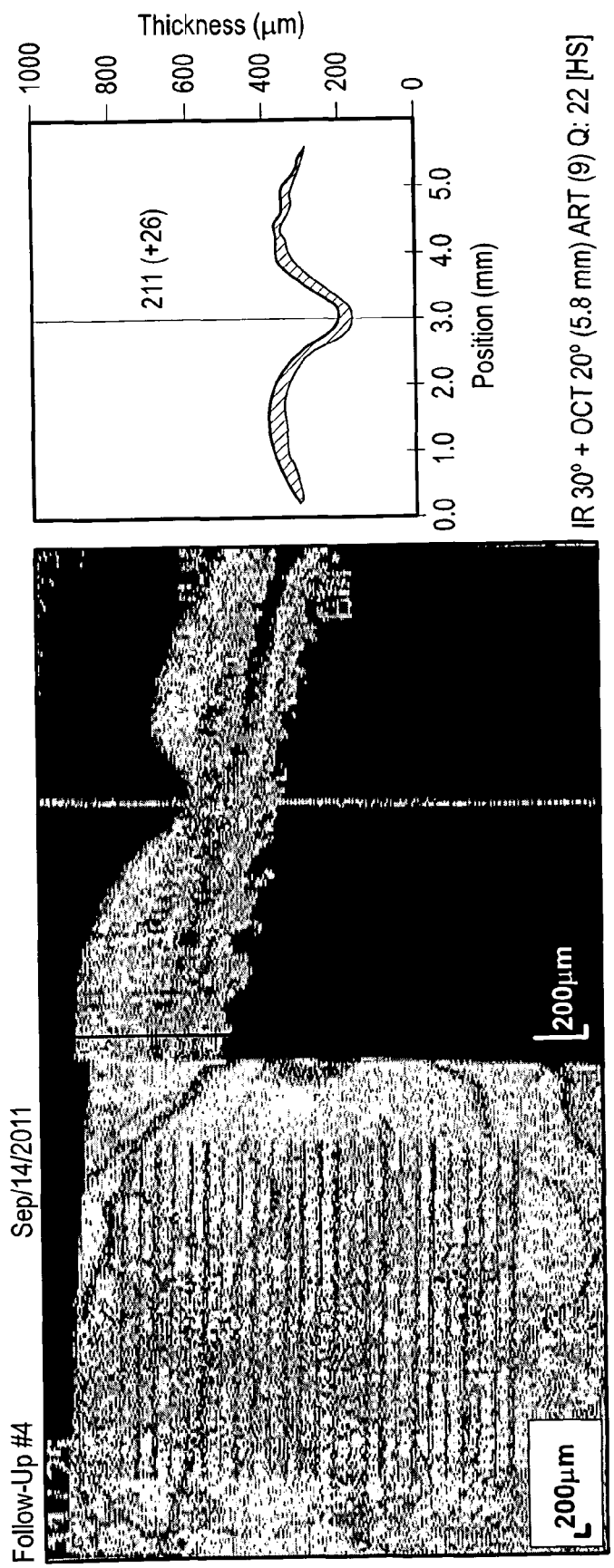
Figure 27:
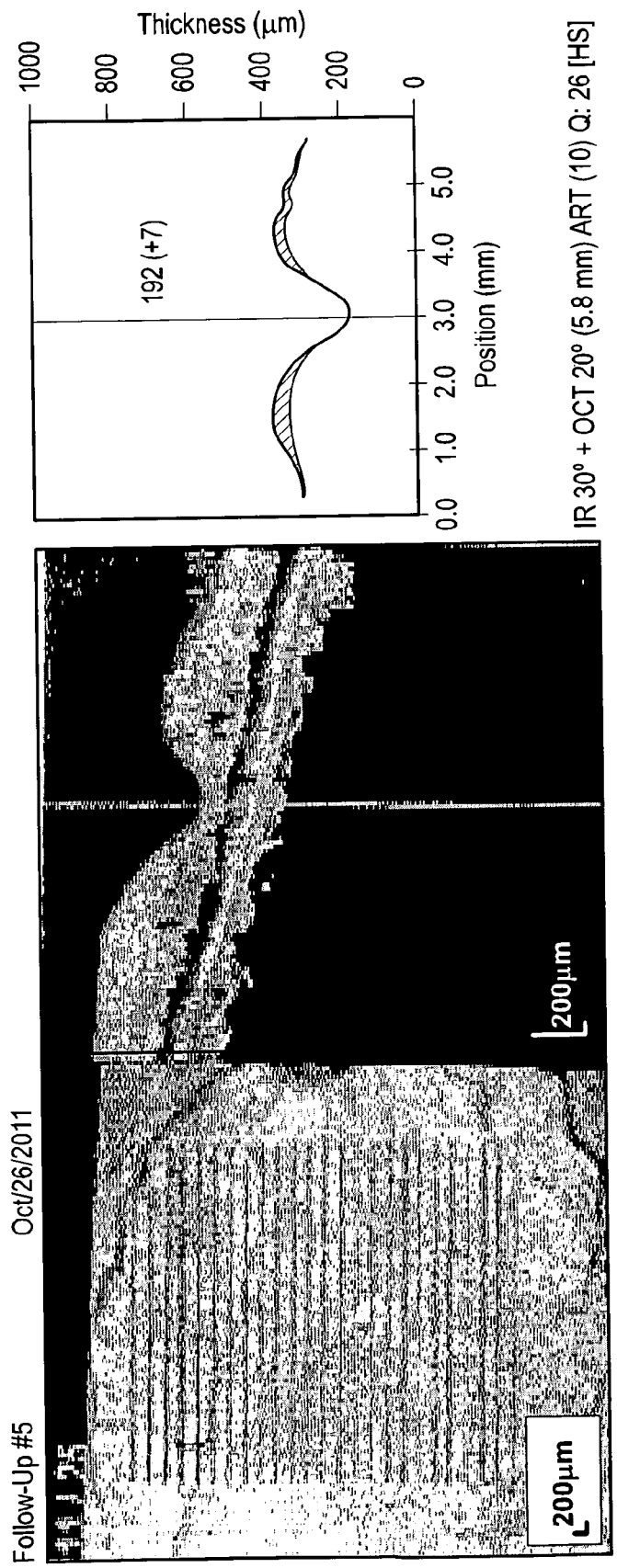
Figure 27:
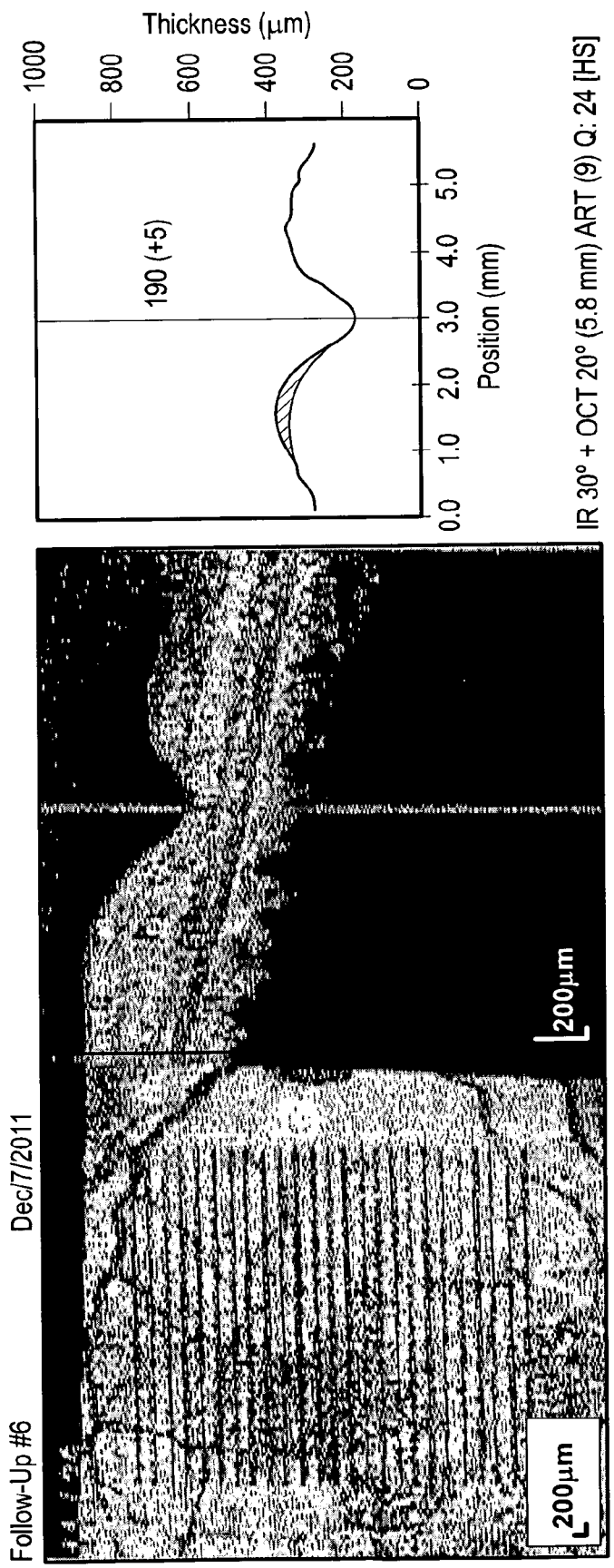
Figure 27:
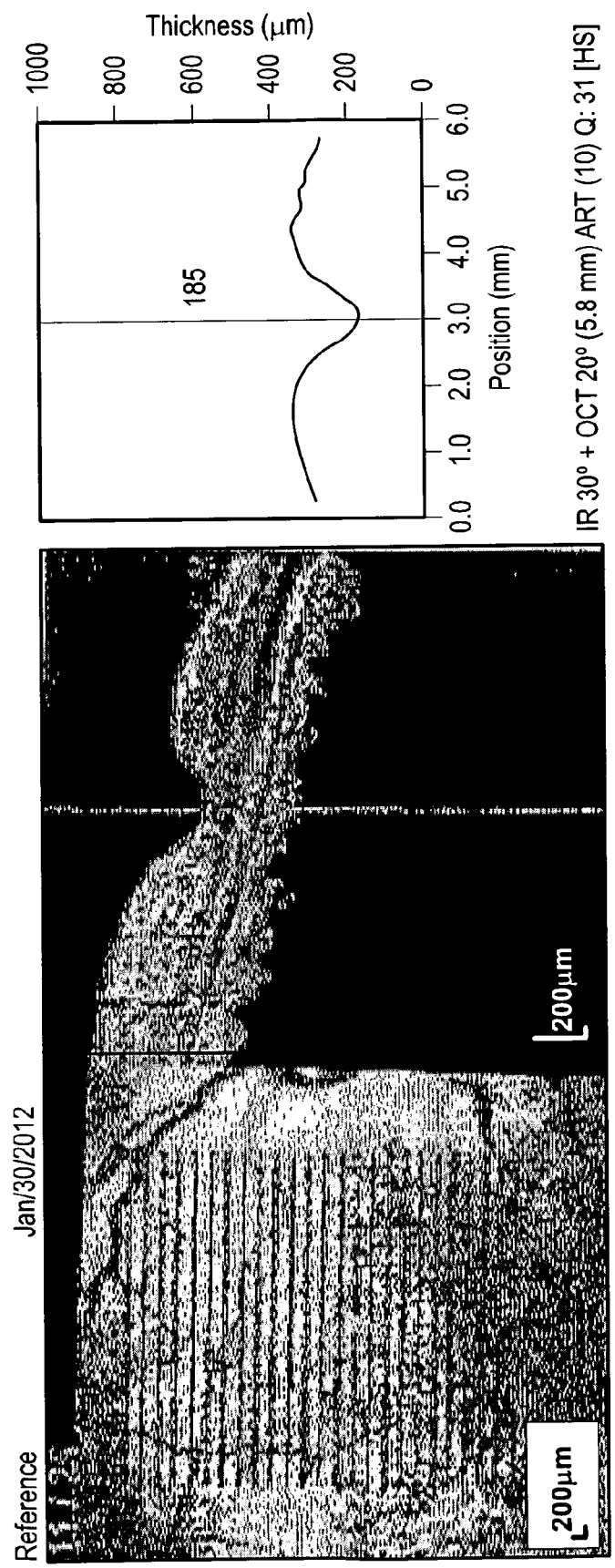
Figure 27:
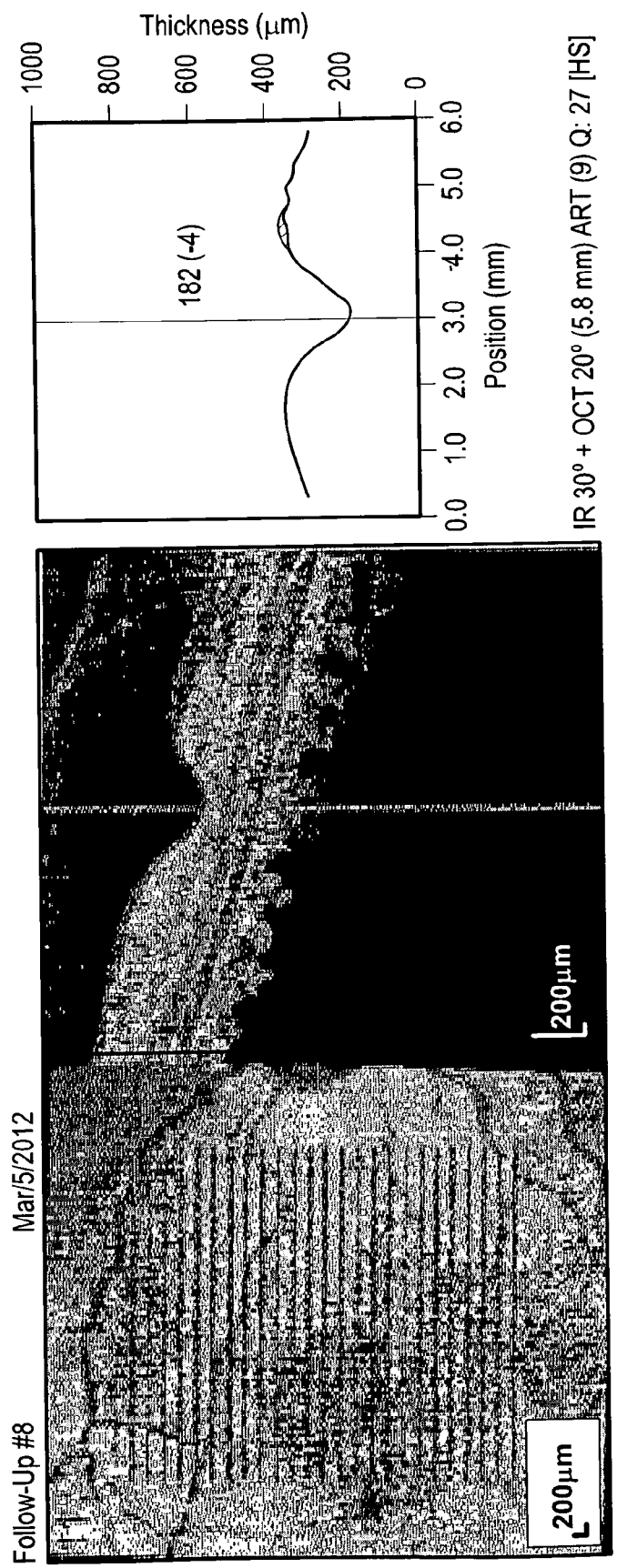
Figure 27:
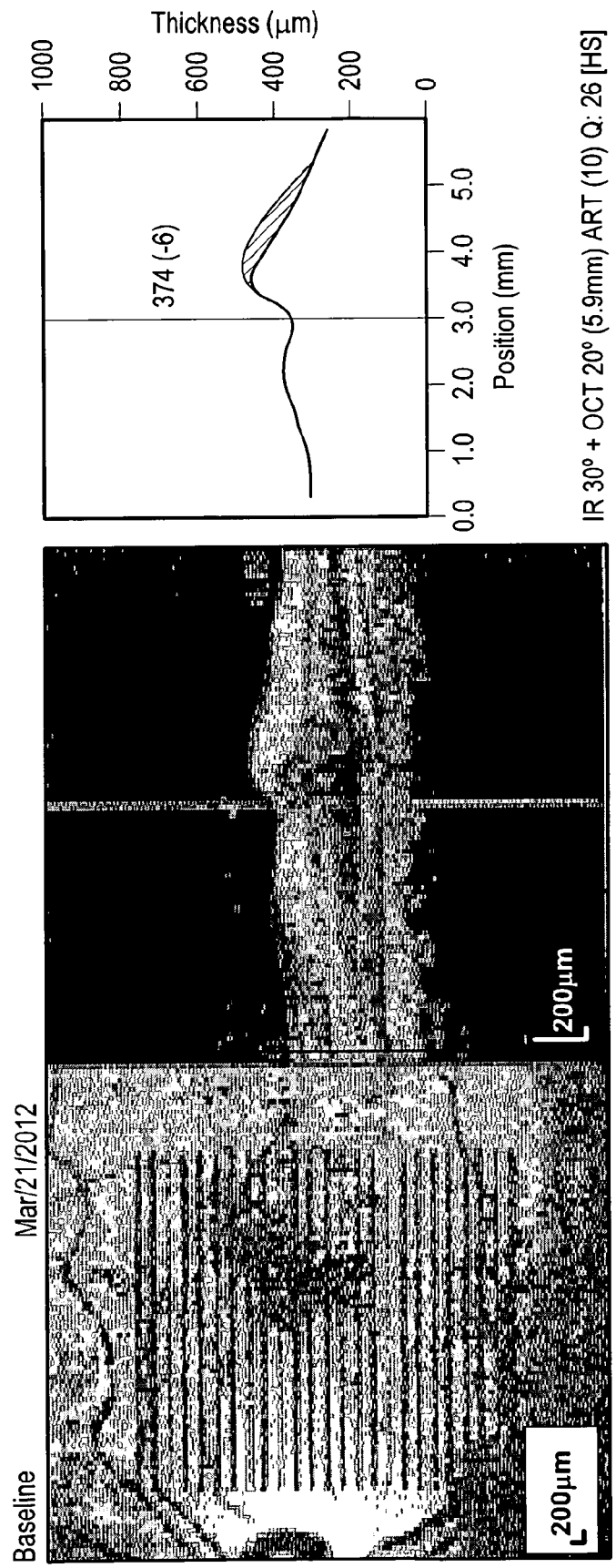
Figure 27:
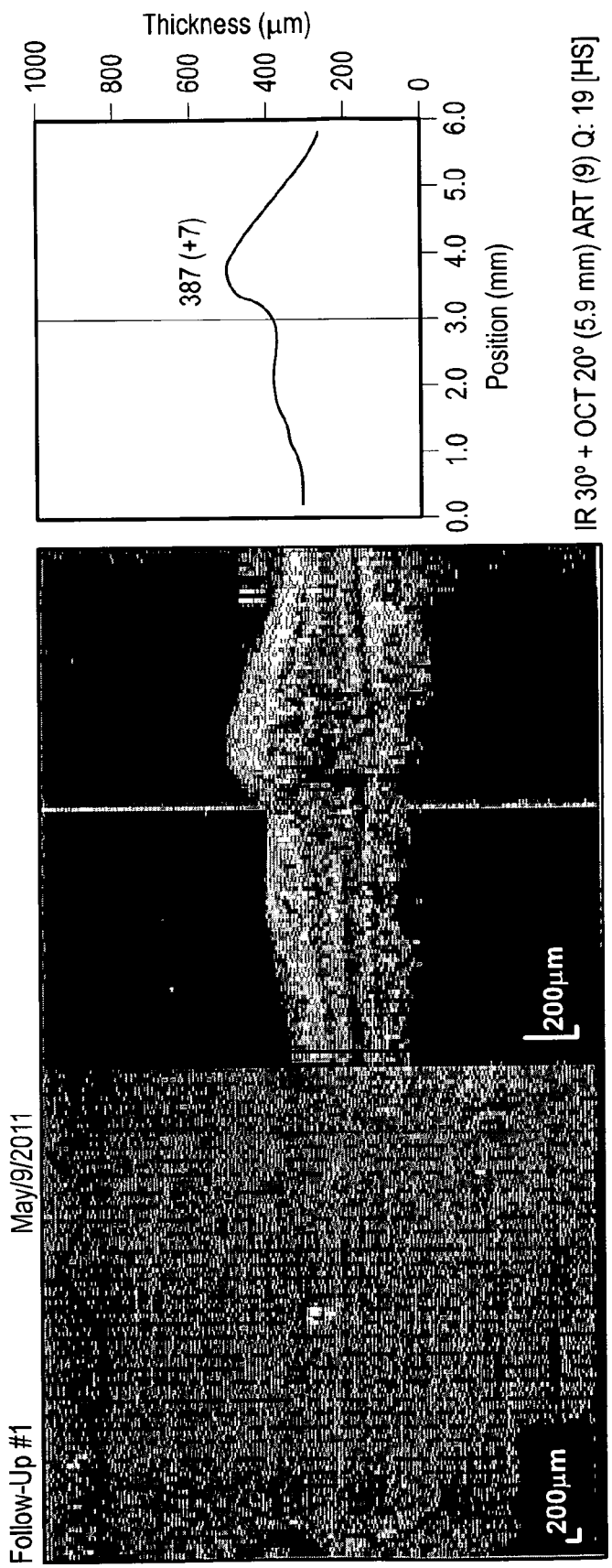
Figure 27:
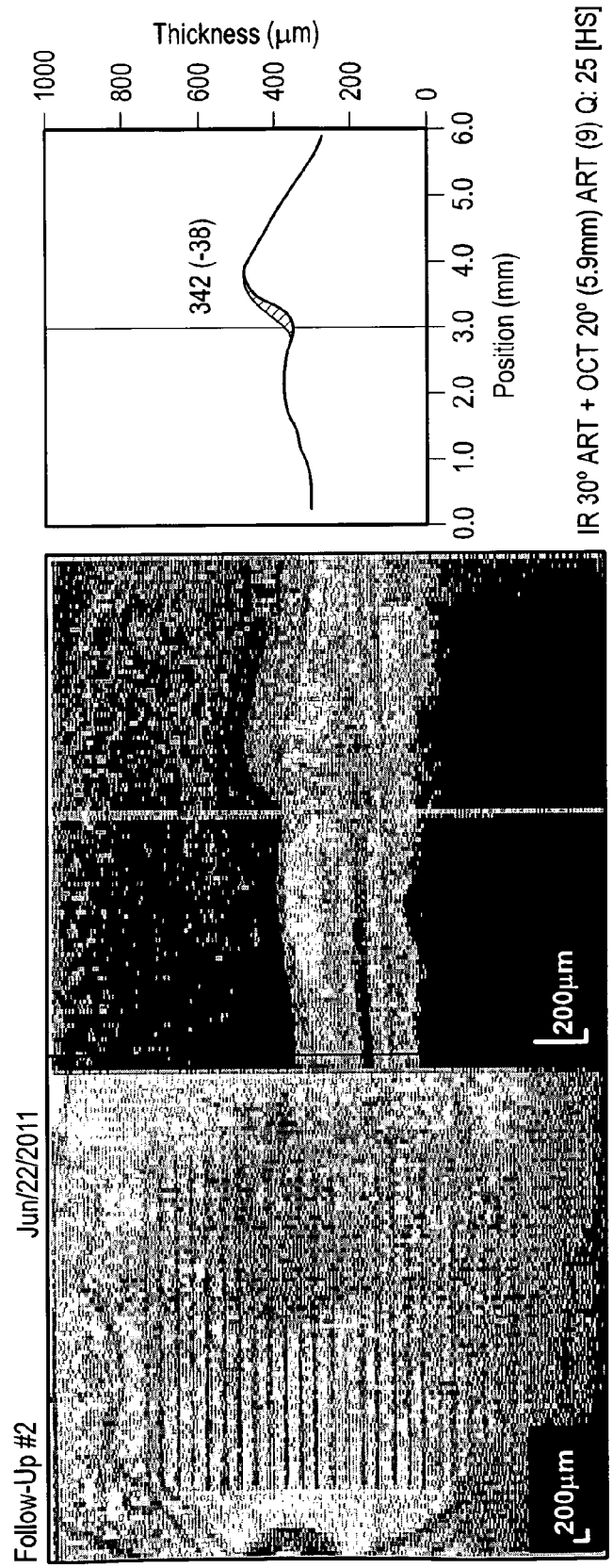
Figure 27:
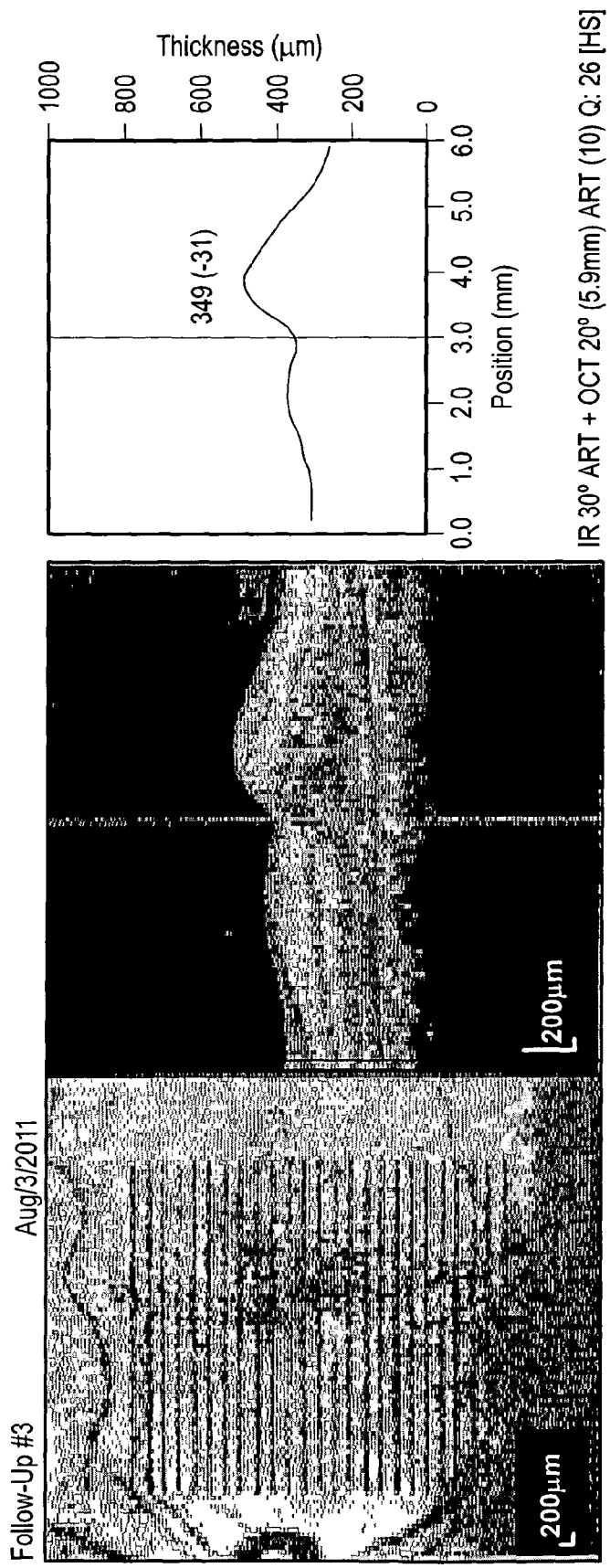
Figure 27:
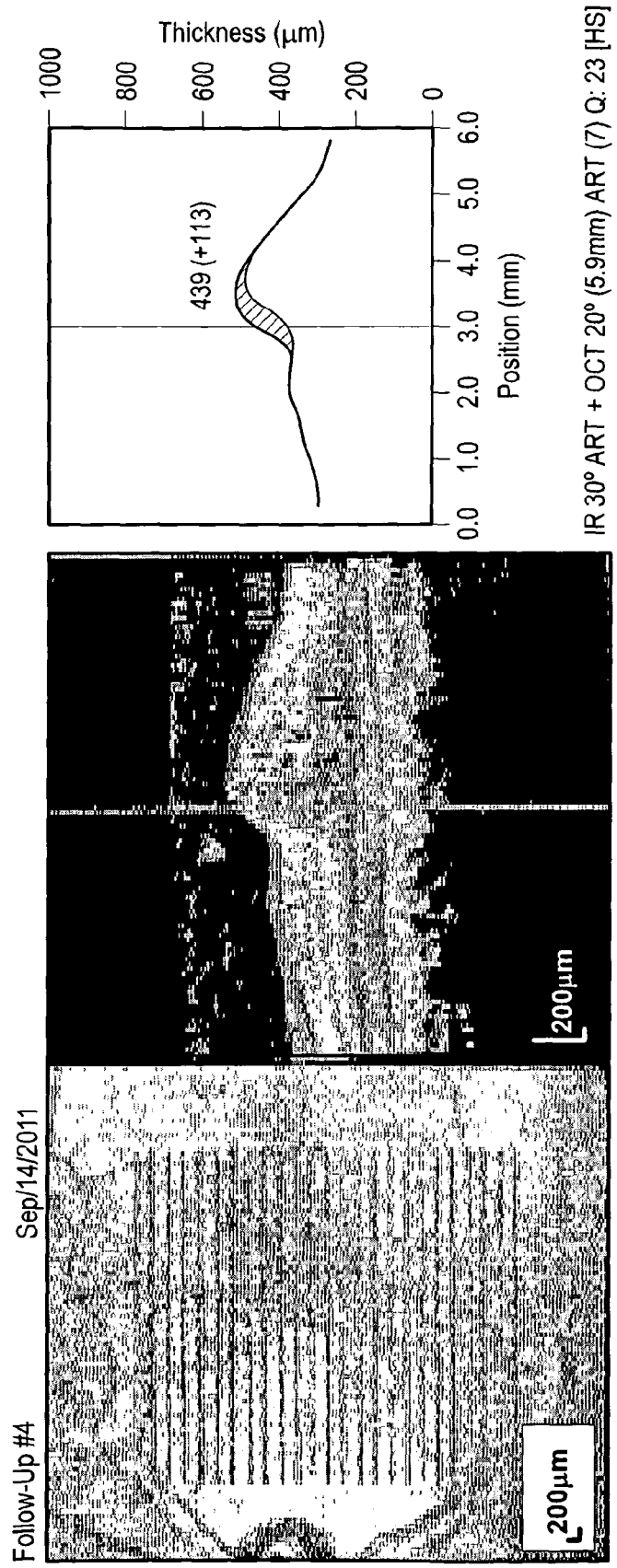
Figure 27:
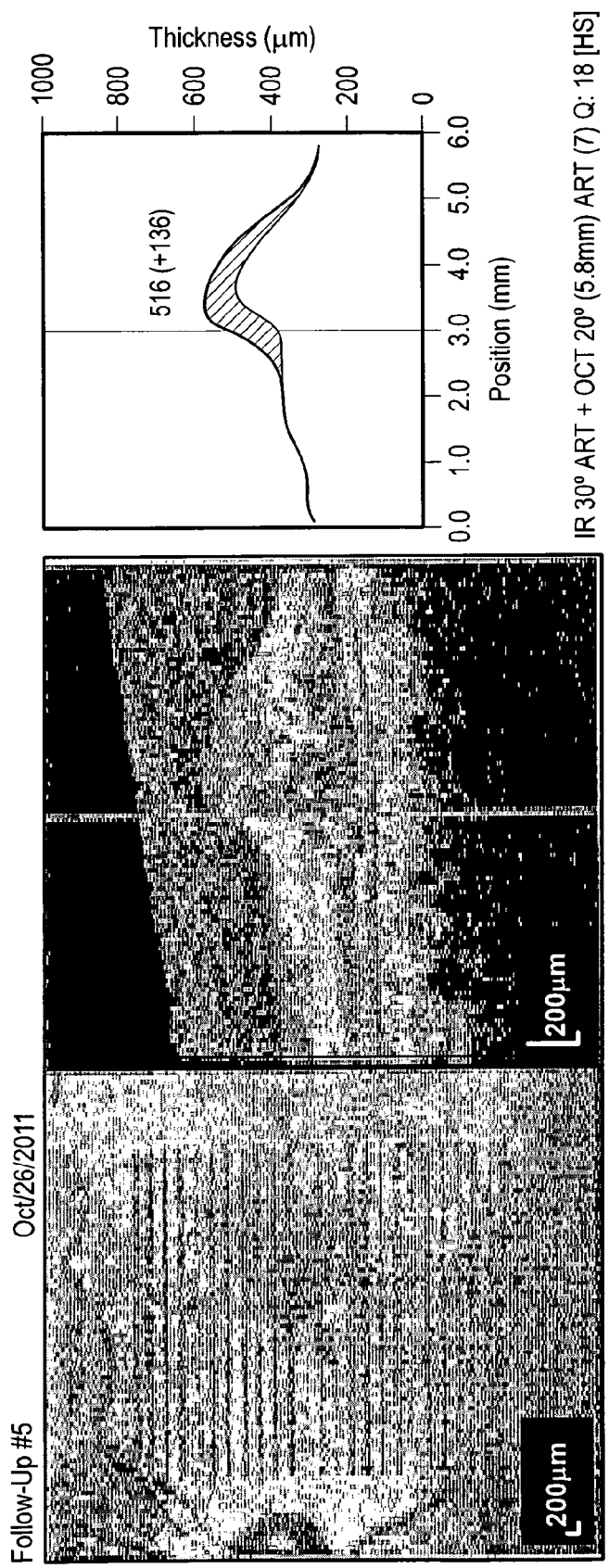
Figure 27:
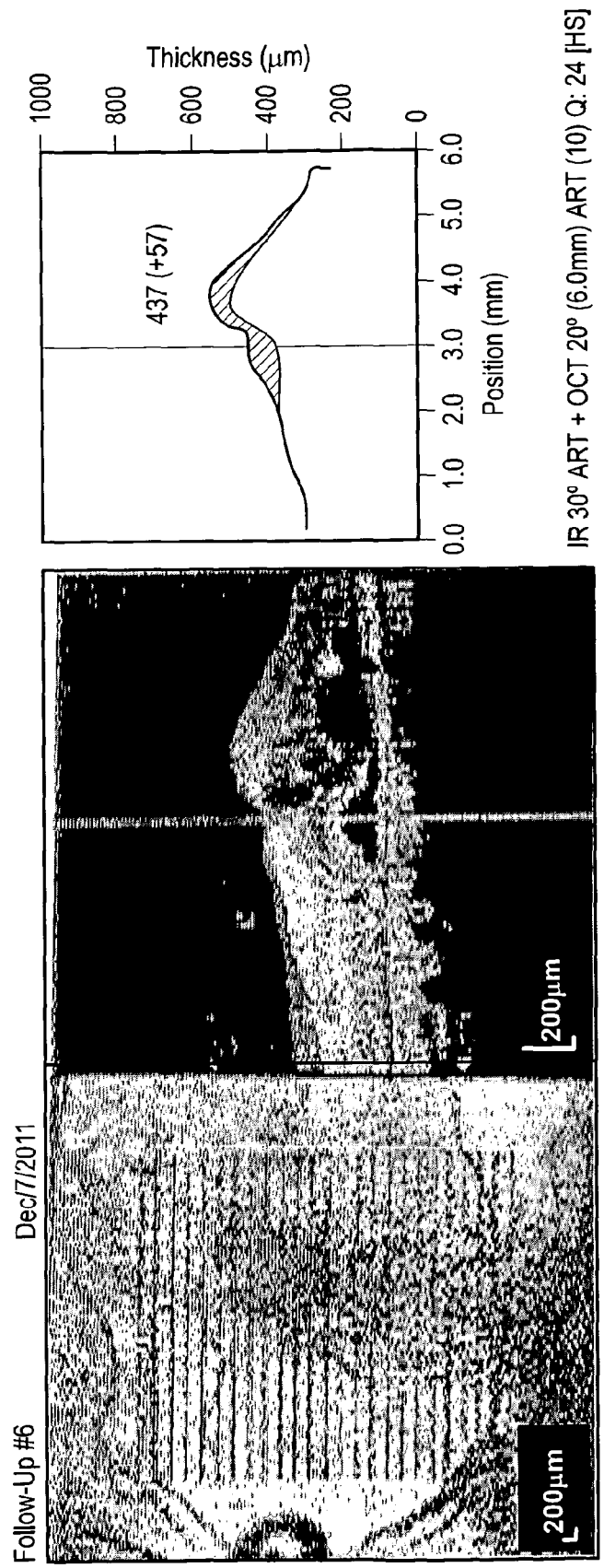
Figure 27:
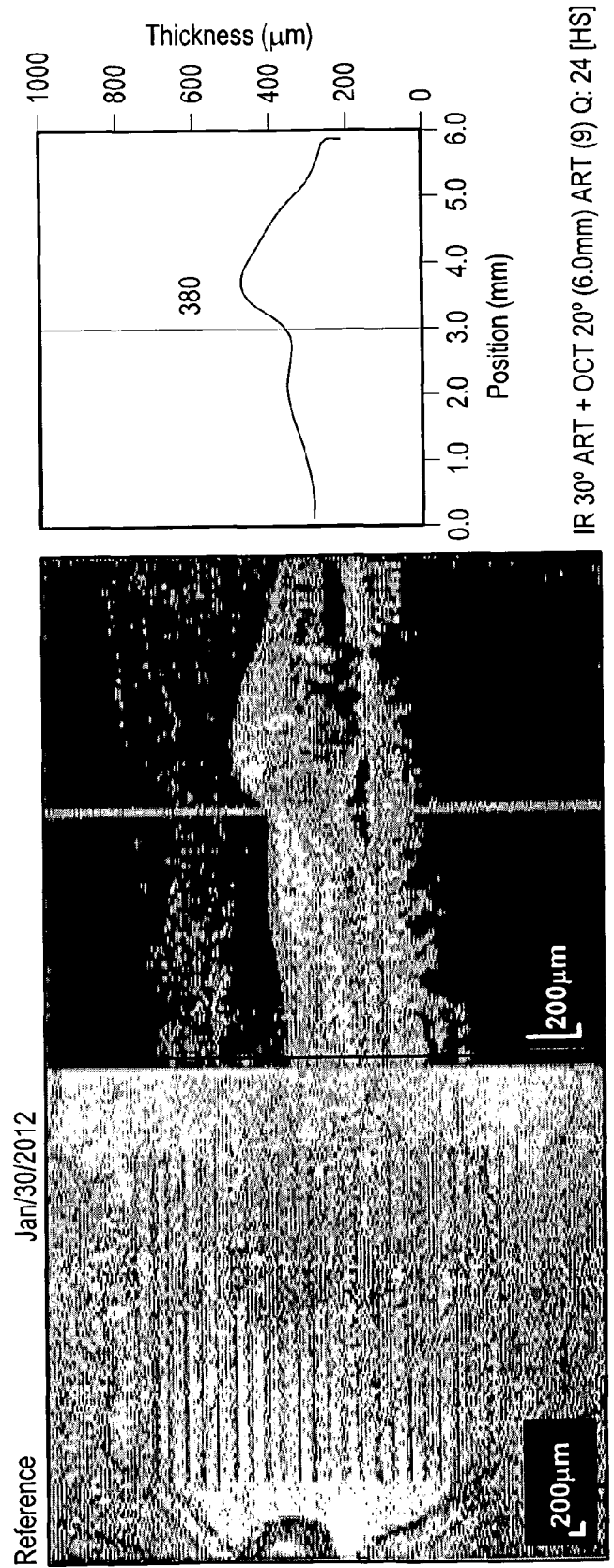
Figure 27:
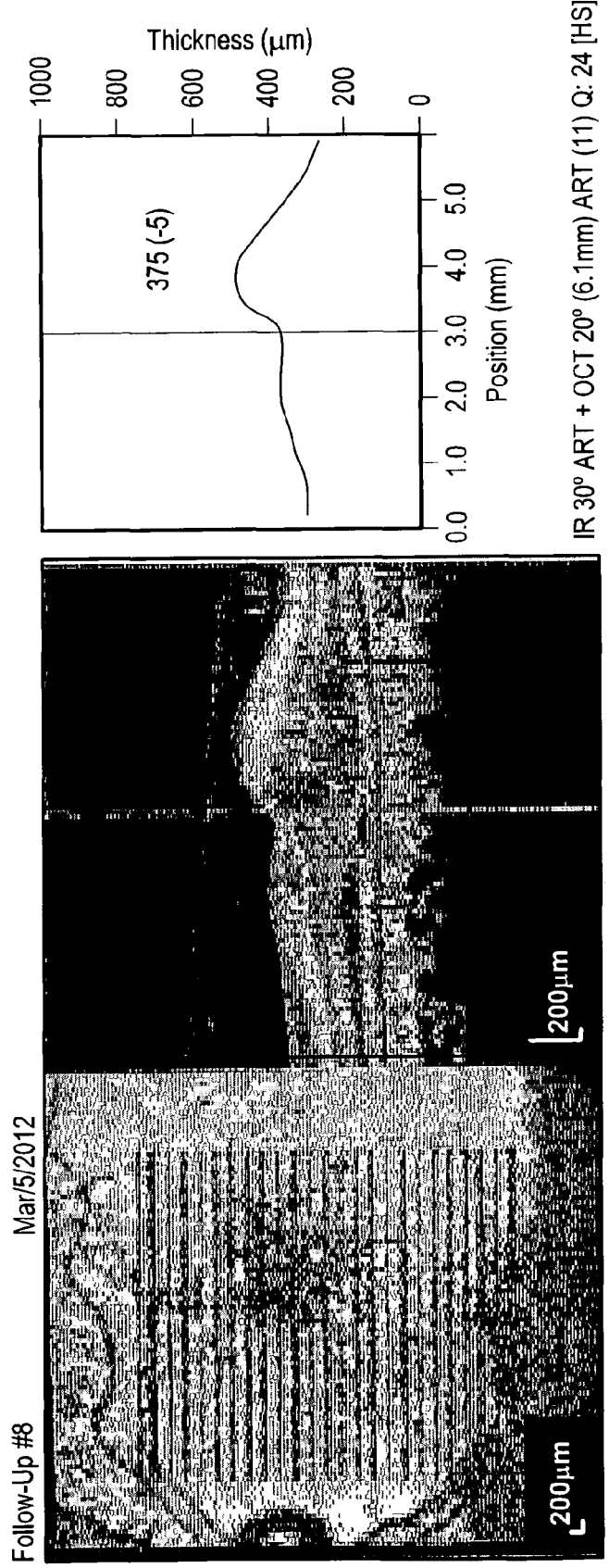

58 year old female presented in 2010 with bilateral macular oedema. She was treated with focal LASER in each eye, two intravitreal Lucentis in the right eye and one intravitreal Lucentis in the left eye. She was started on Omega 3RX® on Mar. 21, 2011. Four months following treatment the fluid resolved in the right eye and there was minimal fluid in the left eye. She gained four lines of vision in the right eye and one line of vision in the left eye (FIG. 27).

Case z)

Figure 28:
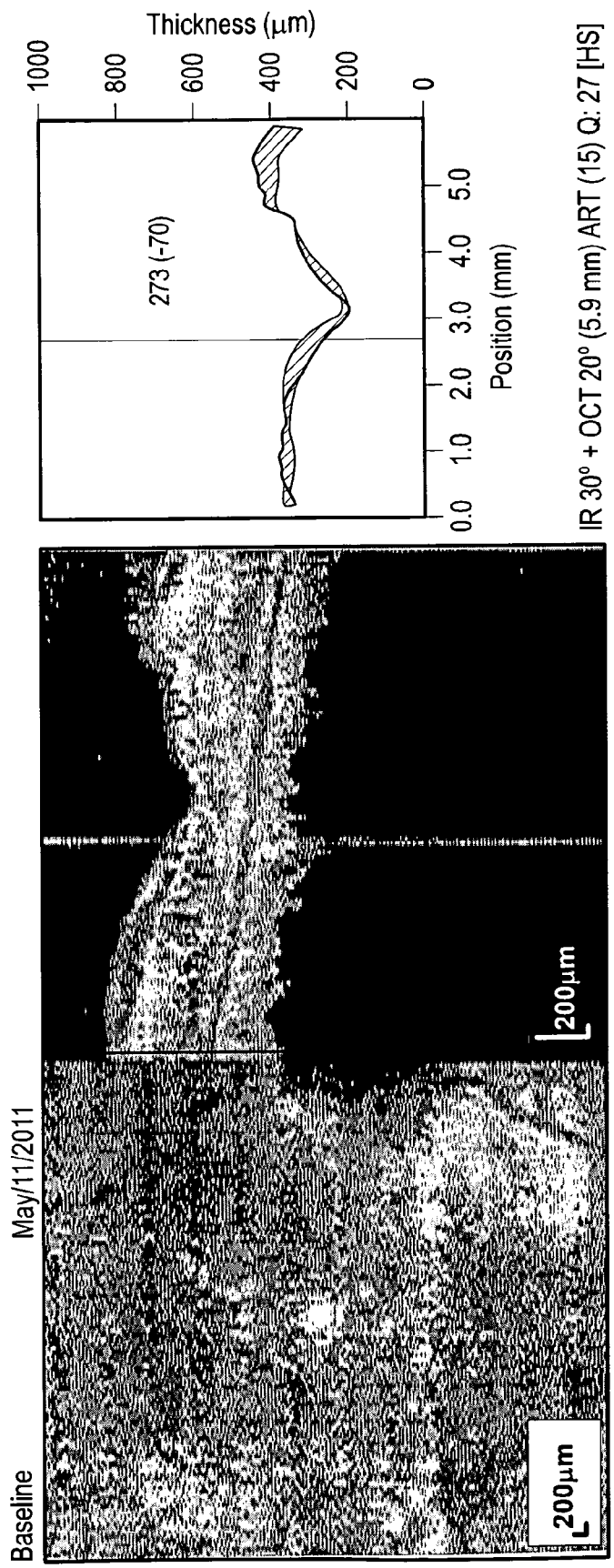
Figure 28:
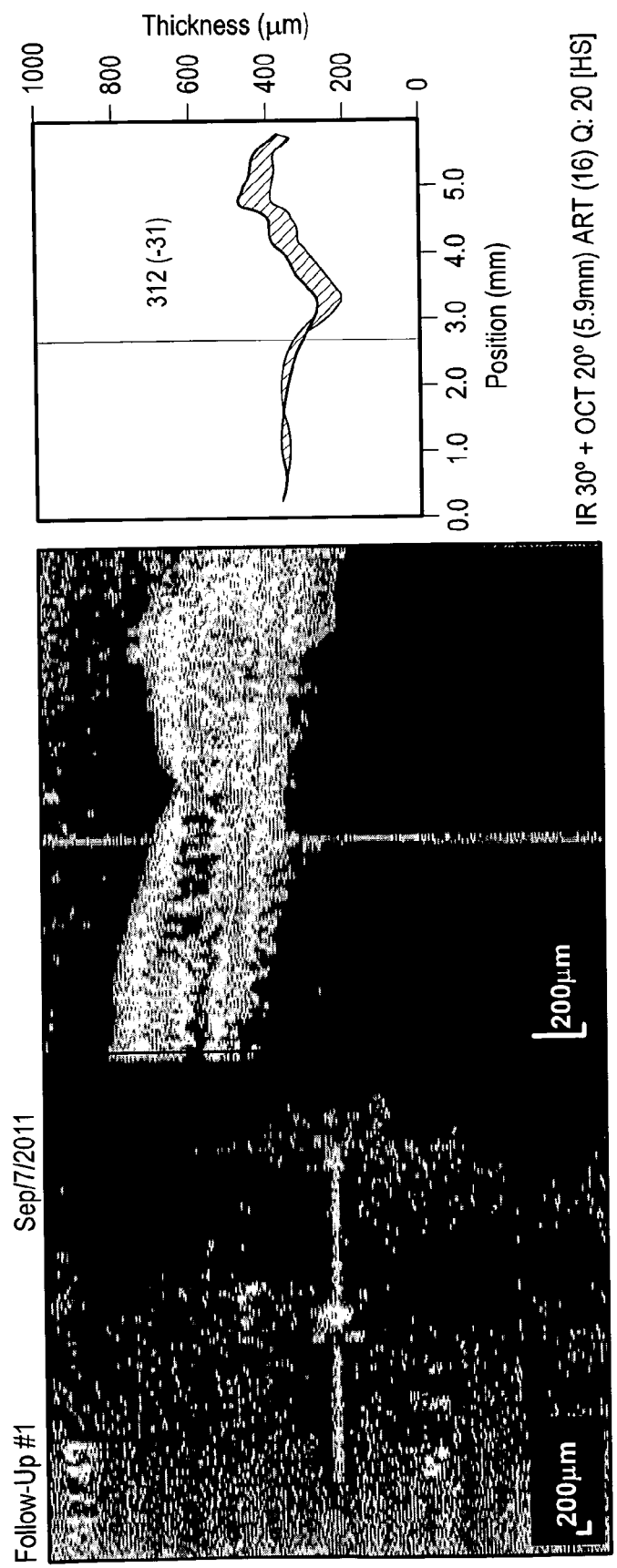
Figure 28:
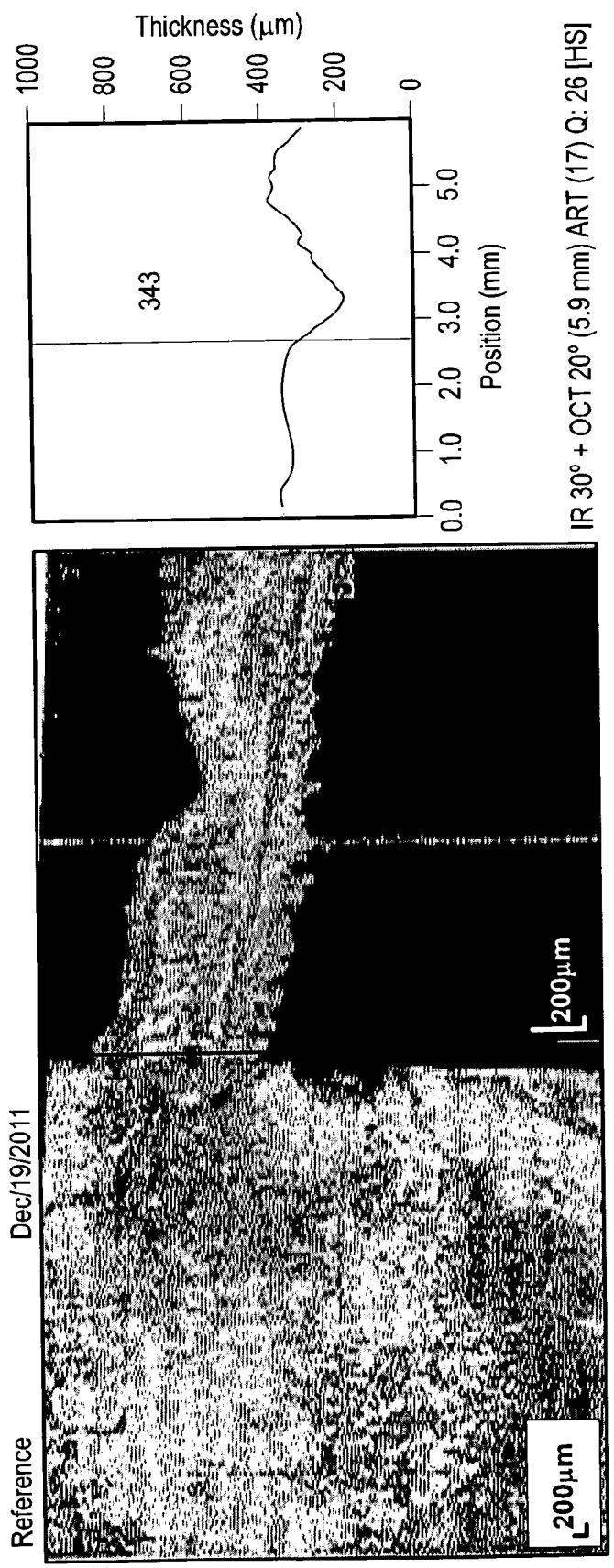
Figure 28:
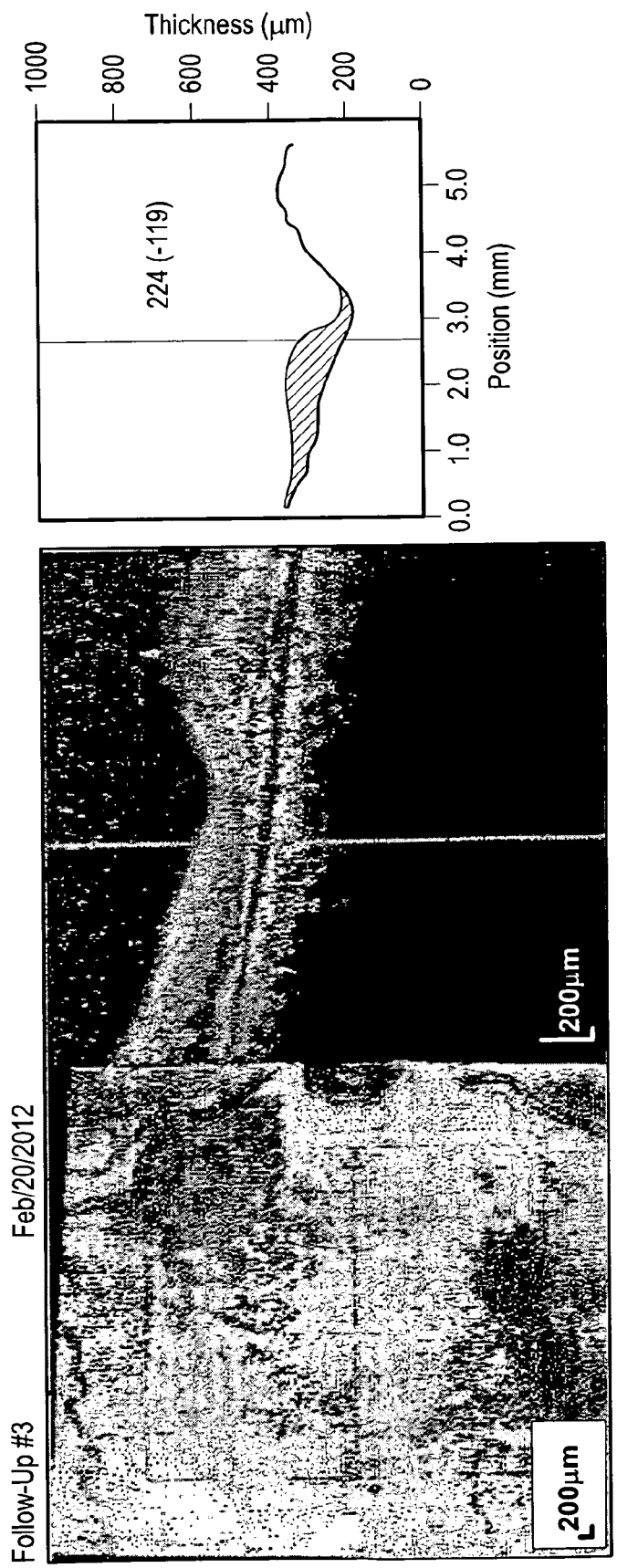
Figure 28:
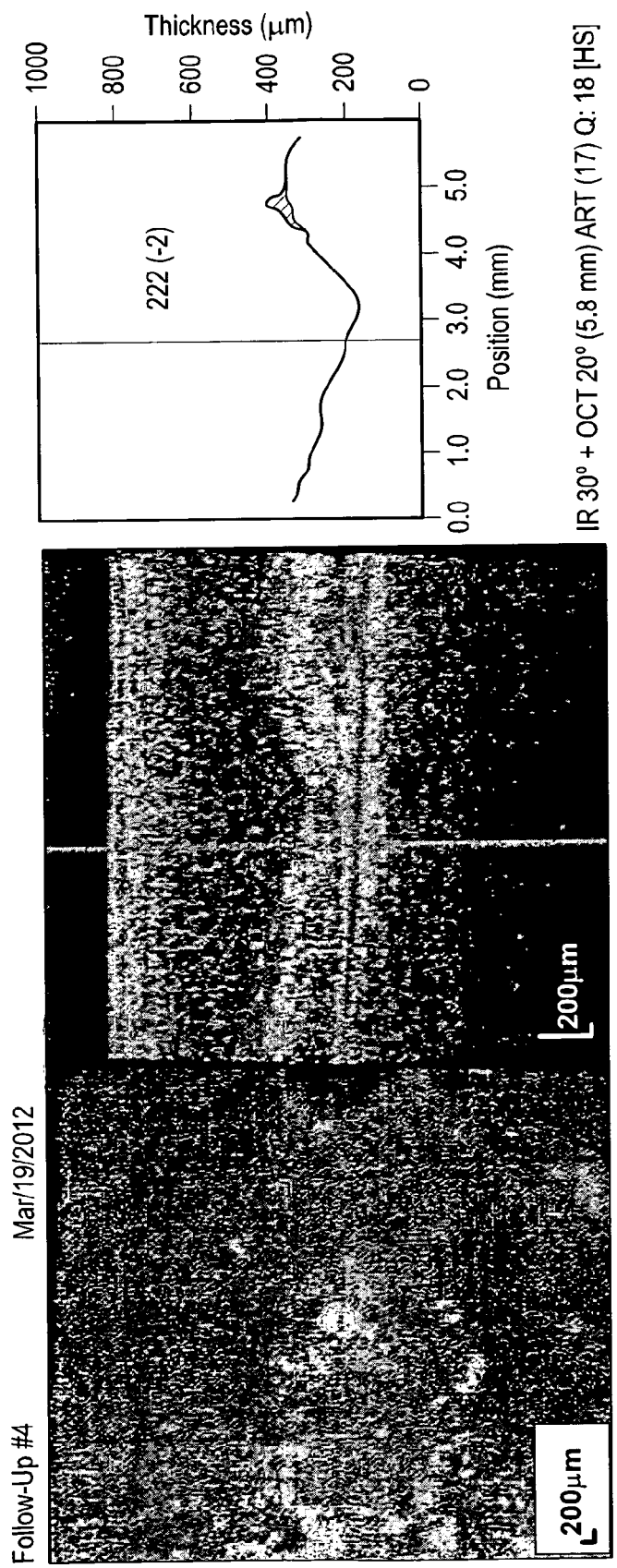
Figure 28:
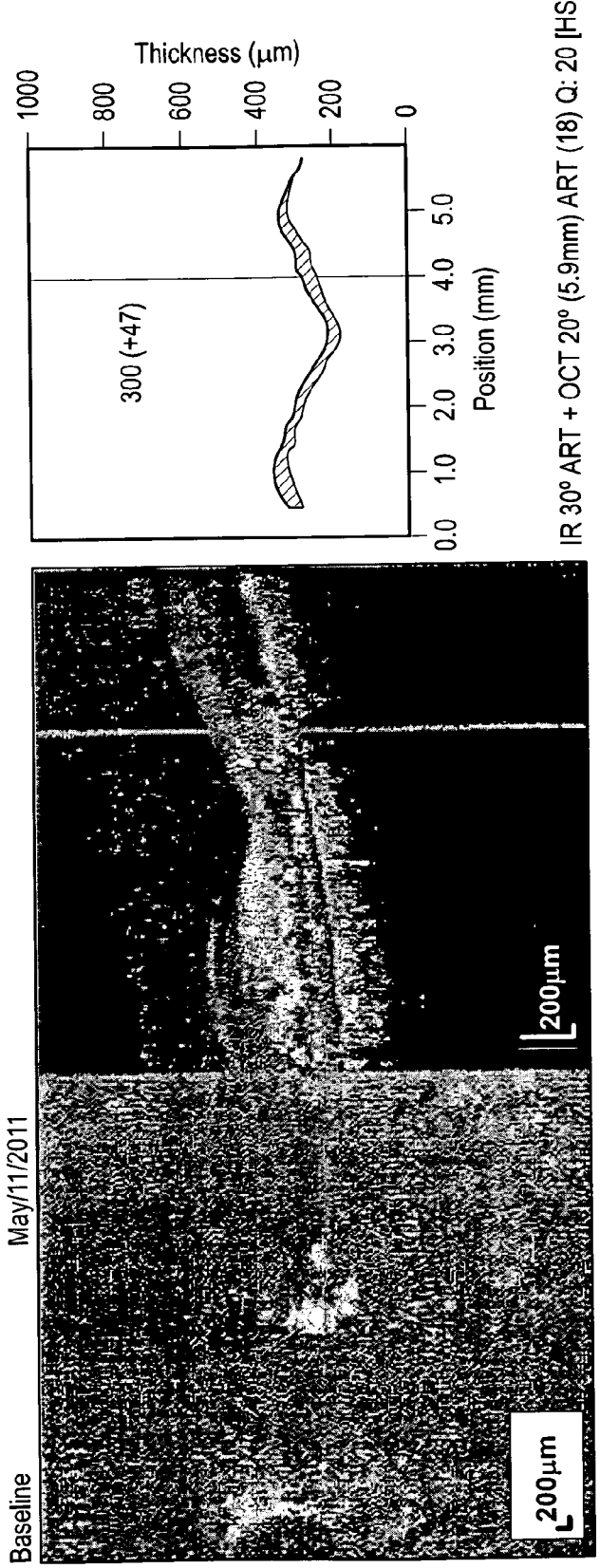
Figure 28:
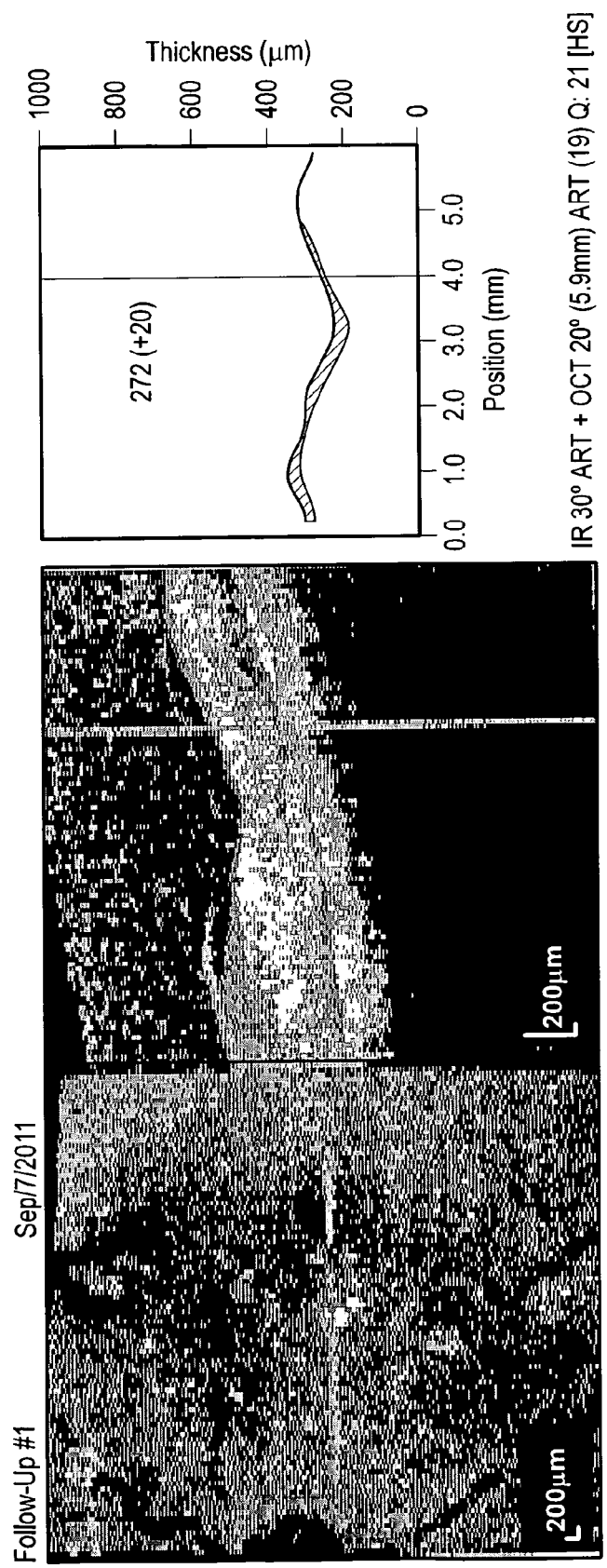
Figure 28:
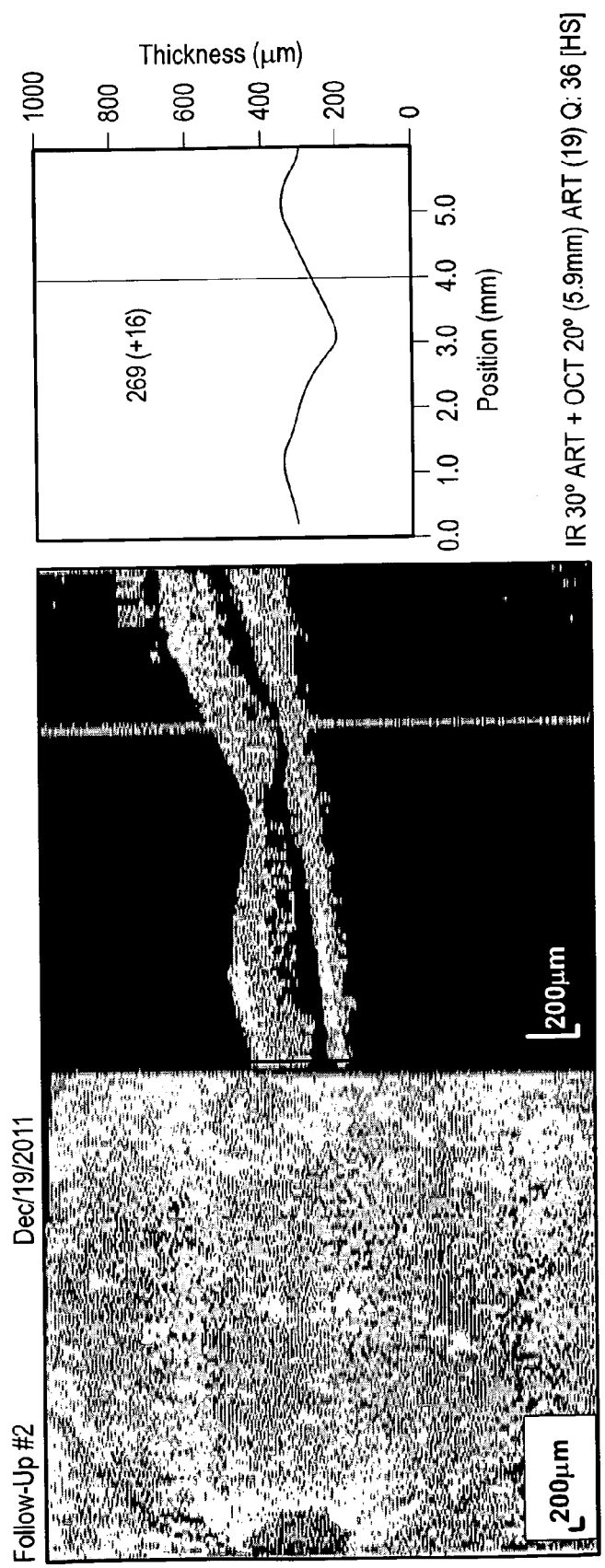
Figure 28:
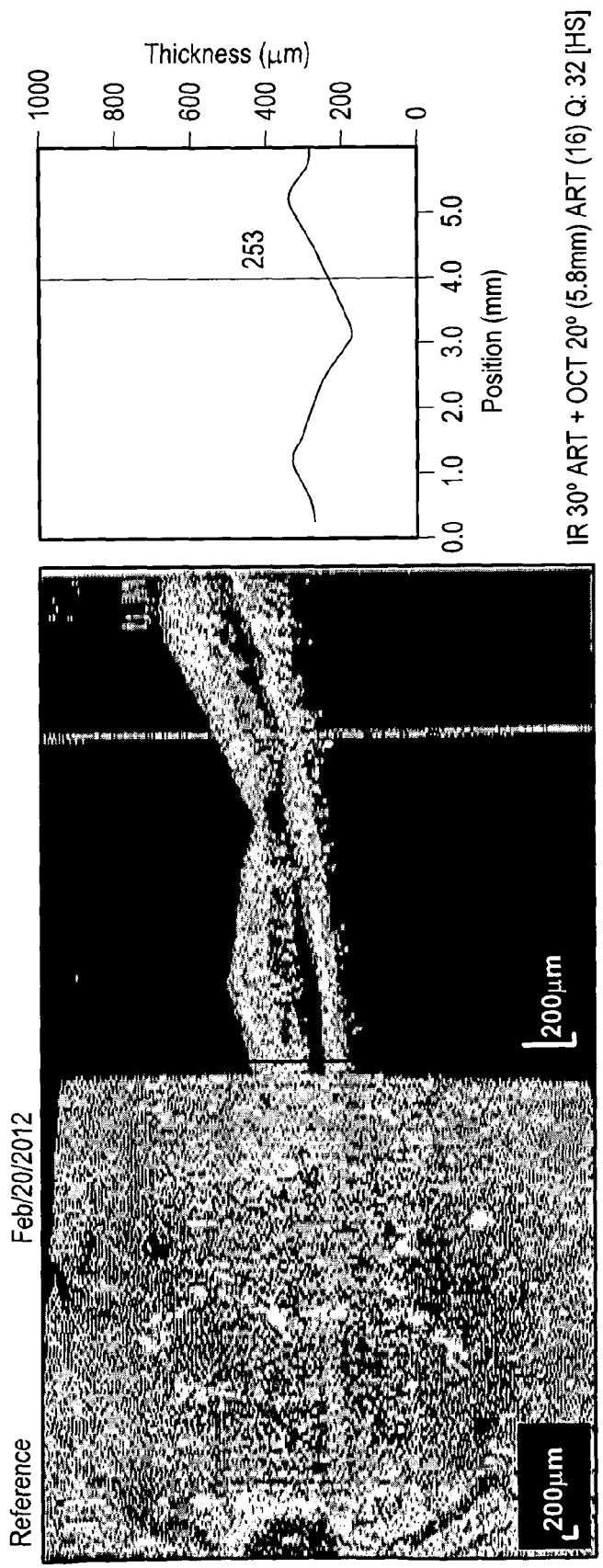
Figure 28:
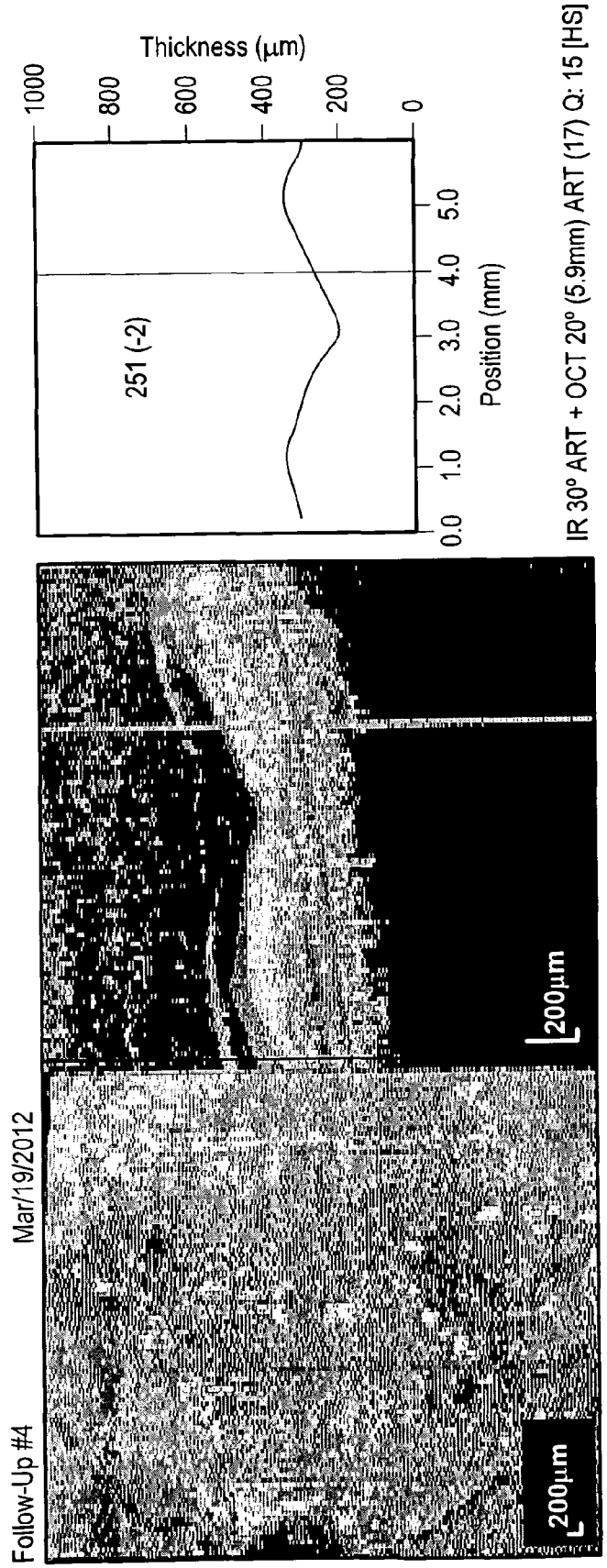

60 year old man presented in 2006 with bilateral macular oedema. He was treated with more than ten intravitreal injections in each eye. Hee also had three sessions of focal LASER treatment in each eye. He was started on Omega 3RX® on Dec. 19, 2011. The fluid resolved within two months of treatment and he gained two lines of vision in each eye (FIG. 28).

Case aa)

Figure 29:
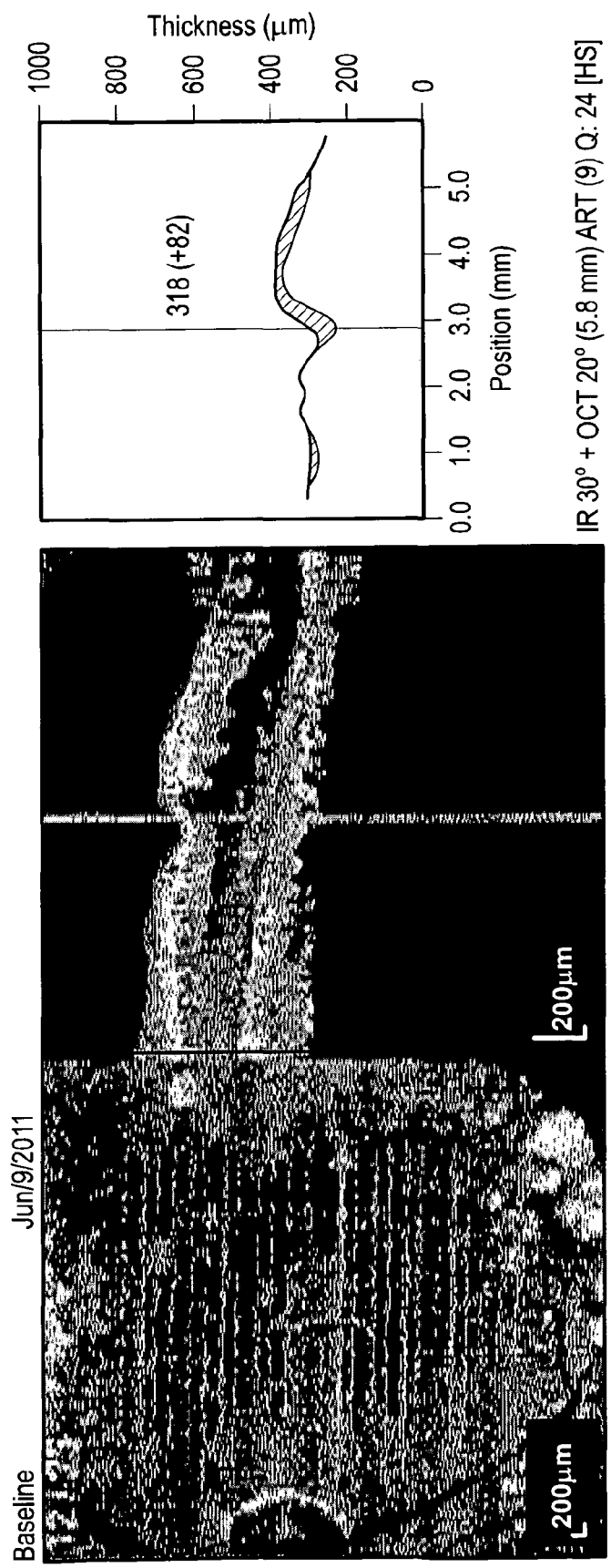
Figure 29:
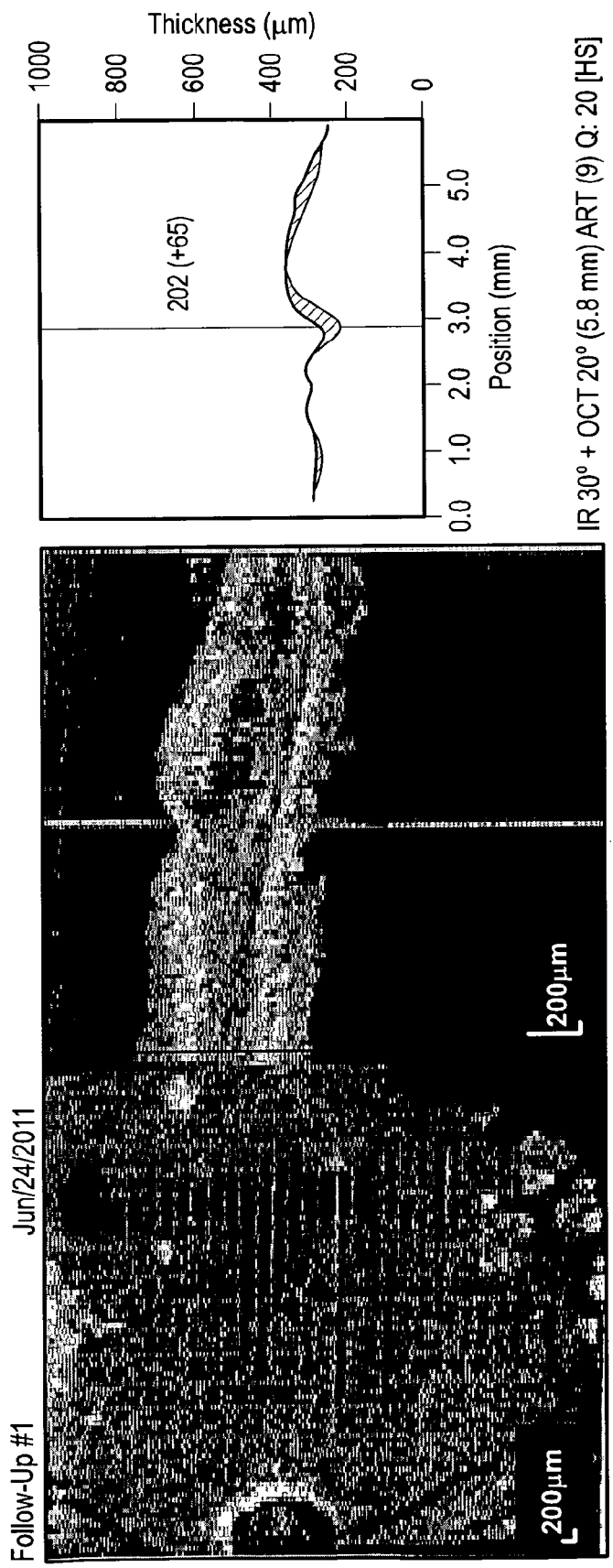
Figure 29:
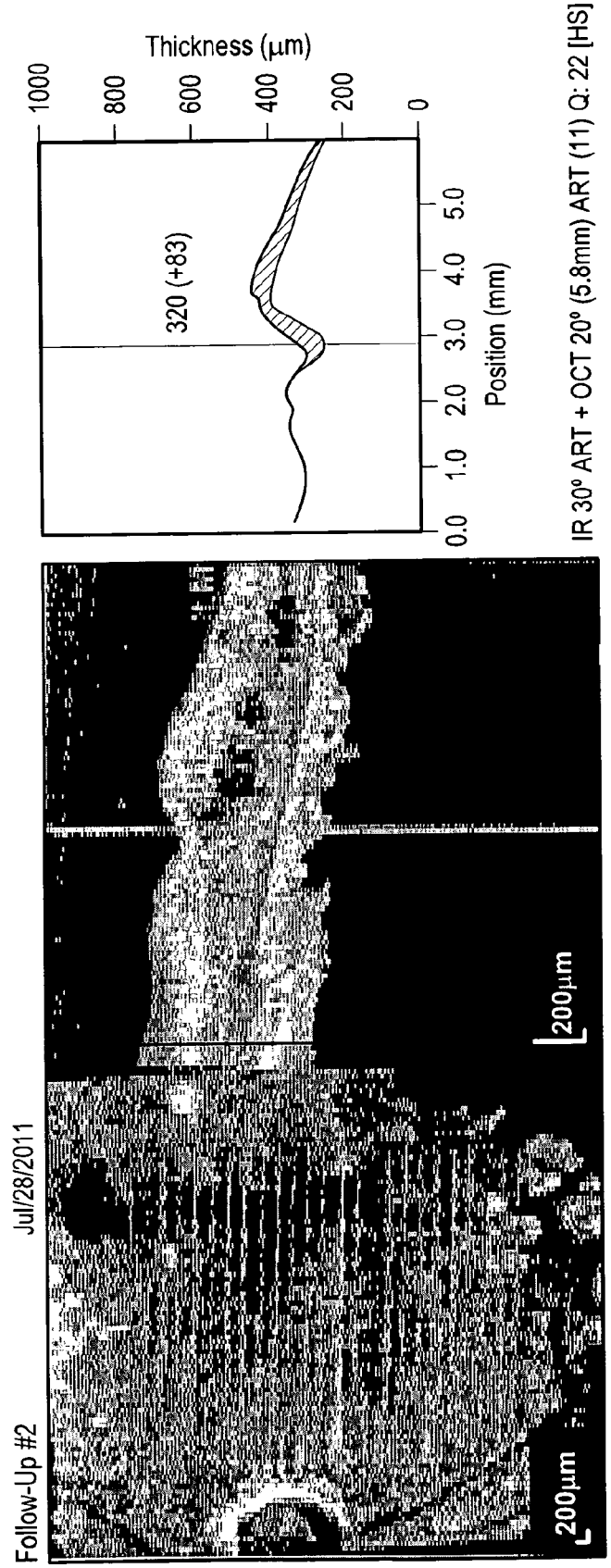
Figure 29:
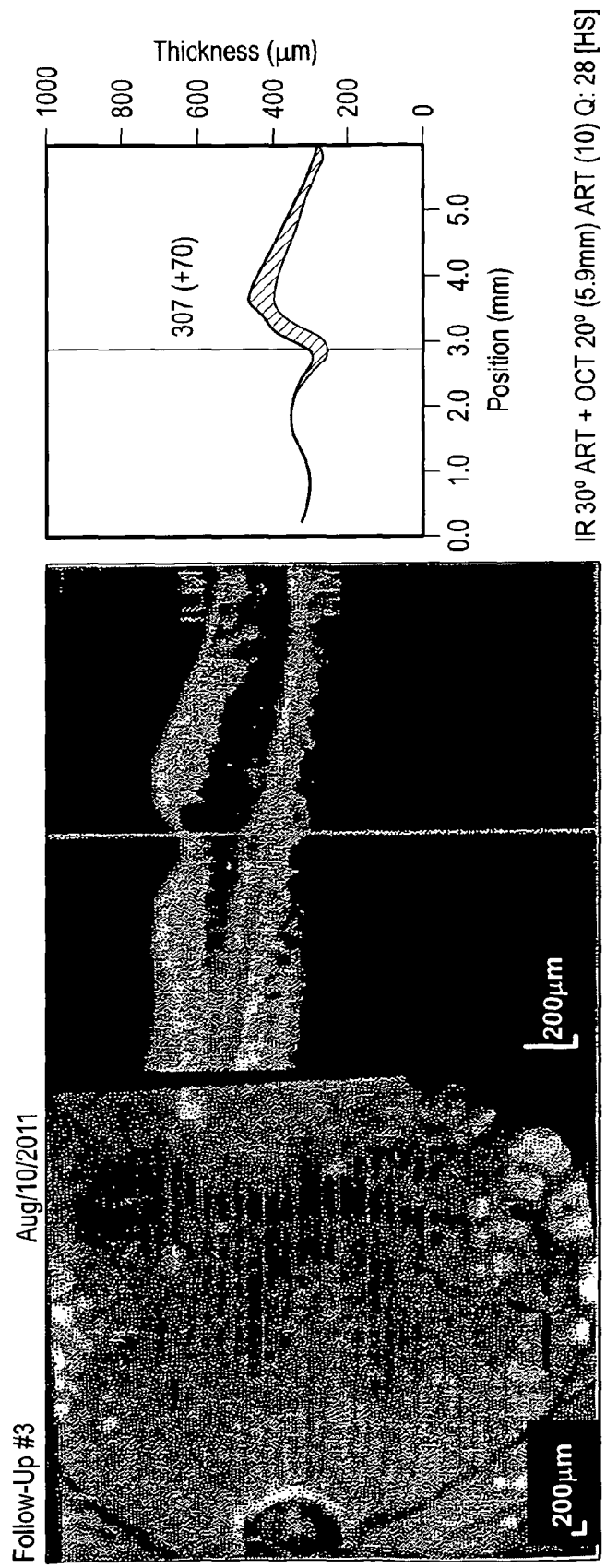
Figure 29:
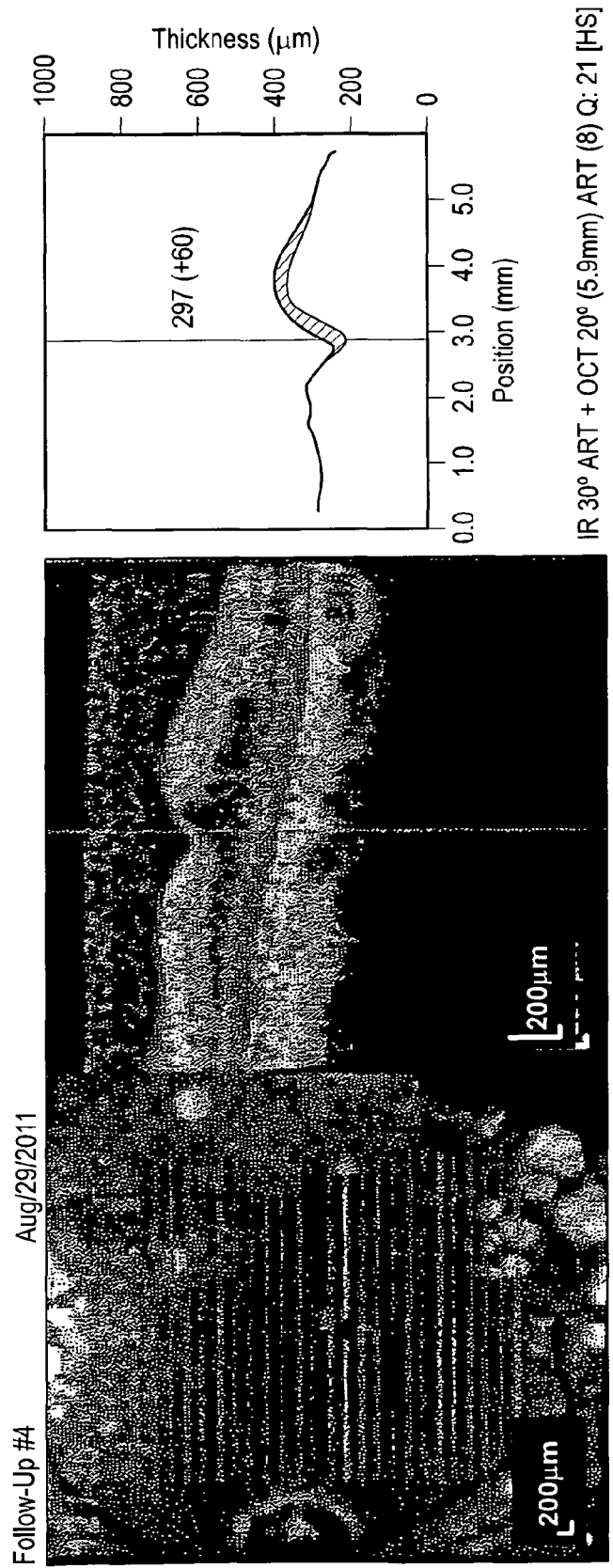
Figure 29:
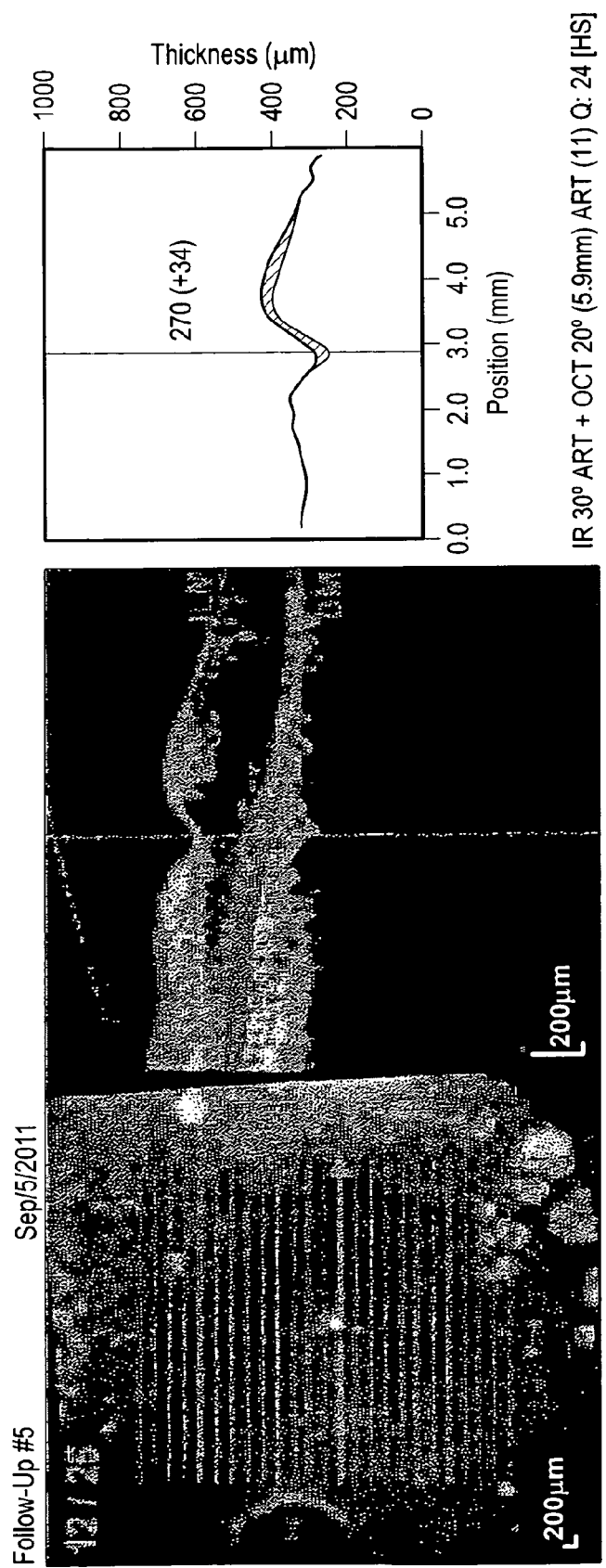
Figure 29:
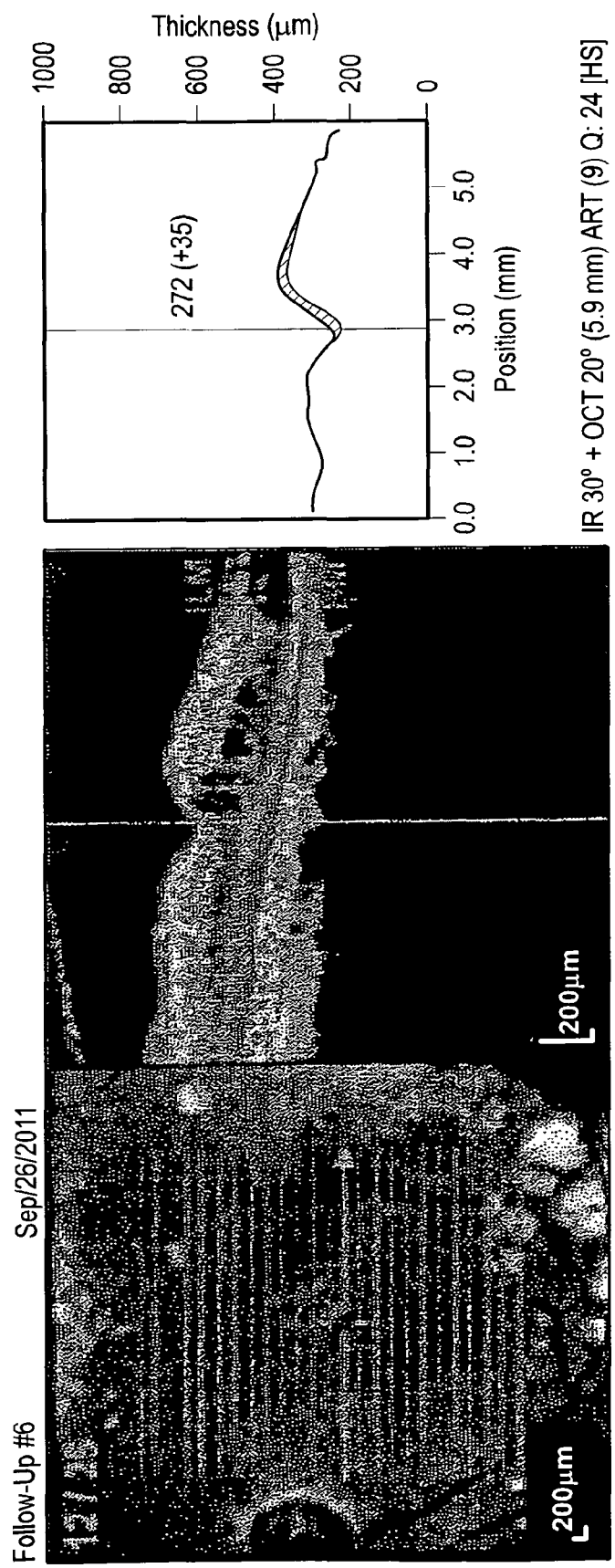
Figure 29:
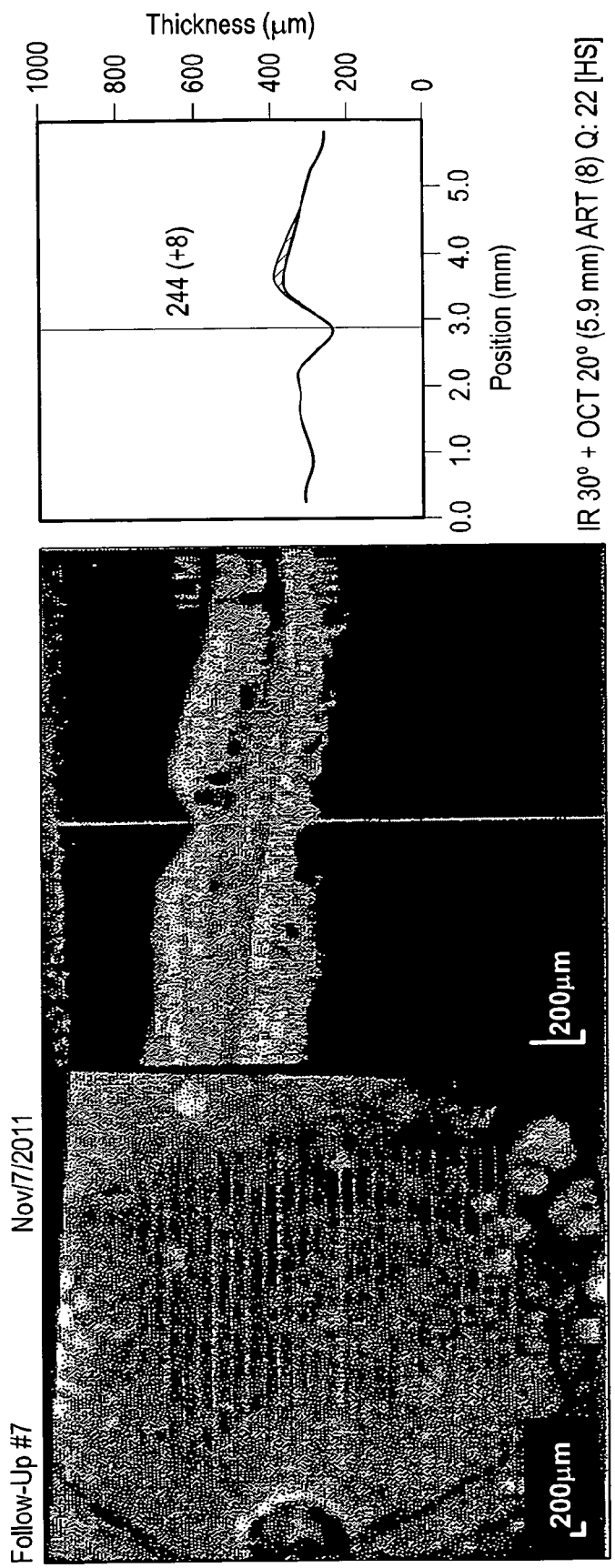
Figure 29:
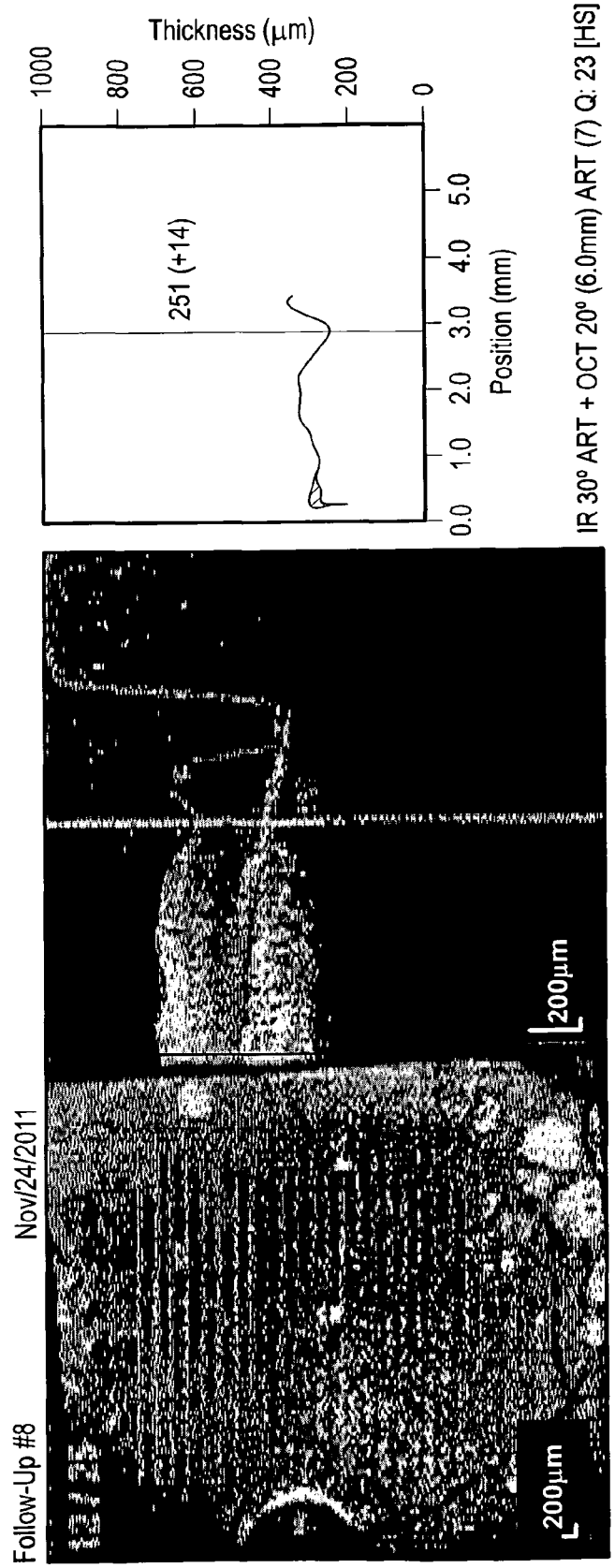
Figure 29:
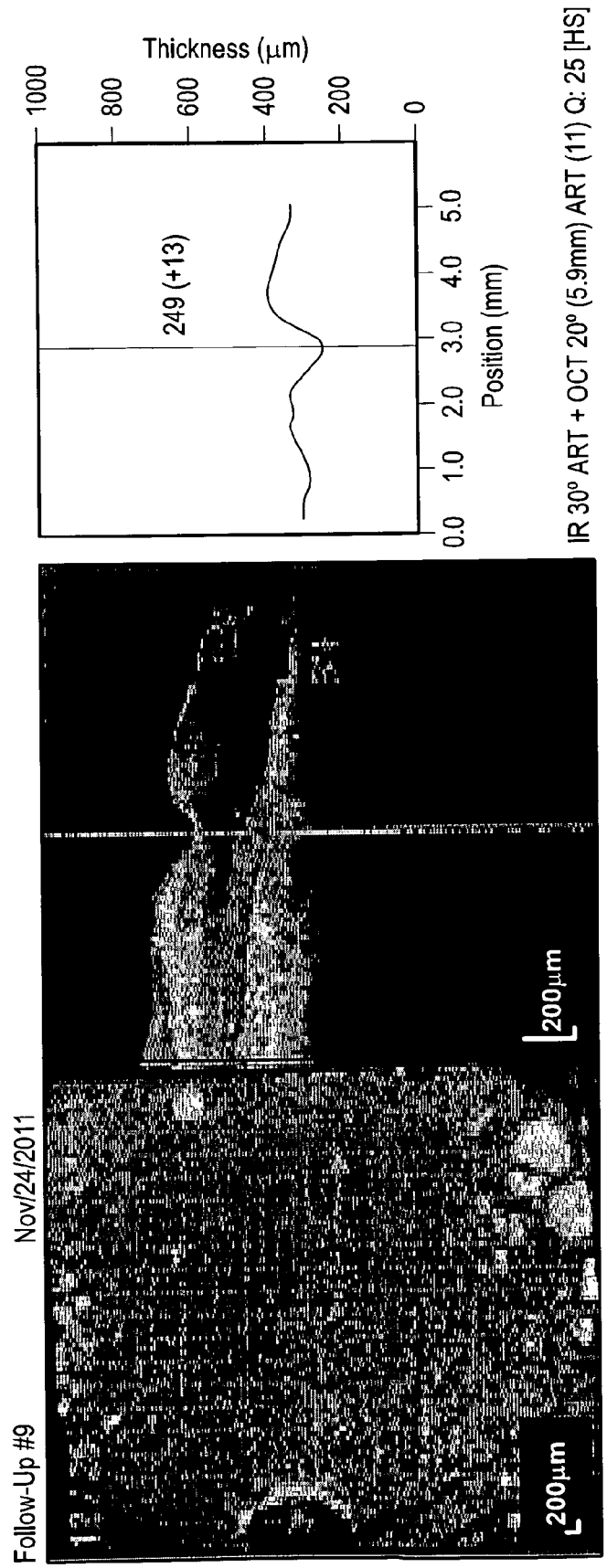
Figure 29:
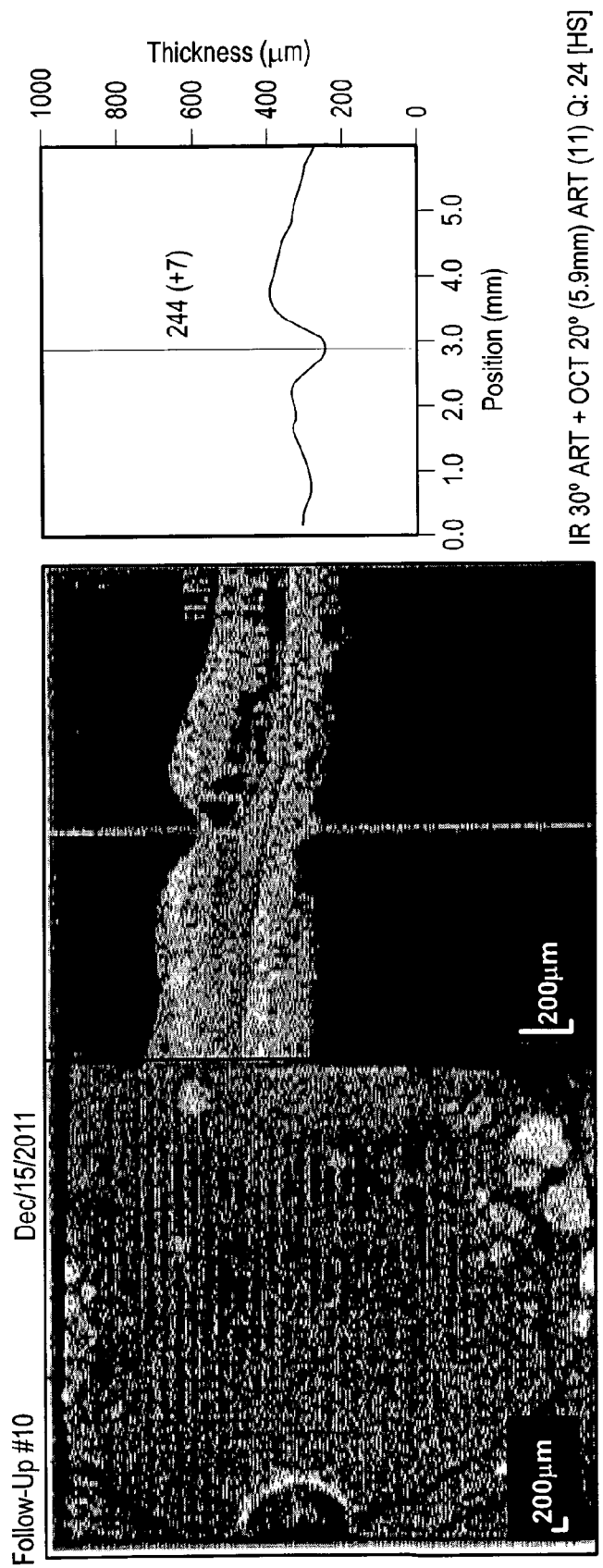
Figure 29:
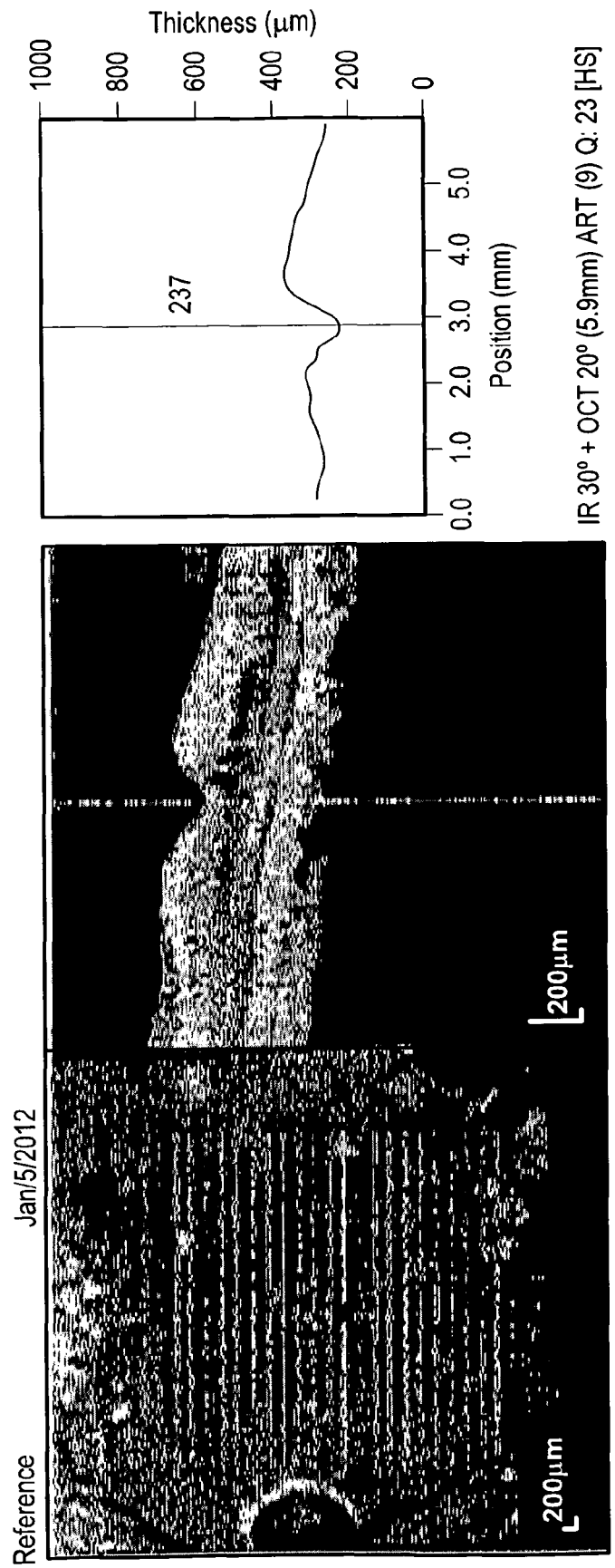
Figure 29:
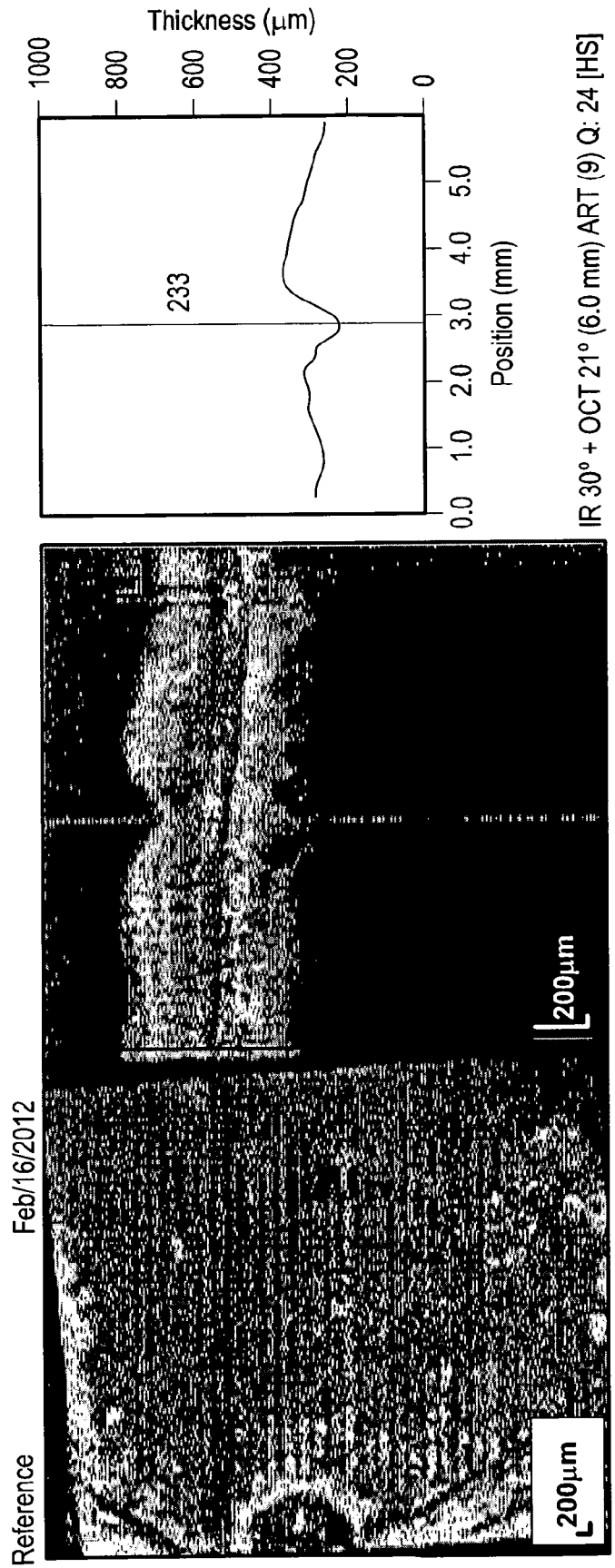

60 year old man presented with left macular oedema in 2011. He was started on Omega 3RX® on Sep. 26, 2011. Most fluid resolved within four months and he gained four lines of vision (FIG. 29).

Case ab)

68 year old man with macular oedema due to diabetes was started on Apr. 14, 2011 with Omega 3RX®. Three months following treatment there was minimal fluid and he gained one line of vision (FIG. 30).

Case ac)

Figure 31:
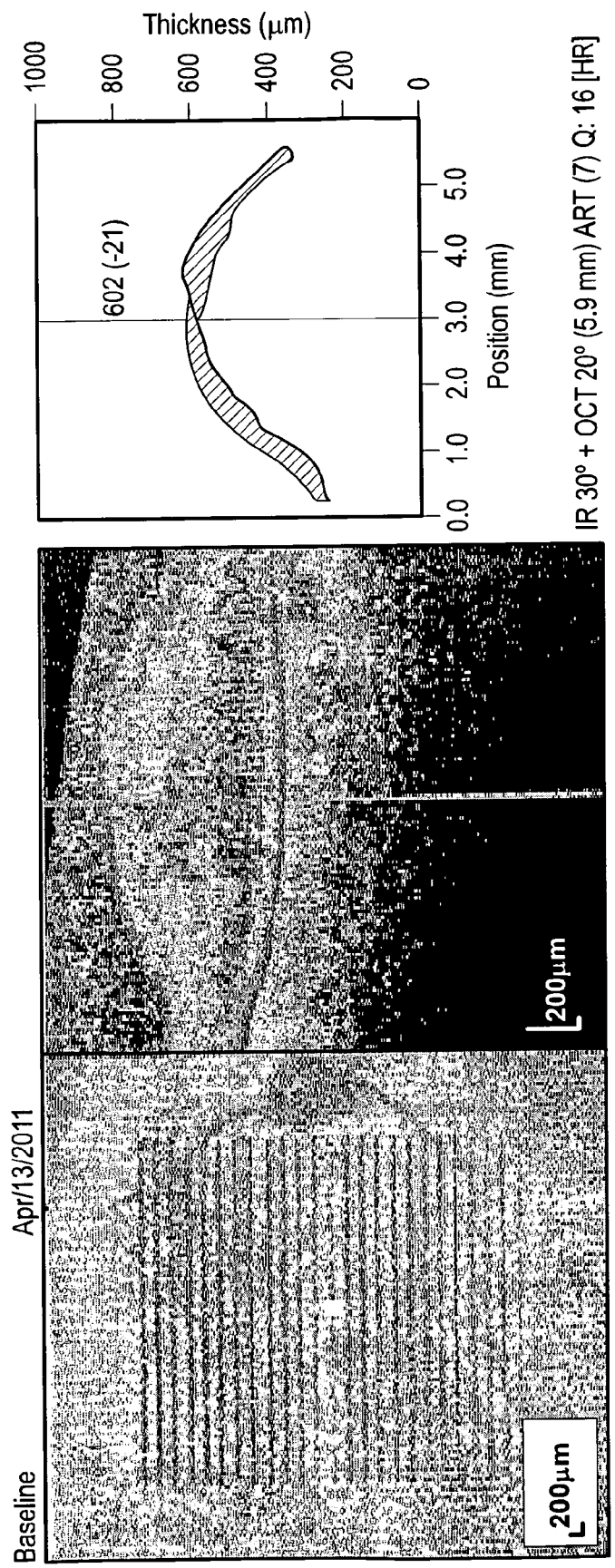
Figure 31:
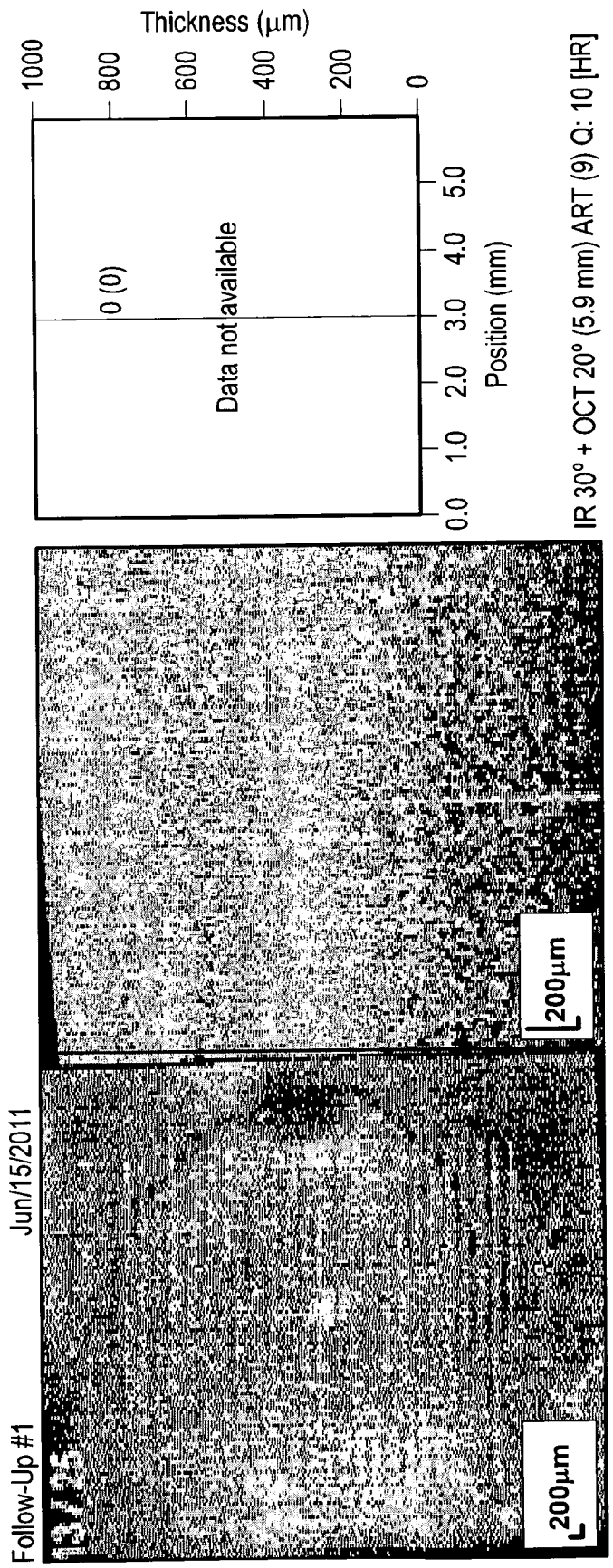
Figure 31:
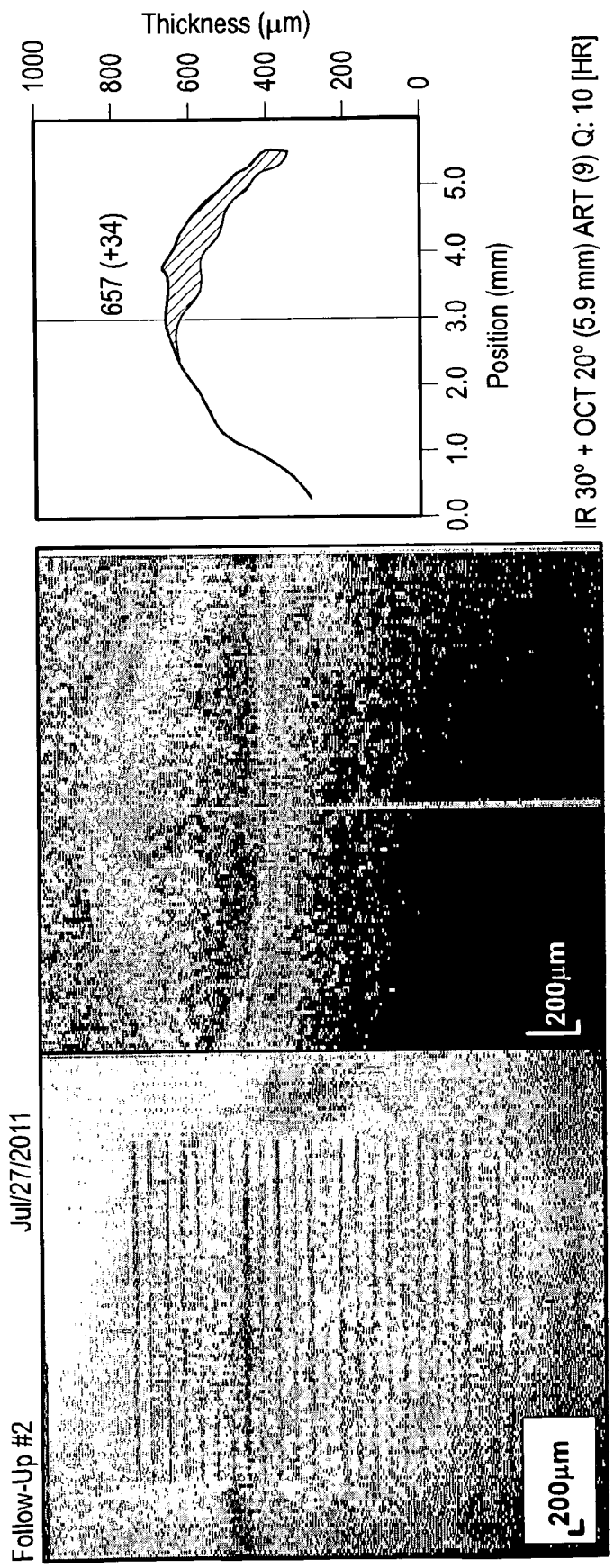
Figure 31:
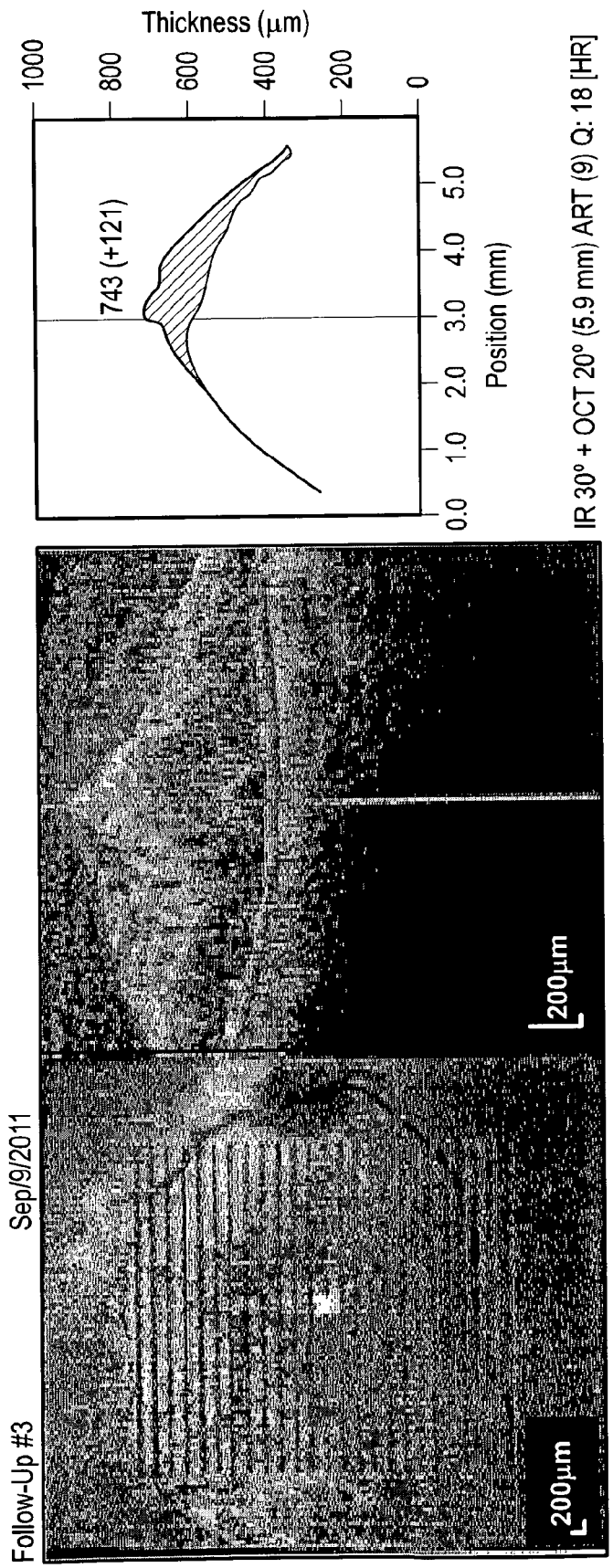
Figure 31:
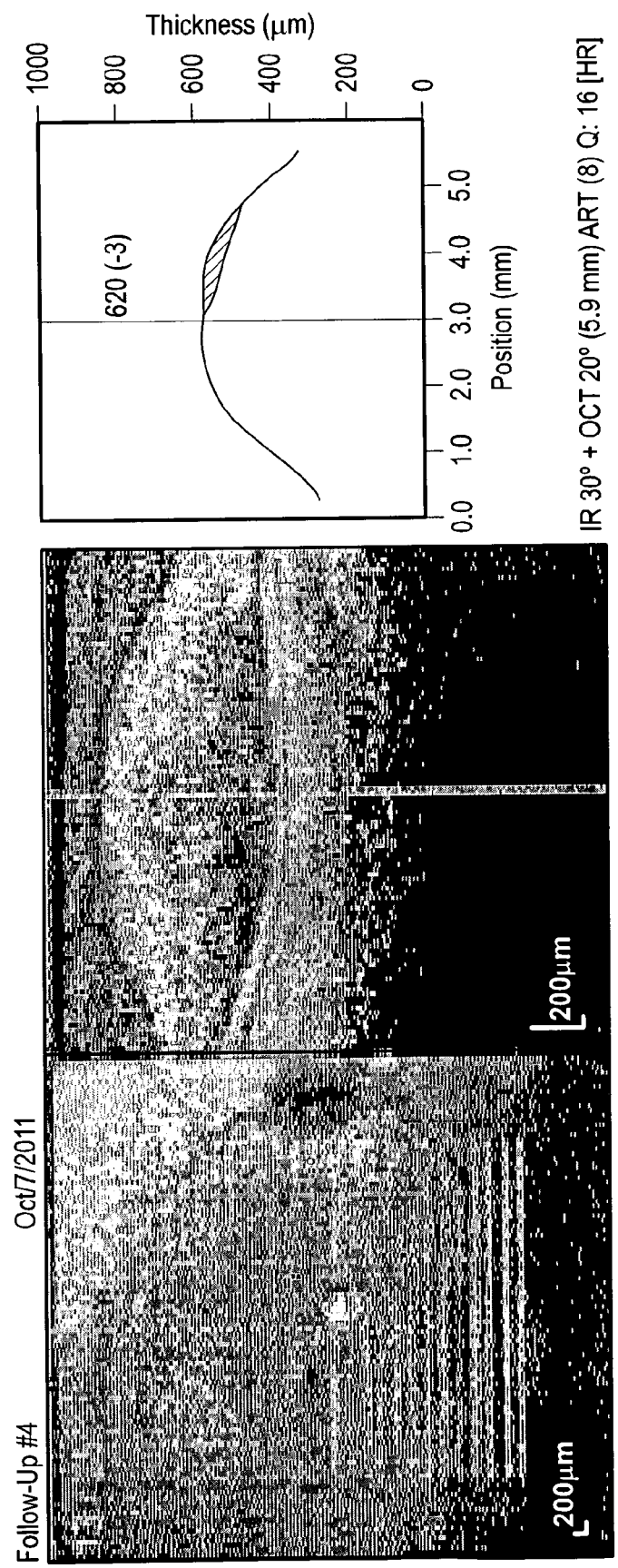
Figure 31:
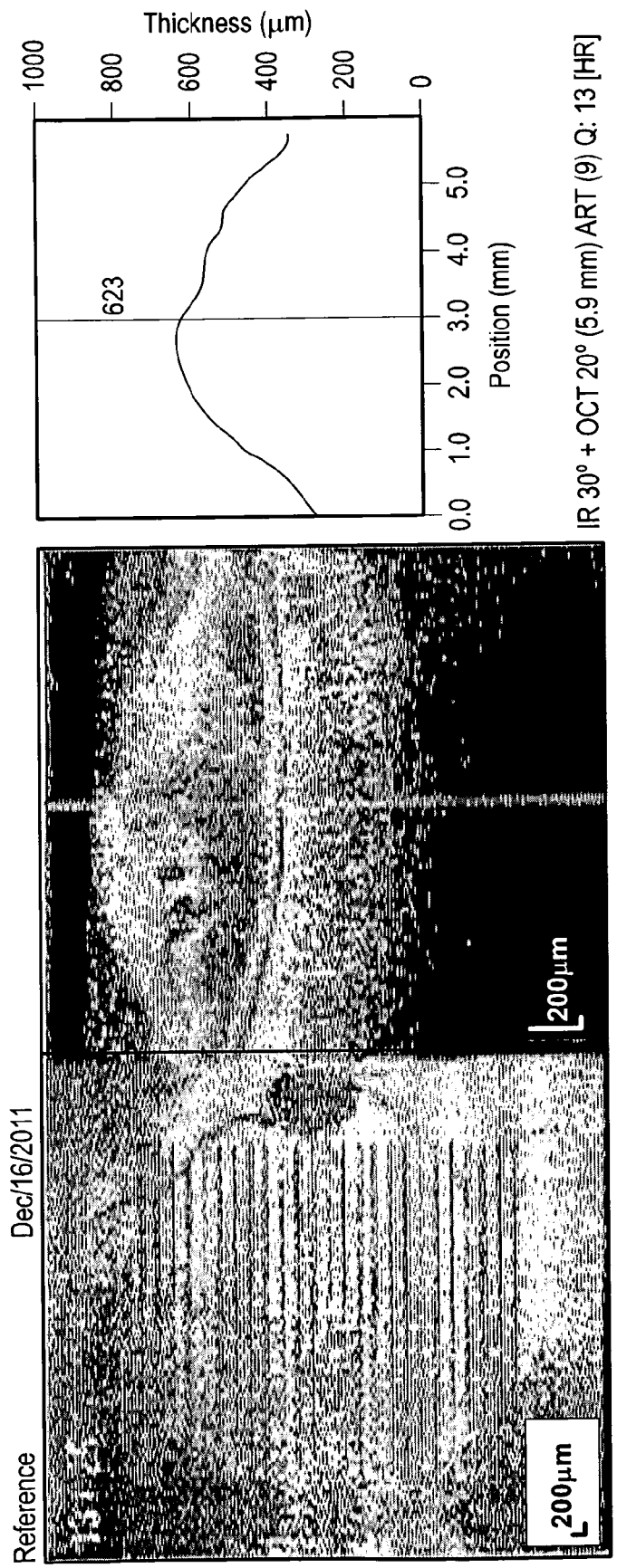
Figure 31:
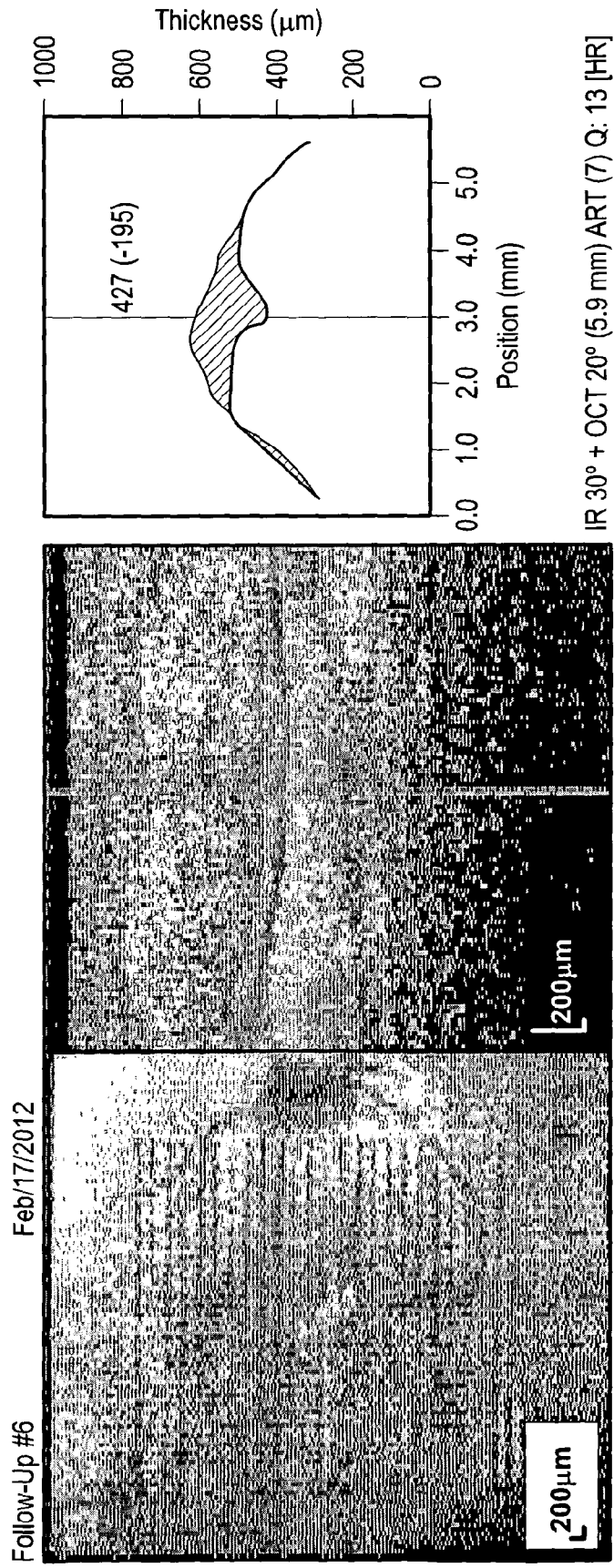
Figure 31:
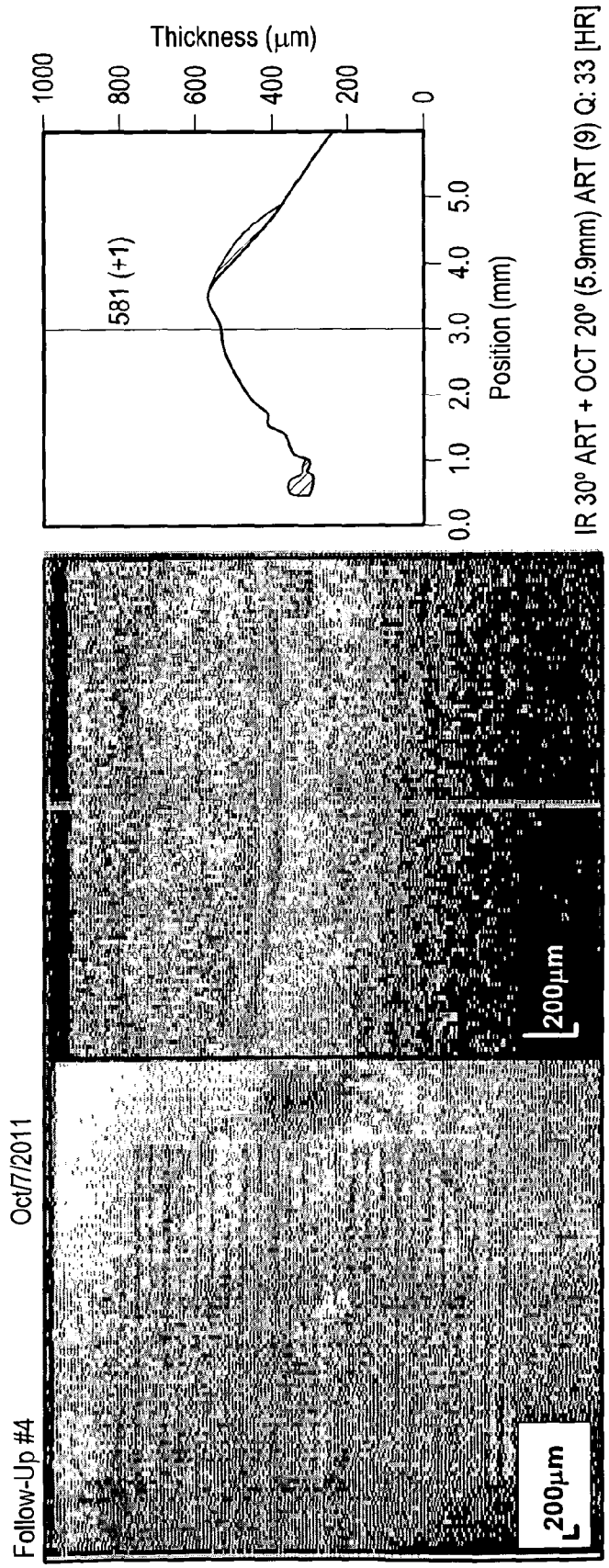
Figure 31:
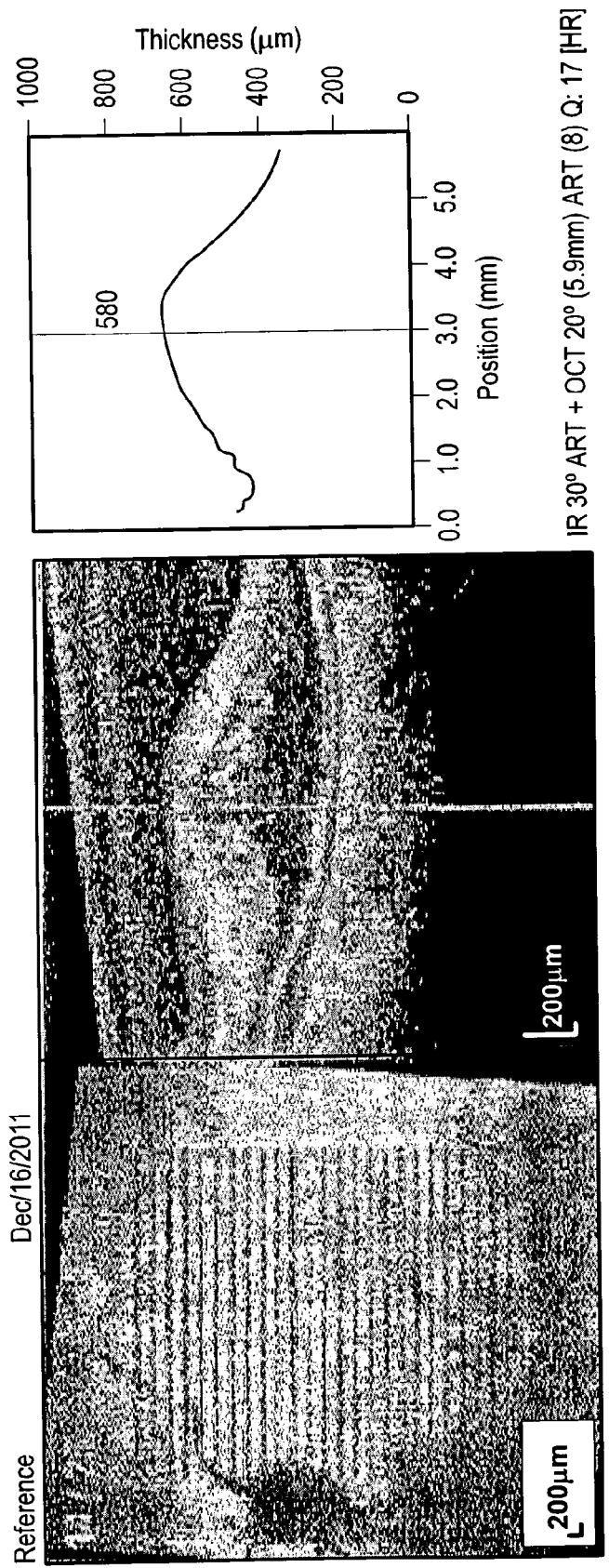
Figure 31:
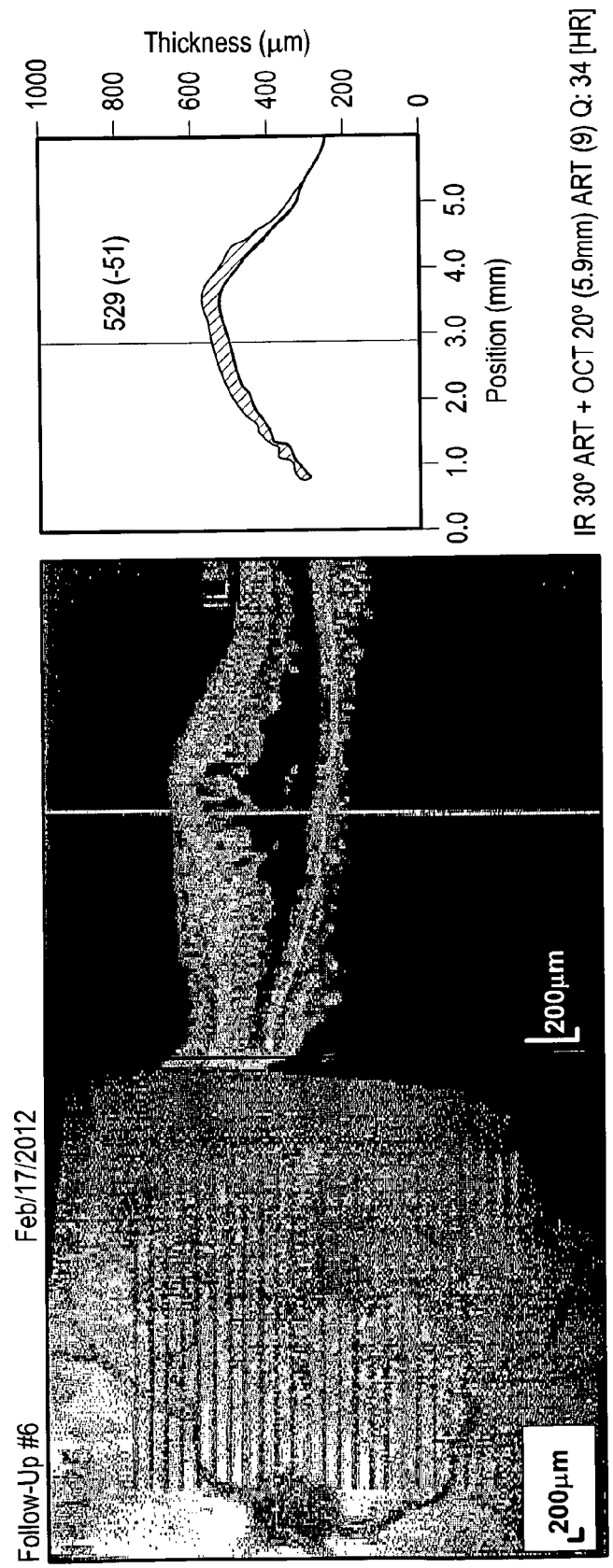

54 year old female presented in 2010 with bilateral diabetic macular oedema. She had bilateral focal LASER in 2010 and she was started on Omega 3RX® on Jan. 7, 2011. Macular oedema was reduced in both eyes following treatment and she gained one line of vision in each eye (FIG. 31).

Case ad)

Figure 32:
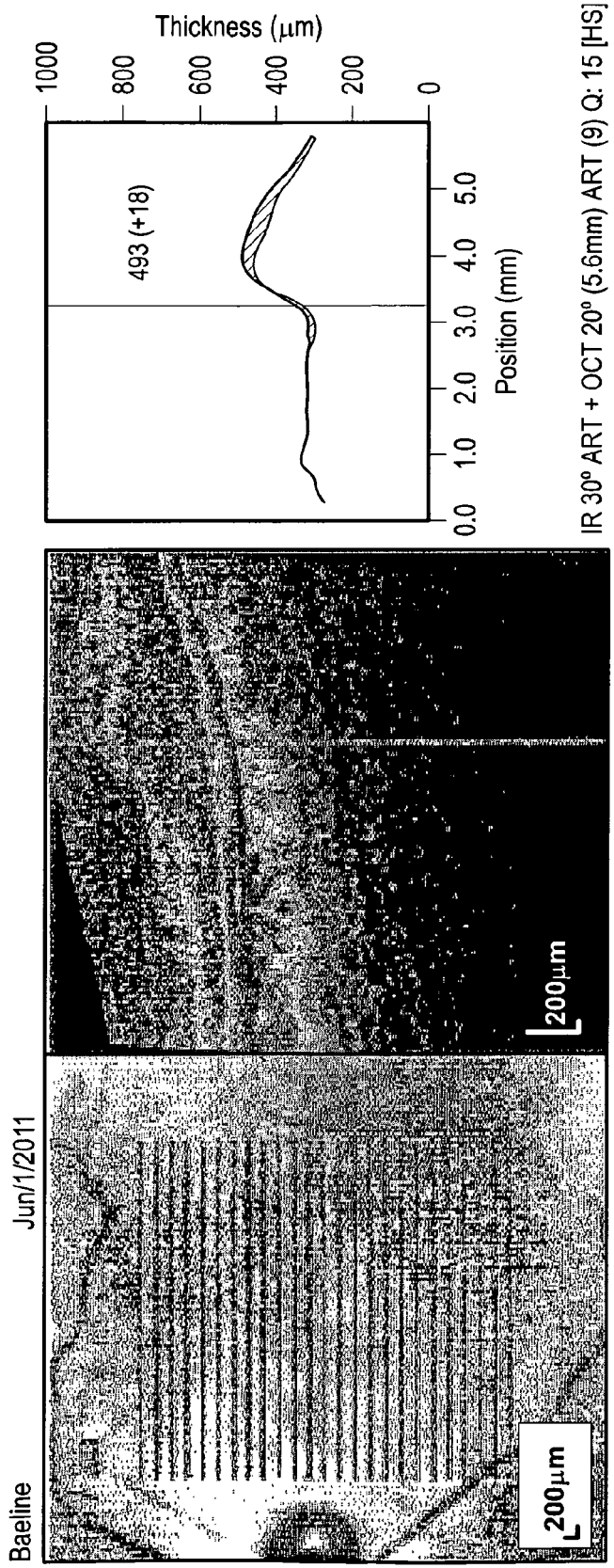
Figure 32:
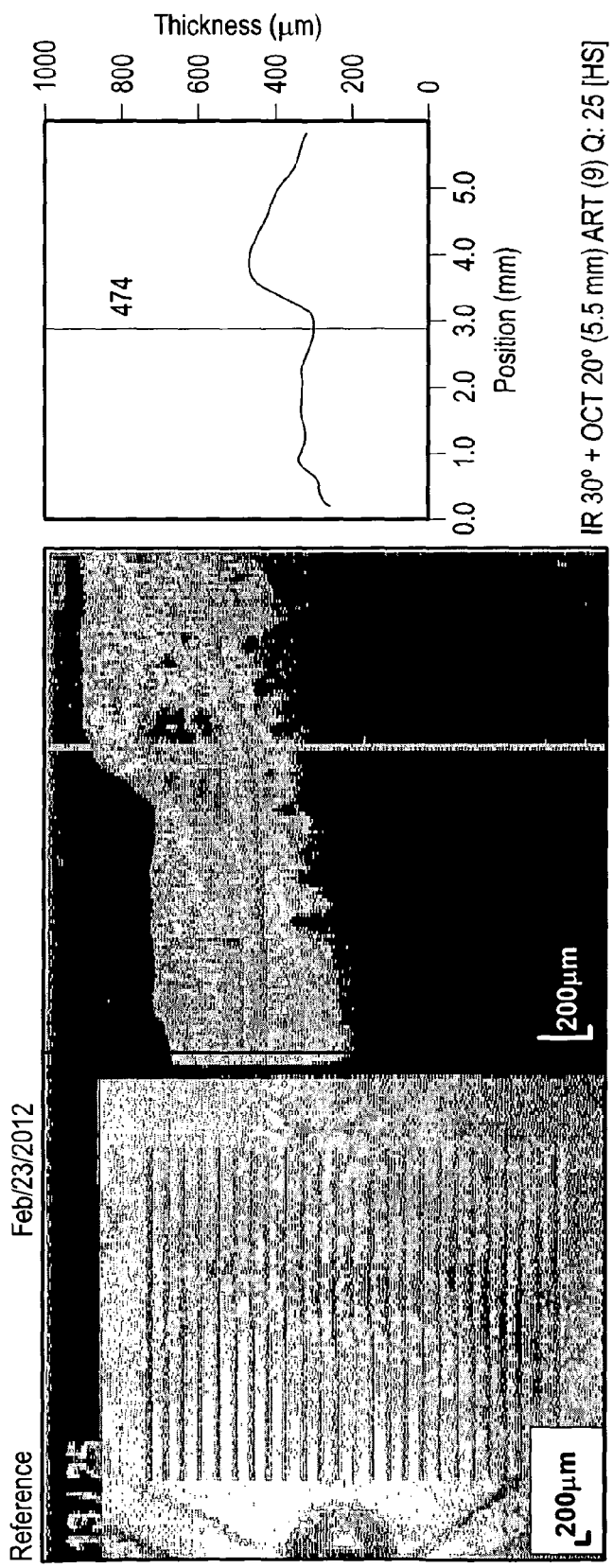
Figure 32:
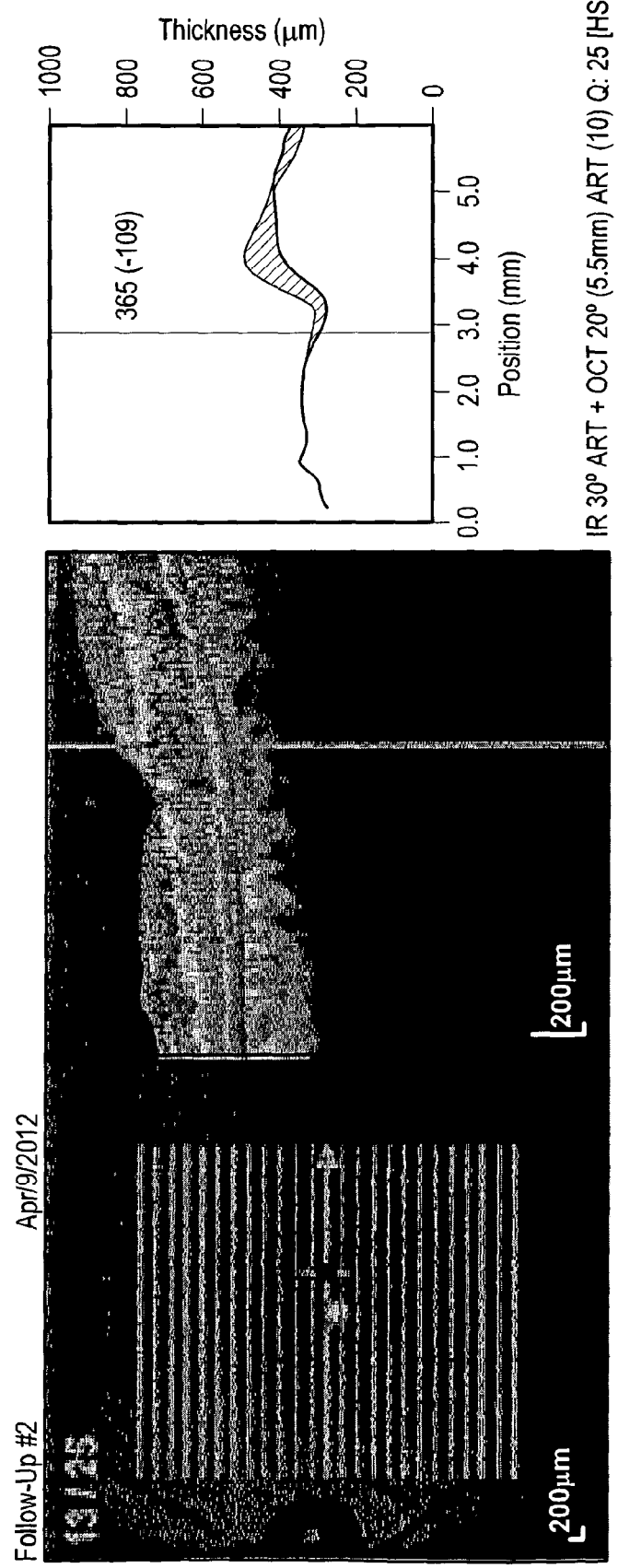

78 year old female presented with left diabetic macular oedema on 1.6.11. She was treated with intravitreal AVASTIN injection. She was started on oral Omega 3RX® on Feb. 23, 2012. Six weeks following treatment the fluid resolved and she gained one line of vision (FIG. 32).

Case ae)

Figure 33:
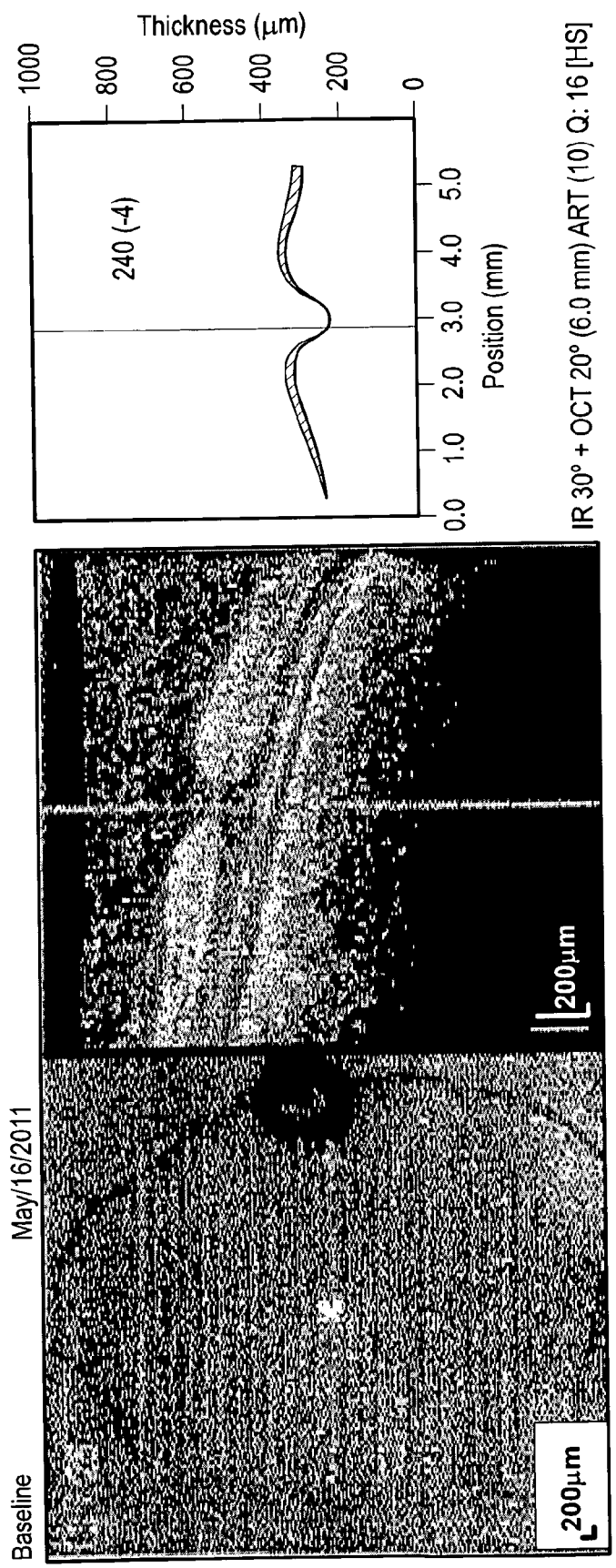
Figure 33:
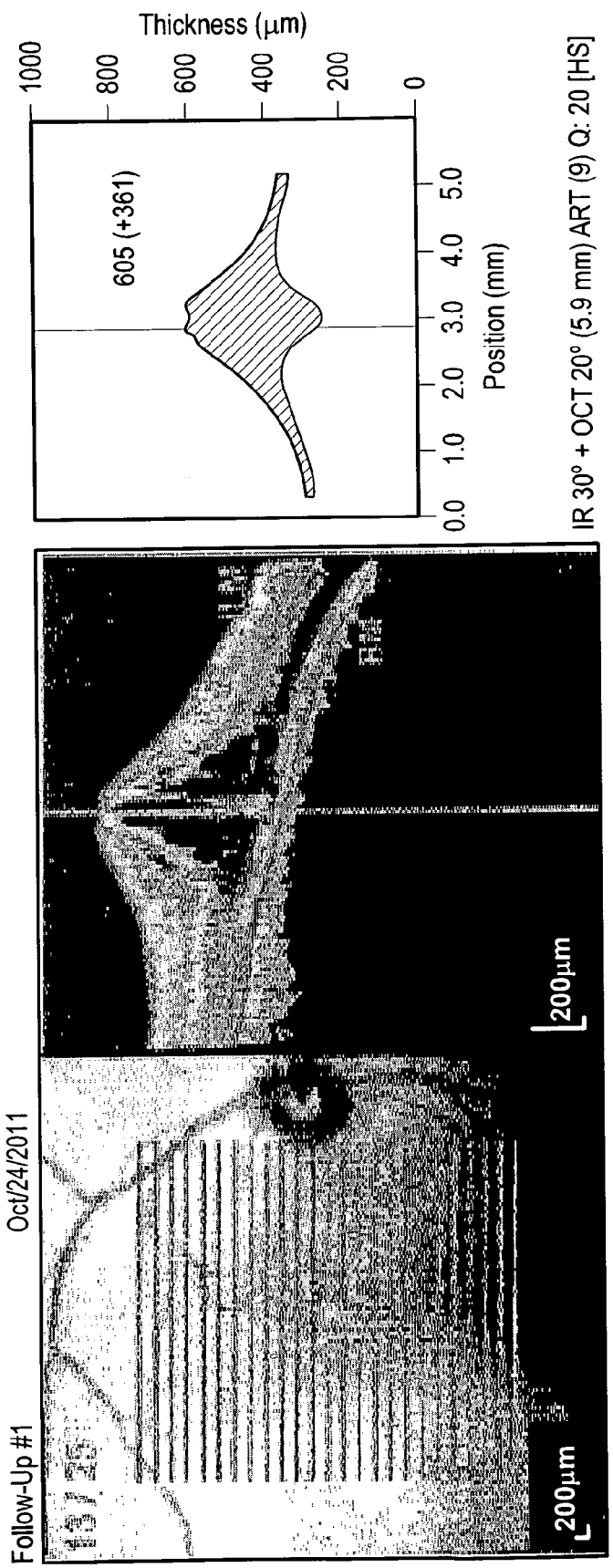
Figure 33:
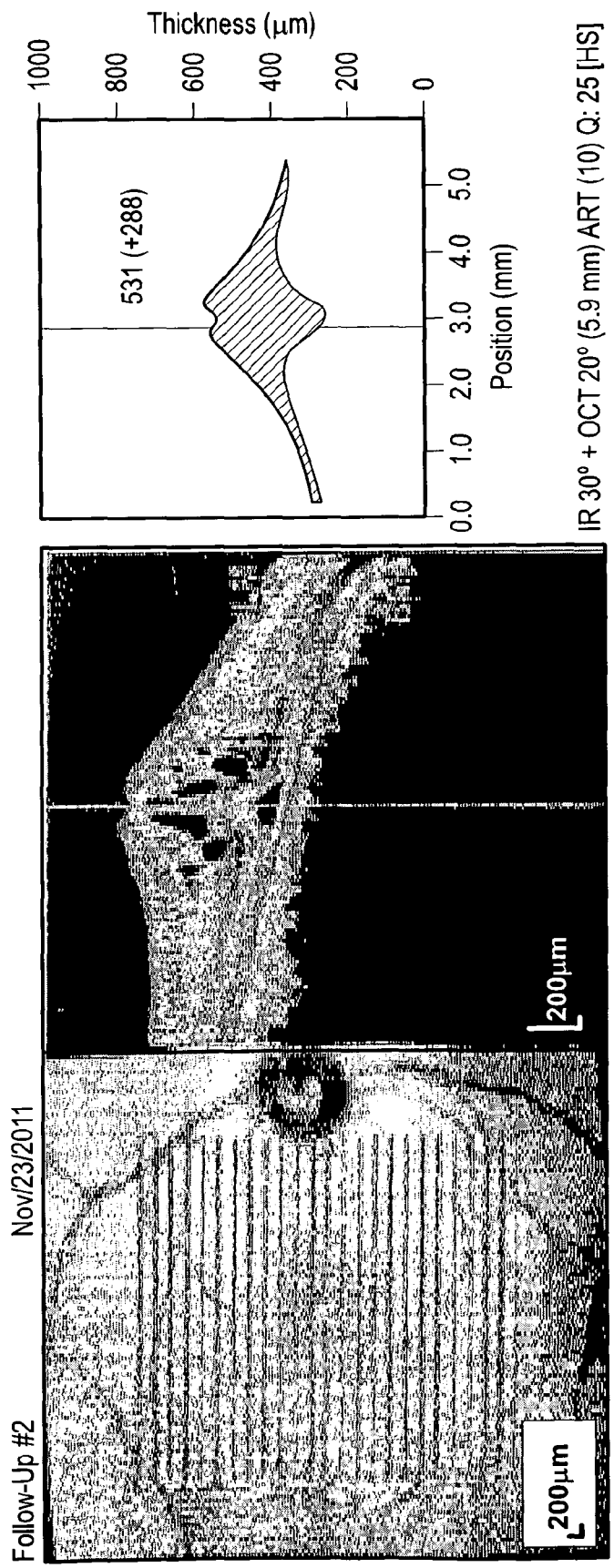
Figure 33:
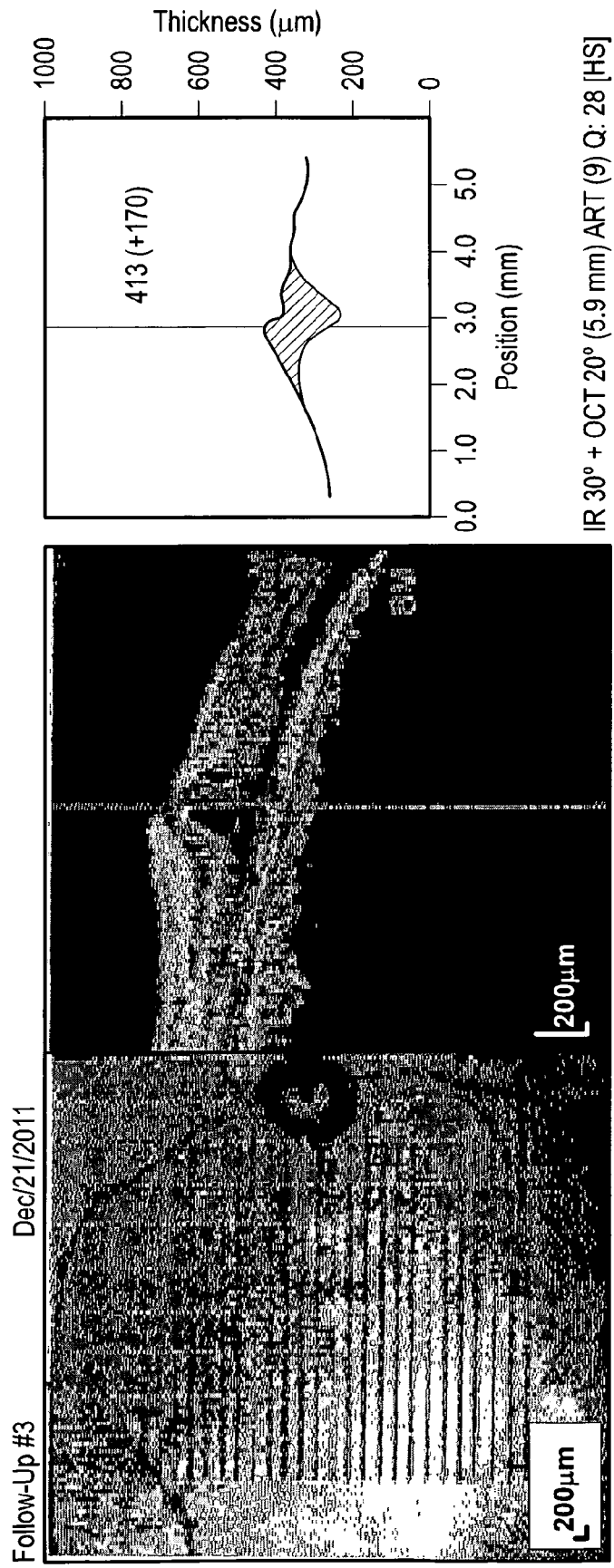
Figure 33:
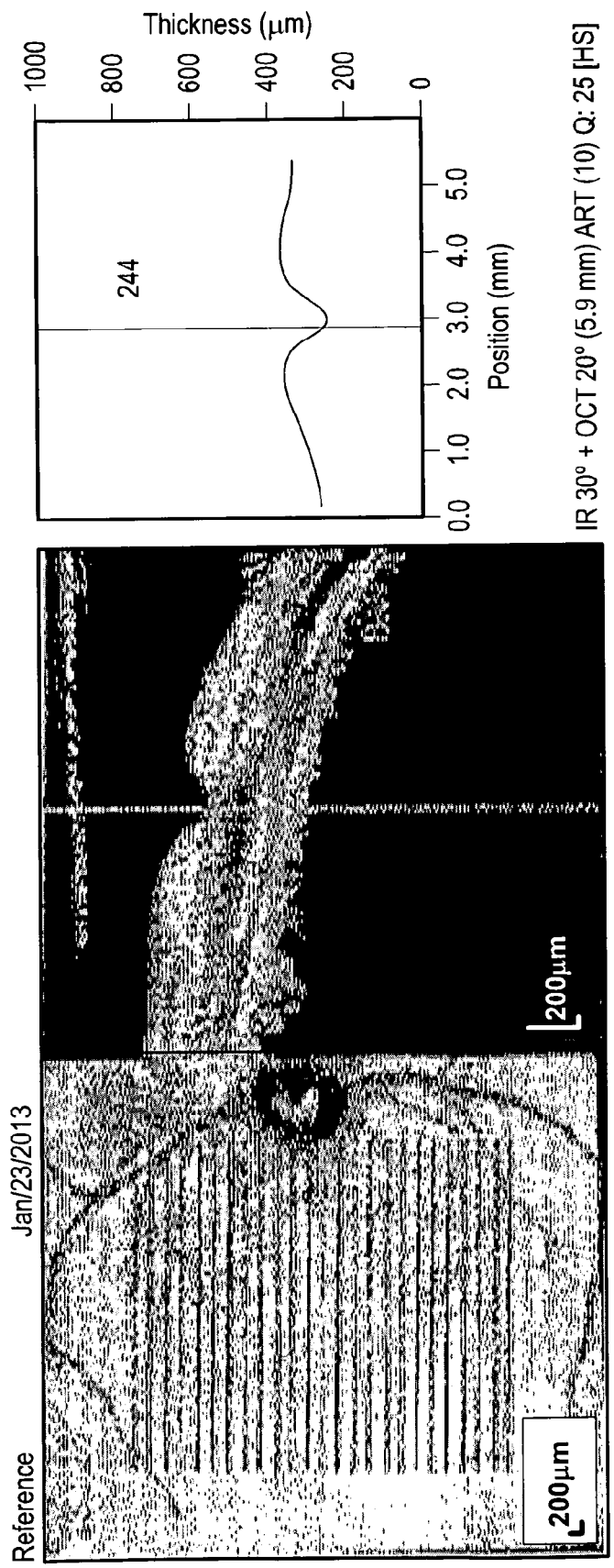
Figure 33:
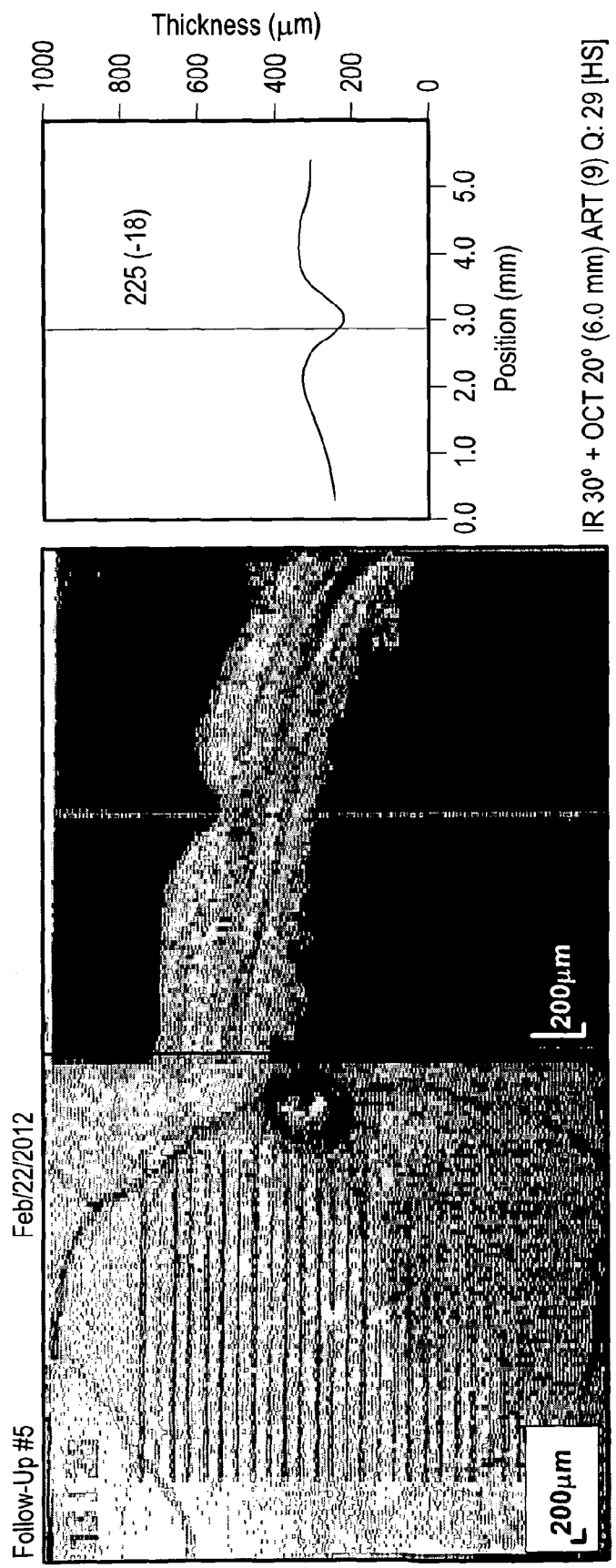
Figure 33:
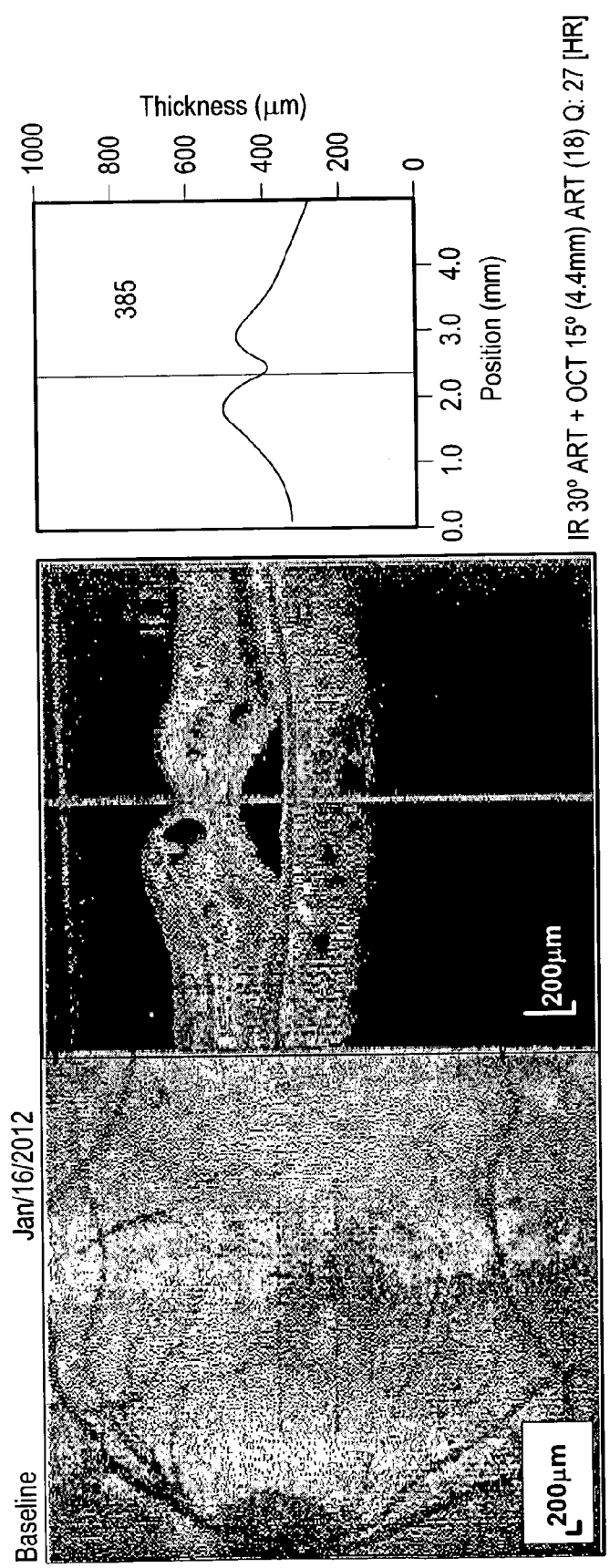
Figure 33:
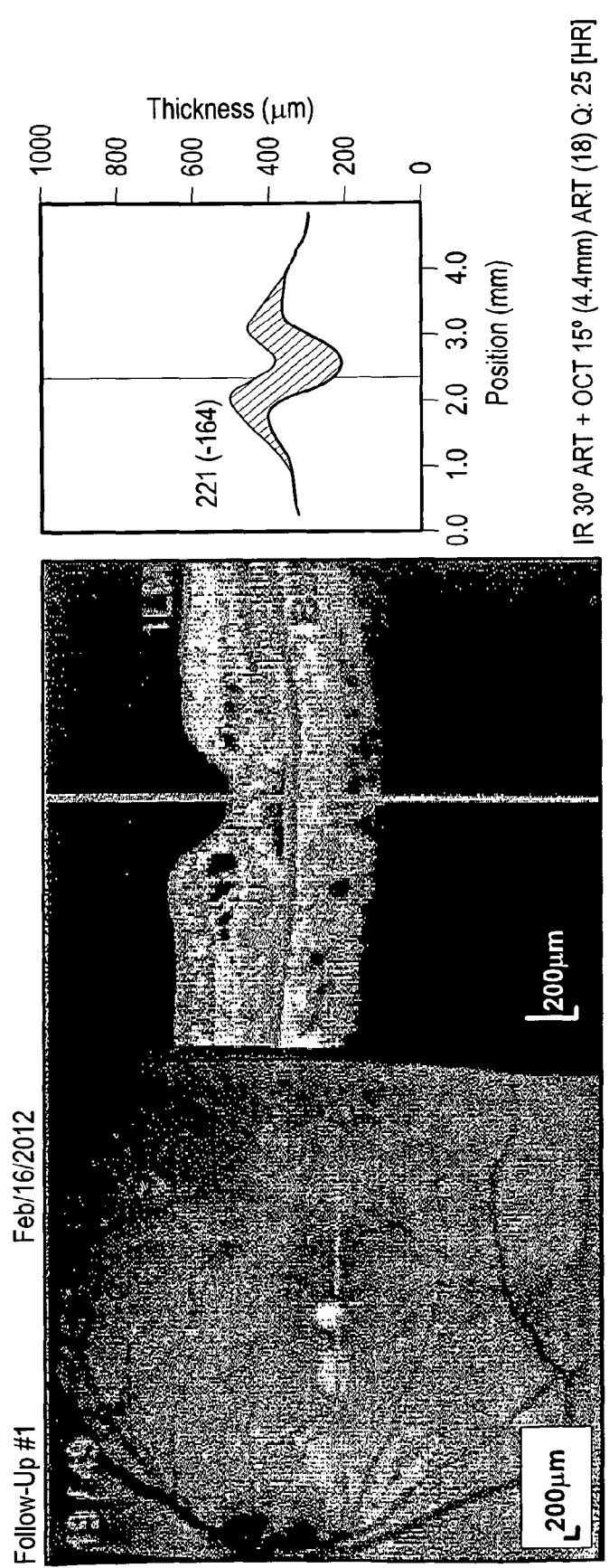

54 year old male had cataract surgery on May 24, 2011 and developed cystoid macular oedema on Oct. 24, 2011. He was started on steroid and non-steroidal eye drops for one month. On Nov. 23, 2011 he was started on Omega 3RX® and two months following treatment the fluid resolved (FIG. 33).

Case af)

Figure 34:
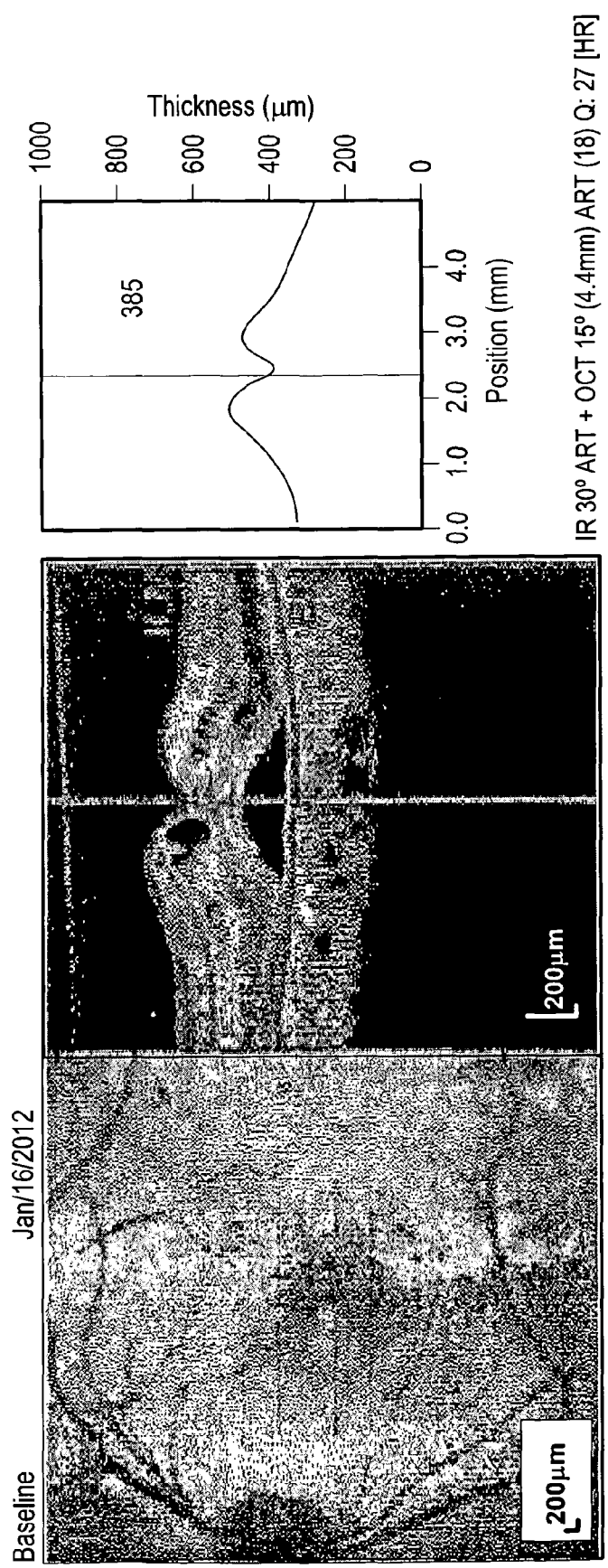
Figure 34:
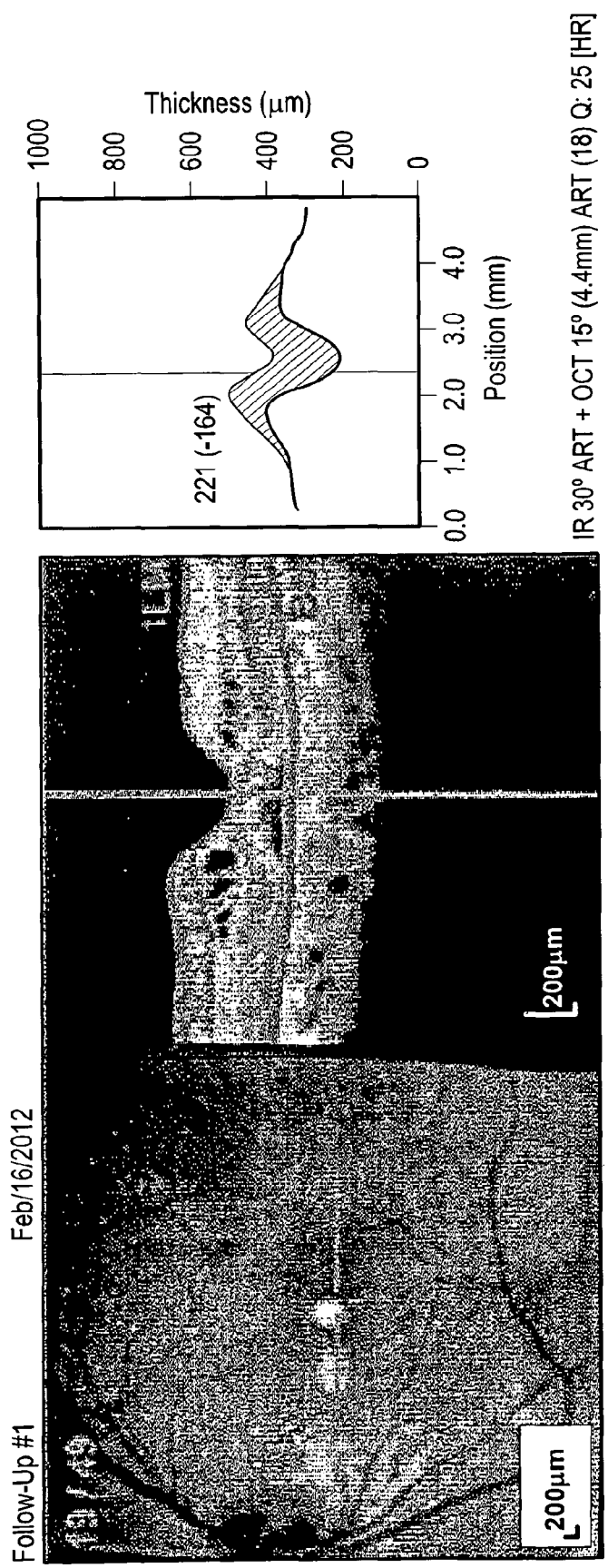

78 year old female who had complicated cataract surgery in 2010 presented with cystoid macular oedema on Jan. 16, 2012. She was started on Omega 3RX® and two months following treatment there was no fluid and she gained one line of vision (FIG. 34).

Case ag)

Figure 35:
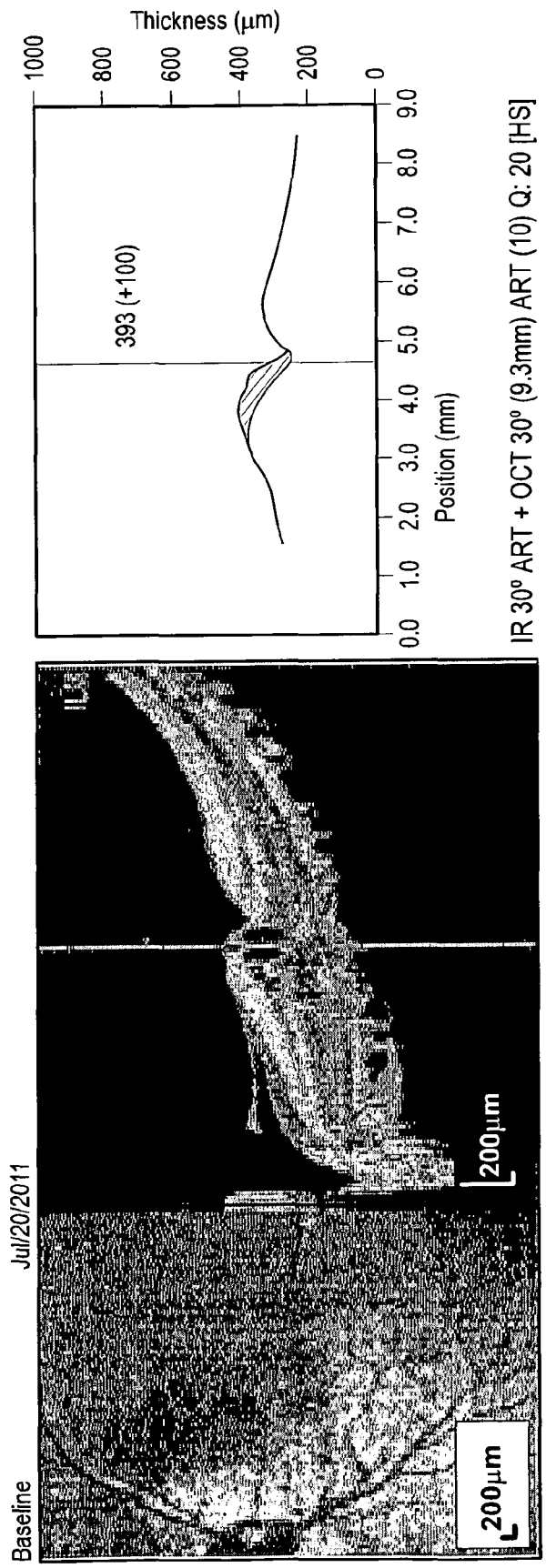
Figure 35:
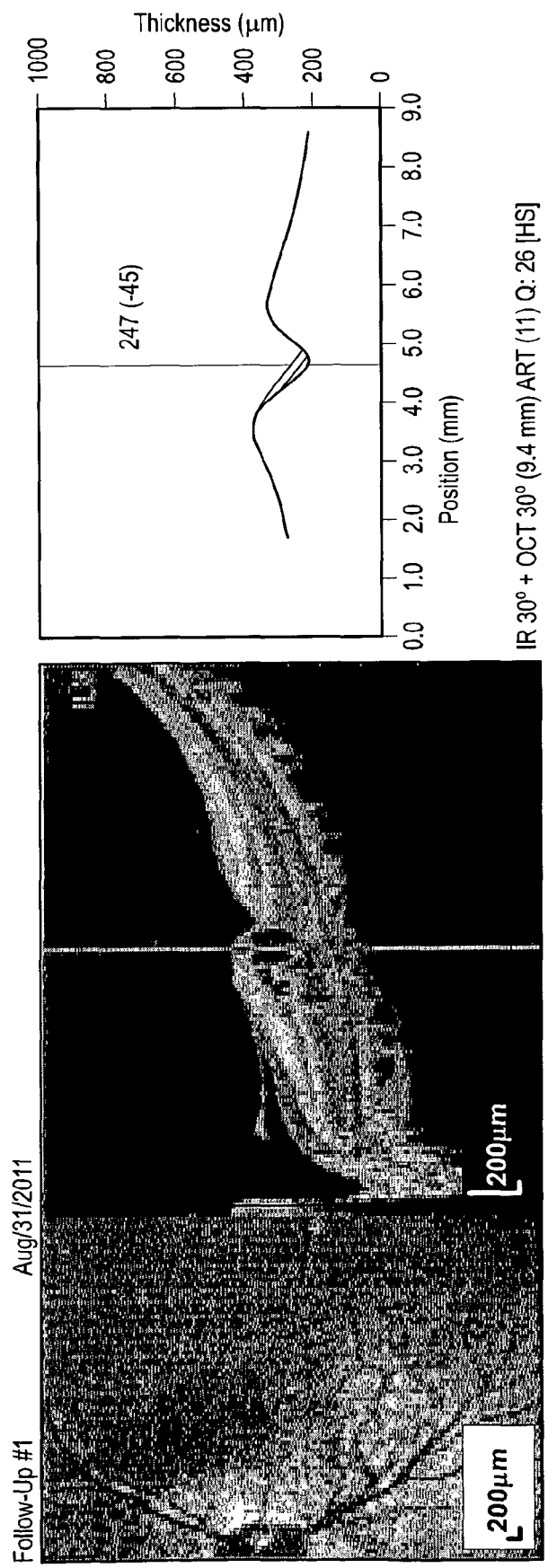
Figure 35:
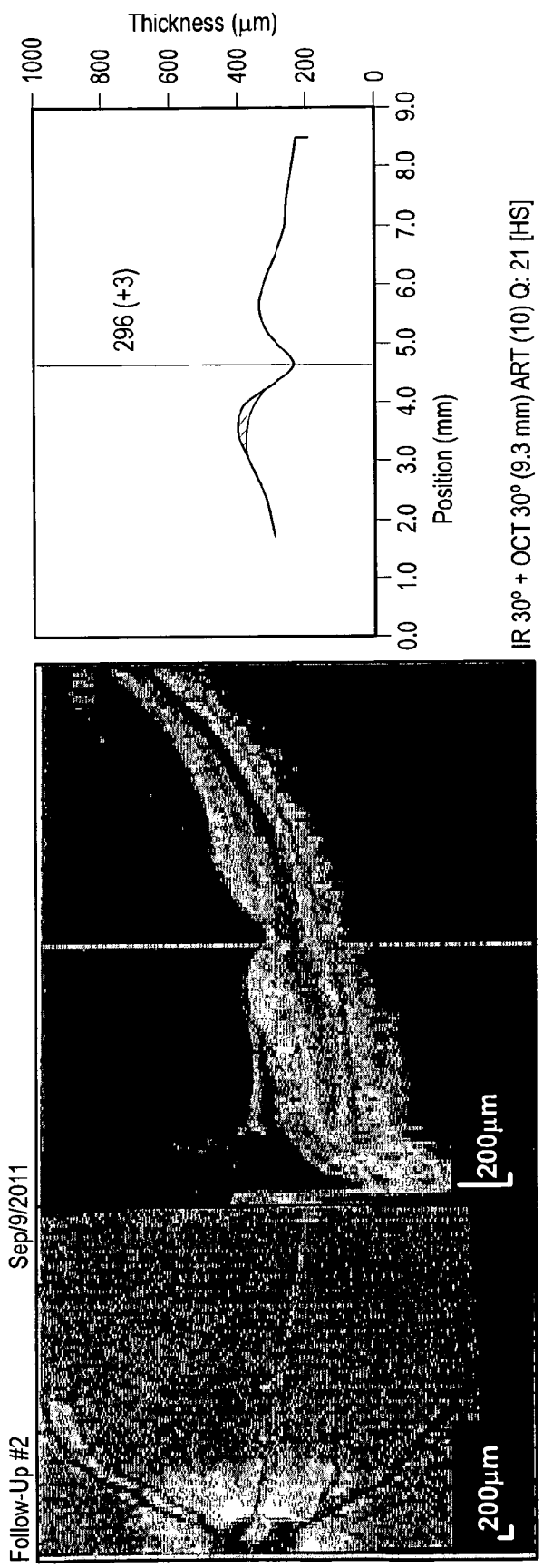
Figure 35:
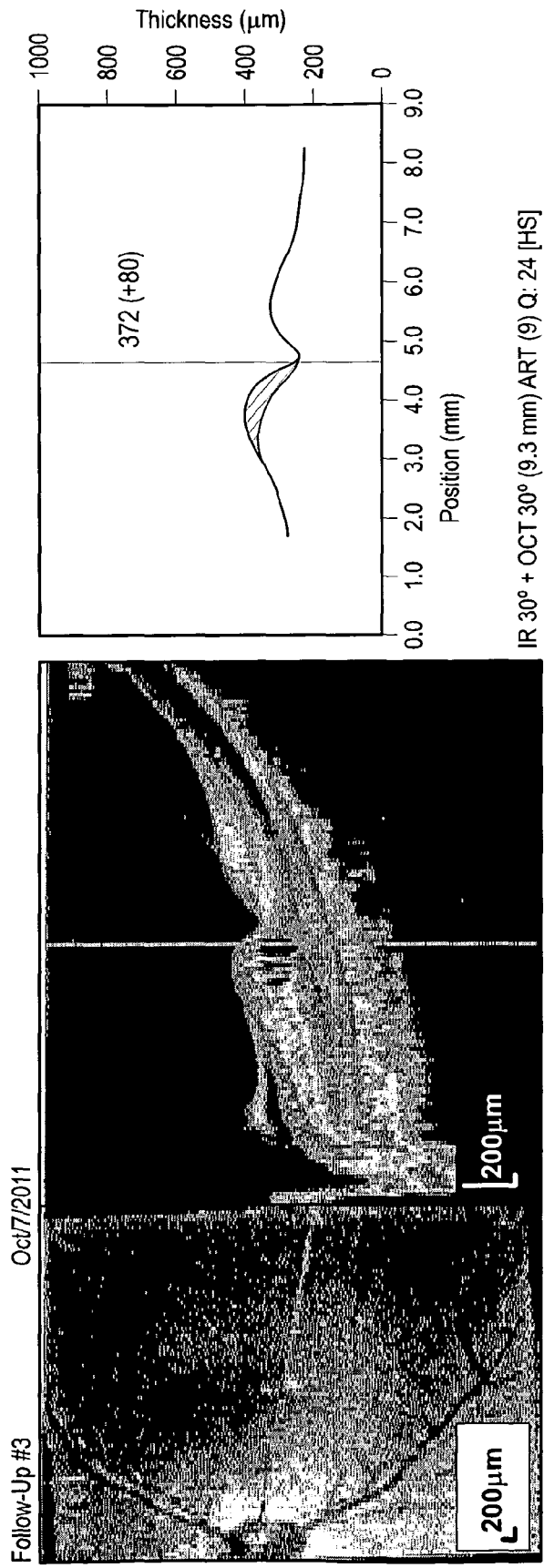
Figure 35:
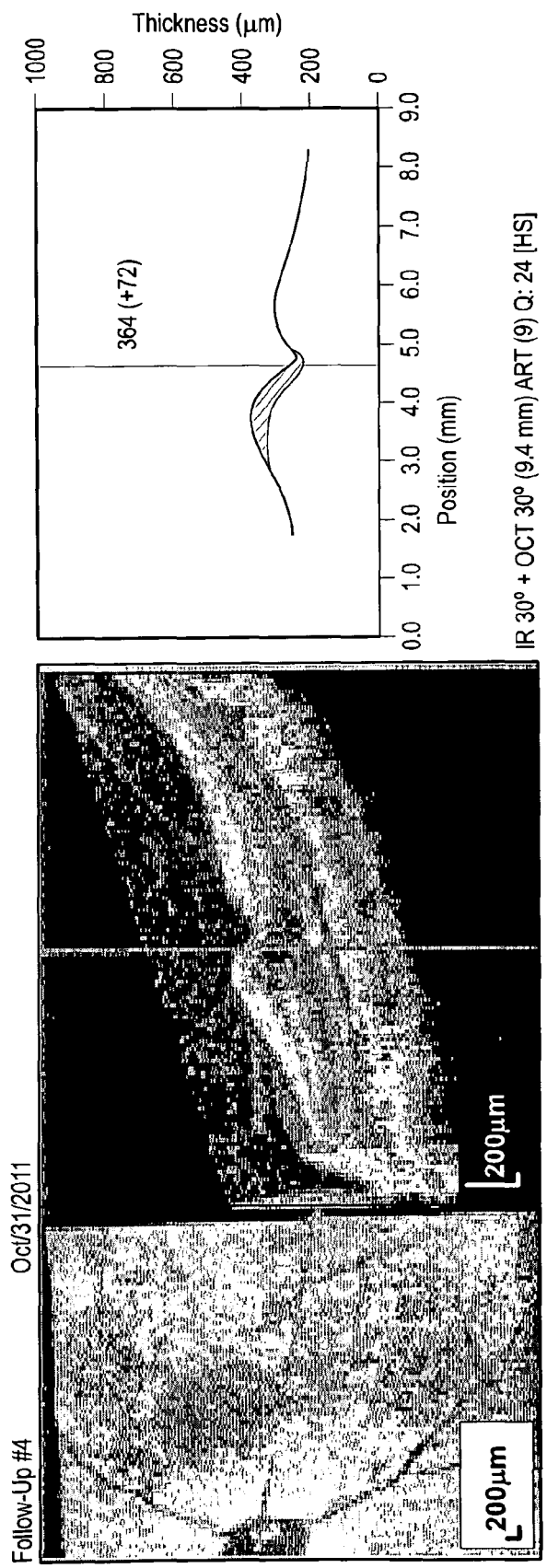
Figure 35:
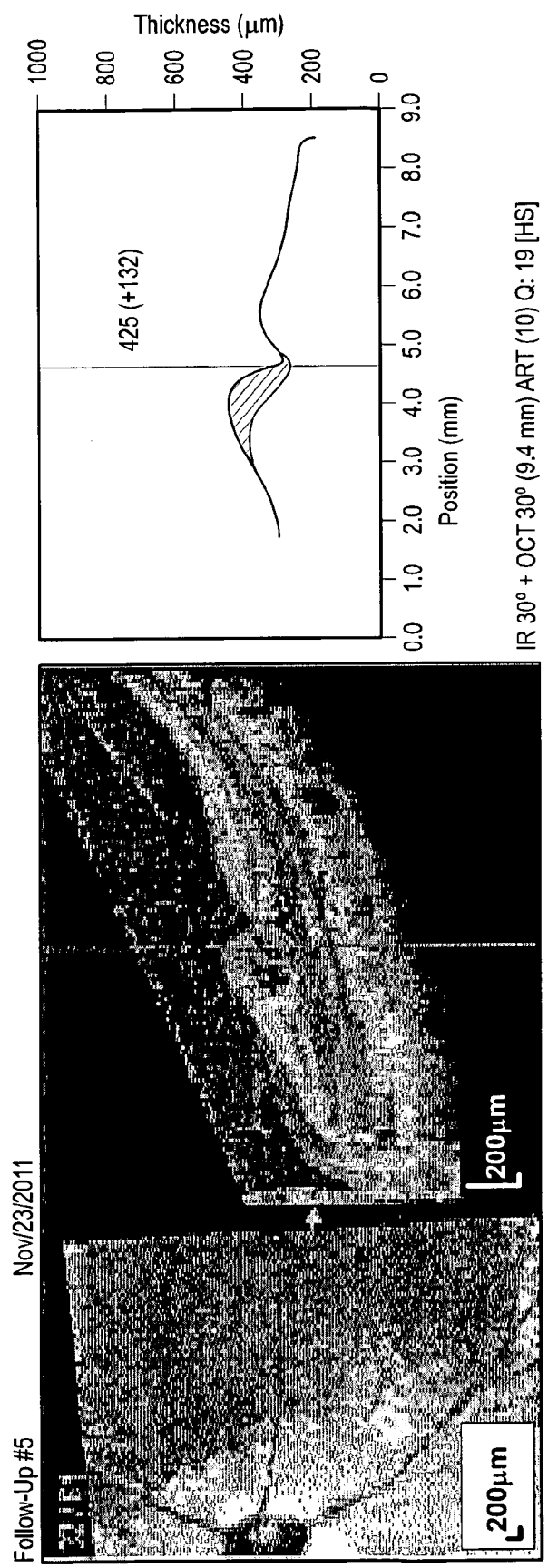
Figure 35:
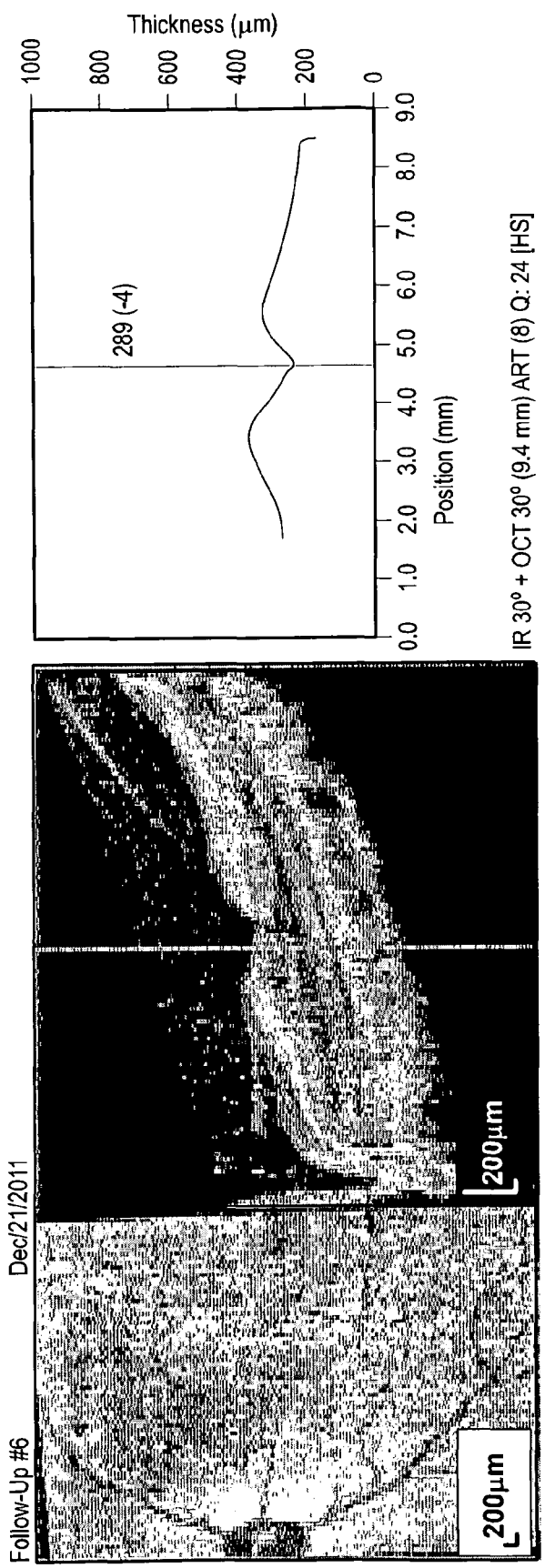
Figure 35:
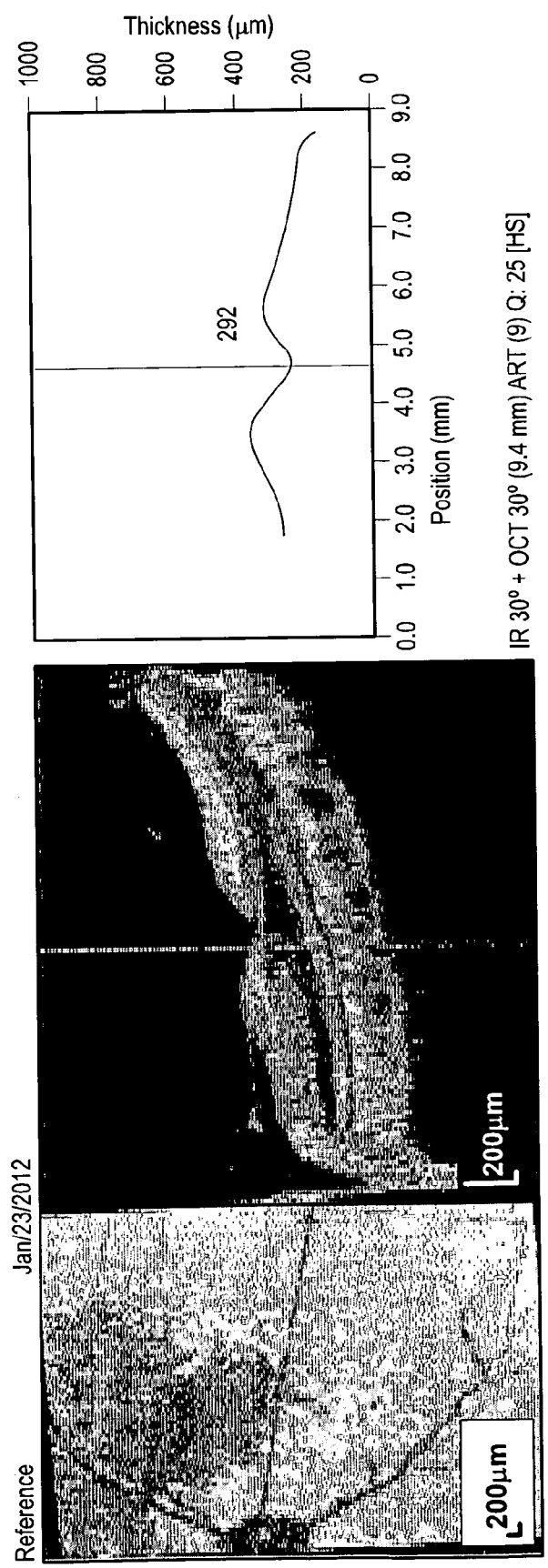
Figure 35:
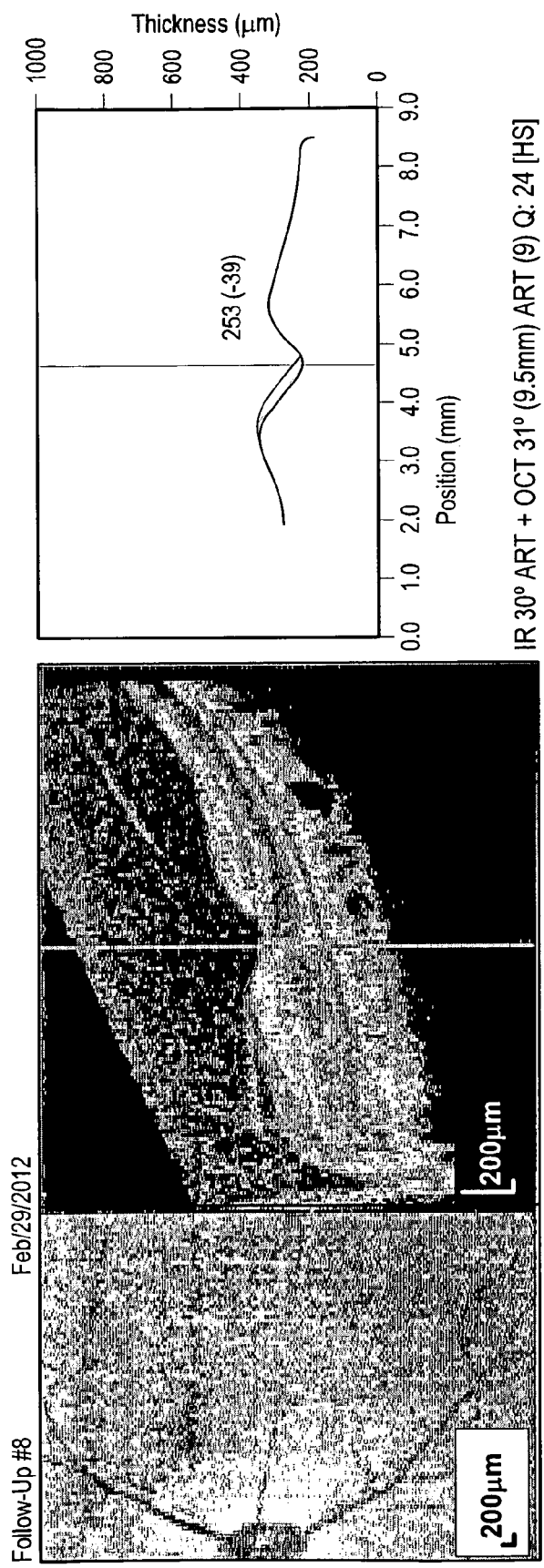
Figure 35:
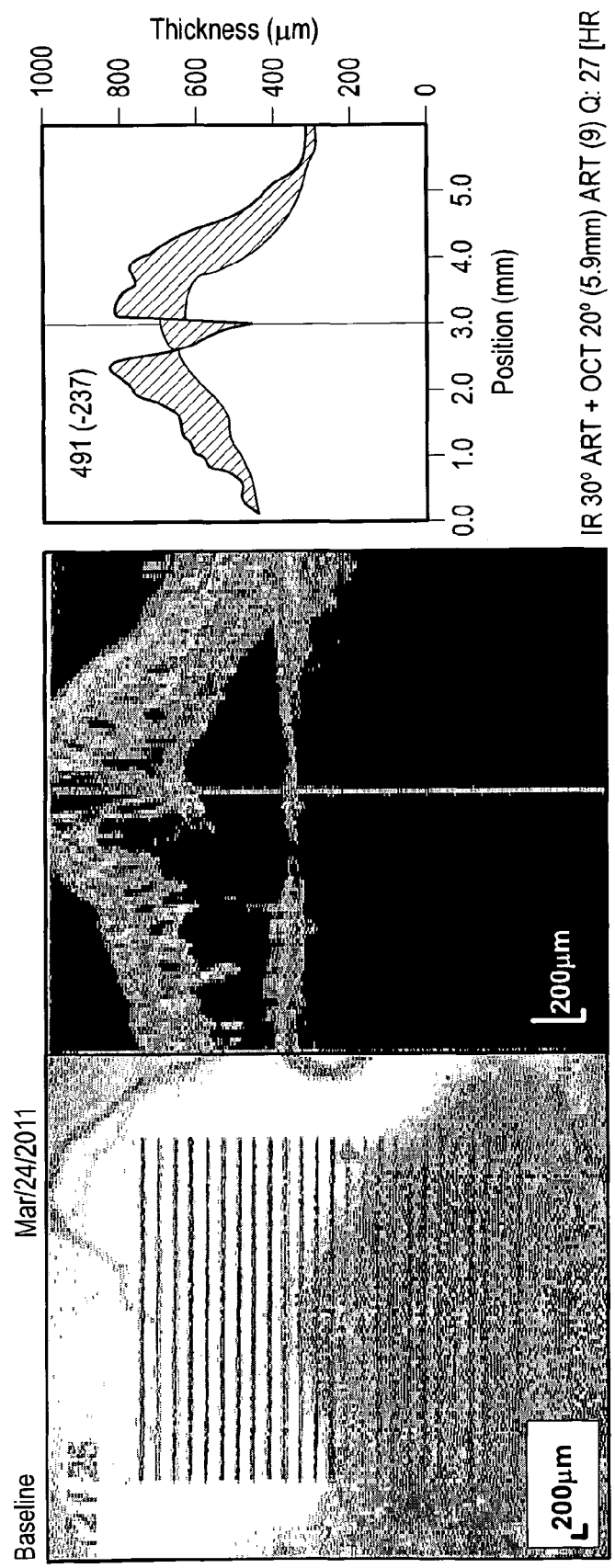
Figure 35:
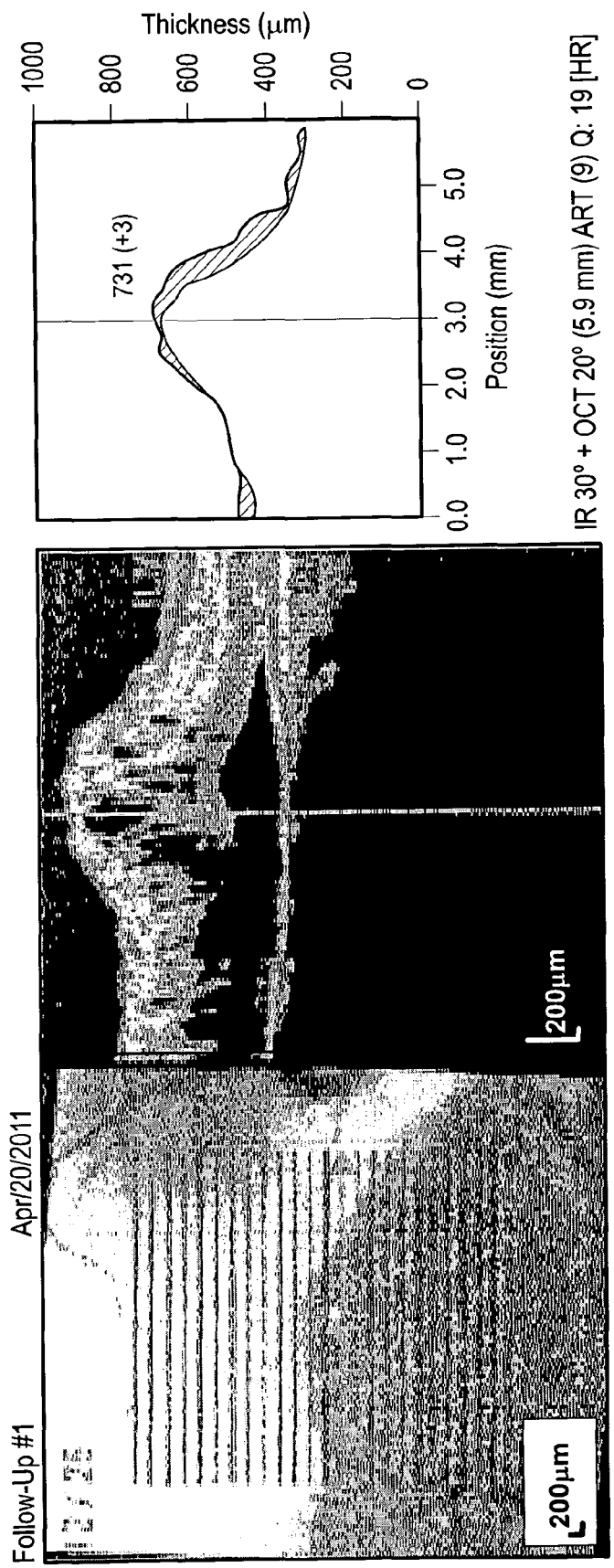
Figure 35:
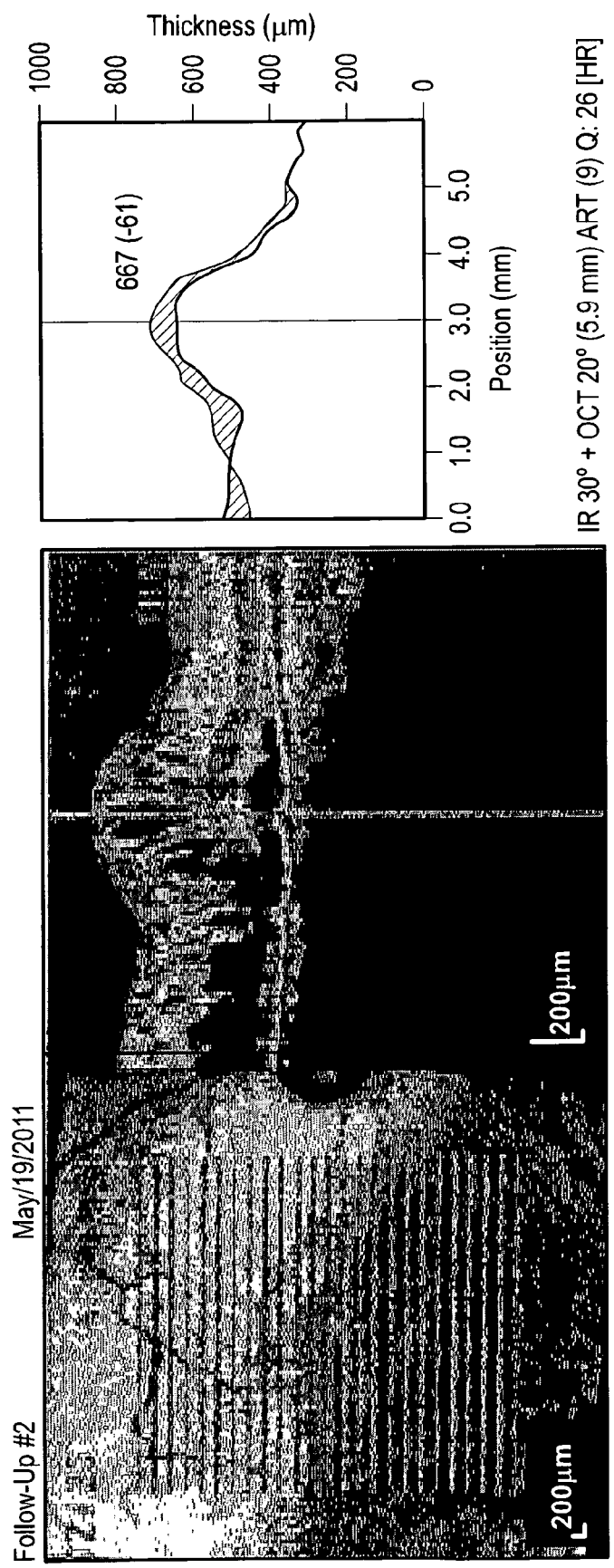
Figure 35:
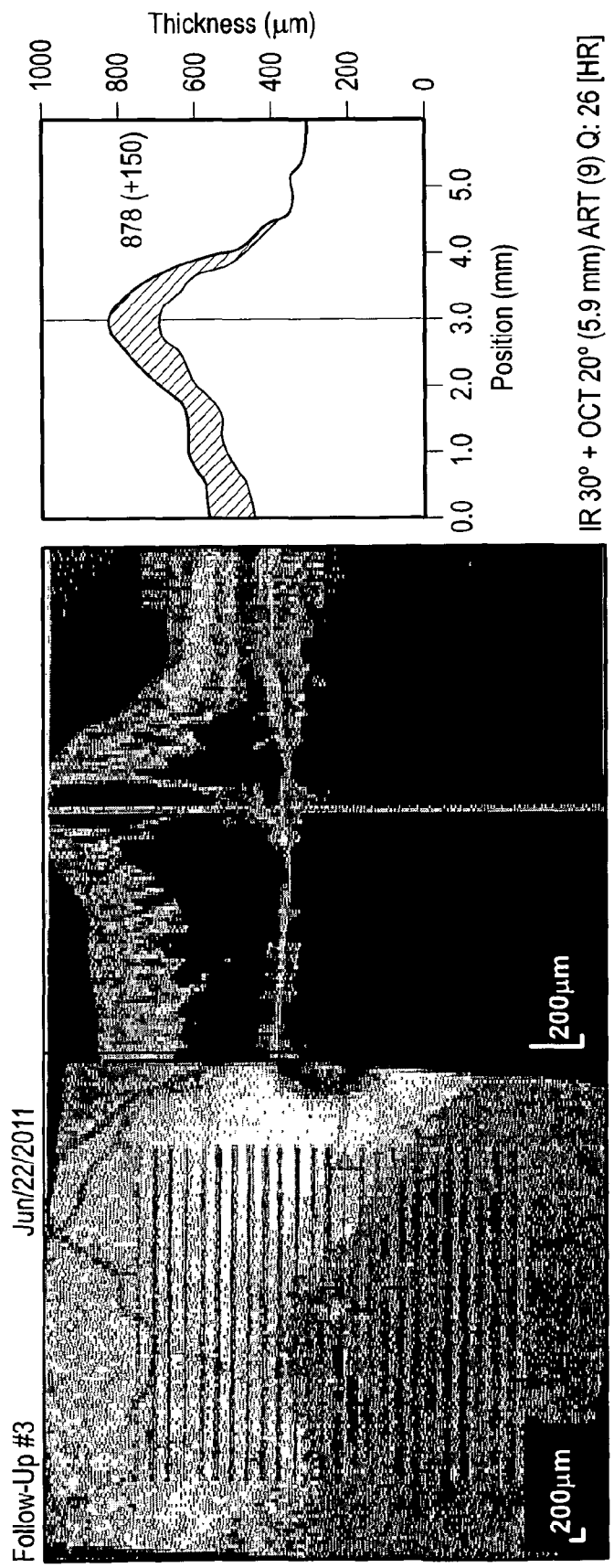
Figure 35:
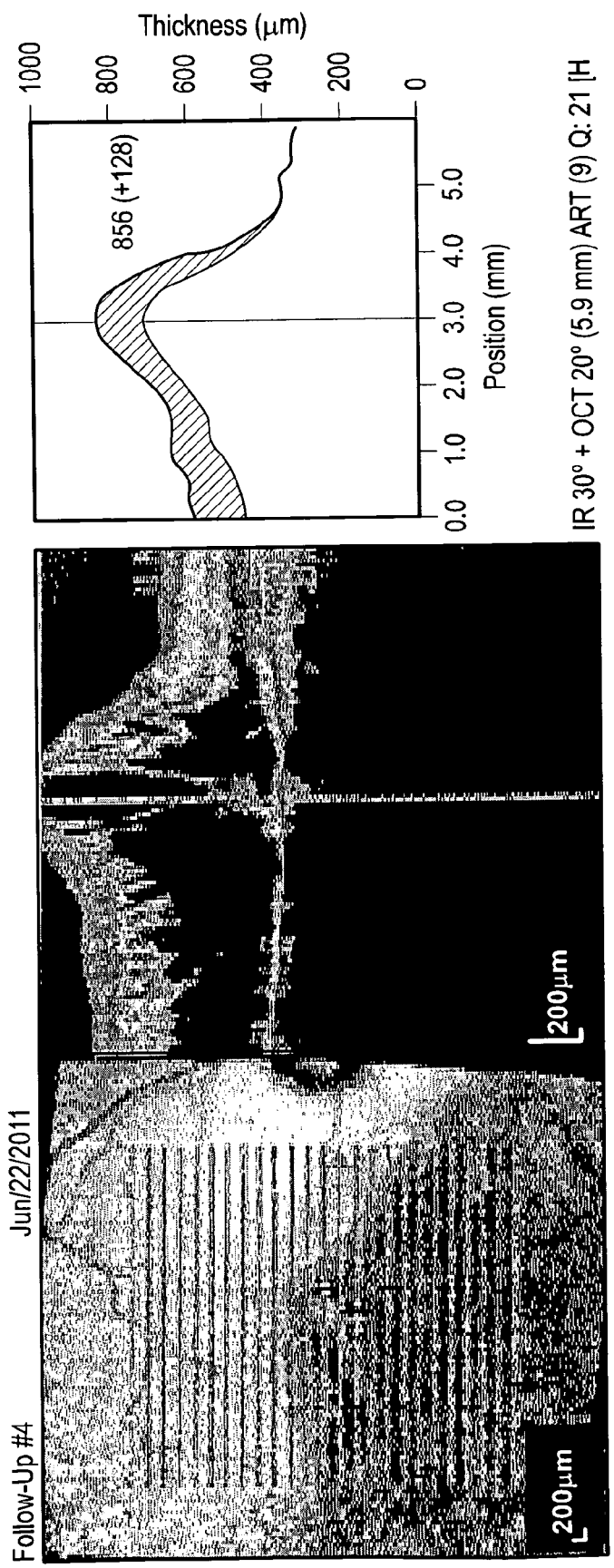
Figure 35:
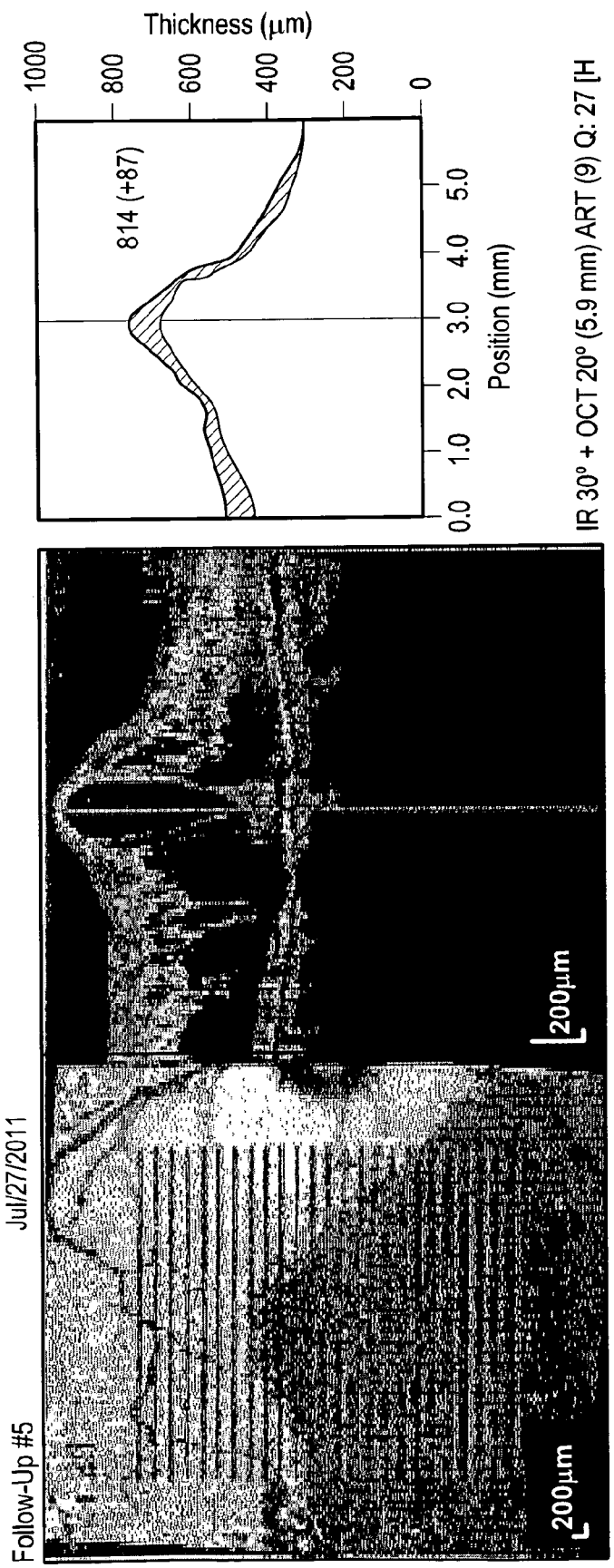
Figure 35:
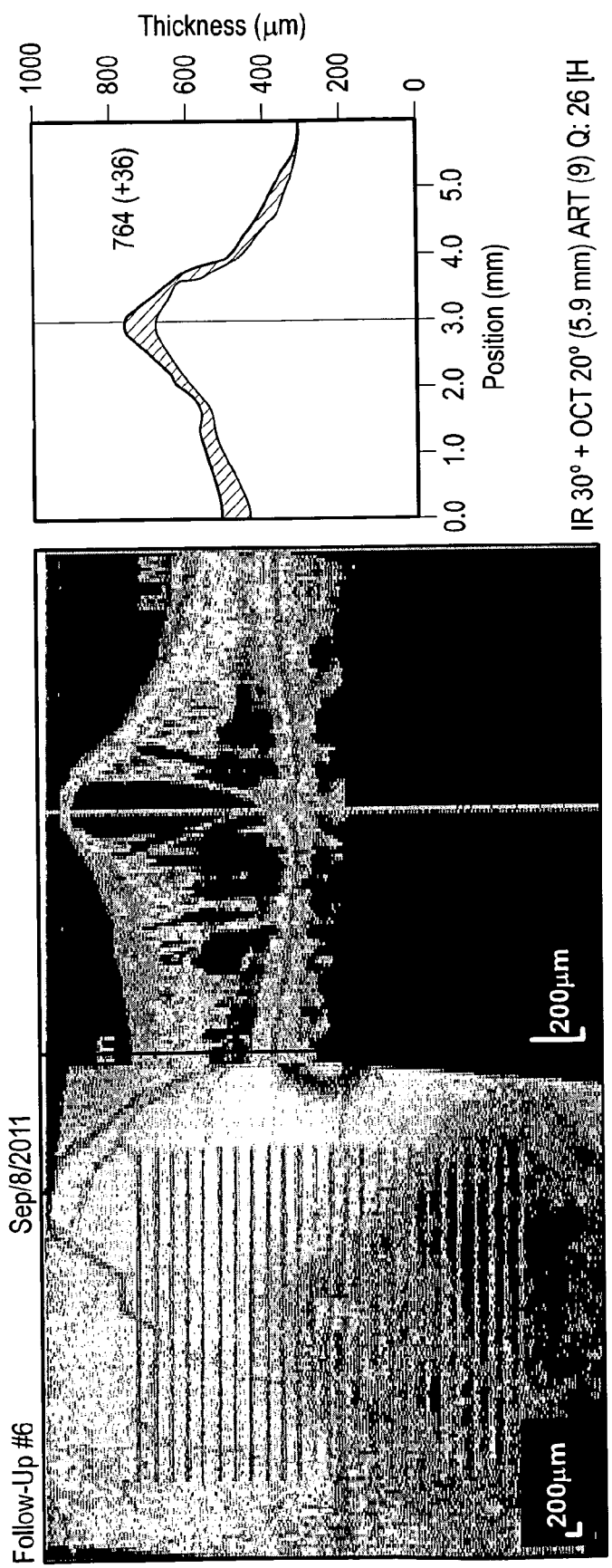
Figure 35:
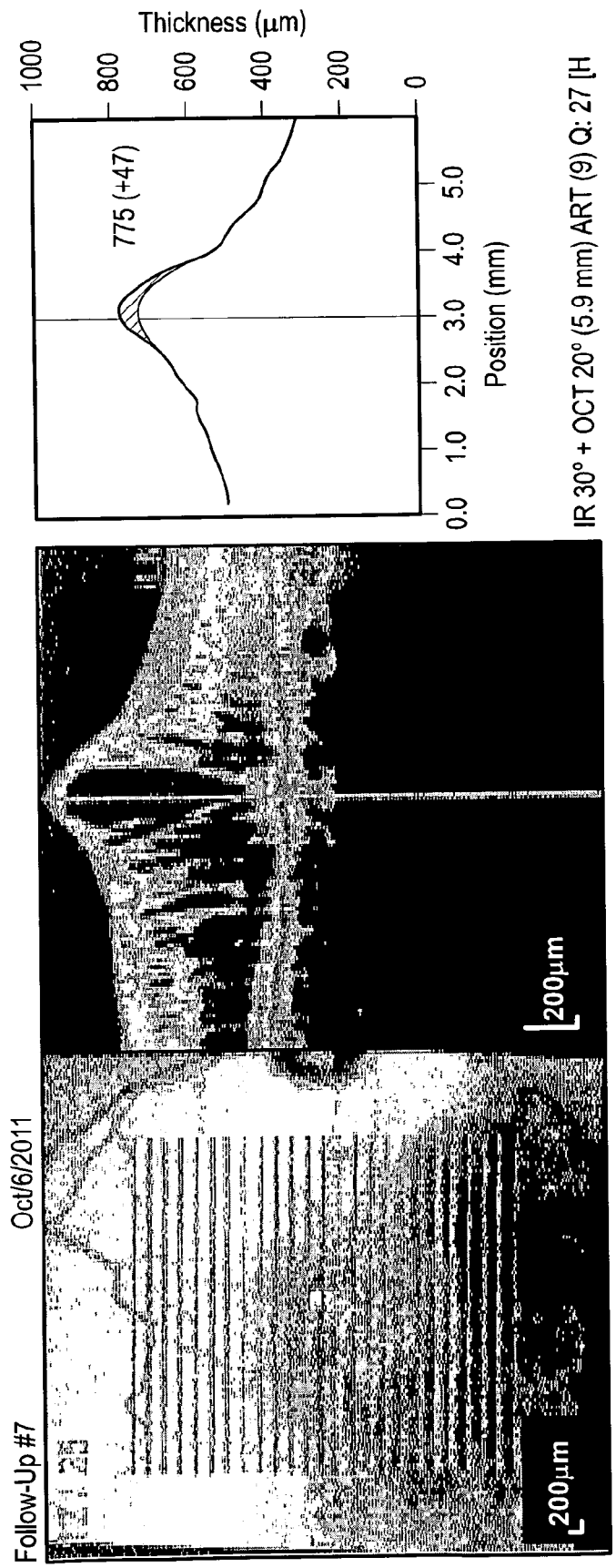
Figure 35:
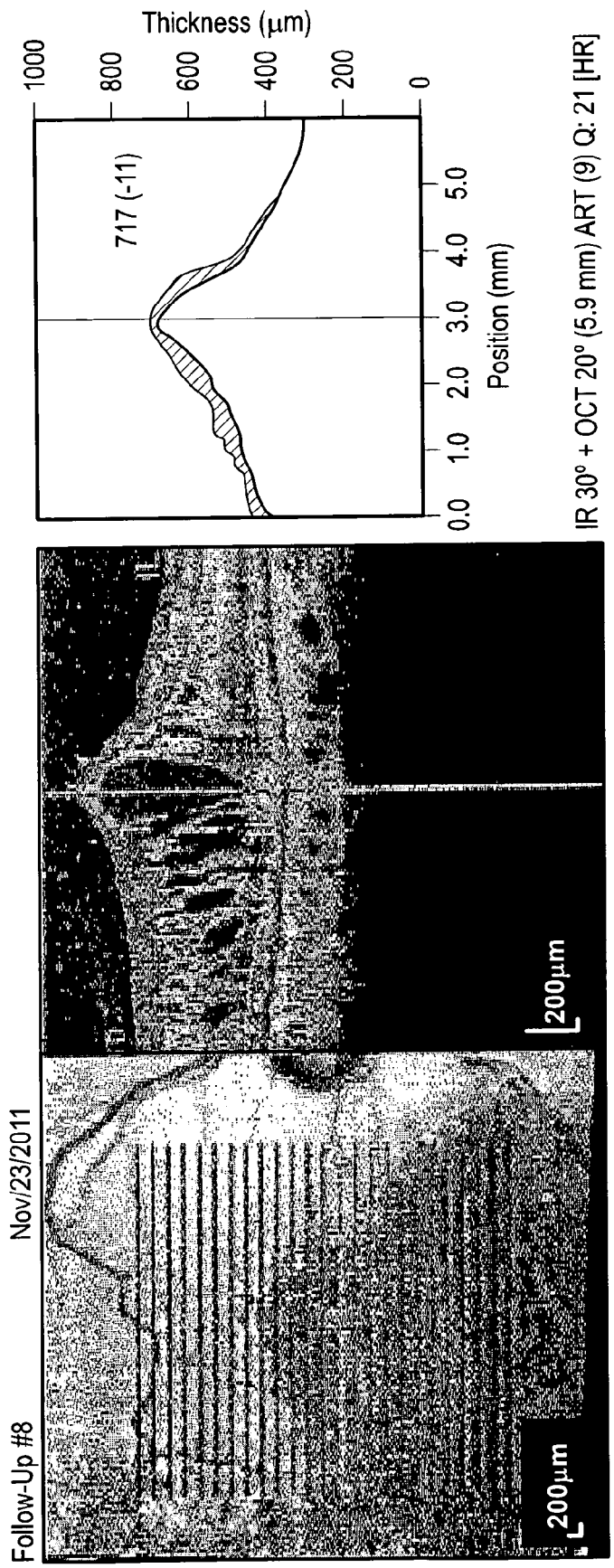
Figure 35:
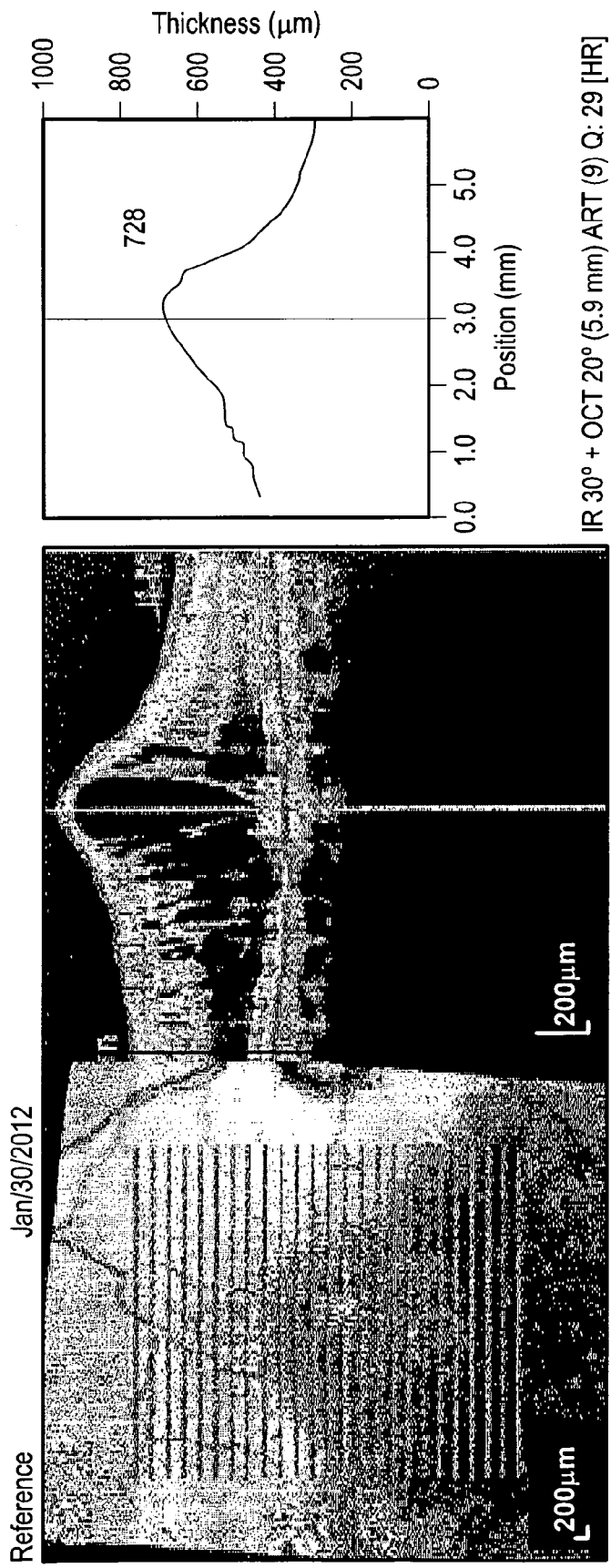
Figure 35:
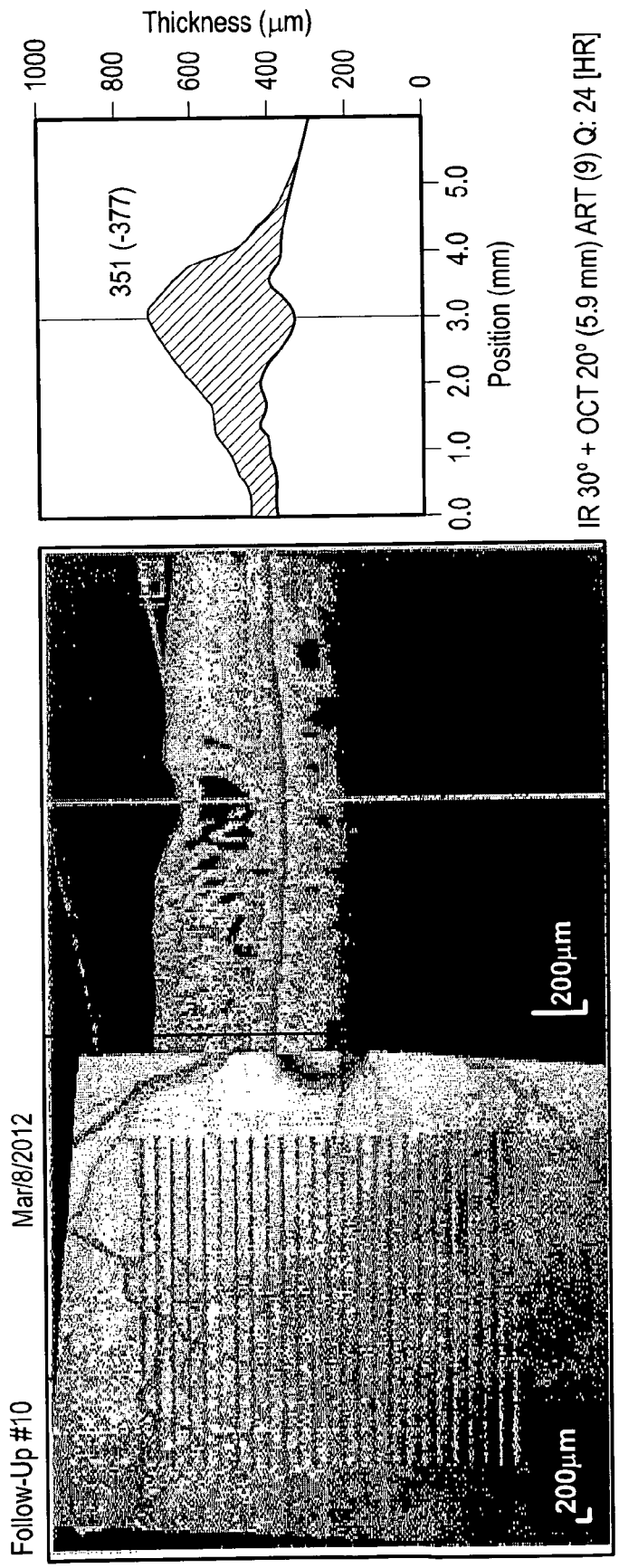

51 year old female had branch retinal vein occlusion on Jul. 20, 2011. She was treated initially with one intravitreal Avastin injection and then with focal LASER on Aug. 9, 2011. She was started on Omega 3RX® on Nov. 23, 2011. The fluid resolved within three months and the vision improved by one line (FIG. 35).

Case ah)

Figure 36:
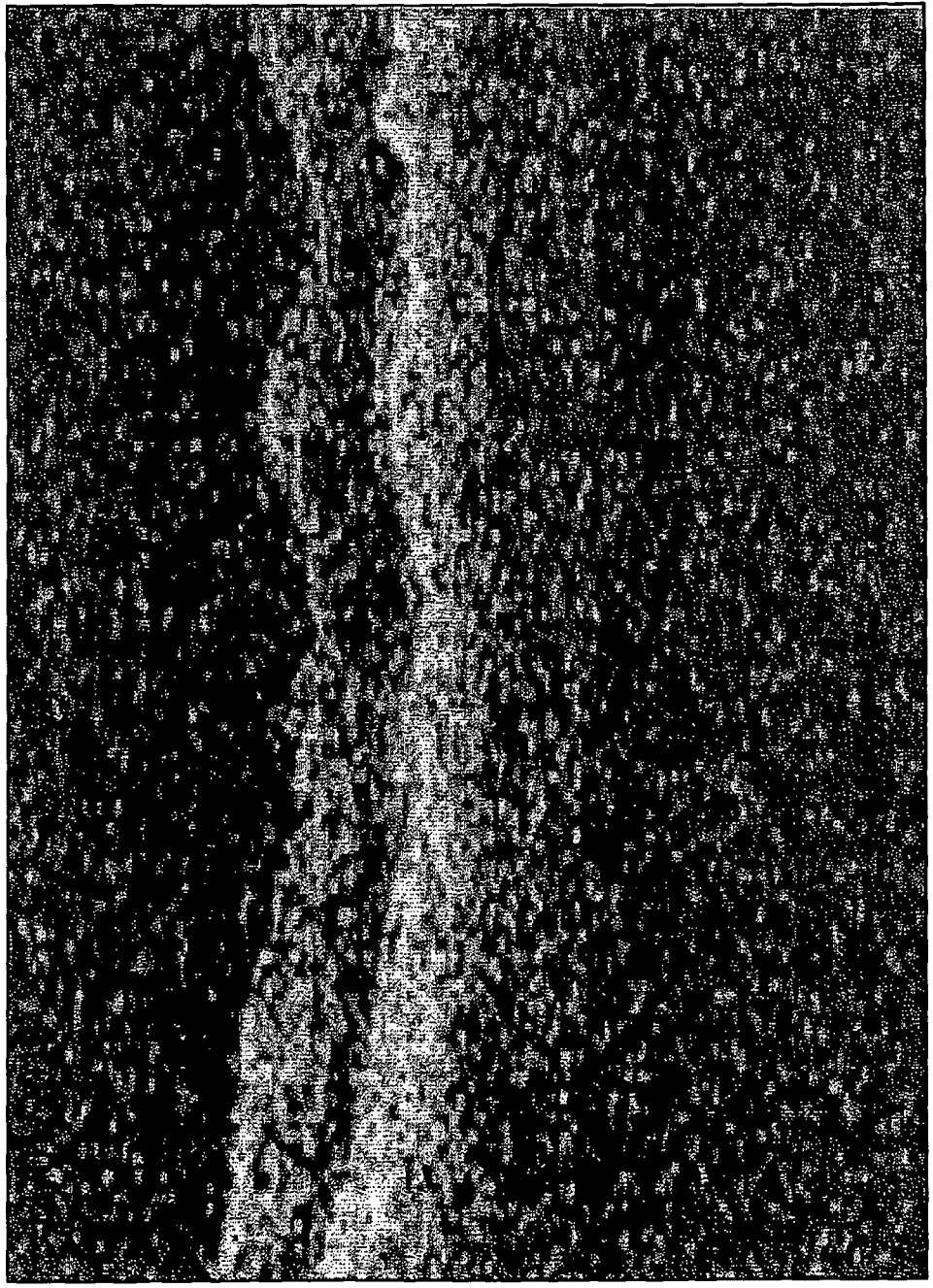
Figure 36:
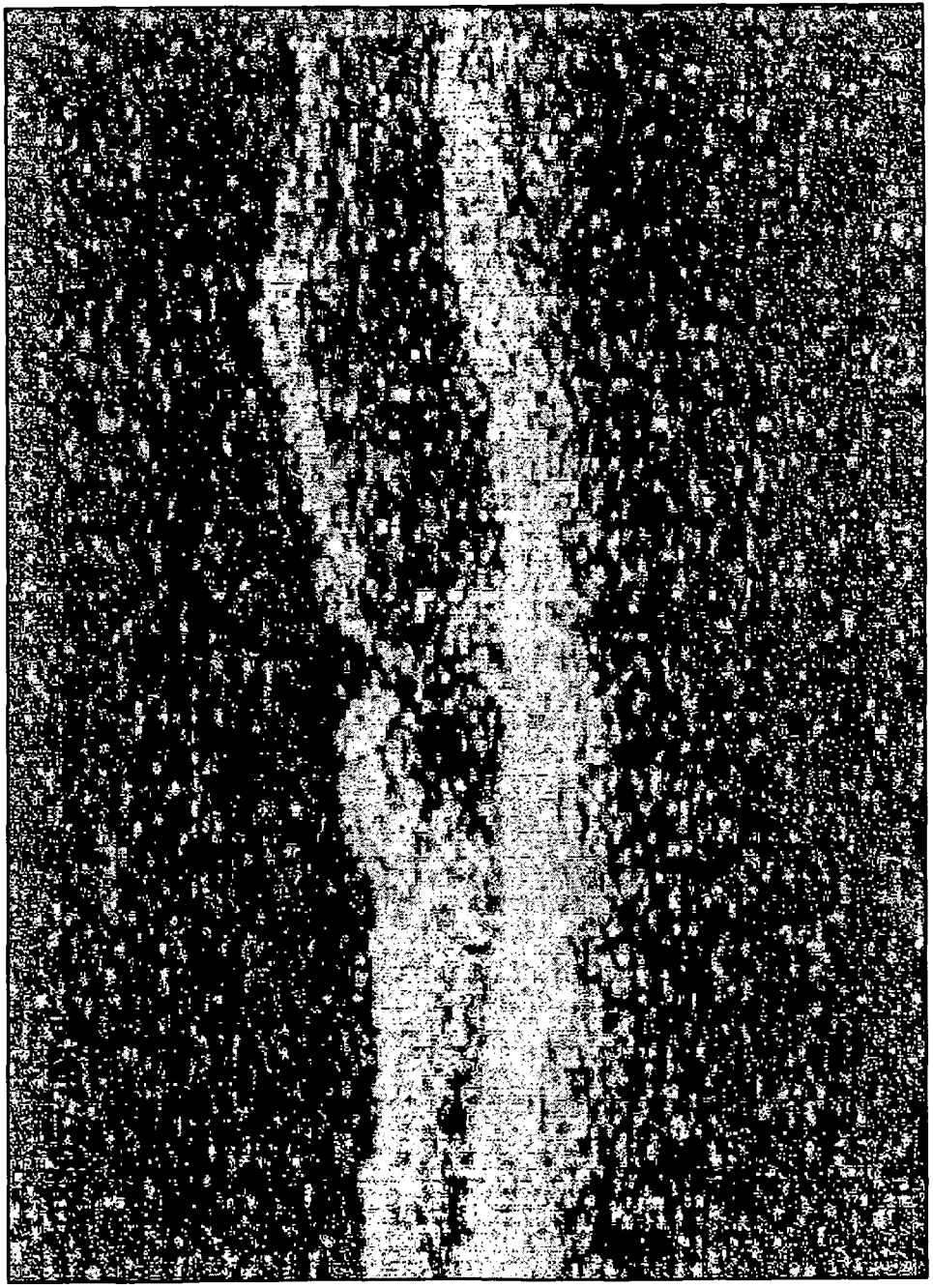
Figure 36:
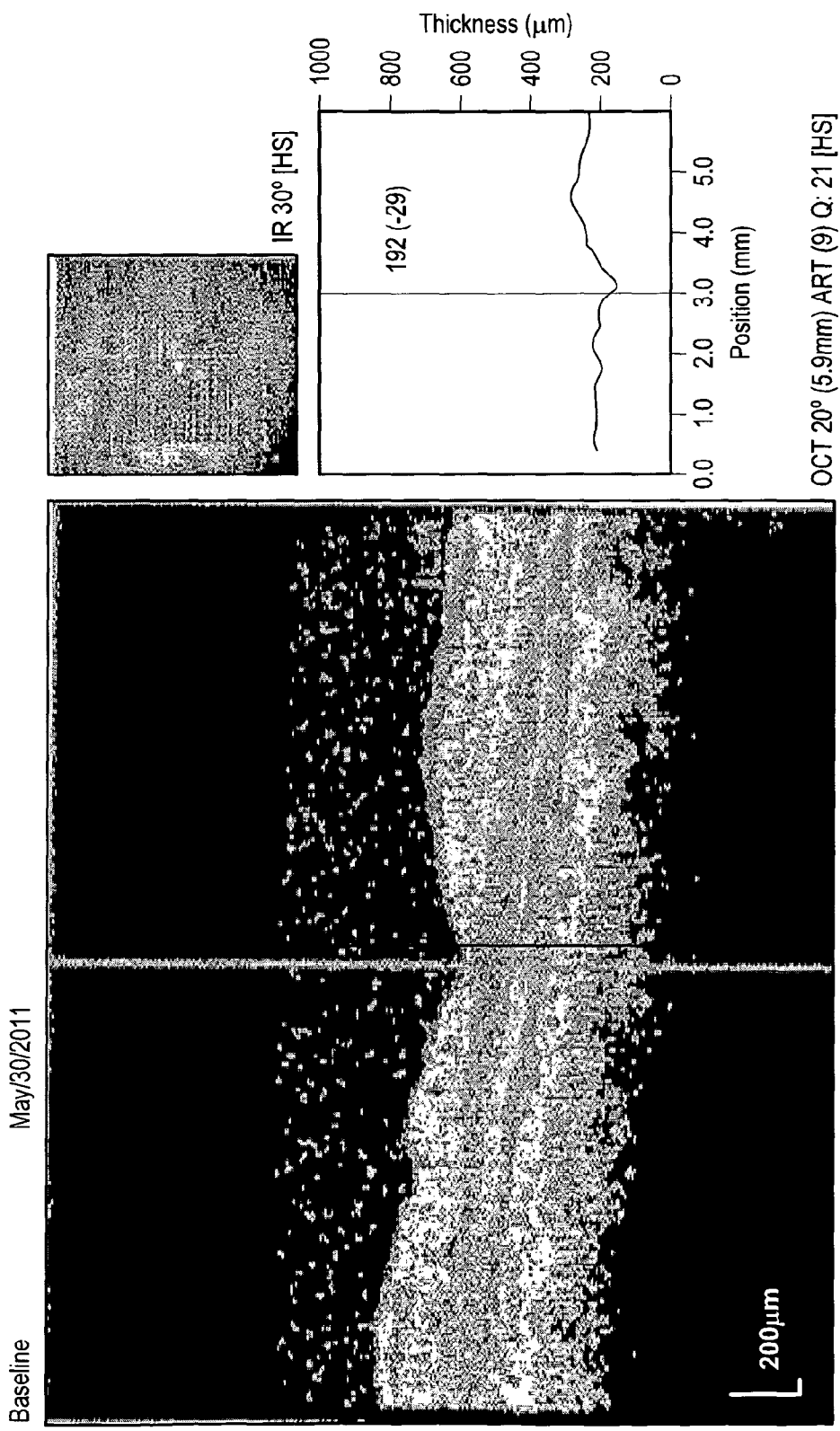
Figure 36:
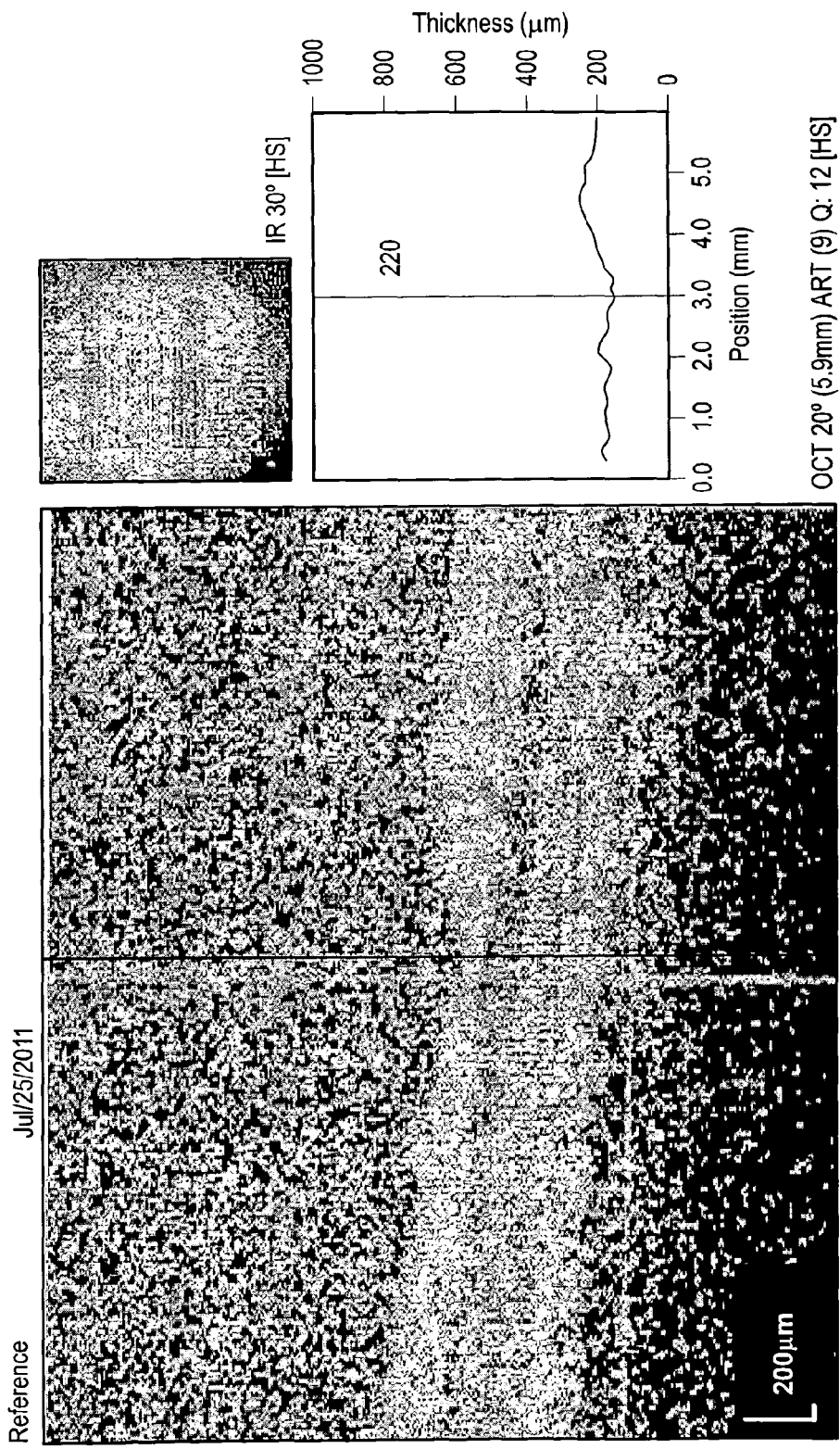
Figure 36:
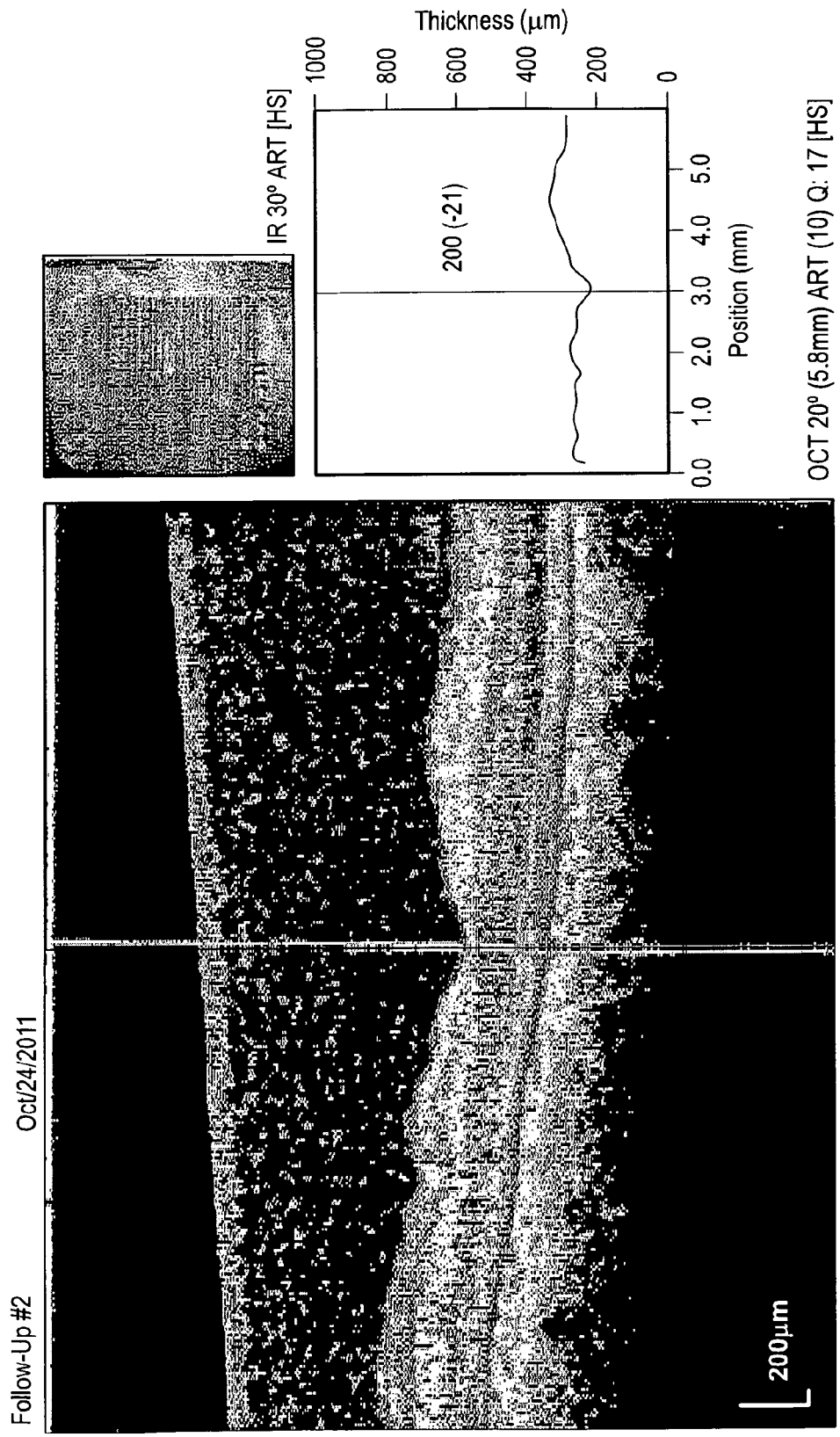

78 year old female presented with right branch retinal vein occlusion in 2008. She has prosthesis in the left eye. She was treated with four intravitreal lucentis and Kenalog injections. She was started on Omega 3RX® on 3.8.10. There was no recurrence of fluid since then and she gained two lines of vision (FIG. 36).

Case ai)

Figure 37:
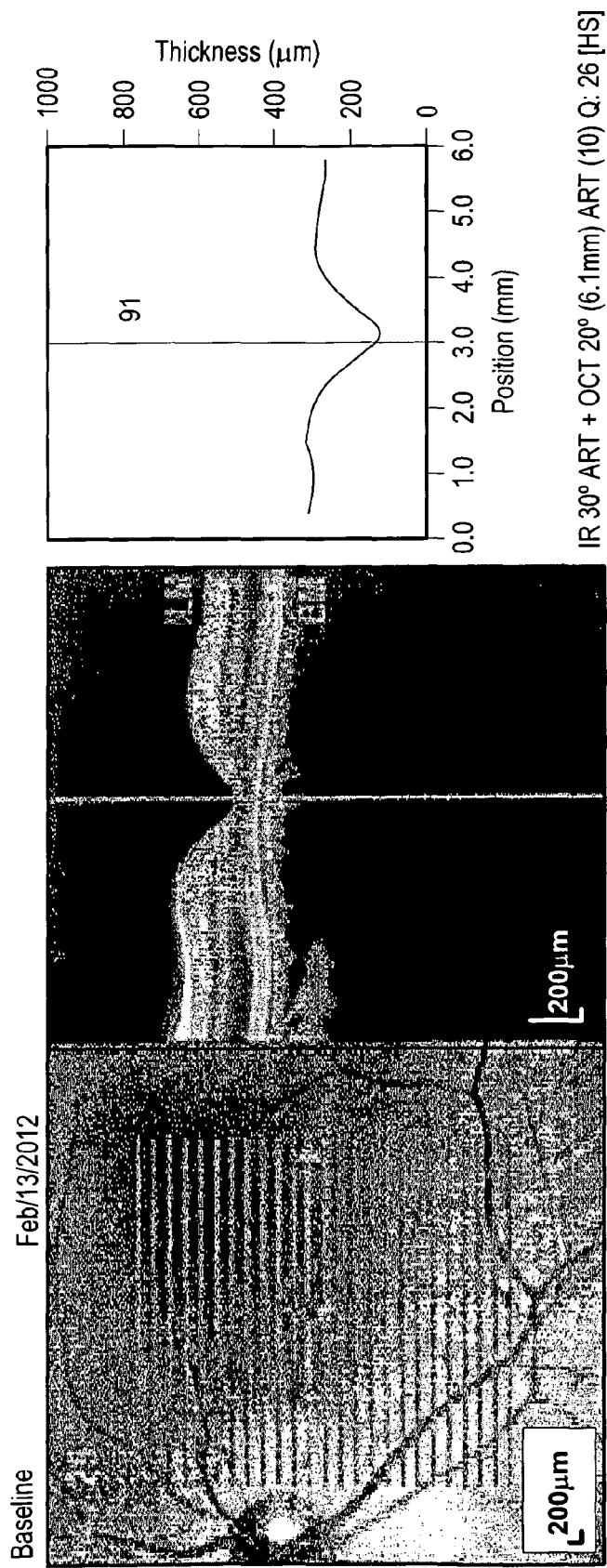
Figure 37:
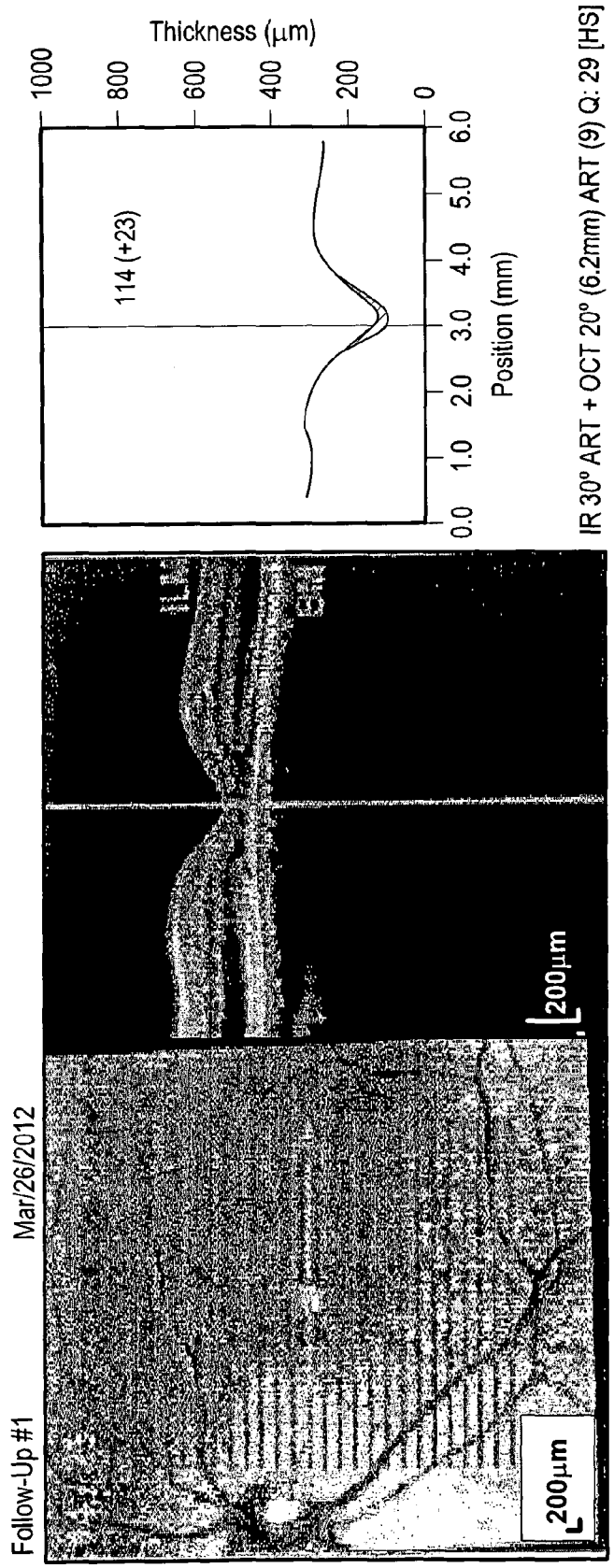

31 year old man with photoreceptor damage due to chloroquin therapy. He was started on Omega 3RX® on Feb. 13, 2012. Photoreceptor thickness increased following treatment and he gained one line of vision (FIG. 37).

Case aj)

Figure 38:
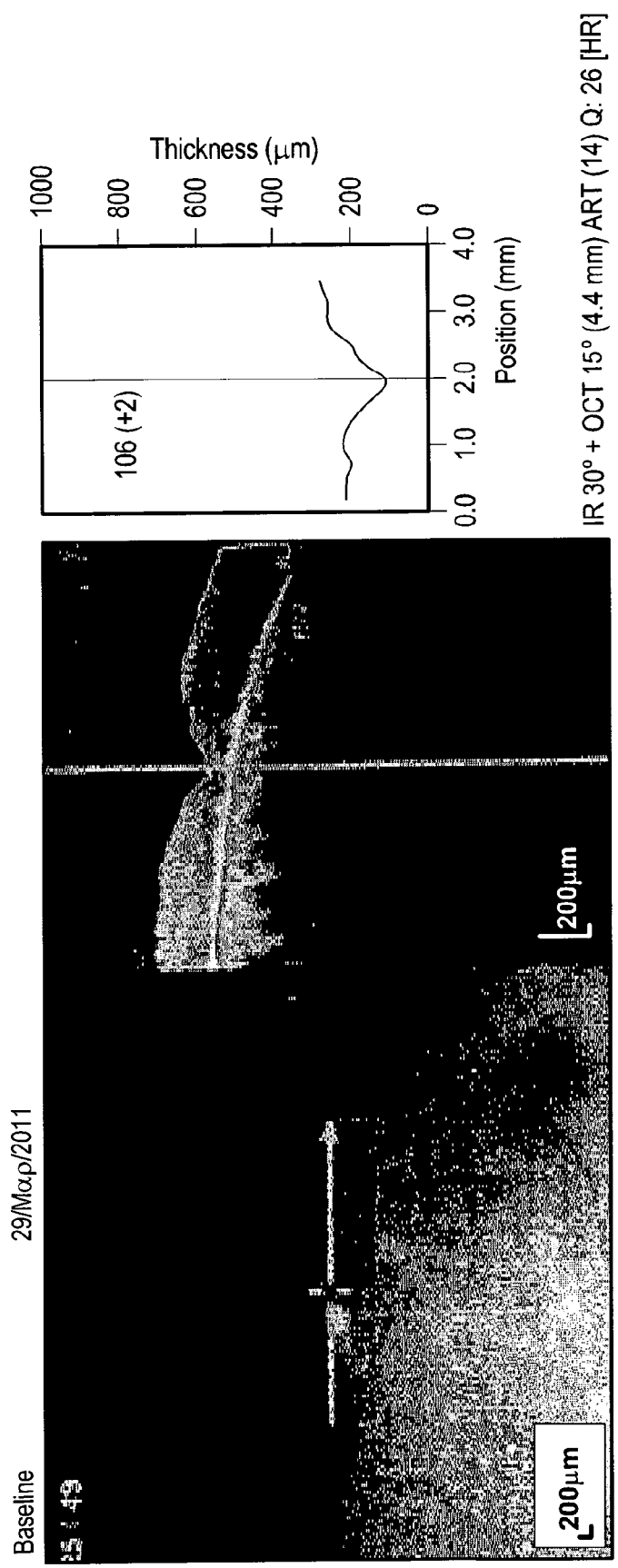
Figure 38:
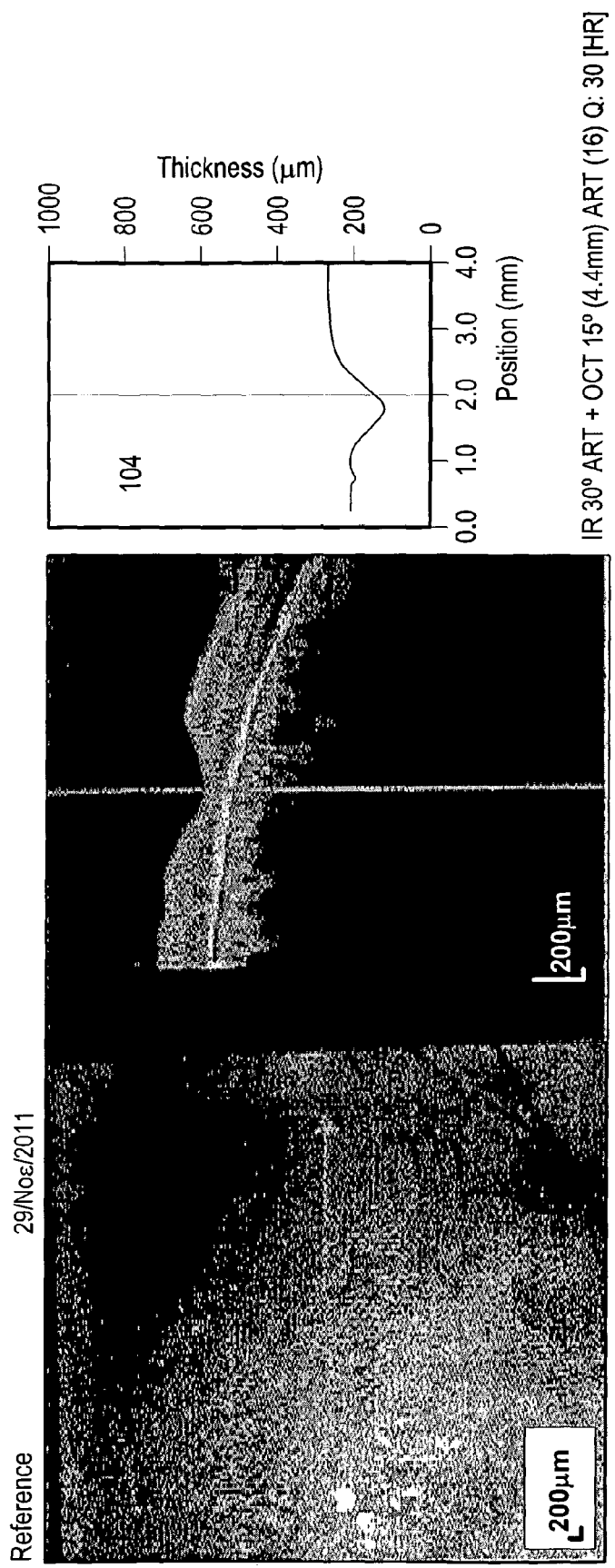
Figure 38:
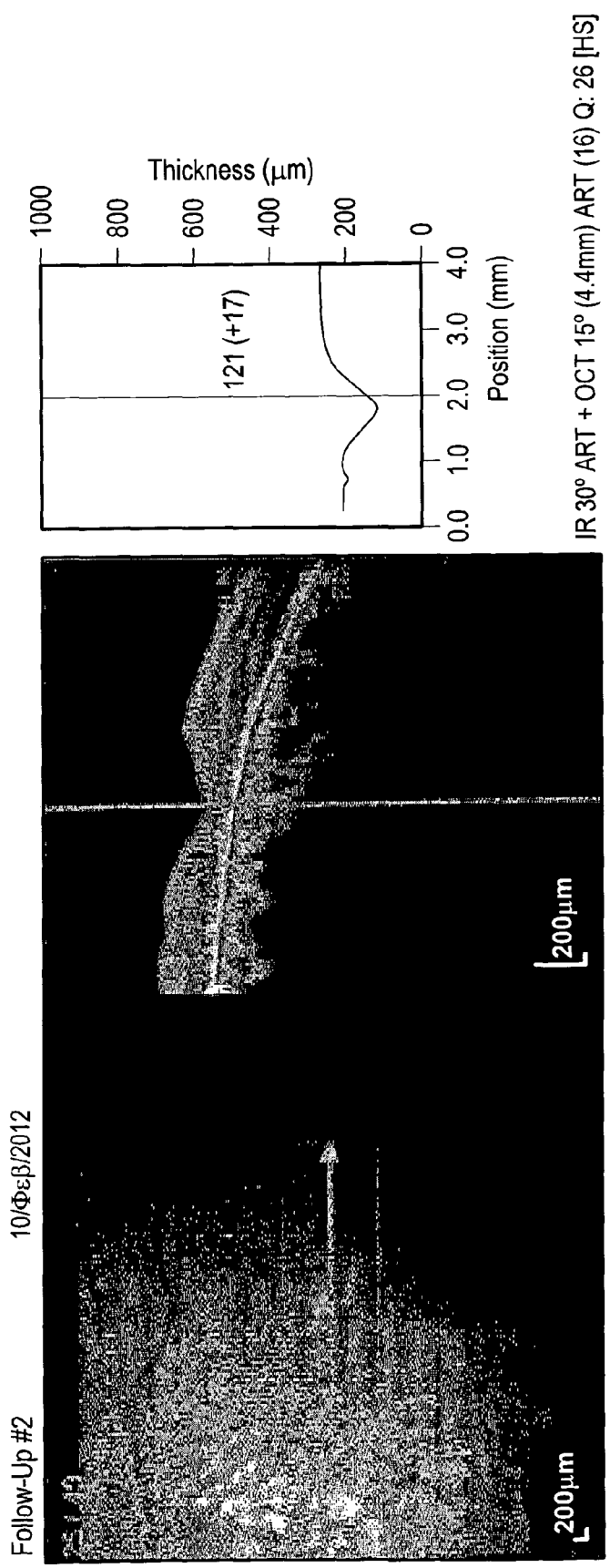

68 year old man who had routine cataract surgery in 2009 developed photoreceptor damage. He was started on Omega 3RX® on Nov. 29, 2012, three months following treatment with photoreceptor thickness increased and he gained two lines of vision (FIG. 38).

Example 5

New Treatment for Macular Oedema and Dry Eyes

The cases presented in this prospective study show that Omega 3RX® in the liquid form (Enerzona) can be of a significant benefit to patients with macular oedema and dry eyes. Each patient in this case presentation had a marked and favourable response with reduction in macular oedema or improvement of dry eyes during Omega 3RX® treatment. The therapy for macular oedema is advantageous to the patient and the clinician compared to the other available treatments. We will now have an opportunity to reduce macular oedema in patients in a way that was not previously possible. The treatment will have a positive impact on a large portion of the population.

OCT (Optical Coherence Tomography) has become an invaluable tool for assessment and therapeutic decision making for patients with macular oedema. It can accurately measure the oedema in the macular area. OCT scans were used to monitor response to treatment in patients.

The therapy with the Omega 3RX® was given orally 2.5-5 ml twice per day in a liquid form. It has been discovered that, if used every day orally on a long term, Omega 3RX® can decrease macular oedema. In addition, no ocular or systemic side effects were seen. This is an alternative therapy to intravitreal injections and laser. To the best of the inventor's knowledge, there is no other oral treatment effective for macular oedema.

Purpose

To evaluate the effect of oral Omega 3RX® liquid in eyes with macular oedema secondary to wet macular oedema, diabetic maculopathy, retinal vein occlusions and following surgery or inflammation and to evaluate the effect of oral Omega 3RX® in dry eyes unresponsive to other treatments.

Method

Prospective study of 91 eyes with macular oedema started with oral Omega 3RX®. Therapy was given orally twice per day. Each day 5-10 mls of Omega 3RX® was used. Macular thickness from OCT scan, visual acuity and complications were noted. Also, a prospective study of 40 eyes with dry eyes unresponsive to any other treatment started on Omega 3RX® orally 5 ml twice per day. The state of the cornea, visual acuity and patients comments were noted.

There were 4 groups of patients in this prospective study:
1) Group 1 consisted of 45 patients with wet macular degeneration;
2) Group 2 consisted of 34 patients with diabetic maculopathy (retinopathy);
3) Group 3 consisted of 12 patients with branch retinal vein occlusions and cystoid macular oedema secondary to inflammation or surgery;
4) Group 4 consisted of 42 severe dry eye patients unresponsive to current therapies.

Results

Group 1: Wet AMD

1. Demographics

The sample included 45 patients, 18 females (40%) and 27 males (60%). Their average age was 71.5 years old, ranging from 43 to 92 years, with a standard deviation of 9.3 years (i.e. 71.5±9.3).

2. Descriptives of Macular Oedema Thickness Per Time Point.

The average initial thickness of the patients was 483.2, ranging from 235 to 1010, with a standard deviation of 159.0 (483.2±159.0).

The following table shows the minimum, maximum, average (mean) and standard deviation of thickness at each time point. In addition, the table shows how many patients were measured at each time point (N).

TABLE 5

Descriptive statistics of thickness at each time point (Wet AMD group)

| Time Point | N (Number of patients) | Minimum Thickness | Maximum Thickness | Mean macular oedema Thickness | Std. Deviation |
|---|---|---|---|---|---|
| INITIAL | 45 | 235 | 1010 | 483.18 | 158.991 |
| 6 weeks | 45 | 166 | 741 | 386.02 | 143.206 |
| 3 months | 39 | 166 | 744 | 350.54 | 127.865 |
| 4.5 months | 31 | 169 | 660 | 315.71 | 118.565 |
| 6 months | 17 | 167 | 591 | 303.88 | 116.239 |
| 7.5 months | 10 | 167 | 395 | 278.00 | 81.930 |
| 9 months | 8 | 167 | 368 | 261.75 | 77.987 |
| 10.5 months | 6 | 167 | 369 | 243.33 | 82.452 |
| 12 months | 4 | 183 | 301 | 222.25 | 55.181 |
| 18 months | 2 | 177 | 220 | 198.50 | 30.406 |

Note:
The reduction in mean oedema thickness at each time point in relation to initial measurement is statistically significant at the 5% level (p < 5%) (for all time points where paired samples t-test was used). The descriptive statistics in Table 5 show that thickness has reduced, on average, at each time point, in relation to the initial measurement.

To get a better insight of the reduction in thickness, descriptive statistics of the reduction in relation to initial thickness were obtained. All the descriptive statistics (mean thickness at each time point, standard deviation, number of patients measured at each time point) are given in Table 6.

TABLE 6

Descriptive statistics of thickness at each time point (Wet AMD group)

| | | Mean Thickness at each time point* | Number of patients | Std. Deviation |
|---|---|---|---|---|
| Pair 1 | INITIAL THICKNESS | 483.18 | 45 | 158.991 |
| | 6 weeks | 386.02 | 45 | 143.206 |
| Pair 2 | INITIAL THICKNESS | 491.69 | 39 | 166.468 |
| | 3 months | 350.54 | 39 | 127.865 |
| Pair 3 | INITIAL THICKNESS | 490.32 | 31 | 154.922 |
| | 4.5 months | 315.71 | 31 | 118.565 |
| Pair 4 | INITIAL THICKNESS | 525.24 | 17 | 184.398 |
| | 6 months | 303.88 | 17 | 116.239 |
| Pair 5 | INITIAL THICKNESS | 588.70 | 10 | 139.003 |
| | 7.5 months | 278.00 | 10 | 81.930 |
| Pair 6 | INITIAL THICKNESS | 602.50 | 8 | 124.681 |
| | 9 months | 261.75 | 8 | 77.987 |
| Pair 7 | INITIAL THICKNESS | 580.50 | 6 | 139.167 |
| | 10.5 months | 243.33 | 6 | 82.452 |
| Pair 8 | INITIAL THICKNESS | 676.00 | 4 | 104.585 |
| | 12 months | 222.25 | 4 | 55.181 |
| Pair 9 | INITIAL THICKNESS | 730.50 | 2 | 116.673 |
| | 18 months | 198.50 | 2 | 30.406 |

*Notice that this is the mean thickness of the patients that were measured at both time points (for example at time point "3 months" 39 patients were measured, so we have the mean of those 39 patients, both at initial measurement and at 3 months. That is why the mean of the initial thickness differs at each time point (it depends on how many patients were measured at the corresponding follow-up time point of interest) (e.g. for 3 months we have the mean initial thickness of 39 patients (now 491.69 instead of 483.18 which was for 45 patients).

In addition, paired samples t-tests were performed, to examine whether the reduction of thickness at each time point in relation to the initial measurement was statistically significant at the 5% level of significance. A reduction is considered statistically significant if the corresponding p-value is lower than 5%. All the results of the paired samples t-tests appear in Table 7.

TABLE 7

Paired samples t-tests to examine for significant reduction in thickness at each time point (Wet AMD group).

| | | Mean Reduction in Thickness | Std. Deviation of reduction in thickness | 95% Confidence Interval of the Mean Thickness | | T | df | p-value |
|---|---|---|---|---|---|---|---|---|
| | | | | Lower | Upper | | | |
| Pair 1 | INITIAL - 6 weeks | 97.156 | 106.237 | 65.239 | 129.073 | 6.135 | 44 | <0.001** |
| Pair 2 | INITIAL - 3 months | 141.154 | 155.325 | 90.803 | 191.504 | 5.675 | 38 | <0.001** |
| Pair 3 | INITIAL - 4.5 months | 174.613 | 144.780 | 121.507 | 227.719 | 6.715 | 30 | <0.001** |
| Pair 4 | INITIAL - 6 months | 221.353 | 179.933 | 128.840 | 313.866 | 5.072 | 16 | <0.001** |
| Pair 5 | INITIAL - 7.5 months | 310.700 | 181.500 | 180.863 | 440.537 | 5.413 | 9 | <0.001** |

TABLE 7-continued

Paired samples t-tests to examine for significant reduction in thickness at each time point (Wet AMD group).

| | | Mean Reduction in Thickness | Std. Deviation of reduction in thickness | 95% Confidence Interval of the Mean Thickness | | T | df | p-value |
|---|---|---|---|---|---|---|---|---|
| | | | | Lower | Upper | | | |
| Pair 6 | INITIAL - 9 months | 340.750 | 176.436 | 193.246 | 488.254 | 5.463 | 7 | <0.001** |
| Pair 7 | INITIAL - 10.5 months | 337.167 | 208.058 | 118.823 | 555.510 | 3.969 | 5 | 0.011* |
| Pair 8 | INITIAL - 12 months | 453.750 | 118.402 | 65.239 | 129.073 | N/A | N/A | N/A |
| Pair 9 | INITIAL - 18 months | 532.000 | 147.078 | 90.803 | 191.504 | N/A | N/A | N/A |

**Reduction is significant at the 1% level of significance (p < 1%)
*Reduction is significant at the 5% level of significance (p < 5%)

Conclusions from the Previous Tables Regarding the Reduction in Thickness:

Looking at the above results, it can be seen that a reduction in oedema thickness has been shown statistically, since the mean reduction in thickness was positive at all time points and additionally the paired samples t-tests showed that this reduction was significant (all p-values were lower than 5%) (i.e. difference between initial and new thickness was significantly different from zero and positive). In addition the reduction was increasing from each time point to the next, starting from a mean reduction of 97.156 at 6 weeks and reaching a mean reduction of 532 at 18 months (exception of this was at 10.5 months, where although there was a significant reduction (p=0.011<0.05) the level of reduction did not increase, it was lower compared to the previous time points, 337 compared to 340) (see the column "Mean reduction in thickness" in the above table;). Overall, the above results show that patients at each time point had, on average, significantly lower levels of thickness compared with the initial measurement and they had even more improvement as time went by.

Initial Vision and Gain in Vision (Number of Lines Gained)

Table 8 below provides descriptives of initial vision.

TABLE 8

| Initial Vision | Frequency (Number of patients) | % |
|---|---|---|
| CF | 6 | 13.3 |
| 6/120 | 6 | 13.3 |
| 6/60 | 9 | 20.0 |
| 6/36 | 1 | 2.2 |
| 6/30 | 2 | 4.4 |
| 6/24 | 1 | 2.2 |
| 6/18 | 4 | 8.9 |
| 6/15 | 3 | 6.7 |
| 6/12 | 3 | 6.7 |

TABLE 8-continued

| Initial Vision | Frequency (Number of patients) | % |
|---|---|---|
| 6/9 | 4 | 8.9 |
| 6/7.5 | 5 | 11.1 |
| 6/4.5 | 1 | 2.2 |
| Total | 45 | 100.0 |

From the above table, it can be seen that most of the patients had very problematic initial vision. More specifically, 20% of patients had vision of 6/60 and 13.3% had vision of 6/120, while another 13.3% had vision CF. Only 2.2% had vision of 6/4.5. Table 9 below shows the gain in lines for patients at different time points-WET AMD

TABLE 9

| Lines gained | 6 weeks (N = 45) | | 3 months (N = 39) | | 4.5 months (N = 31) | | 6 months (N = 21) | | 9 months (N = 10) | | 12 months (N = 6) | | 18 months (N = 2) | |
|---|---|---|---|---|---|---|---|---|---|---|---|---|---|---|
| | f | % | f | % | f | % | f | % | f | % | f | % | f | % |
| 0 | 20 | 44.4 | 12 | 30.8 | 9 | 29.0 | 5 | 23.8 | 2 | 20.0 | 0 | 0 | 0 | 0 |
| 1 | 17 | 37.8 | 15 | 38.5 | 13 | 41.9 | 9 | 42.9 | 3 | 30.0 | 1 | 16.7 | 1 | 50.0 |
| 2 | 6 | 13.3 | 7 | 17.9 | 6 | 19.4 | 5 | 23.8 | 4 | 40.0 | 3 | 50.0 | 0 | 0 |
| 3 or more | 2 | 4.4 | 5 | 12.8 | 3 | 9.7 | 2 | 4.4 | 1 | 10.0 | 2 | 33.4 | 1 | 50.0 |

It can be seen that at 6 weeks, 20 patients (44.4%) had no gain in lines, but at later time points the percentage of zero gain decreases substantially, while on the contrary the percentage of patients with gain in 2 lines increases as time goes by.

Figure 39:
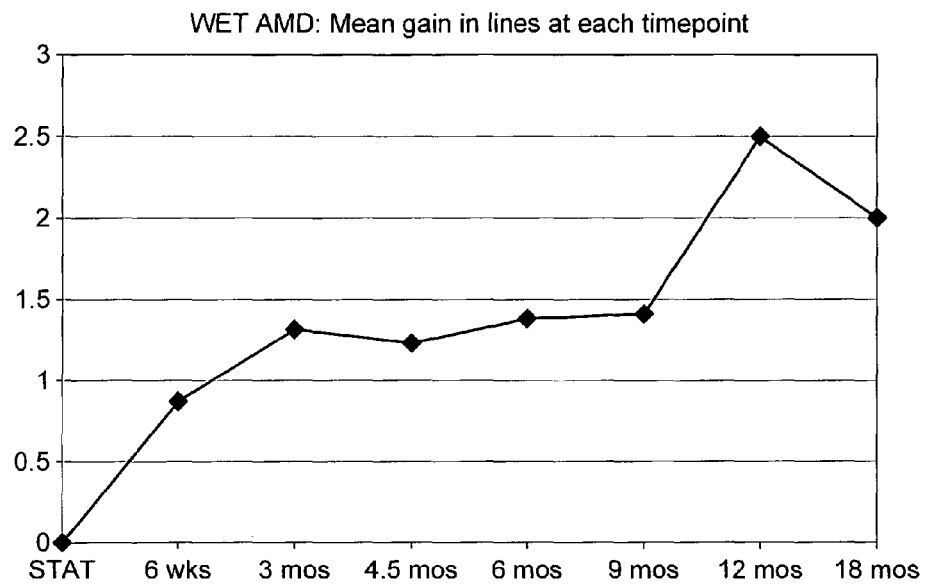
FIG. 39 shows the mean gain in lines of vision (Snellen chart) for patients having macular oedema caused by/associated with wet age-related macular degeneration at various time points following treatment with EPA and DHA.

The raw data regarding gains in lines were further examined, and the mean gain in lines at each time point were plotted, as shown in FIG. 39. From FIG. 39 it can be seen that on average there is a gain in lines of vision (all means are positive) and this gain in lines increases as time goes by.

Figure 40:
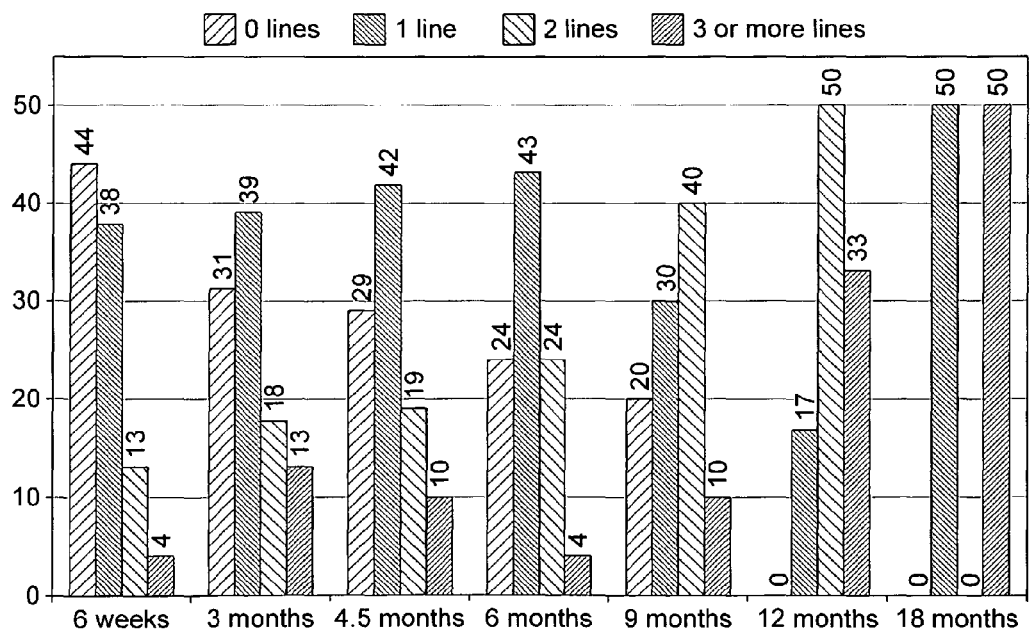
FIG. 40 shows the distribution of the number of lines of vision gained by patients having macular oedema caused by/associated with wet age-related macular degeneration at various time points following treatment with EPA and DHA.

FIG. 40 shows the comparative distributions for each number of lines of vision gained. More specifically it shows the number of patients that had a gain of zero lines at each time point (6 weeks to 18 months), and similarly for a gain of I line at each time point, for 2 and 3 or more lines.

It can be seen that at 6 weeks, most patients had no gain in lines (see blue bars) whereas at 3, 4.5 and 6 months most patients had gain of I line, while at 9 and 12 months most patients had gain of 2 lines (see yellow and red bars). Overall, no patient had zero gains in lines after 9 months (i.e. at 9, 12 or 18 months—no red or light blue at zero).

Figure 41:
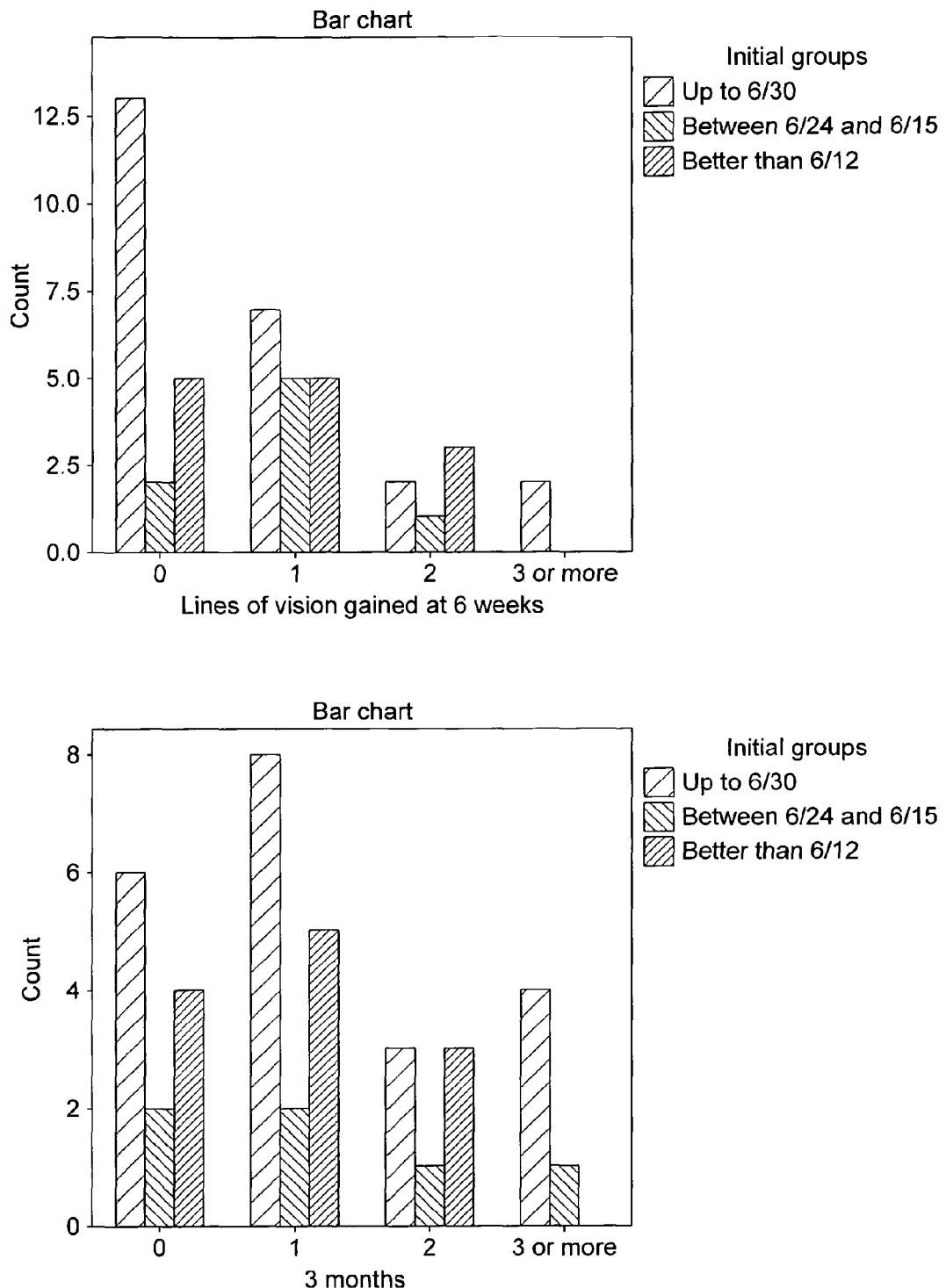
FIG. 41 shows the distribution for number of lines of vision gained by patients having macular oedema caused by/associated with wet age-related macular degeneration grouped into categories according to their initial vision, at various time points following treatment with EPA and DHA.
Figure 41:
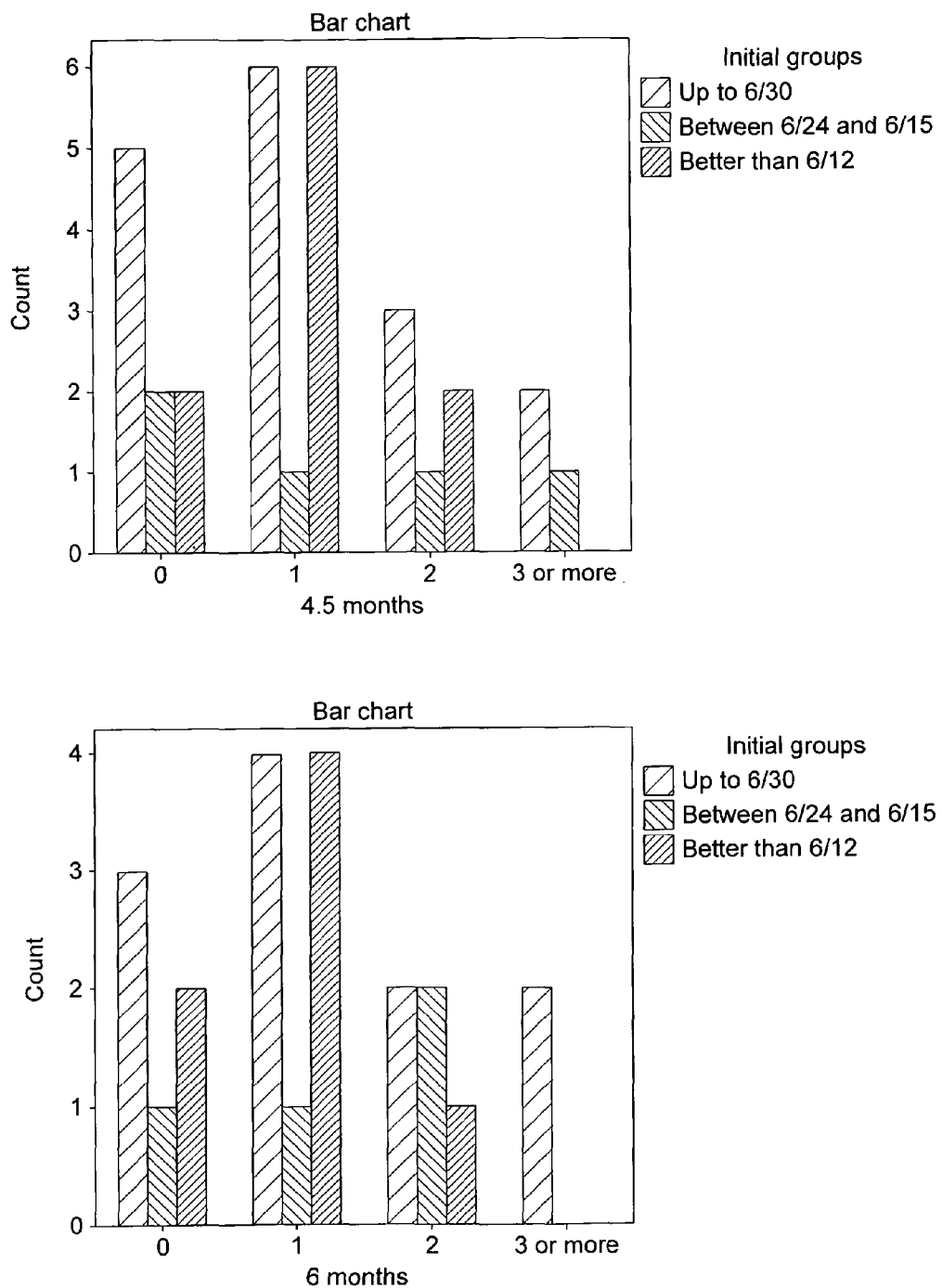
Figure 41:
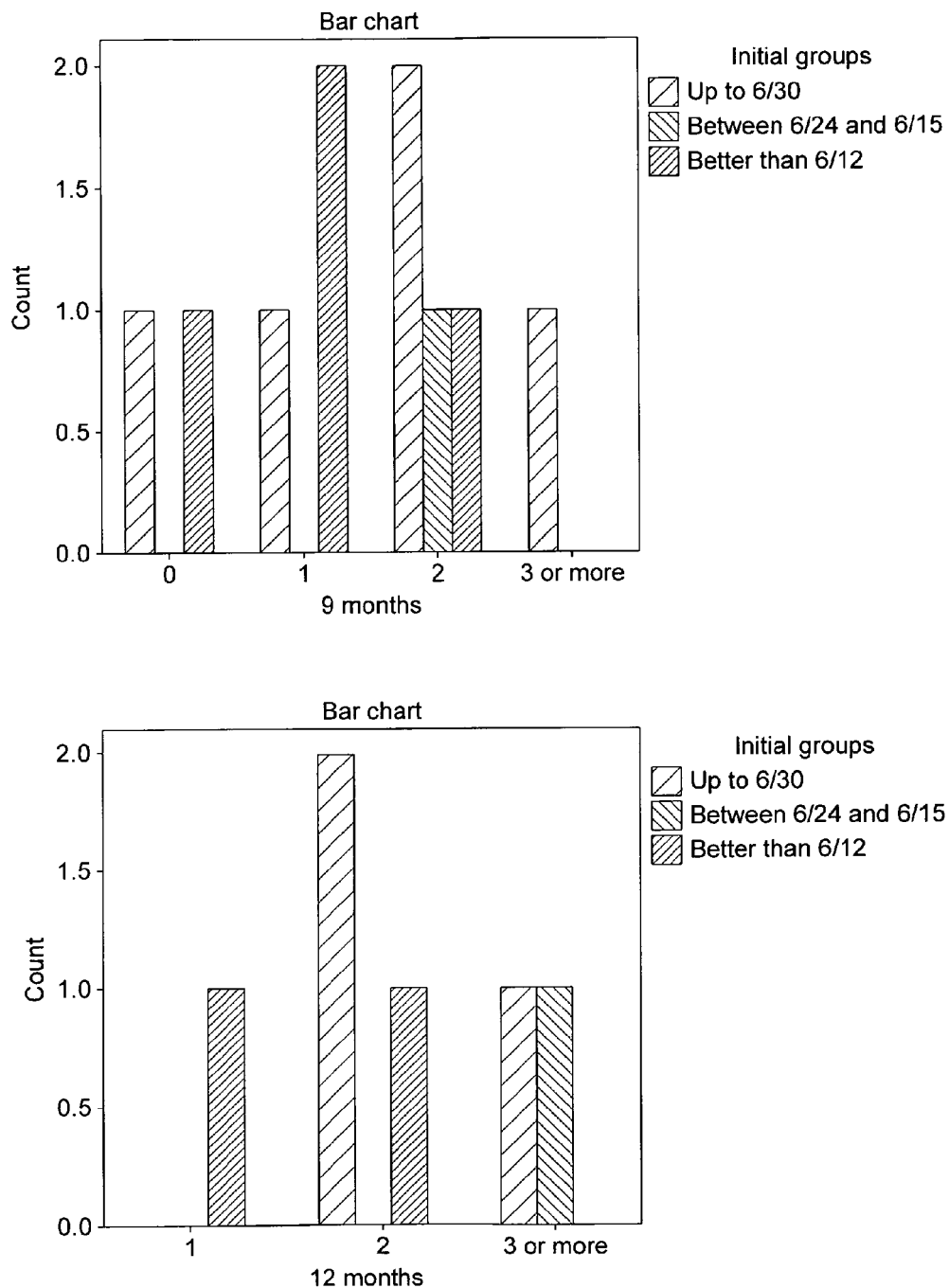
Figure 41:
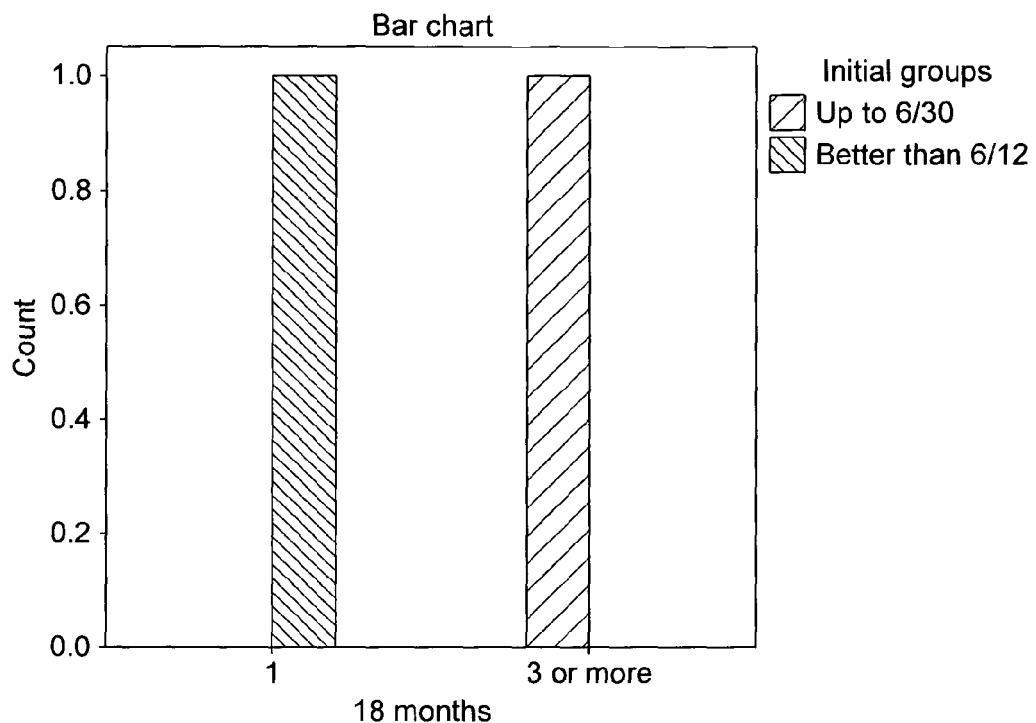

It was examined whether there is a relation between initial vision and number of lines gained (i.e. if people that started with a better vision had more improvement) and we see also how this improvement is through time (from 6 weeks to 18 months). In order to test it with chi-square tests, to see if the relation is statistically significant, grouping of initial vision categories was deemed necessary, due to the small number of patients in each cell. Grouping of initial vision in categories was 0=up to 6/30, 1=between 6/24 and 6/15 and 2=better than 6/12. Each of the graphs in FIG. 41 corresponds to one time-point. The p-value from the chi-square test is as follows (6 weeks P=0.402>5%; 3 months P=0.823>5%; 4.5 months P=0.731>5%; 6 months P=0.436>5%; 9 months, P=0.761>5%; 12 months, P=0.323>5%) If p<0.05 it means that it matters how the initial vision was in terms of the number of lines gained, otherwise the number of lines gained does not depend on the initial vision of the patient. In all the cases, p was larger than 5%.

Number of Injections in Relation to Omega 3RX® Therapy

1. Previous Injections:

For the 45 patients of Wet AMD, the mean number of previous injections was 6.6, with a standard deviation of 5.3:

TABLE 10

| | Number of patients | Minimum | Maximum | Mean | Std. Deviation |
|---|---|---|---|---|---|
| Number of previous injections | 45 | 0.00 | 25.00 | 6.5556 | 5.27669 |

The following table shows the distribution of the number of previous injections (number/percentage of patients who had each number of injections).

TABLE 11

| Number of injections | Number of patients | % of patients |
|---|---|---|
| 0 | 1 | 2.2% |
| 1-3 | 15 | 33.3% |
| 4-6 | 11 | 24.5% |
| 7-12 | 12 | 26.5% |
| ≥15 | 6 | 13.3% |
| Total patients: 45 | | 100% |

Number of months that patients had their last injection before starting Omega 3RX® Treatment:

Mean=4.5 months and standard deviation 6.7 months before Omega 3RX®. More details:

TABLE 12

| Mean | 4.5341 |
|---|---|
| Std. Deviation | 6.74313 |
| Minimum | 0.00 |
| Maximum | 29.00 |
| Number of patients | 44 |

(Note that one patient did not have an injection before or at STAT with Omega 3RX® Treatment, so they are not included in the above sample)

In more detail: Number of months that patients had their last injection before starting Omega 3RX® Treatment:

TABLE 13

| Last injection to initial Omega 3RX ® (months) | Number of patients | % of patients |
|---|---|---|
| STAT | 16 | 36.4 |
| 1-3 months | 13 | 29.5 |
| 4-6 months | 6 | 13.6 |
| 8-12 months | 3 | 6.8 |
| More than 1 year | 6 | 13.6 |
| Total patients: 44 (1 patient did not have an injection before or STAT with Omega 3RX ®) | | 100% |

WET AMD: Number of Avastin injections during treatment with Omega 3RX®.

TABLE 14

| Number of injections | Number of patients | % of patients |
|---|---|---|
| 0 | 29 | 64.4% |
| 1 | 14 | 31.1% |
| 2 | 2 | 4.4% |
| Total: 45 | | 100% |

From the above table it can be seen that most of the patients (64.4%) did not have an injection during their treatment with Omega 3RX®.

The results (about previous and current injections) were put in one table and graph, which shows the time of the previous injections before-STAT or during treatment in relation to the number of injections. The total number of injections can be considered (previous injections+STAT+during treatment for every patient). Note that since some patients had some injections before and some injections at STAT or during treatment, the table shows the time of the last injection for all patients.

TABLE 15

| | | | Time of last injection | | | |
|---|---|---|---|---|---|---|
| | | | Before treatment | STAT | During treatment | Total |
| Number of total injections | 1-3 injections | Number of patients | 5 | 5 | 3 | 13 |
| | | % | 38.5% | 38.5% | 23.1% | 100.0% |
| | 4-6 injections | Number of patients | 6 | 4 | 1 | 11 |
| | | % | 54.5% | 36.4% | 9.1% | 100.0% |
| | 7-12 injections | Number of patients | 11 | 2 | 1 | 14 |
| | | % | 78.6% | 14.3% | 7.1% | 100.0% |

TABLE 15-continued

|  |  |  | Time of last injection | | | |
|---|---|---|---|---|---|---|
|  |  |  | Before treatment | STAT | During treatment | Total |
|  | more than 15 injections | Number of patients | 6 | 0 | 0 | 6 |
|  |  | % | 100.0% | .0% | .0% | 100.0% |
| Total |  | Number of patients | 28 | 11 | 5 | 44 |
|  |  | % | 63.6% | 25.0% | 11.4% | 100.0% |

From the table it can be seen that most patients who had a lot of injections had them before their treatment with Omega 3RX®.

It can be examined how many of the patients who needed a lot of injections before their treatment with Omega 3RX® reduced their number of injections during their treatment. This is given by a cross tabulation:

Table with grouped categories:

TABLE 16

|  |  | Avastin during Omega 3RX ® | | | |
|---|---|---|---|---|---|
|  |  | 0 | 1 | 2 | Total |
| Previous injections | 0 | 1 | 0 | 0 | 1 |
|  | 1 | 0 | 7 | 0 | 7 |
|  | 2 | 1 | 1 | 0 | 2 |
|  | 3 | 4 | 1 | 1 | 6 |
|  | 4-6 | 6 | 4 | 1 | 11 |
|  | 7-10 | 8 | 1 | 0 | 9 |
|  | More than 10 | 9 | 0 | 0 | 9 |
| Total |  | 29 | 14 | 2 | 45 |

From the above tables, looking at the 29 patients (64.4%) who did not need any injection during their therapy with Omega 3RX®, most of them (17 patients or 59%) were those that had had a lot of previous injections (e.g more than 7). It appears that the number of Avastin injections is reduced significantly during therapy with Omega 3RX®.

It was examined whether the gain in lines of vision is related with the number of injections during Omega 3RX® treatment, at the various timepoints. A continuous variable "average gain in lines", which is the average gain in lines over all the time points (6 weeks, 3 months etc.) that data for each patient is available, was created.

1. Gain in Lines in Relation to Injections During Omega 3RX® Treatment:

An independent samples t-test was performed, where the p-value was found to be 0.494. This means that on average it does not affect the gain in lines whether a patient has an Avastin injection during the treatment or not. The mean gain in lines is similar for the two groups (1.07 for those who did not have any injection during the treatment and 1.25 for those who had an injection) (Notice that although 1.25 is higher than 1.07 the results of the test show that this difference is not statistically significant).

Table with Results from t-Test for Relation Between Gain in Lines of Vision and Avastin Injections During Omega 3RX® Treatment.

TABLE 17

| Avastin ® injections during Omega 3RX ® treatment | Number of patients | Mean gain in lines | Std. Deviation | t | p-value |
|---|---|---|---|---|---|
| 0 | 29 | 1.0690 | .92875 | −0.69 | 0.494 |
| 1 or 2 | 16 | 1.2563 | .75186 |  |  |

2. Gain in Lines in Relation to Number of Previous Injections (Before Omega 3Rx Treatment):

The raw data (i.e. not grouped in categories, as given for each patient, e.g. 8, 15 etc.) for the number of previous injections was used and examined with Pearson's correlation coefficient, if the number of previous injections affects the average gain in lines. The results showed that the number of previous injections affects the gain in lines negatively (Pearson's correlation coefficient is equal to −0.354, p-value=0.017<5%). In other words, if a patient had a lot of previous injections before the treatment then he/she will have on average a lower gain in lines of vision (or if he did not have a lot of previous injections then he will have on average a higher gain). This was further investigated when the data for the number of previous injections were now grouped in categories (0-3, 4-6, 7-12, more than 15), using one-way ANOVA and post-hoc Tukey tests. The tests showed that the previous conclusion did not hold for all the levels of previous injections, but a (marginally) significant difference in gains in lines existed only between the patients that had 4-6 previous injections and those that had more than 15 injections, (p=0.069<10%). More specifically, those who had more than 15 previous injections had on average lower gain in lines compared to those that had 4-6 injections (0.38 lines compared to 1.45 lines respectively). So, the group that had the highest mean gain in lines was those who had 4-6 previous injections (if we compared those with 4-6 injections with those in the group 0-3 injections and 7-12 injections, the differences were not, however, statistically significant (p-values 0.967 and 0.595 respectively, both larger than 5%).

Notice, of course, that for all four groups of previous injections the mean gain in lines is positive (so they all had a gain), and the average gain in lines for all patients was 1.14. The next table gives all the descriptive details.

TABLE 18

Table: Number of previous injections in relation to gain in lines of vision

| Number of previous injections | Number of patients | Mean gain in lines of vision | Std. Deviation |
|---|---|---|---|
| 0-3 injections | 16 | 1.2969 | 0.74307 |
| 4-6 injections | 11 | 1.4455 | 0.87105 |
| 7-12 injections | 12 | 1.0125 | 1.02206 |
| ≥15 injections | 6 | 0.3833 | 0.34157 |
| Total | 45 | 1.1356 | 0.86594 |

Group 2: CSMO (Clinically Significant Macular Oedema in Patients with Diabetic Retinopathy)
1. Demographics The sample included 34 patients (10 females, 22 males and 2 patients without a record of gender). Their average age was 64.6 years old, ranging from 53 to 79 years, with a standard deviation of 7.5 years (i.e. 64.6±7.5).

2. Descriptives of Thickness Per Time Point.

The average initial thickness of the patients was 511.9, ranging from 167 to 841, with a standard deviation of 180.3 (511.9±180.3).

The following table shows the minimum, maximum, average (mean) and standard deviation of thickness at each time point. In addition, the table shows how many patients were measured at each time point (N).

TABLE 19

Descriptive statistics of thickness at each time point (CSMO group).

| Time Point | N (Number of patients) | Minimum Thickness | Maximum Thickness | Mean macular oedema Thickness | Std. Deviation |
|---|---|---|---|---|---|
| INITIAL | 34 | 167 | 841 | 511.91 | 180.286 |
| 6 weeks | 34 | 153 | 767 | 445.18 | 181.181 |
| 3 months | 31 | 153 | 947 | 410.00 | 177.355 |
| 4.5 months | 24 | 153 | 927 | 405.71 | 178.622 |
| 6 months | 11 | 242 | 907 | 495.36 | 185.335 |
| 7.5 months | 4 | 255 | 623 | 474.50 | 155.941 |
| 9 months | 7 | 232 | 629 | 391.14 | 151.413 |
| 10.5 months | 4 | 185 | 381 | 297.75 | 93.128 |
| 12 months | 2 | 182 | 375 | 278.50 | 136.472 |

The results for mean thickness show that on average there is a reduction in thickness for all time points in relation to the initial thickness. Note: Reduction in relation to initial measurement is statistically significant at the 5% level (p<5%) (for all time points where paired samples t-test was used). The descriptive statistics in Table 20, show that thickness has reduced, on average, at each time point, in relation to the initial measurement.

To get a better insight of the reduction in thickness, descriptive statistics of the reduction in relation to initial thickness were obtained. All the descriptive statistics (mean thickness at each time point, standard deviation, number of patients measured at each time point) are given in Table 20.

TABLE 20

Descriptive statistics of thickness at each time point (CSMO group)

| | | Mean Thickness at each time point | Number of patients | Std. Deviation |
|---|---|---|---|---|
| Pair 1 | INITIAL THICKNESS | 511.91 | 34 | 180.286 |
| | 6 weeks | 445.18 | 34 | 181.181 |
| Pair 2 | INITIAL THICKNESS | 499.52 | 31 | 186.272 |
| | 3 months | 410.00 | 31 | 192.188 |
| Pair 3 | INITIAL THICKNESS | 536.96 | 24 | 161.380 |
| | 4.5 months | 405.71 | 24 | 180.619 |
| Pair 4 | INITIAL THICKNESS | 604.00 | 11 | 160.789 |
| | 6 months | 495.36 | 11 | 185.335 |
| Pair 5 | INITIAL THICKNESS | 556.75 | 4 | 117.831 |
| | 7.5 months | 474.50 | 4 | 155.941 |
| Pair 6 | INITIAL THICKNESS | 523.14 | 7 | 141.029 |
| | 9 months | 391.14 | 7 | 151.413 |
| Pair 7 | INITIAL THICKNESS | 556.75 | 4 | 117.831 |
| | 10.5 months | 297.75 | 4 | 93.128 |
| Pair 8 | INITIAL THICKNESS | 479.00 | 2 | 110.309 |
| | 12 months | 278.50 | 2 | 136.472 |

In addition, paired samples t-tests were performed, to examine whether the reduction of thickness at each time point in relation to the initial measurement was statistically significant at the 5% level of significance.

TABLE 21

Paired samples t-tests to examine for significant reduction in thickness at each time point (CSMO group)

| | | Mean Reduction in Thickness | Std. Deviation of reduction in thickness | 95% Confidence Interval of the Mean Thickness Lower | 95% Confidence Interval of the Mean Thickness Upper | t | df | p-value |
|---|---|---|---|---|---|---|---|---|
| Pair 1 | INITIAL - 6 weeks | 66.735 | 94.276 | 33.841 | 99.630 | 4.128 | 33 | <0.001** |
| Pair 2 | INITIAL - 3 months | 89.516 | 101.930 | 52.128 | 126.904 | 4.890 | 30 | <0.001** |
| Pair 3 | INITIAL - 4.5 months | 131.250 | 121.081 | 80.122 | 182.378 | 5.310 | 23 | <0.001** |
| Pair 4 | INITIAL - 6 months | 108.636 | 135.701 | 17.471 | 199.802 | 2.655 | 10 | 0.024* |
| Pair 5 | INITIAL - 7.5 months | 82.250 | 165.210 | -180.636 | 345.136 | N/A | N/A | N/A |
| Pair 6 | INITIAL - 9 months | 132.000 | 135.773 | 6.431 | 257.569 | 2.572 | 6 | 0.042* |
| Pair 7 | INITIAL - 10.5 months | 259.000 | 161.086 | 2.676 | 515.324 | N/A | N/A | N/A |
| Pair 8 | INITIAL - 12 months | 200.500 | 246.780 | -2016.733 | 2417.733 | N/A | N/A | N/A |

Reduction is significant at the 5% level, p<5% for all time points—Note that the statistical test is not valid for 7.5, 10.5 and 12 months due to the small number of patients, and thus the p-value is not reported).

Conclusions from all the previous tables, regarding the reduction in thickness: Looking at the above results, it can be seen that a reduction in oedema thickness has been shown statistically, since the mean reduction in thickness was positive at all time points and additionally the paired samples t-tests showed that this reduction was significant (all p-values were lower than 5% at the time points for which the paired samples t-test was performed and was valid).

Overall, the above results show that patients of the CSMO group, at each time point had, on average, significantly lower levels of thickness compared with the initial measurement.
Initial Vision and Gain in Vision (Number of Lines Gained)

The following table provides descriptives of initial vision for the CSMO group.

TABLE 22

| Initial Vision | Frequency (Number of patients) | % |
|---|---|---|
| 6/120 | 4 | 11.8 |
| 6/60 | 8 | 23.5 |
| 6/36 | 1 | 2.9 |
| 6/30 | 3 | 8.8 |
| 6/24 | 3 | 8.8 |
| 6/21 | 1 | 2.9 |
| 6/18 | 3 | 8.8 |
| 6/15 | 3 | 8.8 |
| 6/12 | 3 | 8.8 |
| 6/9 | 2 | 5.9 |
| 6/7.5 | 2 | 5.9 |
| 6/4.5 | 1 | 2.9 |
| Total | 34 | 100.0 |

From the above table, it can be seen that most of the patients had problematic initial vision, where 11.8% had vision of 6/120 and 23.5% 6/60.
Table 23 shows the gain in lines for patients at different time points-CSMO

TABLE 23

| Lines gained | 6 weeks (N = 34) | | 3 months (N = 30) | | 4.5 months (N = 24) | | 6 months (N = 13) | | 9 months (N = 8) | | 10.5 months (N = 4) | | 12 months (N = 2) | |
|---|---|---|---|---|---|---|---|---|---|---|---|---|---|---|
| | f | % | f | % | f | % | f | % | f | % | f | % | f | % |
| 0 | 14 | 41.2 | 9 | 30.0 | 7 | 29.2 | 6 | 46.2 | 4 | 50.0 | 1 | 25.0 | 0 | 0.0 |
| 1 | 16 | 47.1 | 11 | 36.7 | 10 | 41.7 | 2 | 15.4 | 2 | 25.0 | 2 | 50.0 | 0 | 0.0 |
| 2 | 2 | 5.9 | 4 | 13.3 | 1 | 4.2 | 2 | 15.4 | 1 | 12.5 | 0 | 0.0 | 1 | 50.0 |
| 3 or more | 2 | 5.9 | 6 | 20.0 | 6 | 25.0 | 3 | 23.1 | 1 | 12.5 | 1 | 25.0 | 1 | 50.0 |

Figure 42:
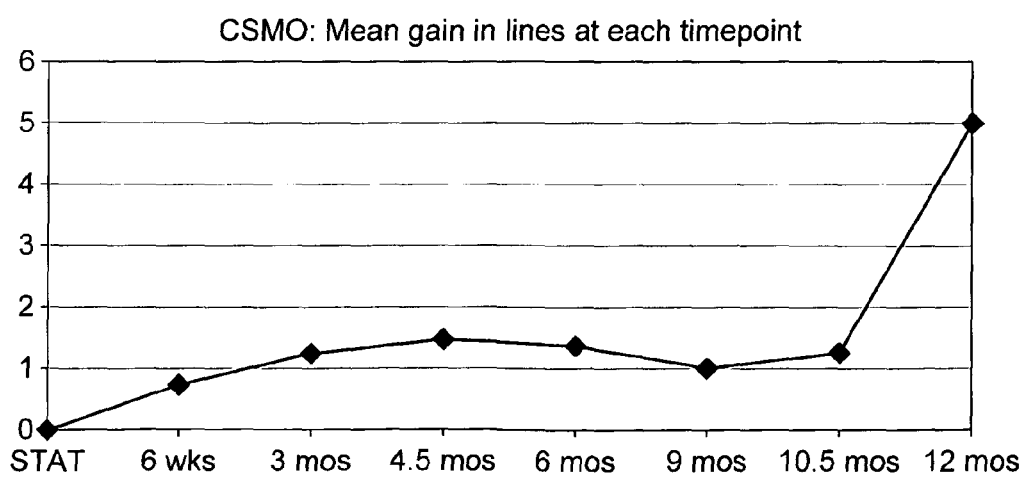
FIG. 42 shows the mean gain in lines of vision (Snellen chart) for patients having macular oedema caused by/associated with diabetic retinopathy at various time points following treatment with EPA and DHA.

The raw data regarding gains in lines were further examined, and the mean gain in lines at each timepoint were plotted, as shown in FIG. 42. From FIG. 42 it can be seen that on average there is gain in lines (all means are positive) and the gain constantly increases slightly as time goes by (there is a large increase at 12 months, but there are only have 2 patients for that time point).

Figure 43:
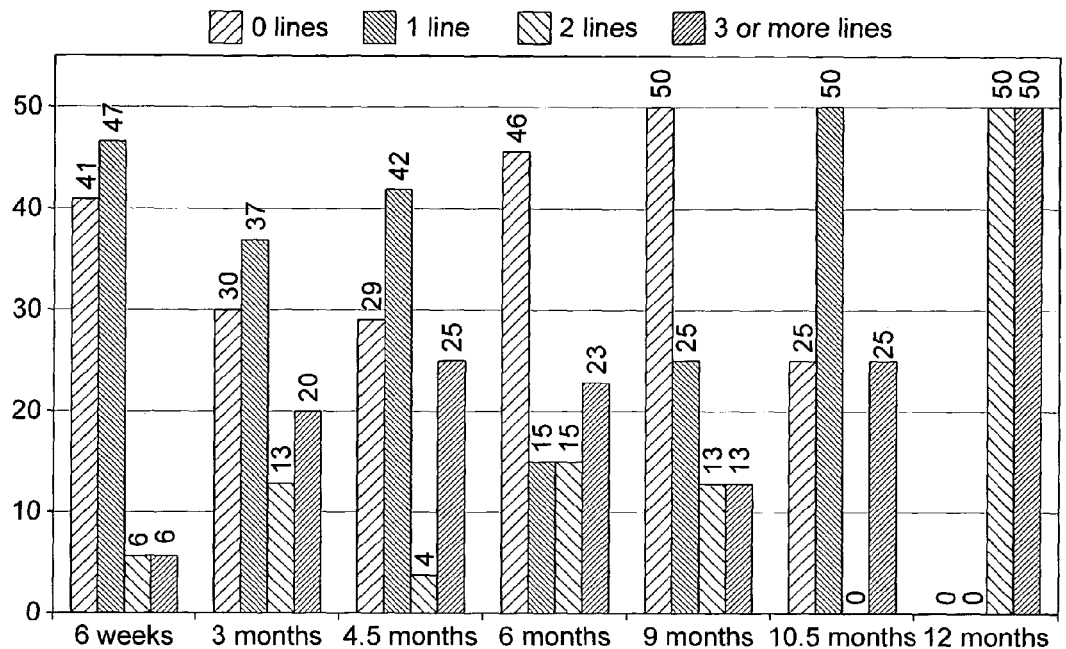
FIG. 43 shows the distribution of the number of lines of vision gained by patients having macular oedema caused by/associated with diabetic retinopathy at various time points following treatment with EPA and DHA.

FIG. 43 shows the comparative distributions for each number of lines of vision gained. More specifically it shows the number of patients that had a gain of zero lines at each time point (6 weeks to 12 months), and similarly for a gain of I line at each time point, for 2 and 3 or more lines.

Figure 44:
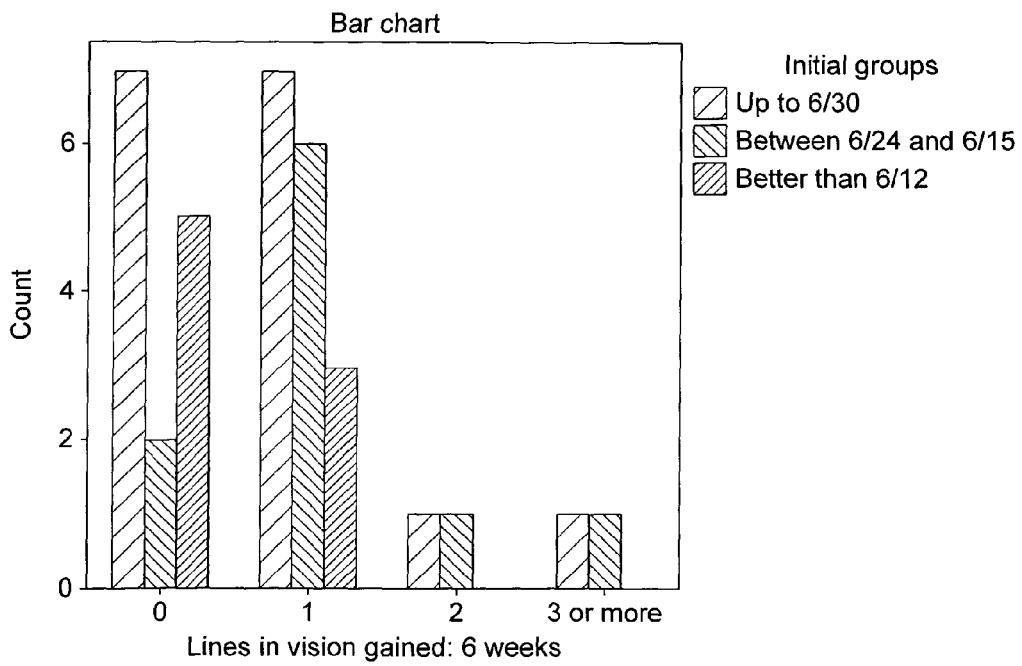
FIG. 44 shows the distribution for number of lines of vision gained by patients having macular oedema caused by/associated with diabetic retinopathy grouped into categories according to their initial vision, at various time points following treatment with EPA and DHA.
Figure 44:
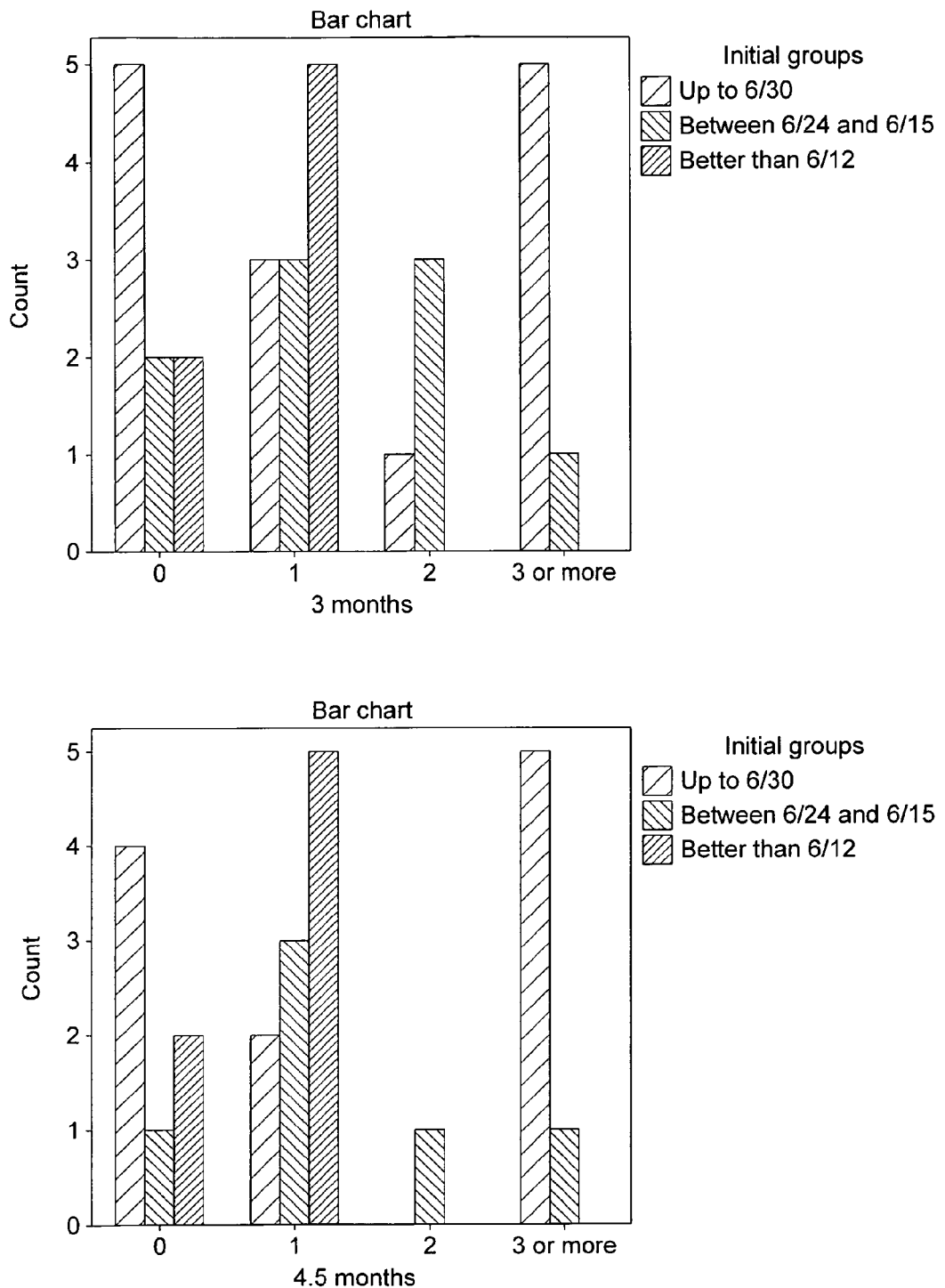

The relation between initial vision and number of lines gained can now be examined (i.e. if people that started with a better vision had more improvement) and it can be seen also how this improvement is through time. Grouping of initial vision in categories was 0=up to 6/30, 1=between 6/24 and 6/15 and 2=better than 6/12. The graphs for the time points which had an adequate number of patients for presentation are shown in FIG. 44. The graphs of FIG. 44 show that there is no relation between initial vision and gain in lines. To explain this in simple words: for example, looking at the graph for 4.5 months, it appears that it does not make a difference if a patient started with a very bad initial vision (up to 6/30) in terms of the gain in lines (e.g. we expected maybe that if someone started off with a good vision that he would get more lines gained, or if he started with a bad vision that he would get fewer lines gained, but none of the two seems to be true). In general, good or bad initial vision does not seem to be related to gain in lines.

Number of Injections in Relation to Omega 3RX® Therapy
2. Previous Injections:

For the 34 patients of CSMO, the mean number of previous injections was 3.5, with a standard deviation of 3.7:

TABLE 24

| | Number of patients | Minimum | Maximum | Mean | Std. Deviation |
|---|---|---|---|---|---|
| Number of previous injections | 34 | .00 | 12.00 | 3.5 | 3.71116 |

The following tables and the pie chart show the distribution of the number of previous injections (number/percentage of patients who had each number of injections).

TABLE 25

| Number of injections | Number of patients | % of patients |
|---|---|---|
| 0 | 7 | 20.6% |
| 1-2 | 15 | 44.1% |
| 6-7 | 7 | 20.6% |
| ≥10 | 5 | 14.7% |
| Total patients: 34 | | 100% |

Number of Months that Patients Had their Last Injection Before Starting Omega 3RX® Treatment:
Mean=14.7 months and standard deviation 13.7 months before Omega 3RX®. More details:

TABLE 26

| Mean | 14.7037 |
|---|---|
| Std. Deviation | 13.67146 |
| Minimum | 0 |
| Maximum | 48 |
| Number of patients | 27 |

(Notice that 7 patients did not have an injection before or at STAT with Omega 3RX® Treatment, so they are not included in the above sample)
In more detail: Number of months that they had their last injection before starting Omega 3RX® Treatment:

TABLE 27

| Last injection to initial Omega 3RX ® (months) | Number of patients | % of patients |
|---|---|---|
| STAT | 1 | 3.7 |
| 1-4 months | 5 | 18.5 |
| 6-9 months | 7 | 25.9 |
| 1-2 years | 10 | 37.0 |
| 3-4 years | 4 | 14.8 |
| Total patients: 27 (7 patients did not have an injection before or STAT with Omega 3RX ®) | | 100% |

CSMO: Number of Avastin® Injections During Treatment with Omega 3RX®.

TABLE 28

| Number of injections | Number of patients | % of patients |
|---|---|---|
| 0 | 29 | 85.3 |
| 1 | 5 | 14.7 |
| Total: 34 | | 100% |

From the above table it can be seen that most of the patients (85.3%) did not have an injection during their treatment with ®.

Focal laser: the following table shows the number of times that patients in the CSMO group had focal laser.

TABLE 29

| Number of times of focal laser | Number of patients | % |
|---|---|---|
| .00 | 12 | 35.3 |
| 1.00 | 14 | 41.2 |
| 2.00 | 4 | 11.8 |
| 3.00 | 4 | 11.8 |
| Total | 34 | 100.0 |

Regarding the time of doing focal laser, of those who had done laser (i.e. 22 patients), 19 patients (86%) had done it before treatment, 2 patients (9%) after the treatment and for one patient the dates of focal laser treatment were not available.

It can be examined how many of the patients who needed a lot of injections before their treatment with Omega 3RX®, reduced their number of injections during their treatment. This will be given by a cross tabulation and a graph.

Table with grouped categories:

TABLE 30

| | | Avastin ® during O3 Rx | | |
|---|---|---|---|---|
| | | 0 | 1 | Total |
| Previous injections | 0 | 5 | 2 | 7 |
| | 1 | 7 | 1 | 8 |
| | 2 | 6 | 1 | 7 |
| | 6-7 | 7 | 0 | 7 |
| | More than 10 | 4 | 1 | 4 |
| Total | | 29 | 5 | 34 |

From the above table, looking at the 29 patients (85.3%) who did not need any injection during their therapy with Omega 3RX®, 7 (24%) had had 6-7 previous injections. It appears that the number of Avastin injections is reduced significantly during therapy with Omega 3RX®.

It can be examined whether the gain in lines of vision is related with the number of injections before and during Omega 3RX® treatment, at the various timepoints.
Gain in Lines in Relation to Injections During Omega 3RX® Treatment:

An independent samples t-test was performed, where the p-value was found to be 0.129. This means that on average it does not affect the gain in lines whether you have an Avastin injection during the treatment or not. The mean gain in lines was 1.27 for those who did not have any injection during the treatment and 0.57 for those who had an injection, but according to the statistical test this difference is not significant ($p=0.129>5\%$)

Table with Results from t-Test for Relation Between Gain in Lines of Vision and Avastin Injections During Omega 3rx Treatment.

TABLE 31

| Avastin ® injections during Omega 3RX ® treatment | Number of patients | Mean gain in lines | Std. Deviation | t | p-value |
|---|---|---|---|---|---|
| 0 | 29 | 1.2659 | 0.89997 | 1.558 | 0.129 |
| 1 | 5 | 0.5680 | 1.08336 | | |

Gain in Lines of Vision in Relation to Number of Previous Injections (Before Omega 3RX® Treatment):

The results showed that the number of previous injections is not significantly related to the gain in lines (Pearson's correlation coefficient is equal to −0.029, p-value=0.029<5%). In other words, it does not make any difference how many injections the patient had before the treatment in terms of the gain in lines of vision that he will have.

Similar results were obtained using a one-way ANOVA test when treating the number of previous injections as categories (p-value=0.161>5%), which again shows that the number of previous injections does not affect the gain in lines of vision.
Group 3: OTHER (4 Eyes with BRVO (Macular Oedema in Patients with Branch Retinal Vein Occlusion) and 8 Eyes with CMO (Patients with Cystoid Macular Oedema)
1. Demographics The sample included 12 patients (6 females, 6 males, 50% each group). Their average age was 53.8 years, ranging from 10 to 78 years, with a standard deviation of 23 years (i.e. 53.8±23).

2. Descriptives of Thickness Per Time Point.

The average initial thickness of the patients was 510.33, ranging from 307 to 820, with a standard deviation of 155.5 (510.3±155.5).

The following table shows the minimum, maximum, average (mean) and standard deviation of thickness at each time point. In addition, the table shows how many patients were measured at each time point (N).

TABLE 32

Descriptive statistics of thickness at each time point.

| Time Point | N (Number of patients) | Minimum Thickness | Maximum Thickness | Mean macular oedema Thickness | Std. Deviation |
|---|---|---|---|---|---|
| INITIAL | 12 | 309 | 820 | 510.33 | 155.522 |
| 6 weeks | 12 | 207 | 767 | 416.75 | 155.682 |
| 3 months | 9 | 163 | 694 | 342.22 | 162.286 |
| 4.5 months | 7 | 155 | 719 | 324.00 | 195.371 |
| 6 months | 4 | 190 | 699 | 337.25 | 242.040 |
| 7.5 months | 3 | 190 | 618 | 351.00 | 232.858 |
| 9 months | 2 | 190 | 245 | 217.50 | 38.891 |
| 10.5 months | 2 | 190 | 256 | 223.00 | 46.669 |
| 12 months | 1 | 190 | 190 | 190.00 | N/A |
| 18 months | 1 | 190 | 190 | 190.00 | N/A |

The descriptive statistics in Table 32 show that thickness has reduced, on average, at each time point, in relation to the initial measurement.

To get a better insight of the reduction in thickness, descriptive statistics of the reduction in relation to initial thickness were obtained. All the descriptive statistics (mean thickness at each time point, standard deviation, number of patients measured at each time point) are given in Table 33.

TABLE 33

Descriptive statistics of thickness at each time point (other group)

| | | Mean Thickness at each time point | Number of patients | Std. Deviation |
|---|---|---|---|---|
| Pair 1 | INITIAL THICKNESS | 510.33 | 12 | 155.522 |
| | 6 weeks | 416.75 | 12 | 155.682 |
| Pair 2 | INITIAL THICKNESS | 493.00 | 9 | 149.044 |
| | 3 months | 342.22 | 9 | 162.286 |
| Pair 3 | INITIAL THICKNESS | 514.14 | 7 | 161.711 |
| | 4.5 months | 324.00 | 7 | 195.371 |
| Pair 4 | INITIAL THICKNESS | 560.75 | 4 | 208.674 |
| | 6 months | 337.25 | 4 | 242.040 |
| Pair 5 | INITIAL THICKNESS | 563.00 | 3 | 255.513 |
| | 7.5 months | 351.00 | 3 | 232.858 |
| Pair 6 | INITIAL THICKNESS | 434.50 | 2 | 177.484 |
| | 9 months | 217.50 | 2 | 38.891 |
| Pair 7 | INITIAL THICKNESS | 434.50 | 2 | 177.484 |
| | 10.5 months | 223.00 | 2 | 46.669 |
| Pair 8 | INITIAL THICKNESS | 309.00 | 1 | n/a |
| | 12 months | 190.00 | 1 | n/a |
| Pair 9 | INITIAL THICKNESS | 309.00 | 1 | n/a |
| | 18 months | 190.00 | 1 | n/a |

In addition, paired samples t-tests were performed, to examine whether the reduction of thickness at each time point in relation to the initial measurement was statistically significant at the 5% level of significance.

TABLE 34

Paired samples t-tests to examine for significant reduction in thickness at each time point (other group)

| | | Mean Reduction in Thickness | Std. Deviation of reduction in thickness | 95% Confidence Interval of the Mean Thickness | | t | df | p-value |
|---|---|---|---|---|---|---|---|---|
| | | | | Lower | Upper | | | |
| Pair 1 | INITIAL - 6 weeks | 93.583 | 101.247 | 29.254 | 157.913 | 3.202 | 11 | 0.008* |
| Pair 2 | INITIAL - 3 months | 150.778 | 85.834 | 84.800 | 216.755 | 5.270 | 8 | <0.001** |
| Pair 3 | INITIAL - 4.5 months | 190.143 | 87.068 | 109.619 | 270.667 | 5.778 | 6 | <0.001** |
| Pair 4 | INITIAL - 6 months | 223.500 | 119.651 | 33.109 | 413.891 | 3.736 | 3 | 0.033* |
| Pair 5 | INITIAL - 7.5 months | 212.000 | 98.382 | −32.394 | 456.394 | n/a | n/a | n/a |
| Pair 6 | INITIAL - 9 months | 217.000 | 138.593 | n/a | n/a | n/a | n/a | n/a |
| Pair 7 | INITIAL - 10.5 months | 211.500 | 130.815 | −963.824 | 1386.824 | n/a | n/a | n/a |
| Pair 8 | INITIAL - 12 months | n/a | n/a | n/a | n/a | n/a | n/a | n/a |
| Pair 9 | INITIAL THICKNESS- 18 months | n/a | n/a | n/a | n/a | n/a | n/a | n/a |

Reduction is significant at the 5% level, p<5% for all time points where the paired samples t-test was performed—Note that the statistical test is not valid for 7.5, 9, 10.5, 12 and 18 months due to the small number of patients, and thus the p-value is not reported).

Conclusions from all the previous tables, regarding the reduction in thickness: Looking at the above results, it can be seen that a reduction in oedema thickness has been shown statistically, since the mean reduction in thickness was positive at all time points and additionally the paired samples t-tests showed that this reduction was significant (all p-values were lower than 5% at the time points for which the paired samples t-test was performed and was valid), in relation to the initial thickness.

Overall, the above results show that patients of the other group, at each time point had, on average, significantly lower levels of thickness compared with the initial measurement.

Initial Vision and Gain in Vision (Number of Lines Gained)

The following table provides descriptives of initial vision for the other group. The same results appear also graphically below, with a bar chart.

TABLE 35

| Initial Vision | Frequency (Number of patients) | % |
|---|---|---|
| CF | 1 | 8.3 |
| 6/36 | 1 | 8.3 |
| 6/24 | 1 | 8.3 |
| 6/18 | 1 | 8.3 |
| 6/15 | 1 | 8.3 |
| 6/12 | 4 | 33.3 |
| 6/9 | 2 | 16.7 |
| 6/7.5 | 1 | 8.3 |
| Total | 12 | 100.0 |

Table 36 shows the gain in lines for patients at different time points-OTHER

TABLE 36

| Lines gained | 6 weeks (N = 12) | | 3 months (N = 9) | | 4.5 months (N = 7) | | 6 months (N = 4) | | 9 months (N = 3) | | 12 months (N = 1) | | 18 months (N = 1) | |
|---|---|---|---|---|---|---|---|---|---|---|---|---|---|---|
| | f | % | f | % | f | % | f | % | f | % | f | % | f | % |
| 0 | 3 | 25.0 | 1 | 11.1 | 0 | 0.0 | 0 | 0.0 | 0 | 0.0 | 0 | 0.0 | 0 | 0.0 |
| 1 | 7 | 58.3 | 3 | 33.3 | 3 | 42.9 | 1 | 25.0 | 1 | 33.3 | 0 | 0.0 | 0 | 0.0 |
| 2 | 2 | 16.7 | 3 | 33.3 | 3 | 42.9 | 2 | 50.0 | 1 | 33.3 | 0 | 0.0 | 0 | 0.0 |
| 3 or more | 0 | 0.0 | 2 | 22.2 | 1 | 14.3 | 1 | 25.0 | 1 | 33.3 | 1 | 100.0 | 1 | 100.0 |

It can be seen from the table that at 6 weeks 25% of patients had no gain, but this number was reduced to zero after 3 months.

Figure 45:
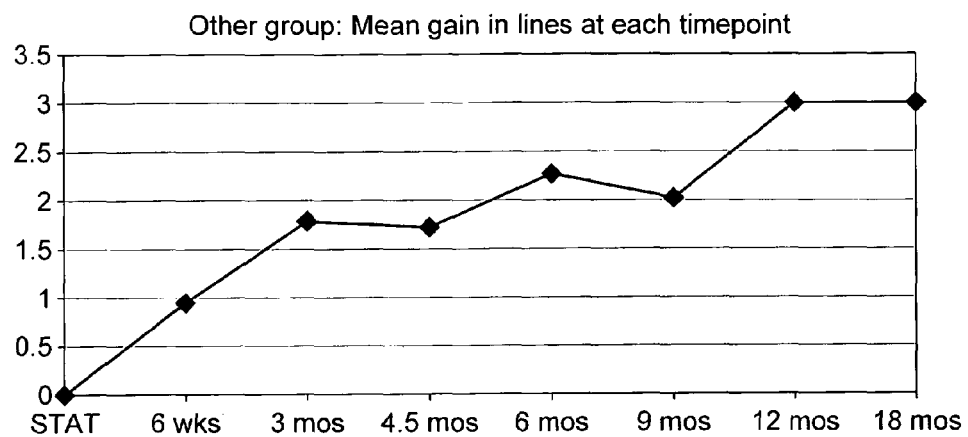
FIG. 45 shows the mean gain in lines of vision (Snellen chart) for patients having macular oedema caused by/associated with branch retinal vein occlusions and/or cystoid macular oedema secondary to inflammation or surgery, at various time points following treatment with EPA and DHA.
Figure 46:
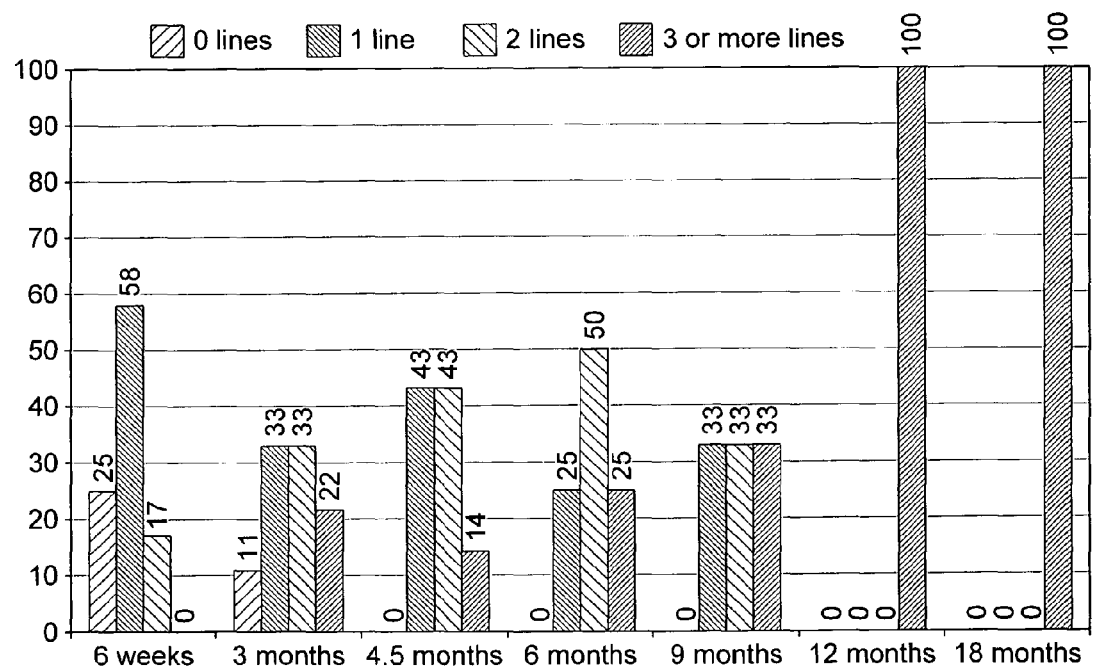
FIG. 46 shows the distribution of the number of lines of vision gained by patients having macular oedema caused by/associated with branch retinal vein occlusions and/or cystoid macular oedema secondary to inflammation or surgery, at various time points following treatment with EPA and DHA.

The raw data regarding gains in lines were further examined, and the mean gain in lines at each time point were plotted, as shown in FIG. 45:

FIG. 46 shows the comparative distributions for each number of lines of vision gained. More specifically it shows the number of patients that had a gain of zero lines at each time point (6 weeks to 18 months), and similarly for a gain of 1 line at each time point, for 2 and 3 or more lines.

It can be seen from Table 36 and FIGS. 45 and 46 that patients had more gain in lines of vision as time went by. More specifically we can see how the zero gain disappears after 3 months and how the gain of 3 or more lines increases.

Number of Injections in Relation to Omega 3RX® Therapy
3. Previous Injections:

For the 12 patients of the other group, the mean number of previous injections was 2.2, with a standard deviation of 3.4:

TABLE 37

| | Number of patients | Minimum | Maximum | Mean | Std. Deviation |
|---|---|---|---|---|---|
| Number of previous injections | 12 | .00 | 10.00 | 2.1667 | 3.43335 |

The following tables show the distribution of the number of previous injections (number/percentage of patients who had each number of injections).

TABLE 38

| Number of injections | Number of patients | % of patients |
|---|---|---|
| 0 | 6 | 50.0 |
| 1 | 2 | 16.7 |
| 2 | 1 | 8.3 |
| 4 | 1 | 8.3 |
| 8 | 1 | 8.3 |
| 10 | 1 | 8.3 |
| Total patients: 12 | | 100% |

Number of Months that Patients Had their Last Injection Before Starting Omega 3RX® Treatment:

Mean=4.3 months and standard deviation 2 months before Omega 3RX®. More details:

TABLE 39

| Mean | 4.2500 |
|---|---|
| Std. Deviation | 2.04328 |
| Minimum | 2.50 |

TABLE 39-continued

| Maximum | 8.00 |
|---|---|
| Number of patients | 6 |

(Notice that 6 patients did not have an injection before or at STAT with Omega 3RX® Treatment, so they are not included in the above sample)

Number of Months that they Had their Last Injection Before Starting Omega 3RX® Treatment:

TABLE 40

| Last injection to initial Omega 3RX ® (months) | Number of patients | % of patients |
|---|---|---|
| 2.50 | 1 | 16.7 |
| 3.00 | 2 | 33.3 |

TABLE 40-continued

| Last injection to initial Omega 3RX ® (months) | Number of patients | % of patients |
|---|---|---|
| 4.00 | 1 | 16.7 |
| 5.00 | 1 | 16.7 |
| 8.00 | 1 | 16.7 |
| Total patients: 6 (6 patients did not have an injection before or STAT with Omega 3RX ®) | | 100% |

Other Group: Number of Avastin® Injections During Treatment with Omega 3RX®.

None of the patients in this group had an injection during treatment with Omega 3RX®. Therefore either the number of injections remained the same (for those who had no previous injections they did not have any during the treatment either) or it was reduced to zero (for those that had some injections before the treatment).

It can now be examined whether the gain in lines of vision is related with the number of injections before Omega 3RX® treatment, at the various timepoints. The continuous variable "average gain in lines", which is the average gain in lines over all the time points that we have data for each patient, was created.

The results showed that the number of previous injections is not related to the gain in lines (correlation coefficient is equal to −0.242, p-value=0.448>5%). In other words, it does not matter how many injections the patient had before the treatment in terms of the gain in lines of vision that he will have.

Similar results were obtained using a one-way ANOVA test when treating the number of previous injections as categories (p-value=0.405>5%), which again shows that the number of previous injections does not affect the gain in lines of vision.

Group 4: Severe Dry Eyes

All 40 eyes with dry eyes unresponsive to any other ocular treatment showed improvement between 70-90% of the superficial punctate keratitis and tear break up time after 1 month following treatment with Omega 3RX®. Also patients reported marked improvement of the dryness, watering and foreign body sensation of their eyes within 1 month of treatment.

These patients had been treated for long periods of time with most of the current therapies available in the market such as steroid eye drops, artificial tear drops and oinmtents, Restasis® eye drops, punctual plugs, other omega 3 supplements etc. with no relief of their symptoms.

The following table shows the classification of dry eyes. The patients had most of the symptoms and signs of severity score 3 and 4 (moderate to severe dry eyes).

TABLE 41

Dry eye severity grading scheme

| | Dry Eye Severity Level | | | |
|---|---|---|---|---|
| | 1 | 2 | 3 | 4 |
| Discomfort, severity and frequency | Mild and/or episodic; occurs under environmental stress | Moderate episodic or chronic, stress or no stress | Severe frequent or constant without stress | Severe and/or disabling and constant |
| Visual symptoms | None or episodic mild fatigue | Annoying and/or activity-limiting episodic | Annoying, chronic and/or constant, limiting activity | Constant and/or possibly disabling |
| Conjunctival injection | None to mild | None to mild | +/− | +/+ + |
| Conjunctival staining | None to mild | Variable | Moderate to marked | Marked |
| Corneal staining (severity/location) | None to mild | Variable | Marked central | Severe punctuate erosions |
| Corneal/tear signs | None to mild | Mild debris, ∇ meniscus | Filamentary keratitis, mucus clumping, Δ tear debris | Filamentary keratitis, mucus clumping, Δ tear debris, ulceration |
| Lid/meibomian | MGD variably present | MGD variably present | Frequent | Trichasis, keratinization, symblepharon |
| TFBUT (sec) | Variable | ≤10 | ≤5 | Immediate |
| Schirmer score (mm/5 min) | Variable | ≤10 | ≤5 | ≤2 |

*Must have signs and symptoms. TFBUT: fluorescein tear break-up time. MGD: meibomian gland disease
The table above shows: The Definition & Classification of Dry Eye Disease Guidelines from the 2007 International Dry Eye Workshop Discussion Oral Omega 3RX® appears to be an effective treatment for macular oedema secondary to wet macular degeneration, diabetic maculopathy, retinal vein occlusions and following surgery or inflammation. Eyes treated with oral Omega 3RX® showed a significant reduction in macular thickness and improvement in visual acuity. Also treatment for severe dry eyes with Omega 3RX® has been shown to produce marked improvement of signs and symptoms of the patients. Treatment seems to be well tolerated with no systemic side effects.

The case studies have shown using OCT scan documentation that, using Omega 3RX® in the liquid form as monotherapy or sometimes in combination with anti-VEGF injections in patients with macular oedema, macular thickness can be reduced or even eliminated in patients with macular oedema resulting in improvement of visual acuity. In addition no ocular or systemic side effects were shown.

There is continued reduction of macular oedema for patients taking the Omega3RX®. Significant reduction over the following months for patients who continue with the treatment has been shown.

Dry eye is one of the common disorders encountered in clinical practise. Ocular surface inflammation is considered an important pathologic factor of dry eye. Patients with dry eyes (moderate to severe dry eyes) who were unresponsive to other treatments have shown improvements after using Omega 3RX®.

Treatment with Omega 3RX® appears to be safe and effective in moderate to severe chronic dry eye.

Omega 3RX® liquid is recommended to be used in the following diseases:
  Age related macular degeneration (wet type)
  Diabetic retinopathy
  Retinal vascular occlusions (branch or central)
  Cystoid macular oedema following surgery or inflammation
  Other causes of oedema such as central serious retinopathy, RPE atrophy
  Dry age related macular degeneration to prevent the risk from developing to wet.
  Dry eyes Oral treatment is a huge advantageous to the patients compared to monthly expensive intravitreal injections.

In some cases, monotherapy may need to be the only treatment. The aim of treatment is to maximise outcomes and minimise side effects. Always the desired end result should be a flat retina without continuous retreatments. Combination therapies may provide better overall outcomes for some patients.

The invention claimed is:

1. A method of treating and/or preventing a condition comprising administering eicosapentaenoic acid (EPA) and docosahexaenoic acid (DHA), or a salt or an ester thereof, to a subject in need thereof, wherein said condition is selected from the group consisting of macular oedema, conditions causing damage to retinal photoreceptors and/or retinal pigment epithelial cells, and dry eyes in a mammal, and wherein a combined dosage of eicosapentaenoic acid and docosahexaenoic acid from 5 mmol to 25 mmol per day is administered, and wherein the eicosapentaenoic acid to the docosahexaenoic acid is in a molar ratio from 1:1 to 5:1, and wherein the dosage of eicosapentaenoic acid is from 4 mmol to 15 mmol per day and the dosage of docosahexaenoic acid is from 2 mmol to 7.5 mmol per day.

2. The method of claim 1, wherein the condition is macular oedema or dry eyes.

3. The method of claim 1, wherein the condition is macular oedema.

4. The method of claim 3, wherein the macular oedema is caused by or associated with wet age-related macular degeneration, diabetic retinopathy, retinal vascular occlusion and/or inflammation of the eye.

5. The method of claim 2, wherein the subject administered with said eicosapentaenoic acid and docosahexaenoic acid poorly responsive or non responsive to treatment with a VEGF inhibitor.

6. The method of claim 1, wherein the condition is dry eyes.

7. The method of claim 6, wherein the condition is moderate or severe dry eyes.

8. The method of claim 6, wherein the subject administered with said eicosapentaenoic acid and docosahexaenoic acid is poorly responsive or non responsive to treatment with steroid eye drops, artificial tear drops, tear lubricating ointments, steroid ointments, punctual plugs and/or cyclosporine eye drops.

9. The method of claim 1, wherein the conditions causing damage to retinal photoreceptors and/or retinal pigment epithelial cells are selected from the group consisting of retinitis pigmentosa, Stargardt's disease, damage caused by exposure to extreme light, damage associated with surgery, damage associated with exposure to chemical toxins, macular dystrophy and dry age-related macular degeneration.

10. The method of claim 1, wherein the molar ratio of eicosapentaenoic acid to docosahexaenoic acid is in the range of from 2:1 to 2.4:1.

11. The method of claim 1, wherein said Eicosapentaenoic acid and docosahexaenoic acid are administered, together with a further therapeutic agent simultaneously, sequentially or separately, said therapeutic agent comprising a VEGF inhibitor, a steroid, a carbonic anhydrase inhibitor and/or cyclosporine.

12. The method of claim 2, wherein the macular oedema is caused by or associated with wet age-related macular degeneration, diabetic retinopathy, retinal vascular occlusion and/or inflammation of the eye.

13. The method of claim 3, wherein the subject administered with said eicosapentaenoic acid and docosahexaenoic acid is poorly responsive or non responsive to treatment with a VEGF inhibitor.

* * * * *